US012735416B2

(12) United States Patent
Du et al.

(10) Patent No.: US 12,735,416 B2
(45) Date of Patent: Sep. 15, 2026

(54) AROMATIC COMPOUND AND USE THEREOF IN PREPARING ANTINEOPLASTIC DRUGS

(71) Applicant: Shanghai Zheye Biotechnology Co. Ltd., Shanghai (CN)

(72) Inventors: Fengtian Du, Shanghai (CN); Haibo Wang, Shanghai (CN); Qiang Zhang, Shanghai (CN)

(73) Assignee: Shanghai Zheye Biotechnology Co. Ltd., Shanghai (CN)

( * ) Notice: Subject to any disclaimer, the term of this patent is extended or adjusted under 35 U.S.C. 154(b) by 1064 days.

(21) Appl. No.: 17/800,750

(22) PCT Filed: Feb. 23, 2021

(86) PCT No.: PCT/CN2021/077516
§ 371 (c)(1),
(2) Date: Aug. 18, 2022

(87) PCT Pub. No.: WO2021/169963
PCT Pub. Date: Sep. 2, 2021

(65) Prior Publication Data

US 2023/0143751 A1 May 11, 2023

(30) Foreign Application Priority Data

Feb. 24, 2020 (CN) ......................... 202010113349.1
Mar. 2, 2020 (CN) ......................... 202010136460.2
(Continued)

(51) Int. Cl.
*C07D 471/04* (2006.01)
*A61P 35/00* (2006.01)
*C07D 401/14* (2006.01)

(52) U.S. Cl.
CPC ............ *C07D 471/04* (2013.01); *A61P 35/00* (2018.01); *C07D 401/14* (2013.01)

(58) Field of Classification Search
CPC ............................ C07D 471/04; C07D 401/14
See application file for complete search history.

(56) References Cited

U.S. PATENT DOCUMENTS

2019/0292182 A1 9/2019 Kuramoto et al.
2019/0374542 A1 12/2019 Allen et al.

FOREIGN PATENT DOCUMENTS

CN 112159405 A * 1/2021 ........... C07D 471/04
WO 2017087528 A1 5/2017
(Continued)

OTHER PUBLICATIONS

Ashenhurst, J. "Alkenes to Alkynes Via Halogenation and Elimination Reactions" https://web.archive.org/web/20190818141829/https://www.masterorganicchemistry.com/2013/06/11/alkynes-via-elimination-reactions/ Jun. 28, 2019 (Year: 2019).*
(Continued)

*Primary Examiner* — Andrew D Kosar
*Assistant Examiner* — John D Mcanany
(74) *Attorney, Agent, or Firm* — Lerner David LLP

(57) ABSTRACT

Provided is a compound containing an aromatic group, or a stereoisomer, a tautomer or a pharmaceutically acceptable salt thereof. Further provided is a method of preparation and use of the compound. The aromatic group-containing compound described herein has a remarkable inhibitory activity on protein, and thus is useful for tumor treatment, such as for the treatment of tumors associated with KRAS G12C mutations.

24 Claims, 2 Drawing Sheets

(30) Foreign Application Priority Data

| | | |
|---|---|---|
| Mar. 12, 2020 | (CN) | 202010168356.1 |
| Mar. 21, 2020 | (CN) | 202010204502.1 |
| May 6, 2020 | (CN) | 202010370560.1 |
| Oct. 11, 2020 | (CN) | 202011080316.8 |
| Oct. 19, 2020 | (CN) | 202011114333.9 |
| Dec. 6, 2020 | (CN) | 202011418298.X |

(56) References Cited

FOREIGN PATENT DOCUMENTS

| | | | |
|---|---|---|---|
| WO | 2018143315 | A1 | 8/2018 |
| WO | 2018217651 | A1 | 11/2018 |
| WO | 2019051291 | A1 | 3/2019 |
| WO | 2019213516 | A1 | 11/2019 |

OTHER PUBLICATIONS

Lanman B.A. et al., "Discovery of a Covalent Inhibitor of KRAS G12C (AMG 510) for the Treatment of Solid Tumors" Journal of Medicinal Chemistry, ACS Publications, Dec. 2019, pp. 52-65. vol. 63.

International Search Report for Application No. PCT/CN2021/077516 mailed Jun. 2, 2021, pp. 1-4.

* cited by examiner

AROMATIC COMPOUND AND USE THEREOF IN PREPARING ANTINEOPLASTIC DRUGS

CROSS REFERENCE TO RELATED APPLICATIONS

The present application is a national phase entry under 35 U.S.C. § 371 of International Application No. PCT/CN2021/077516, filed Feb. 23, 2021, which claims priority from Chinese Patent Applications No. 202010113349.1, filed on Feb. 24, 2020, No. 202010136460.2, filed on Mar. 2, 2020, No. 202010168356.1, filed on Mar. 12, 2020, No. 202010204502.1, filed on Mar. 21, 2020, No. 202010370560.1, filed on May 6, 2020, No. 202011080316.8 filed on Oct. 11, 2020, No. 202011114333.9, filed on Oct. 19, 2020 and No. 202011418298.X, filed on Dec. 6, 2020, all the disclosures of which are hereby incorporated herein by reference.

TECHNICAL FIELD

The present invention relates to an aromatic group-containing compound, and the preparation method thereof and use of such compound in treating diseases.

BACKGROUND ART

As common structural units in pharmaceutical chemistry design, aromatic rings are widely present in drug molecular structures and play an important role in improving drug properties. For drug molecule design, the introduction of other functional groups that are able to produce conjugate action onto an aromatic ring can influence the interaction between the aromatic ring and drug targets, improve the efficacy of the drug molecules, and adjust and control the ability of the drug molecules to agitate or inhibit the target proteins.

It is common to introduce other functional groups that are able to produce conjugate action onto an aromatic ring, including carbonyl compounds (aldehydes, ketones, sulfones, sulfoxides, carboxylic acids and carboxylic acid derivatives, etc.), unsaturated alkanes (olefins, alkynes, etc.). For example, in the molecular structures of the following marketed drugs or drug candidates in clinical stage, the introductions of other functional groups (e.g., carbonyl groups, unsaturated alkanes, olefins, alkynes, etc.) onto the aromatic rings have achieved desirable results in improving drug-likeness of the drug molecules, increasing drug efficacy and reducing toxic side effect. Among them, styrene structural fragments, which exist in many drug molecules, are involved in a wide range of targets and pathways.

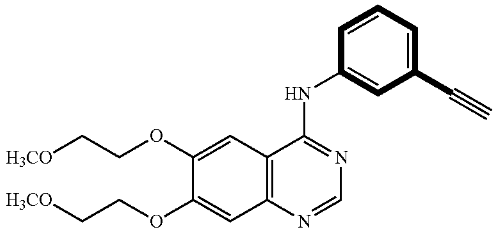

Erlotinib

-continued

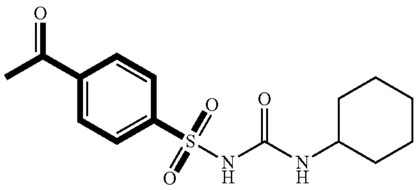

Acetohexamide

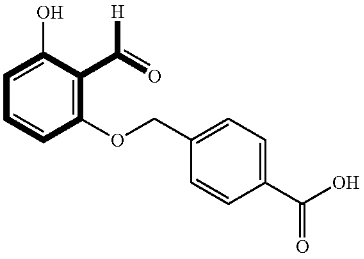

Tucaresol

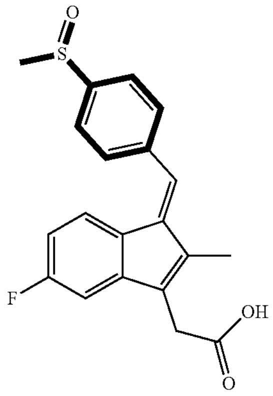

Sulindac

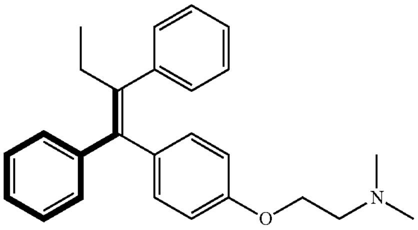

Tamoxifen

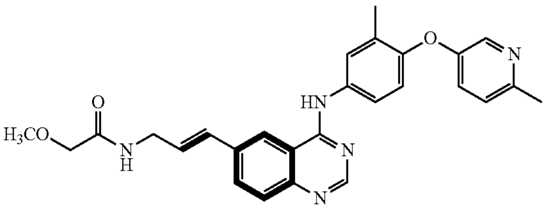

CP-724714

-continued

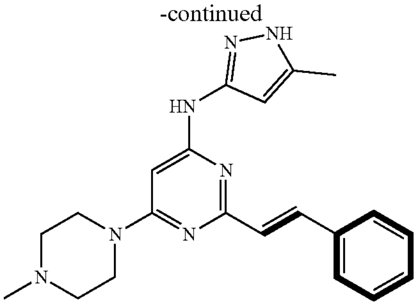

ENMD-2076

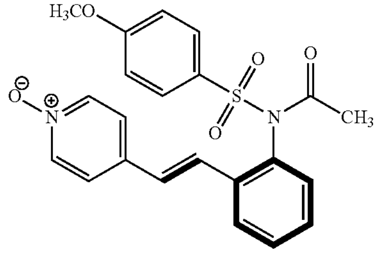

HMN-214

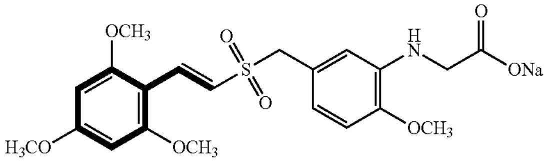

OMO1910

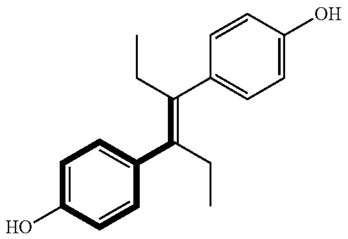

Diethylstilbestrol

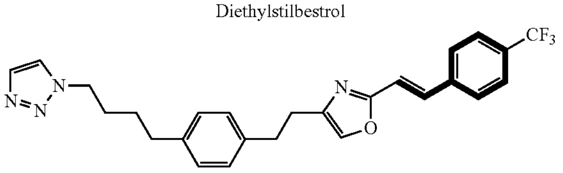

Mubritinib

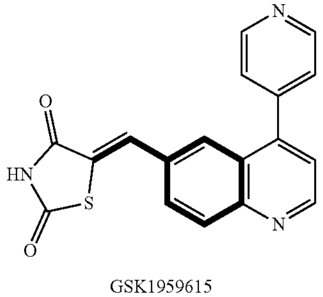

GSK1959615

RAS protein is a guanosine triphosphate (GTP) binding protein, including active GTP-binding conformation and inactive GDP-binding conformation. These two conformations can be transformed into each other under certain conditions, constituting the RAS circulation and regulating the activation of multiple downstream signaling pathways. RAS is known as the "molecular switch" in cell signaling network transmission. Clinical data show that RAS is the gene with the highest mutation rate regarding human tumors. Of all the tumors, approximately 20-30% involve RAS mutations, and there are RAS mutations present in about 98% of pancreatic cancers, 52% of colon cancers, 43% of multiple myelomas, and 32% of lung adenocarcinomas. The most common mutation mode of RAS is point mutation, among which codon 12 mutation is the most common one. KRAS-G12C mutations account for approximately 10-20% of KRAS mutations and 14% of non-small cell lung cancers.

It is very difficult to find drugs targeting RAS. In recent years, since the druggability of KRAS-G12C was discovered, KRAS-G12C inhibitors have become one of the current hot areas in drug research and development. At present, the KRAS-G12C inhibitors under research with rapid progress mainly include AMG510 and MRTX849.

The present invention designs the compounds with structures of general formulas (A), (I), and find that such compounds containing styrene structures exhibit superior effect.

SUMMARY OF THE INVENTION

The present invention provides a compound of formula (A), a stereoisomer, a tautomer or a pharmaceutically acceptable salt thereof,

A

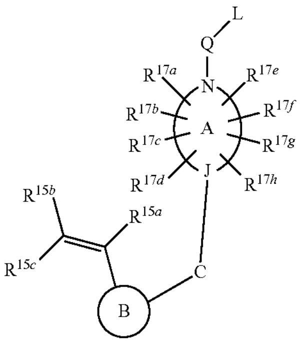

wherein, J is nitrogen atom, or CH;

Ring B is aryl, heteroaryl;

C is the following group:

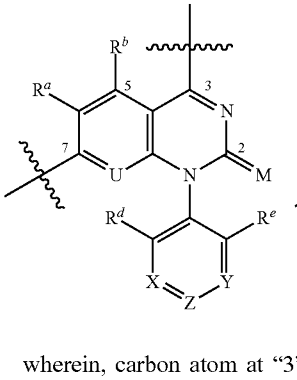

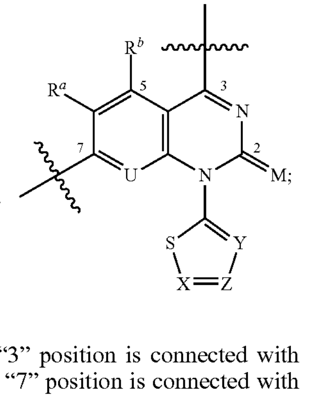

wherein, carbon atom at "3" position is connected with Ring A, carbon atom at "7" position is connected with Ring B;

U is nitrogen atom or $CR^U$, wherein $R^U$ is hydrogen or deuterium;

M is oxygen atom, or sulfur atom;

X is nitrogen atom or $CR^1$, Y is nitrogen atom or $CR^2$, Z is nitrogen atom or $CR^3$;

$R^a$, $R^b$ are independently hydrogen, deuterium, halogen;

$R^d$, $R^e$ are independently hydrogen, deuterium, halogen, alkyl, deuterated alkyl, haloalkyl, hydroxyl, amino, sulfonyl, sulfonamido, amido, alkenyl, alkynyl;

Ring A is nitrogen-containing heterocyclyl;

$R^1$, $R^2$, $R^3$, $R^{15a}$, $R^{15b}$, $R^{15c}$, $R^{17a}$, $R^{17b}$, $R^{17c}$, $R^{17d}$, $R^{17e}$, $R^{17f}$, $R^{17g}$, $R^{17h}$ are independently selected from the group consisting of hydrogen, deuterium, halogen, alkyl, deuterated alkyl, haloalkyl, alkenyl, alkynyl;

Q is —C(O)—, —C(S)—, —S(O)—, —$S(O)_2$—, —$C(^{18}O)$—;

L is alkynyl, alkenyl, haloalkyl.

The present invention provides a compound of formula (I), a stereoisomer, a tautomer or a pharmaceutically acceptable salt thereof,

I

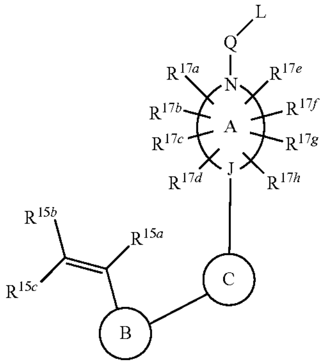

wherein, Ring B is aryl, heteroaryl;

C is the following group:

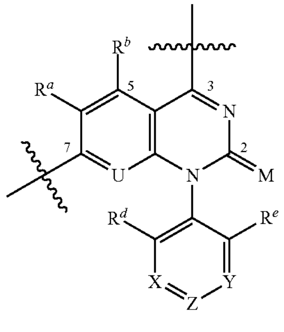

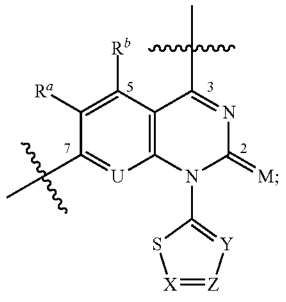

wherein, carbon atom at "3" position is connected with Ring A, carbon atom at "7" position is connected with Ring B;

U is nitrogen atom or $CR^U$, wherein $R^U$ is hydrogen or deuterium;

M is oxygen atom, or sulfur atom;

X is nitrogen atom or $CR^1$, Y is nitrogen atom or $CR^2$, Z is nitrogen atom or $CR^3$;

$R^a$, $R^b$ are independently hydrogen, deuterium, halogen;

$R^d$, $R^e$ are independently hydrogen, deuterium, halogen, alkyl, deuterated alkyl, haloalkyl, hydroxyl, amino, sulfonyl, sulfonamido, amido, alkenyl, alkynyl;

Ring A is 5 to 7-membered nitrogen-containing heterocyclyl;

$R^1$, $R^2$, $R^3$, $R^{15a}$, $R^{15b}$, $R^{15c}$, $R^{17a}$, $R^{17b}$, $R^{17c}$, $R^{17d}$, $R^{17e}$, $R^{17f}$, $R^{17g}$, $R^{17h}$ are independently selected from the group consisting of hydrogen, deuterium, halogen, alkyl, deuterated alkyl, haloalkyl, alkenyl, alkynyl;

Q is —C(O)—, —C(S)—, —S(O)—, —$S(O)_2$—;

L is alkynyl, alkenyl, haloalkyl;

the following structural fragment:

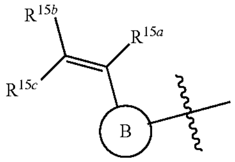

is selected from the following groups:

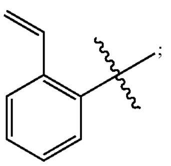

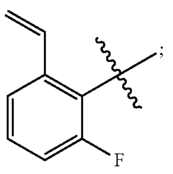

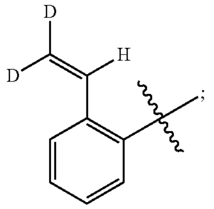

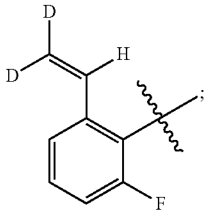

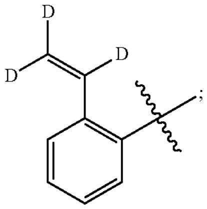

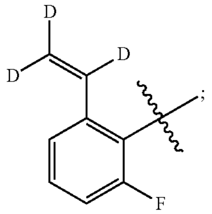

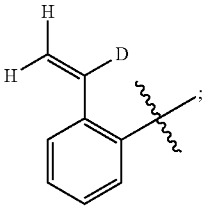

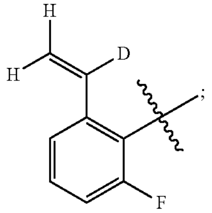

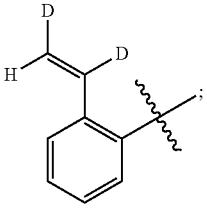

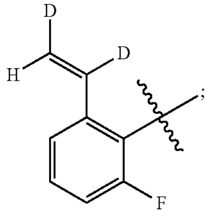

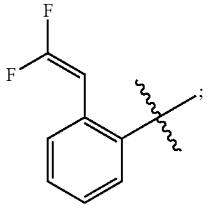

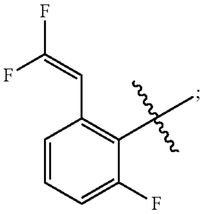 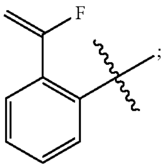 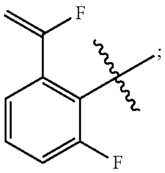
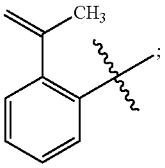 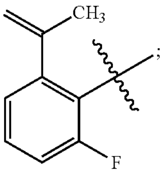 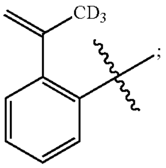
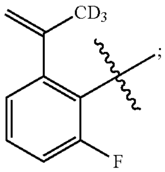 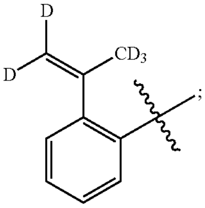
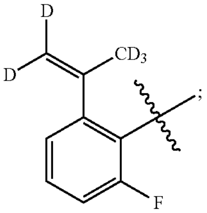 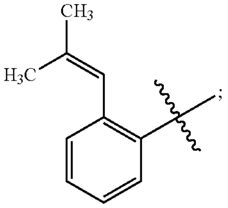
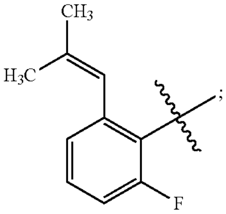 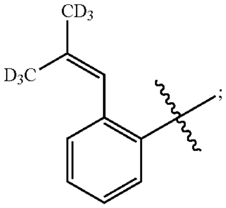
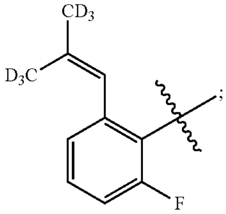 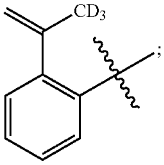
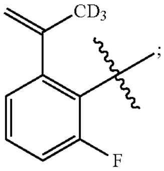 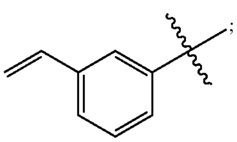
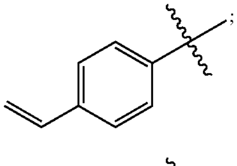 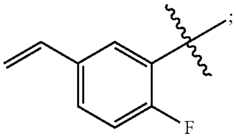
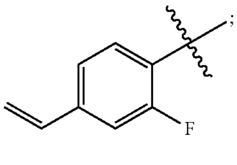 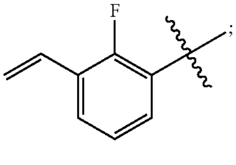
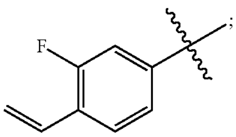 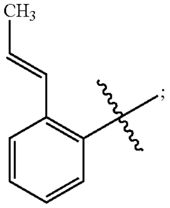
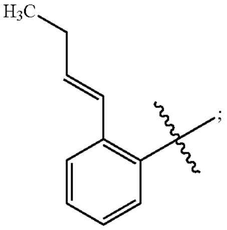 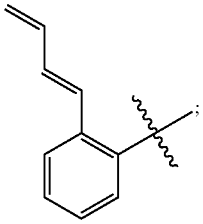
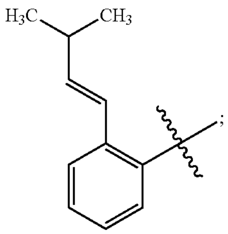 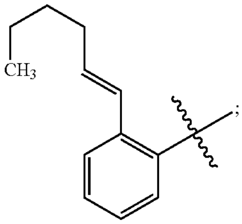
the following structural fragment:
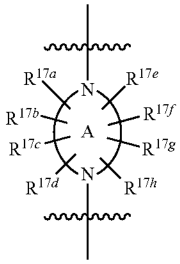
is selected from the following groups:
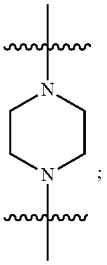 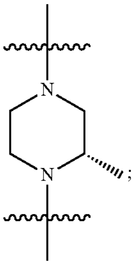 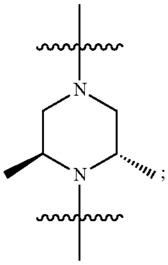
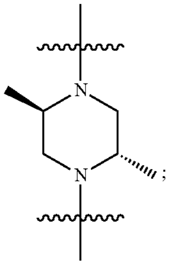 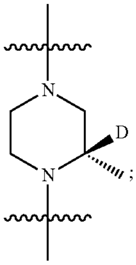 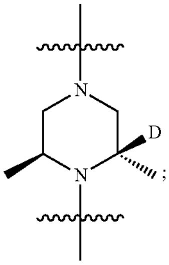

-continued

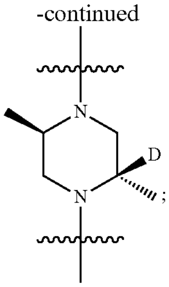;

the following structural fragment:

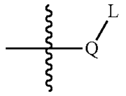

is selected from the following groups:

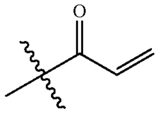; 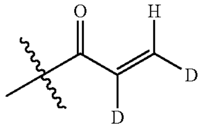; 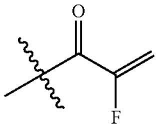;

the following structural fragments:

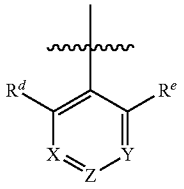

and

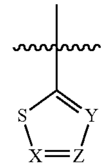

are selected from the following groups:

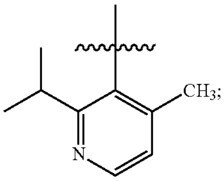CH3; 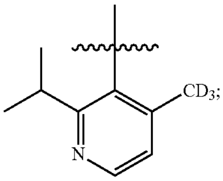CD3;

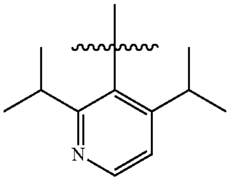; 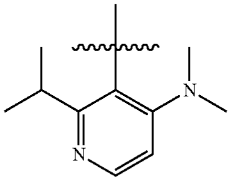;

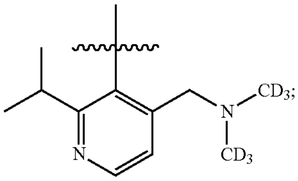CD3; 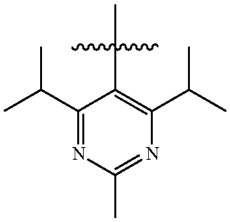;

-continued

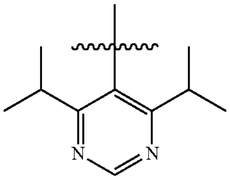; 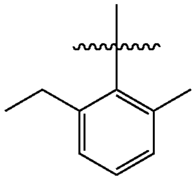;

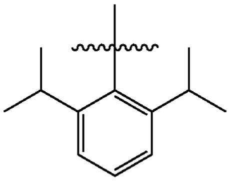; 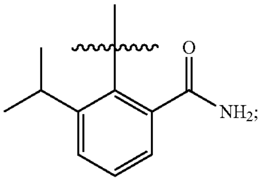NH2;

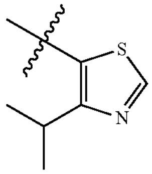; 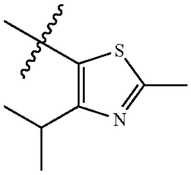;

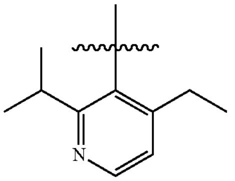.

The present invention provides a compound of formula (I), a stereoisomer, a tautomer or a pharmaceutically acceptable salt thereof,

I

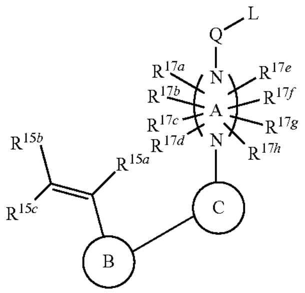

wherein, Ring B is aryl, heteroaryl;
C is the following group:

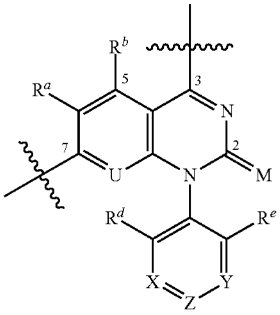 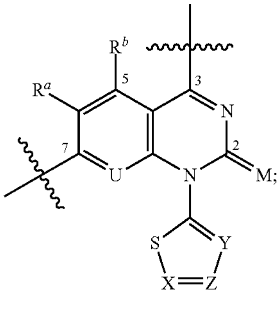;

wherein, carbon atom at "3" position is connected with Ring A, carbon atom at "7" position is connected with Ring B;

U is nitrogen atom or $CR^U$, wherein $R^U$ is hydrogen or deuterium;

M is oxygen atom, or sulfur atom;

X is nitrogen atom or $CR^1$, Y is nitrogen atom or $CR^2$, Z is nitrogen atom or $CR^3$;

$R^a$, $R^b$ are independently hydrogen, deuterium, halogen;

$R^d$, $R^e$ are independently hydrogen, deuterium, halogen, alkyl, deuterated alkyl, haloalkyl, hydroxyl, amino, sulfonyl, sulfonamido, amido, alkenyl, alkynyl;

Ring A is 5 to 7-membered nitrogen-containing heterocyclyl;

$R^1$, $R^2$, $R^3$, $R^{15a}$, $R^{15b}$, $R^{15c}$, $R^{17a}$, $R^{17b}$, $R^{17c}$, $R^{17a}$, $R^{17e}$, $R^{17f}$, $R^{17g}$, $R^{17h}$ are independently selected from the group consisting of hydrogen, deuterium, halogen, alkyl, deuterated alkyl, haloalkyl, alkenyl, alkynyl;

Q is —C(O)—, —C(S)—, —S(O)—, —$S(O)_2$—;

L is alkynyl, alkenyl, haloalkyl;

the following structural fragment:

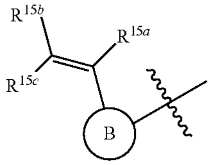

is selected from the following groups:

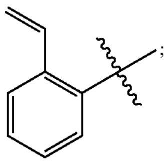;

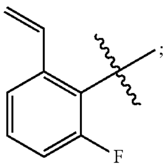;

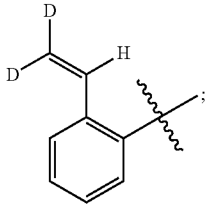;

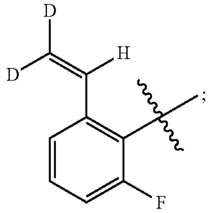;

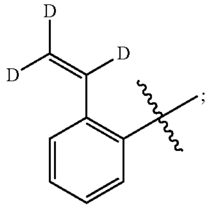;

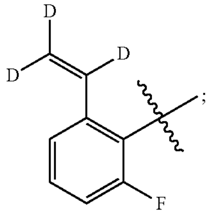;

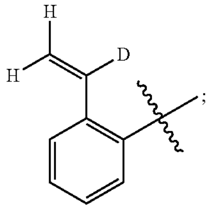;

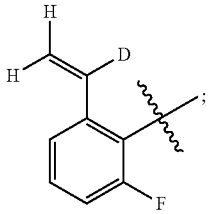;

-continued

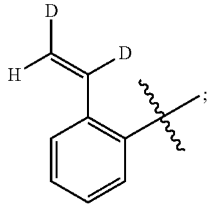;

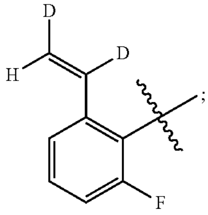;

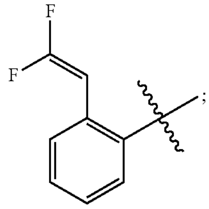;

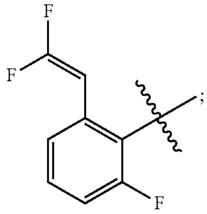;

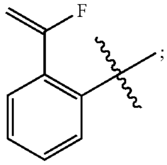;

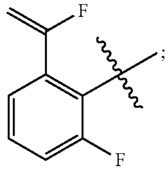;

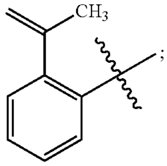;

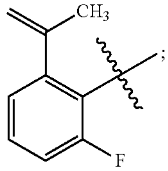;

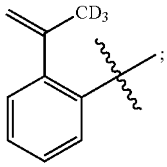;

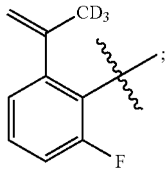;

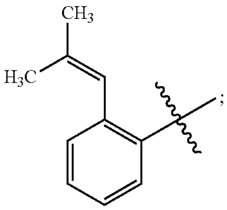;

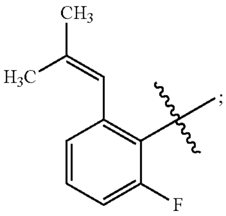;

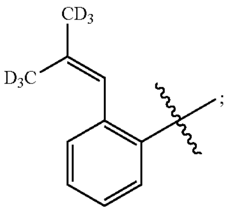;

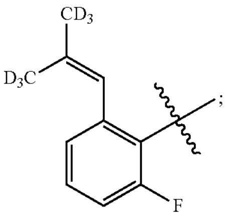;

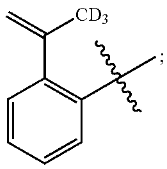;

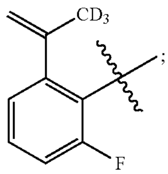;

the following structural fragment:

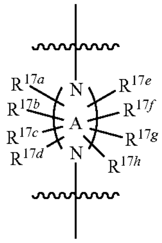
is selected from the following groups:
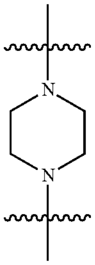 ; 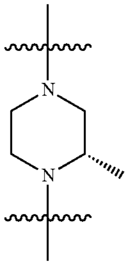 ; 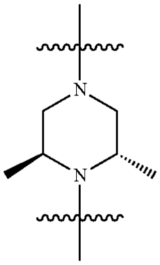 ;
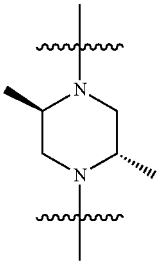 ; 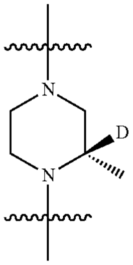 ; 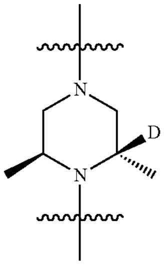 ;
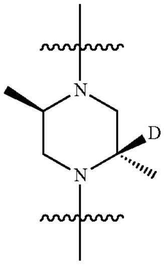 ;
the following structural fragment:
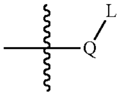
is selected from the following groups:
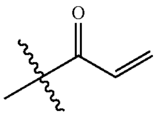 ; 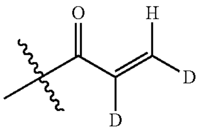 ; 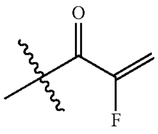 ;
the following structural fragments:
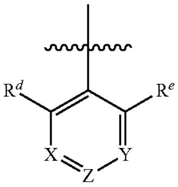 and 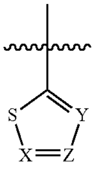
are selected from the following groups:
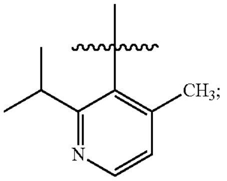 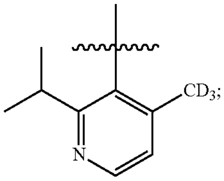
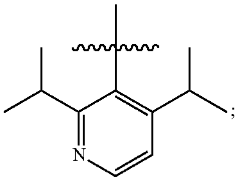 ; 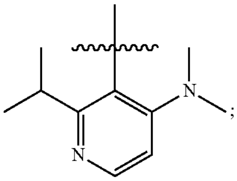 ;
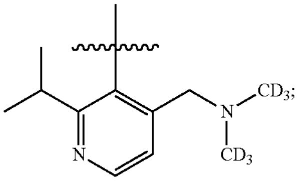
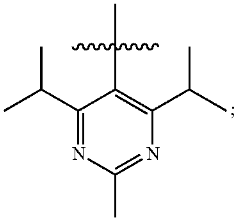 ; 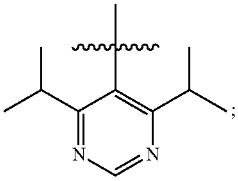 ;
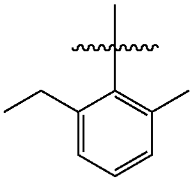 ; 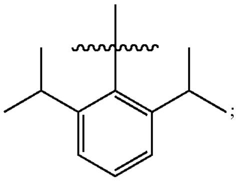 ;
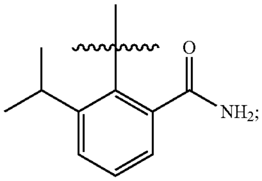 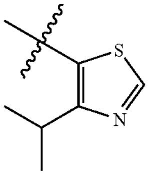 ;
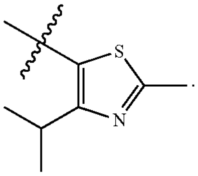 .
The present invention provides the following compounds, stereoisomers, tautomers or pharmaceutically acceptable salts thereof, -continued
1-1
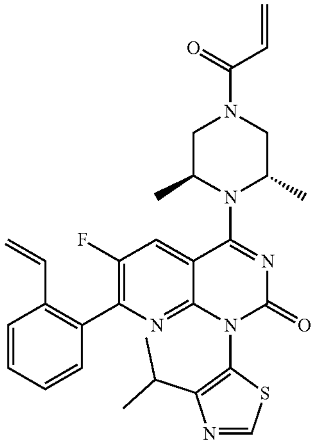
1-2
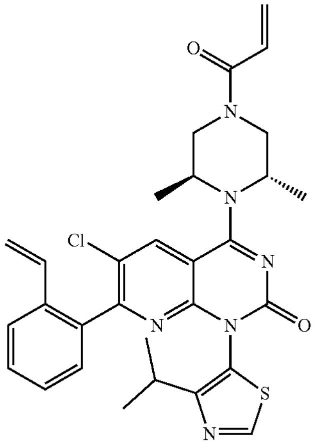
1-3
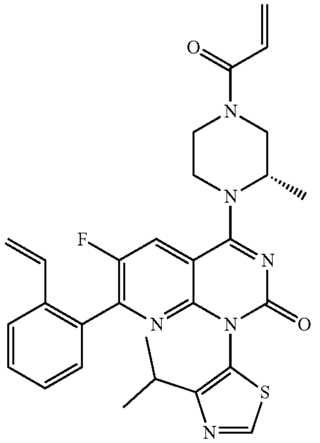
1-4
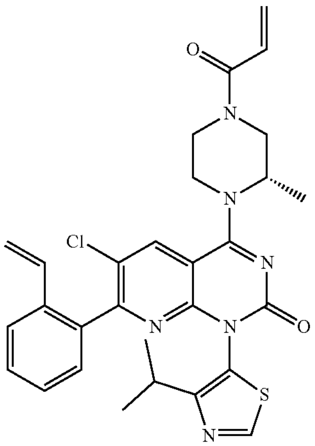
1-5
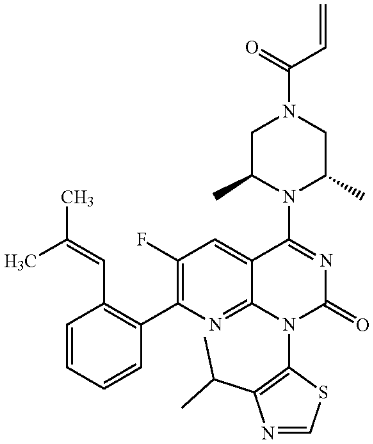
1-6
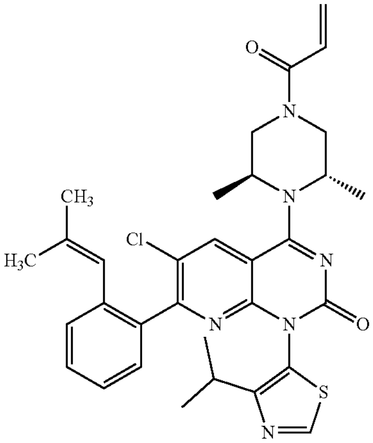

-continued
1-7
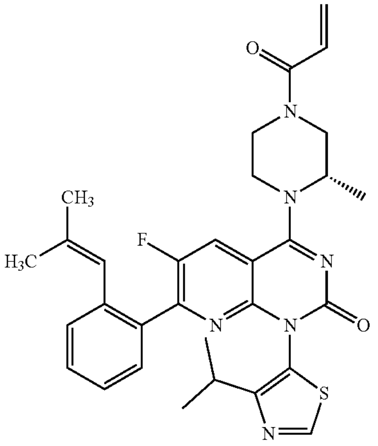
1-8
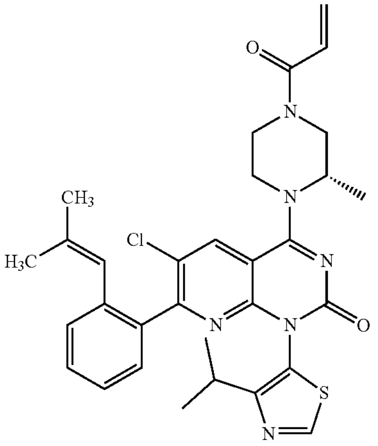
1-9
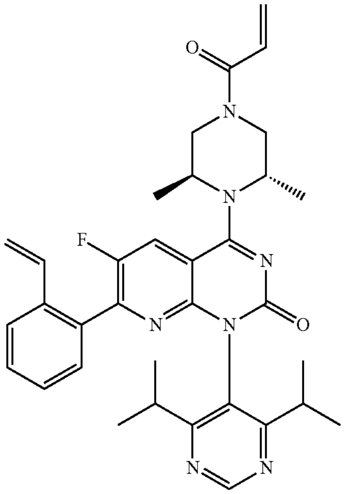
-continued
1-10
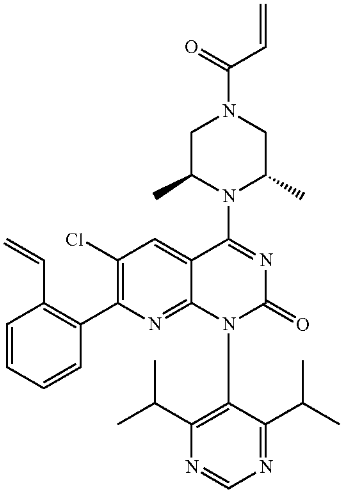
1-11
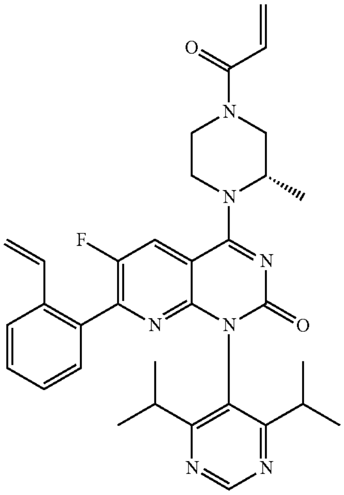
1-12
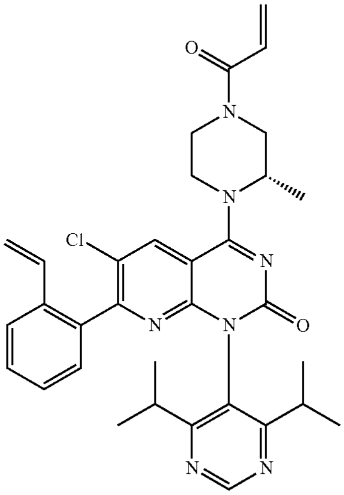

-continued
1-13
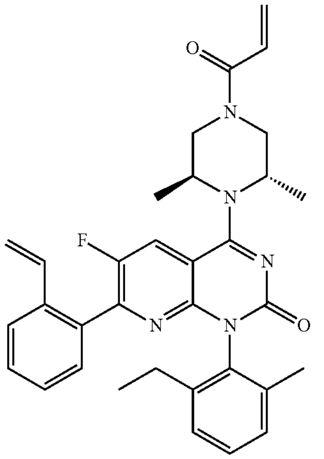
1-14
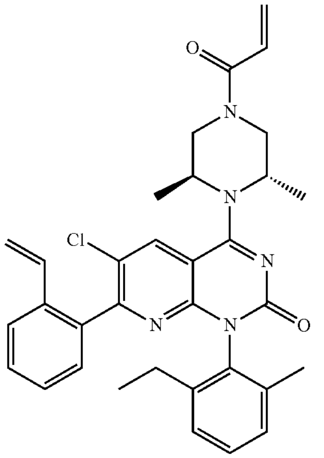
1-15
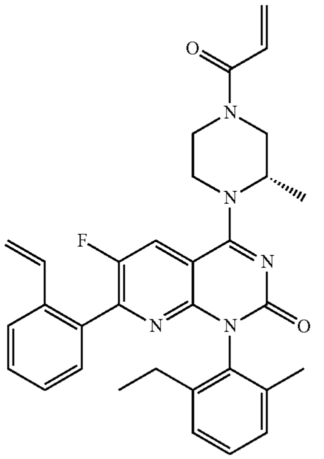
-continued
1-16
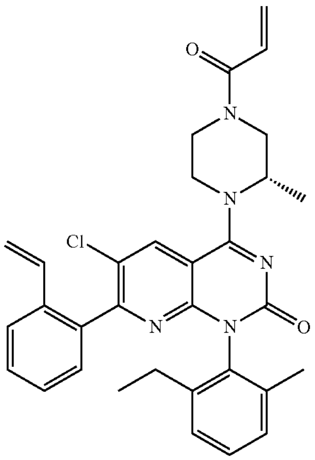
1-17
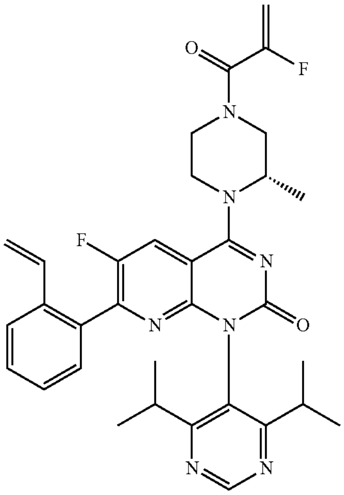
1-18
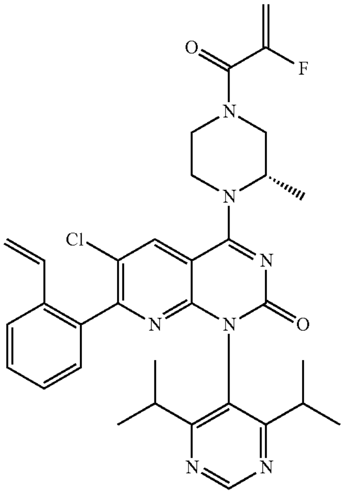

-continued
1-19
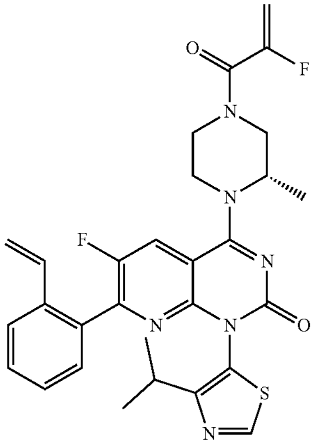
1-20
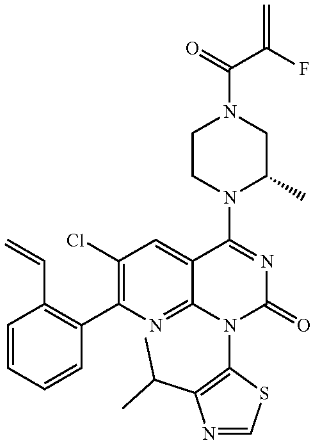
1-21
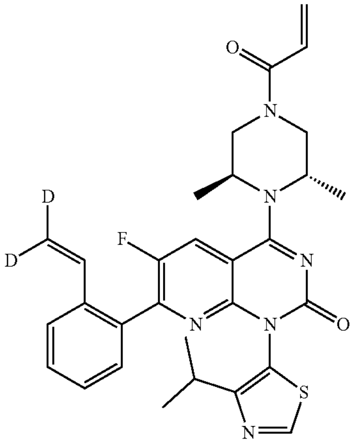
-continued
1-22
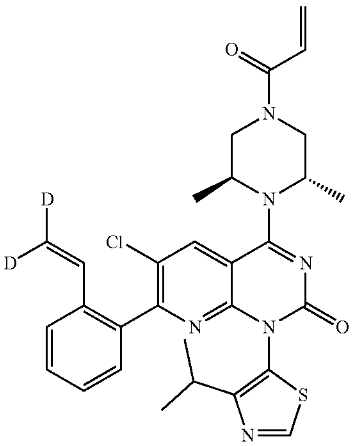
1-23
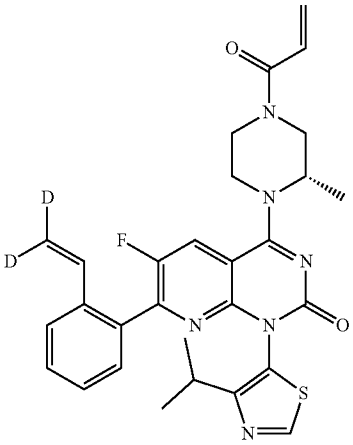
1-24
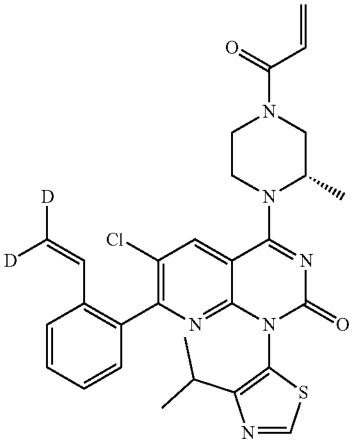

1-25
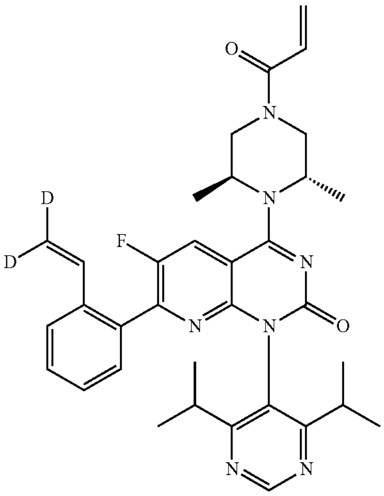
1-26
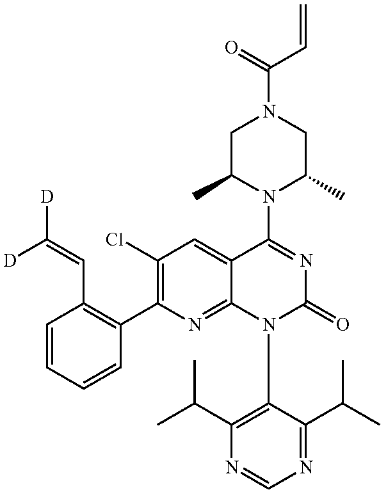
1-27
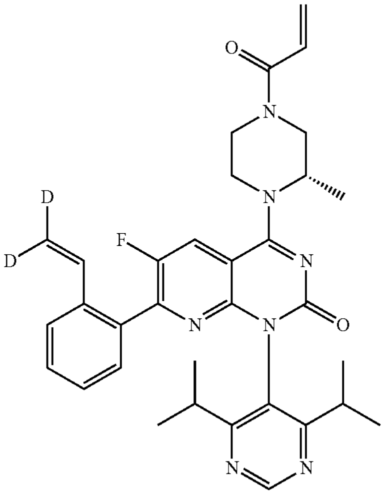
1-28
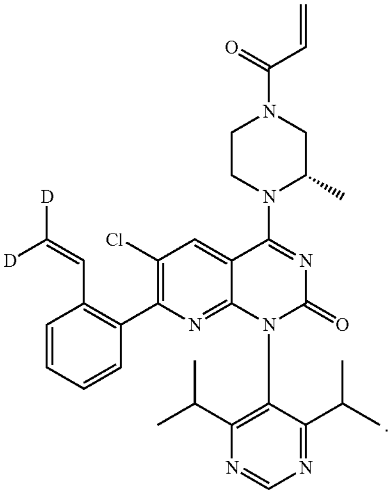
The present invention provides the following compounds, stereoisomers, tautomers or pharmaceutically acceptable salts thereof,
3K-1
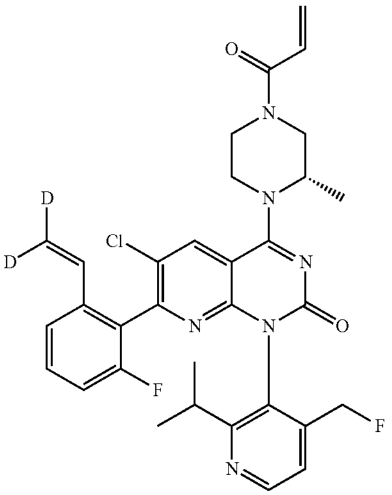
3K-2
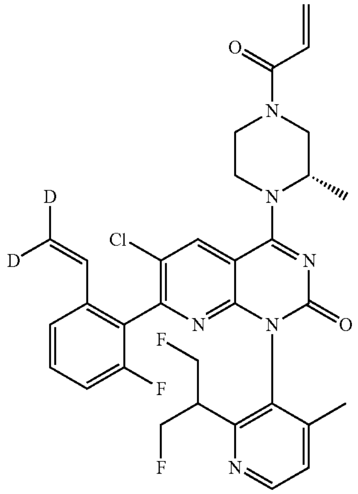

-continued
3K-3
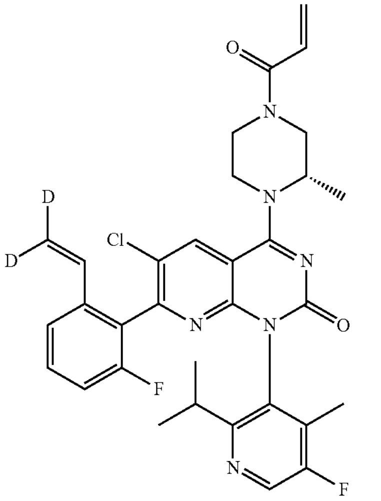
3K-4
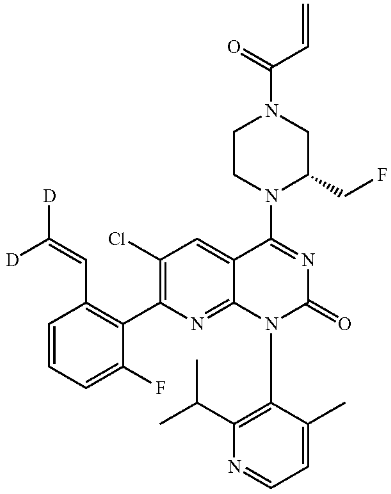
3K-5
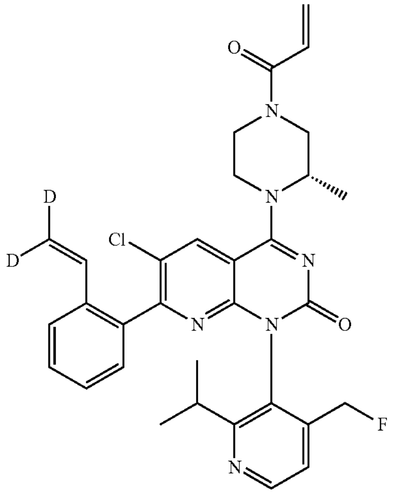
-continued
3K-6
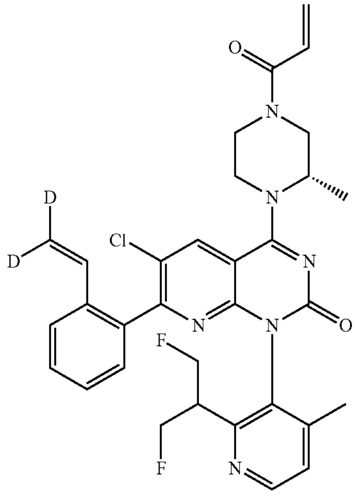
3K-7
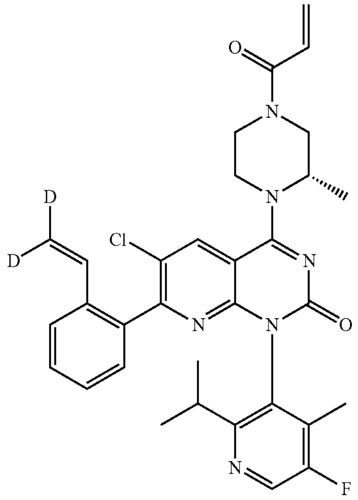
3K-8
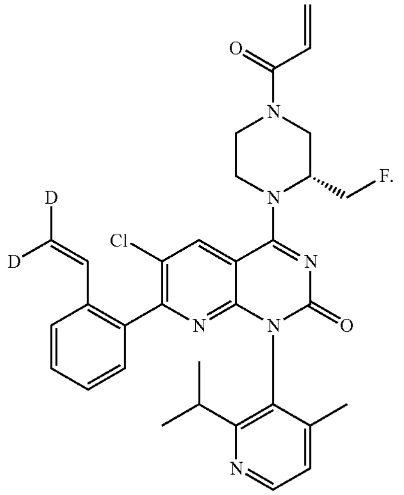
The present invention provides a compound of formula (II), a stereoisomer, a tautomer or a pharmaceutically acceptable salt thereof,

II

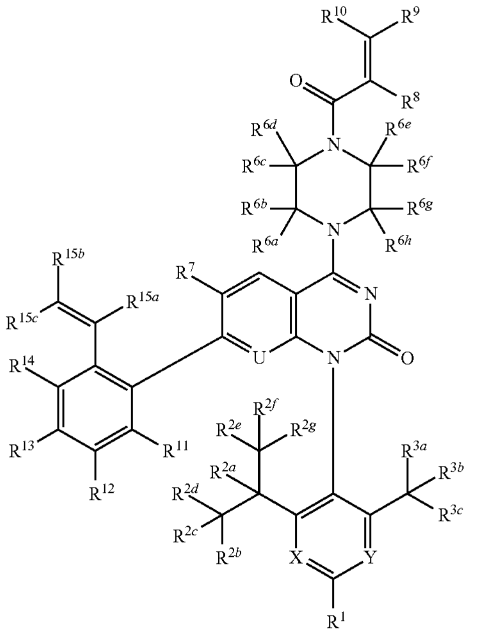

wherein, X is nitrogen atom or $CR^4$, Y is nitrogen atom or $CR^5$;

U is nitrogen atom or $CR^U$, wherein $R^U$ is hydrogen or deuterium;

$R^1$, $R^{2a}$, $R^{2b}$, $R^{2c}$, $R^{2d}$, $R^{2e}$, $R^{2f}$, $R^{2g}$, $R^{3a}$, $R^{3b}$, $R^{3c}$, $R^4$, $R^5$, $R^{12}$, $R^{13}$, $R^{14}$, $R^{15a}$, $R^{15b}$, $R^{15c}$ are independently selected from the group consisting of hydrogen, deuterium, alkyl, deuterated alkyl;

$R^{6a}$, $R^{6b}$, $R^{6c}$, $R^{6d}$, $R^{6e}$, $R^{6f}$, $R^{6g}$, $R^{6h}$ are independently selected from the group consisting of hydrogen, deuterium, methyl, methyl-$d_3$;

$R^7$ is fluorine, chlorine;

$R^8$, $R^9$, $R^{10}$, $R^{11}$ are independently selected from the group consisting of hydrogen, deuterium, fluorine;

structural fragment

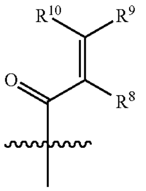

is selected from the following structures:

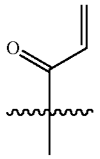 ; 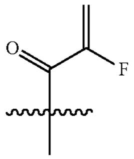 ; 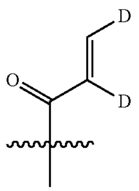 ;

structural fragment

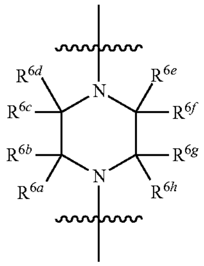

is selected from the following structures:

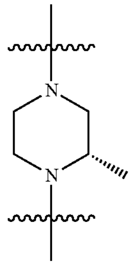 ; 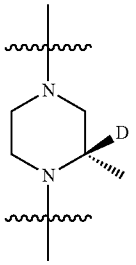 ; 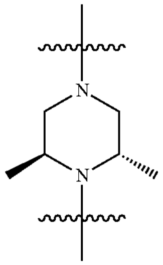 ;

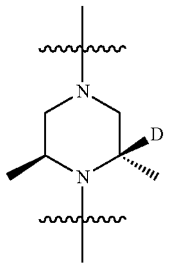 ; 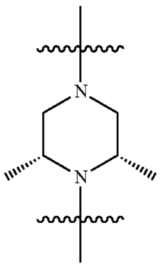 ;

structural fragment

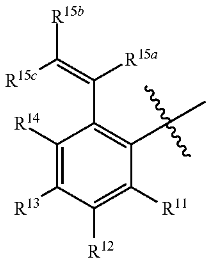

is selected from the following structures:

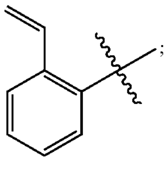 ; 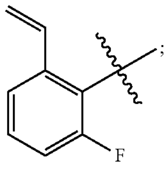 ;

-continued
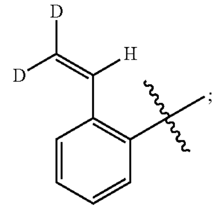
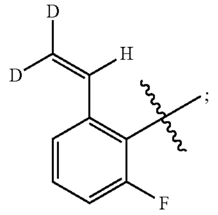
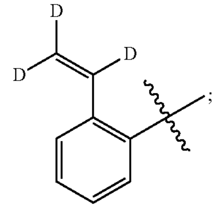
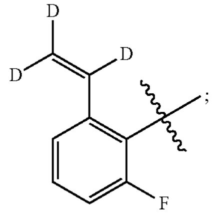
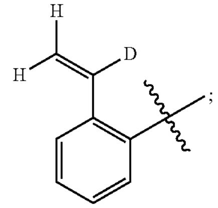
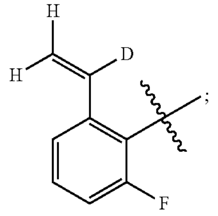
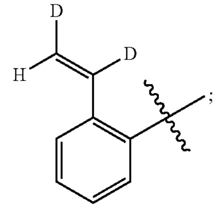
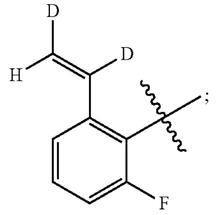
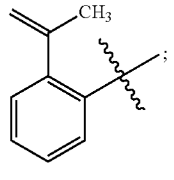
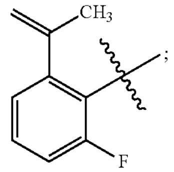
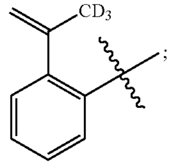
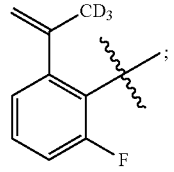
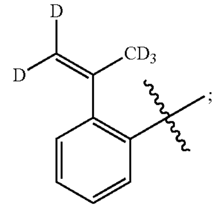
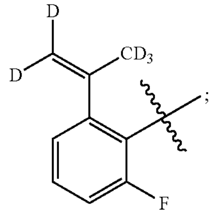
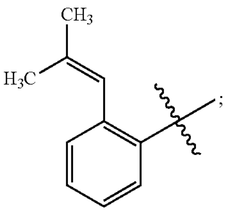
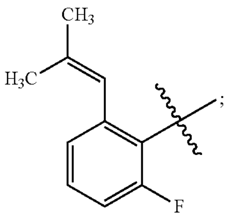
-continued
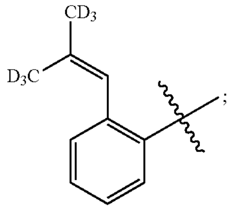
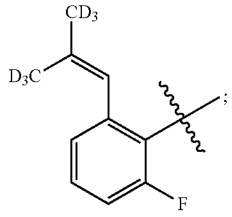
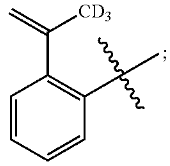
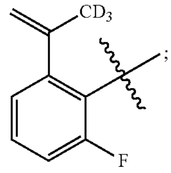
structural fragment
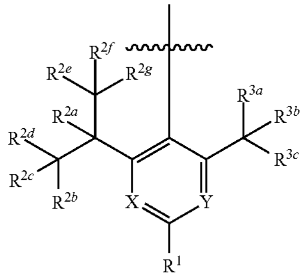
is selected from the following structures:
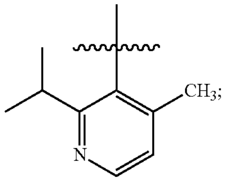
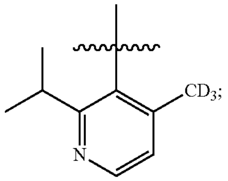
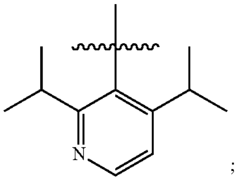
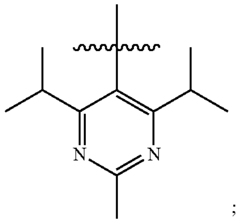
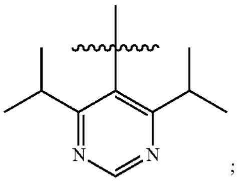
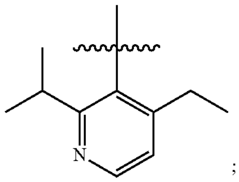
The present invention provides a compound of formula (II-1), a stereoisomer, a tautomer or a pharmaceutically acceptable salt thereof,

II-1

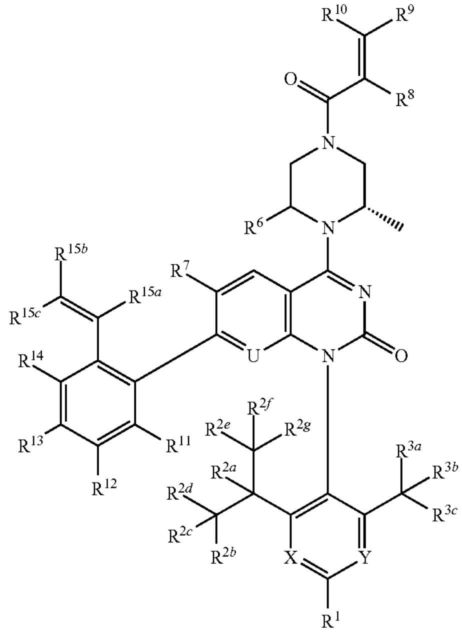

wherein, X is nitrogen atom or $CR^4$, Y is nitrogen atom or $CR^5$;

U is nitrogen atom or $CR^U$, wherein $R^U$ is hydrogen or deuterium;

$R^1$, $R^{2a}$, $R^{2b}$, $R^{2c}$, $R^{2d}$, $R^{2e}$, $R^{2f}$, $R^{2g}$, $R^{3a}$, $R^{3b}$, $R^{3c}$, $R^4$, $R^5$, $R^{12}$, $R^{13}$, $R^{14}$, $R^{15a}$, $R^{15b}$, $R^{15c}$ are independently selected from the group consisting of hydrogen, deuterium, alkyl, deuterated alkyl;

$R^6$ is independently selected from the group consisting of hydrogen, deuterium, methyl, methyl-$d_3$;

$R^7$ is fluorine, chlorine;

$R^8$, $R^9$, $R^{10}$, $R^{11}$ are independently selected from the group consisting of hydrogen, deuterium, fluorine;

structural fragment

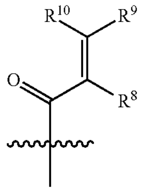

is selected from the following structures:

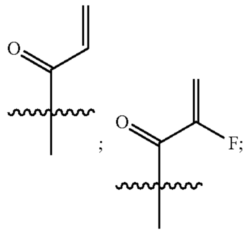

structural fragment

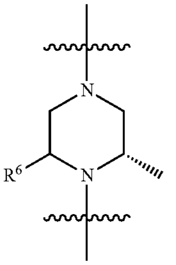

is selected from the following structures:

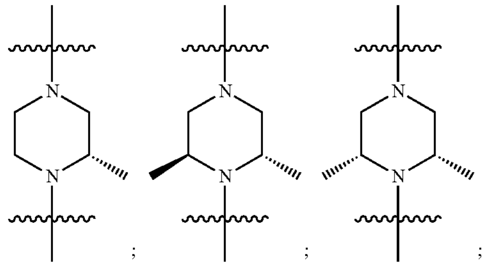

structural fragment

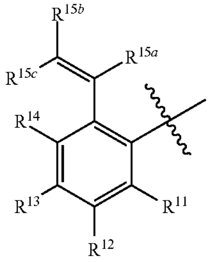

is selected from the following structures:

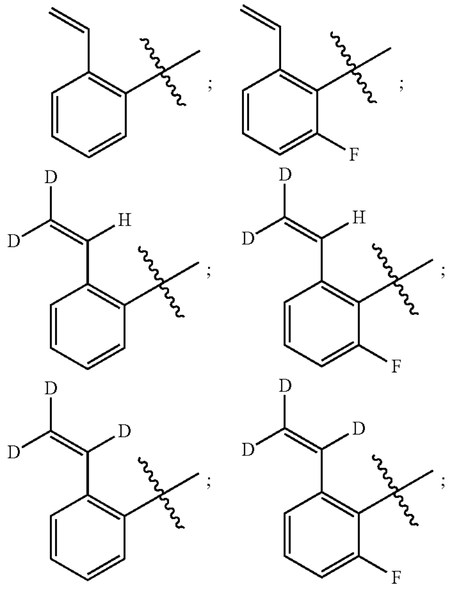

-continued
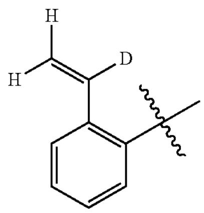 ; 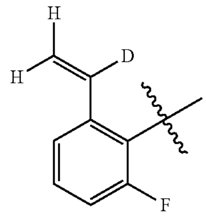 ;
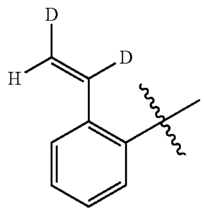 ; 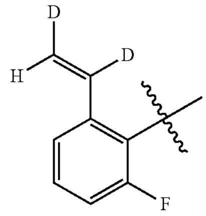 ;
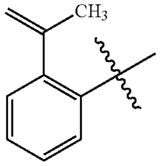 ; 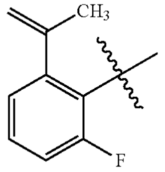 ; 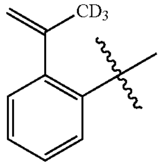 ;
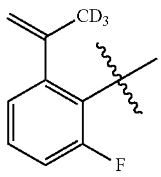 ; 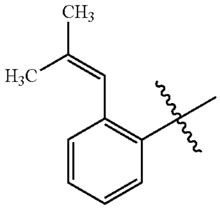 ;
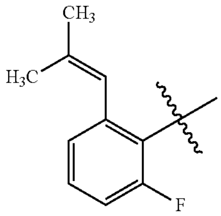 ; 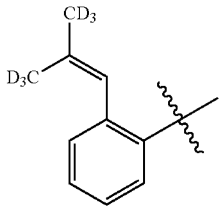 ;
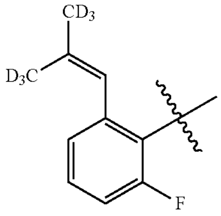 ; 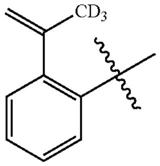 ;
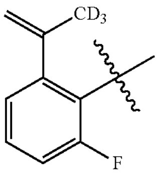 ;
structural fragment
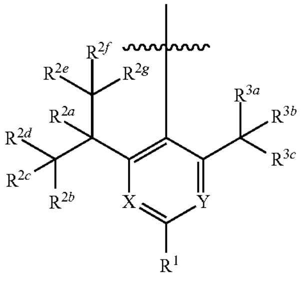
is selected from the following structures:
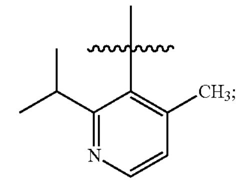 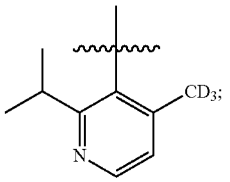
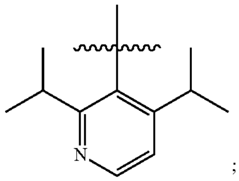 ; 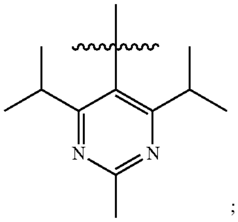 ;
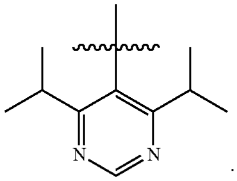 .
The present invention provides the following compounds, stereoisomers, tautomers or pharmaceutically acceptable salts thereof,
2-1
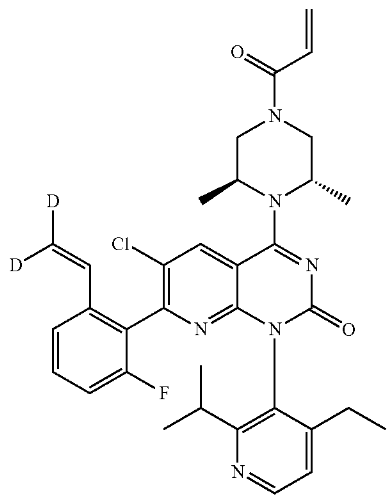

-continued
2-2
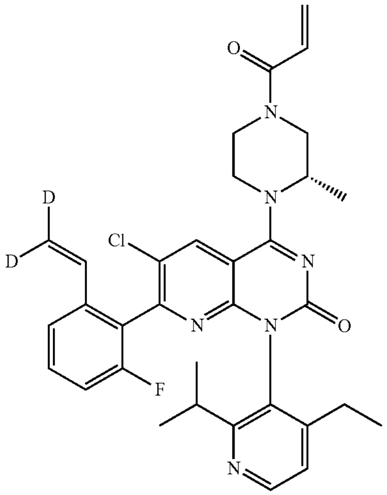
2-3
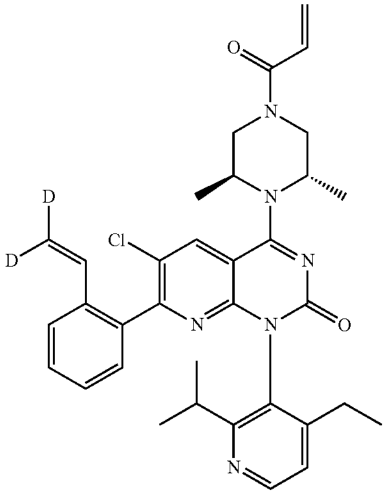
2-4
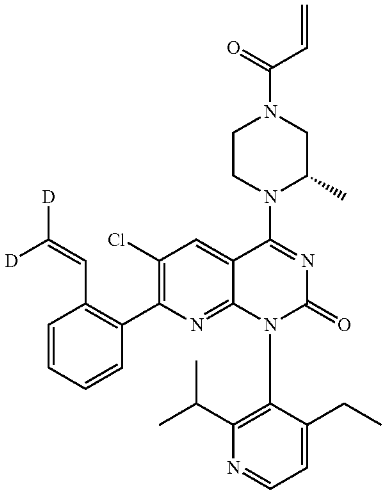
-continued
2-5
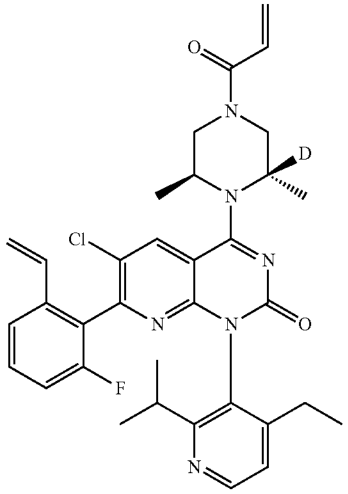
2-6
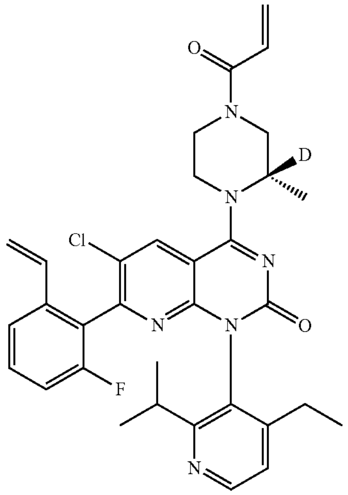
2-7
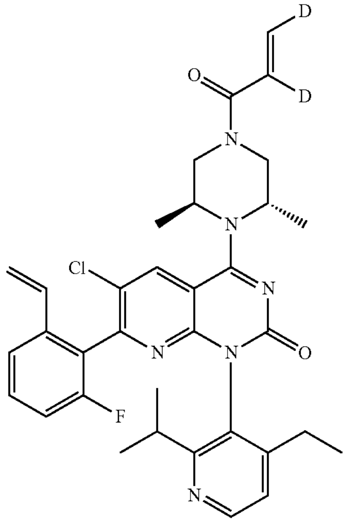

-continued
2-8
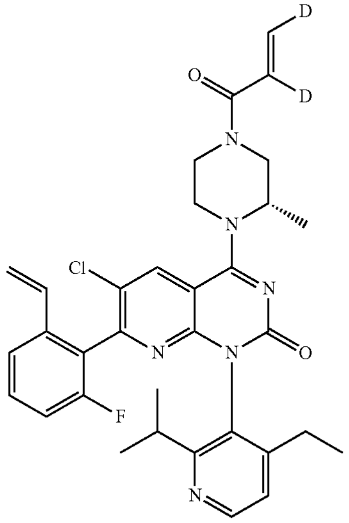
2-9
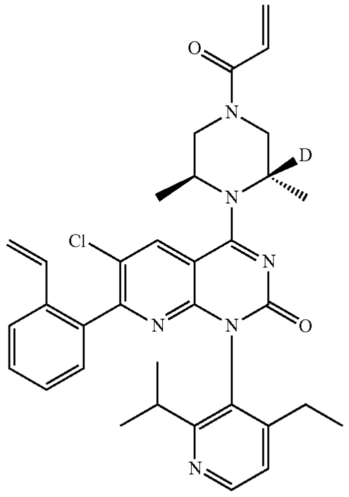
2-10
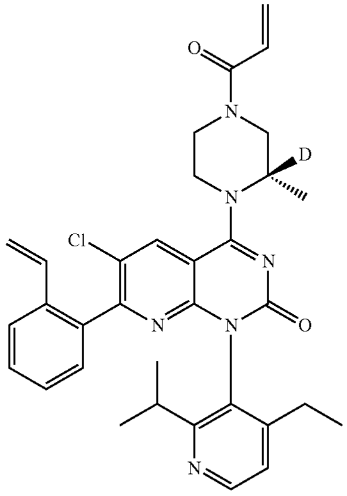
-continued
2-11
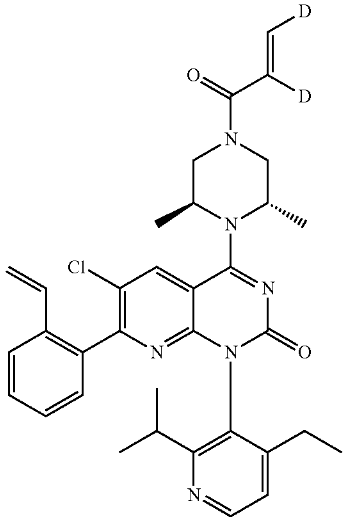
2-12
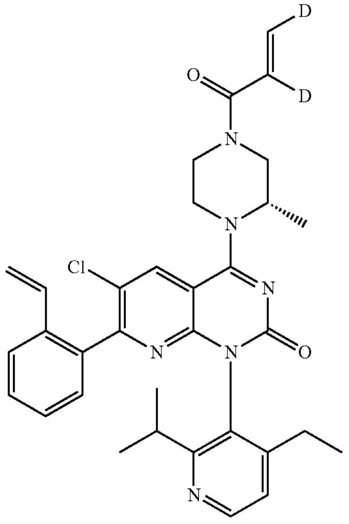
2-13
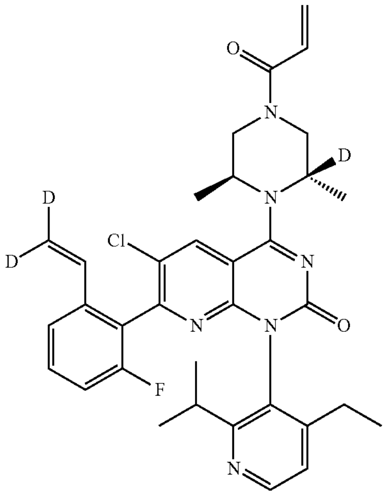

-continued
2-14
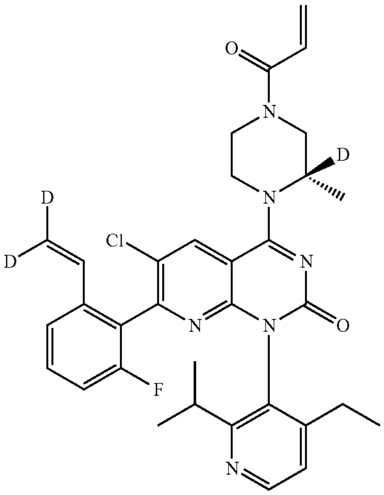
2-15
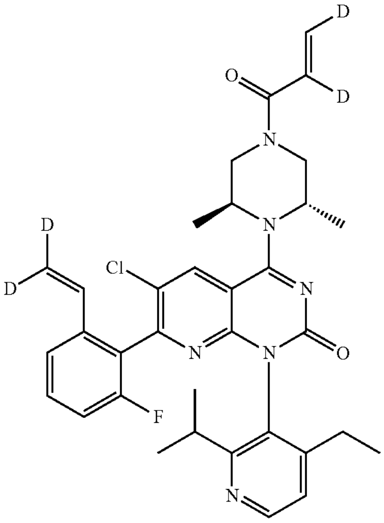
2-16
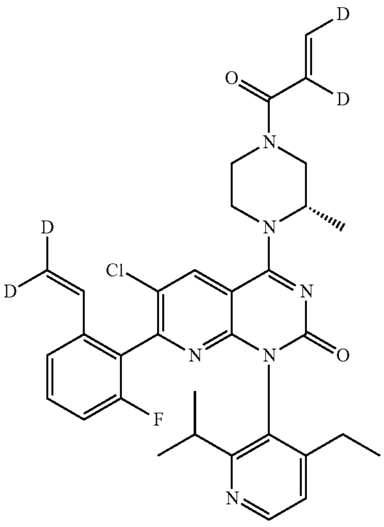
-continued
2-17
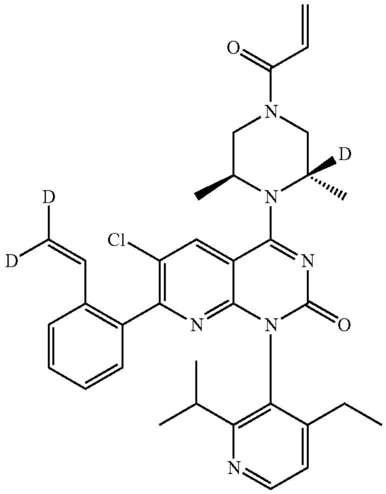
2-18
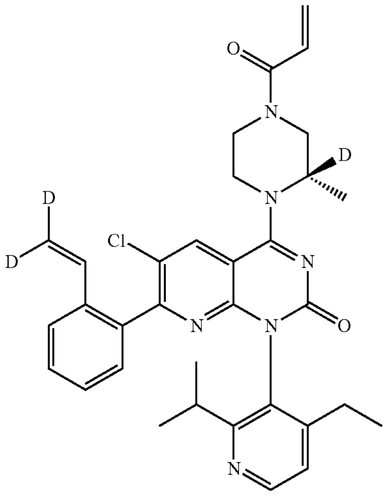
2-19
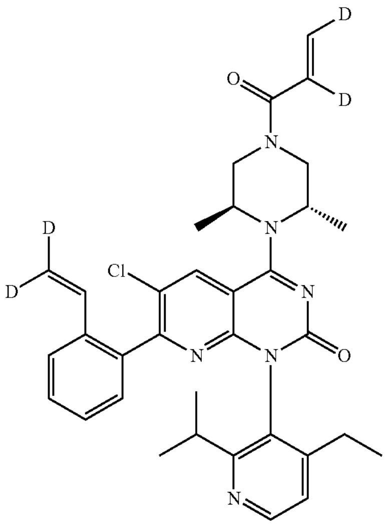

-continued
2-20
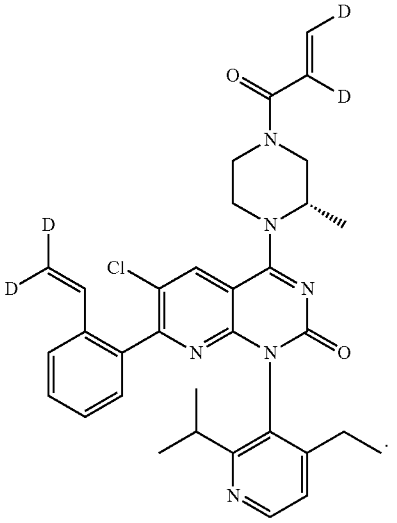
The present invention provides the following compounds, stereoisomers, tautomers or pharmaceutically acceptable salts thereof,
3-1MS
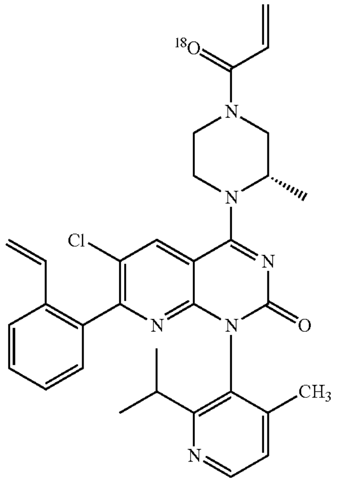
3-3MS
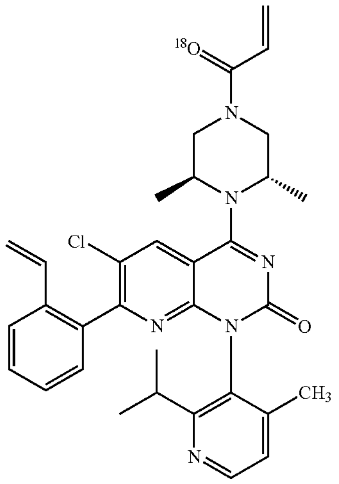
-continued
3-4MS
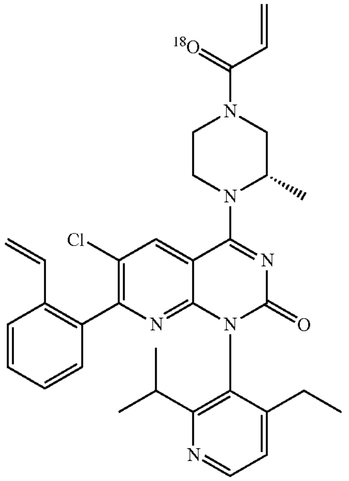
3-5MS
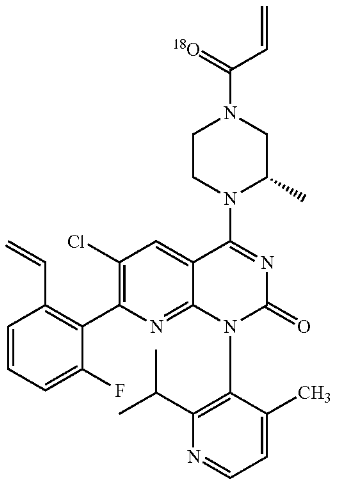
3-7MS
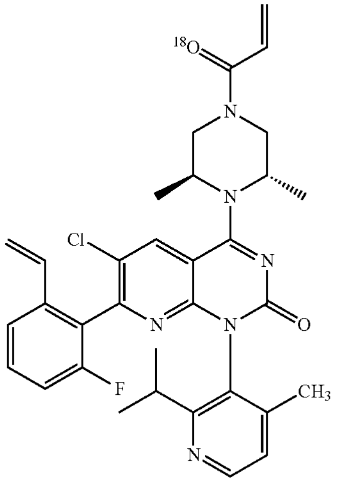

-continued 3-8MS

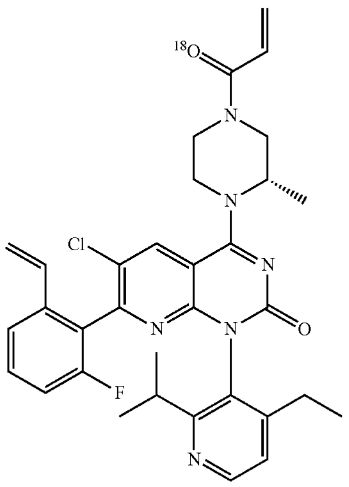

3-9MS

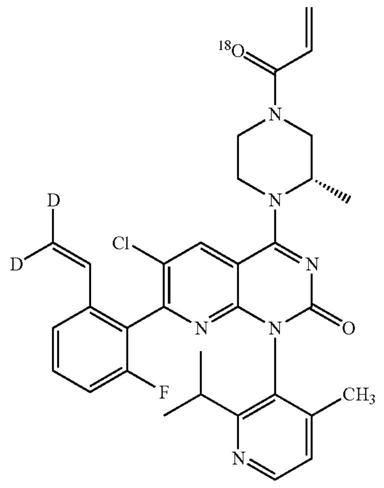

3-11MS

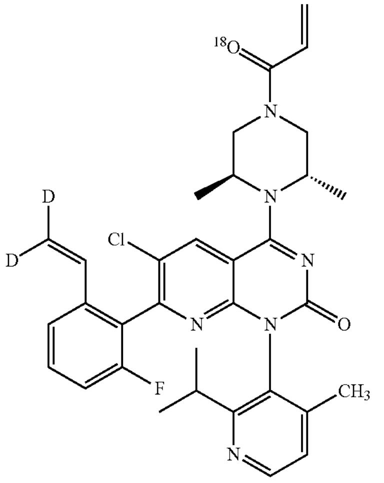

-continued 3-12MS

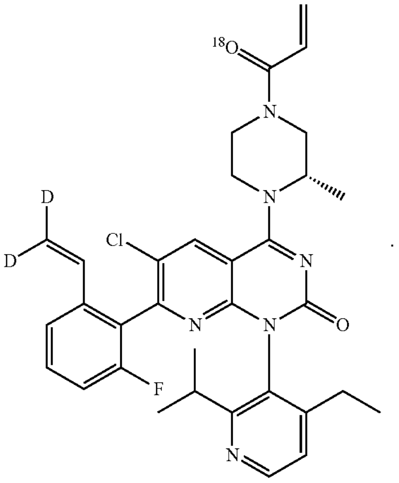

The present invention provides a compound of formula (III), a stereoisomer, a tautomer or a pharmaceutically acceptable salt thereof,

III

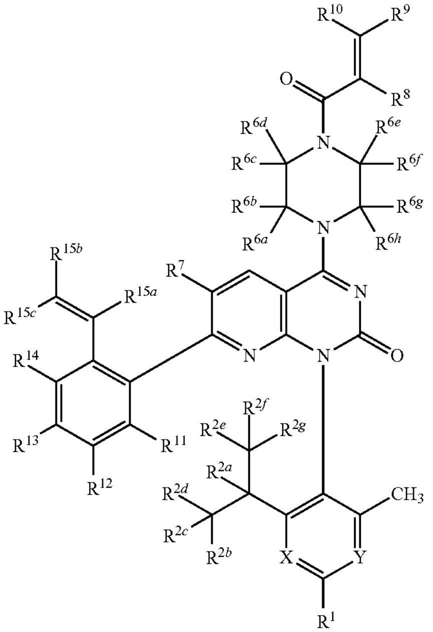

wherein, X is nitrogen atom or $CR^4$, Y is nitrogen atom or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, $R^{15c}$ are independently selected from the group consisting of hydrogen, deuterium, alkyl, deuterated alkyl;

$R^{6a}$, $R^{6b}$, $R^{6c}$, $R^{6d}$, $R^{6e}$, $R^{6f}$, $R^{6g}$, $R^{6h}$ are independently selected from the group consisting of hydrogen, deuterium, methyl, methyl-$d_3$;

$R^7$ is fluorine, chlorine;

$R^8$, $R^9$, $R^{10}$, $R^{11}$ are independently selected from the group consisting of hydrogen, deuterium, fluorine;

structural fragment

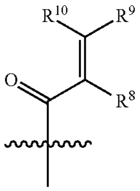
is selected from the following structures:
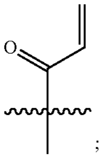
;
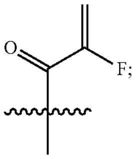
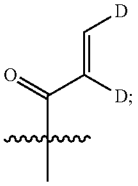
structural fragment
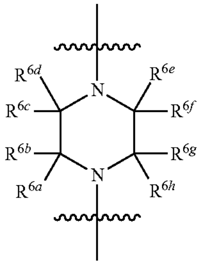
is selected from the following structures:
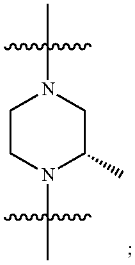
;
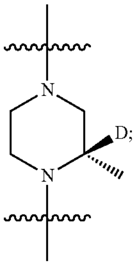
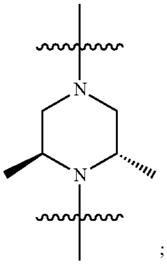
;
-continued
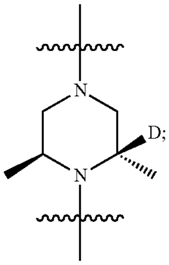
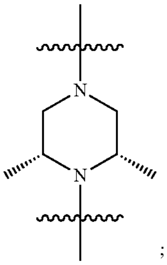
;
structural fragment
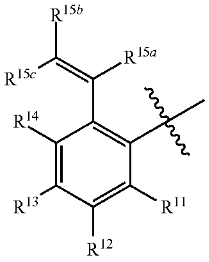
is selected from the following structures:
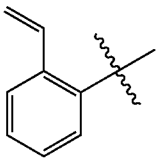
;
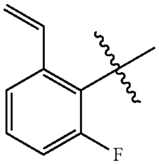
;
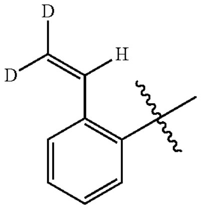
;
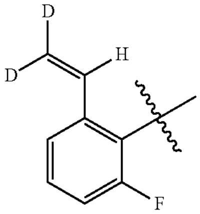
;
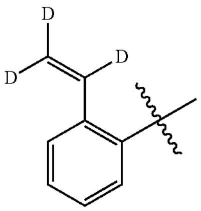
;
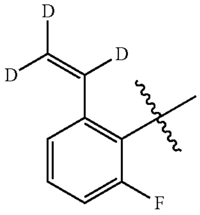
;
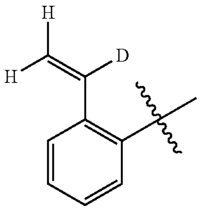
;
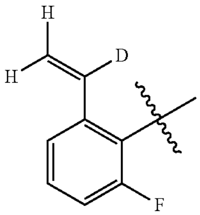
;

-continued

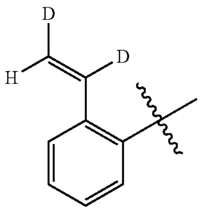 ; 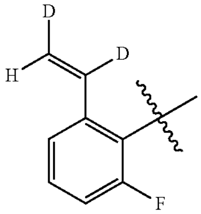 ;

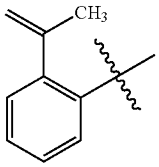 ; 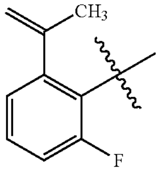 ; 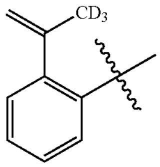 ;

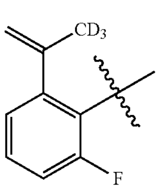 ; 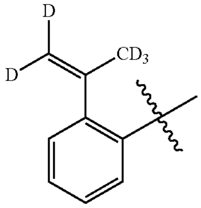 ;

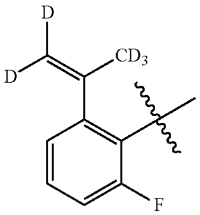 ; 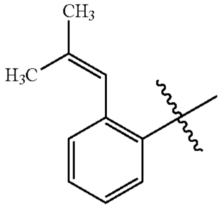 ;

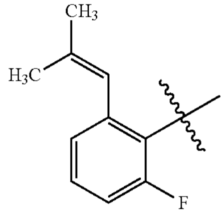 ; 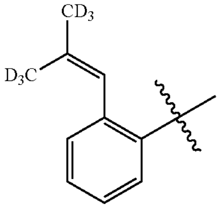 ;

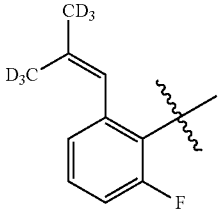 ; 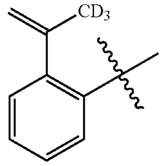 ;

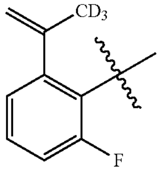 .

The present invention provides a compound of formula (III-1), a stereoisomer, a tautomer or a pharmaceutically acceptable salt thereof,

III-1

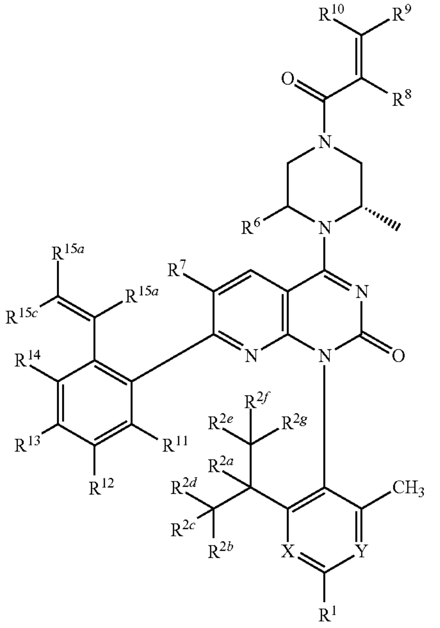

wherein, X is nitrogen atom or $CR^4$, Y is nitrogen atom or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, $R^{15c}$ are independently selected from the group consisting of hydrogen, deuterium, alkyl, deuterated alkyl;

$R^6$ is independently selected from the group consisting of hydrogen, deuterium, methyl, methyl-$d_3$;

$R^7$ is fluorine, chlorine;

$R^8$, $R^9$, $R^{10}$, $R^{11}$ are independently selected from the group consisting of hydrogen, deuterium, fluorine;

structural fragment

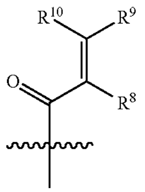

is selected from the following structures:

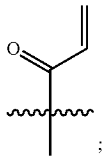 ; 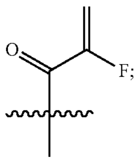

structural fragment

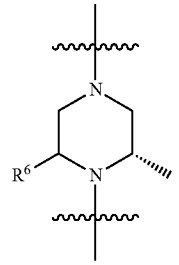
is selected from the following structures:
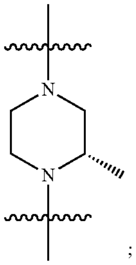 ; 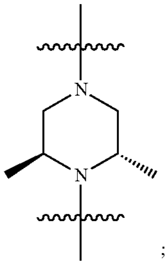 ; 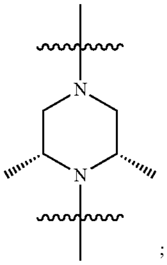 ;
structural fragment
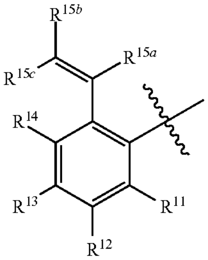
is selected from the following structures:
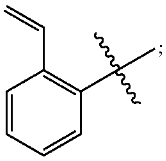 ; 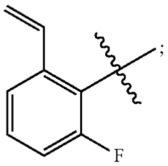 ;
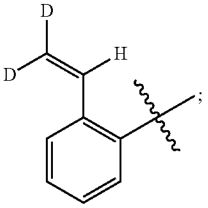 ; 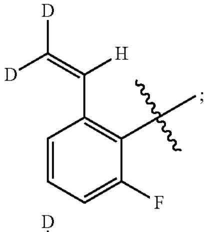 ;
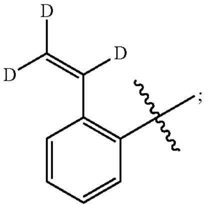 ; 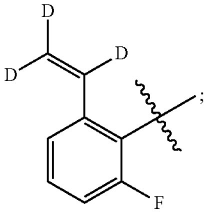 ;
-continued
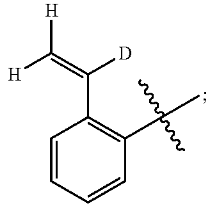 ; 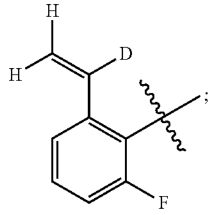 ;
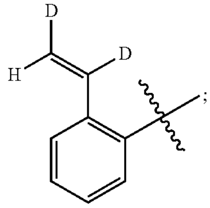 ; 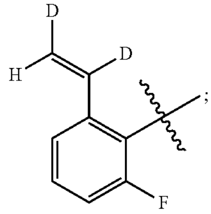 ;
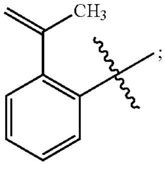 ; 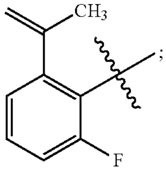 ;
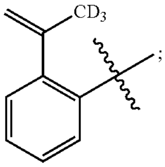 ; 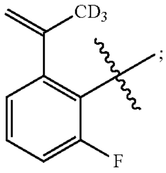 ;
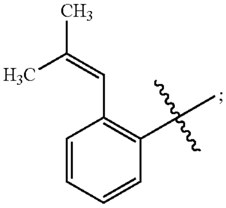 ; 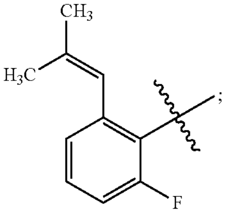 ;
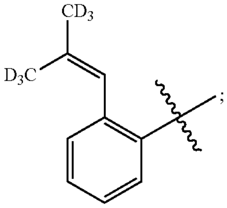 ; 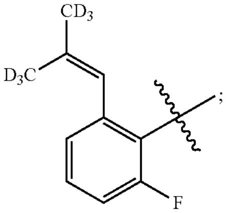 ;
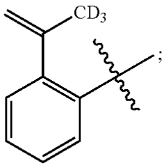 ; 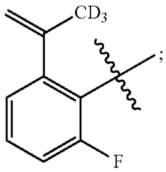 ;
structural fragment

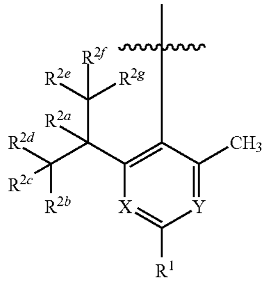
is selected from the following structures:
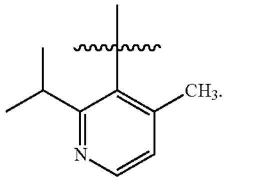 [SMILES: *c1c(C)ccnc1C(C)C]
The present invention provides the following compounds, stereoisomers, tautomers or pharmaceutically acceptable salts thereof,
3-1
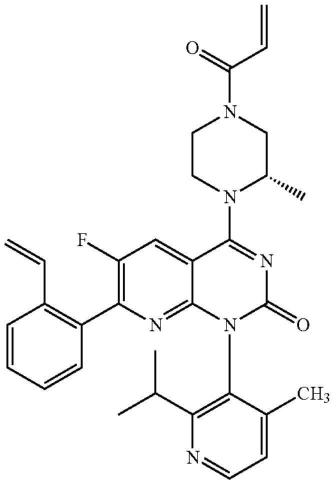
-continued
3-2
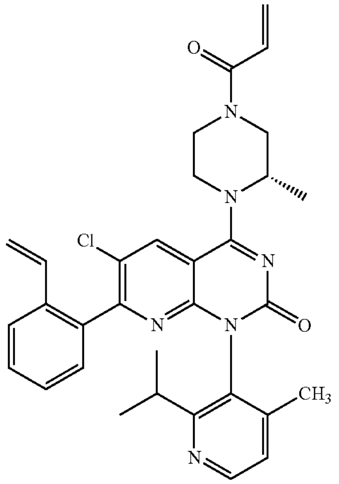
3-3
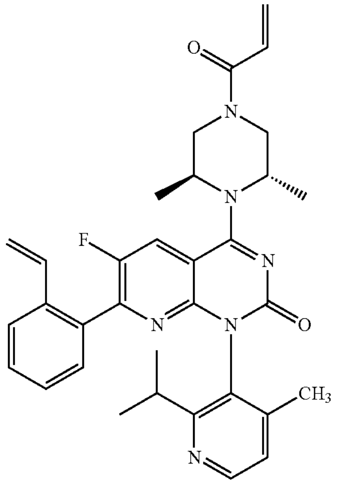
3-4
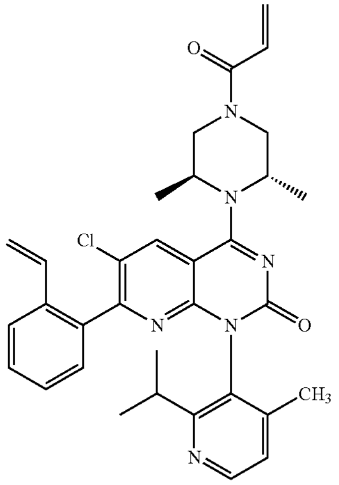

-continued
3-1a
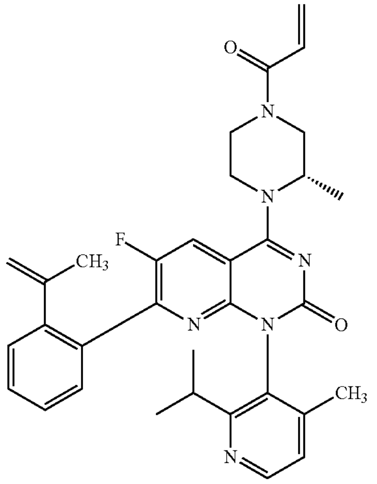
3-2a
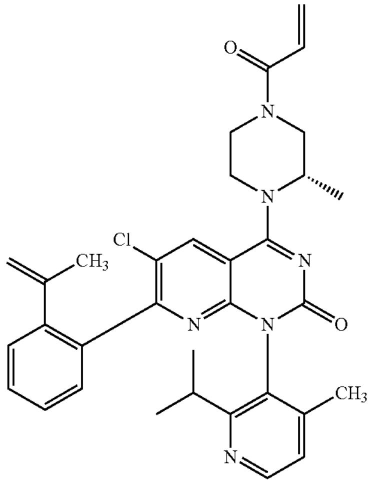
3-3a
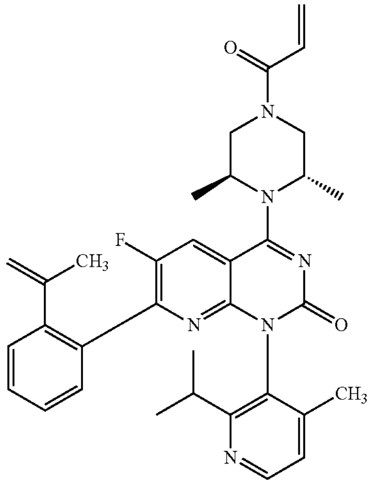
-continued
3-4a
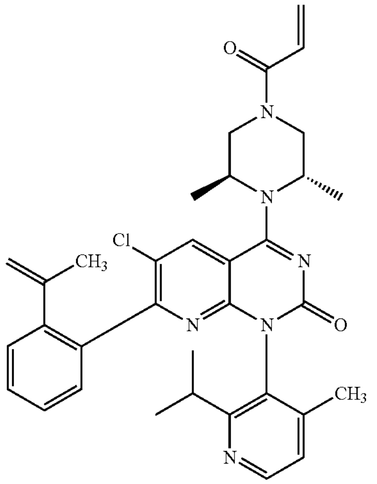
3-5
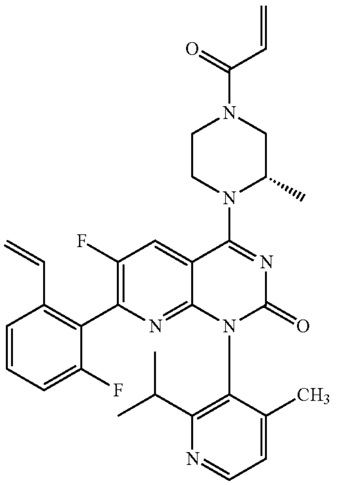
3-6
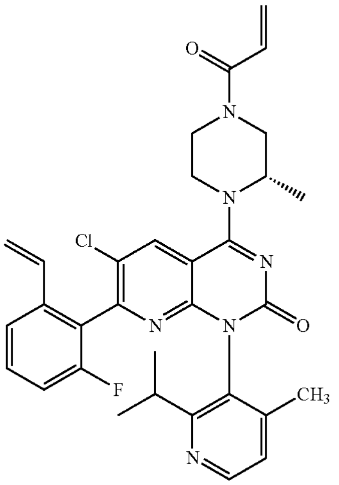

-continued
3-7
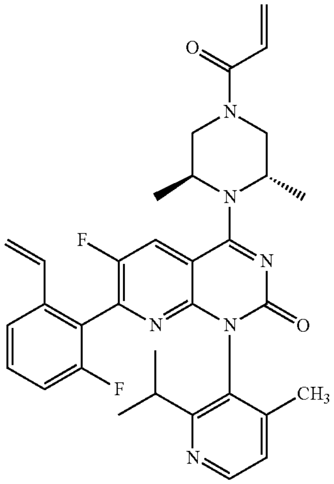
3-8
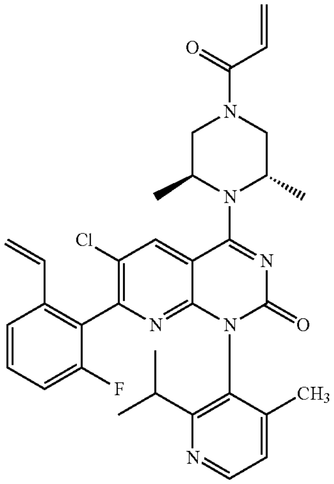
3-17
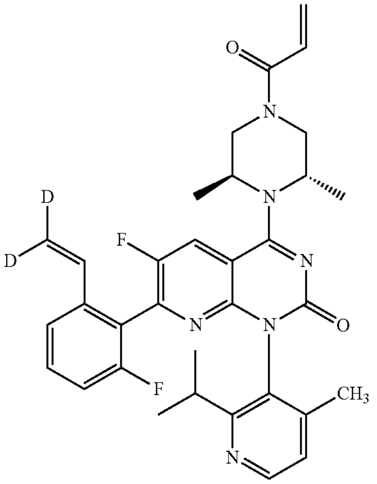
-continued
3-18
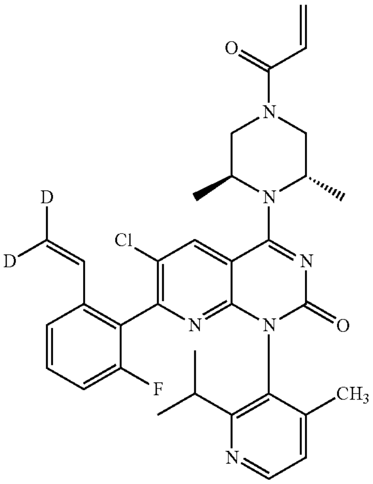
3-19
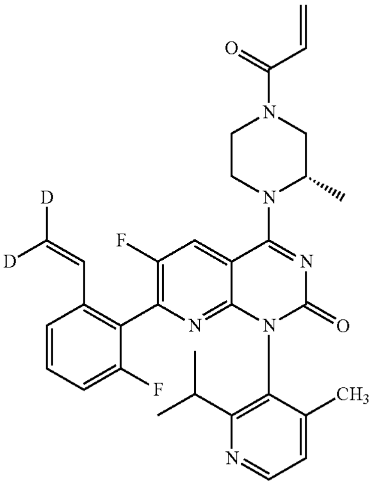
3-20
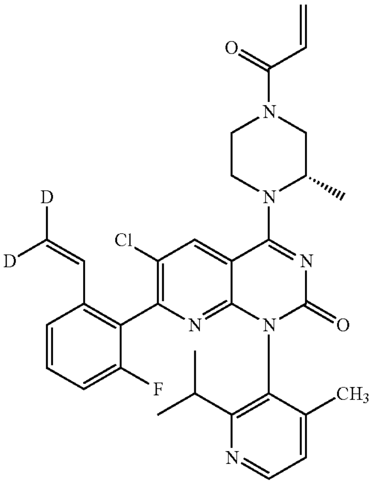

-continued
3-21
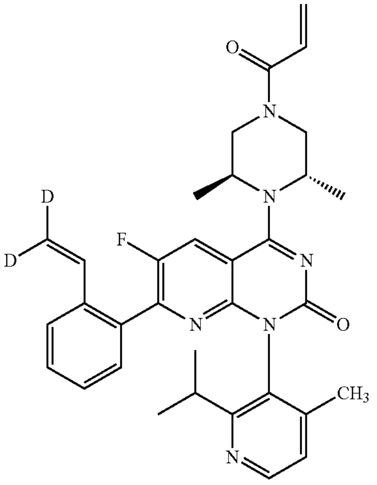
3-22
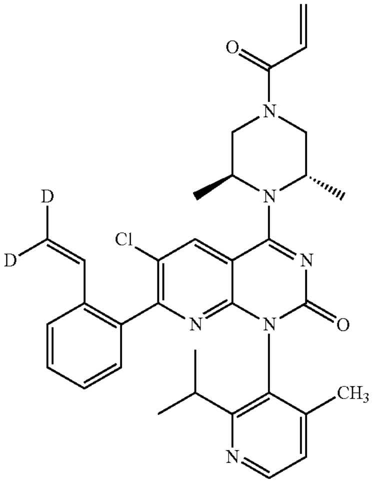
3-23
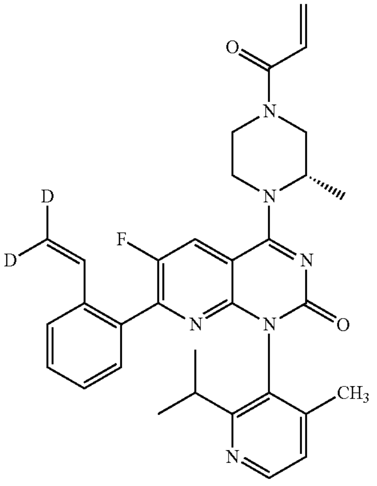
-continued
3-24
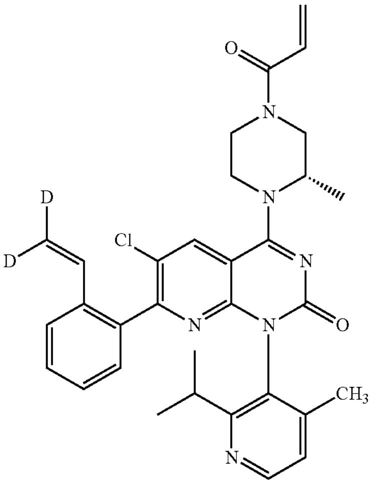
3-25
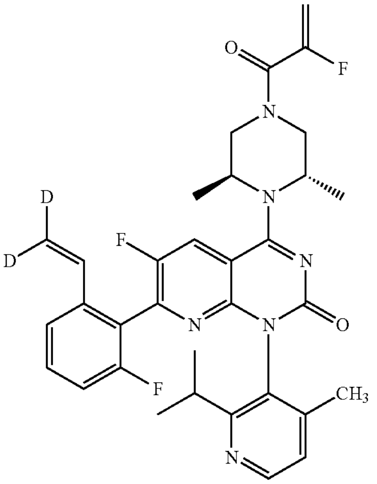
3-26
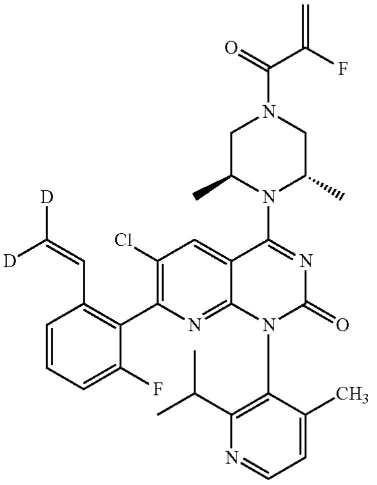

-continued
3-27
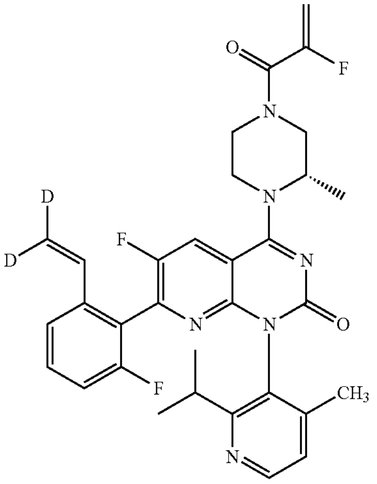
3-28
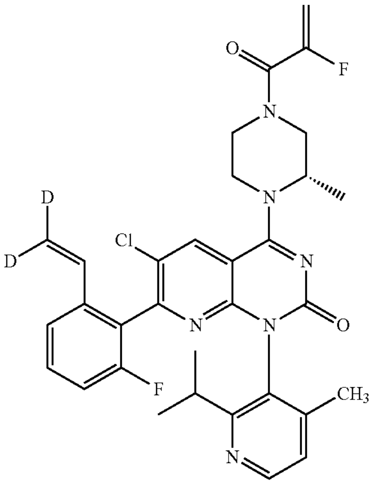
3-29
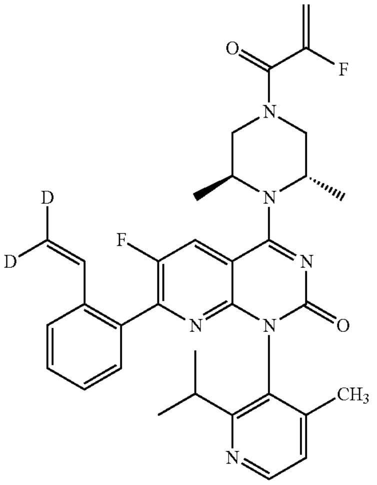
-continued
3-30
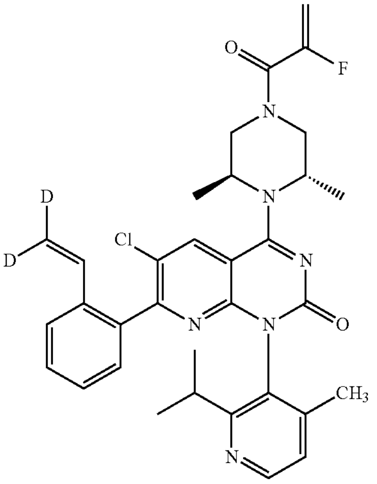
3-31
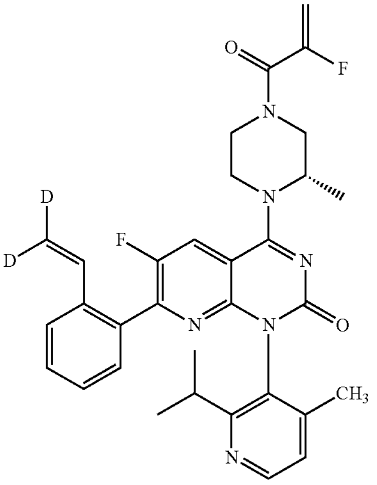
3-32
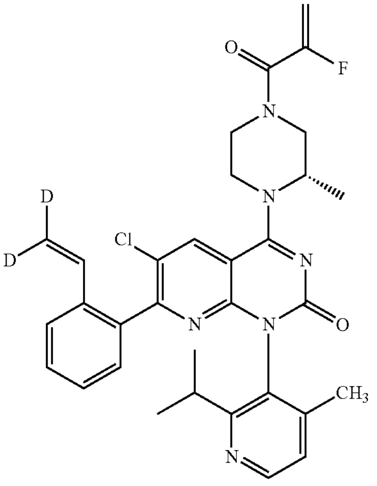

-continued
3-33
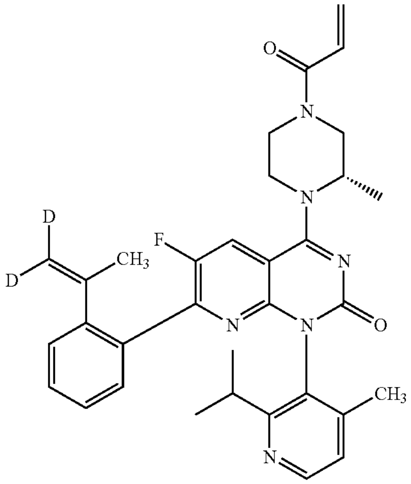
3-34
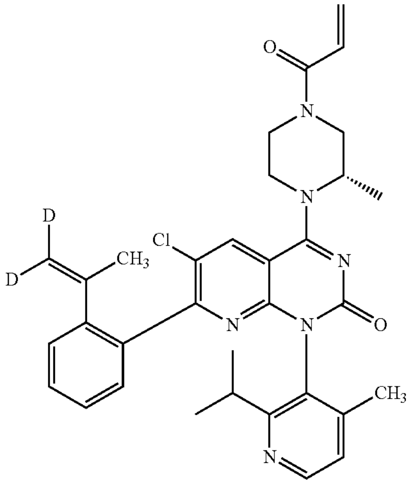
3-35
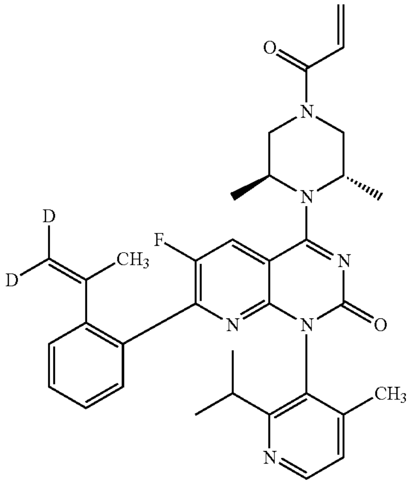
-continued
3-36
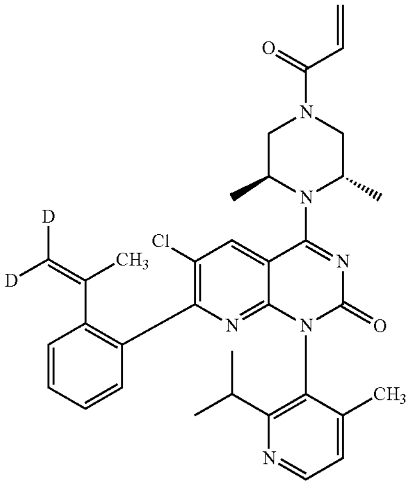
3-37
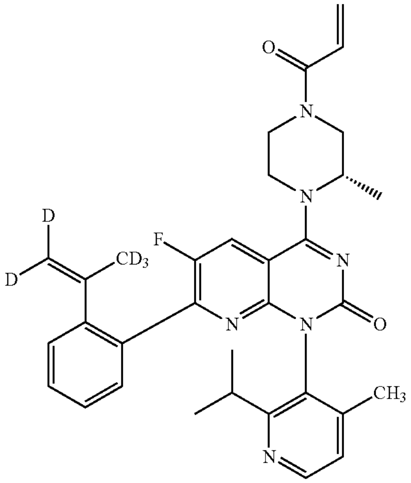
3-38
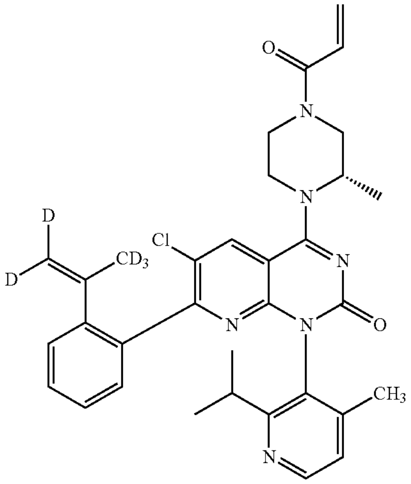

-continued
3-39
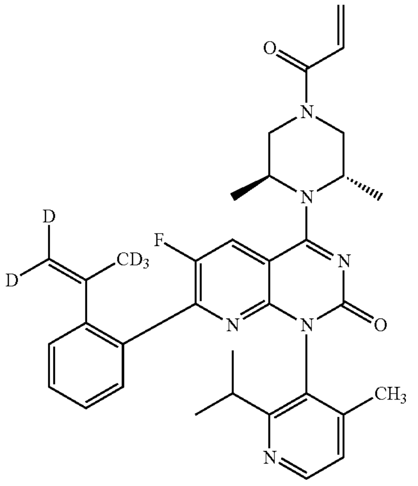
3-40
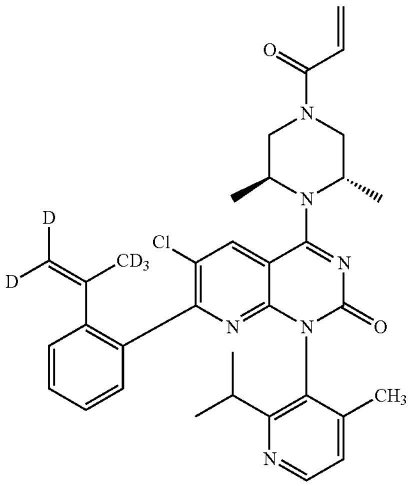
3-41
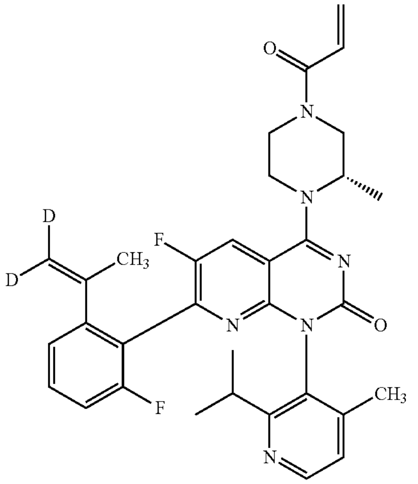
-continued
3-42
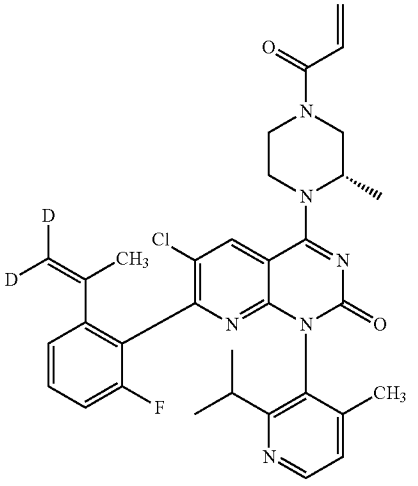
3-43
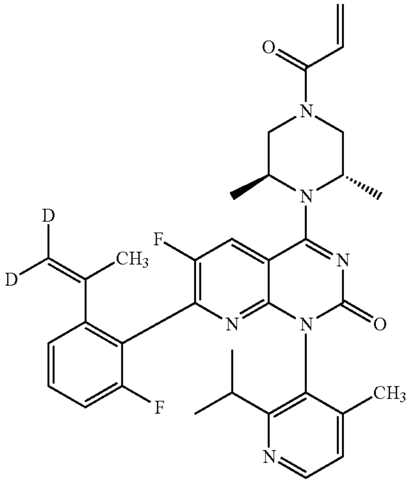
3-44
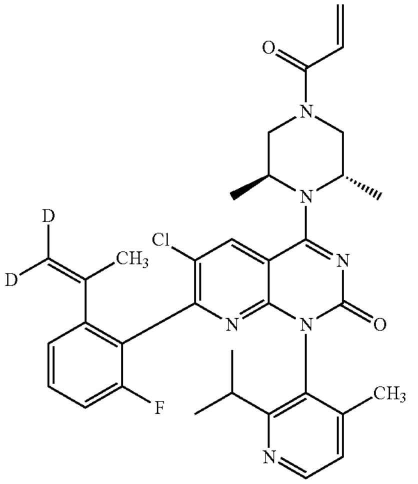

-continued
3-45
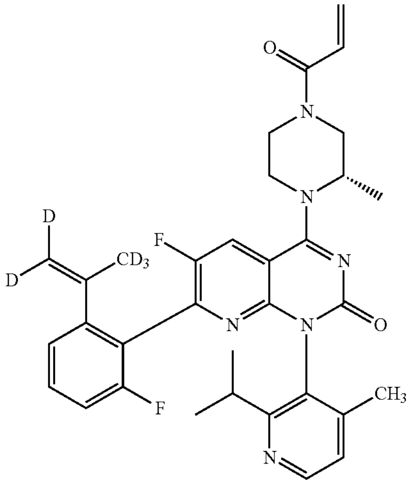
3-46
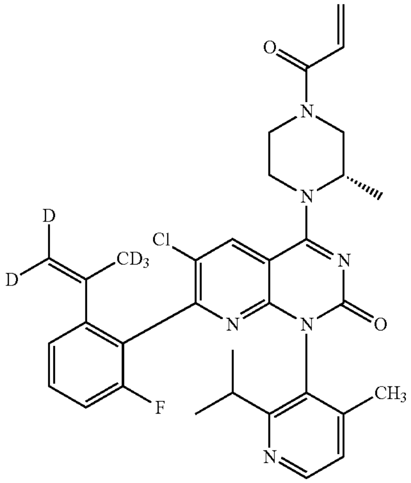
3-47
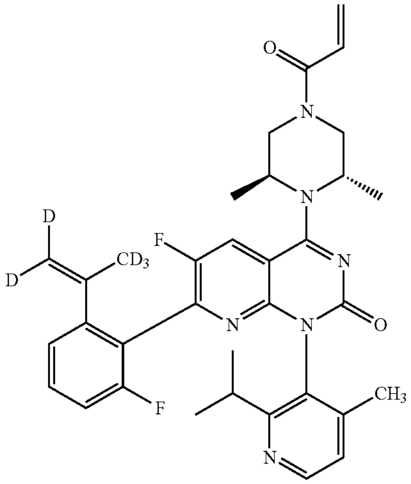
-continued
3-48
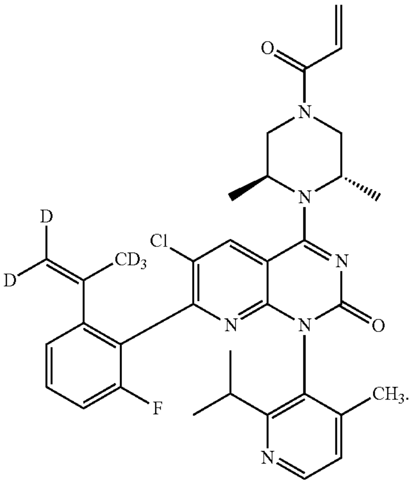
The present invention provides the following compounds, stereoisomers, tautomers or pharmaceutically acceptable salts thereof,
3-49
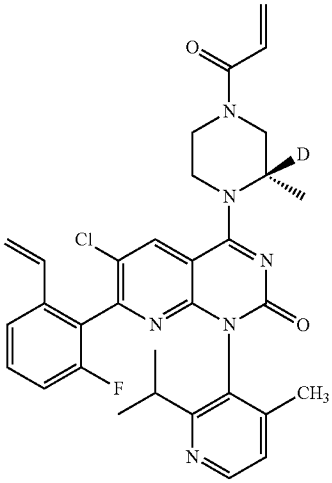
3-50
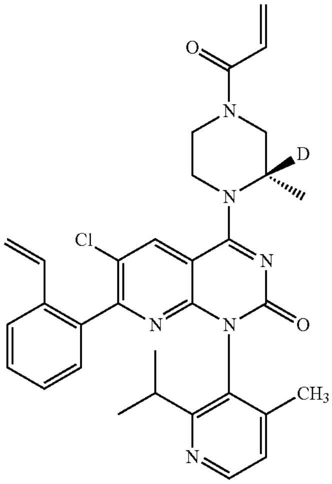

-continued
3-51
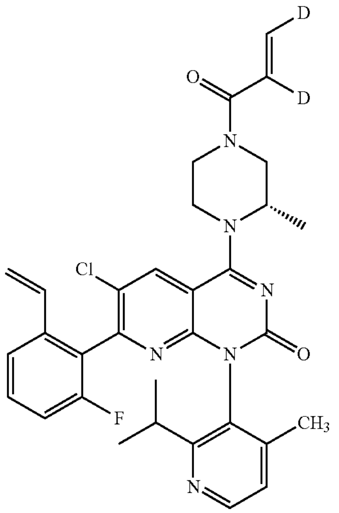
3-52
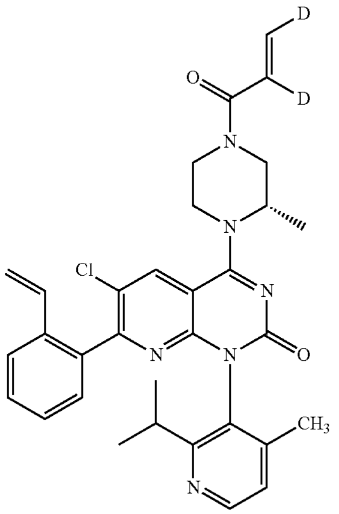
3-53
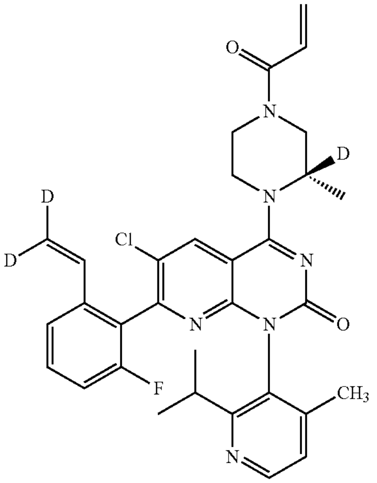
-continued
3-54
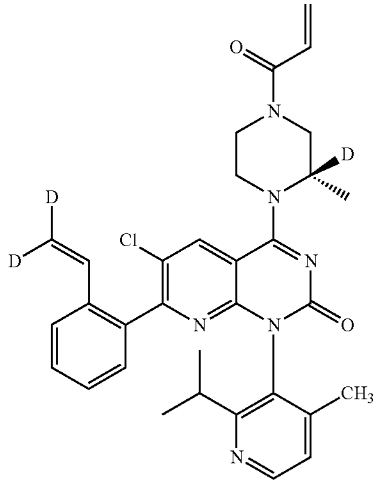
3-55
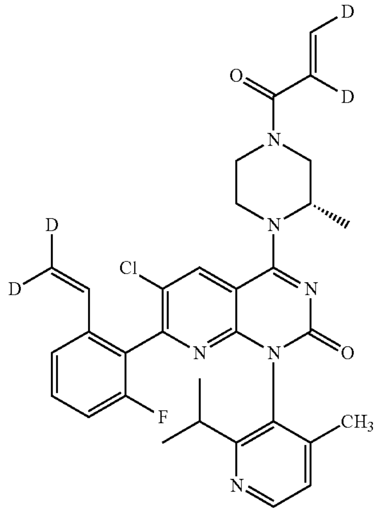
3-56
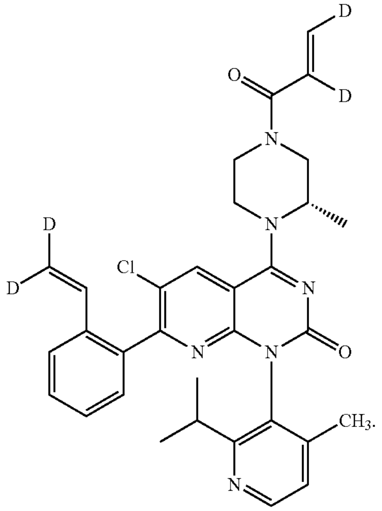
The present invention provides the following compounds, stereoisomers, tautomers or pharmaceutically acceptable salts thereof, -continued
3-1Ca
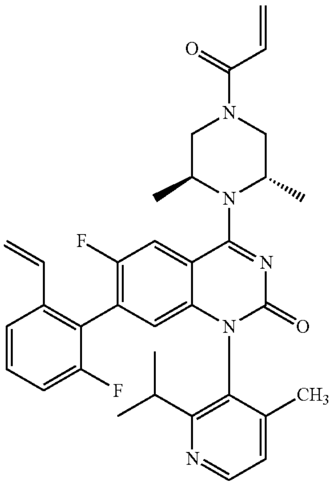
3-2Ca
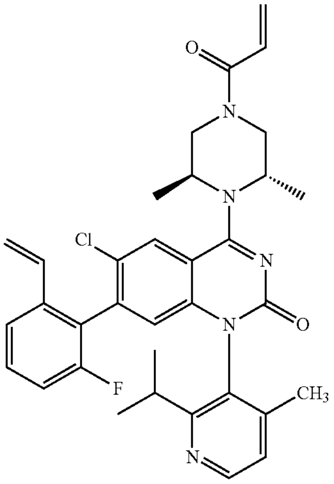
3-3Ca
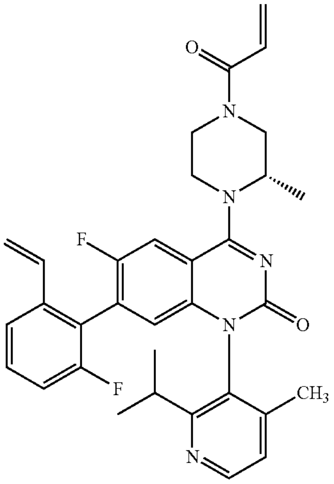
3-4Ca
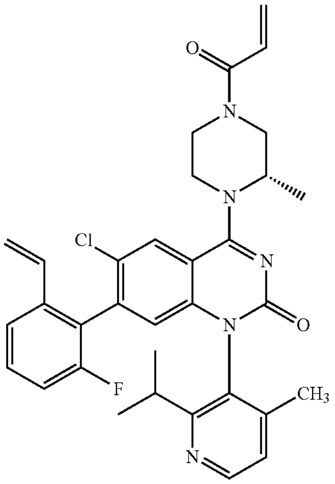
3-1C
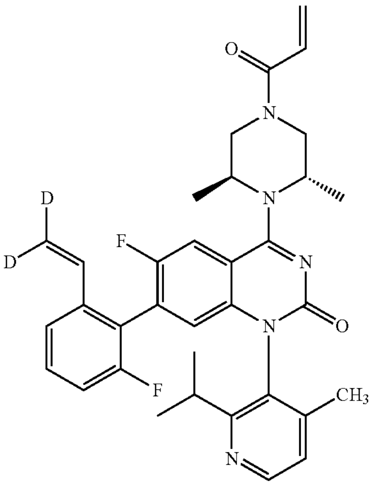
3-2C
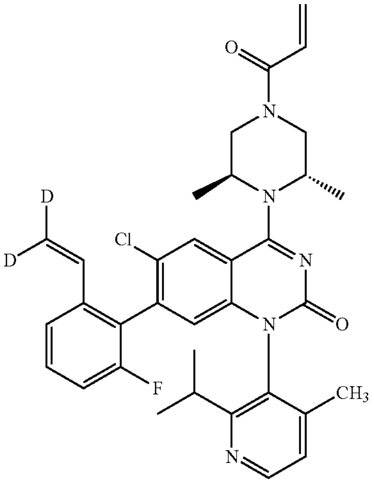

-continued
3-3C
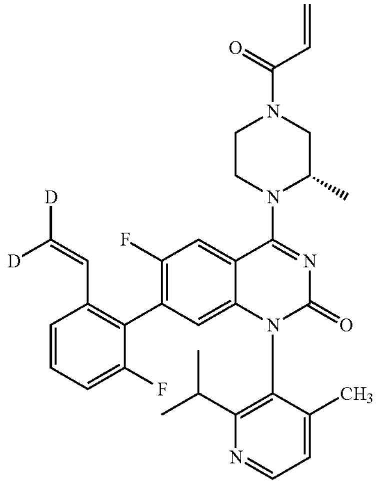
3-4C
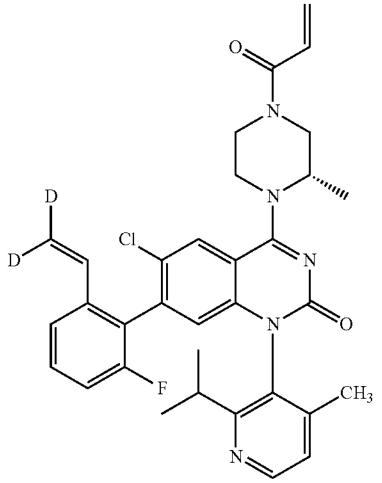
3-5C
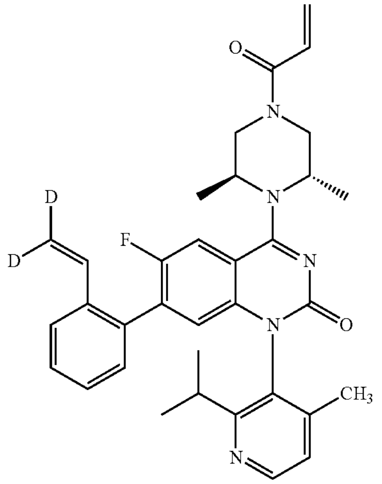
-continued
3-6C
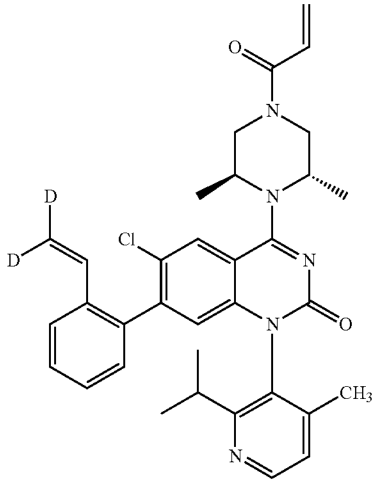
3-7C
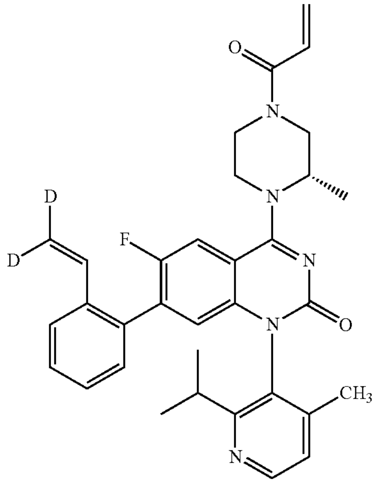
3-8C
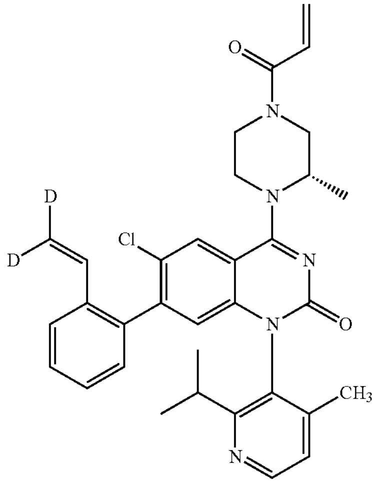

-continued
3-9C
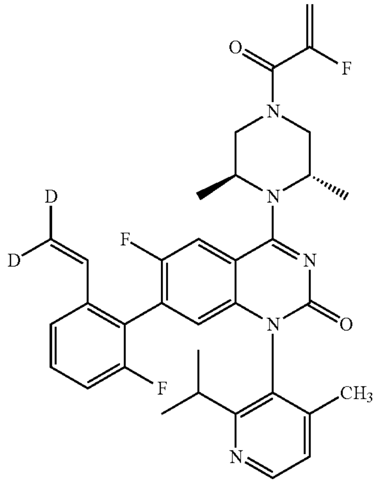
3-10C
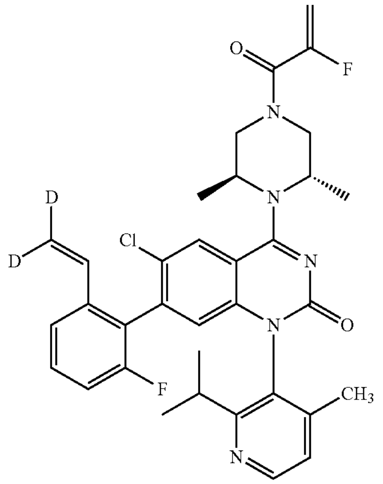
3-11C
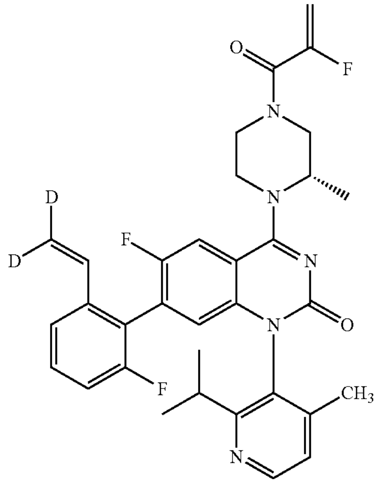
-continued
3-12C
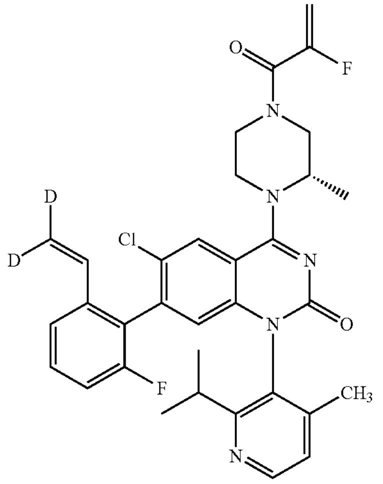
3-13C
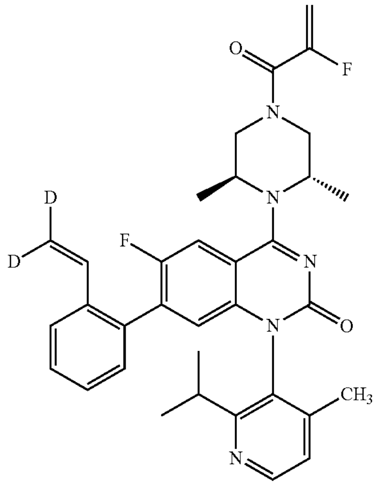
3-14C
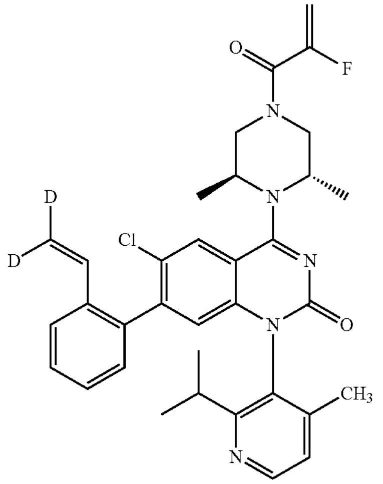

-continued 3-15C

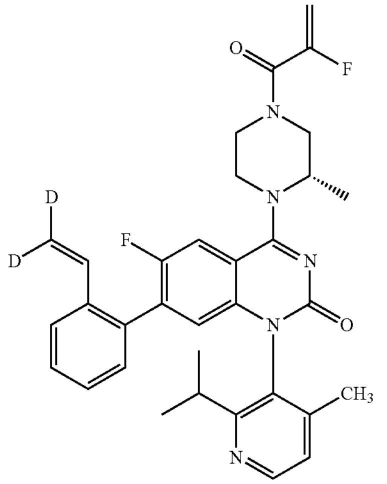

3-16C

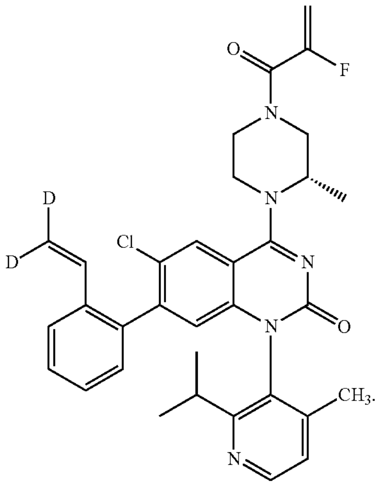

The present invention provides a compound of formula (IV), a stereoisomer, a tautomer or a pharmaceutically acceptable salt thereof,

IV

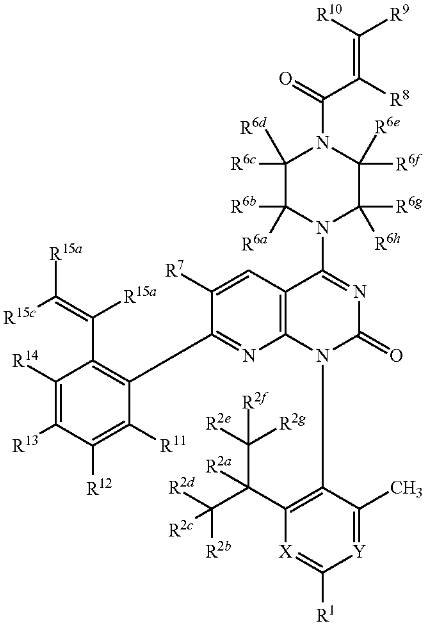

wherein, X is nitrogen atom or $CR^4$, Y is nitrogen atom or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, $R^{15c}$ are independently selected from the group consisting of hydrogen, deuterium, alkyl, deuterated alkyl;

$R^{6a}$, $R^{6b}$, $R^{6c}$, $R^{6d}$, $R^{6e}$, $R^{6f}$, $R^{6g}$, $R^{6h}$ are independently selected from the group consisting of hydrogen, deuterium, methyl, methyl-$d_3$;

$R^7$ is fluorine, chlorine;

$R^8$, $R^9$, $R^{10}$, $R^{11}$ are independently selected from the group consisting of hydrogen, deuterium, fluorine;

structural fragment

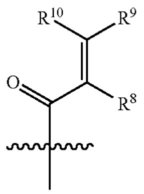

is selected from the following structures:

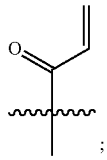
;
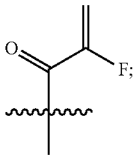
;
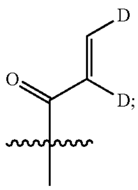
;

structural fragment

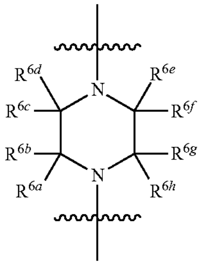
is selected from the following structures:
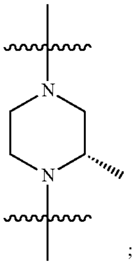 ; 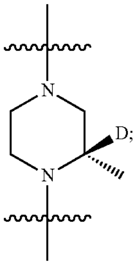 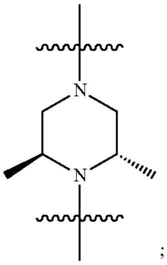 ;
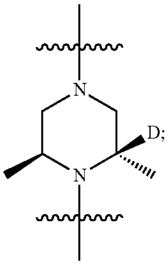 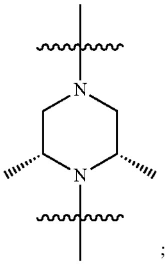 ;
structural fragment
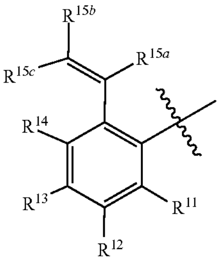
is selected from the following structures:
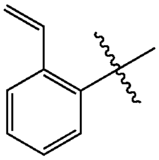 ; 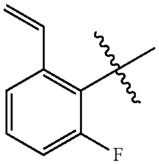 ;
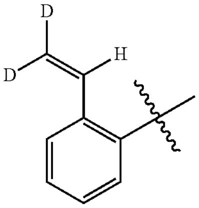 ; 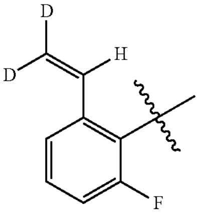 ;
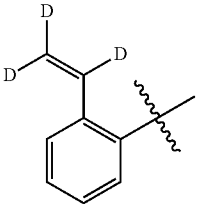 ; 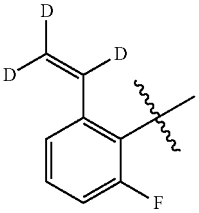 ;
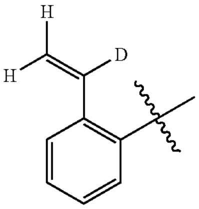 ; 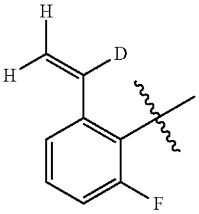 ;
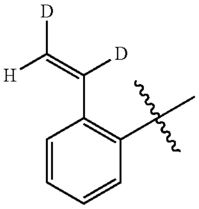 ; 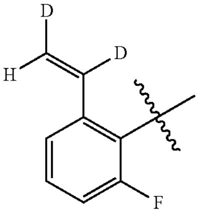 ;
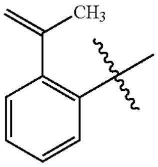 ; 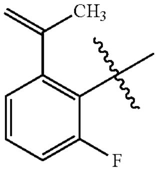 ; 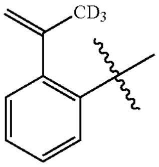 ;
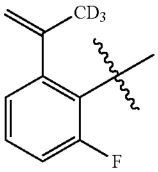 ; 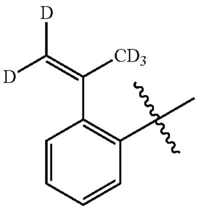 ;
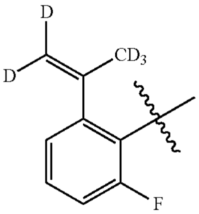 ; 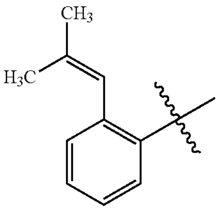 ;

-continued

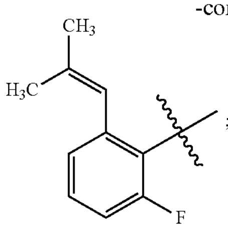 ;

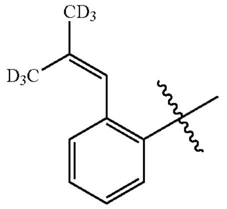 ;

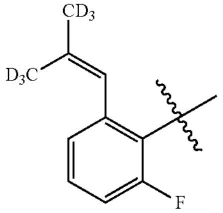 ;

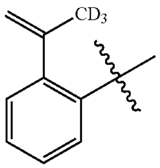 ;

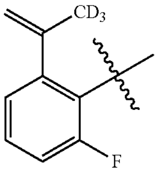 .

The present invention provides a compound of formula (IV-1), a stereoisomer, a tautomer or a pharmaceutically acceptable salt thereof,

IV-1

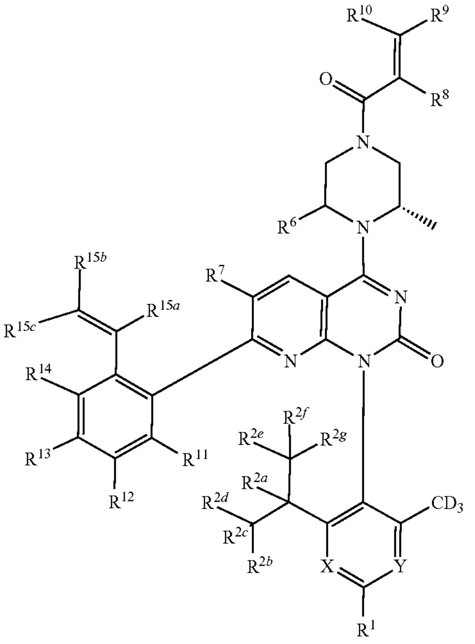

wherein, X is nitrogen atom or $CR^4$, Y is nitrogen atom or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, $R^{15c}$ are independently selected from the group consisting of hydrogen, deuterium, alkyl, deuterated alkyl;

$R^6$ is hydrogen, deuterium, methyl, methyl-$d_3$;

$R^7$ is fluorine, chlorine;

$R^8$, $R^9$, $R^{10}$, $R^{11}$ are independently selected from the group consisting of hydrogen, deuterium, fluorine;

structural fragment

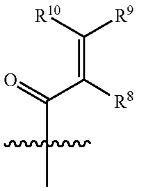

is selected from the following structures:

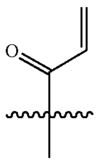 ;

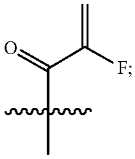 ;

structural fragment

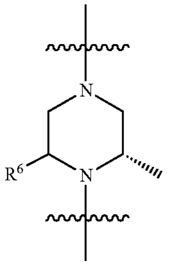

is selected from the following structures:

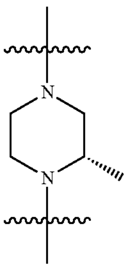 ;

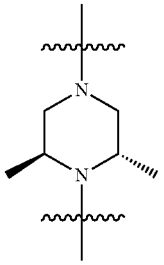 ;

-continued
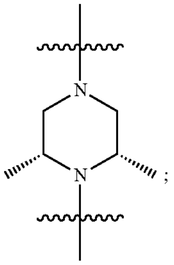
structural fragment
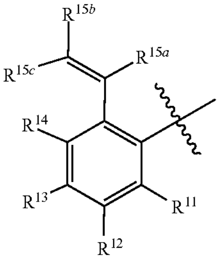
is selected from the following structures:
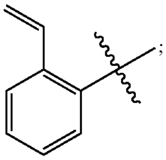
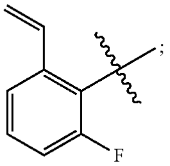
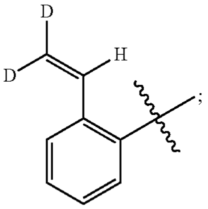
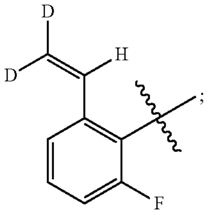
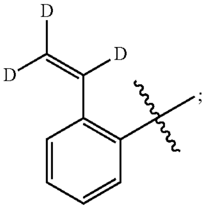
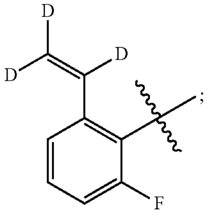
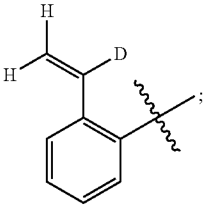
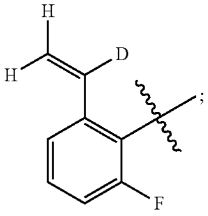
-continued
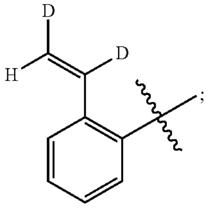
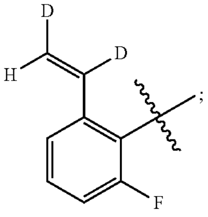
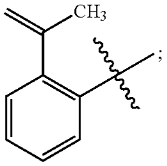
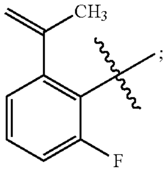
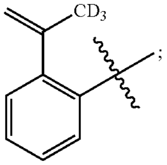
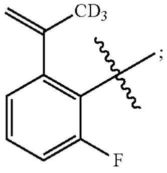
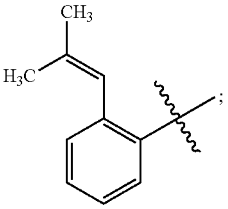
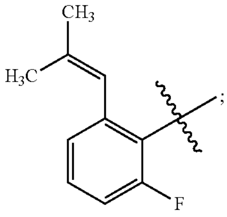
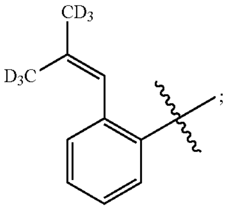
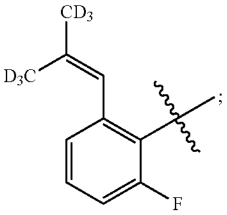
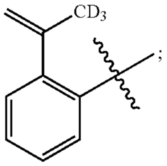
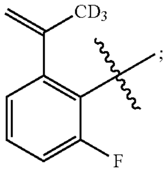
structural fragment
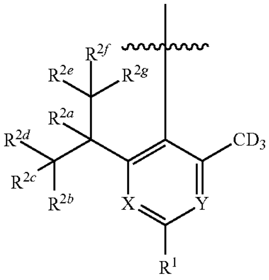
is selected from the following structure:

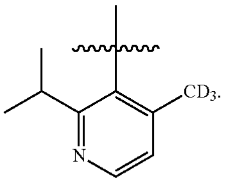
The present invention provides the following compounds, stereoisomers, tautomers or pharmaceutically acceptable salts thereof,
4-1
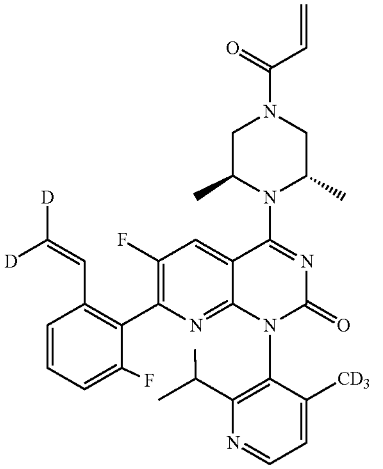
4-2
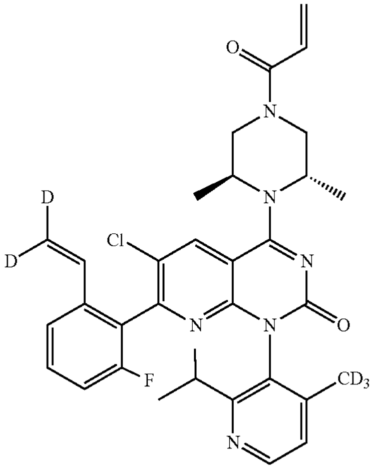
-continued
4-3
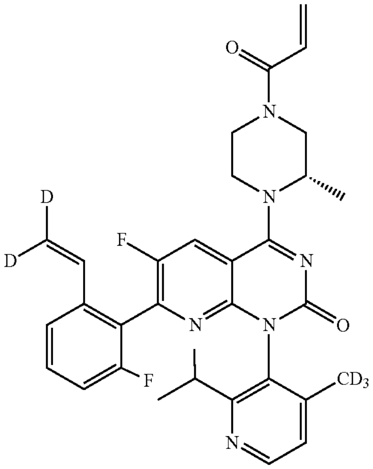
4-4
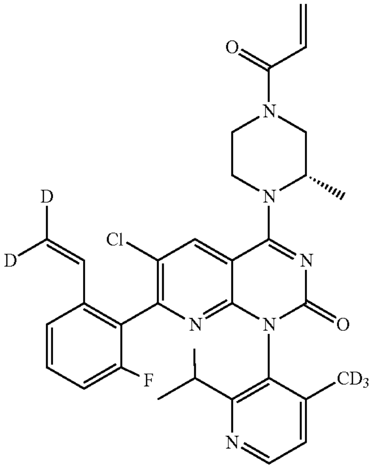
4-5
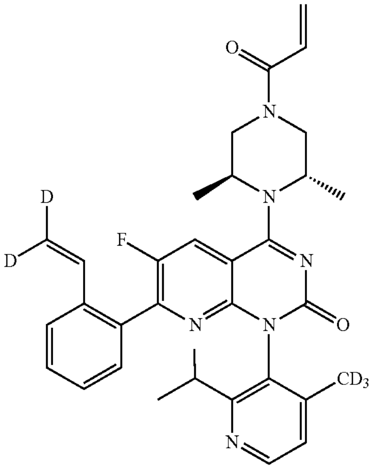

-continued
4-6
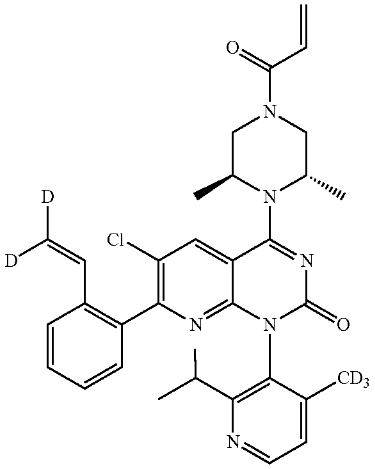
4-7
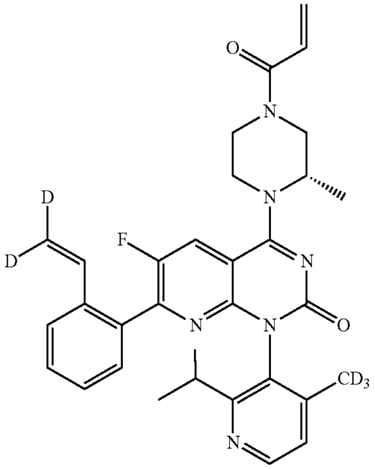
4-8
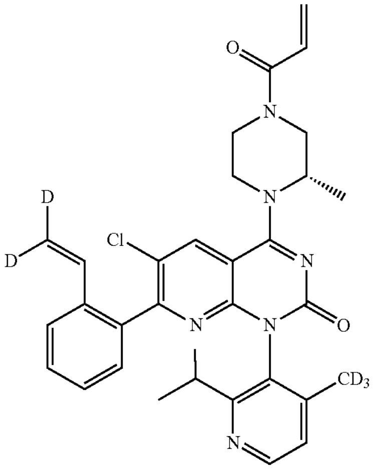
-continued
4-9
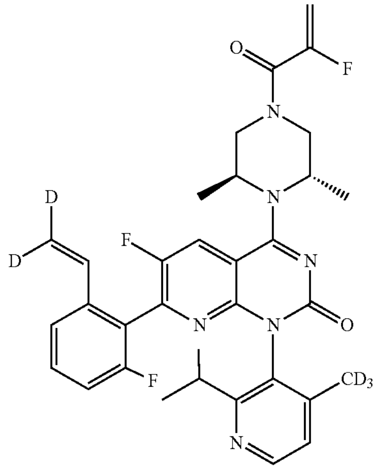
4-10
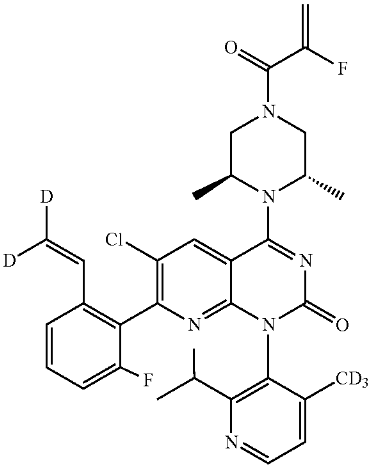
4-11
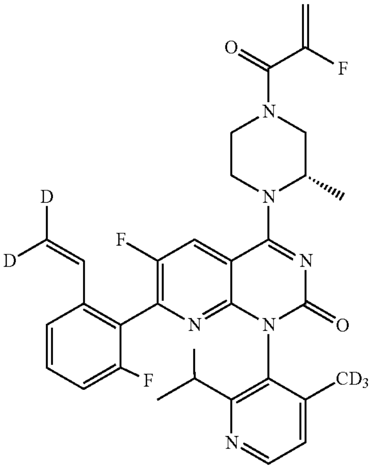

-continued
4-12
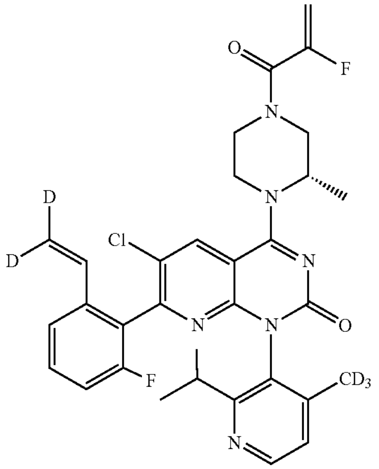
4-13
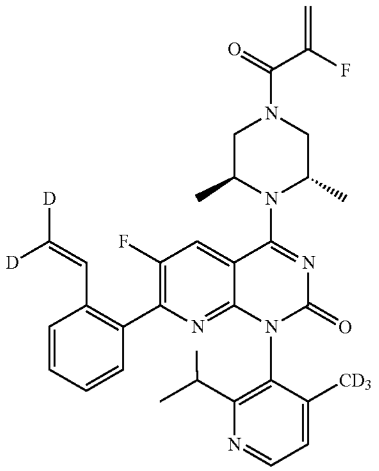
4-14
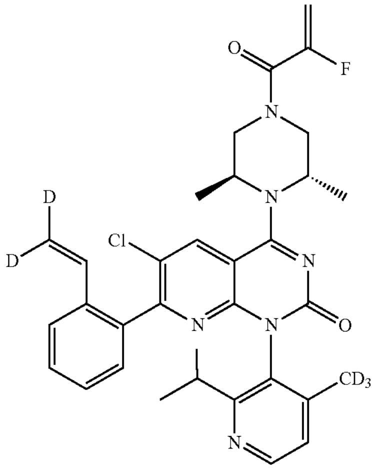
-continued
4-15
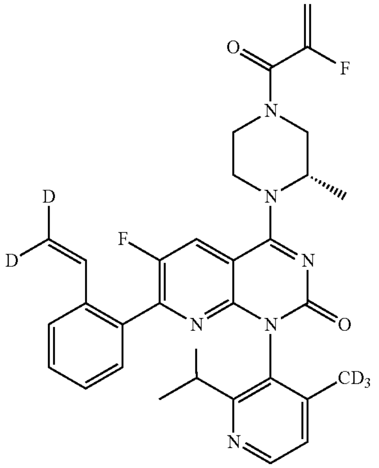
4-16
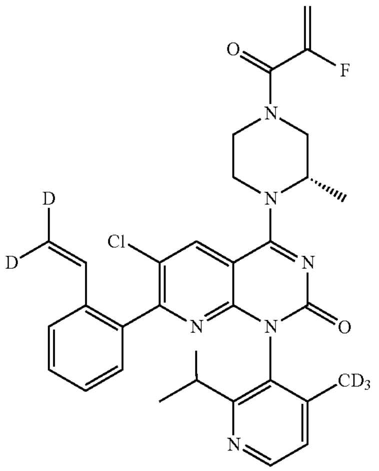
4-17
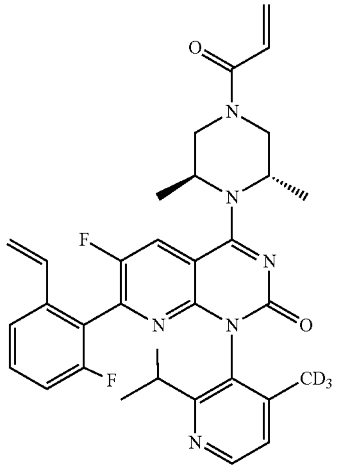

-continued
4-18
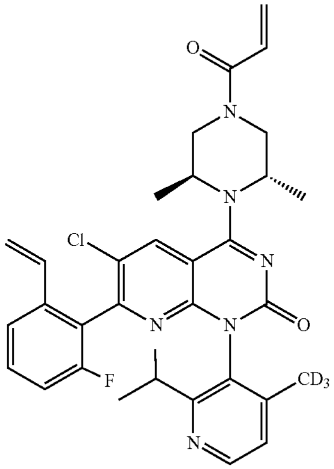
4-19
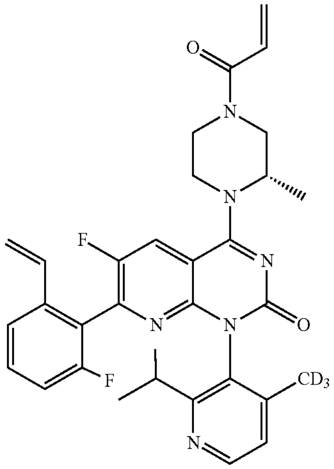
4-20
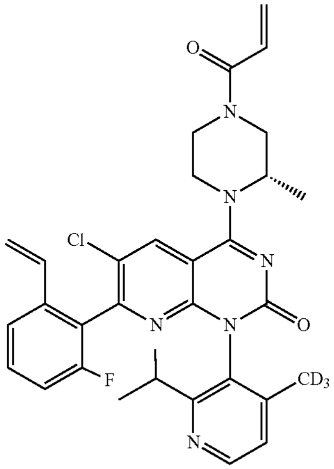
-continued
4-21
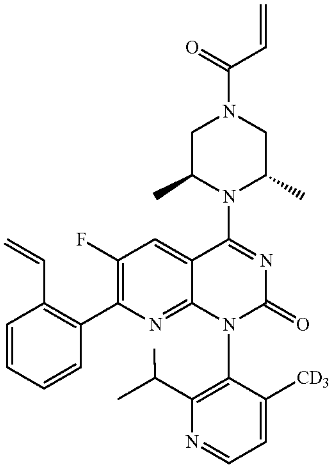
4-22
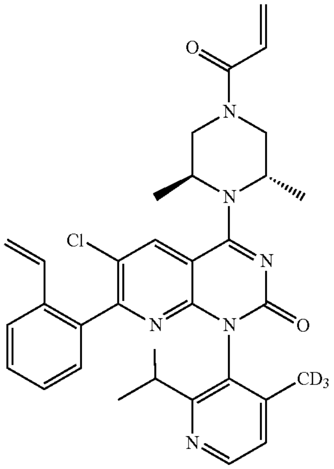
4-23
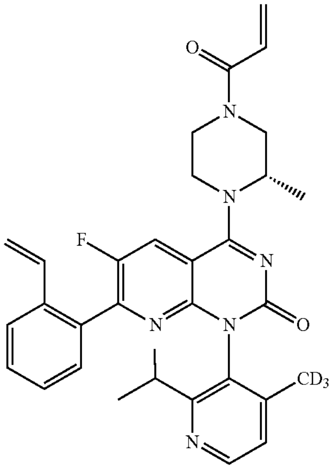

-continued
4-24
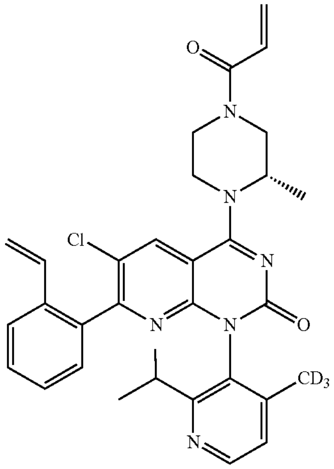
4-25
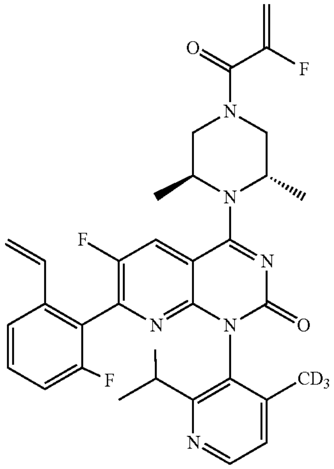
4-26
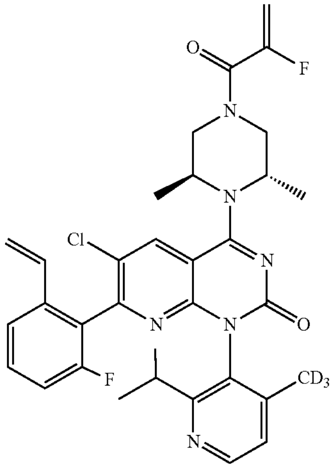
-continued
4-27
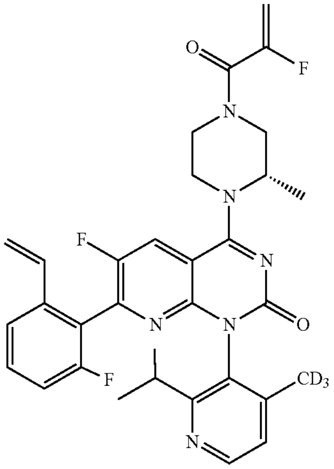
4-28
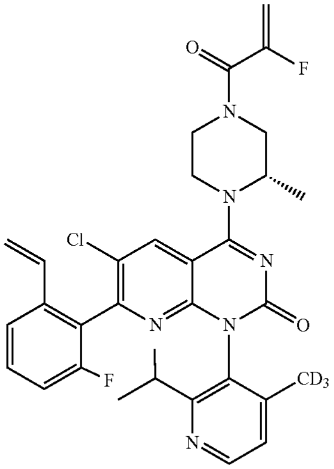
4-29
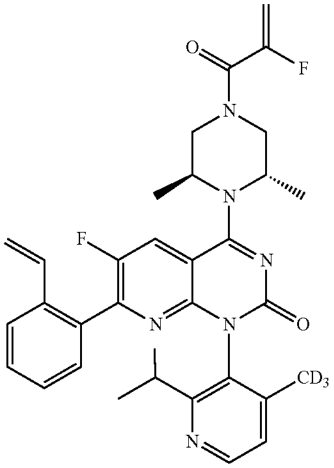

-continued
4-30
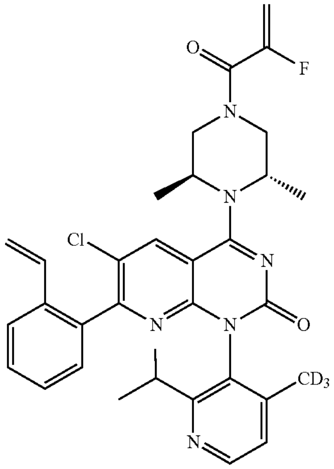
4-31
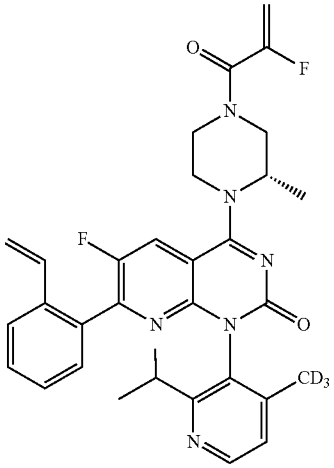
4-32
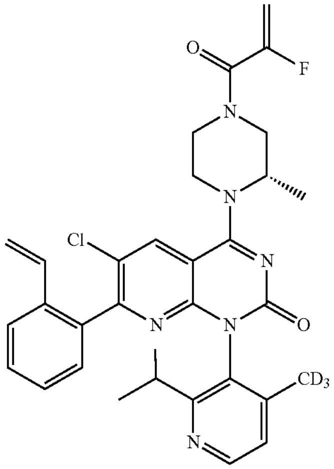
-continued
4-33
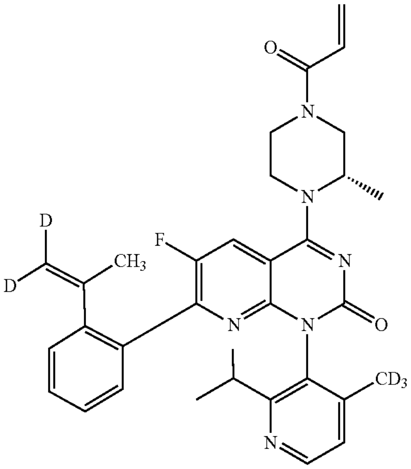
4-34
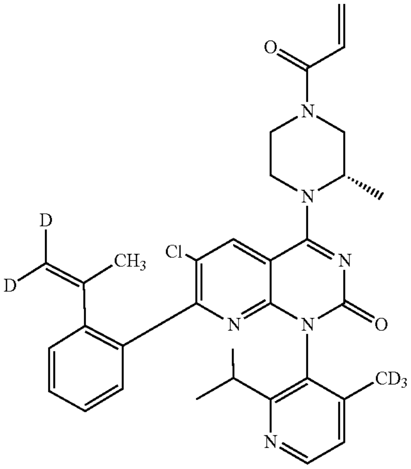
4-35
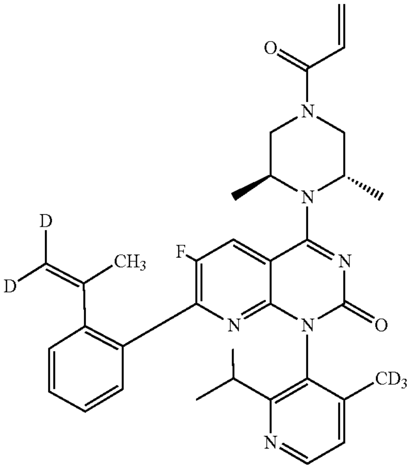

-continued
4-36
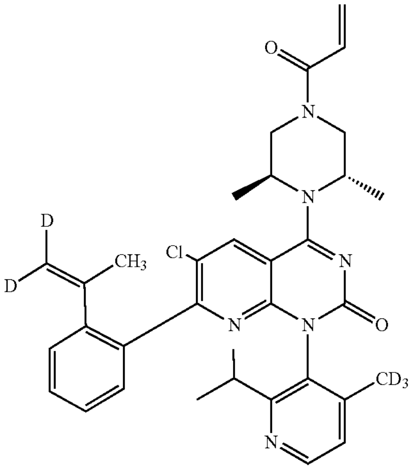
4-37
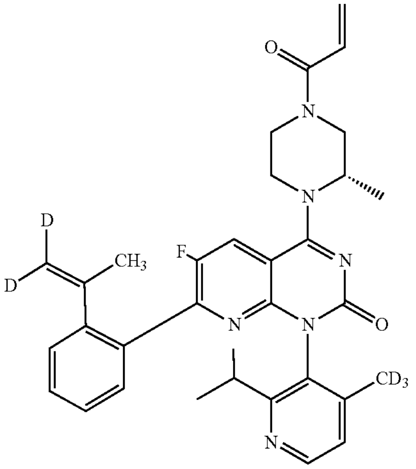
4-38
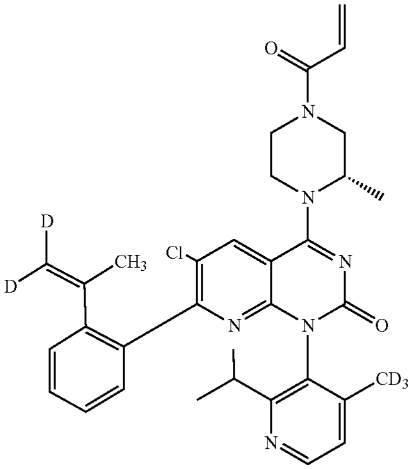
-continued
4-39
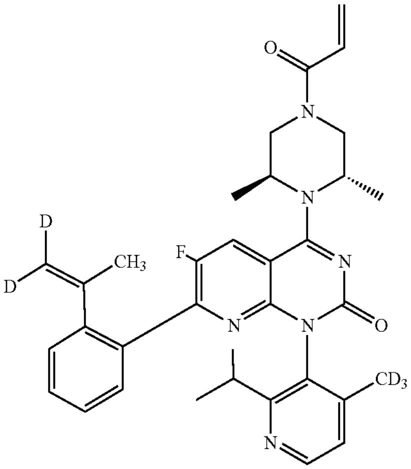
4-40
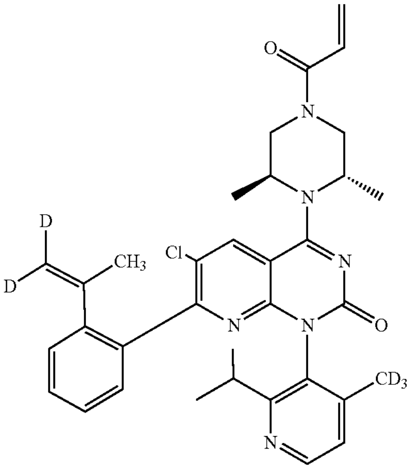
4-41
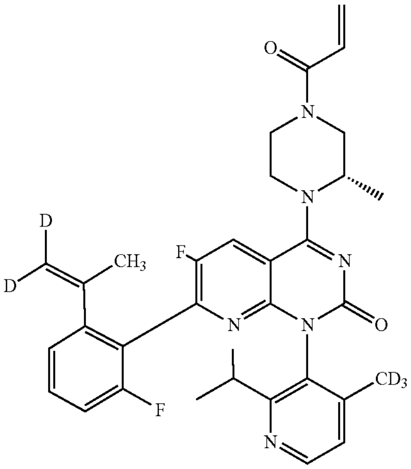

-continued
4-42
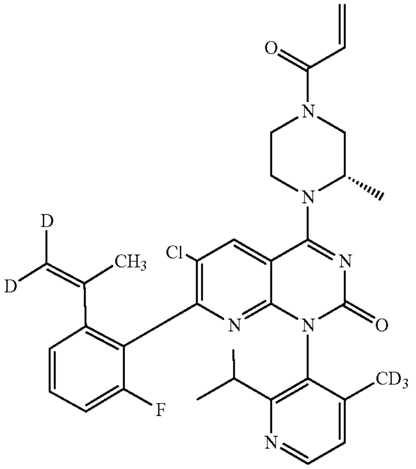
4-43
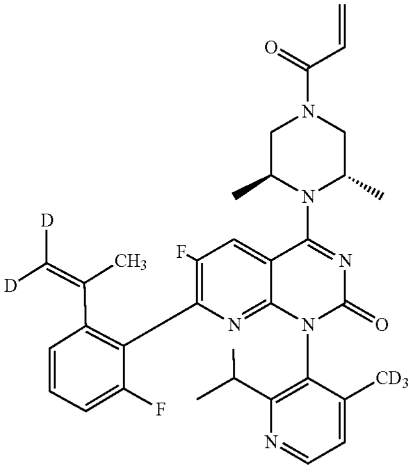
4-44
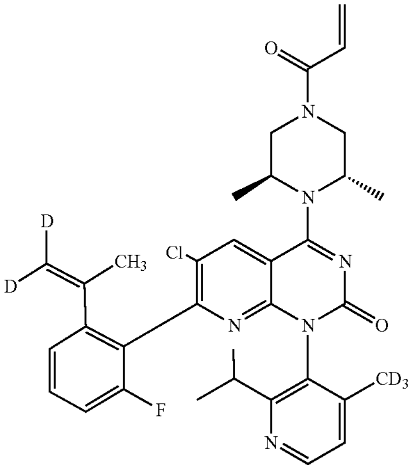
-continued
4-45
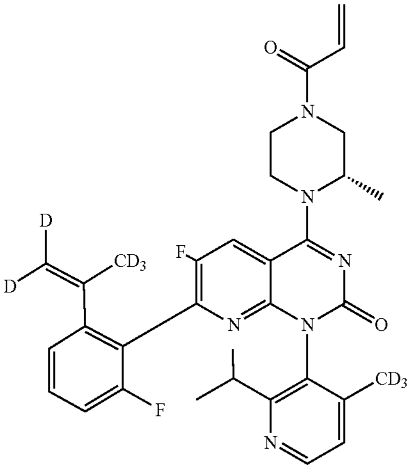
4-46
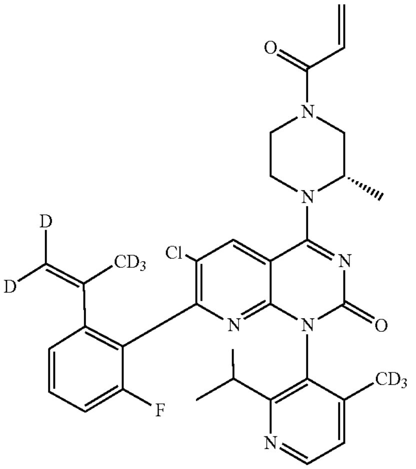
4-47
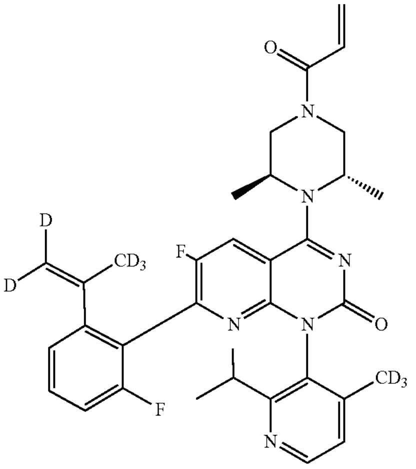

-continued
4-48
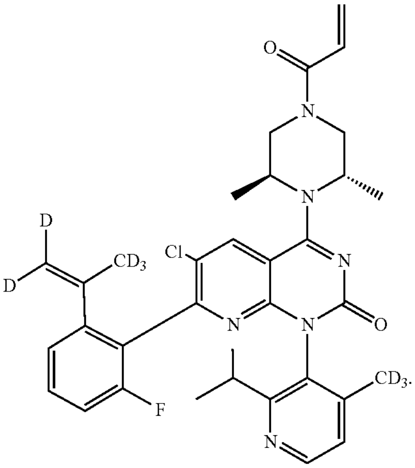
The present invention provides the following compounds, stereoisomers, tautomers or pharmaceutically acceptable salts thereof,
4-1C
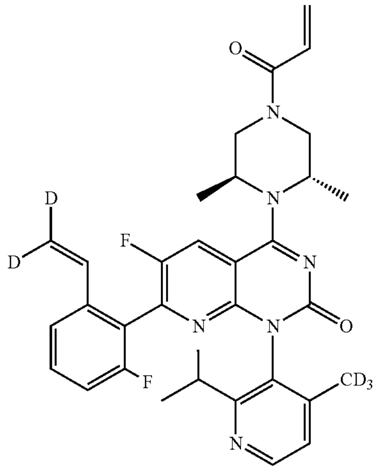
4-2C
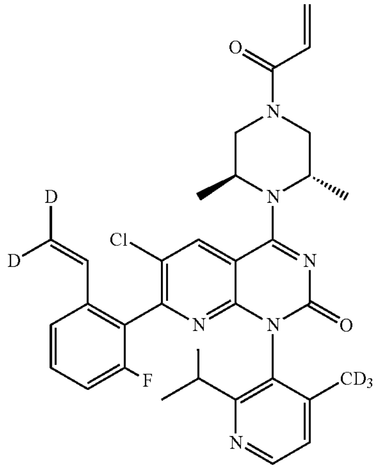
-continued
4-3C
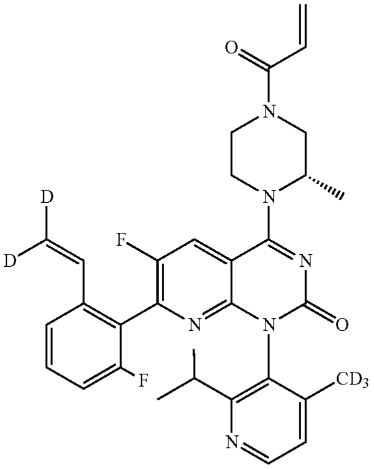
4-4C
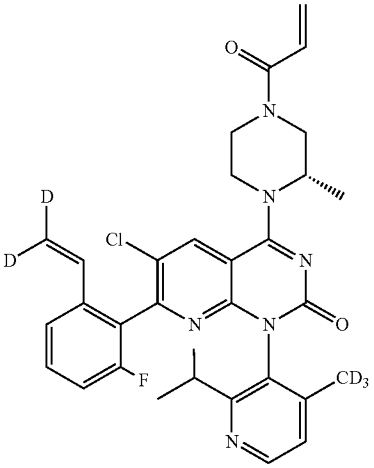
4-5C
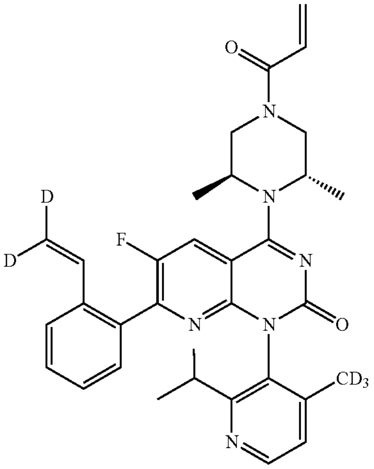

-continued
4-6C
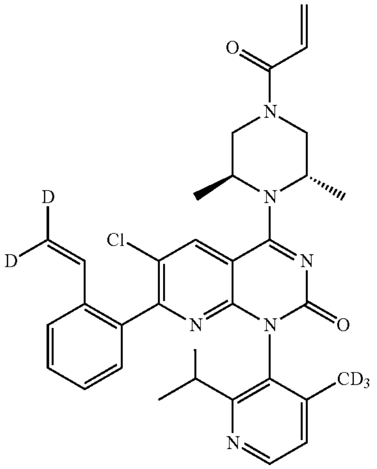
4-7C
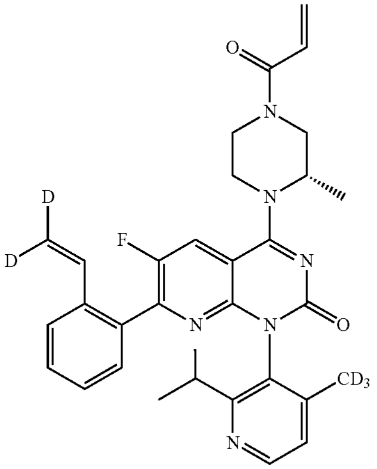
4-8C
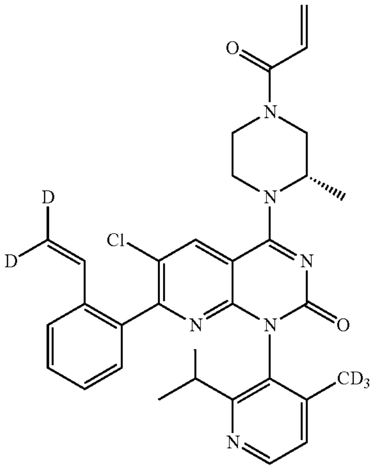
-continued
4-9C
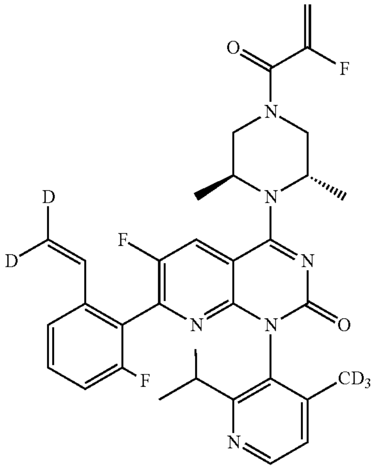
4-10C
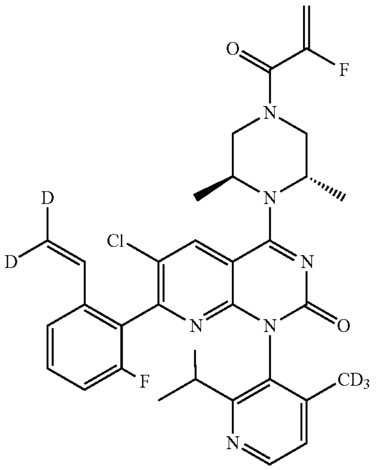
4-11C
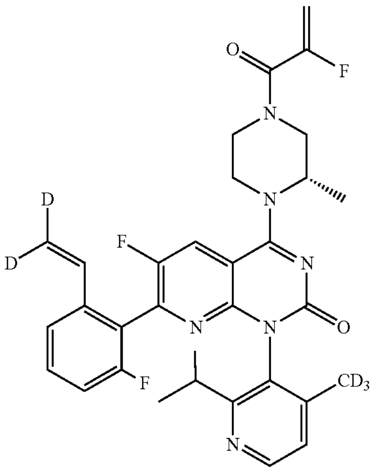

-continued
4-12C
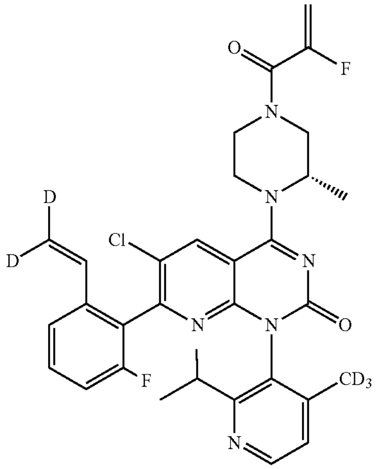
4-13C
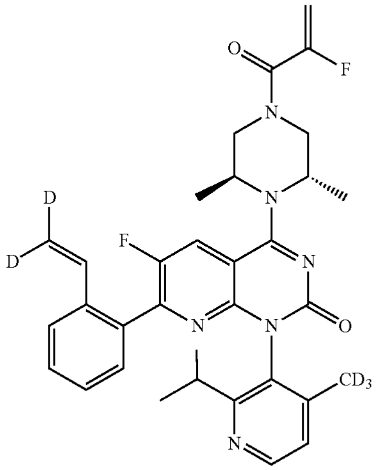
4-14C
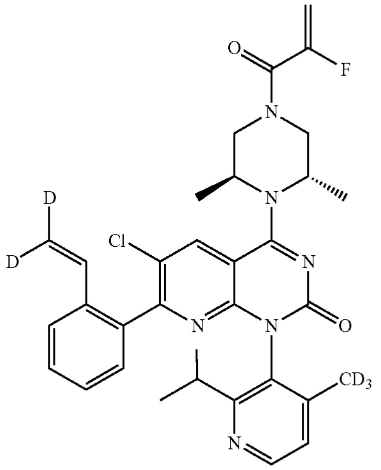
-continued
4-15C
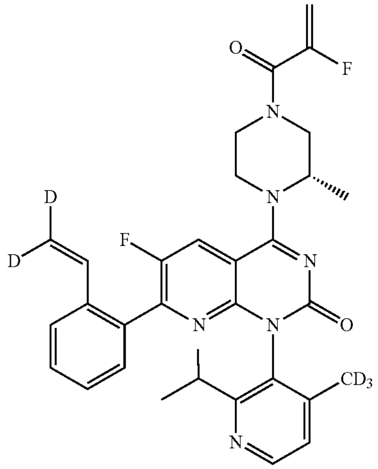
4-16C
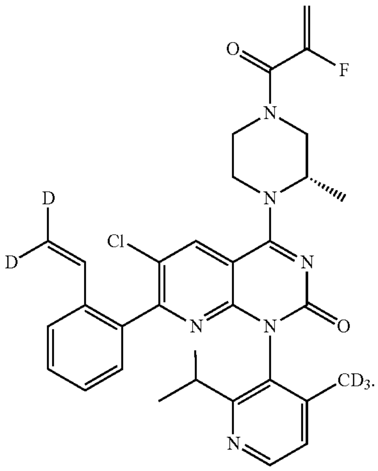
The present invention provides a compound of formula (V), a stereoisomer, a tautomer or a pharmaceutically acceptable salt thereof,

V

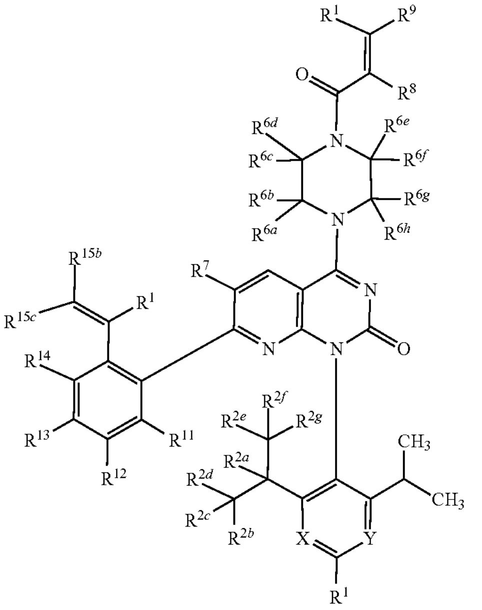

wherein, X is nitrogen atom or $CR^4$, Y is nitrogen atom or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, $R^{15c}$ are independently selected from the group consisting of hydrogen, deuterium, alkyl, deuterated alkyl;

$R^{6a}$, $R^{6b}$, $R^{6c}$, $R^{6d}$, $R^{6e}$, $R^{6f}$, $R^{6g}$, $R^{6h}$ are independently selected from the group consisting of hydrogen, deuterium, methyl, methyl-$d_3$;

$R^7$ is fluorine, chlorine;

$R^8$, $R^9$, $R^{10}$, $R^{11}$ are independently selected from the group consisting of hydrogen, deuterium, fluorine;

structural fragment

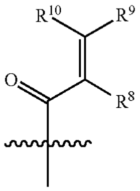

is selected from the following structures:

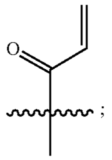

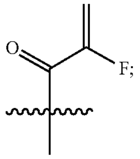

-continued

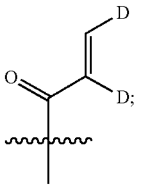

structural fragment

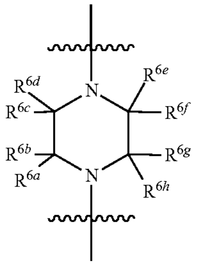

is selected from the following structures:

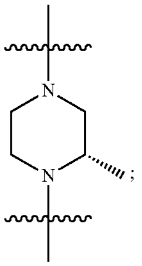

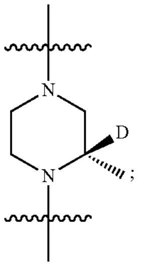

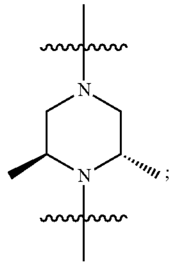

-continued
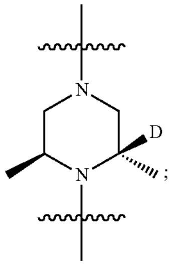 ;
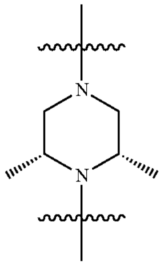 ;
structural fragment
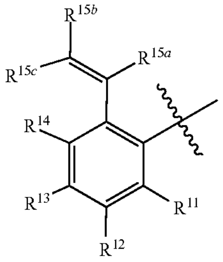
is selected from the following structures:
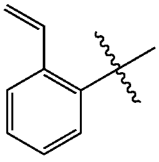 ; 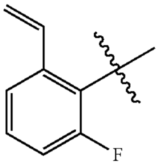 ;
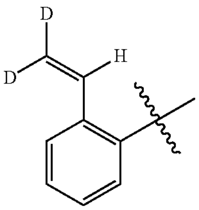 ; 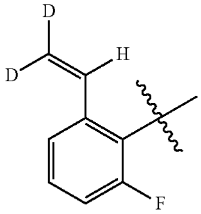 ;
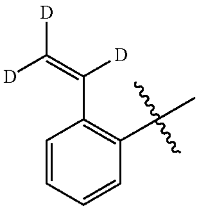 ; 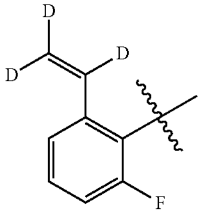 ;
-continued
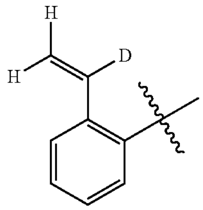 ; 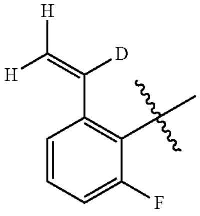 ;
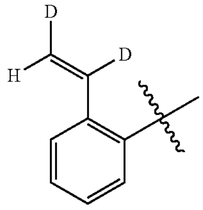 ; 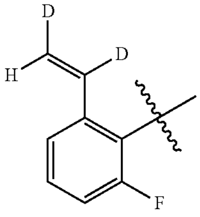 ;
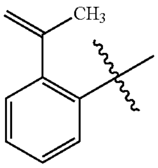 ; 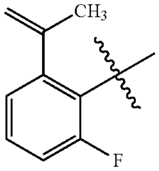 ; 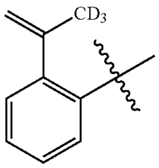 ;
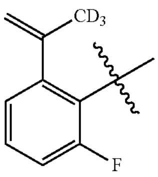 ; 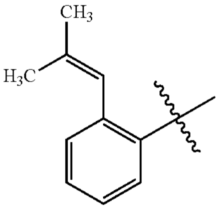 ;
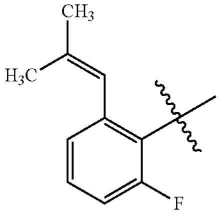 ; 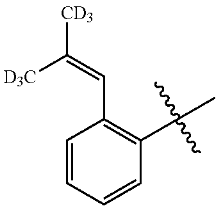 ;
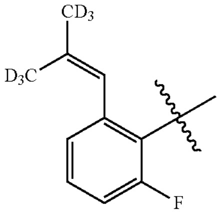 ; 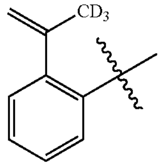 ;
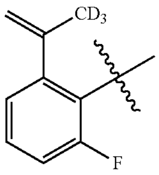 .
The present invention provides a compound of formula (V-1), a stereoisomer, a tautomer or a pharmaceutically acceptable salt thereof,

V-1

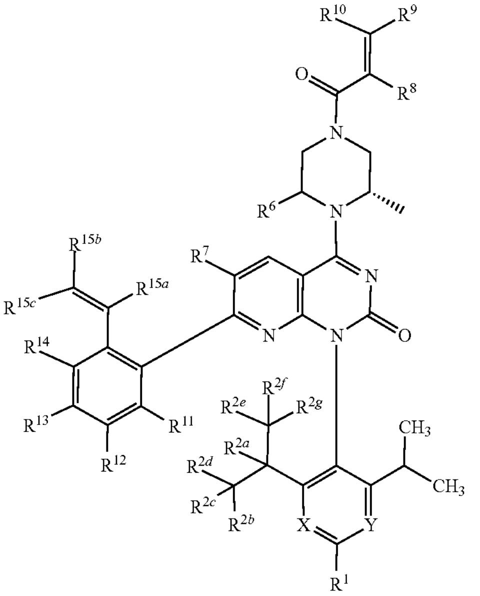

wherein, X is nitrogen atom or $CR^4$, Y is nitrogen atom or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, $R^{15c}$ are independently selected from the group consisting of hydrogen, deuterium, alkyl, deuterated alkyl;

$R^6$ is hydrogen, deuterium, methyl, methyl-$d_3$;

$R^7$ is fluorine, chlorine;

$R^8$, $R^9$, $R^{10}$, $R^{11}$ are independently selected from the group consisting of hydrogen, deuterium, fluorine;

structural fragment

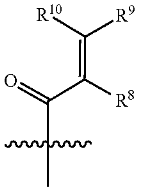

is selected from the following structures:

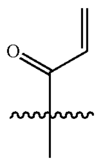

;

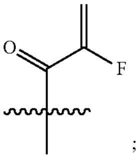

;

structural fragment

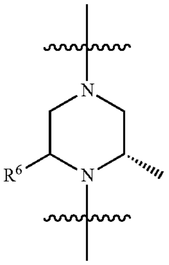

is selected from the following structures:

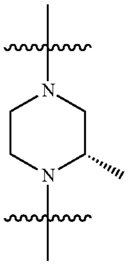

;

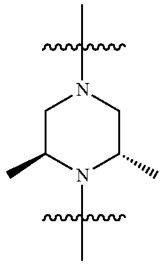

;

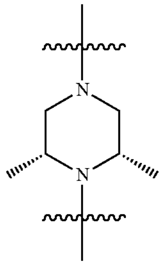

;

structural fragment

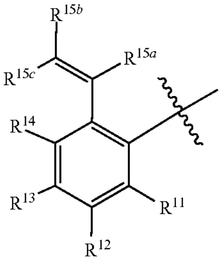

is selected from the following structures:

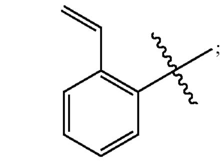;
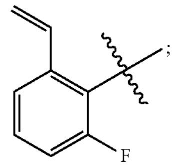;
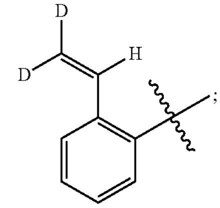;
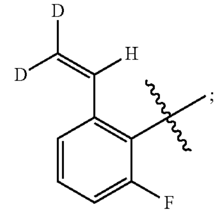;
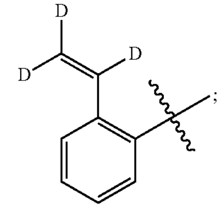;
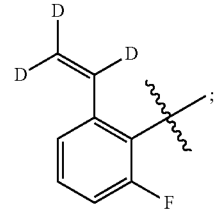;
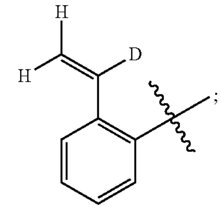;
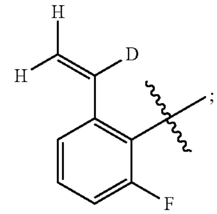;
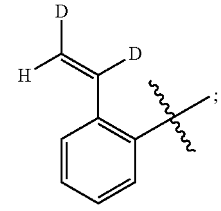;
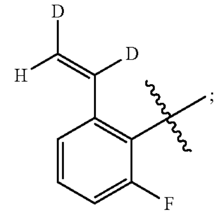;
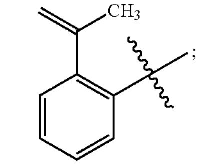;
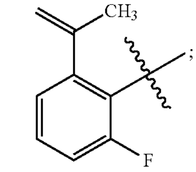;
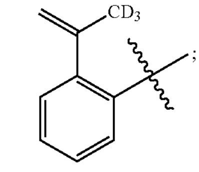;
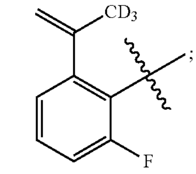;
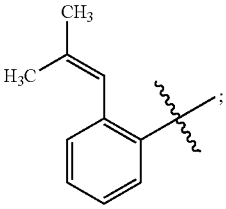;
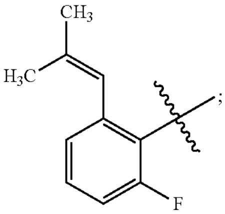;
-continued
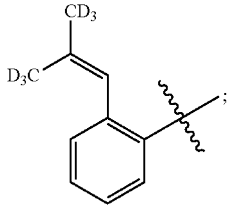;
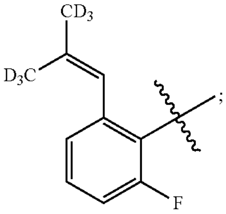;
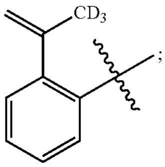;
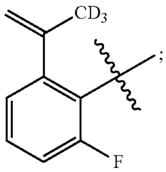;
structural fragment
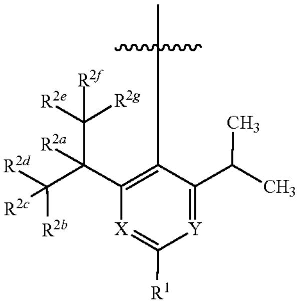
is selected from the following structure:
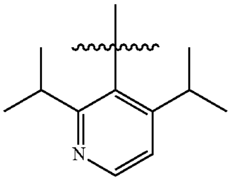.
The present invention provides the following compounds, stereoisomers, tautomers or pharmaceutically acceptable salts thereof, -continued
5-1
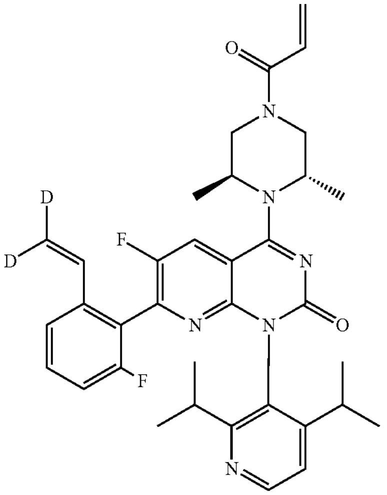
5-2
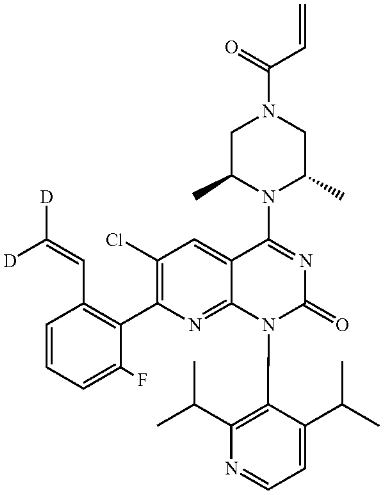
5-3
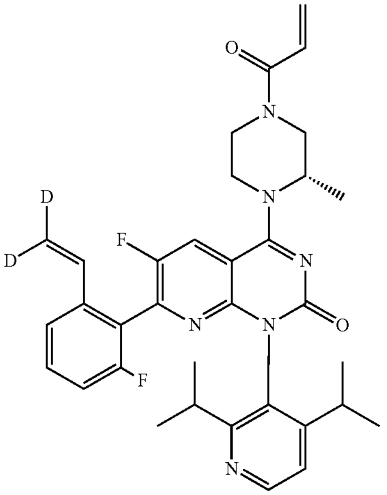
5-4
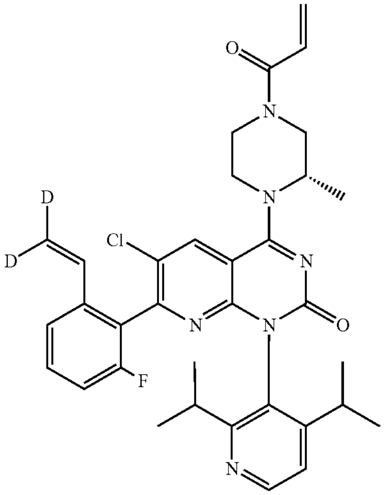
5-5
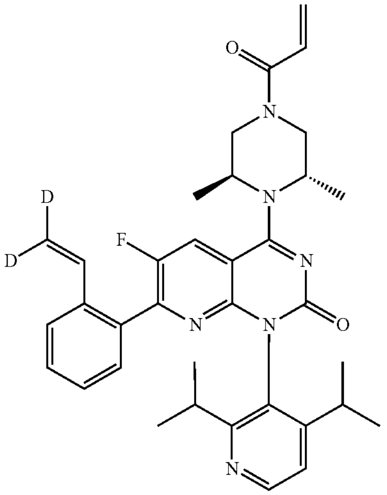
5-6
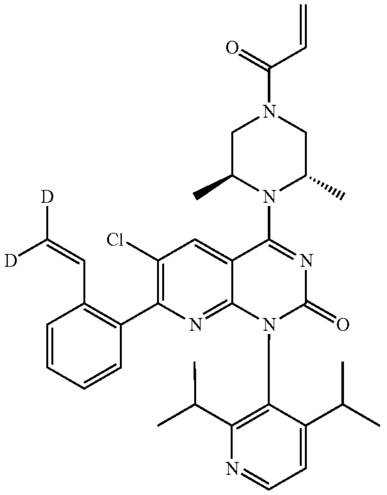

-continued
5-7
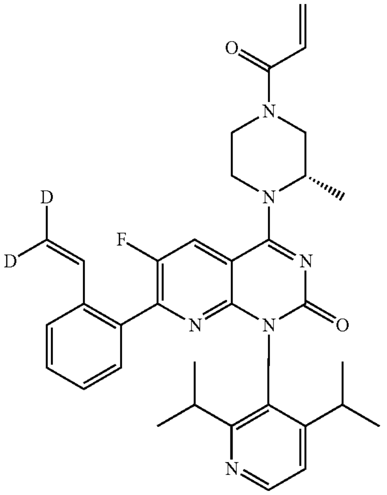
5-8
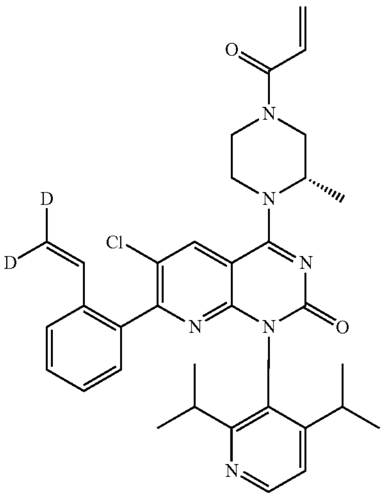
5-9
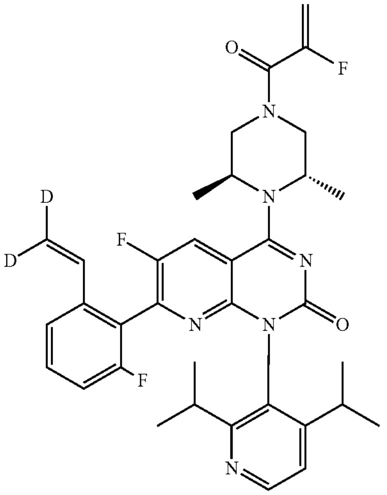
-continued
5-10
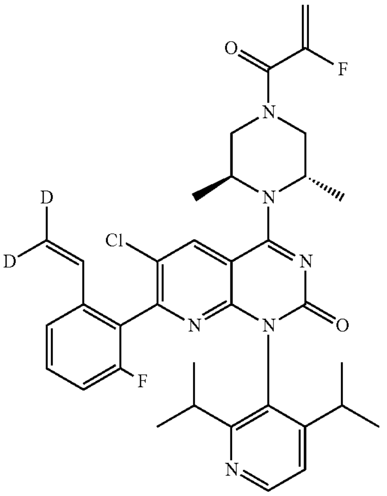
5-11
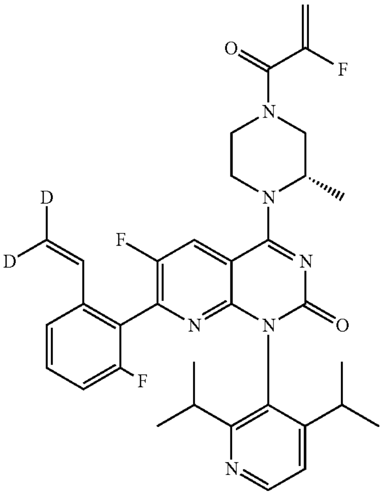
5-12
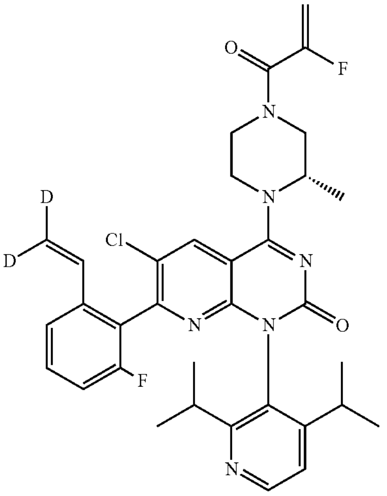

-continued
5-13
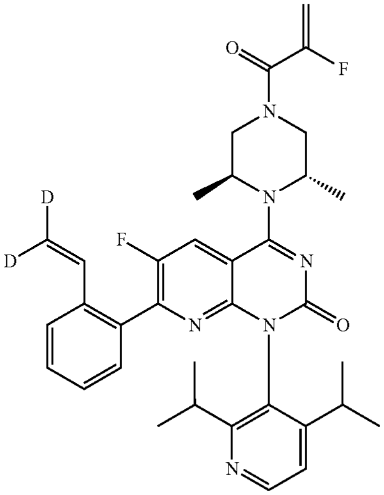
5-14
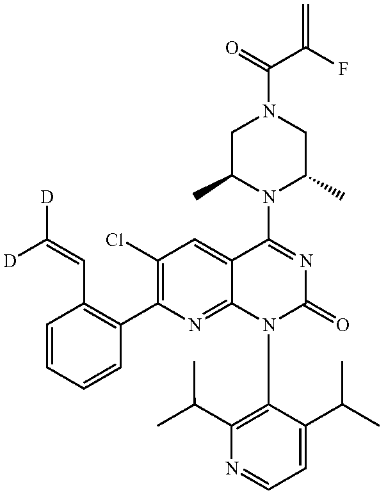
5-15
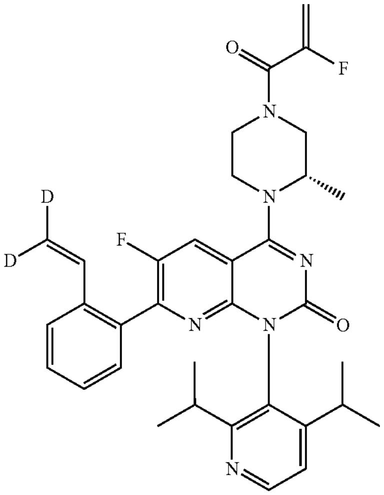
-continued
5-16
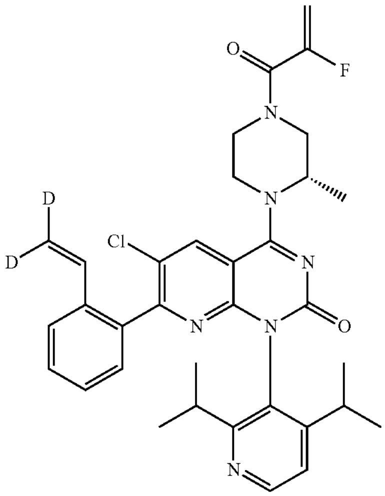
5-17
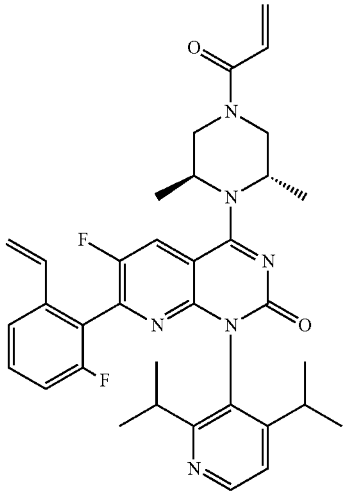
5-18
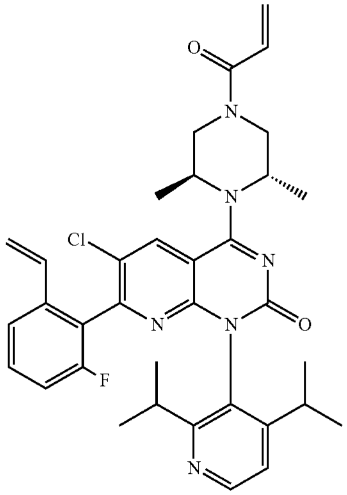

-continued
5-19
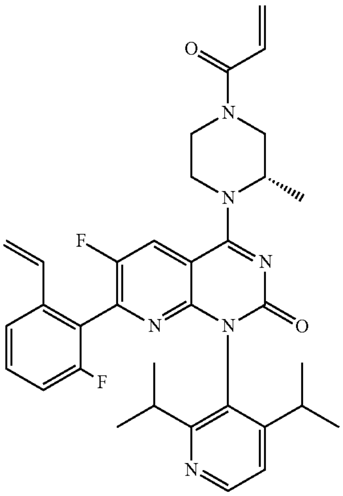
5-20
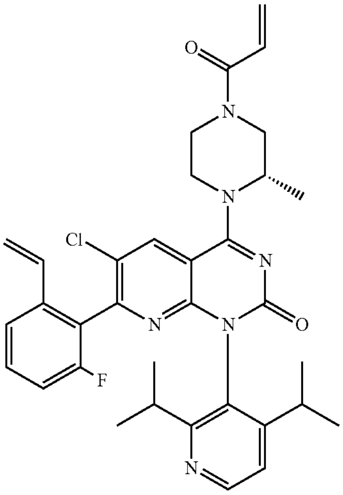
5-21
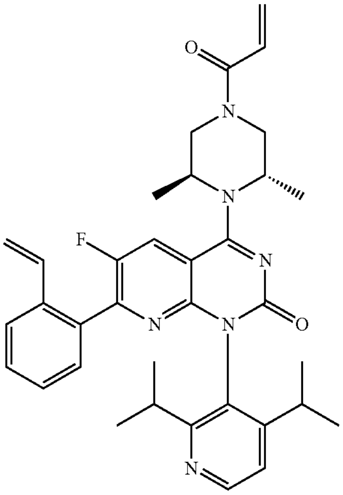
-continued
5-22
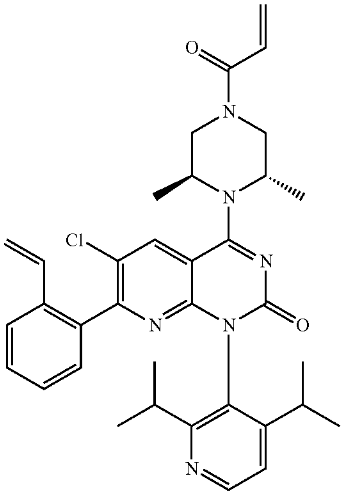
5-23
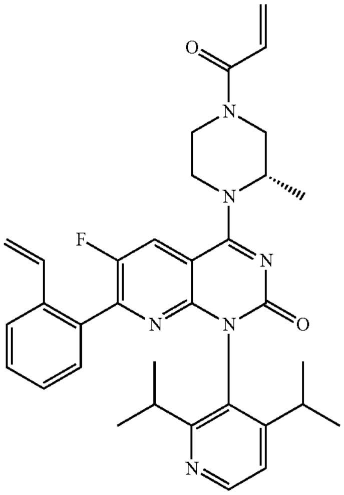
5-24
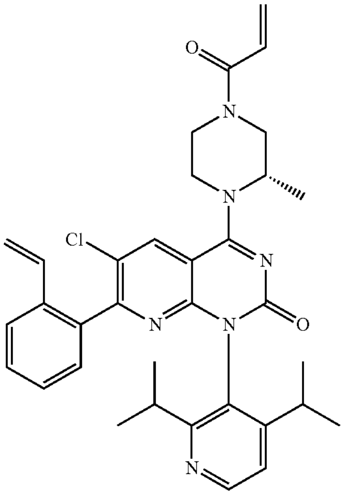

5-25
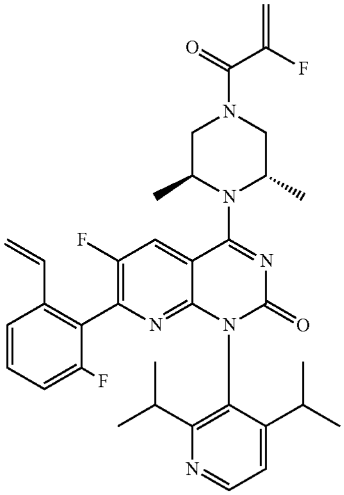
5-26
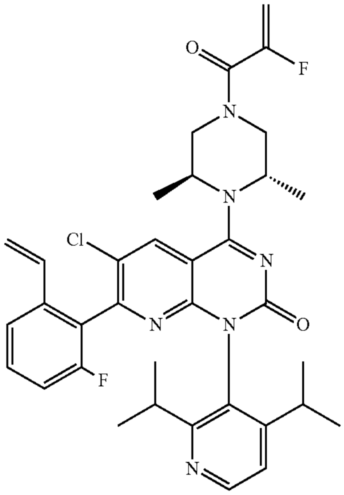
5-27
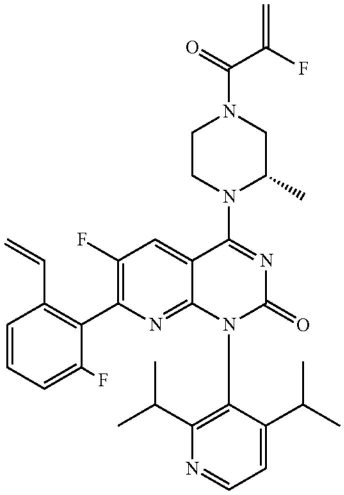
5-28
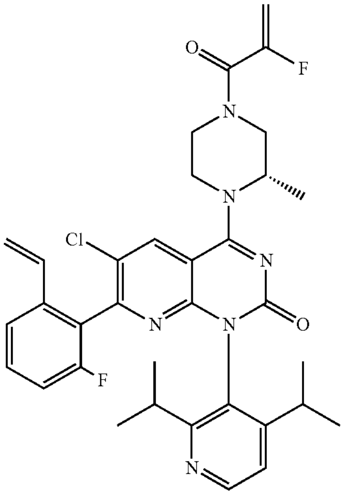
5-29
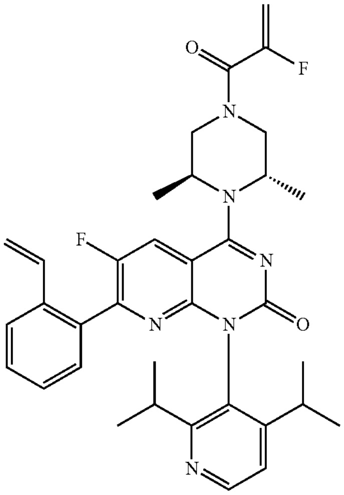
5-30
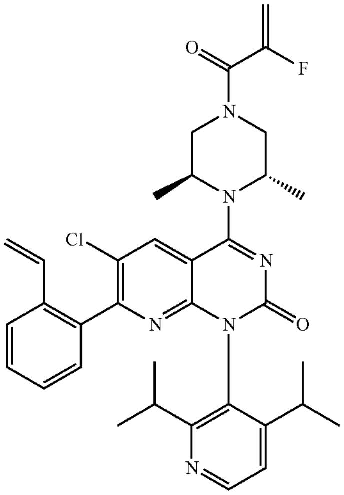

-continued
5-31
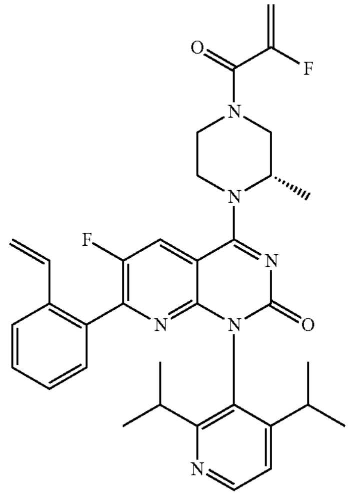
5-32
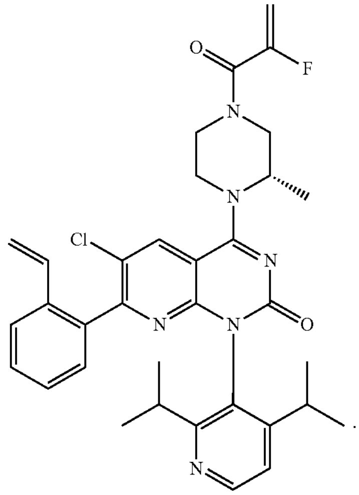
The present invention provides the following compounds, stereoisomers, tautomers or pharmaceutically acceptable salts thereof,
5-1C
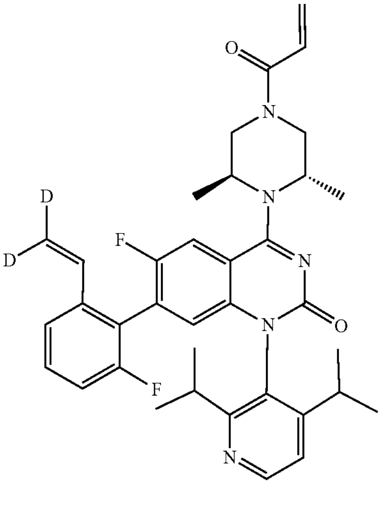
-continued
5-2C
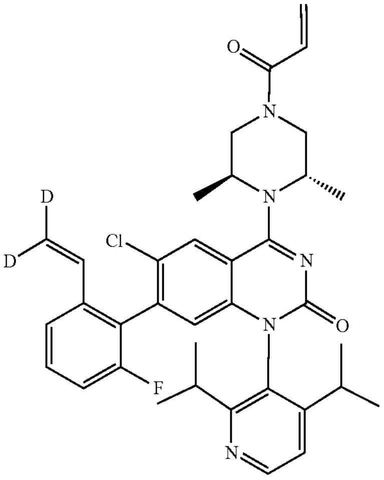
5-3C
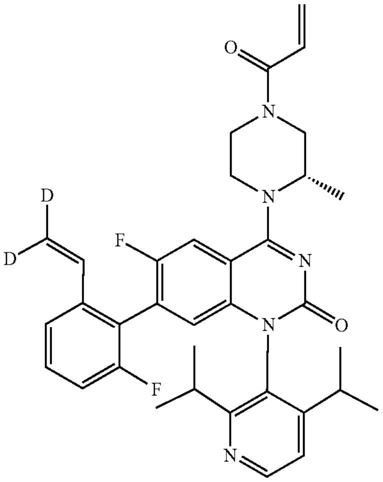
5-4C
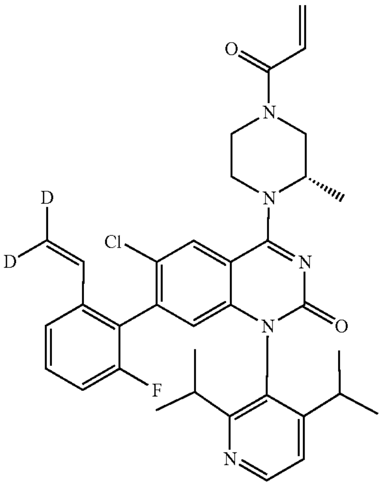

-continued
5-5C
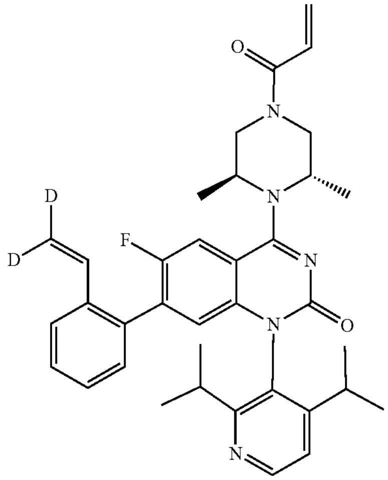
5-6C
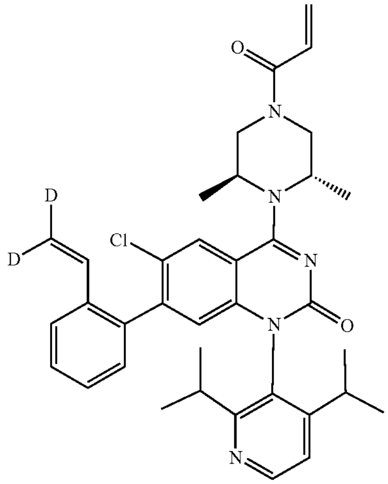
5-7C
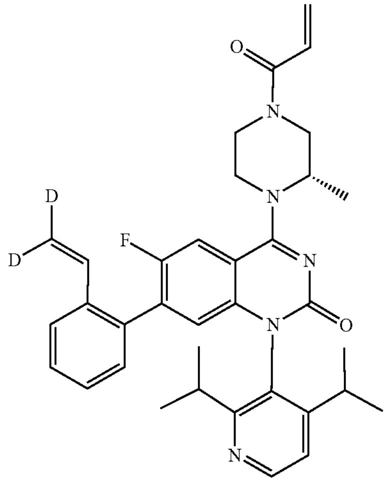
-continued
5-8C
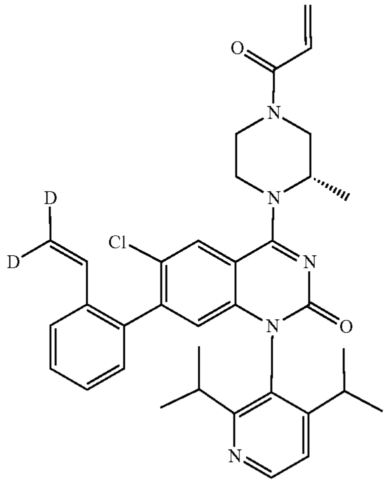
5-9C
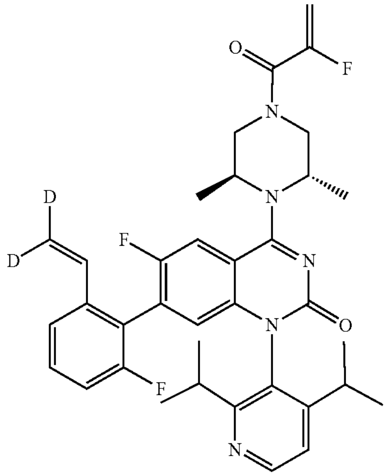
5-10C
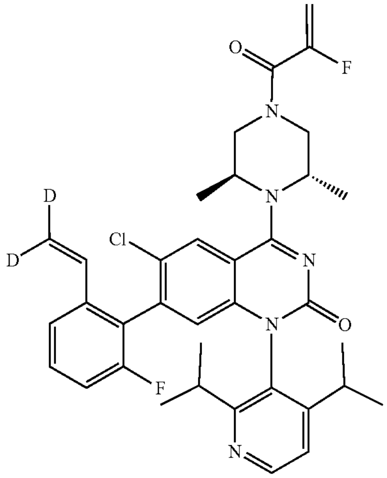

-continued
5-11C
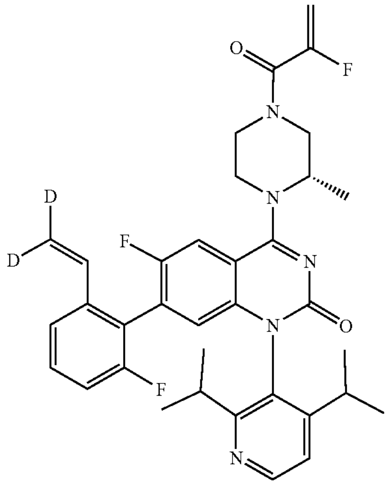
5-12C
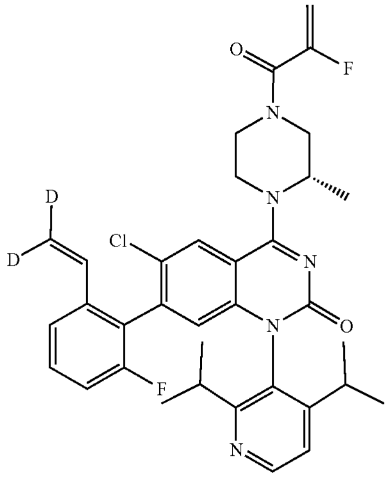
5-13C
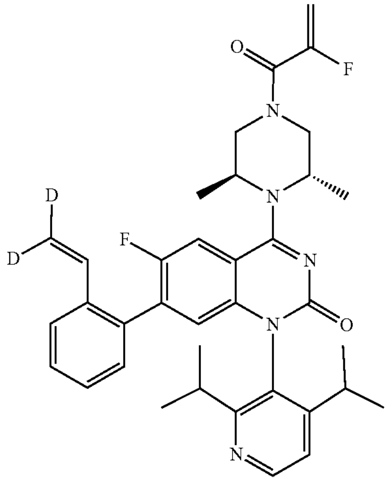
-continued
5-14C
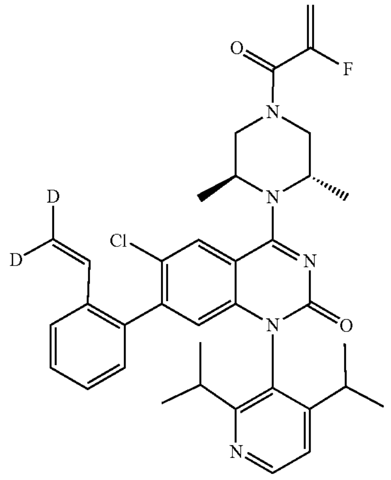
5-15C
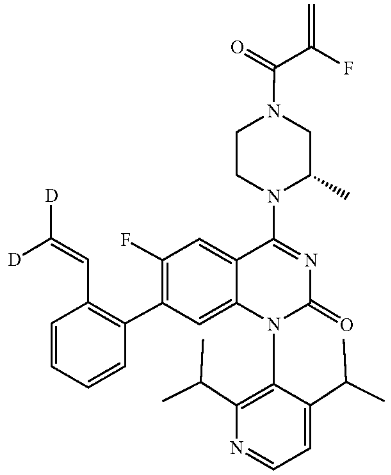
5-16C
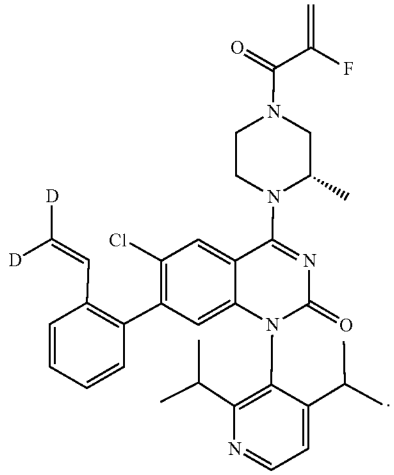
The present invention provides a compound of formula (VI), a stereoisomer, a tautomer or a pharmaceutically acceptable salt thereof,

VI

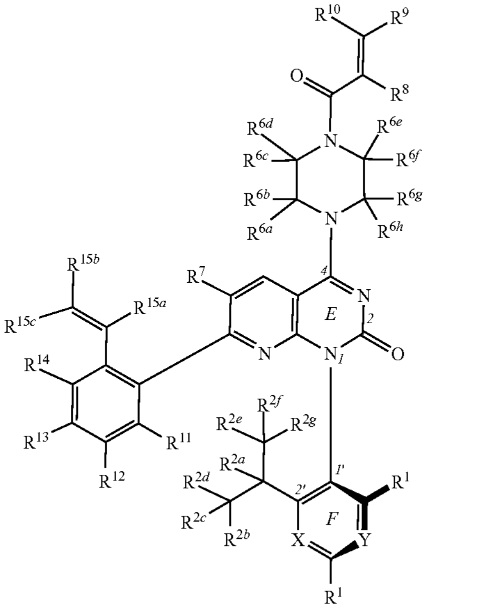

wherein, axial chiral stereoscopic configuration formed by connection of nitrogen atom at position 1 of Ring E and carbon atom at position 1' of Ring F is optically pure;

X is nitrogen atom or $CR^4$, Y is nitrogen atom or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, $R^{15c}$ are independently selected from the group consisting of hydrogen, deuterium, alkyl, deuterated alkyl, halogen;

$R^{6a}$, $R^{6b}$, $R^{6c}$, $R^{6d}$, $R^{6e}$, $R^{6f}$, $R^{6g}$, $R^{6h}$ are independently selected from the group consisting of hydrogen, deuterium, methyl, methyl-$d_3$;

$R^7$ is fluorine, chlorine;

$R^8$, $R^9$, $R^{10}$, $R^{11}$ are independently selected from the group consisting of hydrogen, deuterium, fluorine;

$R^{17}$ is hydrogen, alkyl, deuterated alkyl, haloalkyl, methyl, ethyl, propyl, cyclopropyl, deuterated methyl, deuterated ethyl, deuterated propyl, deuterated cyclopropyl.

The present invention provides a compound of formula (IIIM) with R axial chiral stereoscopic configuration, a tautomer or a pharmaceutically acceptable salt thereof,

IIIM

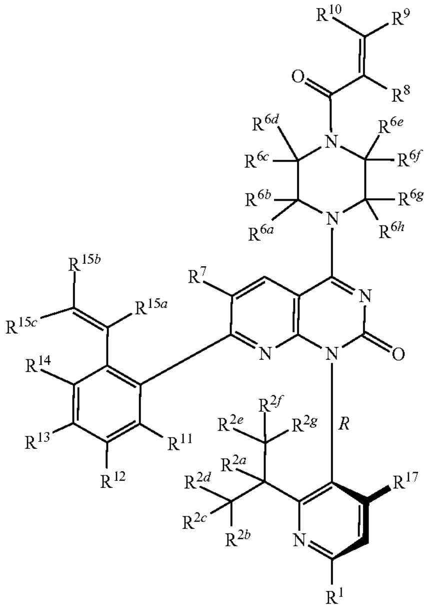

wherein, $R^1$, $R^{2a}$, $R^{2b}$, $R^{2c}$, $R^{2d}$, $R^{2e}$, $R^{2f}$, $R^{2g}$, $R^{12}$, $R^{13}$, $R^{14}$, $R^{15a}$, $R^{15b}$, $R^{15c}$ are independently selected from the group consisting of hydrogen, deuterium, alkyl, deuterated alkyl, alkenyl alkyl, alkynyl alkyl, deuterated alkenyl alkyl, deuterated alkynyl alkyl, halogen;

$R^{6a}$, $R^{6b}$, $R^{6c}$, $R^{6d}$, $R^{6e}$, $R^{6f}$, $R^{6g}$, $R^{6h}$ are independently selected from the group consisting of hydrogen, deuterium, methyl, methyl-$d_3$;

$R^7$ is hydrogen, fluorine, chlorine;

$R^8$, $R^9$, $R^{10}$, $R^{11}$ are independently selected from the group consisting of hydrogen, deuterium, fluorine;

$R^{17}$ is hydrogen, deuterium, fluorine, chlorine, bromine, iodine, methyl, ethyl, deuterated methyl, deuterated ethyl;

structural fragment

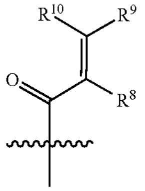

is selected from the following structures:

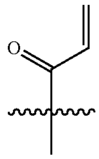

;

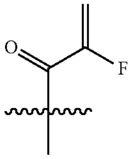

;

-continued
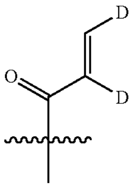
;
structural fragment
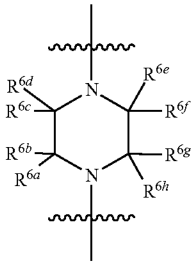
is selected from the following structures:
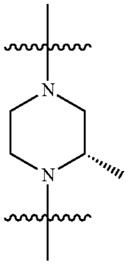
;
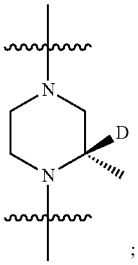
;
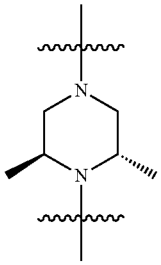
;
-continued
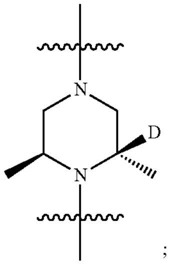
;
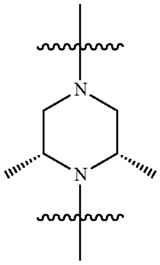
;
structural fragment
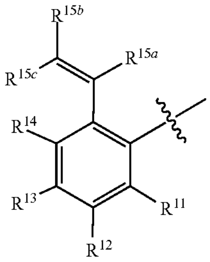
is selected from the following structures:
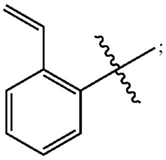
;
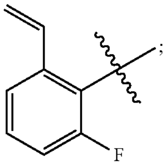
;
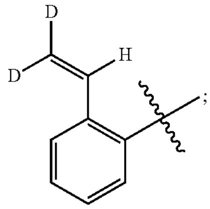
;
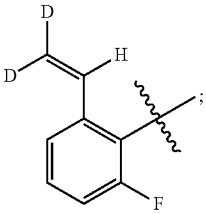
;
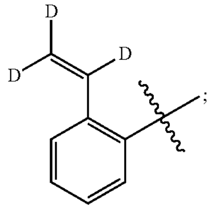
;
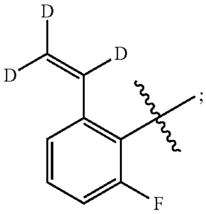
;

-continued
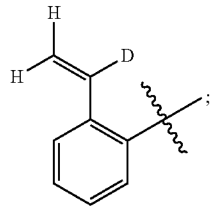
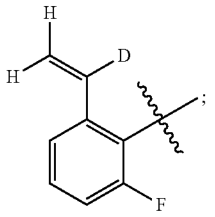
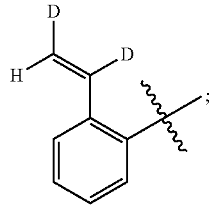
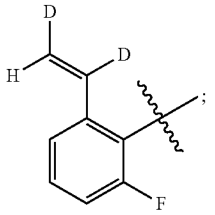
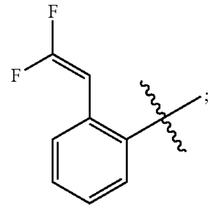
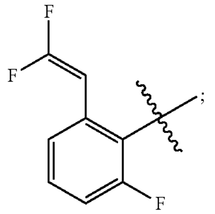
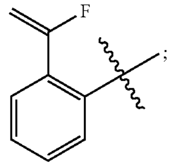
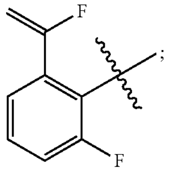
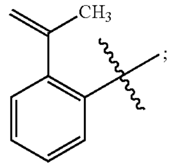
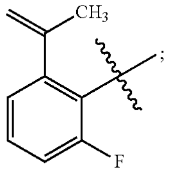
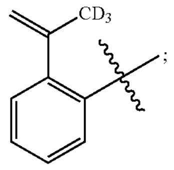
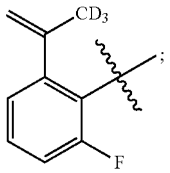
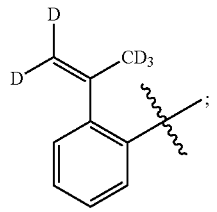
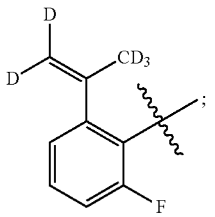
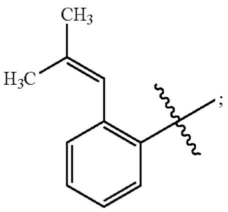
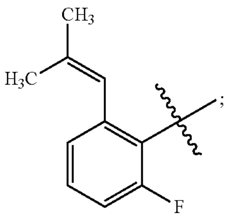
-continued
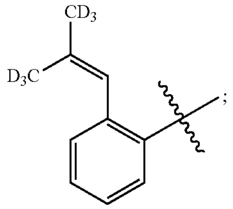
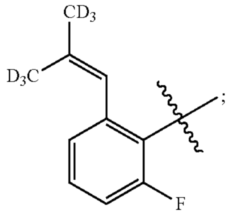
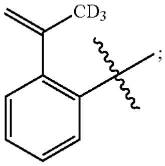
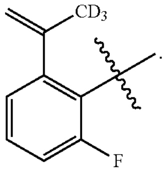
The present invention provides the following compounds with R axial chiral stereoscopic configuration, tautomers or pharmaceutically acceptable salts thereof,
3-1M
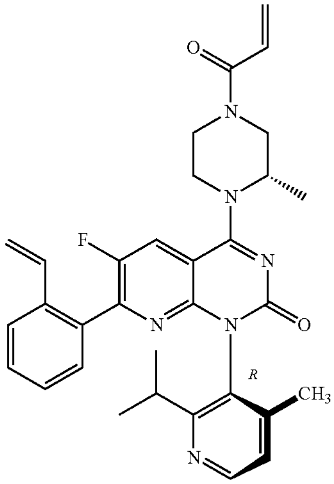
3-2M
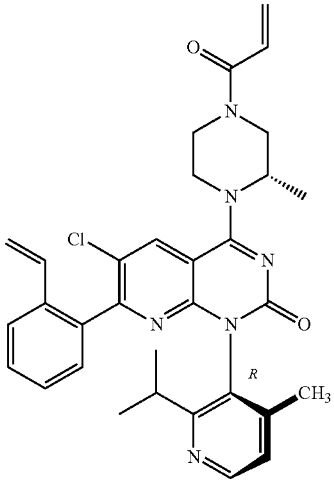

-continued
3-3M
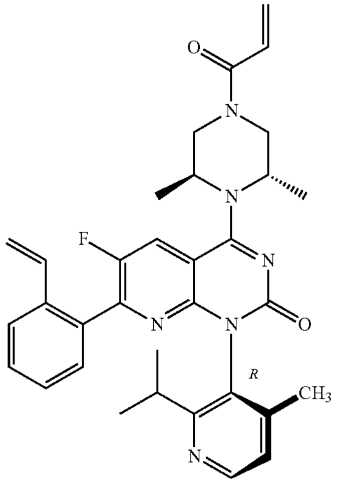
3-4M
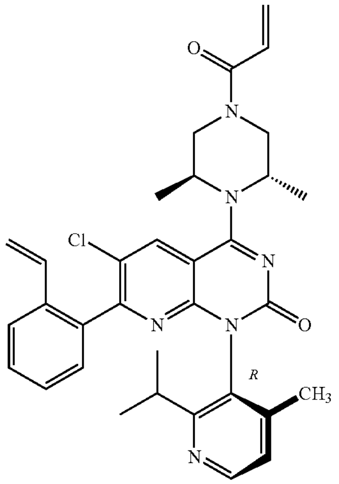
3-5M
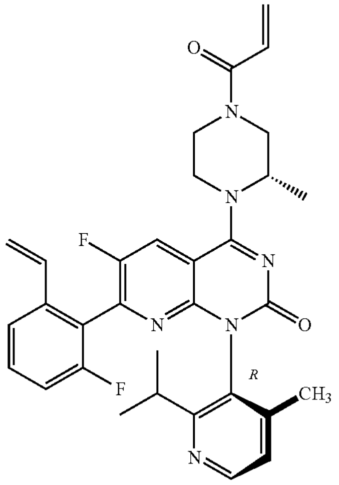
-continued
3-6M
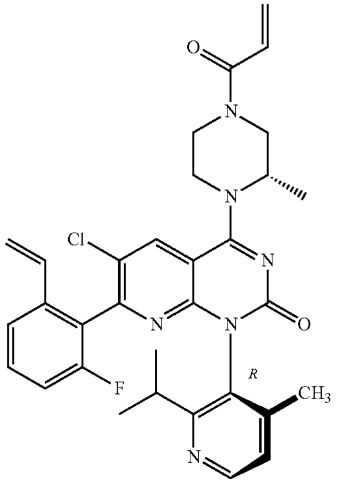
3-7M
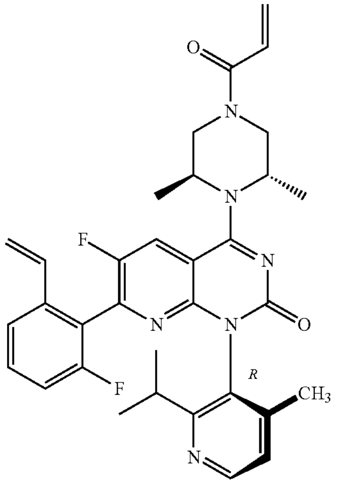
3-8M
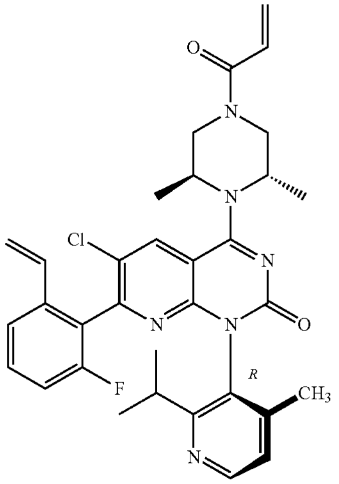

-continued
3-9M
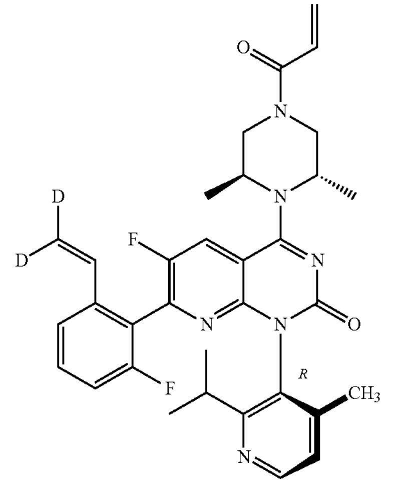
3-10M
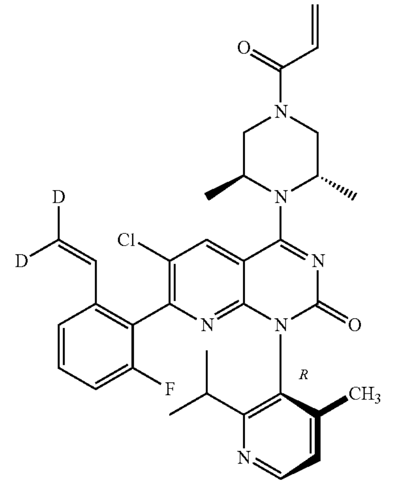
3-11M
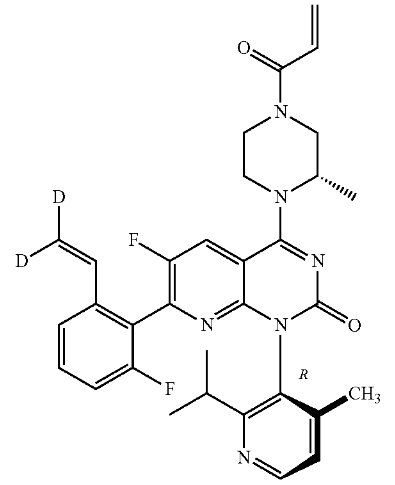
-continued
3-12M
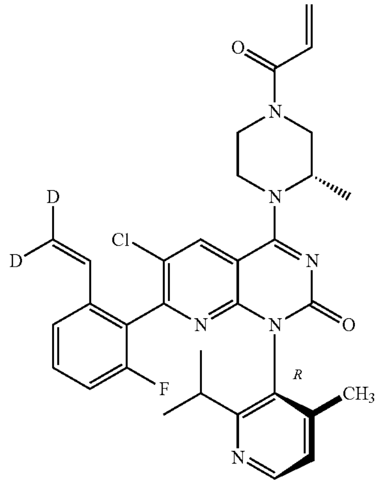
3-13M
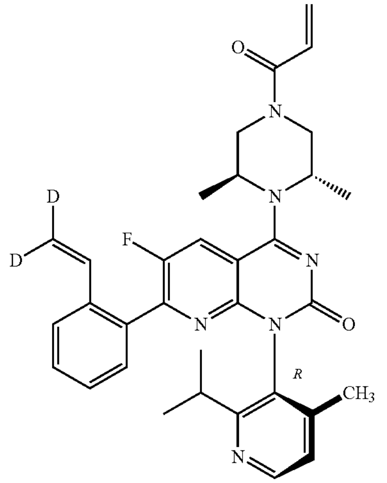
3-14M
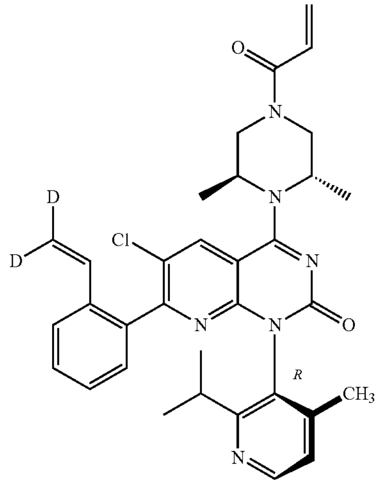

-continued
3-15M
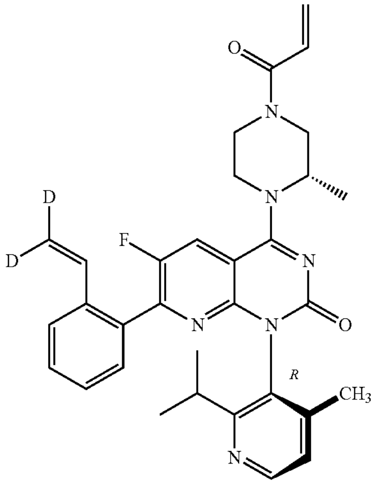
3-16M
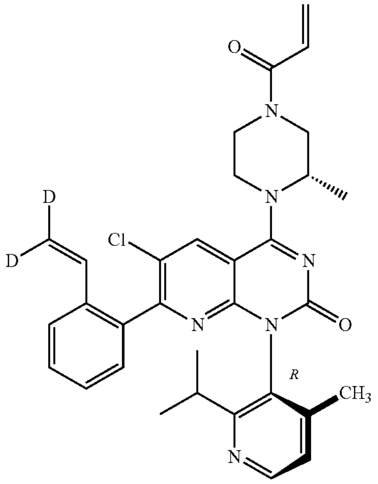
3-17M
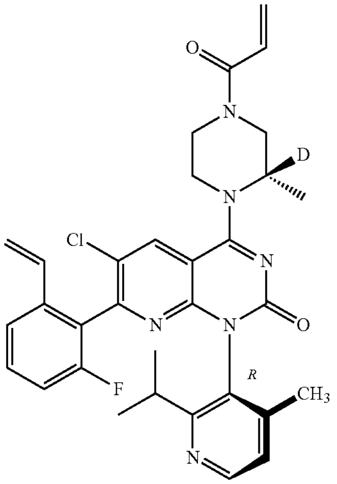
3-18M
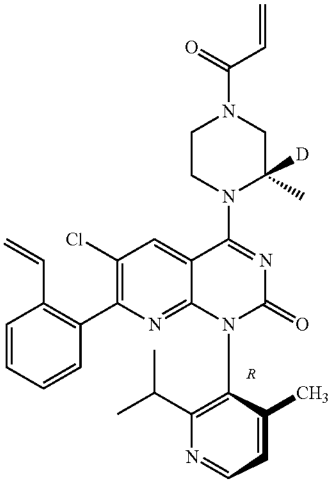
3-19M
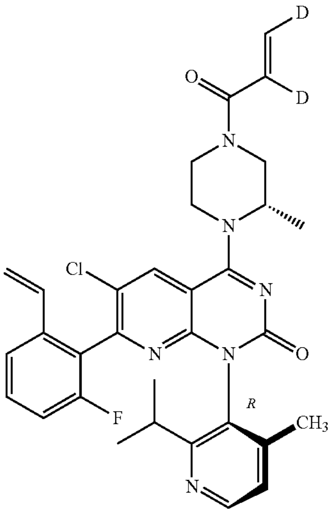
3-20M
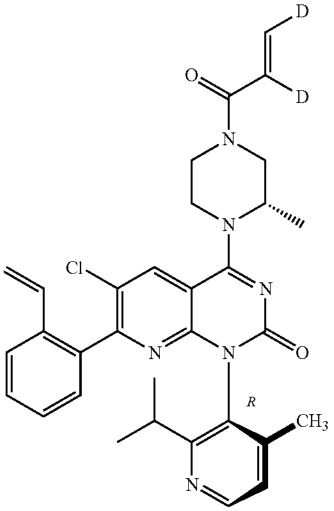

-continued
3-21M
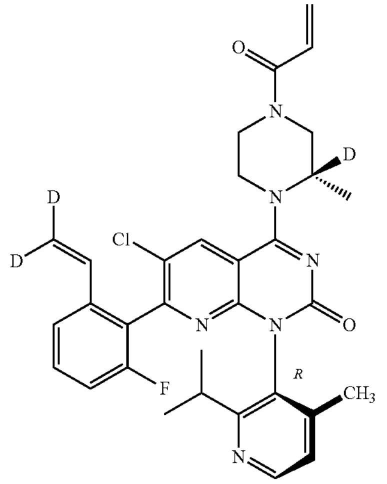
3-22M
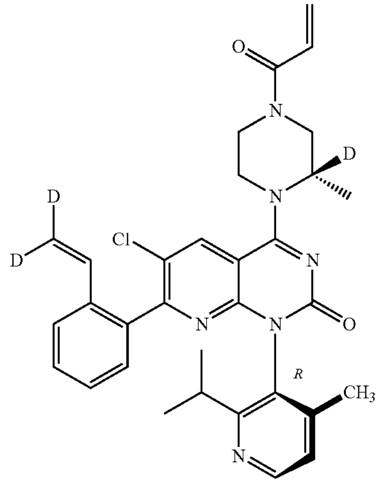
3-23M
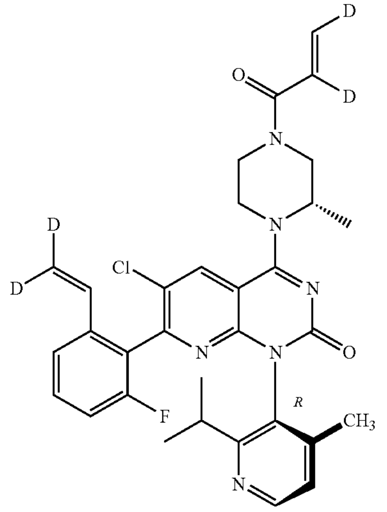
-continued
3-24M
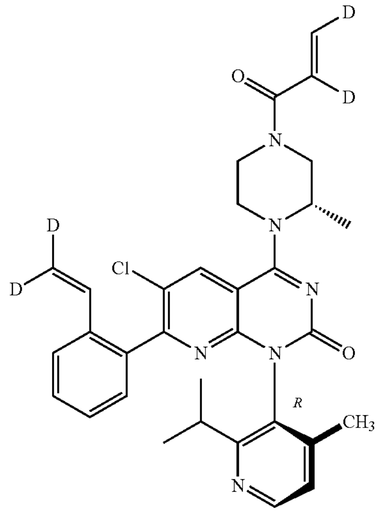
3-25M
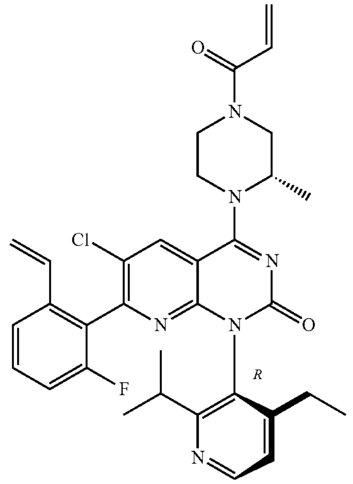
3-26M
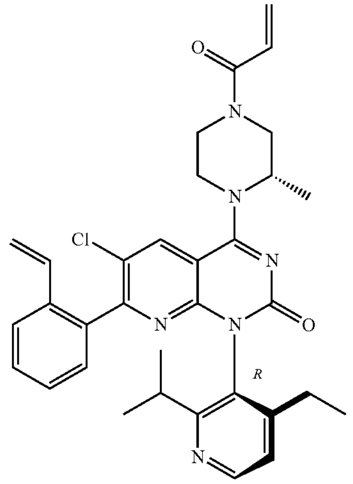

-continued
3-27M
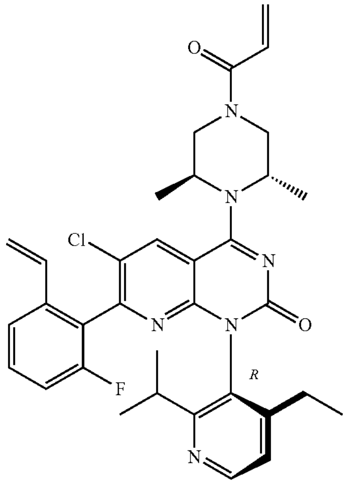
3-28M
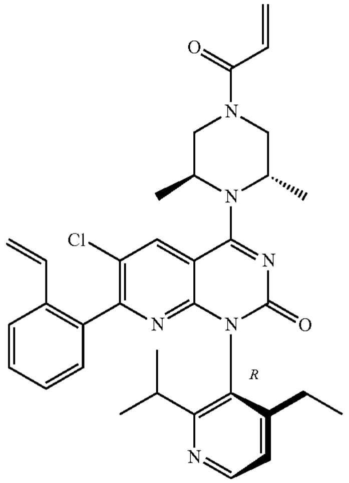
3-29M
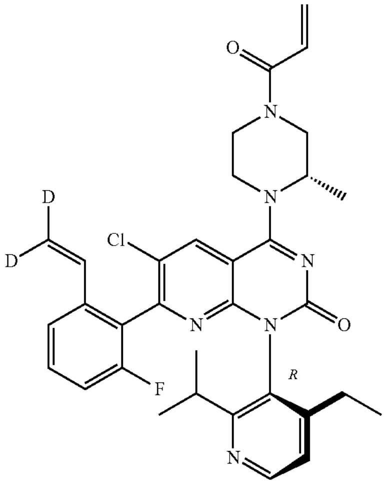
-continued
3-30M
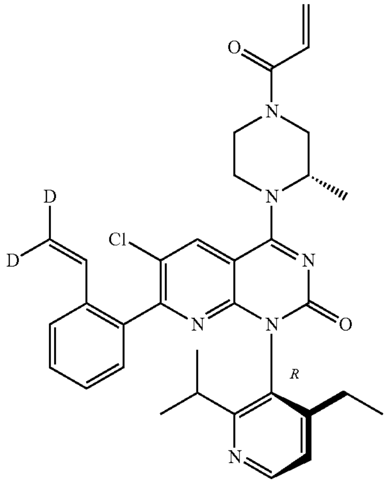
3-31M
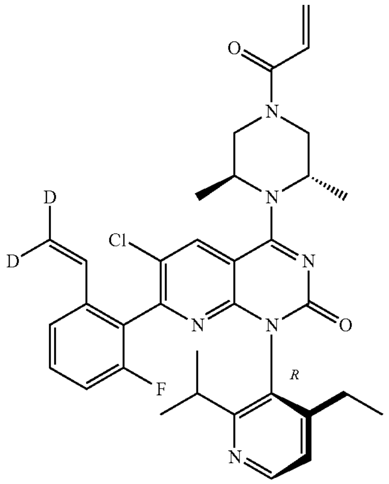
3-32M
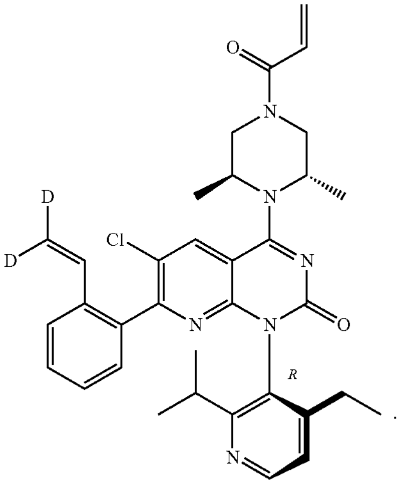
The present invention provides the following compounds with R axial chiral stereoscopic configuration, tautomers or pharmaceutically acceptable salts thereof, -continued
4-1M
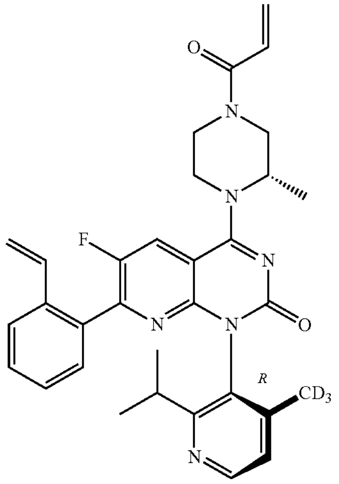
4-2M
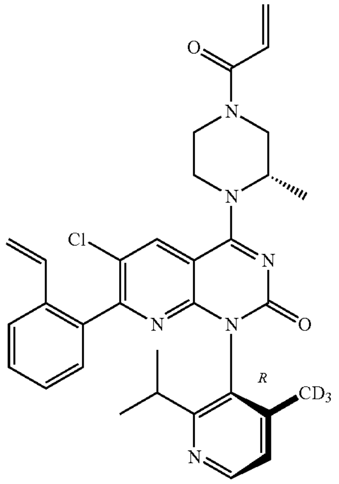
4-3M
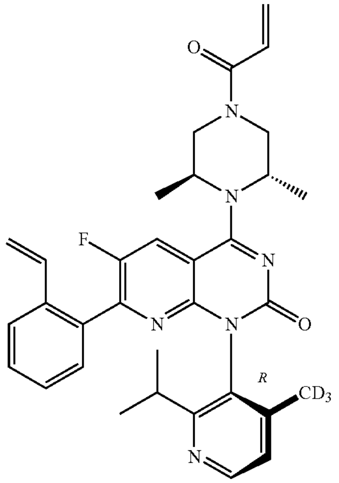
4-4M
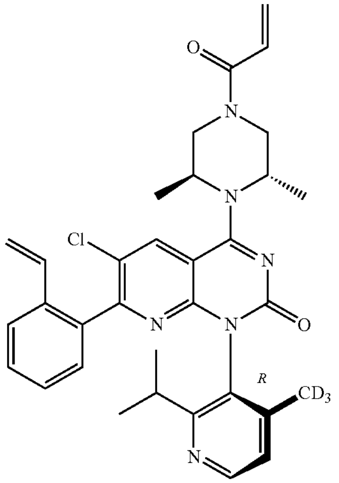
4-5M
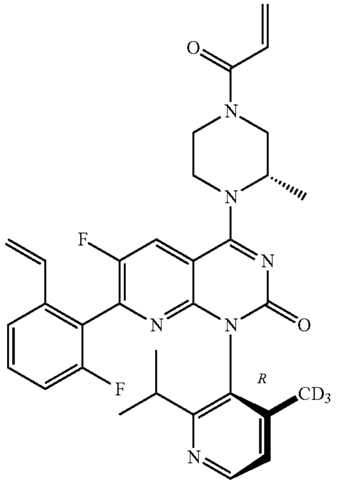
4-6M
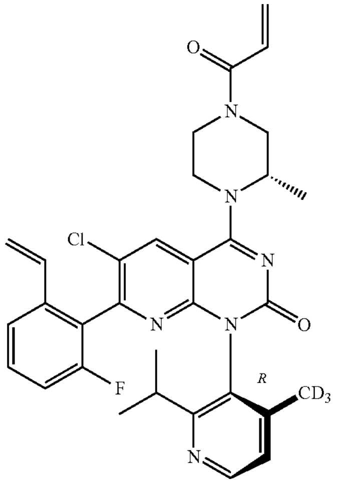

-continued
4-7M
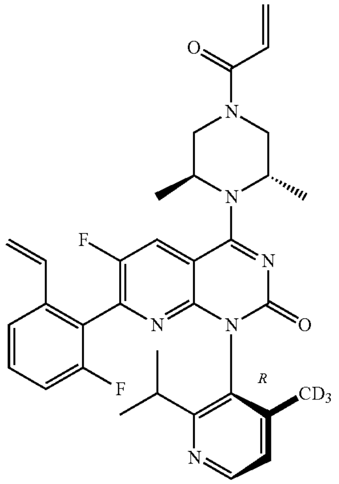
4-8M
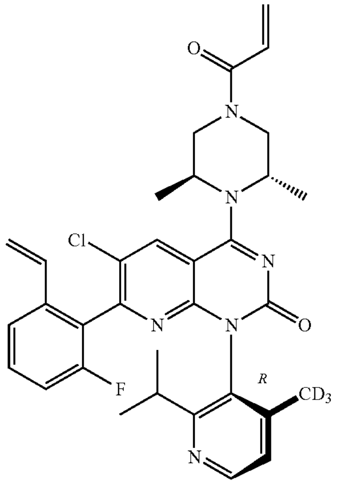
4-9M
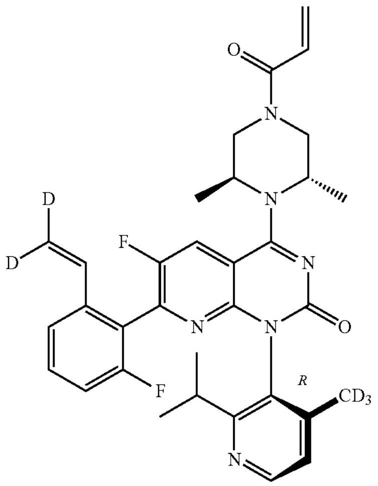
-continued
4-10M
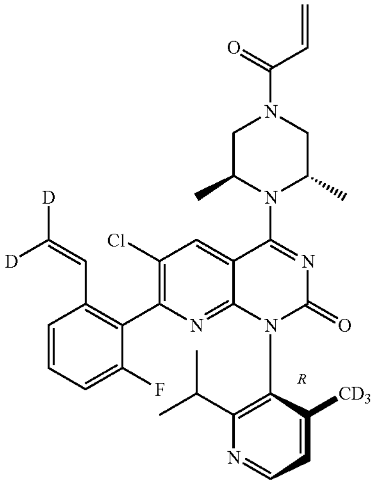
4-11M
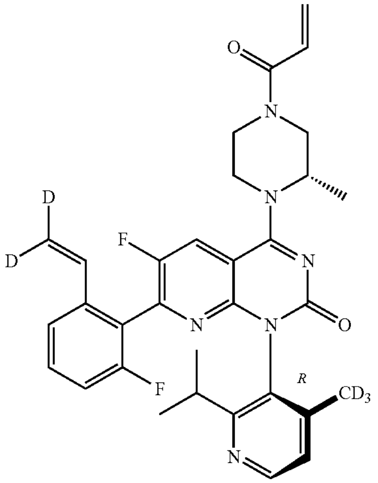
4-12M
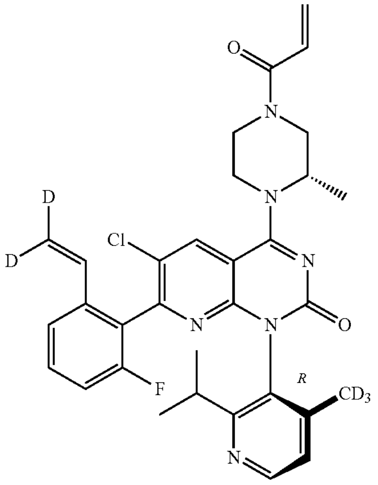

-continued
4-13M
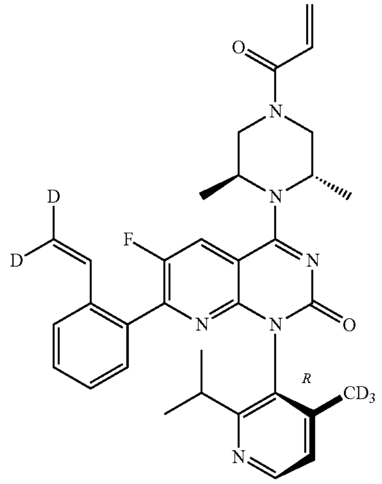
4-14M
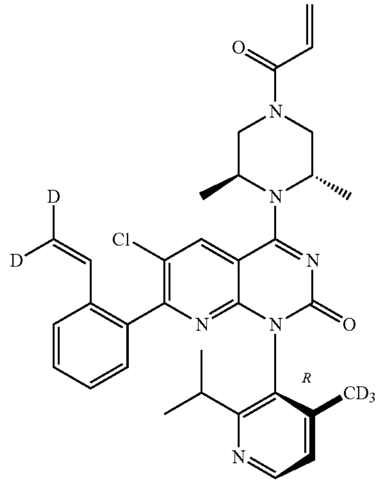
4-15M
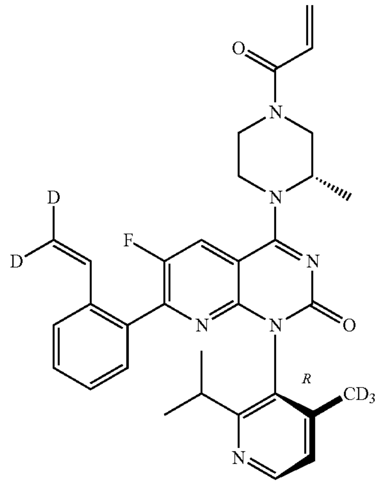
-continued
4-16M
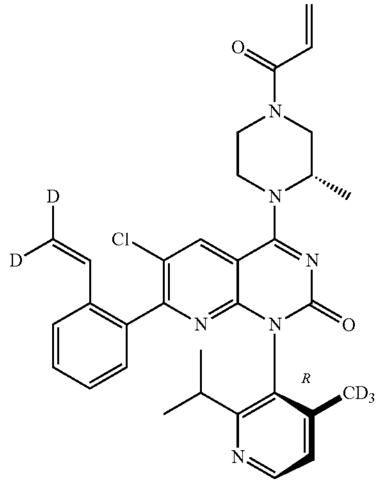
4-17M
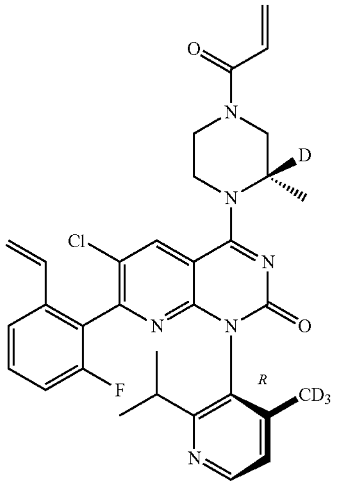
4-18M
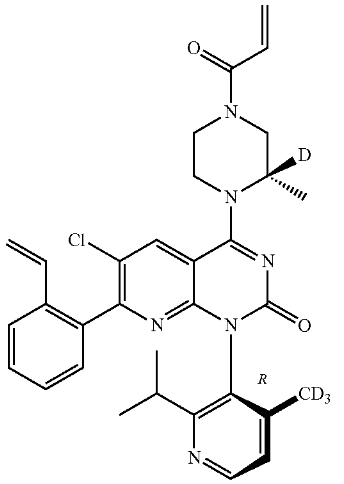

-continued
4-19M
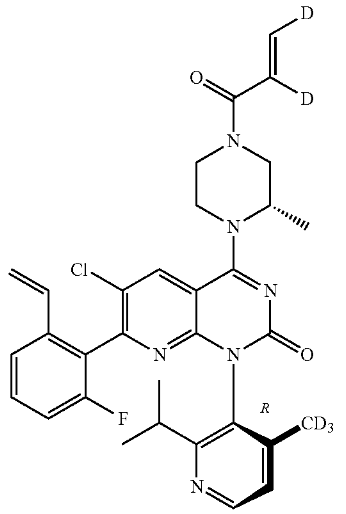
4-20M
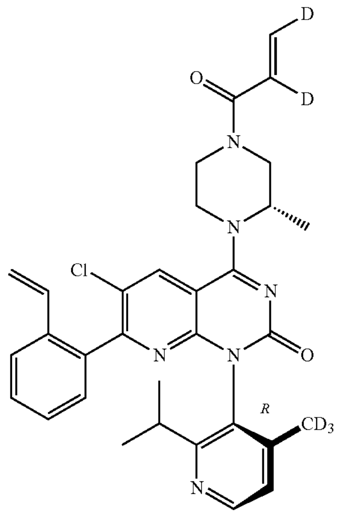
4-21M
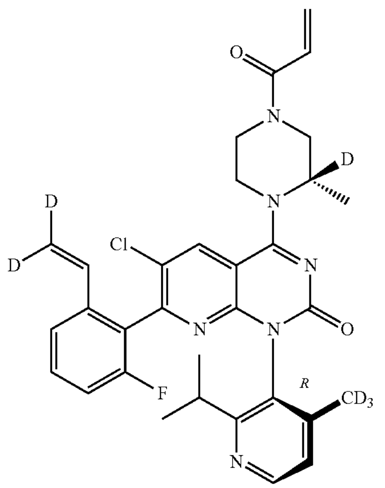
-continued
4-22M
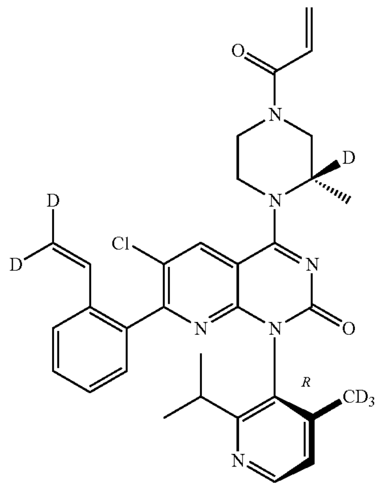
4-23M
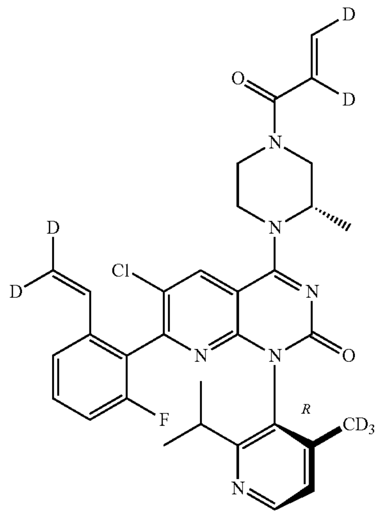
4-24M
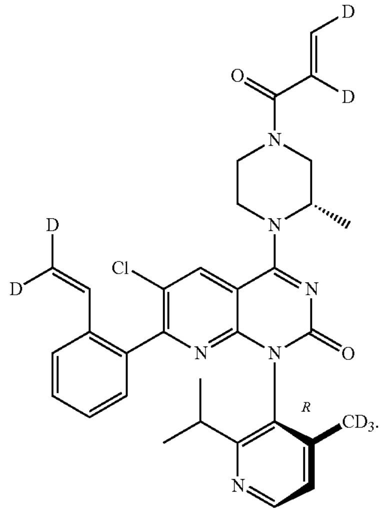
The present invention provides the following compounds with R axial chiral stereoscopic configuration, tautomers or pharmaceutically acceptable salts thereof, 3-1MIS
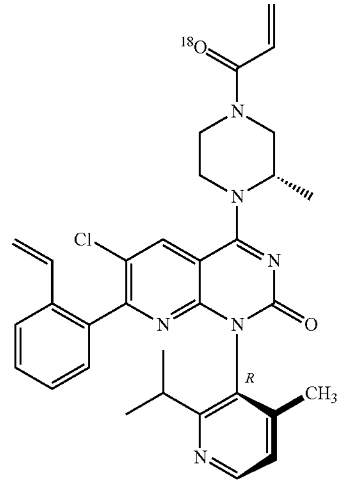
3-3MIS
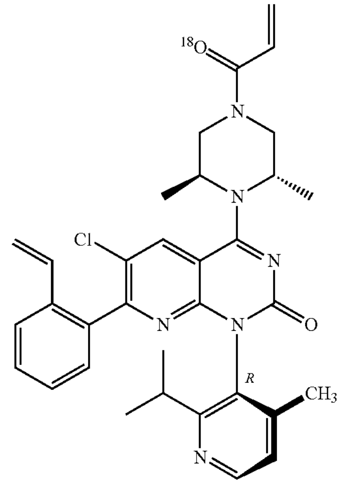
3-4MIS
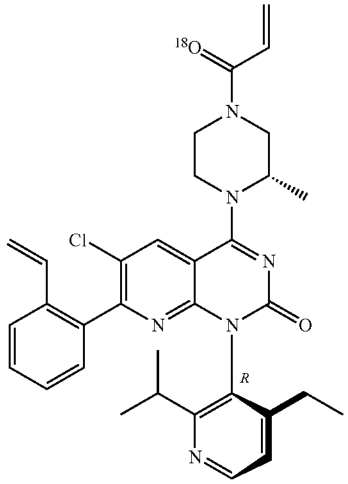
-continued
3-5MIS
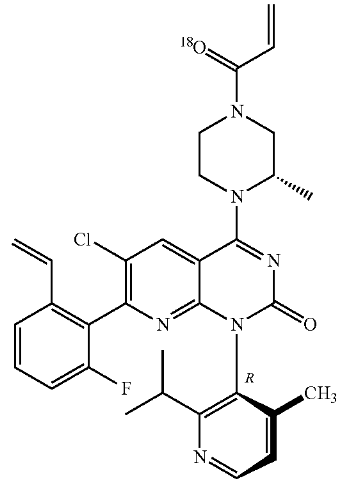
3-7MIS
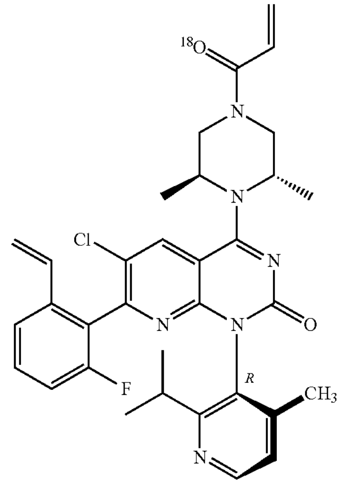
3-8MIS
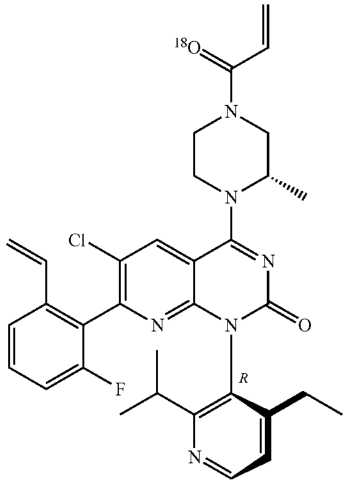

-continued
3-9MIS
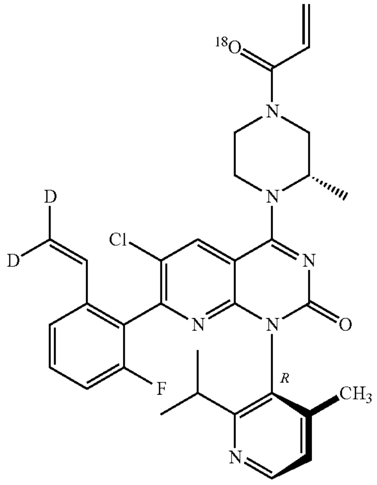
3-11MIS
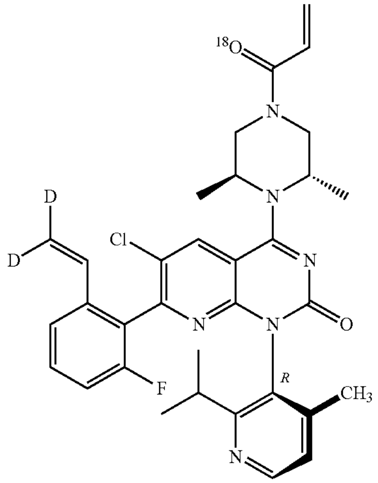
3-12MIS
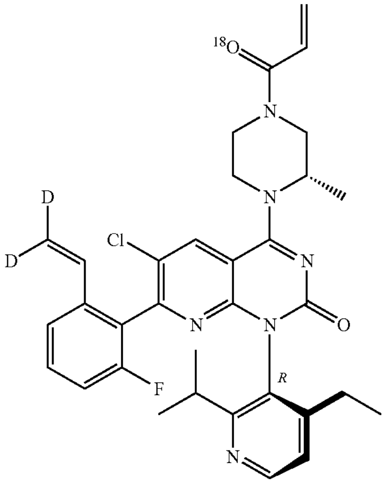
The present invention provides the following compounds with R axial chiral stereoscopic configuration, tautomers or pharmaceutically acceptable salts thereof,
3K-1M
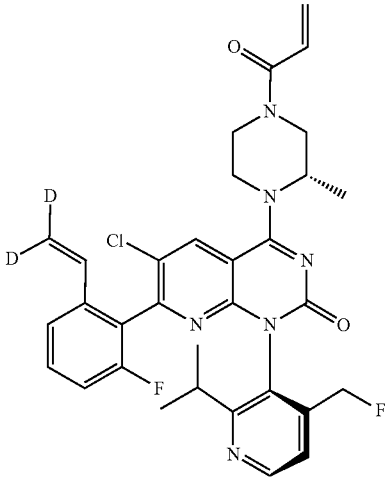
3K-2M
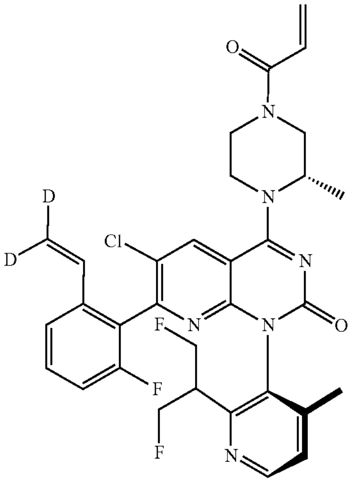
3K-3M
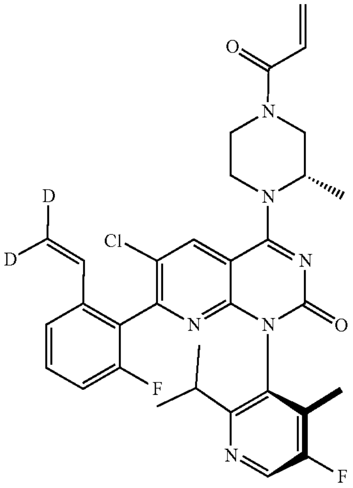

-continued
3K-5M
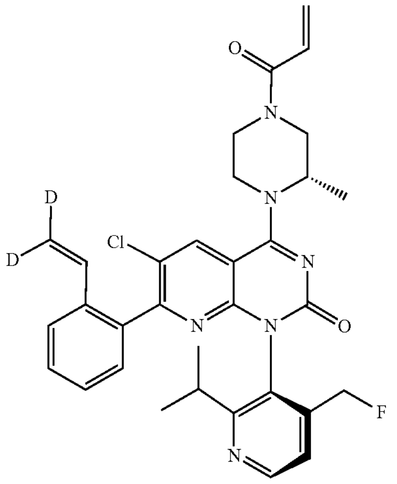
3K-6M
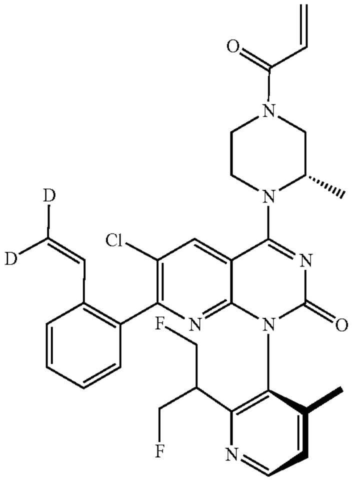
3K-7M
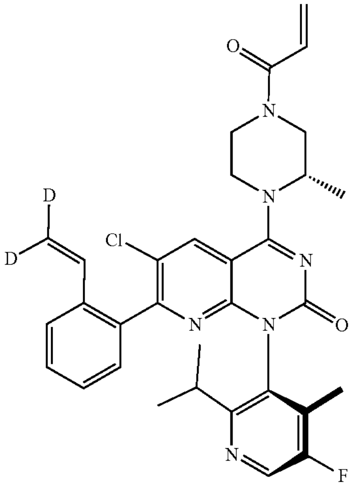
-continued
3K-9M
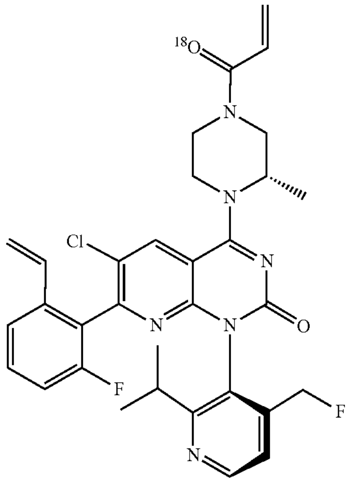
3K-10M
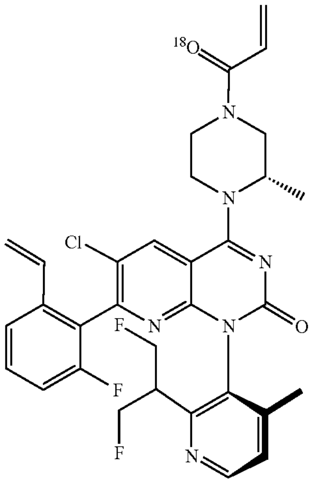
3K-11M
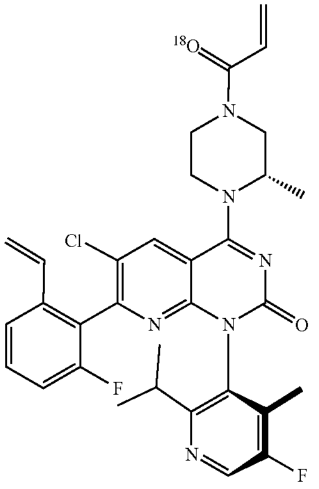

-continued
3K-13M
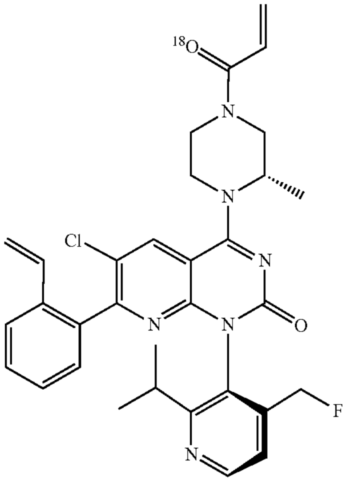
3K-14M
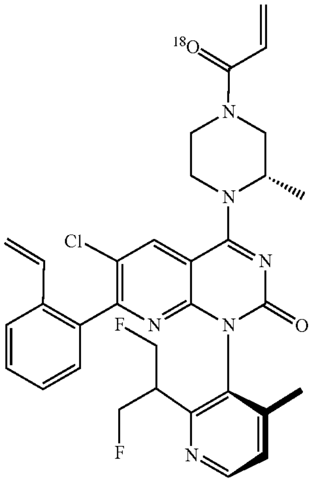
3K-15M
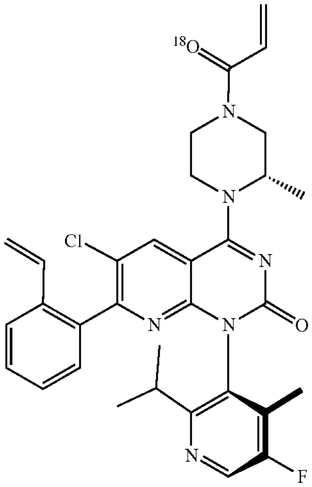
The present invention provides the following compounds, tautomers or pharmaceutically acceptable salts thereof,
3-1
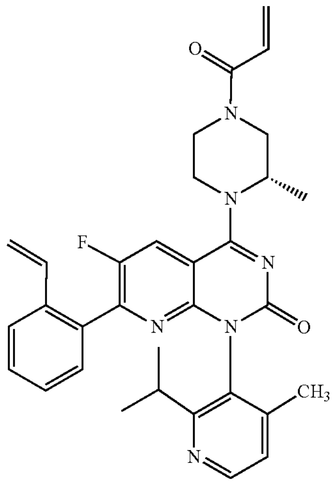
3-2
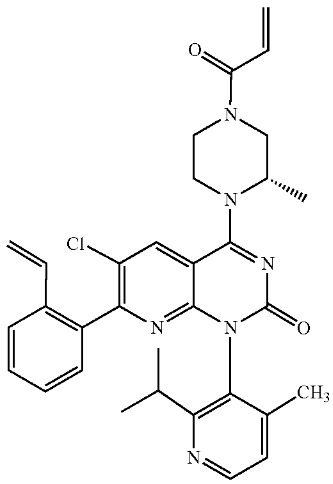
3-5
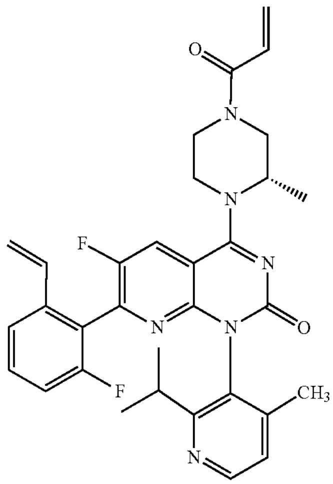

-continued
3-6
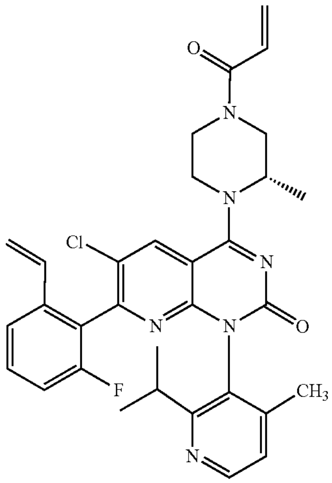
3-8
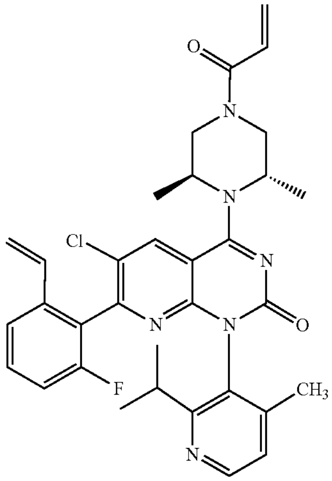
4-17
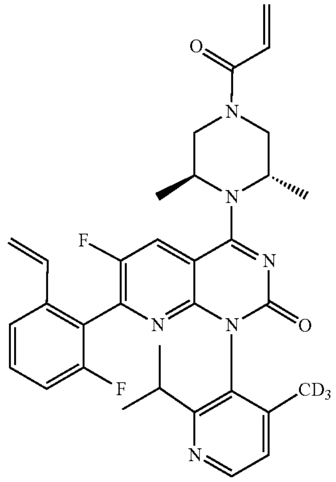
-continued
3-20
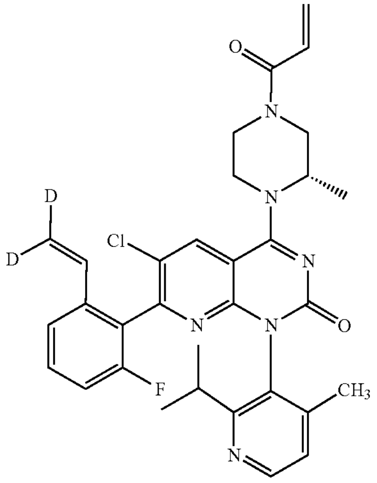
3-21
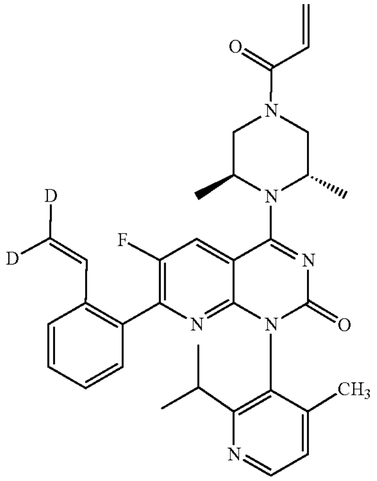
3-6M
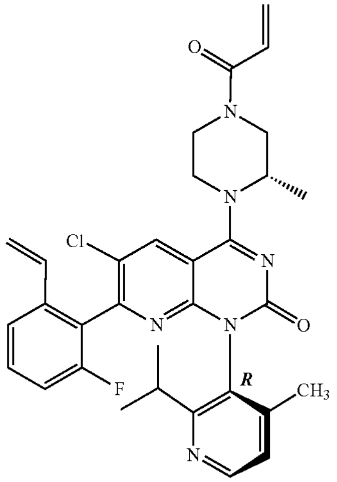

-continued
3-2M
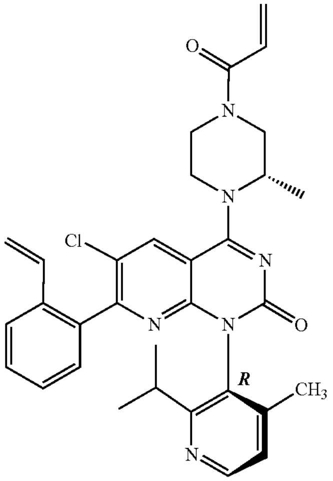
3-12M
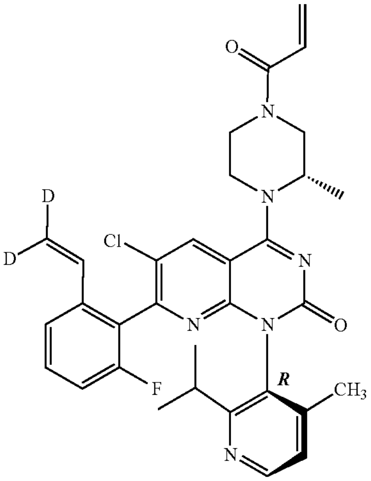
3-16M
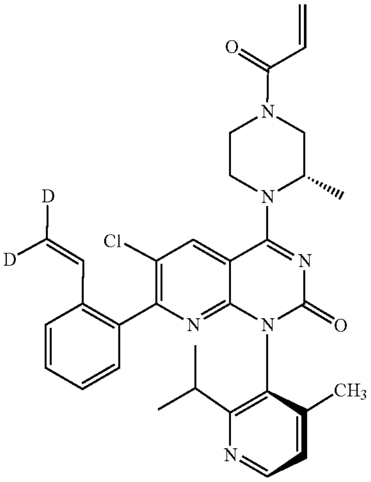
-continued
1-11
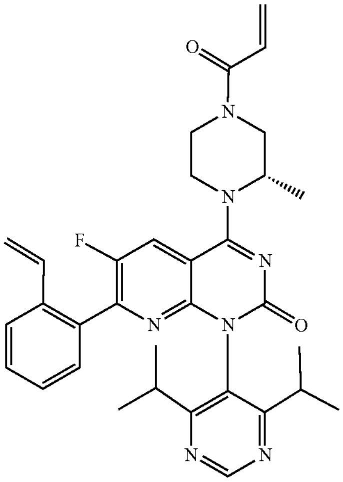
1-12
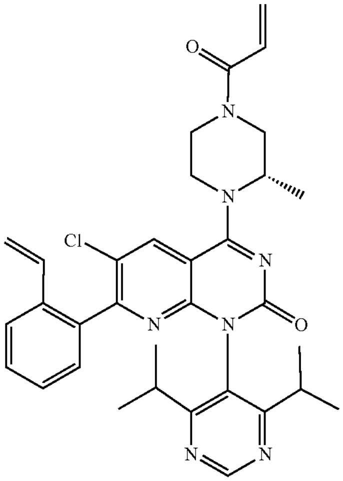
1-27
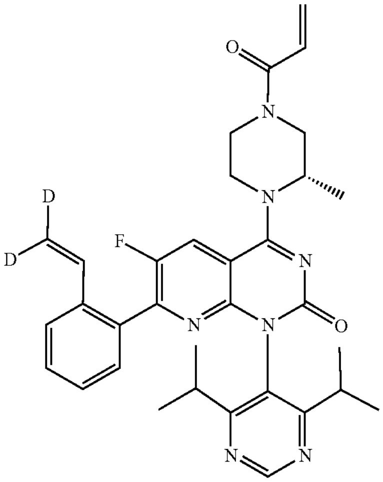

-continued 1-28

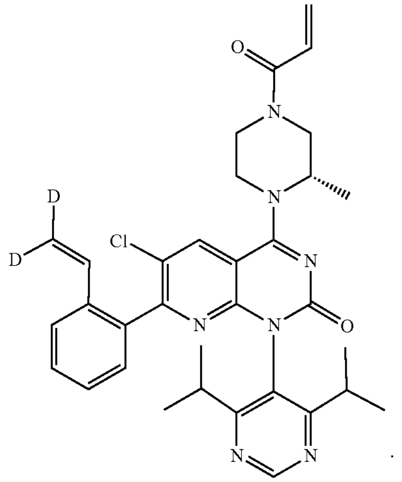

The present invention provides a pharmaceutical composition comprising a therapeutically effective amount of the compound, or the stereoisomer, the tautomer or the pharmaceutically acceptable salt thereof of any one of the present invention and pharmaceutically available carriers.

Further provided is use of the compound or the pharmaceutically available salt thereof according to any one of the present invention or the pharmaceutical composition according to the present invention for the preparation of a medicament for preventing and/or treating diseases associated with KRAS mutation mediated cancers. Use of the compound or the pharmaceutically available salt thereof according to any one of the present invention or the pharmaceutical composition according to the present invention used alone or used in combination with other therapeutic methods including immunotherapy for preventing and/or treating diseases associated with KRAS mutation mediated cancers is included.

Further provided is use of the compound or the pharmaceutically available salt thereof according to any one of the present invention or the pharmaceutical composition according to the present invention for the preparation of a medicament for preventing and/or treating diseases associated with KRAS G12C mutation mediated cancers. Use of the compound or the pharmaceutically available salt thereof according to any one of the present invention or the pharmaceutical composition according to the present invention used alone or used in combination with other therapeutic methods including immunotherapy for preventing and/or treating diseases associated with KRAS G12C mutation mediated cancers is included.

According to the use in the present invention, wherein said various cancer diseases associated with KRAS function are liver cancer, esophageal cancer, gastric cancer, renal cell cancer, sarcoma, bile duct cancer, colon cancer, prostate cancer, ovarian cancer, breast cancer, hematological cancer, pancreatic cancer, MYH-associated polyposis, colorectal cancer, lung cancer, uterine cancer, mesothelioma, cervical cancer, and bladder cancer.

Definitions

All technical and scientific terms used in this description have the meaning commonly understood by those skilled in the art.

The term "hydrogen" as used herein refers to —H.

The term "deuterium" as used herein refers to -D.

The term "halogen" as used herein refers to —F, —Cl, —Br and —I.

The term "fluorine" as used herein refers to —F.

The term "chlorine" as used herein refers to —Cl.

The term "bromine" as used herein refers to —Br.

The term "iodine" as used herein refers to —I.

The term "cyano" as used herein refers to —CN.

The term "amino" as used herein refers to —$NH_2$.

The term "hydroxyl" as used herein refers to —OH.

The term "alkyl" as used herein refers to a saturated aliphatic hydrocarbyl group having from 1 to 10 carbon atoms, and the term includes both straight chain and branched chain hydrocarbon groups. Non-limiting examples of alkyl groups include methyl, ethyl, n-propyl, isopropyl, n-butyl, isobutyl, sec-butyl, tert-butyl, n-pentyl, neopentyl, n-hexyl, and the like. The alkyl group described herein can be optionally substituted with one or more of the following substituents: deuterium, fluorine, chlorine, bromine, iodine, cyano, nitro, hydroxyl, carboxyl, amino, alkyl, alkoxyl, acyl, acyloxy, oxo, amido, ester, amine, cycloalkyl, cycloalkenyl, heterocycloalkyl, alkenyl, alkenyloxy, alkynyl, cycloalkoxy, heterocycloalkyloxy, aryloxy, heteroaryloxy, aryl or heteroaryl.

The term "aryl" as used herein refers to a six- to ten-membered all-carbon monocyclic or fused polycyclic (i.e., a ring that shares a pair of adjacent carbon atoms) group, and polycyclic (i.e., a ring that has a pair of adjacent carbon atoms) group having conjugated 71-electron system. The aryl group can be covalently attached to a defined chemical structure at any carbon atom that results in a stable structure. The aryl groups described herein can be optionally substituted with one or more of the following substituents: deuterium, fluorine, chlorine, bromine, iodine, cyano, nitro, hydroxyl, carboxyl, amino, alkyl, alkoxyl, acyl, amido, ester, amine, sulfonyl, sulfinyl, cycloalkyl, cycloalkenyl, heterocycloalkyl, alkenyl, alkynyl and cycloalkoxyl.

The term "heteroaryl" as used herein refers to an aromatic group consisting of 5 to 10 atoms and containing at least one heteroatom selected from N, O or S. The term may have a single ring (non-limiting examples include furan, thiophene, imidazole, pyrazole, pyridine, pyrazine, oxazole, thiazole, etc.) or multiple fused rings (non-limiting examples include benzothiophene, benzofuran, indole, isoindole, etc.), wherein the fused ring may or may not be an aromatic group containing a heteroatom, assuming that the point of attachment is atoms through an aromatic heteroaryl group. The heteroaryl groups described herein can be optionally substituted with one or more of the following substituents: deuterium, fluorine, chlorine, bromine, iodine, cyano, nitro, hydroxyl, amino, alkyl, alkoxyl, acyl, acyloxy, amido, ester, amine, sulfonyl, sulfinyl, cycloalkyl, cycloalkenyl, heterocycloalkyl, alkenyl, alkynyl and cycloalkoxyl.

Alkenyl is an unsaturated hydrocarbyl group containing a carbon-carbon double bond. The term "alkenyl" as used herein refers to an alkyl group containing a carbon-carbon double bond in its molecule, wherein said alkyl group is as defined hereinbefore. The alkenyl group described herein can be optionally substituted with one or more of the following substituents: deuterium, fluorine, chlorine, bromine, iodine, cyano, nitro, hydroxyl, carboxyl, amino, alkyl, alkoxyl, acyl, amido, ester, amine, sulfonyl, sulfinyl, cycloalkyl, cycloalkenyl, heterocycloalkyl, cycloalkoxy, mercapto, alkylmercapto, deuterated alkylmercapto, sulfonyl, sulfinyl, amino, silyl, phosphonyl, deuterated alkyl, heterocycloalkyl, aryl, heteroaryl, alkynyl, alkenyl, arylalkyl, ester. Non-limiting examples of alkenyl groups include vinyl, propenyl, allyl, isopropenyl, butenyl, isobutenyl and the like.

Alkynyl is an unsaturated hydrocarbyl group containing a carbon-carbon triple bond. The term "alkynyl" as used herein refers to an alkyl group containing a carbon-carbon triple bond in its molecule, wherein said alkyl group is as defined hereinbefore. The alkynyl group can be substituted or unsubstituted, and when substituted, the substituent(s) can be preferably one or more of the following groups which are independently selected from the group consisting of deuterium, fluorine, chlorine, bromine, iodine, cyano, nitro, hydroxyl, carboxyl, amino, alkyl, alkoxyl, acyl, amido, ester, amine, sulfonyl, sulfinyl, cycloalkyl, cycloalkenyl, heterocycloalkyl, cycloalkoxy, mercapto, alkylmercapto, deuterated alkylmercapto, sulfonyl, sulfinyl, amino, silyl, phosphonyl, deuterated alkyl, heterocycloalkyl, aryl, heteroaryl, alkynyl, alkenyl, arylalkyl, ester. Non-limiting examples of alkynyl groups include ethynyl, 1-propinyl, 2-propinyl, 1-, 2- or 3-butynyl and the like.

The term "heterocyclyl" refers to substituted or unsubstituted, saturated or unsaturated aromatic ring and non-aromatic ring containing at least 1 to 5 heteroatoms selected from N, O or S. The aromatic ring and non-aromatic ring can be a three- to ten-membered monocyclic ring, a four- to twenty-membered spiro ring, fused ring or bridged ring. The optionally substituted N, S in the heterocyclyl ring can be oxidized to various oxidation states. A three- to twelve-membered heterocyclic ring is preferred. Non-limiting examples include oxacyclopropyl, oxacyclobutyl, oxacyclopentyl, oxacyclohexyl, oxacyclohexyl, oxacyclooctyl, azacyclopropyl, azacyclobutyl, azacyclopentyl, azacyclohexyl, azacyclopropenyl, 1,3-dioxocyclopentyl, 1,4-dioxocyclopentyl, 1,3-dioxocyclopentyl, 1,3-dioxacyclohexyl, 1,3-dithiocyclohexyl, azacycloheptenyl, morpholinyl, piperazinyl, pyridyl, furyl, thienyl, pyrrolyl, pyranyl, N-alkylpyrrolyl, pyrimidinyl, pyrazinyl, pyridazinyl, imidazolyl, piperidinyl, thiomorpholinyl, dihydropyranyl, thiadiazolyl, oxazolyl, oxadiazolyl, pyrazolyl, 1,4-dioxacyclohexadienyl and the like.

The term "haloalkyl" refers to an alkyl group obtained by substituting the "alkyl" as defined hereinbefore with halogen, wherein halogen includes fluorine, chlorine, bromine, iodine and the like.

The term "alkenyl alkyl" refers to an alkyl group obtained by substituting the "alkyl" as defined hereinbefore with the "alkenyl" as defined hereinbefore.

The term "alkynyl alkyl" refers to an alkyl group obtained by substituting the "alkyl" as defined hereinbefore with the "alkynyl" as defined hereinbefore.

The term "nitrogen-containing heterocyclyl" refers to a ring system containing nitrogen atom(s), such ring system can "combinate" aromatic and non-aromatic ring systems or link other ring systems through "spiro-carbon atom", for example, the ring systems are the following structures:

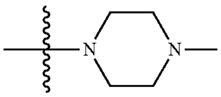

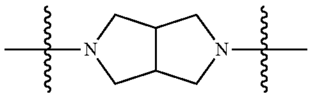

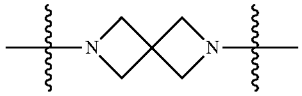

-continued

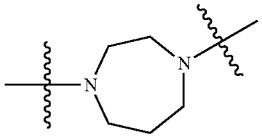

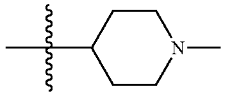

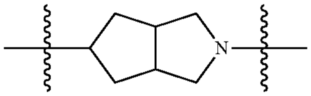

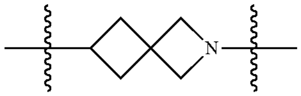

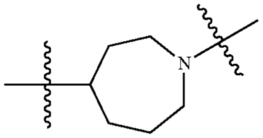

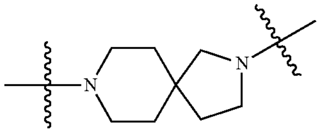

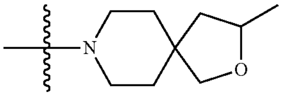

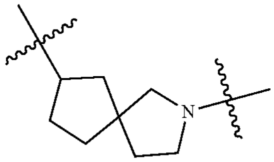

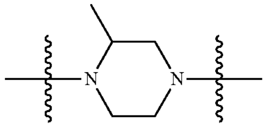

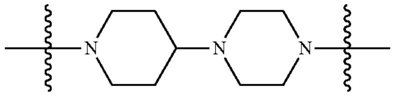

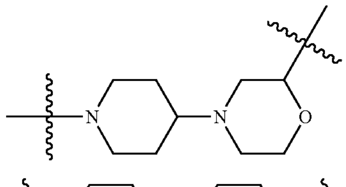

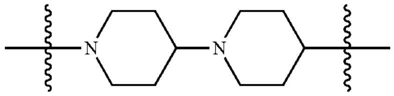

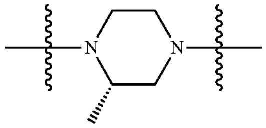

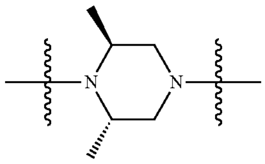

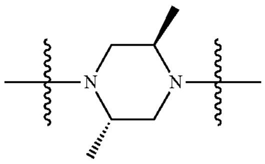

-continued

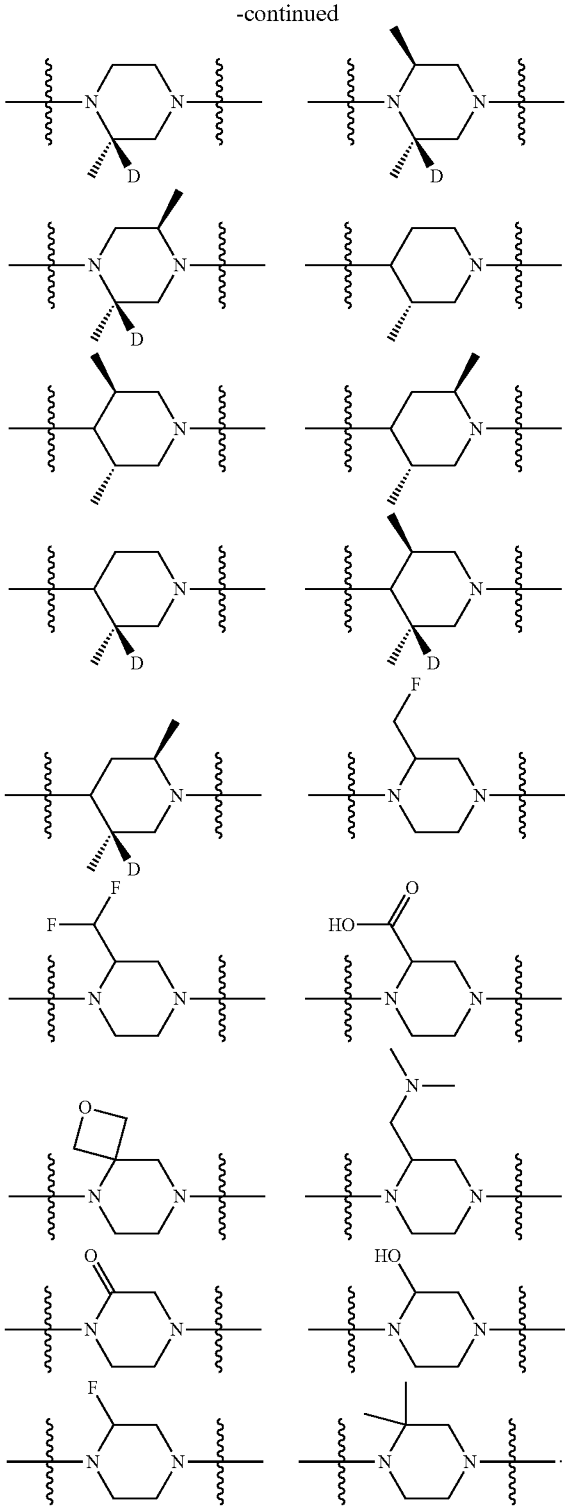

The term "amido" (or "amido group") includes C-amido group and N-amido group, i.e., —C(O)$NR^AR^B$ group and —$NR^A$C(O)$R^B$ group, respectively. $R^A$ and $R^B$ are independently hydrogen or substituted or unsubstituted alkyl, alkenyl, alkynyl, cycloalkyl, aryl, aralkyl, heterocyclyl alkyl or heterocyclyl as defined herein. The amido groups thus include but are not limited to, carbamoyl (—C(O)$NH_2$) and formamido (—NHC(O)H). In some embodiments, the amido group is —$NR^A$C(O)—($C_{1-5}$ alkyl), which is referred to as a "carbonyl amino" group, and in another embodiments, the amido group is —NHC(O)-alkyl, which is referred to as an "alkyl acyl amino" group.

The term "sulfonamido" includes S-sulfonamido group and N-sulfonamido group, i.e., —$SO_2NR^CR^D$ group and —$NR^CSO_2R^D$ group, respectively. $R^C$ and $R^D$ are independently hydrogen or substituted or unsubstituted alkyl, alkenyl, alkynyl, cycloalkyl, aryl, aralkyl, heterocyclyl alkyl or heterocyclyl as defined herein. The sulfonamido groups thus include but are not limited to sulfonyl (—$SO_2NH_2$). In some embodiments herein, the sulfonamido group is —$NHSO_2$-alkyl, which is referred to as an "alkyl sulfonyl amino" group.

The present invention also includes isotopically labeled compounds of the present invention, which are identical to those disclosed above in structure, but in which one or more atoms are replaced by an atom having the same number of protons but a different number of neutrons. Examples of the isotope incorporating into the compound of the present invention include isotopes of hydrogen, carbon, nitrogen, oxygen, sulfur, fluorine, chlorine and iodine, such as $^2H$, $^3H$, $^{13}C$, $^{14}C$, $^{15}N$, $^{18}O$, $^{17}O$, $^{35}S$, $^{18}F$, $^{36}Cl$ and $^{131}I$, etc. The compound of the present invention, the stereoisomer, tautomer or pharmaceutically acceptable salt thereof, and the compound of the above forms containing the above isotopes and/or isotopes of other atoms are within the scope of the present invention. Certain isotopically labeled compounds of the present invention, such as those labeled with $^3H$ or $^{14}C$, can be used in drug tissue distribution assays, and therefore, these $^3H$ or $^{14}C$ isotopes are particularly preferred because of their ease of preparation and detection.

Certain compounds of the present invention that are replaced by heavier isotopes such as $^2H$, $^{18}O$ have certain therapeutic advantages due to better metabolic stability, for example overall performance such as increased in vivo half-life and lower doses, etc., therefore, $^2H$, $^{18}O$ are also preferred in some cases.

DETAILED DESCRIPTION OF THE INVENTION

Figure 1:
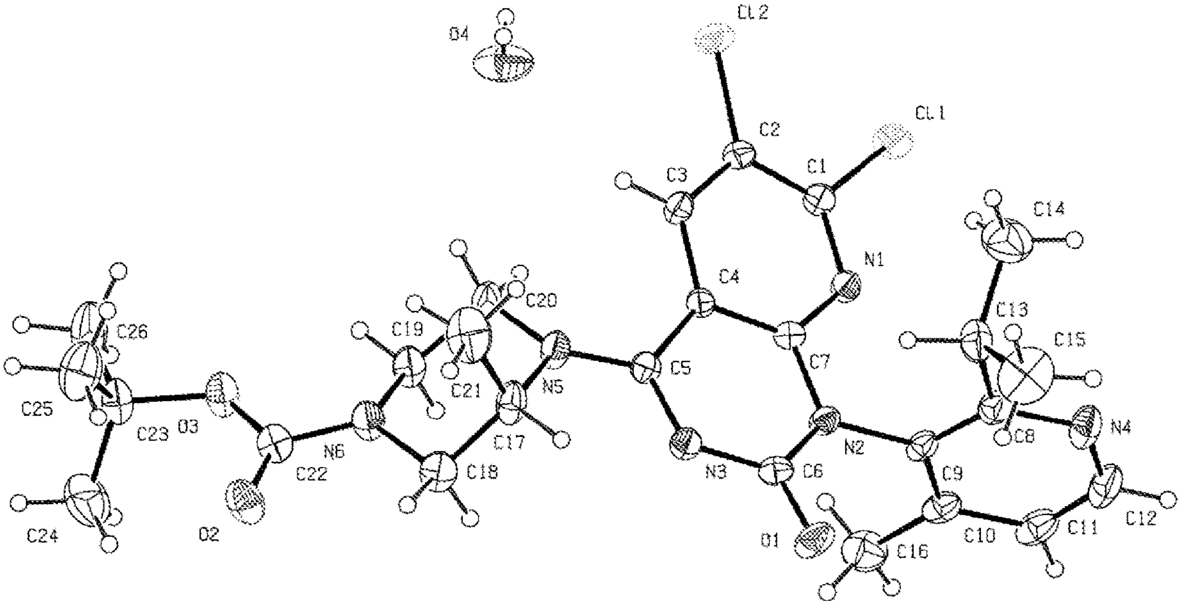
FIG. 1 shows X-ray single-crystal diffractogram of Intermediate 3M.

The following examples are used to further illustrate the present invention, but the present invention is not limited by them. Throughout the present application, various examples of the compounds and methods of the present invention are referred to herein. The present invention is not limited to these examples, and the following examples are merely intended to provide methods for practicing the present invention and are not intended to limit the scope of the present invention by any means.

The compounds provided by the present invention can be prepared by standard synthetic methods well known in the art, and the present description provides general methods for preparing the compounds of the present invention. Starting materials are usually available commercially or can be prepared by methods well known to those skilled in the art.

Process 1 is as follows:

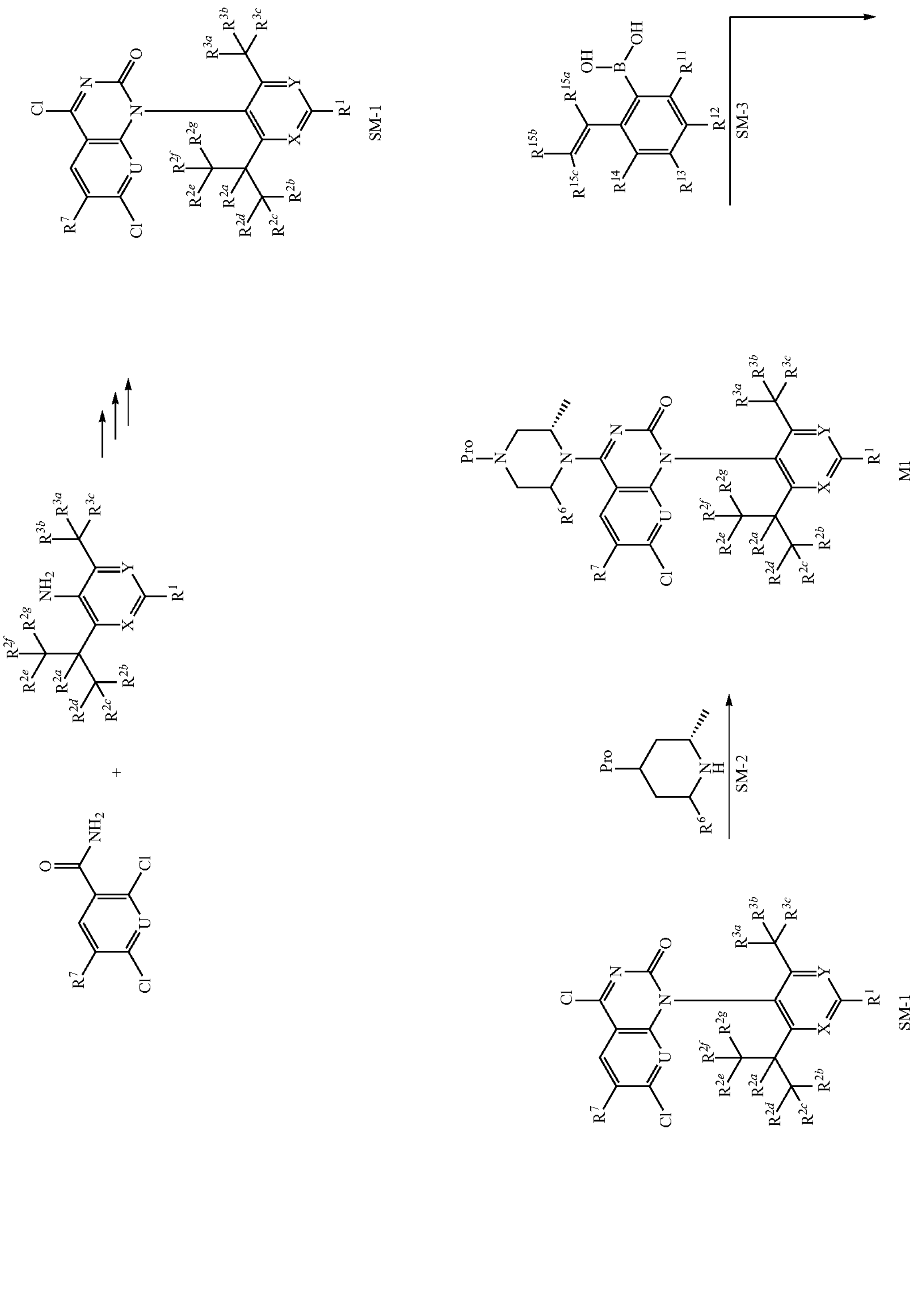
SM-1
SM-3
M1
SM-2
SM-1

-continued
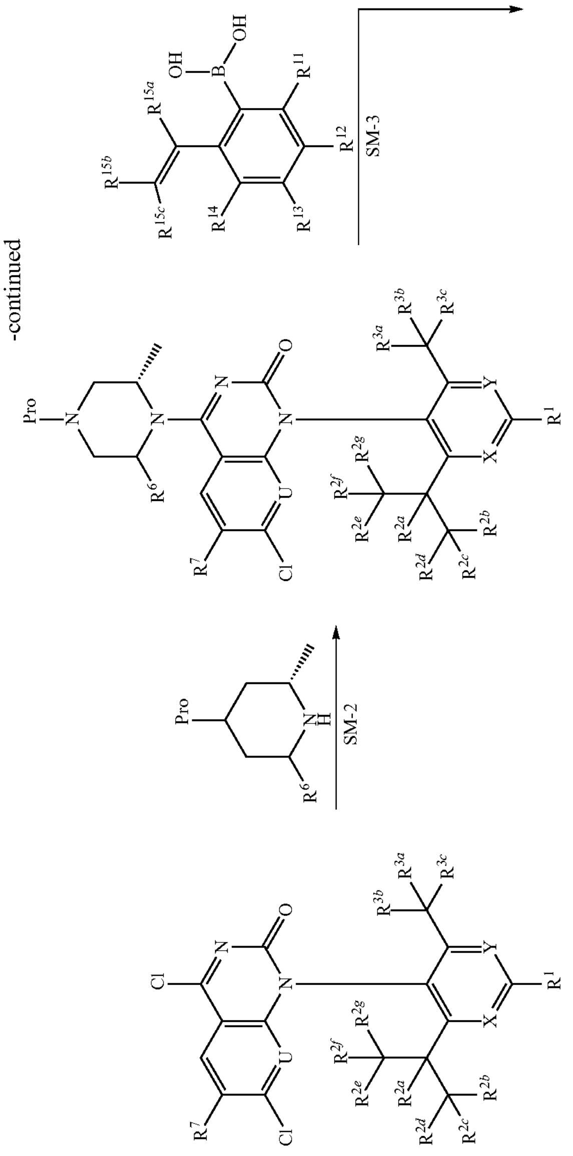
SM-1
M1

-continued
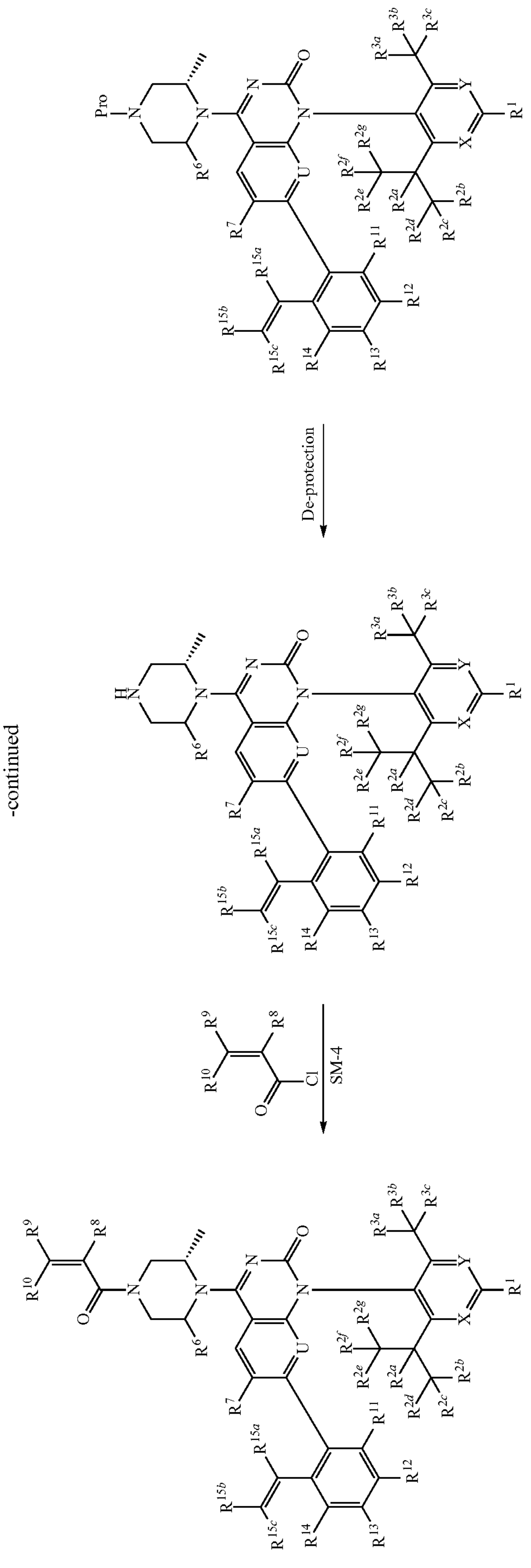
M2
M3
II-1

Firstly, a nucleophilic substitution reaction is performed by SM-1, which is used as the starting material, reacting with SM2 to obtain M1, which is then reacted with SM-3 to obtain M2. After removing the protecting group, M3 is obtained, and then Compound II-1 is obtained through a further reaction.

Process 2 is as follows:

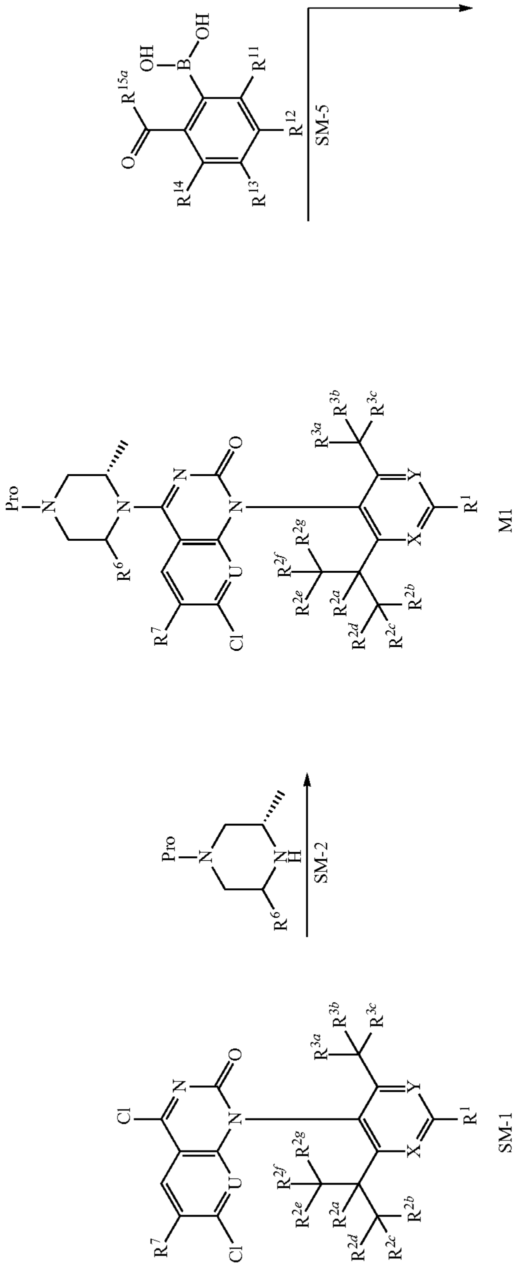
SM-5
M1
SM-2
SM-1
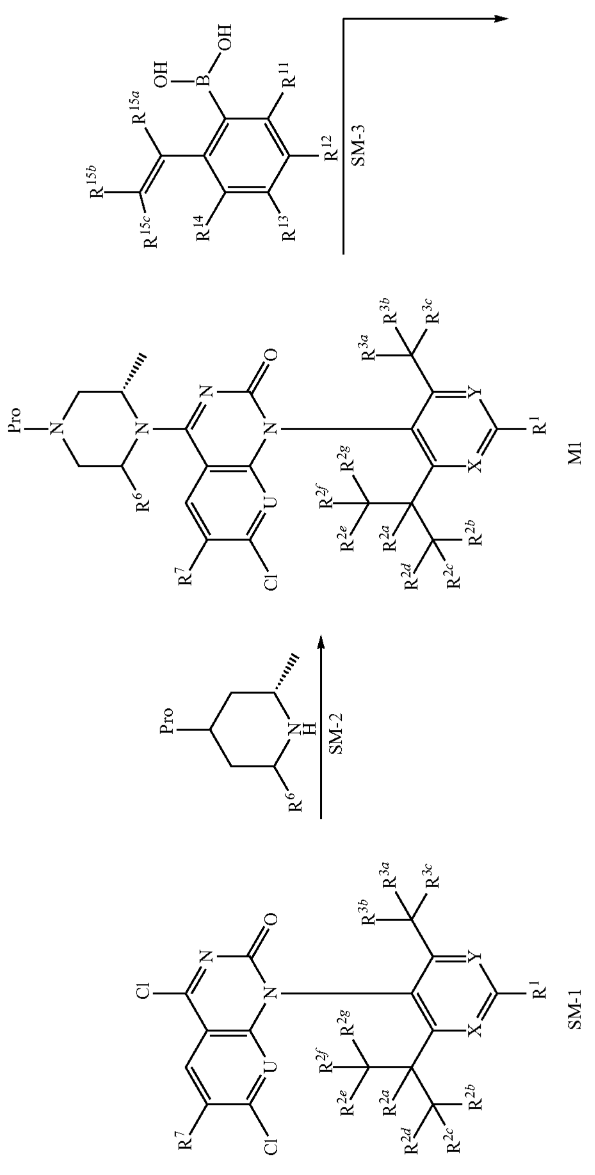
SM-3
M1
SM-2
SM-1

-continued
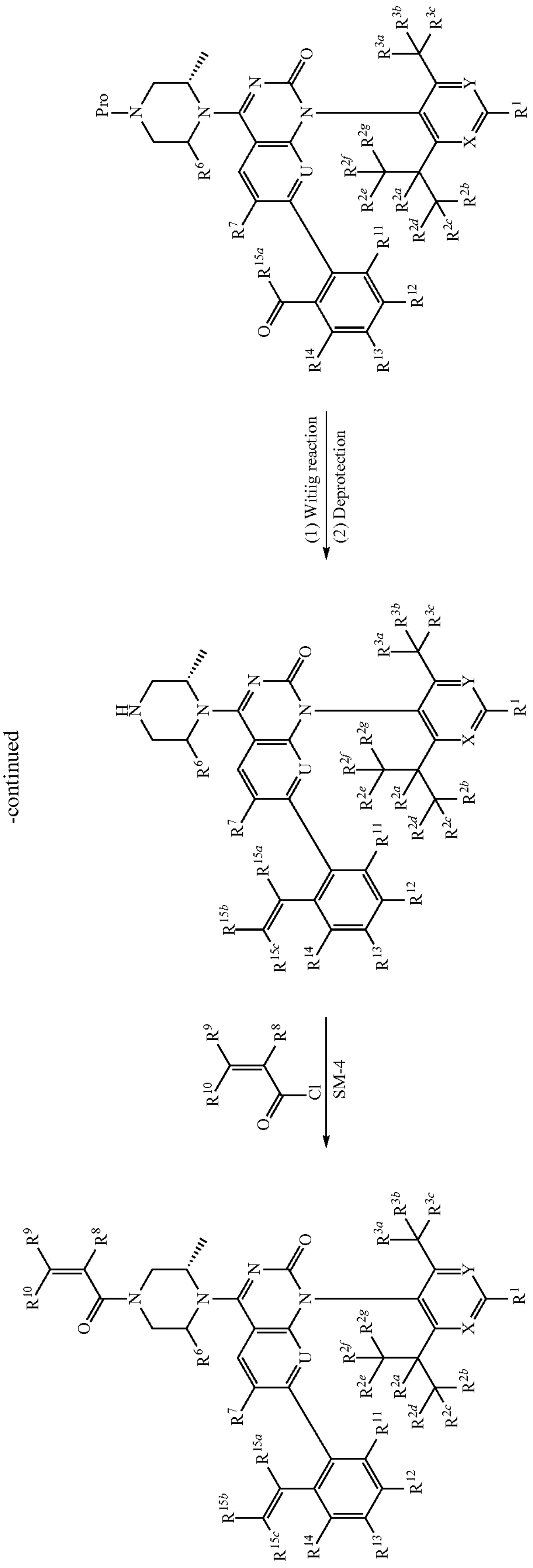
M2'
M3
II-1

Firstly, a nucleophilic substitution reaction is performed by SM-1, which is used as the starting material, reacting with SM2 to obtain M1, which is then reacted with SM-3 to obtain M2'. M2' is then subjected to Wittig reaction and protecting group removal to obtain M3, and then Compound II-1 is obtained through a further reaction.

The compounds of the present invention and the corresponding preparation methods are further explained and enumerated below by way of examples and preparations. It should be understood that although typical or preferred reaction conditions are given in the specific examples, other reaction conditions may be used by those skilled in the art. The optimal reaction conditions may vary with the used particular reaction substrates or solvents, but the said conditions may be determined through common optimization by those skilled in the art.

Preparation of Intermediates

Intermediate 1

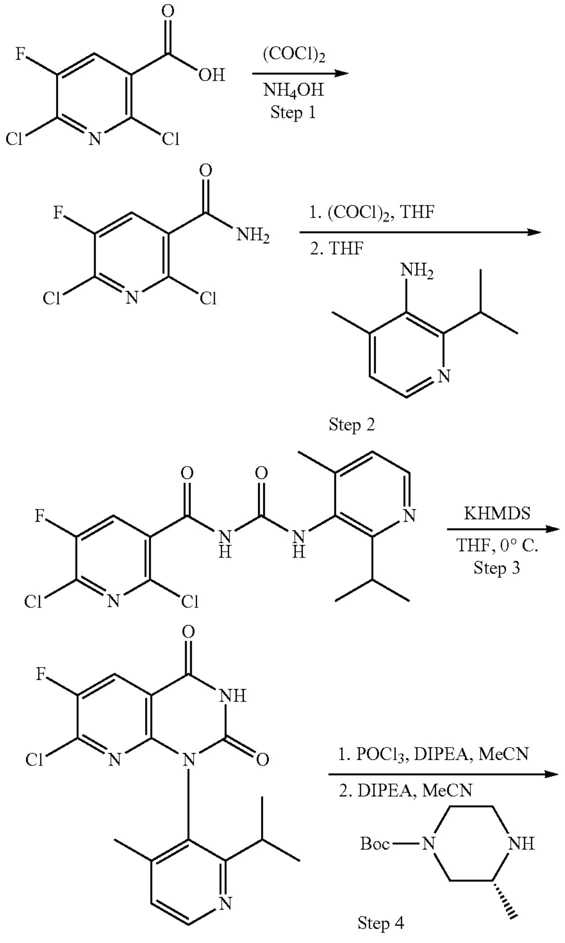

-continued

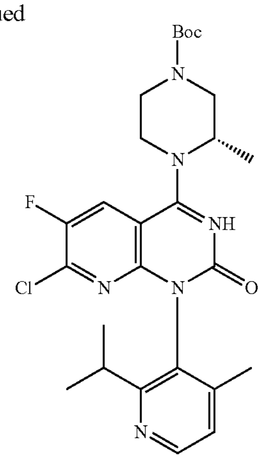

Intermediate 1

Step 1

2,6-Dichloro-5-fluoronicotinic acid (61.0 g), dichloromethane (600 ml) and N,N-dimethylformamide (1 ml) were added into a 2000 ml single-necked flask, cooled to 0° C., dropwise added with a solution of oxalyl chloride (36.9 ml) in dichloromethane (30 ml), gradually warmed to room temperature after the addition and stirred for 16 h. The obtained mixture was concentrated under reduced pressure to dryness, cooled to 0° C., added with 1,4-dioxane (600 ml), then dropwise added with aqueous ammonia (120 ml), and stirred for another 1 h at 0° C. after the addition. The mixture was concentrated under reduced pressure to dryness. The concentrate was triturated with ethyl acetate and n-hexane, stood and filtered. The filter cake was washed with n-hexane and dried. The filtrate was concentrated and purified by silica gel column chromatography to give a total of 38 g of a white solid.

Step 2

At 0° C., a solution of oxalyl chloride (18.5 ml) in dichloromethane (20 ml) was dropwise added, warmed to 75° C. after the addition and stirred for 1 h. The obtained mixture was concentrated under reduced pressure to dryness, cooled to 0° C., added with tetrahydrofuran (300 ml), dropwise added with a solution of 2-isopropyl-4-methylpyridin-3-amine (28.7 g) in tetrahydrofuran (150 ml) and stirred for another 1 h at 0° C. The reaction solution was poured into saturated aqueous solution of ammonium chloride, extracted with ethyl acetate. The organic layers were combined, washed with saturated salt solution, dried over anhydrous sodium sulfate, filtered, and concentrated under reduced pressure until a solid was precipitated. The obtained mixture was cooled to 0° C., kept for 15 min, and filtered. The filter cake was washed with ethyl acetate and petroleum ether, and dried. The filtrate was then purified by silica gel column chromatography, and a total of 51 g of a white solid was obtained.

Step 3

2,6-Dichloro-5-fluoro-N-((2-isopropyl-4-methylpyridin-3-yl)aminocarbonyl)nicotinamide (51.0 g) and tetrahydrofuran (500 ml) were added into a 1000 ml single-necked flask, cooled to 0° C., dropwise added with potassium bis(trimethylsilyl)amide (278 ml), gradually warmed to room temperature after the addition and stirred for 1 h. The reaction solution was poured into saturated aqueous solution of ammonium chloride, extracted with ethyl acetate. The organic layers were combined, washed with saturated salt solution, dried over anhydrous sodium sulfate, filtered, and concentrated under reduced pressure until a solid was precipitated. The obtained mixture was cooled to 0° C., kept for 30 min, and filtered. The filter cake was washed with ethyl acetate and petroleum ether, and dried. The filtrate was concentrated, and purified by silica gel column chromatography. A total of 38 g of a light-yellow solid was obtained.

Step 4

The product from the previous step (24.0 g), acetonitrile (240 ml) and N,N-diisopropylethylamine (68.2 ml) were added into a 500 ml single-necked flask, cooled to 0° C., dropwise added with phosphorus oxychloride (38.5 ml), warmed to 80° C. after the addition and stirred for 2 h. The obtained mixture was concentrated under reduced pressure to dryness, and subjected to azeotropy with tolune twice. Acetonitrile (240 ml) was added into the residue, cooled to 0° C., added with N,N-diisopropylethylamine (68.2 ml), then added with (S)-4-N-tert-butoxycarbonyl-2-methylpiperazine (20.7 g) in batches and stirred at room temperature for 1 h after the addition. Saturated aqueous solution of sodium bicarbonate was slowly poured to quench the reaction. The reaction solution was extracted with ethyl acetate. The organic layers were combined, washed with saturated salt solution, dried over anhydrous sodium sulfate, filtered, and concentrated under reduced pressure until a solid was precipitated. The obtained mixture was cooled to 0° C., kept for 15 min, and filtered. The filter cake was washed with ethyl acetate and petroleum ether, and dried. The filtrate was concentrated, and purified by silica gel column chromatography. A total of 18 g of a yellow solid was obtained. $^1$H NMR (400 MHz, DMSO-$d_6$): δ 8.50 (d, J=4.9 Hz, 1H), 8.38 (d, J=8.5 Hz, 1H), 7.30 (d, J=4.8 Hz, 1H), 4.84 (s, 1H), 4.27-4.10 (m, 1H), 4.03-3.88 (m, 1H), 3.88-3.76 (m, 1H), 3.75-3.58 (m, 2H), 3.38-3.24 (m, 1H), 2.70-2.56 (m, 1H), 1.96 (s, 3H), 1.45 (s, 9H), 1.36-1.29 (m, 3H), 1.07 (d, J=6.7 Hz, 3H), 1.04-0.97 (m, 3H); MS: m/z 531.2, [M+H]$^+$.

Intermediate 2

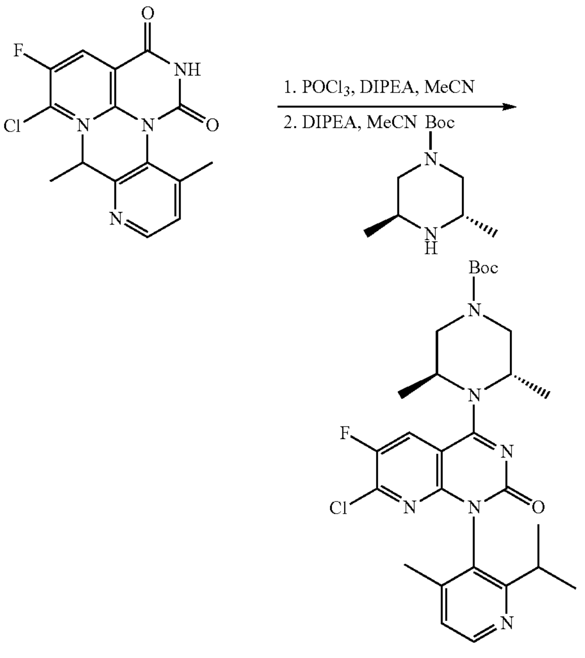

Intermediate 2

7-Chloro-6-fluoro-1-(2-isopropyl-4-methylpyridin-3-yl)pyrido[2,3-d]pyrimidine-2,4(1H,3H)-dione (2.0 g), acetonitrile (20 ml) and N,N-diisopropylethylamine (5.8 ml) were added into a 50 ml single-necked flask, cooled to 0° C., dropwise added with phosphorus oxychloride (3.2 ml), warmed to 80° C. after the addition and stirred for 2 h. The obtained mixture was concentrated under reduced pressure to dryness, and subjected to azeotropy with tolune twice. Acetonitrile (20 ml) was added into the residue, cooled to 0° C., added with N,N-diisopropylethylamine (5.8 ml), then added with tert-butyl-(3S,5S)-3,5-dimethyl-1-piperazinecarboxylate (1.3 g) in batches, and gradually warmed to room temperature after the addition and stirred for 1 h. Saturated aqueous solution of sodium bicarbonate was slowly poured to quench the reaction. The reaction solution was extracted with ethyl acetate. The organic layers were combined, washed with saturated salt solution, dried over anhydrous sodium sulfate, filtered, concentrated under reduced pressure, and then purified by silica gel column chromatography. 2 g of a yellow solid was obtained. $^1$H NMR (400 MHz, DMSO-$d_6$): δ 8.50 (dd, J=4.8, 1.7 Hz, 1H), 8.45 (dd, J=8.6, 6.4 Hz, 1H), 7.28 (d, J=4.8 Hz, 1H), 4.43-4.27 (m, 2H), 3.74 (br s, 2H), 3.48 (br s, 2H), 2.70-2.55 (m, 1H), 1.94 (d, J=4.4 Hz, 3H), 1.45 (s, 9H), 1.30-1.21 (m, 6H), 1.08-1.04 (m, 3H), 1.02 (t, J=6.4 Hz, 3H); MS: m/z 545.3, [M+H]$^+$.

Intermediate 3

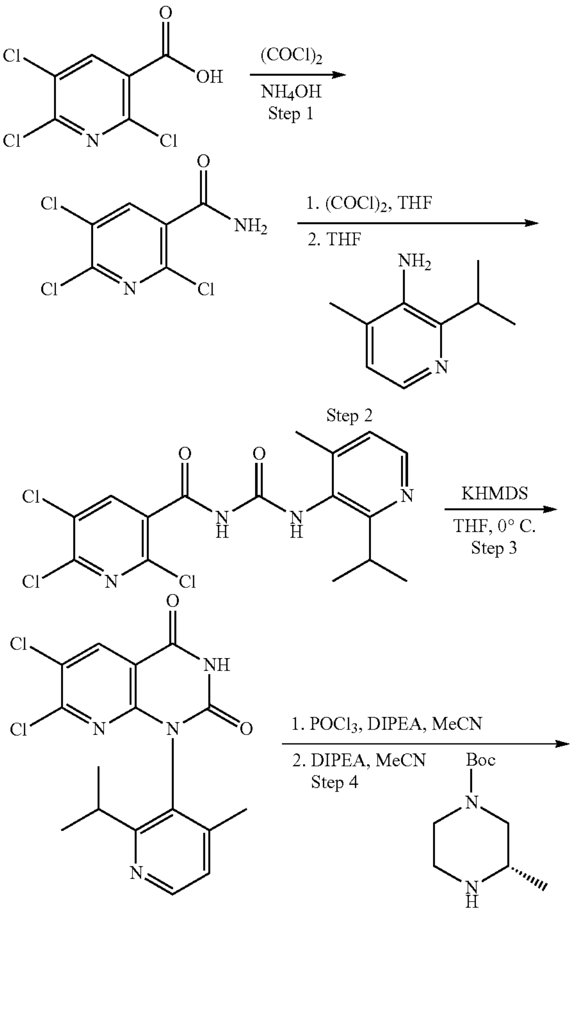

-continued

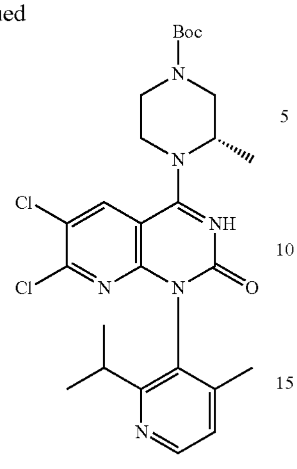

Intermediate 3

Step 1

2,5,6-trichloronicotinic acid (50.0 g) and tetrahydrofuran (500 ml) were added into a 2000 ml single-necked flask, added with N,N'-carbonyldiimidazole (39.4 g) in batches, gradually warmed to 50° C. after the addition and stirred for 2 h. The obtained solution was cooled to room temperature, added with toluene (100 ml), and subjected to reduced pressure distillation until half of the solvent was removed. Then the obtained mixture was cooled to 0° C., dropwise added with aqueous ammonia (60 ml), and stirred for another 1 h at 0° C. after the addition. The resulting mixture was added with water, and then separated. The aqueous phase was extracted with ethyl acetate. The organic phases were combined, washed with saturated salt solution, dried over anhydrous sodium sulfate, filtered, concentrated under reduced pressure, and purified by silica gel column chromatography. 36 g of a white solid was obtained. $^{1}H$ NMR (400 MHz, $CDCl_3$): δ 8.36 (s, 1H), 6.76 (br s, 1H), 6.47 (br s, 1H).

Step 2

2,5,6-trichloronicotinamide (15.4 g) and tetrahydrofuran (150 ml) were added into a 500 ml single-necked flask, cooled to 0° C., dropwise added with a solution of oxalyl chloride (7.0 ml) in dichloromethane (7 ml), warmed to 75° C. after the addition and stirred for 2 h. The reaction solution was concentrated to dryness, cooled to 0° C., added with tetrahydrofuran (150 ml), dropwise added with a solution of 2-isopropyl-4-methylpyridin-3-amine (10.8 g) in tetrahydrofuran (70 ml) and stirred for another 1 h at 0° C. after the addition. The reaction solution was poured into saturated aqueous solution of ammonium chloride, extracted with ethyl acetate. The organic layers were combined, washed with saturated salt solution, dried over anhydrous sodium sulfate, filtered, concentrated under reduced pressure and purified by silica gel column chromatography to give 12 g of a white solid. $^{1}H$ NMR (400 MHz, DMSO-$d_6$): δ 11.34 (s, 1H), 9.58 (br s, 1H), 8.68 (s, 1H), 8.34 (d, J=4.8 Hz, 1H), 7.16 (d, J=4.8 Hz, 1H), 3.33-3.23 (m, 1H), 2.22 (s, 3H), 1.17 (d, J=6.6 Hz, 6H).

Step 3

The product from the previous step (12.0 g, 29.9 mmol) and tetrahydrofuran (150 ml) were added into a 500 ml single-necked flask, cooled to 0° C., dropwise added with potassium bis(trimethylsilyl)amide (74.8 ml, 74.8 mmol), and stirred at room temperature for 1 h after the addition. The reaction solution was poured into saturated aqueous solution of ammonium chloride, extracted with ethyl acetate. The organic layers were combined, washed with saturated salt solution, dried over anhydrous sodium sulfate, filtered, concentrated under reduced pressure, and purified by silica gel column chromatography to give 9.6 g of a light-yellow solid.

Step 4

The product from the previous step (26.0 g), acetonitrile (250 ml) and N,N-diisopropylethylamine (16.4 g) were added into a 500 ml single-necked flask, cooled to 0° C., dropwise added with phosphorus oxychloride (11.9 ml), warmed to 80° C. after the addition and stirred for 2 h. The obtained mixture was concentrated under reduced pressure to dryness, and subjected to azeotropy with tolune twice. Acetonitrile (250 ml) was added into the residue, cooled to 0° C., added with N,N-diisopropylethylamine (16.4 g), then added with (S)-4-N-tert-butoxycarbonyl-2-methylpiperazine (15.0 g) in batches and stirred at room temperature for 1 h after the addition. Saturated aqueous solution of sodium bicarbonate was slowly poured to quench the reaction. The reaction solution was extracted with ethyl acetate. The organic layers were combined, washed with saturated salt solution, dried over anhydrous sodium sulfate, filtered, concentrated under reduced pressure, and purified by silica gel column chromatography to give 23.5 g of a yellow solid. $^{1}H$ NMR (400 MHz, DMSO-$d_6$): δ 8.55-8.43 (m, 2H), 7.26 (d, J=4.9 Hz, 1H), 4.88 (br s, 1H), 4.26-4.09 (m, 1H), 4.02-3.88 (m, 1H), 3.88-3.77 (m, 1H), 3.77-3.61 (m, 1H), 3.33-2.92 (m, 2H), 2.72-2.55 (m, 1H), 1.98-1.90 (m, 3H), 1.45 (s, 9H), 1.36-1.28 (m, 3H), 1.06 (d, J=6.7 Hz, 3H), 1.01 (d, J=6.6 Hz, 3H); MS: m/z 547.2, $[M+H]^+$.

Intermediate 4

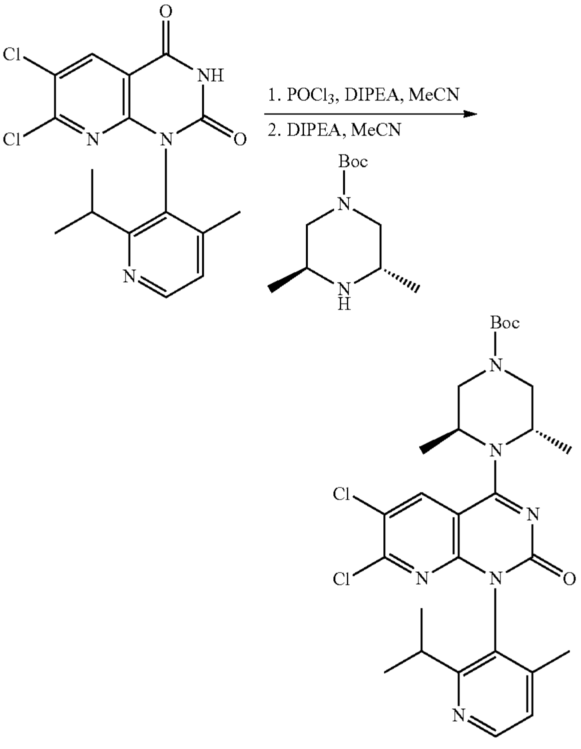

Intermediate 4

6,7-Dichloro-1-(2-isopropyl-4-methylpyridin-3-yl)pyrido[2,3-d]pyrimidine-2,4(1H,3H)-dione (3.0 g), acetonitrile (30 ml) and N,N-diisopropylethylamine (8.1 ml) were added into a 100 ml single-necked flask, cooled to 0° C., dropwise added with phosphorus oxychloride (4.6 ml), warmed to 80° C. after the addition and stirred for 2 h. The obtained mixture was concentrated under reduced pressure to dryness, and subjected to azeotropy with tolune twice. Acetonitrile (30 ml) was added into the residue, cooled to 0° C., added with N,N-diisopropylethylamine (5.8 ml), then added with tert-butyl-(3S,5S)-3,5-dimethyl-1-piperazinecarboxylate (1.8 g) in batches, and stirred at room temperature for 1 h after the addition. Saturated aqueous solution of sodium bicarbonate was slowly poured to quench the reaction. The reaction solution was extracted with ethyl acetate. The organic layers were combined, washed with saturated salt solution, dried over anhydrous sodium sulfate, filtered, concentrated under reduced pressure, and purified by silica gel column chromatography. 2.2 g of a yellow solid was obtained. $^{1}H$ NMR (400 MHz, DMSO-$d_6$): δ 8.53 (d, J=7.2 Hz, 1H), 8.50 (dd, J=4.8, 1.6 Hz, 1H), 7.28 (d, J=4.8 Hz, 1H), 4.47-4.31 (m, 2H), 3.73 (br s, 2H), 3.52 (br s, 2H), 2.71-2.54 (m, 1H), 1.95 (d, J=7.3 Hz, 3H), 1.45 (s, 9H), 1.31-1.24 (m, 6H), 1.08-0.99 (m, 6H); MS: m/z 561.2, $[M+H]^+$.

Intermediate 5

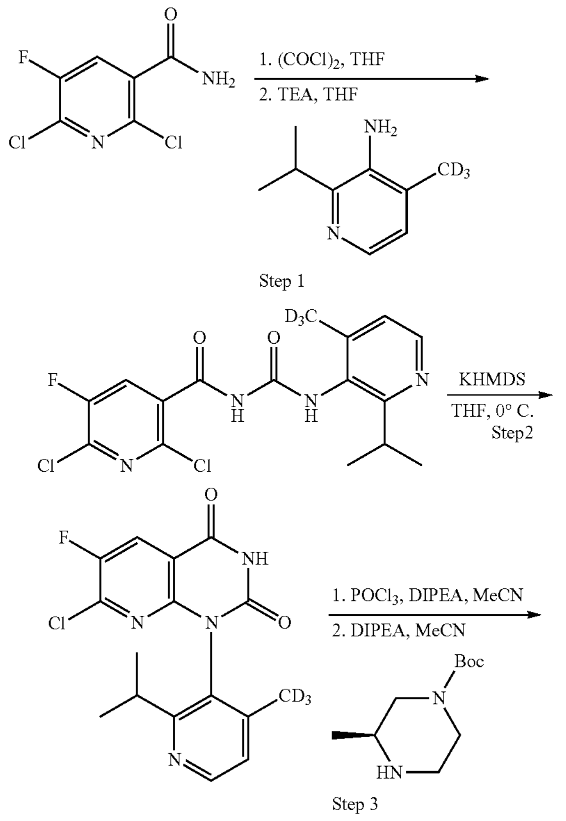

-continued

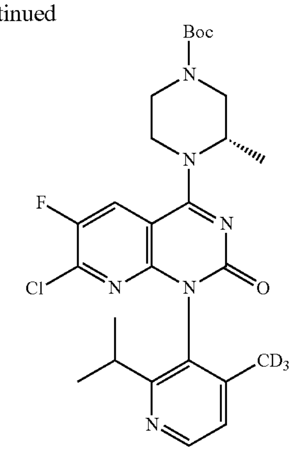

Intermediate 5

Step 1

2,6-Dichloro-5-fluoronicotinamide (1.2 g) and tetrahydrofuran (40 ml) were added into a 250 ml single-necked flask, cooled to 0° C., dropwise added with oxalyl chloride (860 mg), after the addition warmed to 70° C. and stirred for 1 h. The reaction solution was concentrated to dryness, cooled to 0° C., added with tetrahydrofuran (40 ml), dropwise added with a solution of 2-isopropyl-4-(methyl-$d_3$)pyridin-3-amine (783 mg) in tetrahydrofuran (10 ml), 5 min later dropwise added with triethylamine (580 mg), and stirred for another 30 min after the addition. The reaction solution was poured into saturated aqueous solution of ammonium chloride, extracted with ethyl acetate. The organic layers were combined, washed with saturated salt solution, dried over anhydrous sodium sulfate, filtered, concentrated under reduced pressure and purified by silica gel column chromatography to give 1.45 g of an off-white solid. $^{1}H$ NMR (400 MHz, $CDCl_3$): δ 10.38 (s, 1H), 9.79 (s, 1H), 8.45 (d, J=4.9 Hz, 1H), 7.85 (d, J=7.0 Hz, 1H), 7.07 (d, J=4.9 Hz, 1H), 3.33-3.19 (m, 1H), 1.25 (d, J=6.8 Hz, 6H); MS: m/z 388.1, $[M+H]^+$.

Step 2

The product from the previous step (1.45 g) and tetrahydrofuran (20 ml) were added into a 250 ml single-necked flask, cooled to 0° C., dropwise added with potassium bis(trimethylsilyl)amide (8.3 ml), gradually warmed to room temperature and stirred for 1 h after the addition. The reaction solution was poured into saturated aqueous solution of ammonium chloride, extracted with ethyl acetate. The organic layers were combined, washed with saturated salt solution, dried over anhydrous sodium sulfate, filtered, concentrated under reduced pressure, and purified by silica gel column chromatography to give 1.15 g of an off-white solid. $^{1}H$ NMR (400 MHz, $CDCl_3$): δ 8.64 (d, J=4.9 Hz, 1H), 8.28 (d, J=6.6 Hz, 1H), 7.19 (d, J=4.9 Hz, 1H), 6.64 (br s, 1H), 2.80-2.65 (m, 1H), 1.24 (d, J=6.7 Hz, 3H), 1.15 (d, J=6.7 Hz, 3H); MS: m/z 352.1, $[M+H]^+$.

Step 3

The product from the previous step (1.1 g), acetonitrile (20 ml) and N,N-diisopropylethylamine (1.0 g) were added into a 250 ml single-necked flask, cooled to 0° C., dropwise added with phosphorus oxychloride (970 mg), then dropwise added with 2 drops of N-methylmorpholine, and stirred at room temperature for 1 h. The obtained mixture was concentrated under reduced pressure to dryness, and subjected to azeotropy with tolune twice. Acetonitrile (20 ml) was added into the residue, cooled to 0° C., added with N,N-diisopropylethylamine (1.0 g), then added with (S)-4-N-tert-butoxycarbonyl-2-methylpiperazine (632 mg) and stirred at room temperature for 1 h after the addition. Saturated aqueous solution of sodium bicarbonate was slowly poured to quench the reaction. The reaction solution was extracted with ethyl acetate. The organic layers were combined, washed with saturated salt solution, dried over anhydrous sodium sulfate, filtered, concentrated under reduced pressure, and purified by silica gel column chromatography to give 1.2 g of a yellow solid. MS: m/z 534.2, $[M+H]^+$.

Intermediate 6

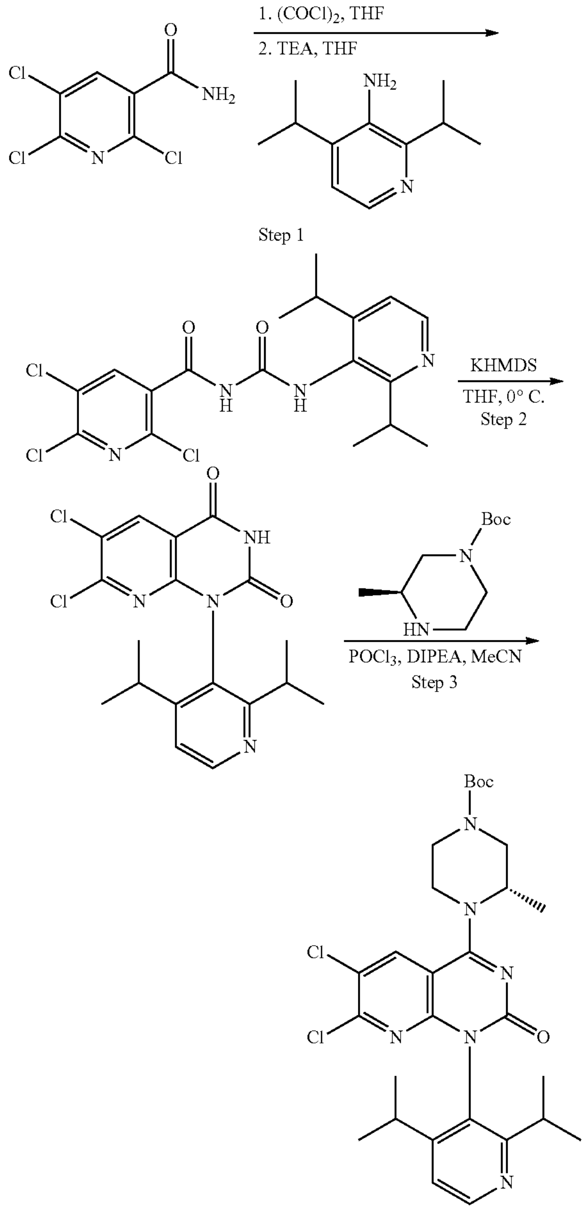

Intermediate 6

Step 1

Dry tetrahydrofuran (100 ml) and oxalyl chloride (3.0 g) were added into a 250 ml flask, added with 2,5,6-trichloronicotinamide (4.6 g) in batches under stirring, and stirred at room temperature for 10 min then at 75° C. for 1 h. The reaction solution was concentrated under reduced pressure to dryness, added with dry tetrahydrofuran (50 ml) and 2,4-diisopropyl-3-aminopyridine (3.0 g), then dropwise added with triethylamine (2.1 g), and stirred for 20 min after the addition. The reaction solution was added with water to quench the reaction, and extracted with ethyl acetate. The organic layers were combined, washed with saturated salt solution, dried over anhydrous sodium sulfate, filtered, concentrated under reduced pressure and purified by silica gel column chromatography to give 6.8 g of a white solid. MS: m/z 429.1, $[M+H]^+$.

Step 2

The product from the previous step (6.7 g) and dry tetrahydrofuran (50 ml) were added into a 250 ml single-necked flask, slowly dropwise added with 1 M of potassium bis(trimethylsilyl)amide (39 ml) under the condition of ice bath, and stirred at room temperature for 40 min after the addition. The reaction solution was poured into 100 ml of saturated aqueous solution of ammonium chloride, and extracted with ethyl acetate. The organic layers were combined, washed with saturated sodium chloride solution, dried over anhydrous sodium sulfate, filtered, concentrated under reduced pressure, and purified by silica gel column chromatography to give 4.58 g of an off-white solid. MS: m/z 393.1, $[M+H]^+$.

Step 3

The product from the previous step (2.0 g), acetonitrile (30 ml), N,N-diisopropylethylamine (4.5 ml) and (S)-tert butyl-3-methylpiperazine-1-carboxylate (1.1 g) were added into a 100 ml single-necked flask, dropwise added with phosphorus oxychloride (0.94 ml), and stirred for another 1 h after the addition. The reaction solution was added with saturated aqueous solution of sodium carbonate to quench the reaction, and extracted with ethyl acetate. The organic layers were combined, washed with saturated sodium chloride solution, dried over anhydrous sodium sulfate, filtered, concentrated under reduced pressure, and purified by silica gel column chromatography to give 1.7 g of a yellow solid. MS: m/z 575.2, $[M+H]^+$.

Intermediate 7

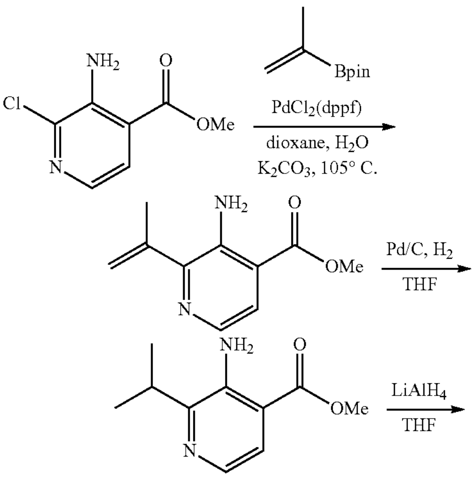

-continued

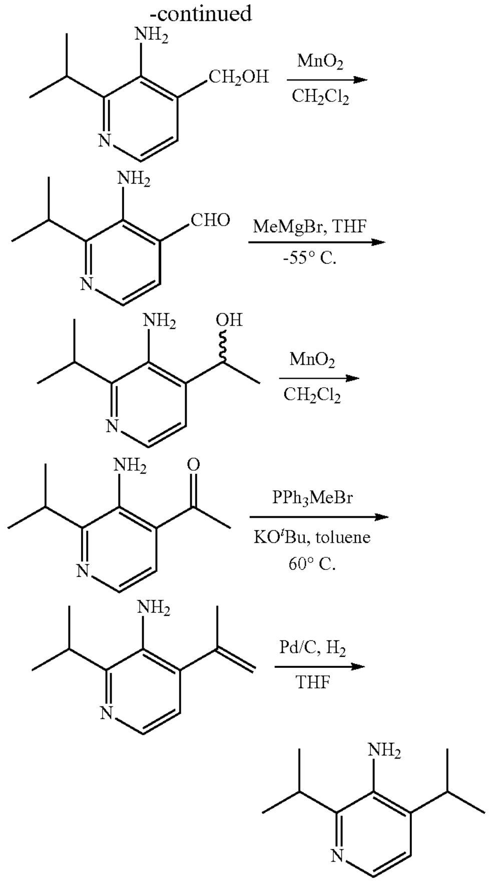

Methyl-3-amino-2-chloro-pyridine-4-carboxylate (9.2 g), isopropenylboronic acid pinacol ester (11.9 g), potassium carbonate (7.6 g), $pdCl_2$(dppf) (5.5 g), 1,4-dioxane (85 ml), and water (17 ml) were added into a flask in sequence, inside which sufficient nitrogen gas replacement was performed after the addition. Then the flask was put in an oil bath at 105° C., and stirred and refluxed for 3 h. The reaction solution was filtered through a celite pad. The filtrate was added with 300 ml of water, extracted with ethyl acetate three times. The ethyl acetate layers were combined, washed twice with saturated salt water, dried over anhydrous sodium sulfate, filtered, concentrated under reduced pressure and purified by silica gel column chromatography to yield 9.3 g of an orange-yellow solid. MS: m/z 193.2, $[M+H]^+$.

Methyl-3-amino-2-isopropenyl-pyridine-4-carboxylate (9.3 g), 5% palladium on carbon (1.86 g), and tetrahydrofuran (120 ml) were added into a flask, inside which sufficient hydrogen gas replacement was performed after the addition. The mixture in the flask was stirred overnight at room temperature under the atmosphere of a hydrogen balloon. The reaction solution was filtered through a celite pad and the filtrate was concentrated to obtain 9.5 g of an oil, which was directly used for the next reaction step.

Methyl-3-amino-2-isopropyl-pyridine-4-carboxylate (19 g) and dry tetrahydrofuran (150 ml) were added into a flask, added with lithium aluminum hydride (17 g) in batches. After the addition, the atmosphere in the flask was replaced with nitrogen gas. The mixture in the flask was refluxed for 3 h at 80° C. The reaction was quenched by slowly dropwise adding with saturated aqueous solution of ammonium chloride, and filtered. The filtrate was extracted twice with ethyl acetate. The organic layers were combined, washed twice with saturated salt solution, dried over anhydrous sodium sulfate, concentrated under reduced pressure to dryness to obtain a product, which was directly used for the next reaction step. MS: m/z 167.1, $[M+H]^+$.

Dichloromethane (300 ml) and activated manganese dioxide (86 g) were added to the product from the previous step, and stirred at room temperature for 2.5 h after the addition. The reaction solution was filtered through a celite pad. The filtrate was concentrated under reduced pressure and purified by silica gel column chromatography to obtain 12 g of a product. 3-Amino-2-isopropylisonicotinaldehyde (8.8 g) and tetrahydrofuran (150 ml) were added into a flask, inside which nitrogen gas replacement was performed. The mixture in the flask was cooled to −55° C., dropwise added with a solution of methylmagnesium bromide in tetrahydrofuran (1 M, 162 ml) and reacted at −55° C. for 1.5 h after the addition. The reaction was quenched by slowly dropwise adding with aqueous solution of ammonium chloride, then added with 400 ml of water, warmed to room temperature, and extracted twice with ethyl acetate. The organic layers were combined, washed once with saturated salt solution, dried over anhydrous sodium sulfate, and concentrated under reduced pressure to dryness. The obtained product was directly used for the next reaction step. MS: m/z 181.1, $[M+H]^+$.

Dichloromethane (200 ml) and activated manganese dioxide (47 g) were added to the product from the previous step, and stirred at room temperature for 2.5 h after the addition. The reaction solution was filtered through a celite pad. The filtrate was concentrated under vacuum and purified by silica gel column chromatography to obtain 7.0 g of a yellow oil. MS: m/z 179.1, $[M+H]^+$.

Methyltriphenylphosphonium bromide (15.4 g), potassium tert-butoxide (4.8 g, 42.8 mmol) and toluene (200 ml) were added into a three-necked flask, and stirred at 60° C. for 2 h after nitrogen gas replacement. The reaction solution was cooled to 40° C., dropwise added with a solution of the product from the previous step (7.0 g) in toluene (20 ml), and stirred for another 30 min after the addition. The reaction was quenched by adding with ammonium chloride solution, then added with water, and extracted twice with toluene. The organic layers were combined, washed once with saturated salt solution, dried over anhydrous sodium sulfate, concentrated under reduced pressure and purified by silica gel column chromatography to obtain 4.7 g of a light-yellow liquid. $^1H$ NMR (400 MHz, $CDCl_3$): δ 8.01 (d, J=4.9 Hz, 1H), 6.81 (d, J=4.9 Hz, 1H), 5.37 (t, J=1.5 Hz, 1H), 5.12 (s, 1H), 3.85 (s, 2H), 3.11-3.01 (m, 1H), 2.08 (s, 3H), 1.33 (d, J=6.8 Hz, 6H); MS: m/z 177.1, $[M+H]^+$.

2-Isopropyl-3-amino-4-isopropenylpyridine (3.0 g), tetrahydrofuran (30 ml) and 5% palladium on carbon (0.6 g) were added into a flask. After the addition, the atmosphere in the flask was replaced with hydrogen gas sufficiently. The mixture in the flask was stirred overnight at room temperature under hydrogen balloon pressure. The reaction solution was filtered through a celite pad and the filtrate was concentrated under reduced pressure to dryness and purified by silica gel column chromatography to obtain 3.0 g of a yellow oil. $^1H$ NMR (400 MHz, $CDCl_3$): δ 8.04 (d, J=5.0 Hz, 1H), 6.93 (d, J=5.0 Hz, 1H), 3.70 (br s, 2H), 3.13-3.01 (m, 1H), 2.97-2.84 (m, 1H), 1.33 (d, J=6.8 Hz, 6H), 1.27 (d, J=6.8 Hz, 6H).

Intermediate 8

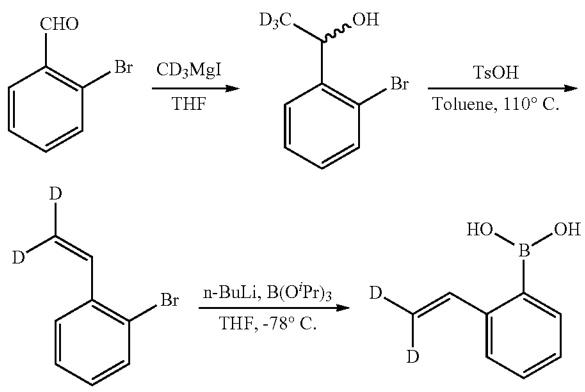

Intermediate 8

Step 1 o-Bromobenzaldehyde (10.0 g) and tetrahydrofuran (100 ml) were added into a three-necked flask, cooled to −45° C. under nitrogen gas protecting, dropwise added with deuterated methylmagnesium iodide (1 M in ether solution, 108.6 ml), and stirred for another 1 h after the addition. The reaction solution was poured into saturated aqueous solution of ammonium chloride, and extracted with ethyl acetate. The organic phases were combined, washed once with saturated salt solution, dried over anhydrous sodium sulfate, filtered, concentrated under reduced pressure to a small amount of liquid residue, and purified by silica gel column chromatography to yield 7.5 g of a colorless liquid.

Step 2

The product from the previous step (500 mg), p-toluenesulfonic acid (105 mg) and toluene (5 ml) were added into a 50 ml single-necked flask, warmed to 90° C. after nitrogen gas replacement and stirred for 2 h. The reaction solution was cooled to room temperature, added with silica gel, stirred at room temperature to dryness, and purified by silica gel column chromatography to yield 200 mg of a colorless liquid. $^1H$ NMR (400 MHz, $CDCl_3$): δ 7.60-7.55 (m, 2H), 7.31 (t, J=7.2 Hz, 1H), 7.14 (td, J=7.7, 1.7 Hz, 1H), 7.07 (br s, 1H).

Step 3

1-Bromo-2-(vinyl-2,2-$d_2$)benzene (1.0 g), dry tetrahydrofuran (20 ml) and triisopropyl borate (3.0 g) were added into a 100 ml three-necked flask, protected by nitrogen gas replacement, cooled to −80° C., slowly dropwise added with n-butyllithium (2.3 ml), and reacted for another 30 min after the addition. The reaction solution was warmed to room temperature, quenched by adding water, and extracted with ethyl acetate. The organic layers were combined, dried over anhydrous sodium sulfate, filtered and concentrated under reduced pressure to obtain a solid crude product. The solid was then triturated in n-hexane to obtain 300 mg of a white solid. $^1H$ NMR (400 MHz, DMSO-$d_6$): δ 8.17 (s, 2H), 7.59 (d, J=7.8 Hz, 1H), 7.44 (dd, J=7.3, 1.1 Hz, 1H), 7.33 (td, J=7.6, 1.2 Hz, 1H), 7.22 (td, J=7.3, 1.1 Hz, 1H), 7.15-7.05 (m, 1H).

Intermediate 11

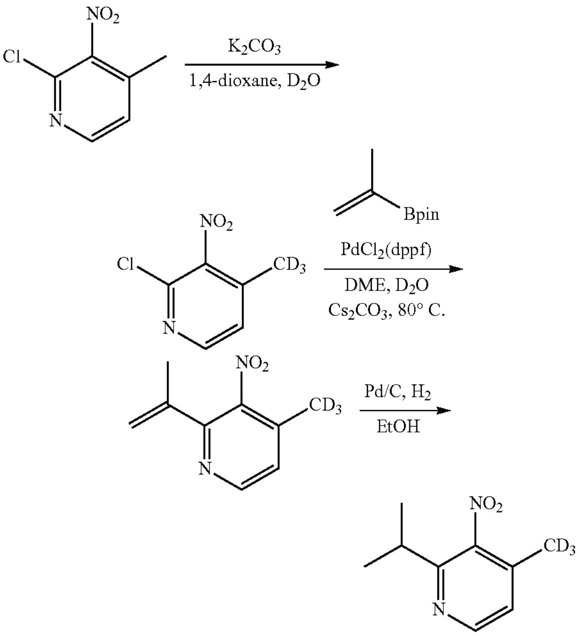

Step 1

2-Chloro-4-methyl-3-nitropyridine (19 g), potassium carbonate (14 g), 1,4-dioxane (100 ml), and heavy water (60 ml) were added into a reaction flask and refluxed at 100° C. for 24 h after the addition. The reaction solution was cooled to room temperature, diluted with water, and extracted with ethyl acetate. The organic layers were combined, washed once with water, dried over anhydrous sodium sulfate, filtered and concentrated under reduced pressure to dryness. The product was obtained by repeating the procedure three times as described above. $^1H$ NMR (400 MHz, $CDCl_3$): δ 8.40 (d, J=5.0 Hz, 1H), 7.27 (d, J=5.0 Hz, 1H). MS: m/z 176.0, $[M+H]^+$.

Step 2

The product from the previous step (15 g), cesium carbonate (85.3 g), 1,2-dimethoxyethane (240 ml), heavy water (60 ml), isopropenylboronic acid pinacol ester (17.6 g), and [1,1'-bis(diphenylphosphino)ferrocene]-palladium dichloride (6.2 g) were added into a 500 ml single-necked flask, inside which nitrogen gas replacement was performed. The mixture in the flask was warmed to 80° C. and refluxed for 3 h. The reaction solution was cooled down, then added with 200 ml of saturated sodium bicarbonate solution, and extracted with ethyl acetate. The organic layers were combined, dried over anhydrous sodium sulfate, filtered, concentrated under reduced pressure and purified by silica gel column chromatography to give 14 g of a light-yellow oil. $^1H$ NMR (400 MHz, $CDCl_3$): δ 8.54 (d, J=5.0 Hz, 1H), 7.18 (d, J=5.0 Hz, 1H), 5.37-5.31 (m, 1H), 5.20 (s, 1H), 2.20 (t, J=1.2 Hz, 3H).

Step 3

The product from the previous step (14 g), anhydrous ethanol (200 ml) and 5% palladium on carbon (7 g) were added into a 500 ml single-necked flask, inside which hydrogen gas replacement was performed. The mixture in the flask was stirred overnight at room temperature under the pressure of a hydrogen bag. The reaction solution was filtered through a celite pad to remove palladium on carbon. The filtrate was concentrated under reduced pressure and purified by silica gel column chromatography to obtain 8.0 g of a light-yellow oil. $^1$H NMR (400 MHz, $CDCl_3$): δ 7.96 (d, J=4.8 Hz, 1H), 6.85 (d, J=4.8 Hz, 1H), 3.63 (br s, 2H), 3.12-2.97 (m, 1H), 1.31 (d, J=6.8 Hz, 6H).

Intermediate 12

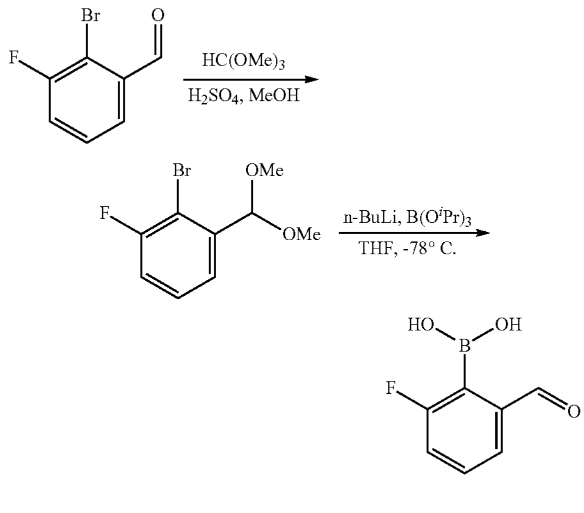

Step 1

2-Bromo-3-fluorobenzaldehyde (20.0 g), methanol (40 ml) and concentrated sulfuric acid (0.5 ml) were added into a 100 ml single-necked flask, then dropwise added with trimethyl orthoformate (13.6 g), and warmed to 70° C. after the addition and stirred for 2 h. After the reaction, the reaction solution was cooled to 0° C., slowly added with sodium methanol to adjust the pH to 8-9, then diluted with water, and extracted with ethyl acetate. The organic layers were combined, washed once with saturated salt solution, dried over anhydrous sodium sulfate, filtered, and concentrated under reduced pressure to give 21 g of a white solid. $^1$H NMR (400 MHz, $CDCl_3$): δ 7.42 (d, J=7.8 Hz, 1H), 7.36-7.27 (m, 1H), 7.12 (td, J=8.2, 1.3 Hz, 1H), 5.58 (s, 1H), 3.40 (s, 6H).

Step 2

The product from the previous step (10.0 g) and tetrahydrofuran (100 ml) were added into a 500 ml three-necked flask, cooled to −78° C., dropwise added with a solution of n-butyllithium in n-hexane (2.5 M, 24 ml) and stirred for another 1 h after the addition, then dropwise added with triisopropyl borate (9.8 g) and stirred for another 2 h after the addition. After the reaction, the reaction solution was slowly added with 3N of diluted hydrochloric acid to adjust the pH to 2-3, and extracted with ethyl acetate. The organic layers were combined, washed once with saturated salt solution, dried over anhydrous sodium sulfate, filtered, concentrated under reduced pressure and purified by silica gel column chromatography to obtain 5.3 g of a white solid. $^1$H NMR (400 MHz, Acetone-$d_6$): δ 10.06 (d, J=2.4 Hz, 1H), 7.77 (d, J=7.5 Hz, 1H), 7.65-7.57 (m, 1H), 7.44 (s, 2H), 7.38 (td, J=8.2, 0.7 Hz, 1H).

Intermediate 13

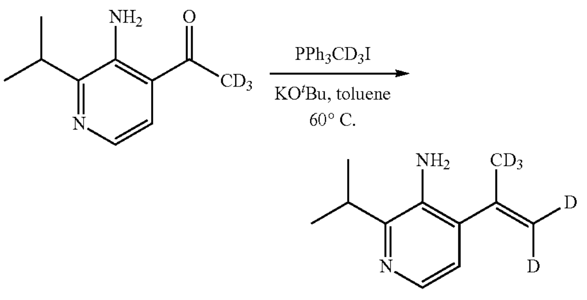

Methyl-$d_3$-triphenylphosphonium iodide (169 mg), potassium tert-butoxide (46 mg) and dry toluene (10 ml) were added into a reaction flask, inside which nitrogen gas replacement was performed after the addition. The reaction was carried out at 60° C. for 1 h. A solution of 1-(3-amino-2-isopropylpyridin-4-yl)ethan-1-one-2,2,2-$d_3$ (50 mg) in toluene (4 ml) was added slowly and the reaction was continued for another 30 min. The reaction solution was dropwise added with aqueous solution of ammonium chloride to quench the reaction, and extracted with ethyl acetate. The organic layers were combined, washed with saturated salt solution, dried over anhydrous sodium sulfate, filtered, concentrated under reduced pressure and purified by silica gel column chromatography to obtain 32 mg of a light-yellow liquid. $^1$H NMR (400 MHz, $CDCl_3$): δ 8.00 (d, J=4.9 Hz, 1H), 6.79 (d, J=4.9 Hz, 1H), 3.84 (br s, 2H), 3.11-2.97 (m, 1H), 1.32 (d, J=6.8 Hz, 6H). MS: m/z 182.2, $[M+H]^+$.

Intermediate 14

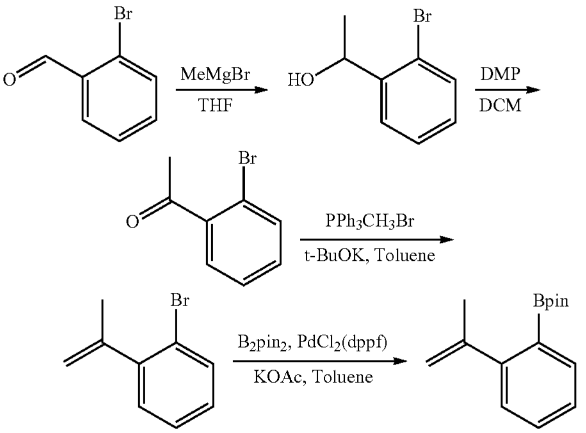

Step 1

2-Bromobenzaldehyde (3.2 g) and dry tetrahydrofuran (20 ml) were added into a 100 ml reaction flask, cooled to 0° C. by ice bath, dropwise added with methylmagnesium bromide solution (19.1 ml) and reacted for another 1 h after the addition. The reaction was quenched by slowly adding saturated aqueous solution of ammonium chloride and the obtained solution was extracted with ethyl acetate. The organic layers were combined, dried over anhydrous sodium sulfate, filtered, concentrated under reduced pressure and purified by silica gel column chromatography to obtain 2.1 g of a colorless oil.

Step 2

The product from the previous step (2.1 g) and dichloromethane (30 ml) were added into a 100 ml reaction flask, added with Dyess-Martin oxidant (6.7 g) in batches with stirring at room temperature, and after the addition stirred for 1 h at room temperature. After the reaction, the reaction was quenched by adding water and the obtained solution was extracted with dichloromethane. The organic layers were combined, washed once with saturated sodium chloride solution, dried over anhydrous sodium sulfate, filtered, concentrated under reduced pressure and purified by silica gel column chromatography to obtain 1.8 g of a colorless oil product.

Step 3

Methyltriphenylphosphonium bromide (6.5 g), toluene (100 ml) and potassium tert-butoxide (2.1 g) were added into a 250 ml single-necked flask, and warmed to 60° C. to react for 1 h. The reaction solution was cooled to room temperature, added with the product from the previous step (1.8 g), and stirred to react for 30 min at room temperature. The reaction was quenched by adding saturated solution of ammonium chloride, and the obtained solution was extracted with ethyl acetate. The organic layers were combined, washed once with saturated sodium chloride solution, dried over anhydrous sodium sulfate, filtered, concentrated under reduced pressure and purified by silica gel column chromatography to obtain 1.34 g of a product.

Step 4

The product from the previous step (1.34 g), biboronic acid pinacol ester (3.45 g), potassium acetate (1.33 g) and [1,1'-bis(diphenylphosphino)ferrocene]-palladium dichloride (512 mg) were added into a 100 ml single-necked flask, inside which nitrogen gas replacement was performed for protection. The mixture in the flask was warmed to 80° C. and reacted for 36 h. The reaction solution was cooled to room temperature, then added with water and separated. The aqueous layer was then extracted with ethyl acetate. The organic layers were combined, washed once with saturated sodium chloride solution, dried over anhydrous sodium sulfate, filtered, concentrated under reduced pressure and purified by silica gel column chromatography to yield 1.2 g of a light-yellow oil.

Referring to the above preparation scheme, the following intermediates were obtained:

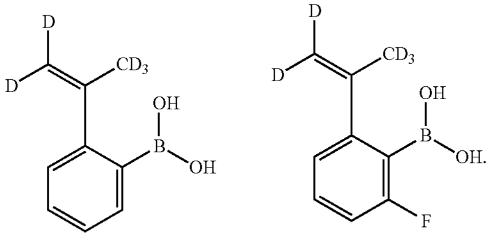 [SMILES: [2H]C([2H])=C(c1ccccc1B(O)O)C([2H])([2H])[2H] ; [2H]C([2H])=C(c1cccc(F)c1B(O)O)C([2H])([2H])[2H]]

Intermediate 15

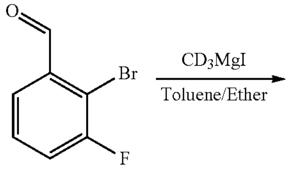

-continued

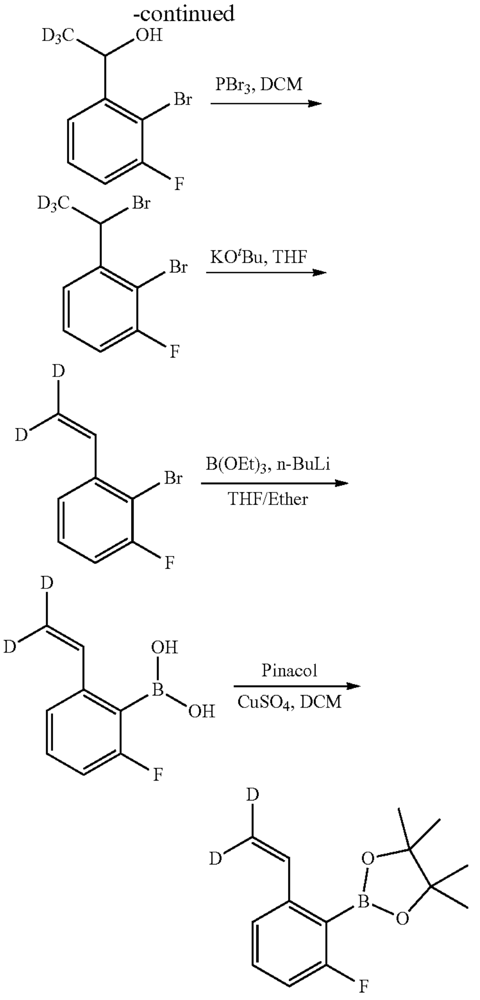

Step 1

2-Bromo-3-fluorobenzaldehyde (50 g), toluene (500 ml) and ether (165 ml) were added into a 2000 ml three-necked flask, cooled to an inner temperature of 0° C. after nitrogen gas replacement, and dropwise added with methyl-$d_3$-magnesium iodide (394 ml). After the addition, the stirring was continued for 15-30 min. The ice bath was removed to allow the temperature to naturally return back to room temperature and the stirring was continued for 1 h until TLC showed that the reaction of the raw materials was completed. The reaction solution was cooled to an inner temperature of less than 5° C., dropwise added with saturated aqueous solution of ammonium chloride (150 ml), then added with water (50 ml), stirred for 5 minutes, and separated into two layers. The aqueous layer was extracted twice with ethyl acetate. The organic phases were combined, washed once with saturated salt solution, dried over anhydrous sodium sulfate overnight, filtered, and concentrated under reduced pressure to obtain 56.7 g of a light-yellow liquid, which was directly used for the next reaction step. $^1H$ NMR (400 MHz, $CDCl_3$): δ 7.38-7.31 (m, 1H), 7.31-7.23 (m, 1H), 7.05-6.96 (m, 1H), 5.19 (s, 1H), 3.06 (s, 1H).

Step 2

The raw material from the previous step (56.7 g, 246 mmol calculated based on 100% yield from the previous step) and dichloromethane (547 ml) were added into a 2000 ml three-necked flask, cooled to an inner temperature of less than 5° C. after nitrogen gas replacement, and dropwise added with phosphorus tribromide (11.5 ml). After the addition, the stirring was continued for 15 min. Then the ice bath was removed to allow the temperature to naturally return back to room temperature and the stirring was continued for 2 h until TLC showed that the raw materials consumption was completed. The reaction solution was cooled to an inner temperature of less than 5° C., dropwise added with saturated aqueous solution of sodium bicarbonate (approximately 300 ml) to adjust the pH to 8-9, stood and separated into two layers. The aqueous phase was extracted twice with dichloromethane. The organic phases were combined, washed once with saturated salt solution, dried over anhydrous sodium sulfate for 30 min, filtered, and distilled under reduced pressure to remove the solvent. 58.5 g of a yellow liquid was obtained, which was used directly for the next reaction step without purification. $^1$H NMR (400 MHz, $CDCl_3$): δ 7.47 (dt, J=7.9, 1.1 Hz, 1H), 7.39-7.30 (m, 1H), 7.08 (td, J=8.2, 1.4 Hz, 1H), 5.59 (s, 1H).

Step 3

The raw material from the previous step (58.5 g) and tetrahydrofuran (600 ml) were added into a 2000 ml three-necked flask, cooled to an inner temperature of less than 5° C. after nitrogen gas replacement, and added with potassium tert-butoxide (37 g) in batches. After the addition, the stirring was continued for 15 min. Then the ice bath was removed to allow the temperature to naturally return back to room temperature and the stirring was continued for 1.5 h. A surplus of the raw materials was shown by TLC. Then the obtained mixture in the flak was cooled to an inner temperature of less than 5° C. and supplemented with potassium tert-butoxide (5 g). After the addition, the ice bath was removed to allow the temperature to naturally return back to room temperature and the stirring was continued for 0.5 h. TLC showed that the conversion of the raw materials was completed. The reaction solution was cooled to an inner temperature of less than 5° C., dropwise added with saturated aqueous solution of ammonium chloride (approximately 100 ml), then added with water (50 ml) and ether (200 ml), stirred for 5 min, stood and separated into two layers. The aqueous phase was extracted twice with ether. The organic phases were combined, washed once with saturated salt solution, dried over anhydrous sodium sulfate overnight, and filtered. The filtrate was distilled under reduced pressure to remove most of ether to obtain 177 g of a yellow liquid, which was directly used for the next reaction step.

Step 4

The raw material from the previous step, tetrahydrofuran (60 ml), ether (600 ml) and triethyl borate (44 ml, 257 mmol) were added into a 2000 ml three-necked flask, cooled to an inner temperature of less than −70° C. after nitrogen gas replacement, dropwise added with n-butyllithium (119 ml), naturally rewarmed after the addition, and stirred for 30 min. A large surplus of the raw materials was shown by TLC. Then the obtained mixture in the flak was cooled to an inner temperature of less than −70° C. again, supplemented with triethyl borate (44 ml) and n-butyllithium (119 ml), naturally rewarmed after the addition, and stirred for 30 min. A complete conversion of the raw materials was shown by TLC. The reaction solution was slowly added into about 400 ml of saturated aqueous solution of ammonium chloride to quench the reaction, adjusted to a pH of 3~4 with 6N of hydrochloric acid, stood and separated into two layers. The aqueous phase was extracted twice with methyl tert-butyl ether. The organic phases were combined, washed once with saturated salt solution, dried over anhydrous magnesium sulfate, and filtered through a celite pad. The filtrate was concentrated to dryness, diluted with petroleum ether, and purified by silica gel column chromatography to obtain 18 g of a light-yellow liquid. MS: m/z 191.1, [M+Na]$^+$.

Step 5

The raw material from the previous step (12.5 g), anhydrous dichloromethane (250 ml) and pinacol (10.5 g) were added into a 500 ml single-necked flask, added with anhydrous copper sulfate (35.6 g) in batches, stirred for 2 h at room temperature after the addition, then supplemented with anhydrous copper sulfate (11.8 g), and stirred for another 1 h after the addition. After the reaction, the reaction solution was filtered through a celite pad and the filtrate was concentrated and purified by silica gel column chromatography to give 9.7 g of a yellow liquid. $^1$H NMR (400 MHz, DMSO-$d_6$): δ 7.50-7.40 (m, 2H), 7.10-7.02 (m, 1H), 6.89 (s, 1H), 1.32 (s, 12H). MS: m/z 273.1, [M+Na]$^+$.

Intermediate 16

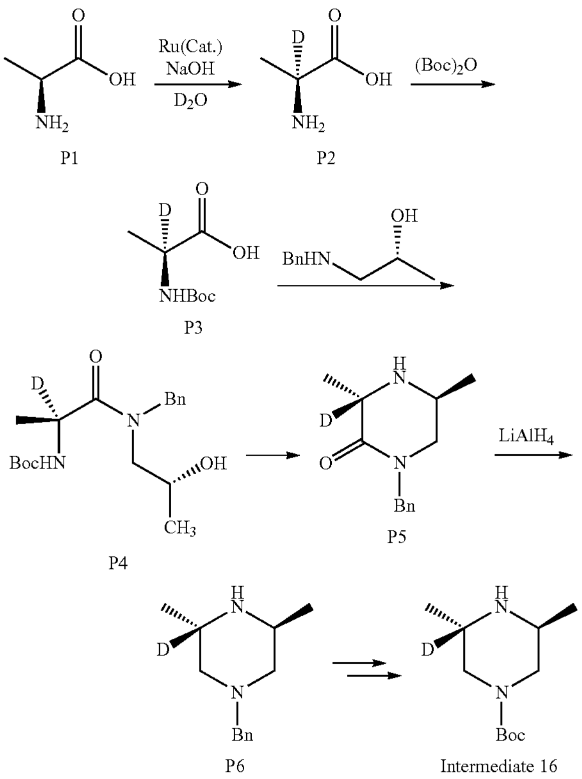

Using P1 as the raw material, deuteration substitution was carried out to obtain P2 and finally Intermediate 16 was prepared (References: Organic Process Research & Development (2017), 21(11), 1741-1744, CN103265498 et al.).

Referring to the patent US2013079554A1 et al., the corresponding alkynyl compound was subjected to catalytic hydrogenation by using Lindlar catalyst, and then subjected to acylating chlorination to obtain the following Intermediate 17:

Intermediate 17

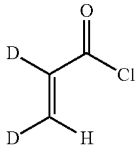

Intermediate 18

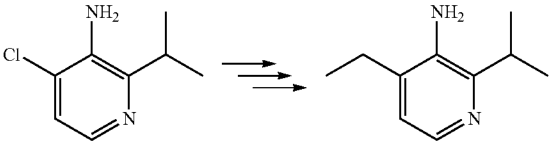

X1 Intermediate 18

X1 was used as the raw material, which was subjected to chemical reaction conversion to obtain Intermediate 18 (References: US20190374542 et al.).

Alternatively, another preparation method was adopted, and the specific preparation method was as follows:

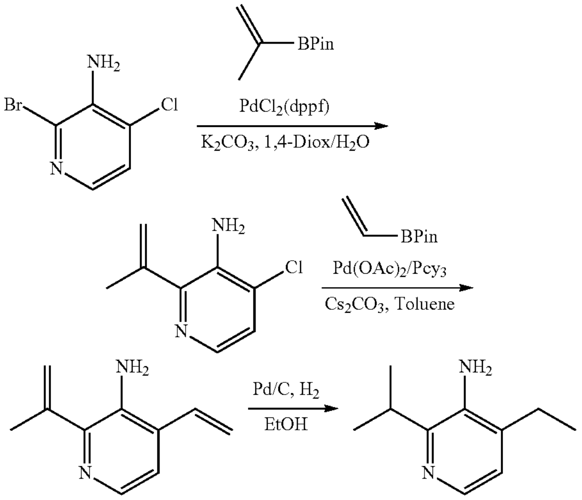

Step 1

2-Bromo-4-chloro-pyridin-3-amine (9.2 g), isopropenylboronic acid pinacol ester (11.9 g), potassium carbonate (7.6 g), $PdCl_2$(dppf) (5.5 g), 1,4-dioxane (85 ml) and water (17 ml) were added into a 250 ml flask, subjected to nitrogen gas replacement, warmed to 105° C. and stirred for 3 h. After the reaction, the reaction solution was cooled to room temperature and filtered. The filtrate was added with water and extracted with ethyl acetate. The organic layers were combined, washed twice with saturated salt solution, dried over anhydrous sodium sulfate, and filtered. The resulting filtrate was concentrated and purified by silica gel column chromatography to yield 9.3 g of an orange-yellow solid. $^1$H NMR (400 MHz, $CDCl_3$): δ 7.92 (d, J=5.2 Hz, 1H), 7.11 (d, J=5.1 Hz, 1H), 5.54-5.51 (m, 1H), 5.36-5.34 (m, 1H), 4.37 (s, 2H), 2.18 (t, J=1.3 Hz, 3H).

Step 2

The product from the previous step (10.0 g), vinylboronic acid pinacol ester (13.8 g), $Pcy_3$ (1.0 g), palladium acetate (0.5 g), cesium carbonate (38.8 g) and toluene (200 ml) were added into a 500 ml flask, subjected to nitrogen gas replacement, warmed to 120° C. and stirred for 12 h. After the reaction, the reaction solution was cooled to room temperature, added with water and extracted with ethyl acetate. The organic layers were combined, washed twice with saturated salt solution, dried over anhydrous sodium sulfate, and filtered. The resulting filtrate was concentrated and purified by silica gel column chromatography to yield 7.1 g of a brown oil. $^1$H NMR (400 MHz, $CDCl_3$): δ 8.01 (d, J=4.9 Hz, 1H), 7.06 (d, J=4.9 Hz, 1H), 6.76 (dd, J=17.4, 11.1 Hz, 1H), 5.80 (dd, J=17.4, 1.2 Hz, 1H), 5.54-5.48 (m, 2H), 5.30-5.28 (m, 1H), 4.05 (s, 2H), 2.18 (t, J=1.2 Hz, 3H). MS: m/z 161.1, $[M+H]^+$.

Step 3

The product from the previous step (7.1 g), ethanol (150 ml) and palladium on carbon (0.7 g) were added into a 250 ml single-necked flask, subjected to hydrogen gas replacement, and stirred overnight at room temperature. After the reaction, the reaction solution was filtered, and the filtrate was concentrated and purified by silica gel column chromatography to yield 5.5 g of a purplish red oil. $^1$H NMR (400 MHz, $CDCl_3$): δ 8.02 (d, J=4.9 Hz, 1H), 6.88 (d, J=4.9 Hz, 1H), 3.66 (s, 2H), 3.12-3.01 (m, 1H), 2.52 (q, J=7.6 Hz, 2H), 1.32 (d, J=6.7 Hz, 6H), 1.28 (t, J=7.5 Hz, 3H). MS: m/z 165.1, $[M+H]^+$.

Then, by referring to the preparation schemes of Intermediate 1, Intermediate 2, Intermediate 3 and Intermediate 4, the following intermediates were prepared:

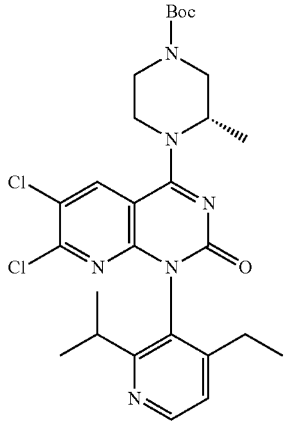

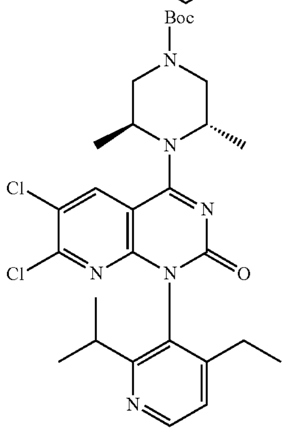

The specific preparation method was as follows:

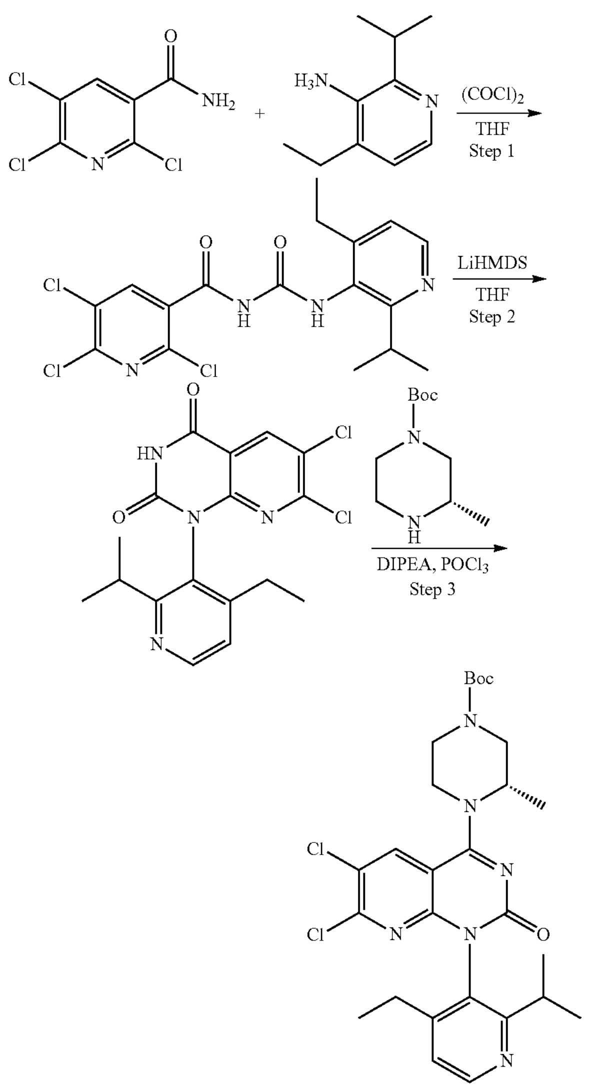

Step 1

Tetrahydrofuran (50 ml) was added into a 250 ml three-necked flask, subjected to nitrogen gas replacement, cooled to −5° C., slowly dropwise added with oxalyl chloride (2.9 g), stirred for 10 min, added with 2,5,6-trichloronicotinamide (4.4 g) in batches, warmed to 45° C. and stirred for 1 h. After the reaction, the reaction solution was concentrated to dryness, added with tetrahydrofuran (25 ml), subjected to nitrogen gas replacement, cooled to −5° C., slowly dropwise added with a solution of 2-isopropyl-4-ethylpyridin-3-amine (2.1 g) in tetrahydrofuran (18 ml), and stirred for 1 h at room temperature. After the reaction, the resulting solution was concentrated to dryness, added with water and an appropriate amount of saturated aqueous solution of sodium carbonate to a pH of 7~8, and extracted with dichloromethane. The organic layers were combined, washed once with saturated salt solution, dried over anhydrous sodium sulfate, and filtered. The filtrate was concentrated to give a crude product as pink solid. The crude product was added with the mixed solvent (petroleum ether:ethyl acetate=10:1, 110 ml), stirred at room temperature for 1 h, and filtered. The filter cake was dried to obtain 6.3 g of an off-white solid. MS: m/z 415.1, $[M+H]^+$.

Step 2

The product from the previous step (6.3 g) and tetrahydrofuran (160 ml) were added into a 500 ml three-necked flask, subjected to nitrogen gas replacement, cooled to 10-15° C., dropwise added with LiHMDS (1 M in THF, 33.5 ml), and stirred for 2 h at room temperature. After the reaction, the reaction solution was added with saturated aqueous solution of ammonium chloride to quench the reaction, and extracted with ethyl acetate. The organic layers were combined, washed once with saturated salt solution, dried over anhydrous sodium sulfate, and filtered. The filtrate was concentrated until a large amount of solid was precipitated, added with MTBE (10 ml), and filtered. The filter cake was dried to obtain 3.8 g of a white solid. MS: m/z 379.1, $[M+H]^+$.

Step 3

The product from the previous step (3.8 g), tetrahydrofuran (95 ml), DIPEA (7.8 g) and (S)-4-N-tert-butylcarbonyl-2-methylpiperazine (2.0 g) were added into a 250 ml three-necked flask, subjected to nitrogen gas replacement, slowly dropwise added with phosphorus trichloride (3.1 g) under cooling by ice bath, warmed to 30° C., stirred for 15 min, added with (S)-4-N-tert-butylcarbonyl-2-methylpiperazine (1.0 g), and stirred for 30 min. After the reaction, the reaction solution was added with saturated aqueous solution of ammonium chloride to quench the reaction, and extracted with ethyl acetate. The organic layers were combined, washed once with saturated salt solution, dried over anhydrous sodium sulfate, and filtered. The filtrate was concentrated to give 5.7 g of a brown solid. MS: m/z 561.2, $[M+H]^+$.

By referring to the supercritical liquid chromatography (SFC) separation method documented in patent WO2019051291, the following intermediates were prepared and separated.

Intermediate 5M

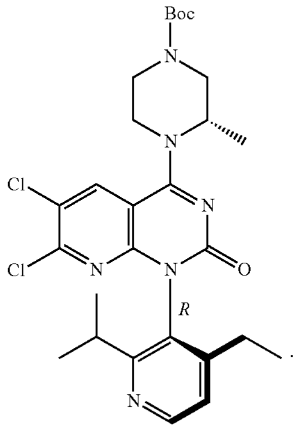

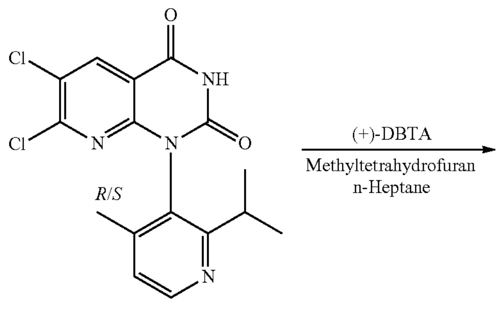

A

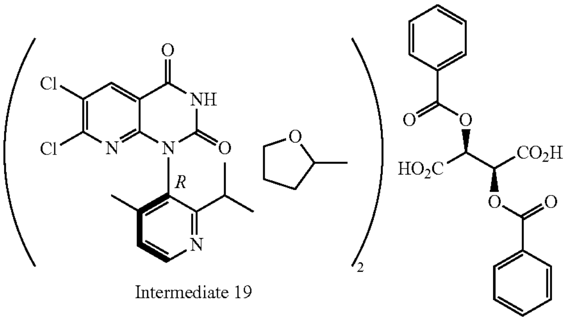

Intermediate 19

5.00 g of Compound A (prepared according to WO2020050890, WO2019051291) was weighed and added into a 250 ml round bottom flask, added with 50 ml of methyltetrahydrofuran and stirred under nitrogen protection at 75° C. for 30 min until the dissolution was completed and a clear solution was obtained. A solution of 10 g of (+)-DBTA dissolved in 20 ml of methyltetrahydrofuran was added into the clear solution. After mixing the above two methyltetrahydrofuran solutions, 50 ml of n-heptane was further added dropwise at 75° C., and then the above mixture was stirred for another 8 h at 25° C. The solid was filtered and subjected to forced-air drying at 50° C. for 5 h to obtain 4 g of the target compound (>99% ee). $^{1}$H NMR (400 MHz, DMSO-$d_6$) δ12.31 (br.s, 1H), 8.60 (s, 1H), 8.53-8.52 (m, 1H), 7.99-7-96 (m, 2H), 7.71-7-67 (m, 1H), 7.57-7.53 (m, 2H), 7.29-7.28 (m, 1H), 5.77 (s, 1H), 3.86-3.72 (m, 2H), 3.58-3.52 (m, 1H), 2.94-2.84 (m, 1H), 2.05 (s, 3H), 1.97-1.90 (m, 1H), 1.85-1.74 (m, 1H), 1.36-1.24 (m, 1H), 1.13-1.12 (m, 3H), 1.09-1.07 (m, 3H), 1.02-1.00 (m, 3H); $^{13}$C NMR (100 MHz, DMSO-$d_6$) δ168.0, 165.2, 164.6, 160.5, 151.7, 150.1, 149.9, 149.7, 146.3, 139.7, 134.1, 129.8, 129.6, 129.3, 128.7, 124.4, 124.1, 112.8, 74.8, 72.0, 67.2, 33.2, 30.0, 25.9, 22.7, 22.3, 21.4, 17.5.

Then, by referring to the preparation scheme of Intermediate 3, the following Intermediate 3M was prepared (for the single-crystal structure thereof, see FIG. 1 of the description):

Intermediate 3M

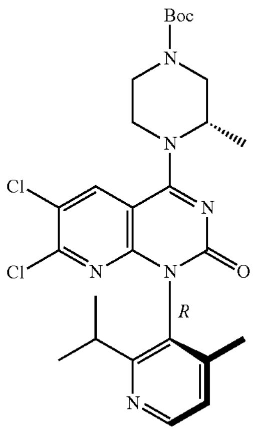

Structural characterization data of Intermediate 3M ($^{1}$H NMR (400 MHz, $CDCl_3$))

| serial number | chemical shift (ppm) | multiplicity (J value/Hz) | proton number |
|---|---|---|---|
| 1 | 8.57 | d (4.9) | 1 |
| 2 | 8.05 | s | 1 |
| 3 | 7.14 | dd (4.9, 0.6) | 1 |
| 4 | 5.01-4.64 | m | 1 |
| 5 | 4.45-3.82 | m | 3 |
| 6 | 3.68 | br s | 1 |
| 7 | 3.44-2.91 | m | 2 |
| 8 | 2.72-2.54 | m | 1 |
| 9 | 2.03 | s | 3 |
| 10 | 1.51 | s | 9 |
| 11 | 1.49 | d (6.8) | 3 |
| 12 | 1.22 | d (6.8) | 3 |
| 13 | 1.13 | d (6.7) | 3 |

By referring to the preparation scheme of Intermediate 19, the following Intermediate 20 was prepared by using (−)-DBTA as the resolution reagent:

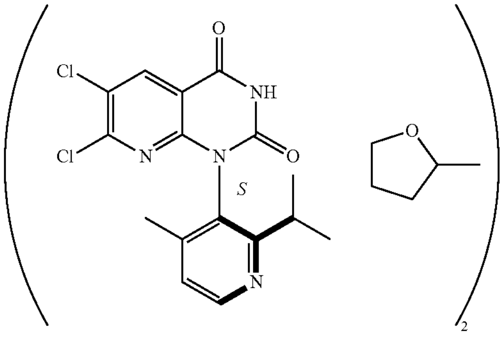

Intermediate 20

-continued

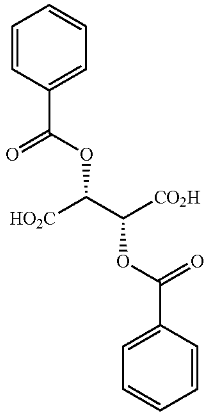

The following Intermediate 3P was prepared:

Intermediate 3P

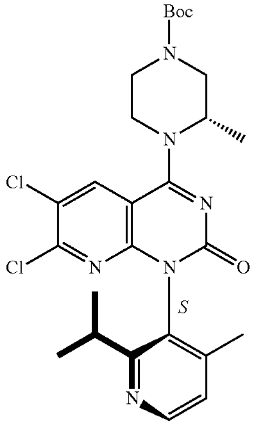

By referring to the preparation scheme of Intermediate 4, the following intermediates were prepared by using Intermediate 19 and Intermediate 20:

Intermediate 4M

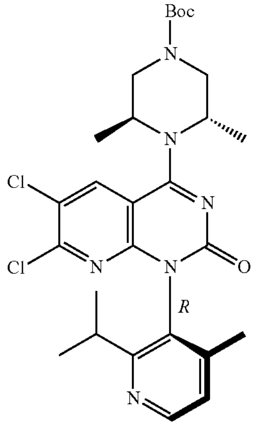

-continued

Intermediae 4P

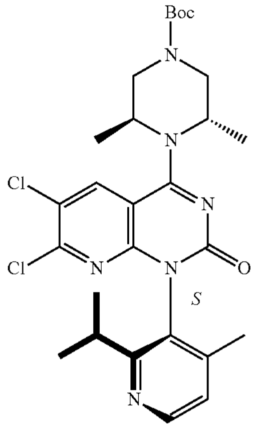

Intermediate 22

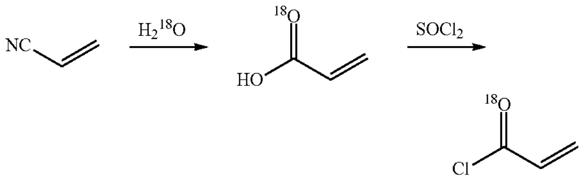

Intermediate 22

By referring to literature methods, Intermediate 22 was prepared by using vinyl cyanide as the raw material and heavy-oxygen water as the isotope source (References: Journal of Biosciences (Bangalore, India) (2009), 34(1), 21-26, JP61282089, US20030148480 et al.).

The specific preparation method was as follows:

25 ml of $H_2{}^{18}O$ with a pH of 7.2, about 2 ml of acrylonitrile and 10 mg of nitrilase were added into a reaction flask and reacted at 28° C. overnight after the addition. The reaction solution was slowly added with a solution of HCl in dioxane to adjust the pH to 2~3, and then extracted twice with dichloromethane. The organic phase was dried over anhydrous sodium sulfate, filtered, and concentrated to dryness to obtain a yellow oil. Then the oil was dissolved in dichloromethane solution, added with thionyl chloride, and refluxed for 2 h. The resulting solution was concentrated under reduced pressure to obtain an acyl chloride product, which was directly used in the reaction.

Intermediate 23

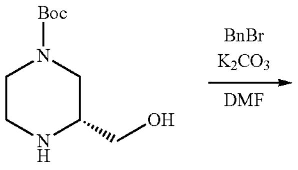

-continued

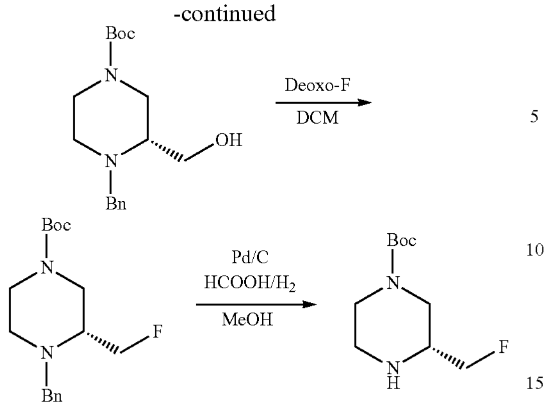

Step 1

Tert-butyl-(R)-3-(hydroxymethyl)piperazine-1-carboxylate (12 g), N,N-dimethylformamide (120 ml) and potassium carbonate (23 g) were added into a 250 ml three-necked flask, subjected to nitrogen gas replacement, slowly dropwise added with benzyl bromide (14.2 g) under cooling by ice bath, and stirred for 2 h at 0° C. After the reaction, the resulting solution was subjected to suction filtration. The filtrate was added with saturated salt solution, and extracted with methyl tert-butyl ether. The organic phases were combined, washed with saturated salt solution, dried over anhydrous sodium sulfate, and concentrated to dryness. The residue was added with an appropriate amount of n-hexane for crystallization, stirred at room temperature, filtered, and dried to obtain 13.8 g of a white solid. $^1$HNMR (400 MHz, $CDCl_3$): δ 7.37-7.26 (m, 5H), 4.05 (d, J=13.3 Hz, 1H), 3.88 (dd, J=11.4, 5.4 Hz, 1H), 3.76-3.50 (m, 3H), 3.49-3.05 (m, 3H), 2.86-2.42 (m, 3H), 2.33-2.24 (m, 1H), 1.47 (s, 9H). MS: m/z 307.2, $[M+H]^+$.

Step 2

The product from the previous step (6.2 g) and dichloromethane (150 ml) were added into a 250 ml three-necked flask, subjected to nitrogen gas replacement, cooled to −20° C., slowly dropwise added with a solution of Deoxo-F (9.0 g) in dichloromethane (81 ml), kept at −20° C. and stirred for 2 h, then rewarmed to room temperature and stirred for 2 h. After the reaction, the resulting solution was added with saturated aqueous solution of sodium bicarbonate to adjust the pH of aqueous phase to 7~8, and extracted with dichloromethane. The organic phases were combined, dried over anhydrous sodium sulfate, and filtered. The filtrate was concentrated and purified by silica gel column chromatography to yield 5.9 g of a colorless oily liquid. MS: m/z 309.2, $[M+H]^+$.

Step 3

The product from the previous step (2.8 g, 9.1 mmol), methanol (40 ml), formic acid (3 g) and 5% Pd/C (3.5 g) were added into a 100 ml single-necked flask, subjected to hydrogen gas replacement, and stirred at room temperature for 10 h to complete the reaction. The reaction solution was filtered through a celite pad. The filtrate was added with aqueous solution of sodium bicarbonate to adjust the pH of aqueous phase to 7~8, and extracted with dichloromethane. The organic phases were combined, dried over anhydrous sodium sulfate, and filtered. The filtrate was concentrated and purified by silica gel column chromatography to yield 1.1 g of a colorless oily liquid. $^1$HNMR (400 MHz, $CDCl_3$): δ 4.52-4.24 (m, 2H), 4.05-3.76 (m, 2H), 3.07-2.83 (m, 3H), 2.82-2.48 (m, 2H), 2.03 (s, 1H), 1.47 (s, 9H). MS: m/z 219.2, $[M+H]^+$.

Preparation of Compounds

Example 1

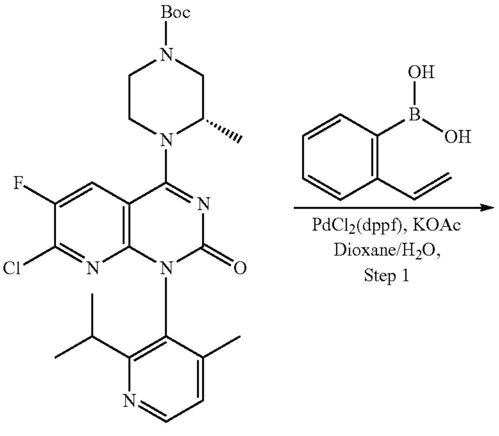

Intermediate 1

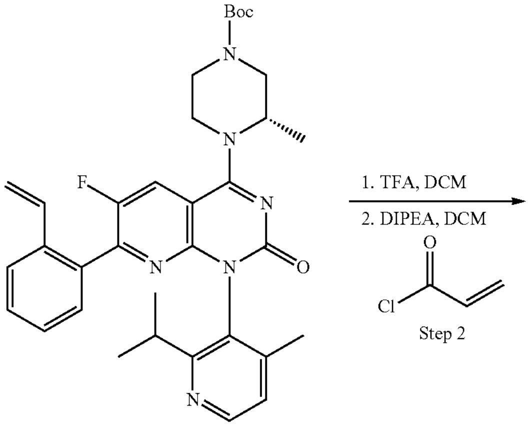

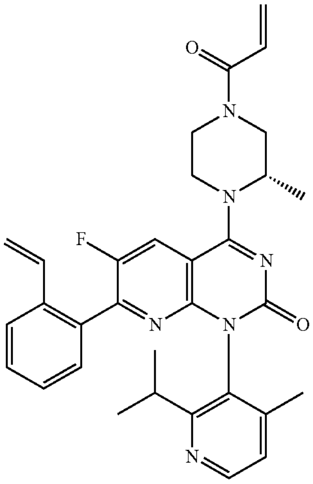

3-1

Step 1

Tert-butyl-(S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (1.0 g), 2-vinylphenylboronic acid (429 mg), potassium acetate (560 mg), 1,4-dioxane (20 ml), water (4 ml) and [1,1'-bis(diphenylphosphino)ferrocene] palladium dichloride (139 mg)

were added into a 50 ml single-necked flask, warmed to 95° C. after nitrogen gas replacement, and stirred overnight. After the reaction, the reaction solution was cooled to room temperature, diluted with water, and extracted with ethyl acetate. The organic layers were combined, washed with saturated salt solution, dried over anhydrous sodium sulfate, filtered, concentrated under reduced pressure and purified by silica gel column chromatography to obtain 0.98 g of a light-yellow solid. MS: m/z 599.3, $[M+H]^+$.

Step 2

The product from the previous step (980 mg) and dichloromethane (15 ml) were added into a 50 ml single-necked flask, dropwise added with trifluoroacetic acid (9 ml) at 10° C.~15° C. and stirred for another 1.5 h after the addition. The reaction solution was concentrated to dryness, and the residue was added with dichloromethane (10 ml), cooled to 0° C., added with N,N-diisopropylethylamine (1.1 g), then slowly dropwise added with a solution of acryloyl chloride (179 mg) in dichloromethane (1 ml), and stirred for 30 min after the addition. The reaction was quenched by slowly pouring saturated aqueous solution of ammonium chloride, and the obtained solution was extracted with ethyl acetate. The organic layers were combined, washed with saturated salt solution, dried over anhydrous sodium sulfate, filtered, concentrated under reduced pressure and purified by silica gel column chromatography to obtain 627 mg of a light-yellow solid. $R_f$: 0.58 (DCM:MeOH=10:1). $^1H$ NMR (400 MHz, $CDCl_3$): δ 8.49 (d, J=4.8 Hz, 1H), 7.84 (dd, J=9.0, 1.9 Hz, 1H), 7.57 (d, J=7.8 Hz, 1H), 7.42 (t, J=7.5 Hz, 1H), 7.30 (t, J=7.4 Hz, 1H), 7.22 (d, J=7.7 Hz, 1H), 7.09 (d, J=4.8 Hz, 1H), 6.74-6.56 (m, 1H), 6.56-6.37 (m, 2H), 5.83 (d, J=10.4 Hz, 1H), 5.55 (d, J=17.3 Hz, 1H), 5.11 (d, J=11.0 Hz, 1H), 5.23-4.24 (m, 3H), 4.09-3.48 (m, 3H), 3.43-2.99 (m, 1H), 2.86-2.57 (m, 1H), 2.06 (s, 3H), 1.62-1.43 (m, 3H), 1.24 (d, J=6.9 Hz, 3H), 1.05 (d, J=6.3 Hz, 3H); MS: m/z 553.2739, $[M+H]^+$.

Example 2

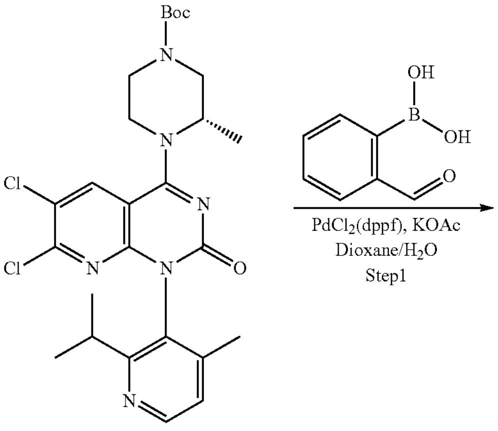

Intermediate 3

-continued

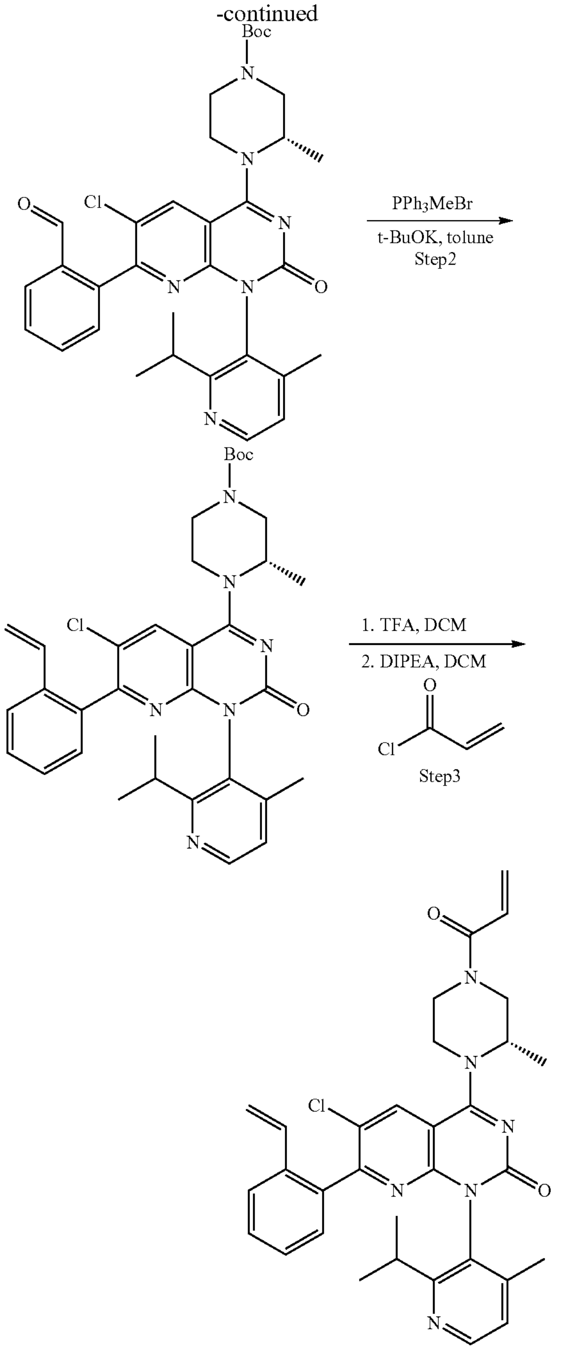

3-2

Step 1

Tert-butyl-(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (2.0 g), 2 -formylphenylboronic acid (769 mg), potassium acetate (1.0 g), 1,4-dioxane (40 ml), water (8 ml) and [1,1'-bis(diphenylphosphino)ferrocene] palladium dichloride (263 mg) were added into a 50 ml single-necked flask, warmed to 105° C. after nitrogen gas replacement, and stirred for 2 h. After the reaction, the resulting solution was cooled to room temperature, diluted with water, and extracted with ethyl acetate. The organic layers were combined, washed with saturated salt solution, dried over anhydrous sodium sulfate, filtered, concentrated under reduced pressure and purified by silica gel column chromatography to obtain 1.8 g of a yellow solid.

Step 2

Methyltriphenylphosphonium bromide (1.4 g), potassium tert-butoxide (454 mg) and toluene (20 ml) were added into a 100 ml three-necked flask, warmed to 65° C. after nitrogen gas replacement, and stirred for 1 h. A solution of the product from the previous step (1.0 g) in toluene (30 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 750 mg of a light-yellow solid.

Step 3

The product from the previous step (750 mg) and dichloromethane (10 ml) were added into a 50 ml single-necked flask, dropwise added with trifluoroacetic acid (10 ml) at 10° C.~15° C. and stirred for another 1 h after the addition. The reaction solution was concentrated to dryness, and the residue was added with dichloromethane (10 ml), cooled to 0° C., added with N,N-diisopropylethylamine (1.2 ml), then slowly dropwise added with a solution of acryloyl chloride (166 mg) in dichloromethane (1 ml), and stirred for 30 min after the addition. The reaction was quenched by slowly pouring saturated aqueous solution of ammonium chloride, and the obtained solution was extracted with ethyl acetate. The organic layers were combined, washed with saturated salt solution, dried over anhydrous sodium sulfate, filtered, concentrated under reduced pressure and purified by silica gel column chromatography to obtain 400 mg of a white solid. $R_f$: 0.57 (DCM:MeOH=10:1). $^1$H NMR (400 MHz, DMSO-$d_6$): δ 8.44 (t, J=8.1 Hz, 1H), 8.36 (d, J=4.8 Hz, 1H), 7.69 (d, J=7.7 Hz, 1H), 7.42 (td, J=7.6, 1.0 Hz, 1H), 7.33 (td, J=7.5, 1.0 Hz, 1H), 7.17 (d, J=5.3 Hz, 1H), 7.09 (d, J=7.4 Hz, 1H), 6.95-6.81 (m, 1H), 6.35-6.13 (m, 2H), 5.78 (dd, J=10.8, 2.2 Hz, 1H), 5.70 (d, J=17.4 Hz, 1H), 5.16 (d, J=11.3 Hz, 1H), 4.98 (br s, 1H), 4.48-4.23 (m, 2H), 4.23-4.04 (m, 1H), 3.91-3.71 (m, 1H), 3.71-3.41 (m, 1H), 3.31-3.04 (m, 1H), 2.81-2.64 (m, 1H), 1.93 (s, 3H), 1.35 (t, J=7.1 Hz, 3H), 1.07 (d, J=6.7 Hz, 3H), 0.92 (d, J=6.7 Hz, 3H); MS: m/z 569.2477, [M+H]$^+$.

Example 2-1

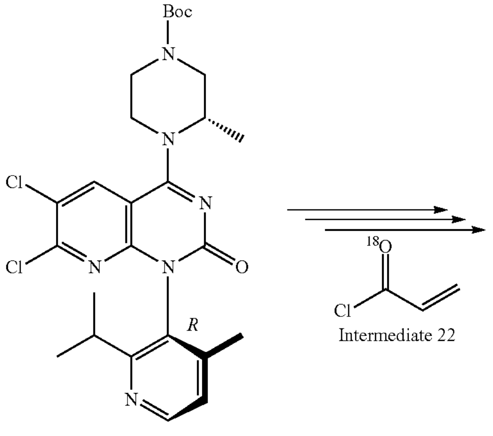

Intermediate 22

Intermediate 3M

-continued

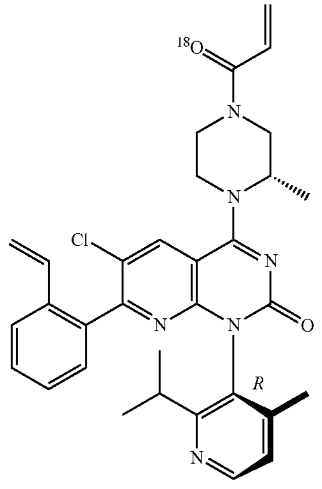

3-1MIS

Referring to the method of Example 2, Compound 3-1MIS was prepared by using Intermediate 3M and Intermediate 22 as the raw materials. $R_f$: 0.56 (DCM:MeOH=10:1). The specific preparation method was as follows:

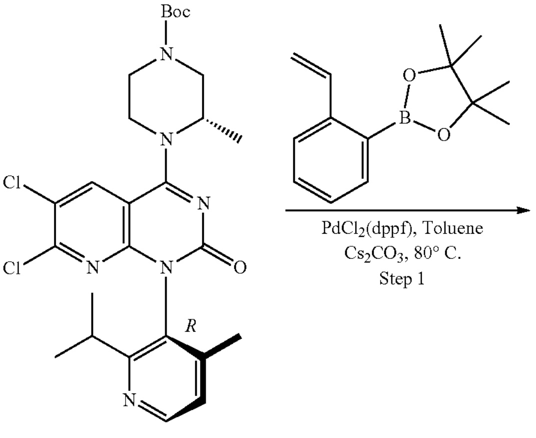

Intermediate 3M

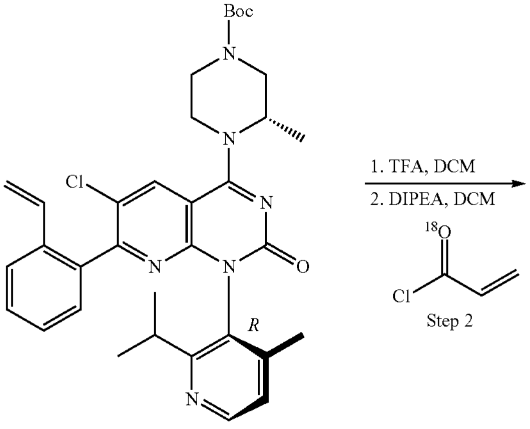

-continued

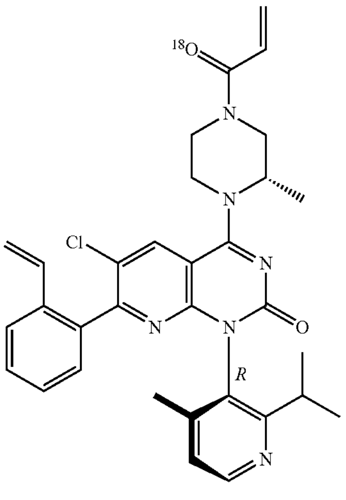

3-1MIS

Step 1

Tert-butyl-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (Intermediate 3M), cesium carbonate, toluene, [1,1'-bis(diphenylphosphino)ferrocene] palladium dichloride and 2-(6-vinylphenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7-8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of O-18 labeled acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 2-2

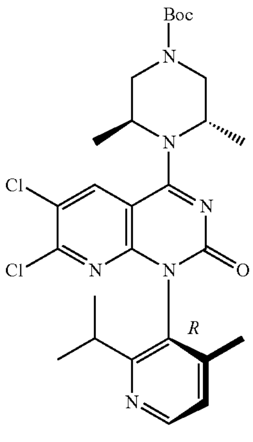

Intermediate 4M

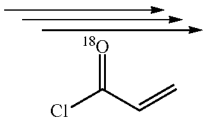

Intermediate 22

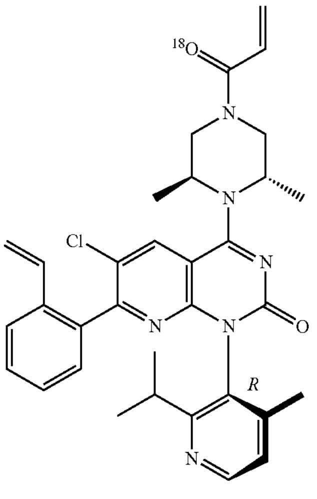

3-3MIS

Referring to the method of Example 2, Compound 3-3MIS was prepared by using Intermediate 4M and Intermediate 22 as the raw materials. $R_f$: 0.55 (DCM:MeOH=10:1). The specific preparation method was as follows:

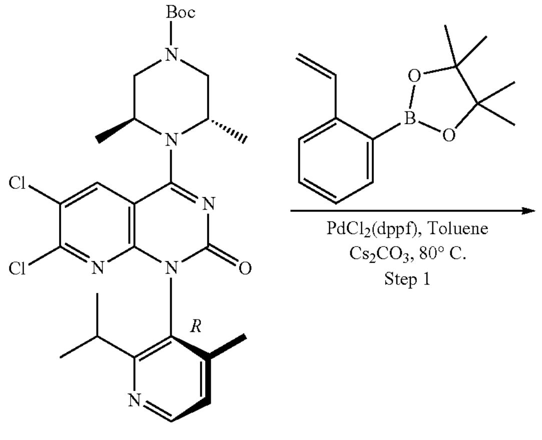

Intermediate 4M

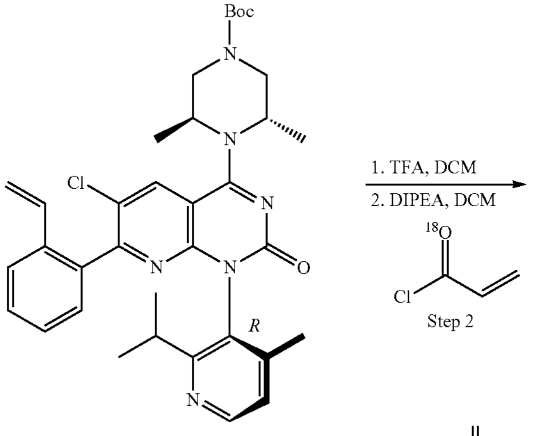

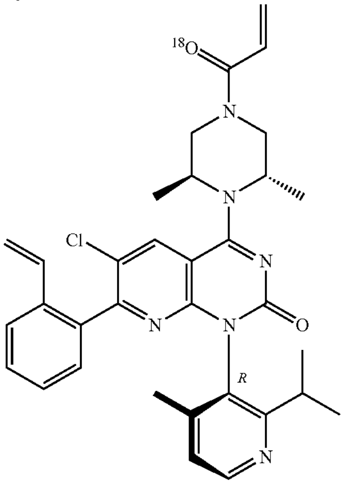

3-3MIS

Step 1

Tert-butyl-4-(6,7-dichloro-1-(2-isopropyl-4-methylpyridin-3-yl)-2-oxo-1,2-dihydropyrido[2,3 -d]pyrimidin-4-yl)-dimethylpiperazine-1-carboxylate (Intermediate 4M), cesium carbonate, toluene, [1,1'-bis(diphenylphosphino)ferrocene] palladium dichloride and 2-(6-vinylphenyl)-4,4,5,5-tetramethyl-1,3,2-dioxaborinane were added into a single-necked flask, inside which nitrogen gas replacement was performed after the addition. The mixture in the flask was warmed up to react. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7-8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of O-18 labeled acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 2-3

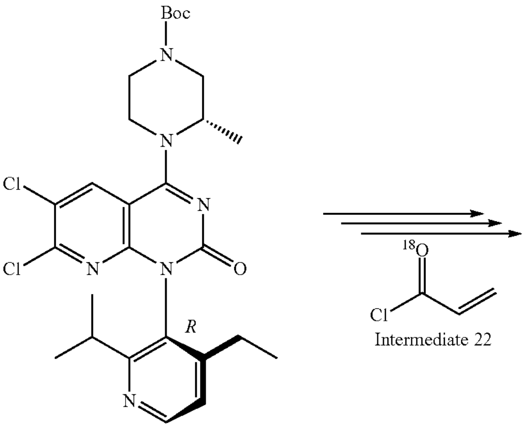

Intermediate 22

Intermediate 5M

-continued

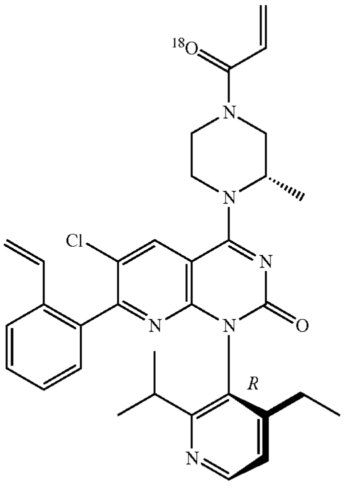

3-4MIS

-continued

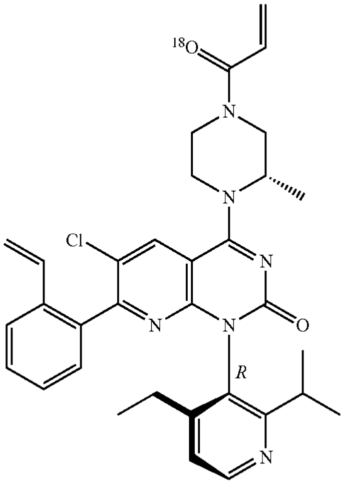

3-4MIS

Referring to the method of Example 2, Compound 3-4MIS was prepared by using Intermediate 5M and Intermediate 22 as the raw materials. $R_f$: 0.57 (DCM:MeOH=10:1). The specific preparation method was as follows:

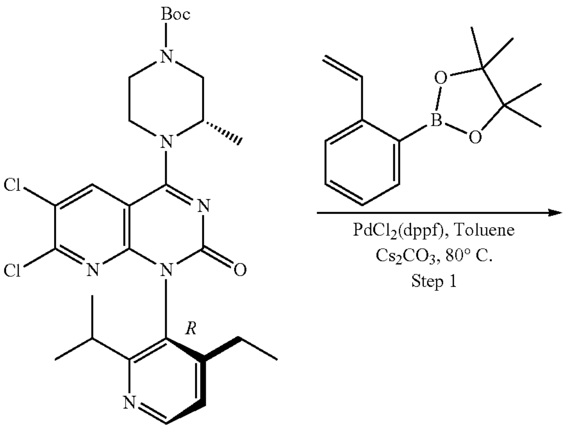

Intermediate 5M

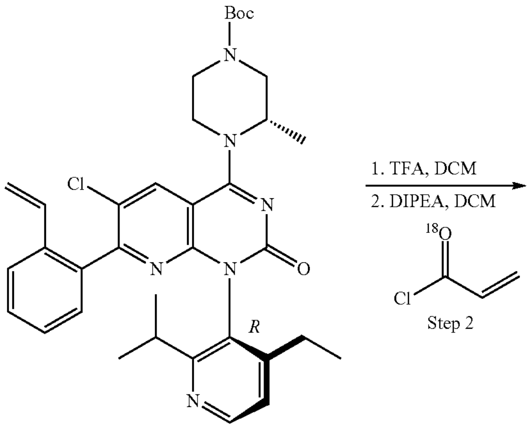

Step 1

Tert-butyl-4-(6,7-dichloro-1-(2-isopropyl-4-ethylpyridin-3-yl)-2-oxo-1,2-dihydropyrido[2,3-d]pyrimidin-4-yl)-3-methylpiperazine-1-carboxylate (Intermediate 5M), cesium carbonate, toluene, [1,1'-bis(diphenylphosphino)ferrocene] palladium dichloride and 2-(6-vinylphenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7~8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of O-18 labeled acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 3

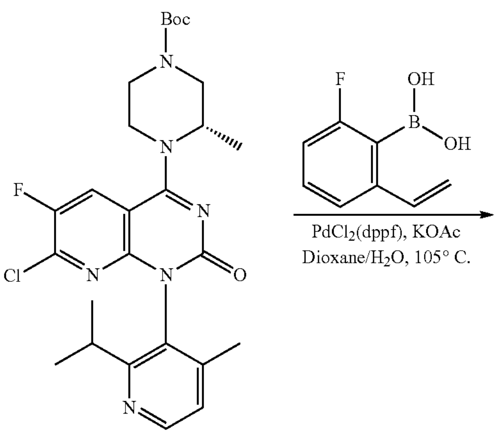

Intermediate 1

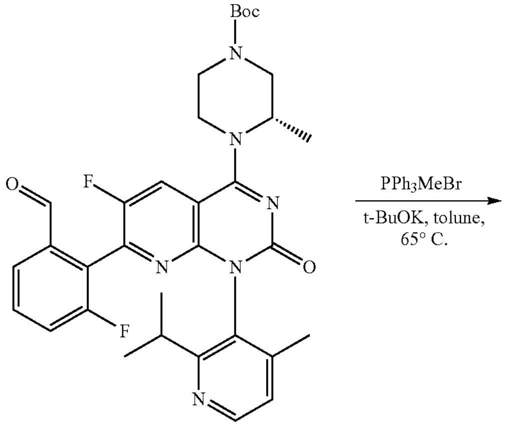

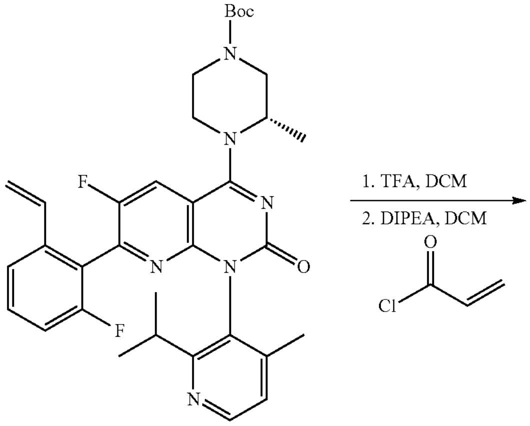

-continued

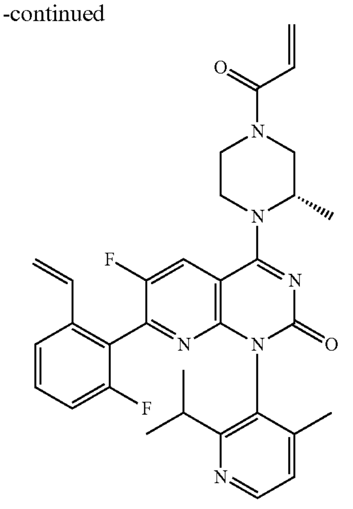

3-5

Step 1

Tert-butyl-(S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (2.0 g), 2-fluoro-6-formylphenylboronic acid (949 mg), potassium acetate (1.1 g), 1,4-dioxane (20 ml), water (4 ml) and [1,1'-bis(diphenylphosphino)ferrocene] palladium dichloride (270 mg) were added into a 50 ml single-necked flask, warmed to 105° C. after nitrogen gas replacement and stirred for 2 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 1.5 g of a yellow solid.

Step 2

Methyltriphenylphosphonium bromide (2.2 g), potassium tert-butoxide (678 mg) and toluene (20 ml) were added into a 100 ml three-necked flask, warmed to 65° C. after nitrogen gas replacement, and stirred for 1 h. A solution of the product from the previous step (1.5 g) in toluene (30 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 1.2 g of a light-yellow solid.

Step 3

The product from the previous step (630 mg) and dichloromethane (10 ml) were added into a 50 ml single-necked flask, dropwise added with trifluoroacetic acid (10 ml) at 10° C.~15° C. and stirred for 1 h at room temperature after the addition. The reaction solution was concentrated to dryness, and the residue was added with dichloromethane (10 ml), cooled to 0° C., added with N,N-diisopropylethylamine (1 ml), then slowly dropwise added with a solution of acryloyl chloride (138 mg) in dichloromethane (1 ml), and stirred for 30 min after the addition. The reaction was quenched by slowly pouring saturated aqueous solution of ammonium chloride, and the obtained solution was extracted with dichloromethane. The organic layers were combined, washed with saturated salt solution, dried over anhydrous sodium sulfate, filtered, concentrated under reduced pressure and purified by silica gel column chromatography to obtain 313 mg of a white solid. $R_f$: 0.54 (DCM:MeOH=10:1). $^1$H NMR (400 MHz, $CDCl_3$): δ 8.49 (d, J=4.9 Hz, 1H), 7.87 (dd, J=8.4, 3.7 Hz, 1H), 7.44-7.31 (m, 2H), 7.09 (d, J=5.0 Hz, 1H), 7.07-7.00 (m, 1H), 6.76-6.52 (m, 1H), 6.43 (dd, J=16.7, 1.2 Hz, 1H), 6.31 (dd, J=17.4, 11.0 Hz, 1H), 5.84 (dd, J=10.4, 1.8 Hz, 1H), 5.57 (d, J=17.2, Hz, 1H), 5.28-4.20 (m, 3H), 5.14 (d, J=11.0 Hz, 1H), 4.10-3.49 (m, 3H), 3.44-3.00 (m, 1H), 2.89-2.58 (m, 1H), 2.07-1.93 (m, 3H), 1.64-1.45 (m, 3H), 1.27-1.22 (m, 3H), 1.13-0.96 (m, 3H); MS: m/z 571.2656, $[M+H]^+$.

Example 4

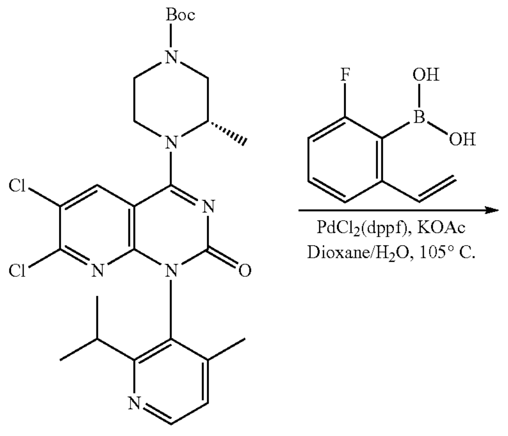

Intermediate 3

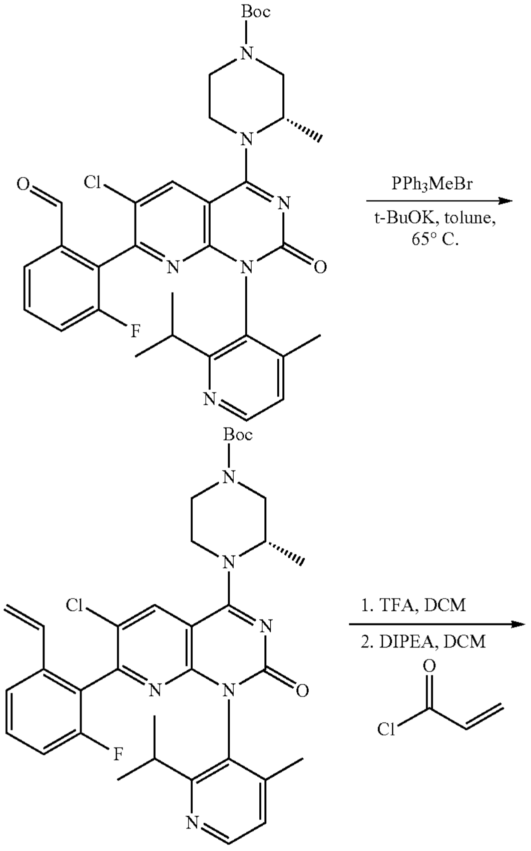

-continued

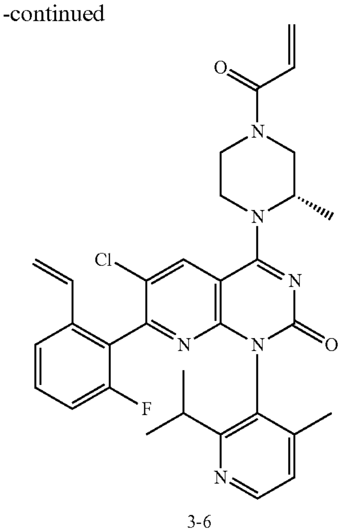

3-6

Step 1

Tert-butyl-(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (2.0 g), 2-fluoro-6-formylphenylboronic acid (920 mg), potassium acetate (1.1 g), 1,4-dioxane (20 ml), water (4 ml) and [1,1'-bis(diphenylphosphino)ferrocene] palladium dichloride (270 mg) were added into a 50 ml single-necked flask, warmed to 105° C. after nitrogen gas replacement and stirred for 2 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 1.7 g of a yellow solid.

Step 2

Methyltriphenylphosphonium bromide (2.4 g), potassium tert-butoxide (751 mg) and toluene (20 ml) were added into a 100 ml three-necked flask, warmed to 65° C. after nitrogen gas replacement, and stirred for 1 h. A solution of the product from the previous step (1.7 g) in toluene (30 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 1.3 g of a light-yellow solid.

Step 3

The product from the previous step (600 mg) and dichloromethane (10 ml) were added into a 50 ml single-necked flask, dropwise added with trifluoroacetic acid (10 ml) at 10° C.~15° C. and stirred for 1 h at room temperature after the addition. The reaction solution was concentrated to dryness, and the residue was added with dichloromethane (10 ml), cooled to 0° C., added with N,N-diisopropylethylamine (0.9 ml), then slowly dropwise added with a solution of acryloyl chloride (129 mg) in dichloromethane (1 ml), and stirred for 30 min after the addition. The reaction was quenched by slowly pouring saturated aqueous solution of ammonium chloride, and the obtained solution was extracted with dichloromethane. The organic layers were combined, washed with saturated salt solution, dried over anhydrous sodium sulfate, filtered, concentrated under reduced pressure and purified by silica gel column chromatography to obtain 355 mg of a white solid. $R_f$: 0.55 (DCM:MeOH=10:1). $^1H$ NMR (400 MHz, $CDCl_3$): δ 8.47 (dd, J=4.9, 0.9 Hz, 1H), 8.14 (s, 1H), 7.42-7.30 (m, 2H), 7.09-6.95 (m, 2H), 6.74-6.53 (m, 1H), 6.43 (dd, J=16.7, 1.6 Hz, 1H), 6.24-6.09 (m, 1H), 5.84 (dd, J=10.4, 1.8 Hz, 1H), 5.67-5.50 (m, 1H), 5.30-4.22 (m, 4H), 4.10-3.49 (m, 3H), 3.46-2.99 (m, 1H), 2.78 (br s, 1H), 2.05-1.92 (m, 3H), 1.67- 1.43 (m, 3H), 1.27-1.19 (m, 3H), 1.04 (dd, J=12.8, 6.7 Hz, 3H); MS: m/z 587.2364, [M+H]'''.

Example 4-1

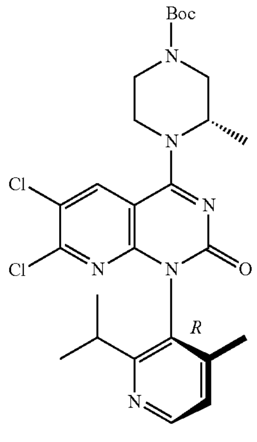

Intermediate 3M

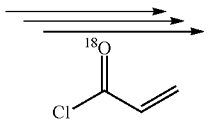

Intermediate 22

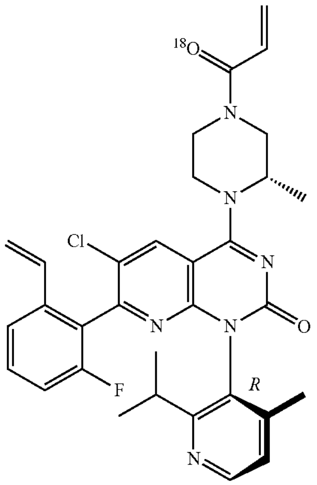

3-5MIS

Referring to the method of Example 2, Compound 3-5MIS was prepared by using Intermediate 3M and Intermediate 22 as the raw materials. $R_f$: 0.55 (DCM:MeOH=10:1). The specific preparation method was as follows:

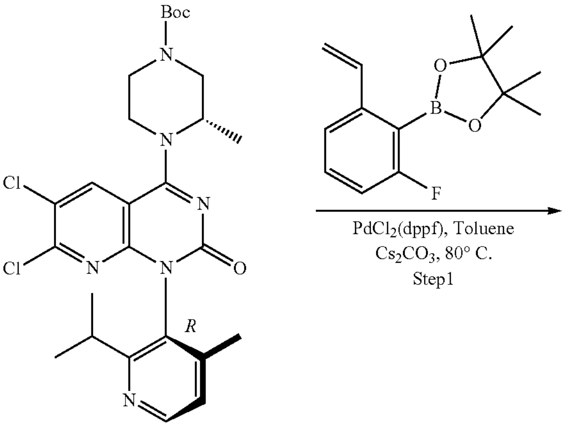

Intermediate 3M

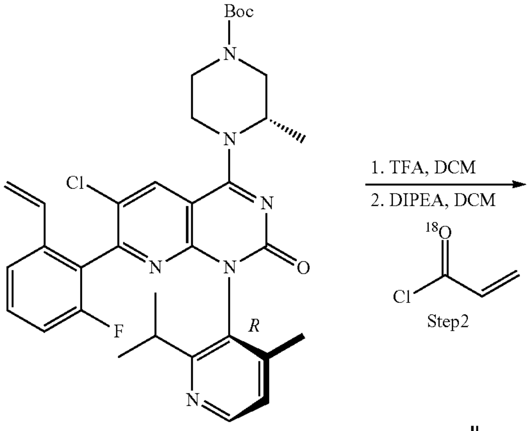

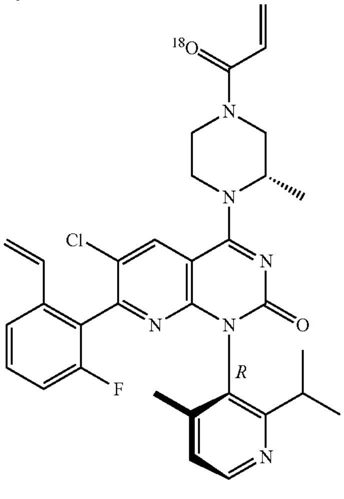

3-5MIS

Step 1

Tert-butyl-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (Intermediate 3M), cesium carbonate, toluene, [1,1'-bis(diphenylphosphino)ferrocene] palladium dichloride and 2-(2-fluoro-6-vinylphenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7-8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of O-18 labeled acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 4-2

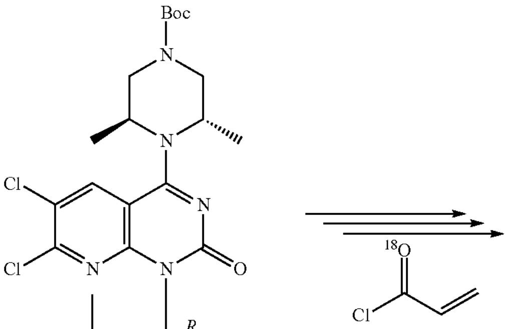

Intermediate 22

Intermediate 4M

-continued

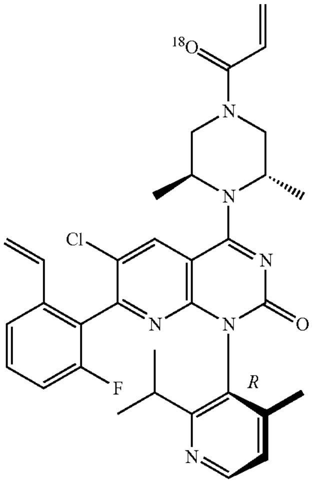

3-7MIS

Referring to the method of Example 2, Compound 3-7MIS was prepared by using Intermediate 4M and Intermediate 22 as the raw materials. $R_f$: 0.56 (DCM:MeOH=10:1). The specific preparation method was as follows:

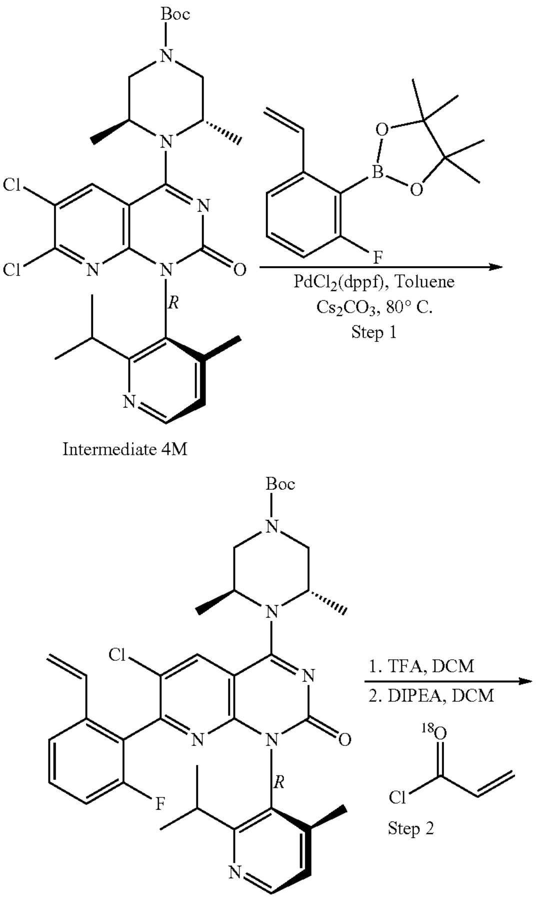

Intermediate 4M

-continued

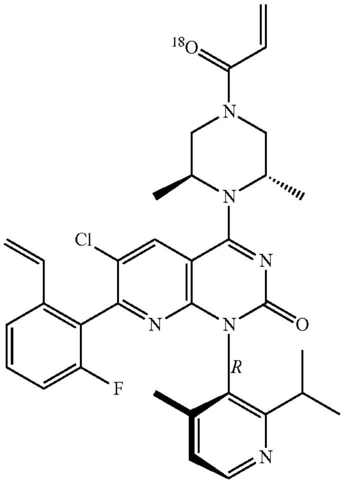

3-7MIS

Step 1

Tert-butyl-4-(6,7-dichloro-1-(2-isopropyl-4-methylpyridin-3-yl)-2-oxo-1,2-dihydropyrido[2,3-d]pyrimidin-4-yl)-dimethylpiperazine-1-carboxylate (Intermediate 4M), cesium carbonate, toluene, [1,1'-bis(diphenylphosphino)ferrocene] palladium dichloride and 2-(2-fluoro-6 -vinylphenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7~8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of O-18 labeled acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 4-3

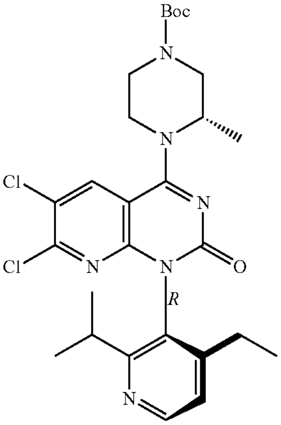

Intermediate 5M

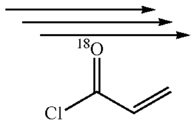

Intermediate 22

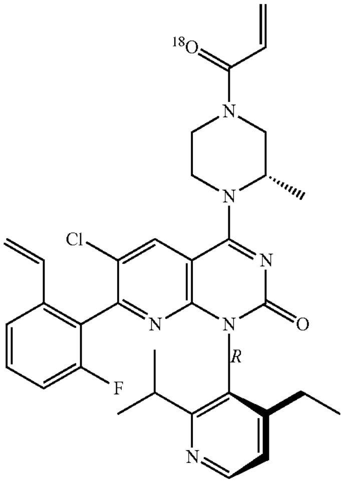

3-8MIS

Referring to the method of Example 2, Compound 3-8MIS was prepared by using Intermediate 5M and Intermediate 22 as the raw materials. $R_f$: 0.55 (DCM:MeOH=10:1). The specific preparation method was as follows:

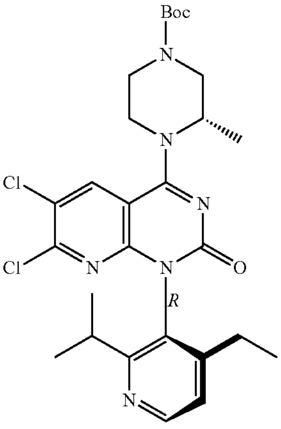

Intermediate 5M

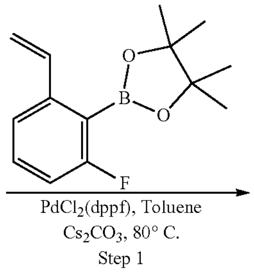

-continued

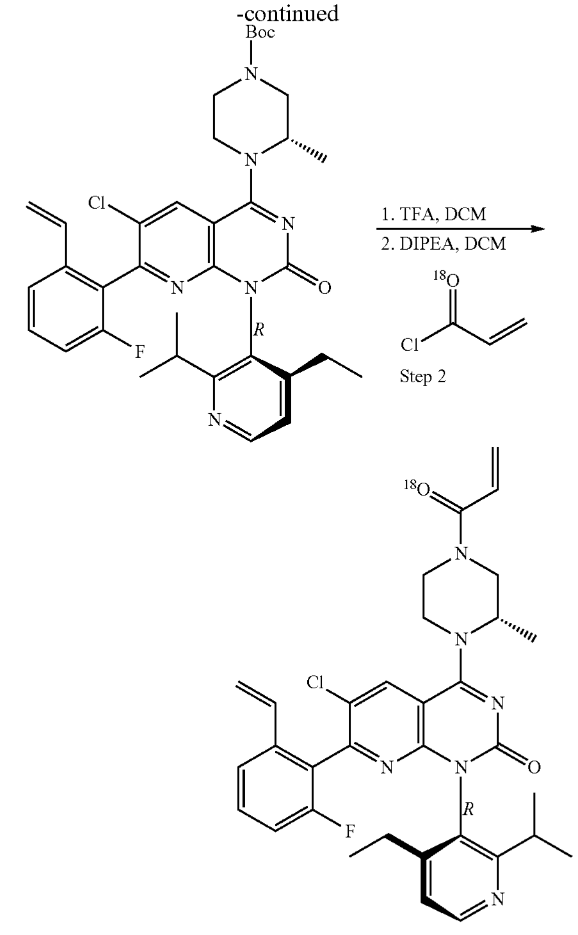

3-8MIS

Step 1

Tert-butyl-4-(6,7-dichloro-1-(2-isopropyl-4-ethylpyridin-3-yl)-2-oxo-1,2-dihydropyrido[2,3-d]pyrimidin-4-yl)-3-methylpiperazine-1-carboxylate (Intermediate 5M), cesium carbonate, toluene, [1,1'-bis(diphenylphosphino)ferrocene] palladium dichloride and 2-(2-fluoro-6-vinylphenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7~8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of O-18 labeled acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 5

3-19

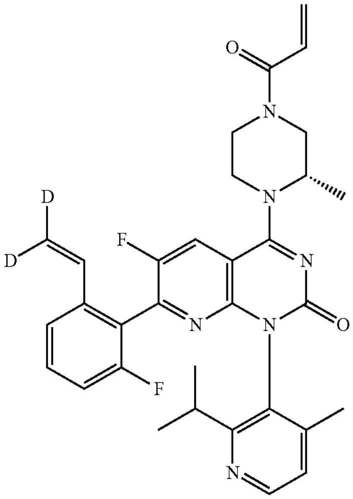

Referring to the preparation method of Example 3, Compound 3-19 was prepared by using Intermediate 1 as the raw material with methyltriphenylphosphonium bromide replaced by methyl-$d_3$-triphenylphosphonium iodide. $R_f$: 0.55 (DCM:MeOH=10:1). The specific preparation method was as follows:

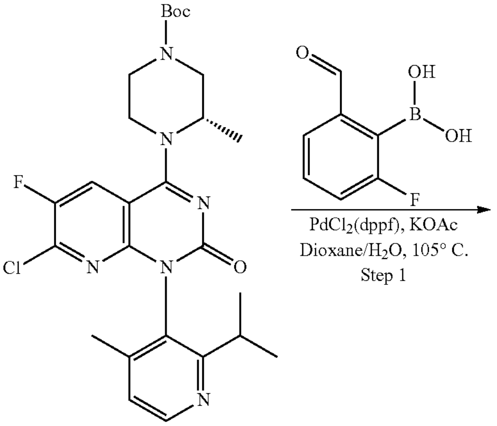

-continued

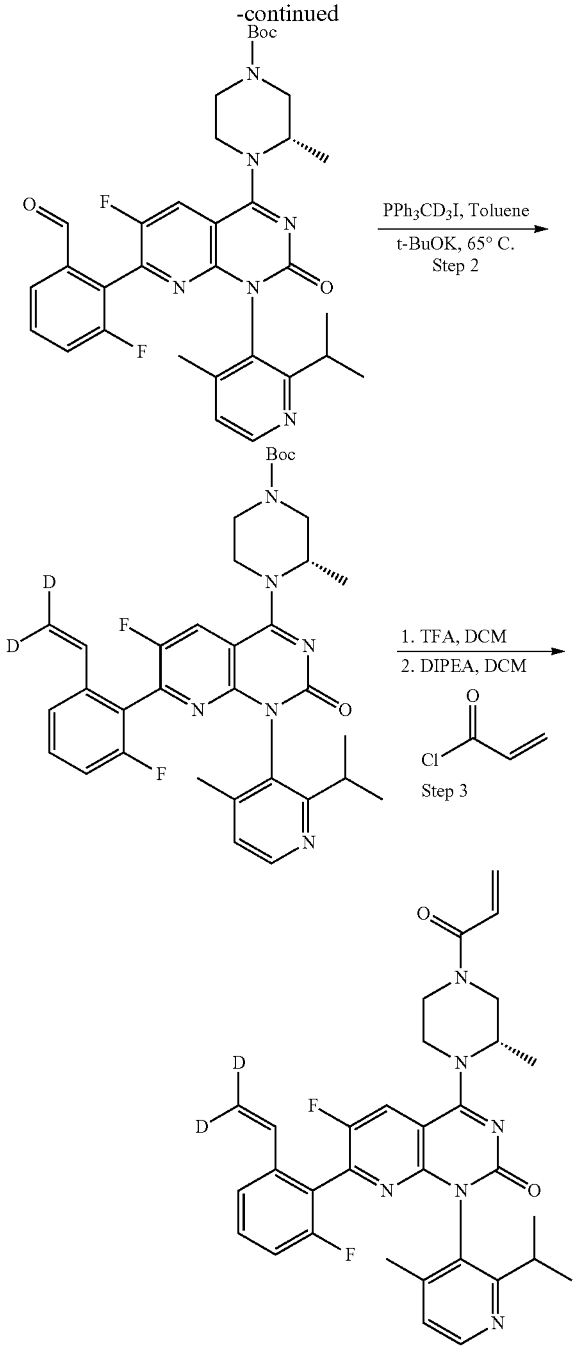

3-19

Step 1

Tert-butyl-(S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (1.5 g), 2-fluoro-6-formylphenylboronic acid (712 mg), potassium acetate (829 g), 1,4-dioxane (20 ml), water (4 ml) and [1,1'-bis(diphenylphosphino)ferrocene] palladium dichloride (205 mg) were added into a 50 ml single-necked flask, warmed to 105° C. after nitrogen gas replacement and stirred for 2 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 1.2 g of a yellow solid. MS: m/z 619.3, $[M+H]^+$.

Step 2

Methyl-$d_3$-triphenylphosphonium iodide (1.97 g), potassium tert-butoxide (543 mg) and toluene (40 ml) were added into a 100 ml reaction flask, warmed to 65° C. under nitrogen gas protection, and stirred for 1 h. A solution of the product from the previous step (1.2 g) in toluene (30 ml) was dropwise added into the reaction flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 700 mg of a light-yellow solid. MS: m/z 619.3, $[M+H]^+$.

Step 3

The product from the previous step (600 mg) and dichloromethane (15 ml) were added into a 50 ml single-necked flask, dropwise added with trifluoroacetic acid (15 ml) at 10° C.~15° C. and stirred at room temperature for 1 h after the addition. After the reaction, the reaction solution was cooled to 0° C., slowly added with saturated aqueous solution of sodium bicarbonate to adjust the pH to 7-8 and extracted with dichloromethane. The organic layers were combined, dried over anhydrous sodium sulfate, filtered, and concentrated under reduced pressure to obtain 503 mg of a yellow solid. MS: m/z 519.3, $[M+H]^+$.

The product from the previous step (120 mg), dichloromethane (10 ml) and N,N-diisopropylethylamine (60 mg) were added into a 50 ml three-necked flask, cooled to 0° C. under nitrogen gas protection, then slowly dropwise added with acryloyl chloride (32 mg), and stirred for 30 min after the addition. After the reaction, the resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 78 mg of an off-white solid. $^1H$ NMR (400 MHz, $CDCl_3$): δ 8.48 (d, J=4.9 Hz, 1H), 7.87 (dd, J=8.4, 3.7 Hz, 1H), 7.43-7.32 (m, 2H), 7.08 (d, J=5.0 Hz, 1H), 7.07-7.00 (m, 1H), 6.75-6.53 (m, 1H), 6.43 (dd, J=16.7, 1.4 Hz, 1H), 6.36-6.23 (m, 1H), 5.84 (dd, J=10.4, 1.8 Hz, 1H), 5.28-4.24 (m, 3H), 4.10-3.49 (m, 3H), 3.44-3.00 (m, 1H), 2.88-2.60 (m, 1H), 2.09-1.93 (m, 3H), 1.65-1.44 (m, 3H), 1.27-1.19 (m, 3H), 1.12-0.97 (m, 3H); MS: m/z 573.2821, $[M+H]^+$.

Example 6

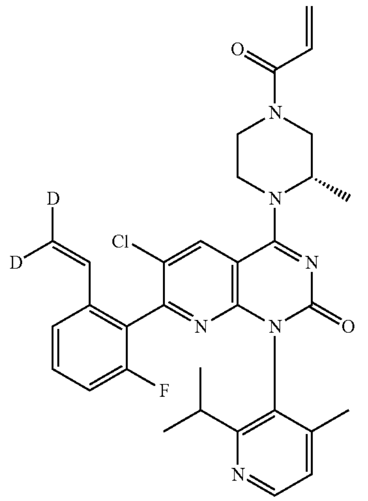

3-20

Referring to the preparation method of Example 4, Compound 3-20 was prepared by using Intermediate 3 as the raw material with methyltriphenylphosphonium bromide replaced by methyl-$d_3$-triphenylphosphonium iodide. $R_f$: 0.56 (DCM:MeOH=10:1). The specific preparation method was as follows:

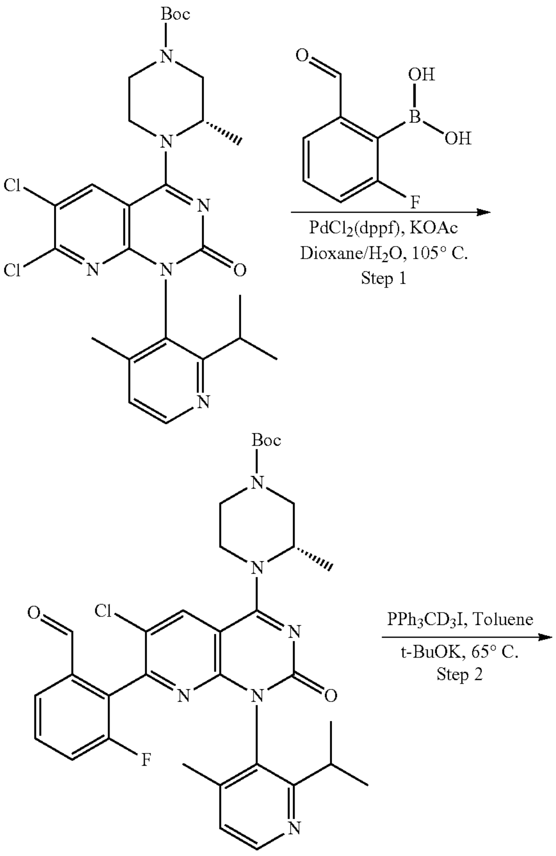

-continued

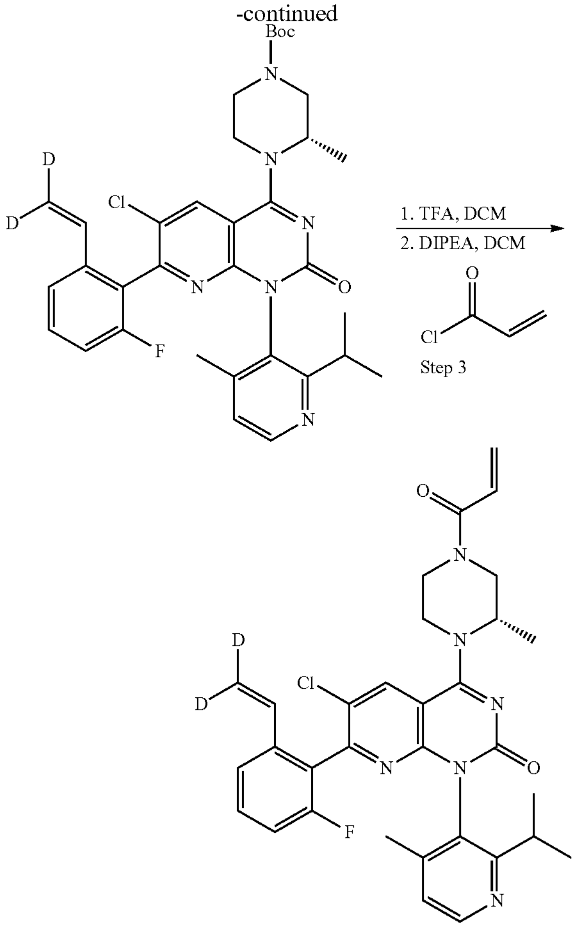

3-20

Step 1

Tert-butyl-(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (2.0 g), 2-fluoro-6-formylphenylboronic acid (920 mg), potassium acetate (1.1 g), 1,4-dioxane (20 ml), water (4 ml) and [1,1'-bis(diphenylphosphino)ferrocene] palladium dichloride (270 mg) were added into a 50 ml single-necked flask, warmed to 105° C. after nitrogen gas replacement and stirred for 2 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 1.7 g of a yellow solid. MS: m/z 635.3, $[M+H]^+$.

Step 2

Methyl-$d_3$-triphenylphosphonium iodide (730 mg), potassium tert-butoxide (200 mg) and toluene (20 ml) were added into a 50 ml three-necked flask, warmed to 65° C. after nitrogen gas replacement, and stirred for 1 h. A solution of the product from the previous step (450 mg) in toluene (10 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 210 mg of a light-yellow solid. MS: m/z 635.3, $[M+H]^+$.

Step 3

The product from the previous step (210 mg) and dichloromethane (10 ml) were added into a 50 ml single-necked flask, dropwise added with trifluoroacetic acid (10 ml) at 10° C.~15° C. and stirred at room temperature for 1 h after the addition. The reaction solution was concentrated to dryness, and the residue was added with dichloromethane (10 ml), cooled to 0° C., added with N,N-diisopropylethylamine (213 mg), then slowly dropwise added with a solution of acryloyl chloride (36 mg) in dichloromethane (1 ml), and stirred for 10 min after the addition. The reaction was quenched by slowly pouring saturated aqueous solution of ammonium chloride, and the obtained solution was extracted with dichloromethane. The organic layers were combined, washed with saturated salt solution, dried over anhydrous sodium sulfate, filtered, concentrated under reduced pressure and purified by silica gel column chromatography to obtain 110 mg of an off-white solid. $^1$H NMR (400 MHz, DMSO-$d_6$): δ 8.55-8.43 (m, 1H), 8.36 (dd, J=4.8, 1.5 Hz, 1H), 7.56 (t, J=8.8 Hz, 1H), 7.51-7.42 (m, 1H), 7.22 (t, J=8.7 Hz, 1H), 7.17 (t, J=4.9 Hz, 1H), 6.95-6.79 (m, 1H), 6.28-6.07 (m, 2H), 5.78 (dd, J=10.3, 2.2 Hz, 1H), 5.11-4.85 (m, 1H), 4.48-4.24 (m, 2H), 4.23-4.03 (m, 1H), 3.93-3.71 (m, 1H), 3.71-3.40 (m, 1H), 3.32-3.02 (m, 1H), 2.86-2.60 (m, 1H), 1.97-1.79 (m, 3H), 1.41-1.29 (m, 3H), 1.07 (t, J=7.3 Hz, 3H), 0.96-0.83 (m, 3H); MS: m/z 589.2457, $[M+H]^+$.

Example 7

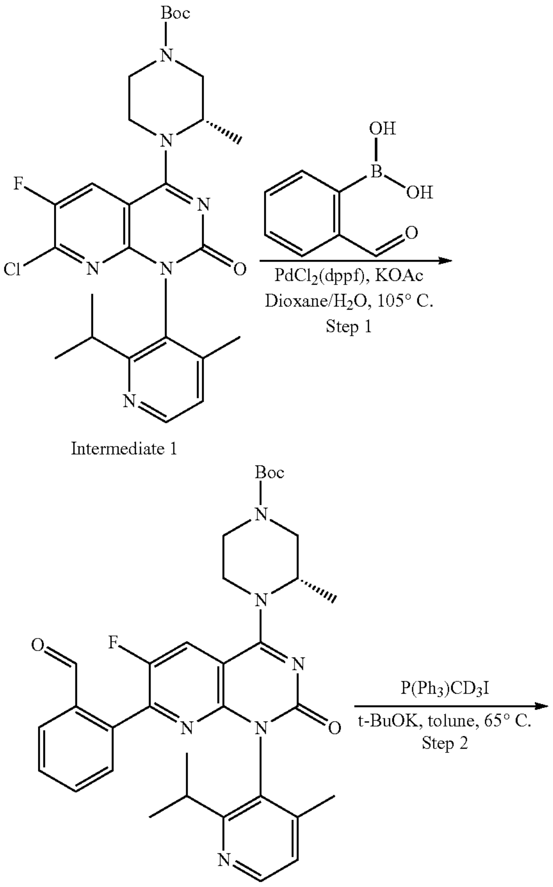

-continued

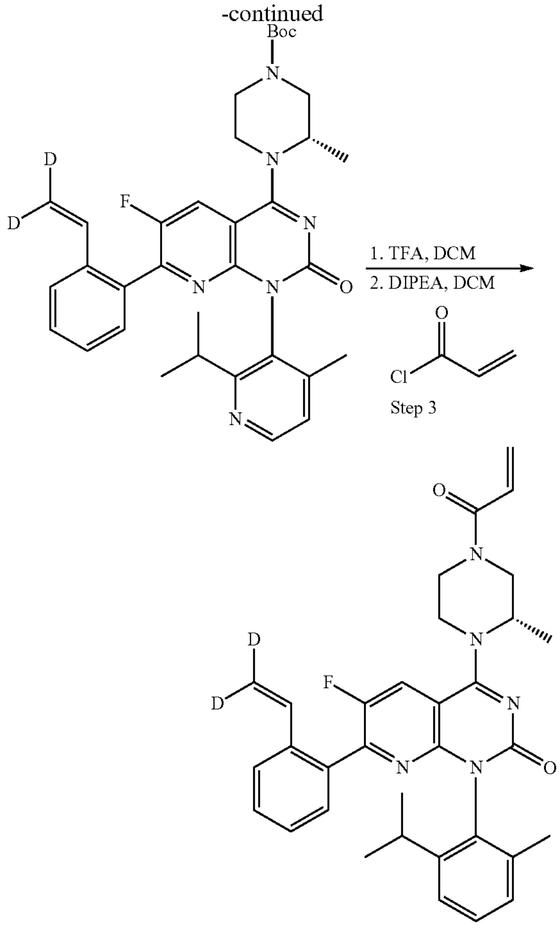

3-23

Step 1

Tert-butyl-(S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (2.0 g), 2-formylphenylboronic acid (848 mg), potassium acetate (1.1 g), 1,4-dioxane (20 ml), water (4 ml) and [1,1'-bis(diphenylphosphino)ferrocene] palladium dichloride (271 mg) were added into a 50 ml single-necked flask, warmed to 105° C. after nitrogen gas replacement, and stirred for 2 h. After the reaction, the reaction solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 1.4 g of a yellow solid.

Step 2

Methyl-$d_3$-triphenylphosphonium iodide (2.4 g), potassium tert-butoxide (652 mg) and toluene (20 ml) were added into a 100 ml three-necked flask, warmed to 65° C. after nitrogen gas replacement, and stirred for 1 h. A solution of the product from the previous step (1.4 g) in toluene (30 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 750 mg of a light-yellow solid. $^1$H NMR (400 MHz, DMSO-$d_6$): 8.38 (d, J=4.8 Hz, 1H), 8.29 (t, J=10.1 Hz, 1H), 7.70 (d, J=7.7 Hz, 1H), 7.46 (td, J=7.6, 1.0 Hz, 1H), 7.35 (td, J=7.5, 1.0 Hz, 1H), 7.23-7.15 (m, 2H), 6.53-6.40 (m, 1H), 4.99-4.79 (m, 1H), 4.34-4.18 (m, 1H), 4.11-3.90 (m, 1H), 3.85 (d, J=13.3 Hz, 1H), 3.77-3.59 (m, 1H), 3.32-3.00 (m, 2H), 2.77-2.64 (m, 1H), 1.96-1.86 (m, 3H), 1.46 (s, 9H), 1.36 (t, J=7.2 Hz, 3H), 1.07 (dd, J=6.7, 1.8 Hz, 3H), 0.92 (dd, J=6.9, 1.6 Hz, 3H).

Step 3

The product from the previous step (200 mg) and dichloromethane (5 ml) were added into a 50 ml single-necked flask, dropwise added with trifluoroacetic acid (5 ml) at 0° C., gradually warmed to 10-15° C. after the addition and stirred for 1 h. After the reaction, the reaction solution was cooled to 0° C., slowly added with saturated aqueous solution of sodium bicarbonate to adjust the pH to 8-9 and extracted with dichloromethane. The organic layers were combined, dried over anhydrous sodium sulfate, filtered, and concentrated under reduced pressure to obtain 120 mg of a yellow oil. $^1$H NMR (400 MHz, DMSO-$d_6$): δ 8.38 (d, J=4.8 Hz, 1H), 8.24 (dd, J=16.0, 9.6 Hz, 1H), 7.69 (d, J=7.8 Hz, 1H), 7.45 (t, J=7.4 Hz, 1H), 7.35 (t, J=7.5 Hz, 1H), 7.24-7.14 (m, 2H), 6.53-6.41 (m, 1H), 4.91-4.71 (m, 1H), 4.26-4.08 (m, 1H), 3.68-3.48 (m, 1H), 3.04-2.90 (m, 2H), 2.87-2.64 (m, 3H), 1.97-1.87 (m, 3H), 1.52-1.42 (m, 3H), 1.07 (d, J=6.6 Hz, 3H), 0.93 (d, J=6.6 Hz, 3H).

Step 4

The product from the previous step (120 mg), dichloromethane (10 ml) and N,N-diisopropylethylamine (47 mg) were added into a 50 ml single-necked flask, cooled to 0° C., slowly dropwise added with acryloyl chloride (26 mg), and stirred for another 30 min after the addition. The resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 38 mg of a light-yellow solid. $^1$H NMR (400 MHz, $CDCl_3$): δ 8.49 (d, J=4.9 Hz, 1H), 7.83 (dd, J=9.0, 2.1 Hz, 1H), 7.57 (d, J=7.8 Hz, 1H), 7.41 (td, J=7.6, 1.0 Hz, 1H), 7.29 (td, J=7.5, 1.1 Hz, 1H), 7.22 (d, J=7.7 Hz, 1H), 7.09 (d, J=5.0 Hz, 1H), 6.75-6.47 (m, 2H), 6.42 (d, J=16.1 Hz, 1H), 5.82 (dd, J=10.4, 1.8 Hz, 1H), 5.23-4.22 (m, 3H), 4.09-3.48 (m, 3H), 3.43-2.99 (m, 1H), 2.86-2.58 (m, 1H), 2.10-1.97 (m, 3H), 1.63-1.43 (m, 3H), 1.24 (d, J=6.8 Hz, 3H), 1.05 (d, J=6.5 Hz, 3H); MS: m/z 555.2873, [M+H]$^+$.

Example 8

3-24

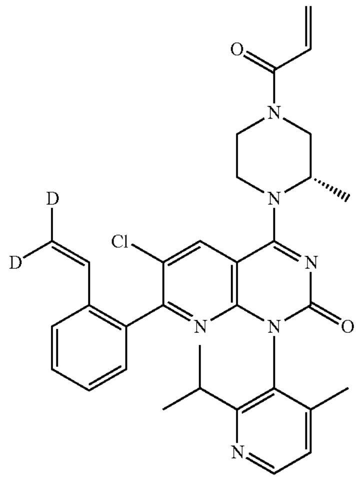

Referring to the preparation method of Example 2, Compound 3-24 was prepared by using Intermediate 3 as the raw material with methyltriphenylphosphonium bromide replaced by methyl-$d_3$-triphenylphosphonium iodide. $R_f$: 0.52 (DCM:MeOH=10:1). The specific preparation method was as follows:

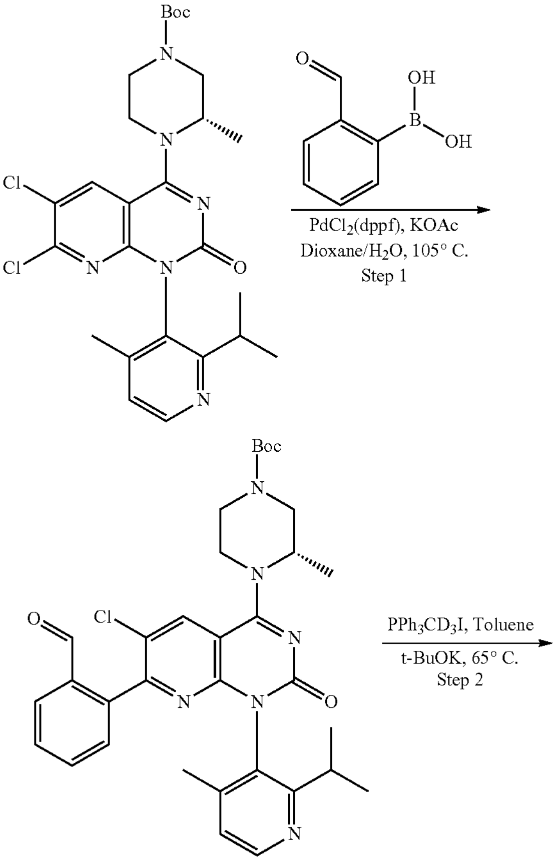

-continued

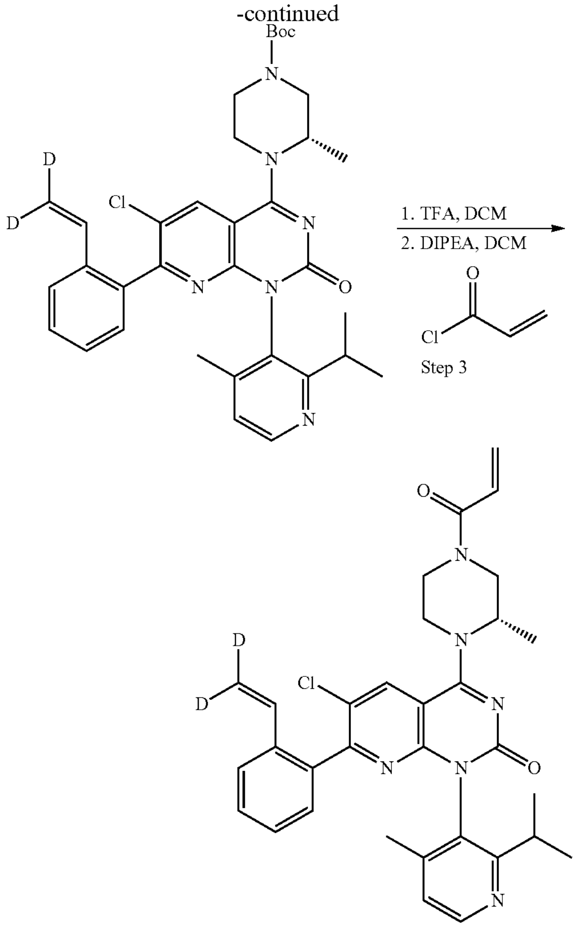

3-24

Step 1

Tert-butyl-(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (2.0 g), 2-formylphenylboronic acid (769 mg), potassium acetate (1.0 g), 1,4-dioxane (40 ml), water (8 ml) and [1,1'-bis(diphenylphosphino)ferrocene] palladium dichloride (263 mg) were added into a 50 ml single-necked flask, warmed to 105° C. after nitrogen gas replacement, and stirred for 2 h. After the reaction, the resulting solution was cooled to room temperature, diluted with water, and extracted with ethyl acetate. The organic layers were combined, washed with saturated salt solution, dried over anhydrous sodium sulfate, filtered, concentrated under reduced pressure and purified by silica gel column chromatography to obtain 1.8 g of a yellow solid. MS: m/z 617.3, $[M+H]^+$.

Step 2

Methyl-$d_3$-triphenylphosphonium iodide (800 mg), potassium tert-butoxide (220 mg) and toluene (20 ml) were added into a 50 ml three-necked flask, warmed to 65° C. after nitrogen gas replacement, and stirred for 1 h. A solution of the product from the previous step (480 mg) in toluene (10 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 320 mg of a light-yellow solid. MS: m/z 617.3, $[M+H]^+$.

Step 3

The product from the previous step (320 mg) and dichloromethane (10 ml) were added into a 50 ml single-necked flask, dropwise added with trifluoroacetic acid (10 ml) at 10° C.~15° C. and stirred at room temperature for 1 h after the addition. The reaction solution was concentrated to dryness, and the residue was added with dichloromethane (10 ml), cooled to 0° C., added with N,N-diisopropylethylamine (336 mg), then slowly dropwise added with a solution of acryloyl chloride (56 mg) in dichloromethane (1 ml), and stirred for 10 min after the addition. The reaction was quenched by slowly pouring saturated aqueous solution of ammonium chloride, and the obtained solution was extracted with dichloromethane. The organic layers were combined, washed with saturated salt solution, dried over anhydrous sodium sulfate, filtered, concentrated under reduced pressure and purified by silica gel column chromatography to obtain 120 mg of an off-white solid. $^1H$ NMR (400 MHz, DMSO-$d_6$): δ 8.49-8.39 (m, 1H), 8.36 (d, J=4.9 Hz, 1H), 7.69 (d, J=7.6 Hz, 1H), 7.42 (td, J=7.6, 0.9 Hz, 1H), 7.33 (td, J=7.5, 1.0 Hz, 1H), 7.17 (d, J=4.9 Hz, 1H), 7.09 (d, J=7.5 Hz, 1H), 6.95-6.79 (m, 1H), 6.34-6.14 (m, 2H), 5.78 (dd, J=10.4, 2.3 Hz, 1H), 5.07-4.87 (m, 1H), 4.48-4.24 (m, 2H), 4.23-4.04 (m, 1H), 3.91-3.71 (m, 1H), 3.71-3.40 (m, 1H), 3.31-3.03 (m, 1H), 2.80-2.64 (m, 1H), 1.96-1.87 (m, 3H), 1.35 (t, J=7.1 Hz, 3H), 1.07 (d, J=6.7 Hz, 3H), 0.92 (d, J=6.7 Hz, 3H); MS: m/z 571.2570, $[M+H]^+$.

Example 8-1M

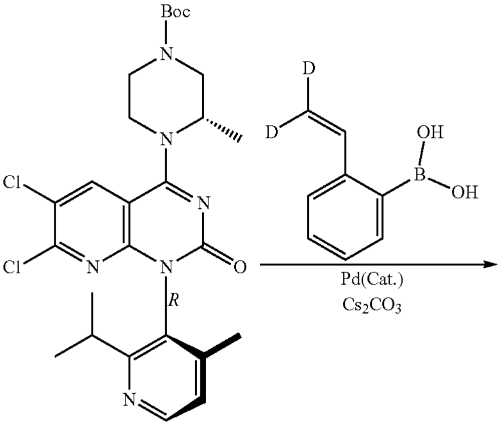

Intermediate 3M

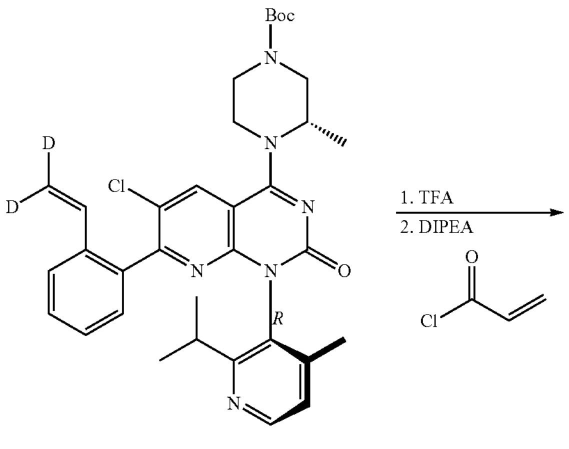

-continued

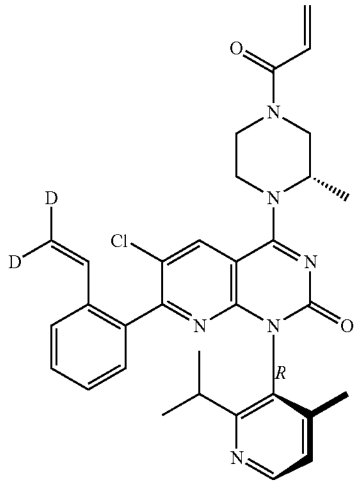

3-16M

Referring to the preparation scheme of Example 28, Compound 3-16M was prepared by using Intermediate 3M as the raw material. $R_f$: 0.52 (DCM:MeOH=10:1). $^1$H NMR (400 MHz, $CDCl_3$): δ 8.57-8.52 (m, 1H), 8.12 (s, 1H), 7.58-7.56 (m, 1H), 7.42-7.38 (m, 1H), 7.30-7.26 (m, 1H), 7.13-7.11 (m, 1H), 7.08-7.06 (m, 1H), 6.73-6.55 (m, 1H), 6.46-6.41 (m, 1H), 6.37-6.30 (m, 1H), 5.85-5.82 (m, 1H), 4.81-2.76 (m, 8H), 2.06-2.03 (m, 3H), 1.64-1.52 (m, 3H), 1.27-1.25 (m, 3H), 1.07-1.06 (m, 3H).

Example 8-1P

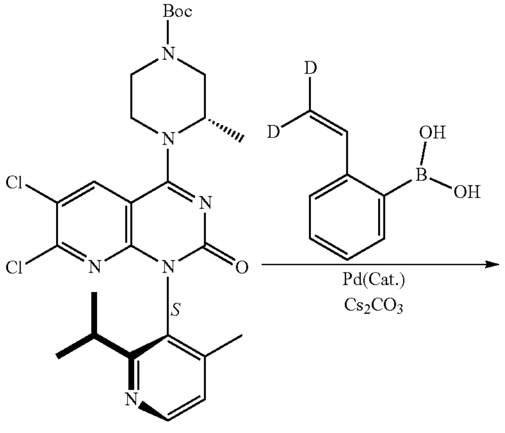

Intermediate 3P

-continued

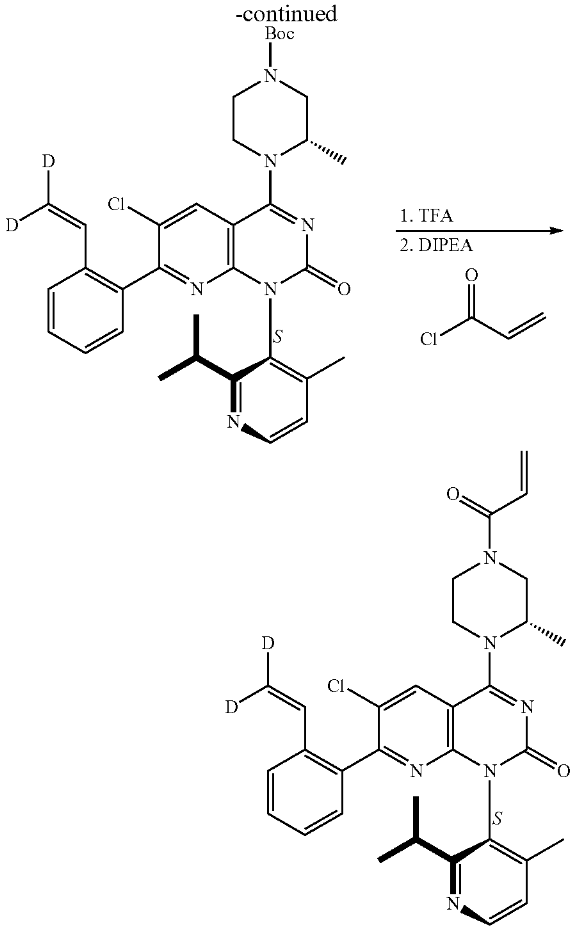

3-16P

Referring to the preparation scheme of Example 28, Compound 3-16P was prepared by using Intermediate 3P as the raw material. $R_f$: 0.52 (DCM:MeOH=10:1).

Example 9

3-25

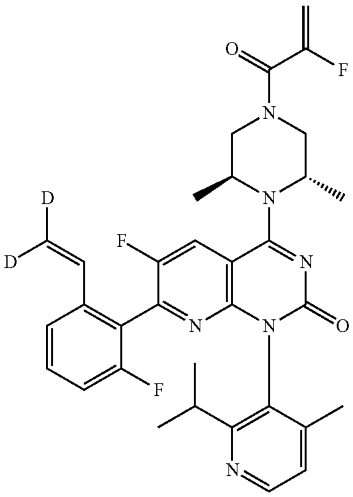

Referring to the preparation method of Example 3, Compound 3-25 was prepared by using Intermediate 2 as the raw material with methyltriphenylphosphonium bromide replaced by methyl-$d_3$-triphenylphosphonium iodide, and using fluorinated acrylic acid for the final amide bond construction. $R_f$: 0.54 (DCM:MeOH=10:1). The specific preparation method was as follows:

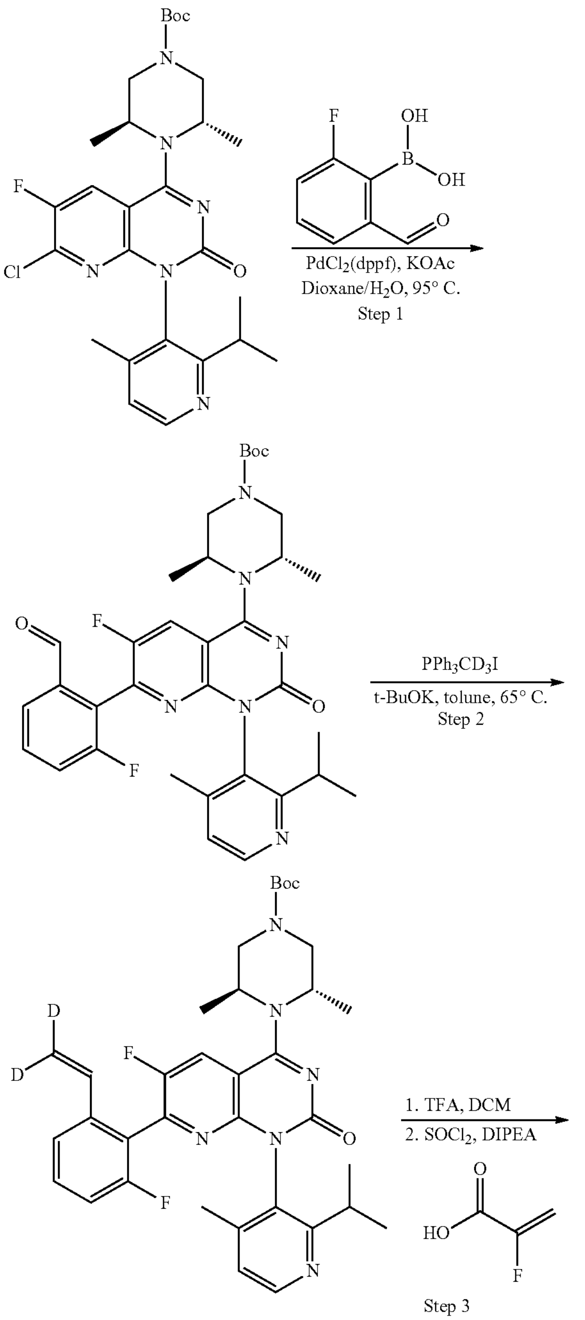

-continued

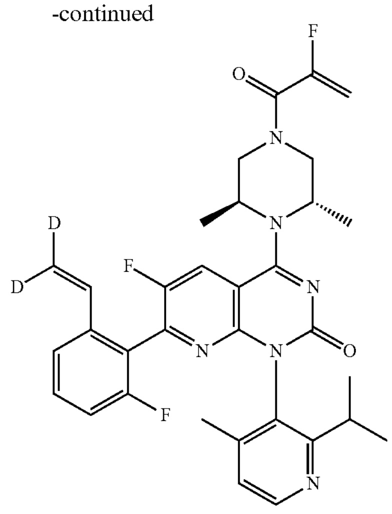

3-25

Step 1

Tert-butyl-(3S,5S)-4-(7-chloro-6-fluoro-1-(2-isopropyl-4-methylpyridin-3-yl)-2-oxo-1,2-dihydropyrido[2,3-d]pyrimidin-4-yl)-3,5-dimethylpiperazine-1-carboxylate (545 mg), 2-fluoro-6-formylphenylboronic acid (252 mg), potassium acetate (441 mg, 4.5 mmol), 1,4-dioxane (15 ml), water (3 ml) and [1,1'-bis(diphenylphosphino)ferrocene] palladium dichloride (73 mg) were added into a 50 ml single-necked flask, warmed to 95° C. after nitrogen gas replacement and stirred for 3 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 600 mg of a yellow solid. $^1H$ NMR (400 MHz, DMSO-$d_6$): δ 9.75 (s, 1H), 8.51-8.40 (m, 1H), 8.37 (dd, J=4.8, 1.8 Hz, 1H), 7.85-7.73 (m, 2H), 7.69 (td, J=8.9, 1.5 Hz, 1H), 7.17 (d, J=4.7 Hz, 1H), 4.52-4.30 (m, 2H), 3.89-3.66 (m, 2H), 3.61-3.42 (m, 2H), 2.73-2.57 (m, 1H), 1.91 (d, J=6.2 Hz, 3H), 1.46 (s, 9H), 1.33 (d, J=6.4 Hz, 3H), 1.28 (d, J=6.3 Hz, 3H), 1.05 (dd, J=6.7, 2.4 Hz, 3H), 0.87 (dd, J=6.6, 4.3 Hz, 3H). MS: m/z 633.3, $[M+H]^+$.

Step 2

Methyl-$d_3$-triphenylphosphonium iodide (869 mg), potassium tert-butoxide (240 mg) and toluene (20 ml) were added into a 100 ml reaction flask, warmed to 65° C. under nitrogen gas protection, and stirred for 1 h. A solution of the product from the previous step (540 mg) in toluene (10 ml) was dropwise added into the reaction flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 400 mg of a light-yellow solid. MS: m/z 633.3, $[M+H]^+$.

Step 3

The product from the previous step (120 mg) and dichloromethane (5 ml) were added into a 50 ml single-necked flask, dropwise added with trifluoroacetic acid (5 ml) at 0° C. and stirred at room temperature for 1 h after the addition. After the reaction, the reaction solution was cooled to 0° C., slowly added with saturated aqueous solution of sodium bicarbonate to adjust the pH to 7-8 and extracted with dichloromethane. The organic layers were combined, dried over anhydrous sodium sulfate, filtered, and concentrated under reduced pressure to obtain 101 mg of a light-yellow solid. 2-Fluoroacrylic acid (25 mg) and dichloromethane (5 ml) were added into another flask, slowly dropwise added with sulfoxide chloride (36 mg), and stirred at room temperature for 30 min after the addition.

The product after removing Boc (101 mg) was dissolved in dichloromethane (10 ml), added with N,N-diisopropylethylamine (139 mg), cooled to 0° C. under nitrogen gas protection, then slowly dropwise added with above prepared 2-fluoroacryloyl chloride, and stirred for 30 min after the addition. After the reaction, the resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 45 mg of a yellow solid. $^1$H NMR (400 MHz, $CDCl_3$): δ 8.48 (d, J=4.9 Hz, 1H), 7.98 (d, J=8.1 Hz, 1H), 7.43-7.32 (m, 2H), 7.08 (d, J=4.9 Hz, 1H), 7.06-6.98 (m, 1H), 6.36-6.21 (m, 1H), 5.41 (dd, J=47.4, 3.5 Hz, 1H), 5.24 (dd, J=16.8, 3.6 Hz, 1H), 4.44-4.24 (m, 2H), 4.07-3.50 (m, 4H), 2.68 (br s, 1H), 2.10-1.97 (m, 3H), 1.48-1.35 (m, 6H), 1.25-1.16 (m, 3H), 1.11-0.96 (m, 3H). MS: m/z 605.2823, $[M+H]^+$.

Example 10

3-27

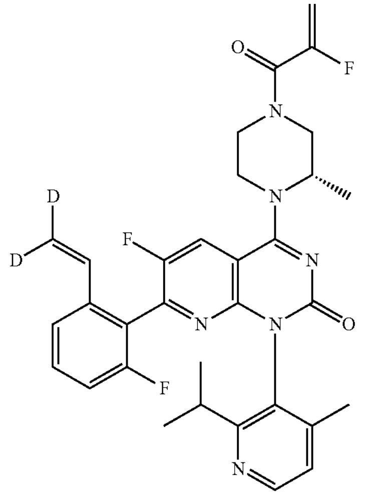

Referring to the preparation method of Example 3, Compound 3-27 was prepared by using Intermediate 1 as the raw material with methyltriphenylphosphonium bromide replaced by methyl-$d_3$-triphenylphosphonium iodide, and using fluorinated acrylic acid for the final amide bond construction. $R_f$: 0.54 (DCM:MeOH=10:1). The specific preparation method was as follows:

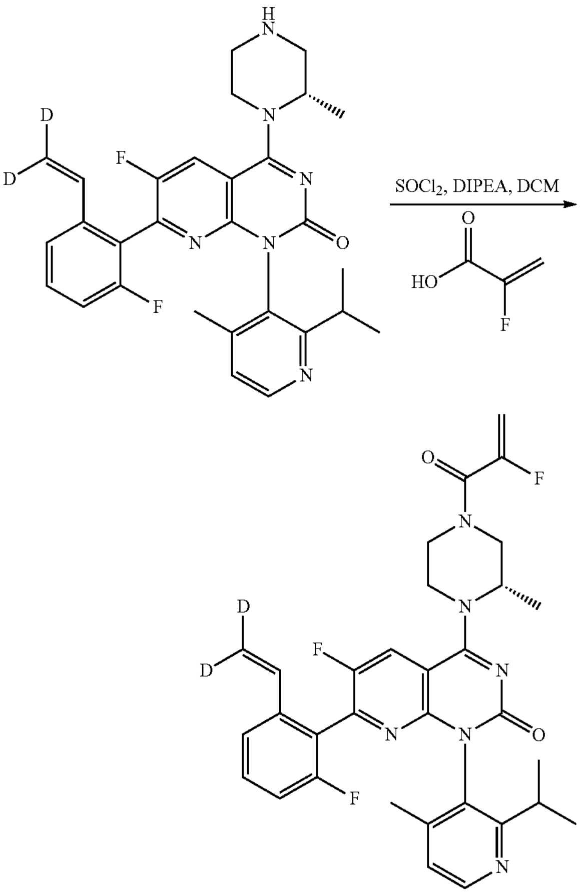

3-27

2-Fluoroacrylic acid (65 mg) and dichloromethane (10 ml) were added into a 25 ml single-necked flask, slowly dropwise added with sulfoxide chloride (95 mg), and stirred at room temperature for 30 min after the addition. 6-Fluoro-7-(2-fluoro-6-(vinyl-2,2-$d_2$)phenyl)-1-(2-isopropyl-4-methylpyridin-3-yl)-4-((S)-2-methylpiperazin-1-yl)pyrido[2,3-d]pyrimidin-2(1H)-one (250 mg), dichloromethane (10 ml) and N,N-diisopropylethylamine (310 mg) were added into another 50 ml reaction flask, cooled to 0° C. under nitrogen gas protection, then slowly dropwise added with above prepared 2-fluoroacryloyl chloride, and stirred for 30 min after the addition. After the reaction, the resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 115 mg of an off-white solid. $^1$H NMR (400 MHz, $CDCl_3$): δ 8.48 (d, J=4.9 Hz, 1H), 7.86 (dd, J=8.4, 4.8 Hz, 1H), 7.43-7.32 (m, 2H), 7.08 (d, J=4.9 Hz, 1H), 7.07-7.00 (m, 1H), 6.36-6.23 (m, 1H), 5.43 (dd, J=47.4, 3.5 Hz, 1H), 5.26 (dd, J=16.8, 3.6 Hz, 1H), 5.10-4.79 (m, 1H), 4.72-4.26 (m, 2H), 4.17-3.48 (m, 3H), 3.48-3.02 (m, 1H), 2.85-2.62 (m, 1H), 2.08-1.93 (m, 3H), 1.62-1.46 (m, 3H), 1.27-1.16 (m, 3H), 1.12-0.96 (br s, 3H); MS: m/z 591.2730, $[M+H]^+$.

Example 11

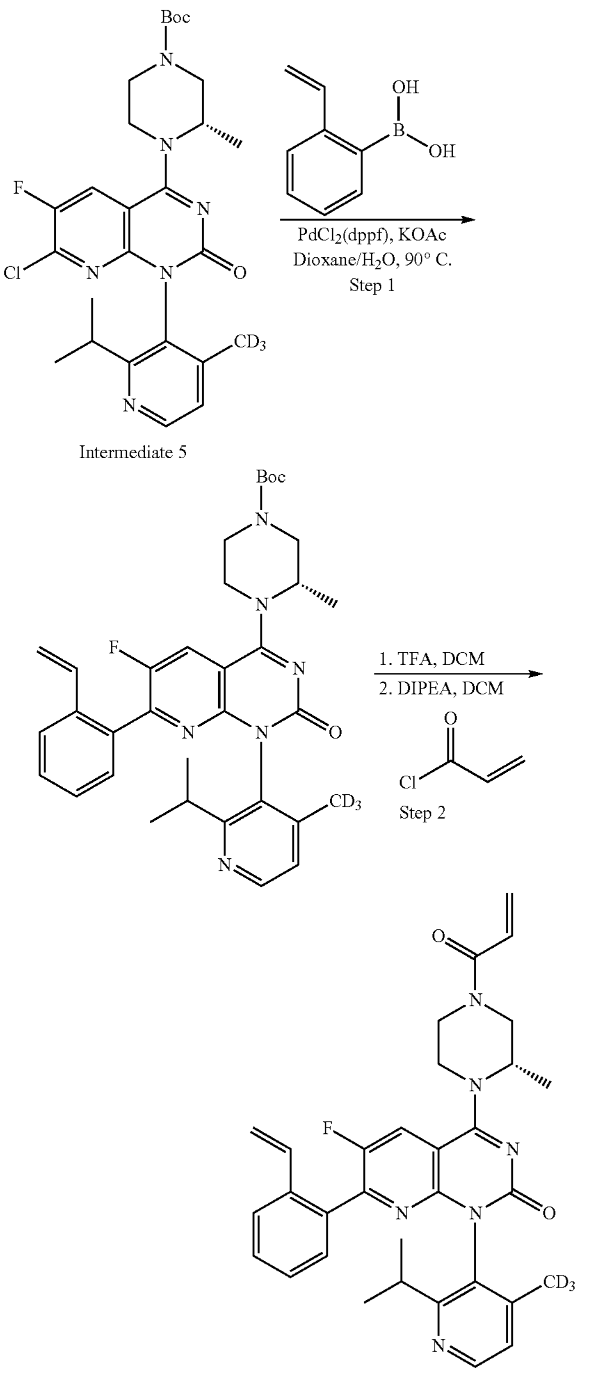

Intermediate 5

4-23

Step 1

The product from the previous step (1.15 g), 2-vinylphenylboronic acid (482 mg), potassium acetate (1.1 g), 1,4-dioxane (20 ml), water (1 ml) and [1,1'-bis(diphenylphosphino)ferrocene]palladium dichloride (159 mg) were added into a 50 ml single-necked flask, warmed to 90° C. after nitrogen gas replacement, and stirred for 4 h. After the reaction, the reaction solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 1.15 g of a yellow solid. MS: m/z 602.3, $[M+H]^+$.

Step 2

The product from the previous step (1.1 g) and dichloromethane (20 ml) were added into a 50 ml single-necked flask, dropwise added with trifluoroacetic acid (10 ml) at 10° C.~15° C. and stirred at room temperature for 1 h after the addition. The reaction solution was concentrated to dryness, and the residue was added with dichloromethane (20 ml), cooled to 0° C., added with N,N-diisopropylethylamine (2 ml), then slowly dropwise added with a solution of acryloyl chloride (151 mg) in dichloromethane (2 ml), and stirred for 30 min after the addition. The reaction was quenched by slowly pouring saturated aqueous solution of ammonium chloride, and the obtained solution was extracted with dichloromethane. The organic layers were combined, washed with saturated salt solution, dried over anhydrous sodium sulfate, filtered, concentrated under reduced pressure and purified by silica gel column chromatography to obtain 515 mg of an off-white solid. $R_f$: 0.57 (DCM: MeOH=10:1). $^1$H NMR (400 MHz, $CDCl_3$): δ 8.50 (dd, J=4.9, 0.6 Hz, 1H), 7.83 (dd, J=9.1, 2.1 Hz, 1H), 7.57 (d, J=7.8 Hz, 1H), 7.42 (t, J=7.6 Hz, 1H), 7.30 (t, J=7.6 Hz, 1H), 7.22 (d, J=7.7 Hz, 1H), 7.09 (d, J=4.9 Hz, 1H), 6.75-6.35 (m, 3H), 5.83 (d, J=10.5 Hz, 1H), 5.55 (d, J=17.4 Hz, 1H), 5.24-4.23 (m, 3H), 5.11 (d, J=11.0 Hz, 1H), 4.09-3.48 (m, 3H), 3.44-2.99 (m, 1H), 2.85-2.60 (m, 1H), 1.62-1.43 (m, 3H), 1.24 (d, J=6.8 Hz, 3H), 1.05 (d, J=6.4 Hz, 3H); MS: m/z 556.2936, $[M+H]^+$.

Example 12

4-3

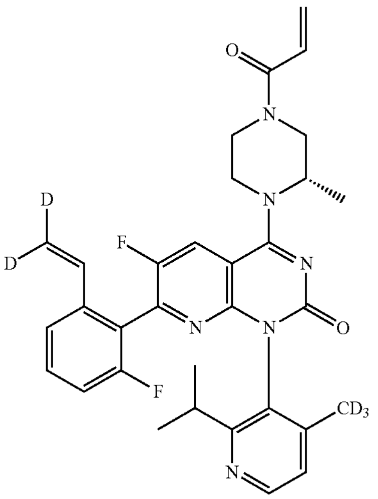

Referring to the preparation method of Example 3, Compound 4-3 was prepared by using Intermediate 5 as the raw material with methyltriphenylphosphonium bromide replaced by methyl-$d_3$-triphenylphosphonium iodide. $R_f$: 0.53 (DCM:MeOH=10:1). The specific preparation method was as follows:

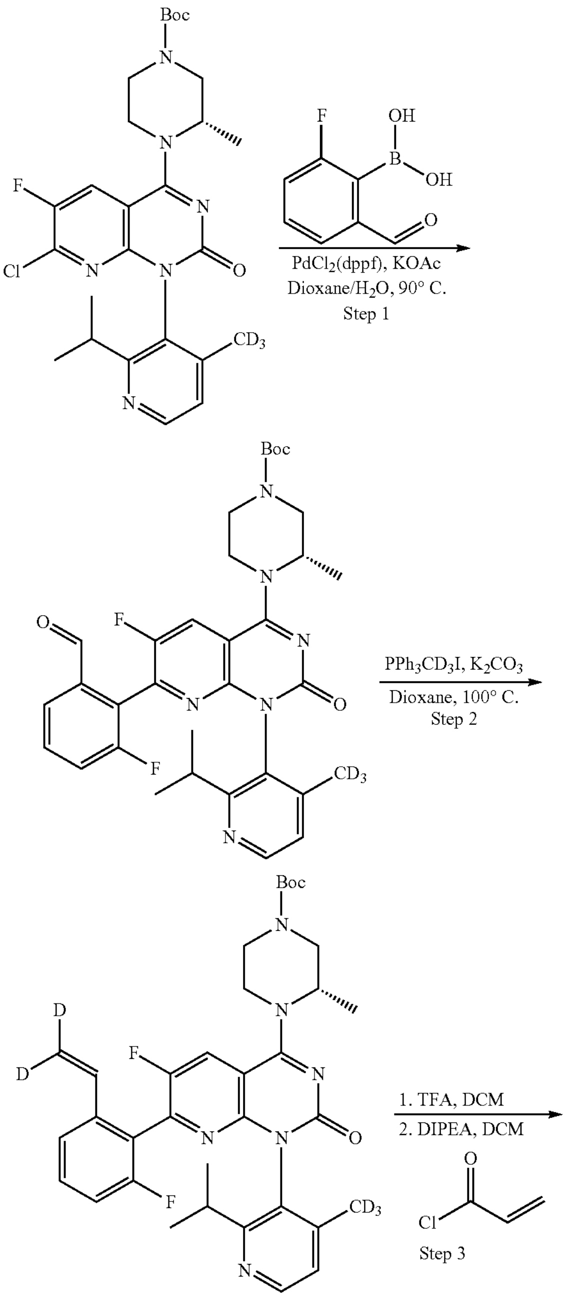

-continued

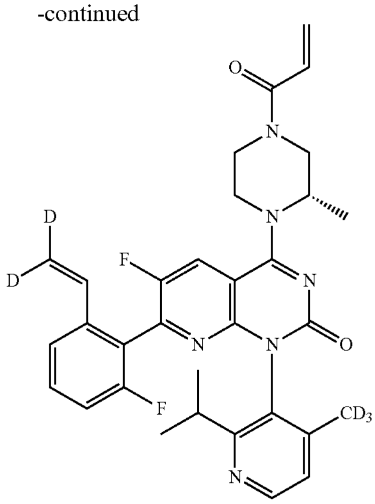

4-3

Step 1

Tert-butyl-(S)-4-(7-chloro-6-fluoro-1-(2-isopropyl-4-(methyl-$d_3$)pyridin-3-yl)-2-oxo-1,2-dihydropyrido[2,3-d]pyrimidin-4-yl)-3-methylpiperazine-1-carboxylate (1.2 g), 2-fluoro-6-formylphenylboronic acid (570 mg), potassium acetate (668 mg, 6.8 mmol), 1,4-dioxane (25 ml), water (1.2 ml) and [1,1'-bis(diphenylphosphino)ferrocene] palladium dichloride (220 mg) were added into a 50 ml single-necked flask, warmed to 90° C. after nitrogen gas replacement and stirred for 4 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 1.0 g of a yellow solid. MS: m/z 622.3, $[M+H]^+$.

Step 2

The product from the previous step (1.0 g), methyl-$d_3$-triphenylphosphonium iodide (788 mg), potassium carbonate (334 mg) and 1,4-dioxane (20 ml) were added into a 50 ml reaction flask, warmed to 100° C. under nitrogen gas protection, and stirred for 3 h. After the reaction, the obtained solution was cooled to room temperature, added with water, and extracted with ethyl acetate. The organic layers were combined, washed with saturated salt solution, dried over anhydrous sodium sulfate, filtered, concentrated under reduced pressure and purified by silica gel column chromatography to obtain 780 mg of a yellow solid. MS: m/z 622.3, $[M+H]^+$.

Step 3

The product from the previous step (780 mg) and dichloromethane (40 ml) were added into a 50 ml single-necked flask, dropwise added with trifluoroacetic acid (10 ml) at 0° C. and stirred at room temperature for 1 h after the addition. After the reaction, the reaction solution was cooled to 0° C., slowly added with saturated aqueous solution of sodium bicarbonate to adjust the pH to 7-8 and extracted with dichloromethane. The organic layers were combined, dried over anhydrous sodium sulfate, filtered, and concentrated under reduced pressure to dryness. 650 mg of an off-white solid was obtained.

The product after removing Boc (325 mg) was dissolved in dichloromethane (20 ml), added with N,N-diisopropylethylamine (243 mg), cooled to 0° C. under nitrogen gas protection, dropwise added with a solution of acryloyl chloride (63 mg) in dichloromethane (2 ml), and stirred for another 30 min after the addition. After the reaction, the resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 260 mg of an off-white solid. $^{1}H$ NMR (400 MHz, $CDCl_3$): δ 8.46 (d, J=4.8 Hz, 1H), 7.87 (dd, J=8.4, 4.4 Hz, 1H), 7.41-7.30 (m, 2H), 7.09-6.95 (m, 2H), 6.74-6.50 (m, 1H), 6.41 (d, J=16.7 Hz, 1H), 6.35-6.22 (m, 1H), 5.81 (d, J=10.4 Hz, 1H), 5.25-4.20 (m, 3H), 4.09-3.49 (m, 3H), 3.43-2.98 (m, 1H), 2.89-2.55 (m, 1H), 1.64-1.39 (m, 3H), 1.27-1.17 (m, 3H), 1.02 (br s, 3H). MS: m/z 576.2938, $[M+H]^+$.

Example 13

4-8

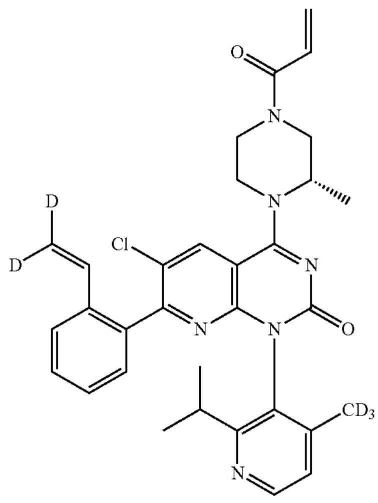

Referring to the preparation method of Example 2, Compound 4-8 was prepared with methyltriphenylphosphonium bromide replaced by methyl-$d_3$-triphenylphosphonium iodide. $R_f$ 0.55 (DCM:MeOH=10:1). The specific preparation method was as follows:

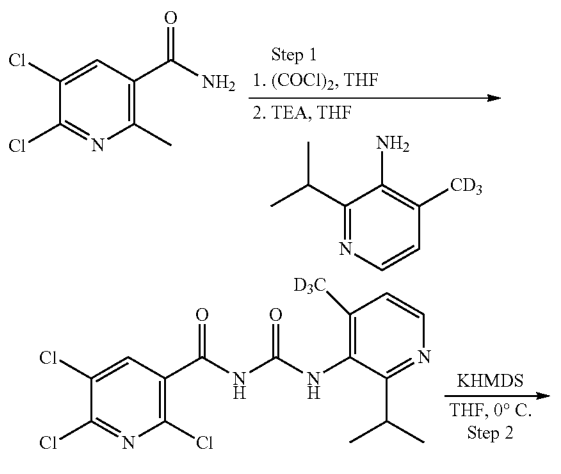

-continued

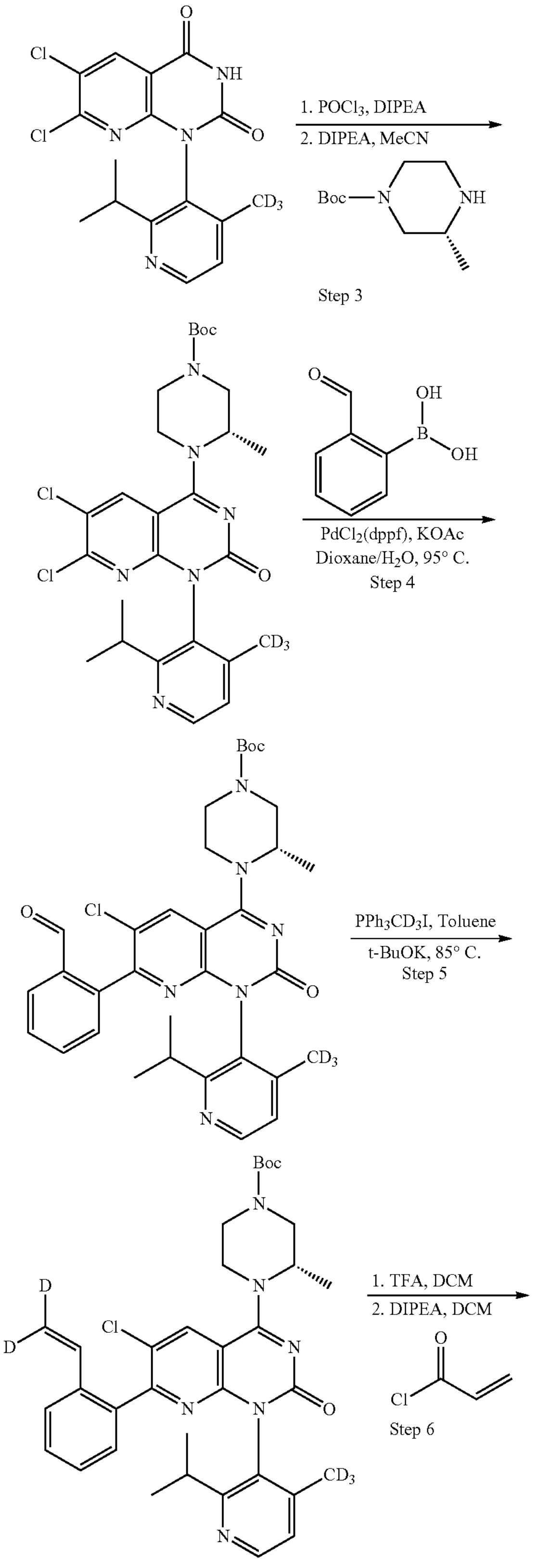

-continued

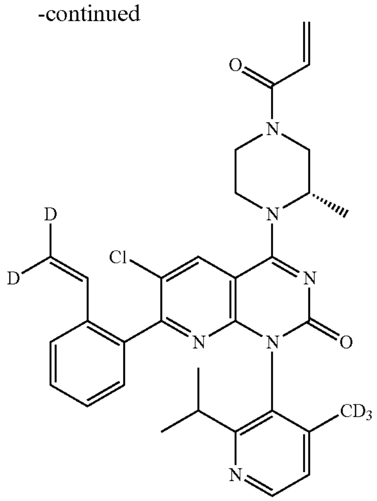

4-8

Step 1

2,5,6-Trichloronicotinamide (1.9 g) and tetrahydrofuran (50 ml) were added into a 100 ml reaction flask, cooled to 0° C., dropwise added with oxalyl chloride (1.3 g), warmed to 70° C. after the addition and stirred for 1 h. The reaction solution was concentrated to dryness, cooled to 0° C., added with tetrahydrofuran (50 ml), dropwise added with 2-isopropyl-4-(methyl-$d_3$)pyridin-3-amine (1.2 g), then added with triethylamine (0.87 g), and stirred at 15° C.~20° C. for another 0.5 h after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 1.56 g of a white solid. MS: m/z 404.1, $[M+H]^+$.

Step 2

The product from the previous step (1.5 g) and tetrahydrofuran (45 ml) were added into a 100 ml reaction flask, cooled to 0° C., dropwise added with potassium bis(trimethylsilyl)amide (8.2 ml), and stirred at room temperature for 1 h after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 1.2 g of a white solid. MS: m/z 368.1, $[M+H]^+$.

Step 3

The product from the previous step (1.2 g), acetonitrile (30 ml) and N,N-diisopropylethylamine (0.85 g) were added into a 100 ml single-necked flask, cooled to below 10° C., dropwise added with phosphoryl trichloride (0.76 g), then added with 2 drops of N-methylmorpholine, and stirred for reaction at 10° C.~20° C. for 1 h after the addition. The reaction solution was concentrated to dryness under reduced pressure, added with acetonitrile (30 ml), N,N-diisopropylethylamine (0.85 g) and tert-butyl-(S)-3-methylpiperazine-1-carboxylate (0.66 g) in turn, and stirred at room temperature for 1 h after the addition. The reaction solution was poured into water and extracted with ethyl acetate. The organic layers were combined, washed with saturated sodium chloride solution, dried over anhydrous sodium sulfate, filtered, concentrated under reduced pressure and purified by silica gel column chromatography to obtain 1.1 g of a yellow solid. MS: m/z 550.2, $[M+H]^+$.

Step 4

The product from the previous step (520 mg), 2-formylphenylboronic acid (220 mg), potassium acetate (280 mg), 1,4-dioxane (20 ml), water (4 ml) and [1,1'-bis(diphenylphosphino)ferrocene]palladium dichloride (139 mg) were added into a 50 ml single-necked flask, warmed to 95° C. after nitrogen gas replacement, and stirred for 5 h. After the reaction, the resulting solution was cooled to room temperature, diluted with water, and extracted with ethyl acetate. The organic layers were combined, washed with saturated salt solution, dried over anhydrous sodium sulfate, filtered, concentrated under reduced pressure and purified by silica gel column chromatography to obtain 480 mg of a yellow solid. MS: m/z 620.3, $[M+H]^+$.

Step 5

Methyl-$d_3$-triphenylphosphonium iodide (800 mg), potassium tert-butoxide (220 mg) and toluene (20 ml) were added into a 100 ml three-necked flask, warmed to 65° C. after nitrogen gas replacement, and stirred for 1 h. A solution of the product from the previous step (480 mg) in toluene (30 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 320 mg of a light-yellow solid.

Step 6

The product from the previous step (320 mg) and dichloromethane (10 ml) were added into a 50 ml single-necked flask, dropwise added with trifluoroacetic acid (10 ml) at 0° C. and stirred for 1 h at 10° C.~15° C. after the addition. After the reaction, the reaction solution was cooled to 0° C., slowly added with saturated aqueous solution of sodium bicarbonate to adjust the pH to 7-8 and extracted with dichloromethane. The organic layers were combined, dried over anhydrous sodium sulfate, filtered, and concentrated under reduced pressure to dryness. A light-yellow solid was obtained. The concentrate was added with dichloromethane (10 ml) and N,N-diisopropylethylamine (134 mg), cooled to 0° C. under nitrogen gas protection, then slowly dropwise added with a solution of acryloyl chloride (71 mg) in dichloromethane (3 ml), and stirred for 30 min after the addition. After the reaction, the resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 150 mg of a white solid. $^1$H NMR (400 MHz, $CDCl_3$): δ 8.46 (d, J=4.9 Hz, 1H), 8.11 (s, 1H), 7.56 (d, J=7.8 Hz, 1H), 7.40 (td, J=7.6, 0.9 Hz, 1H), 7.28 (td, J=7.5, 1.2 Hz, 1H), 7.11-7.04 (m, 2H), 6.75-6.54 (m, 1H), 6.50-6.29 (m, 2H), 5.83 (dd, J=10.4, 1.8 Hz, 1H), 5.29-4.22 (m, 3H), 4.10-3.52 (m, 3H), 3.44-3.01 (m, 1H), 2.84-2.60 (m, 1H), 1.63-1.44 (m, 3H), 1.24 (d, J=6.8 Hz, 3H), 1.05 (d, J=6.7 Hz, 3H). MS: m/z 574.2776, $[M+H]^+$.

Example 14

4-9

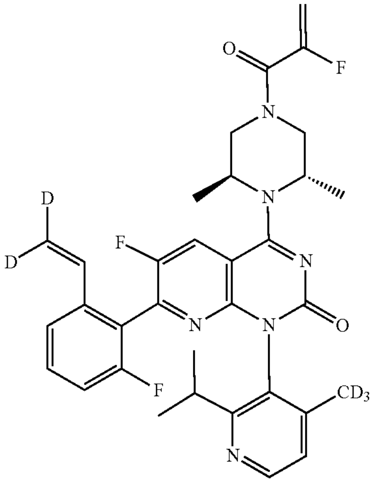

Referring to the preparation method of Example 3, Compound 4-9 was prepared by using methyl-$d_3$-triphenylphosphonium iodide instead of methyltriphenylphosphonium bromide and using fluorinated acrylic acid for the final amide bond construction. $R_f$: 0.53 (DCM:MeOH=10:1). The specific preparation method was as follows:

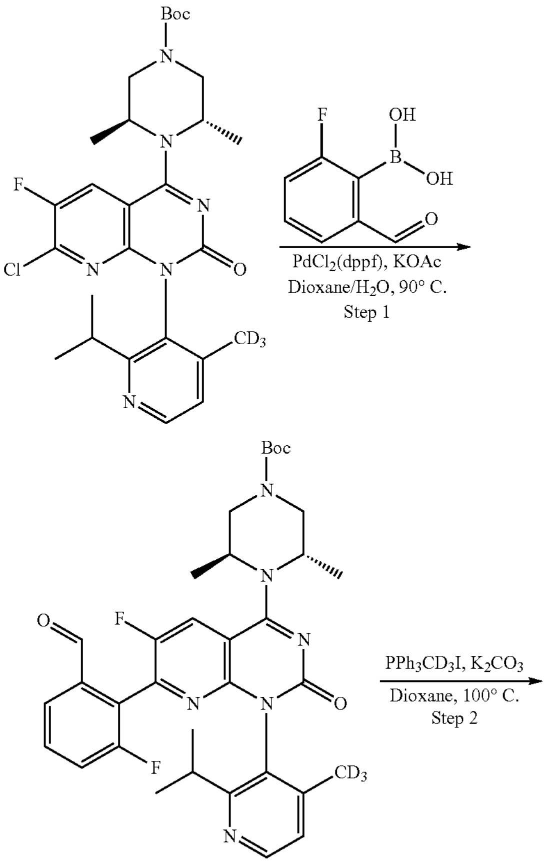

-continued

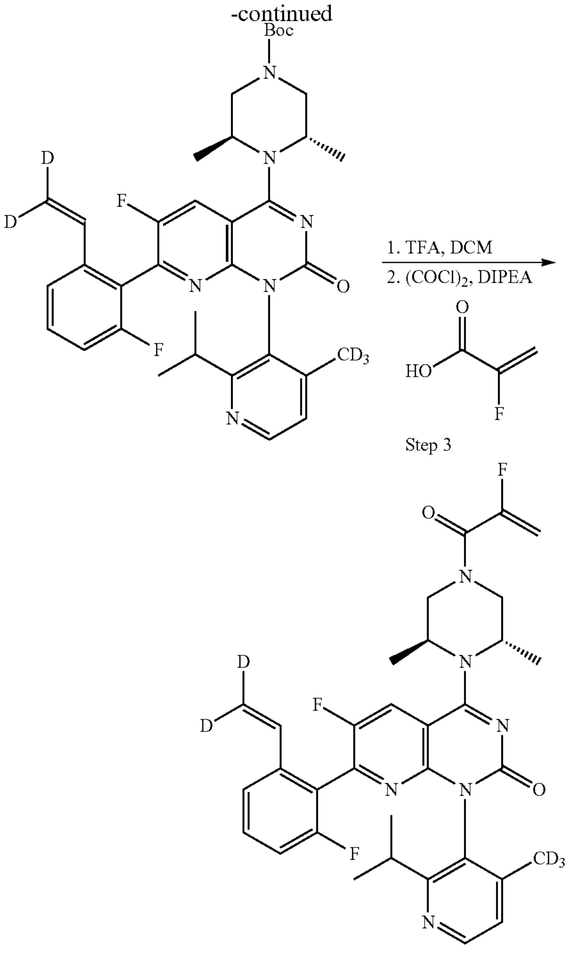

4-9

Step 1

Tert-butyl-(3S,5S)-4-(7-chloro-6-fluoro-1-(2-isopropyl-4-(methyl-$d_3$)pyridin-3-yl)-2-oxo-1,2-dihydropyrido[2,3-d]pyrimidin-4-yl)-3,5-dimethylpiperazine-1-carboxylate (400 mg), 2-fluoro-6-formylphenylboronic acid (184 mg), potassium acetate (215 mg), 1,4-dioxane (10 ml), water (0.5 ml) and [1,1'-bis(diphenylphosphino)ferrocene] palladium dichloride (53 mg) were added into a 50 ml single-necked flask, warmed to 90° C. after nitrogen gas replacement and stirred for 4 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 350 mg of a yellow solid. MS: m/z 636.3, $[M+H]^+$.

Step 2

The product from the previous step (350 mg), methyl-$d_3$-triphenylphosphonium iodide (269 mg), potassium carbonate (114 mg) and 1,4-dioxane (10 ml) were added into a 50 ml reaction flask, warmed to 100° C. under nitrogen gas protection, and stirred for 3 h. After the reaction, the obtained solution was directly concentrated under reduced pressure and then purified by silica gel column chromatography to obtain 308 mg of a light-yellow solid. MS: m/z 636.4, $[M+H]^+$.

Step 3

The product from the previous step (150 mg) and dichloromethane (15 ml) were added into a 50 ml single-necked flask, dropwise added with trifluoroacetic acid (4 ml) at 0° C. and stirred at room temperature for 1 h after the addition. After the reaction, the reaction solution was cooled to 0° C., slowly added with saturated aqueous solution of sodium bicarbonate to adjust the pH to 7-8 and extracted with dichloromethane. The organic layers were combined, dried over anhydrous sodium sulfate, filtered, and concentrated under reduced pressure to obtain 130 mg of a yellow solid. 2-Fluoroacrylic acid (44 mg) and dichloromethane (5 ml) were added into another flask, slowly dropwise added with oxalyl chloride (64 mg) and 2 drops of N,N-dimethylformamide, and stirred at room temperature for 30 min after the addition.

The product after removing Boc (130 mg) was dissolved in dichloromethane (10 ml), added with N,N-diisopropylethylamine (93 mg), cooled to 0° C. under nitrogen gas protection, then slowly dropwise added with the above prepared 2-fluoroacryloyl chloride, and stirred for 30 min after the addition. After the reaction, the resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 91 mg of a white solid. $^1H$ NMR (400 MHz, $CDCl_3$): δ 8.51 (d, J=4.9 Hz, 1H), 7.98 (d, J=8.2 Hz, 1H), 7.45-7.34 (m, 2H), 7.12 (d, J=4.6 Hz, 1H), 7.09-7.00 (m, 1H), 6.37-6.21 (m, 1H), 5.44 (dt, J=47.4, 3.4 Hz, 1H), 5.26 (dd, J=16.8, 3.6 Hz, 1H), 4.46-4.26 (m, 2H), 4.10-3.51 (m, 4H), 2.71 (br s, 1H), 1.47 (d, J=6.2 Hz, 3H), 1.41 (d, J=6.3 Hz, 3H), 1.30-1.19 (m, 3H), 1.13-0.97 (m, 3H). MS: m/z 608.2981, $[M+H]^+$.

Example 15

4-11

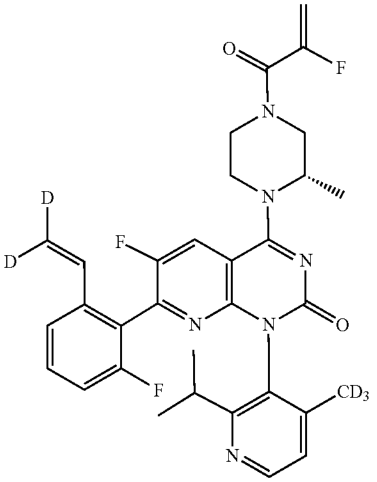

Referring to the preparation method of Example 3, Compound 4-11 was prepared by using Intermediate 5 as the raw material with methyltriphenylphosphonium bromide replaced by methyl-$d_3$-triphenylphosphonium iodide, and using fluorinated acrylic acid for the final amide bond construction. $R_f$: 0.52 (DCM:MeOH=10:1). The specific preparation method was as follows:

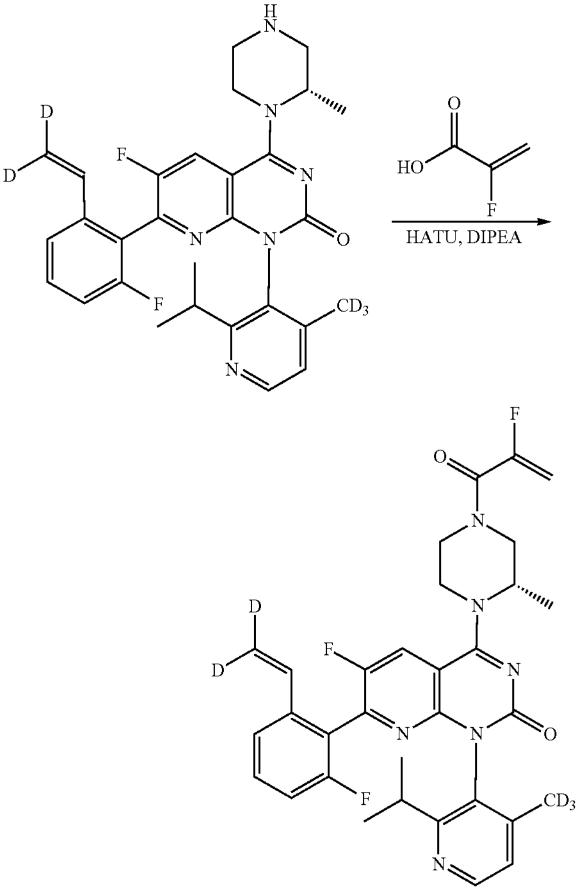

4-11

6-Fluoro-7-(2-fluoro-6-(vinyl-2,2-$d_2$)phenyl)-1-(2-isopropyl-4-(methyl-$d_3$)pyridin-3-yl)-4-((S)-2-methylpiperazin-1-yl)pyrido[2,3-d]pyrimidin-2(1H)-one (325 mg), dichloromethane (20 ml), N,N-diisopropylethylamine (243 mg), 2-fluoroacrylic acid (85 mg) and 2-(7-azabenzotriazol-1-yl)-N,N,N',N'-tetramethyluronium hexafluorophosphate (256 mg) were added into a reaction flask, and stirred at room temperature for 30 min after the addition. After the reaction, the resulting solution was diluted with water and extracted with dichloromethane. The organic layers were combined, washed with saturated salt solution, dried over anhydrous sodium sulfate, filtered, concentrated under reduced pressure and purified by silica gel column chromatography to obtain 240 mg of a yellow solid. $^1H$ NMR (400 MHz, $CDCl_3$): δ 8.48 (d, J=4.7 Hz, 1H), 7.97-7.79 (m, 1H), 7.49-7.31 (m, 2H), 7.16-6.95 (m, 2H), 6.40-6.20 (m, 1H), 5.51-4.80 (m, 3H), 4.74-4.23 (m, 2H), 4.11-3.01 (m, 4H), 2.76 (br s, 1H), 1.67-1.46 (m, 3H), 1.28-1.16 (m, 3H), 1.03 (br s, 3H). MS: m/z 594.2843, $[M+H]^+$.

Example 16

4-16

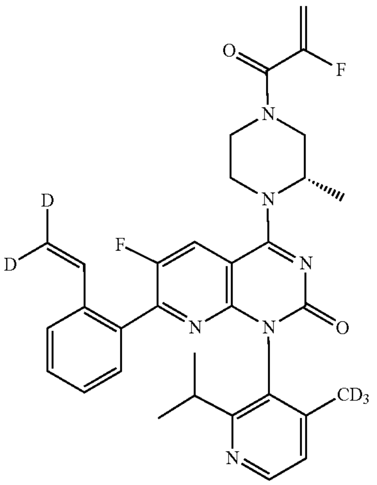

Referring to the preparation method of Example 2, Compound 4-16 was prepared by using methyl-$d_3$-triphenylphosphonium iodide instead of methyltriphenylphosphonium bromide and using fluorinated acrylic acid for the final amide bond construction. $R_f$: 0.53 (DCM:MeOH=10:1).

Example 17

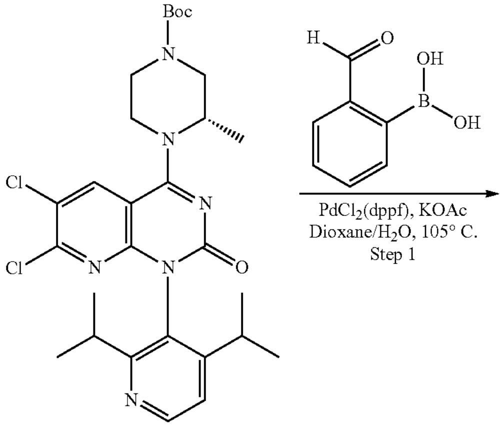

Intermediate 6

-continued

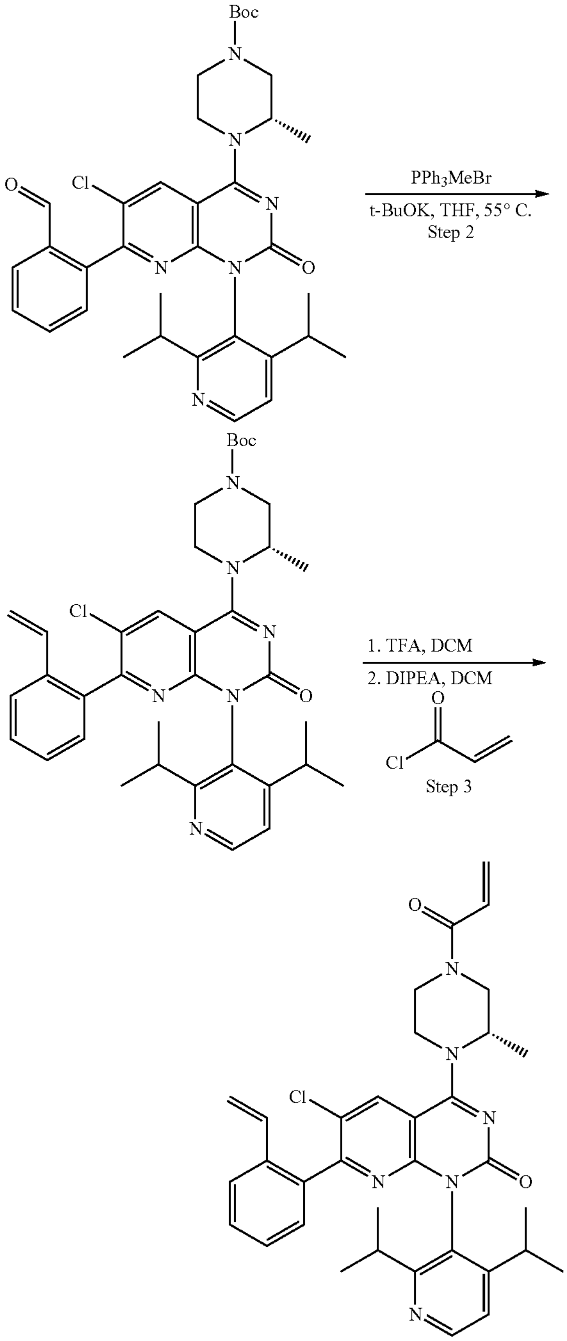

5-24

Step 1

The product from the previous step (1.65 g), 2-formylphenylboronic acid (650 mg), potassium acetate (843 mg), 1,4-dioxane (50 ml), water (5 ml) and [1,1'-bis(diphenylphosphino)ferrocene]palladium dichloride (212 mg) were added into a 100 ml single-necked flask, warmed to 105° C. after nitrogen gas replacement and stirred for 2.5 h. After the reaction, the resulting solution was diluted with water and extracted with ethyl acetate. The organic layers were combined, washed with saturated salt solution, dried over anhydrous sodium sulfate, filtered, concentrated under reduced pressure and purified by silica gel column chromatography to obtain 1.66 g of a yellow solid. MS: m/z 645.3, $[M+H]^+$.

Step 2

Methyltriphenylphosphonium bromide (714 mg), potassium tert-butoxide (224 mg) and dry tetrahydrofuran (20 ml) were added into a 100 ml three-necked flask, warmed to 55° C. after nitrogen gas replacement, and stirred for 1 h. A solution of the product from the previous step (644 mg) in tetrahydrofuran (5 ml) was dropwise added into the flask and the obtained mixture was stirred for another 20 min after the addition. The reaction solution was concentrated to dryness, added with water and extracted with ethyl acetate. The organic layers were combined, washed with saturated salt solution, dried over anhydrous sodium sulfate, filtered, concentrated under reduced pressure and purified by silica gel column chromatography to obtain 640 mg of a light-yellow solid. MS: m/z 643.3, $[M+H]^+$.

Step 3

The product from the previous step (640 mg) and dichloromethane (15 ml) were added into a 50 ml single-necked flask, dropwise added with trifluoroacetic acid (10 ml) at 10° C.~15° C. and stirred at room temperature for 1 h after the addition. The reaction solution was concentrated to dryness, and the residue was added with dichloromethane (15 ml), cooled to 0° C., added with N,N-diisopropylethylamine (646 mg), then slowly dropwise added with a solution of acryloyl chloride (109 mg) in dichloromethane (1 ml), and stirred for 10 min after the addition. The reaction was quenched by slowly pouring saturated aqueous solution of ammonium chloride, and the obtained solution was extracted with dichloromethane. The organic layers were combined, washed with saturated salt solution, dried over anhydrous sodium sulfate, filtered, concentrated under reduced pressure and purified by silica gel column chromatography to obtain 300 mg of an off-white solid. $R_f$: 0.55 (DCM: MeOH=10:1). $^1$H NMR (400 MHz, $CDCl_3$): δ 8.55 (d, J=5.1 Hz, 1H), 8.12 (s, 1H), 7.58 (d, J=7.8 Hz, 1H), 7.39 (t, J=7.4 Hz, 1H), 7.27 (t, J=7.3 Hz, 1H), 7.14 (d, J=5.2 Hz, 1H), 7.01 (d, J=7.5 Hz, 1H), 6.75-6.51 (m, 1H), 6.43 (d, J=16.6 Hz, 1H), 6.36-6.22 (m, 1H), 5.83 (dd, J=10.4, 1.6 Hz, 1H), 5.58 (d, J=17.4 Hz, 1H), 5.11 (d, J=11.0 Hz, 1H), 5.25-4.20 (m, 3H), 4.11-3.51 (m, 3H), 3.47-2.96 (m, 1H), 2.80-2.35 (m, 2H), 1.63-1.44 (m, 3H), 1.30-1.15 (m, 6H), 1.09-0.93 (m, 6H); MS: m/z 597.2760, $[M+H]^+$.

Example 18

5-3

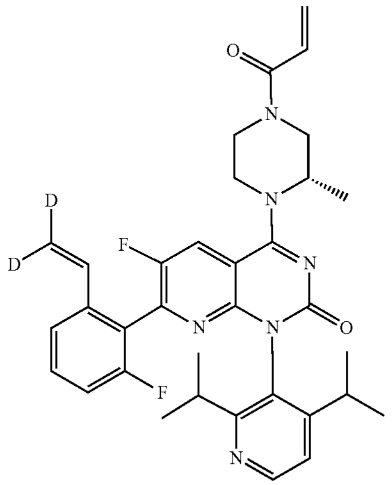

Referring to the preparation method of Example 3, Compound 5-3 was prepared by using methyl-$d_3$-triphenylphosphonium iodide instead of methyltriphenylphosphonium bromide. $R_f$: 0.54 (DCM:MeOH=10:1). The specific preparation method was as follows:

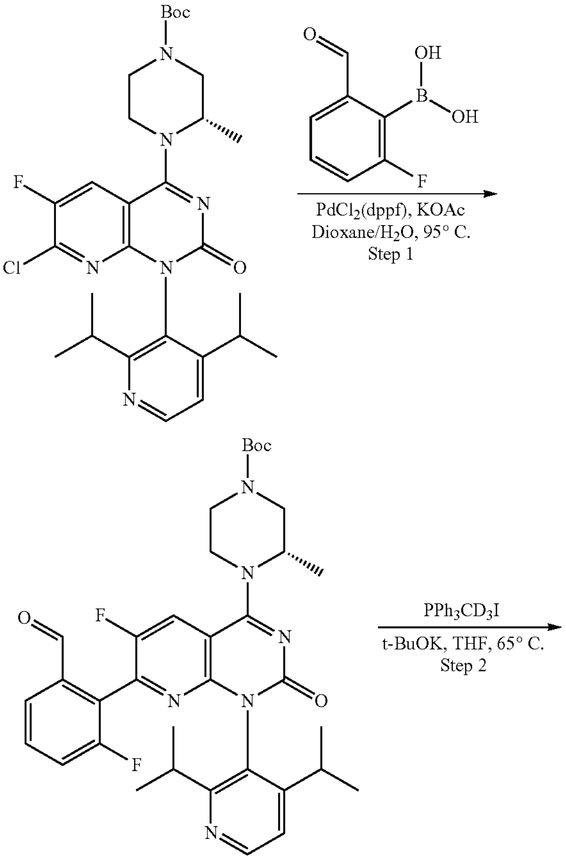

-continued

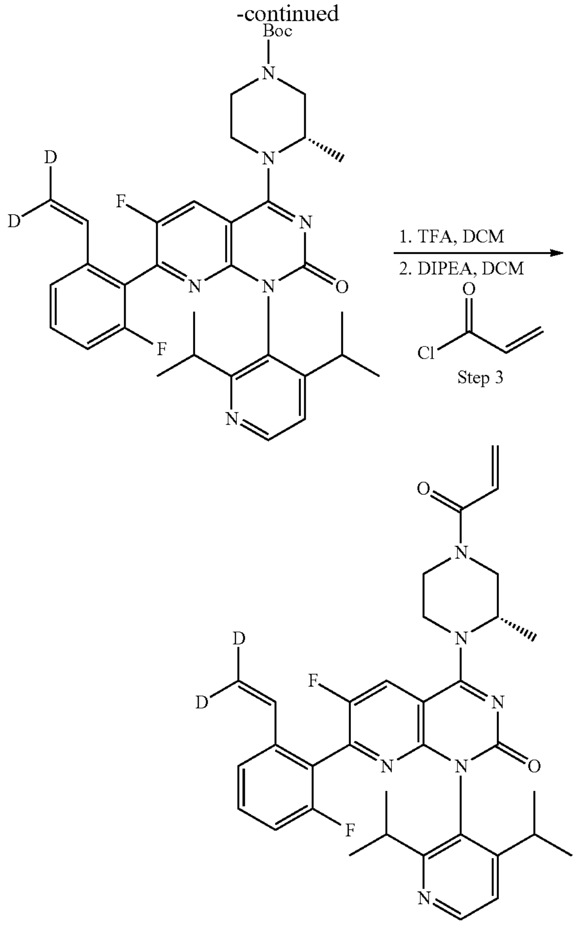

5-3

Step 1

Tert-butyl-(S)-4-(7-chloro-1-(2,4-diisopropylpyridin-3-yl)-6-fluoro-2-oxo-1,2-dihydropyrido[2,3-d]pyrimidin-4-yl)-3-methylpiperazine-1-carboxylate (1.0 g), 2-fluoro-6-formylphenylboronic acid (454 mg), potassium acetate (527 mg), 1,4-dioxane (20 ml), water (4 ml) and [1,1'-bis(diphenylphosphino)ferrocene] palladium dichloride (124 mg) were added into a 100 ml single-necked flask, warmed to 95° C. after nitrogen gas replacement and stirred for 4 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 692 mg of a yellow solid. $^1$H NMR (400 MHz, $CDCl_3$): δ 9.79 (d, J=1.3 Hz, 1H), 8.54 (d, J=5.1 Hz, 1H), 7.87 (d, J=8.4 Hz, 1H), 7.72 (dd, J=7.6, 1.1 Hz, 1H), 7.68-7.61 (m, 1H), 7.40 (td, J=8.6, 1.2 Hz, 1H), 7.13 (d, J=5.2 Hz, 1H), 5.07-4.77 (m, 1H), 4.48-3.88 (m, 3H), 3.78-3.56 (m, 1H), 3.47-3.07 (m, 2H), 2.76-2.48 (m, 2H), 1.54 (s, 12H), 1.25-1.18 (m, 6H), 1.01-0.91 (m, 6H). MS: m/z 647.3, $[M+H]^+$.

Step 2

Methyl-$d_3$-triphenylphosphonium iodide (1.35 g), potassium tert-butoxide (360 mg) and tetrahydrofuran (30 ml) were added into a 50 ml three-necked flask, warmed to 60° C. after nitrogen gas replacement, and stirred for 2 h. A solution of the product from the previous step (692 mg) in tetrahydrofuran (10 ml) was dropwise added into the flask and the obtained mixture was warmed to 65° C. after the addition and stirred for 30 min. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 600 mg of a light-yellow solid. MS: m/z 647.4, $[M+H]^+$.

Step 3

The product from the previous step (460 mg), dichloromethane (10 ml) and trifluoroacetic acid (10 ml) were added into a 50 ml single-necked flask, and stirred at room temperature for 1 h after the addition. After the reaction, the reaction solution was cooled to 0° C., slowly added with saturated aqueous solution of sodium bicarbonate to adjust the pH to alkalescence and extracted with dichloromethane. The organic layers were combined, dried over anhydrous sodium sulfate, filtered, and concentrated under reduced pressure to dryness. The concentrate (150 mg) was dissolved in dichloromethane (10 ml), then added with N,N-diisopropylethylamine (70 mg), cooled to 0° C. under nitrogen gas protection, slowly dropwise added with acryloyl chloride (37 mg), and stirred for 30 min after the addition. After the reaction, the resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 110 mg of a white solid. $^1$H NMR (400 MHz, $CDCl_3$): δ 8.57 (d, J=5.1 Hz, 1H), 7.88 (d, J=8.3 Hz, 1H), 7.43-7.33 (m, 2H), 7.17 (d, J=5.0 Hz, 1H), 7.07-7.00 (m, 1H), 6.75-6.53 (m, 1H), 6.43 (d, J=16.7 Hz, 1H), 6.31-6.17 (m, 1H), 5.84 (dd, J=10.4, 1.7 Hz, 1H), 5.24-4.22 (m, 3H), 4.10-3.51 (m, 3H), 3.44-3.01 (m, 1H), 2.85-2.36 (m, 2H), 1.64-1.45 (m, 3H), 1.28-1.14 (m, 6H), 1.12-0.90 (m, 6H). MS: m/z 601.2771, $[M+H]^+$.

Example 19

5-8

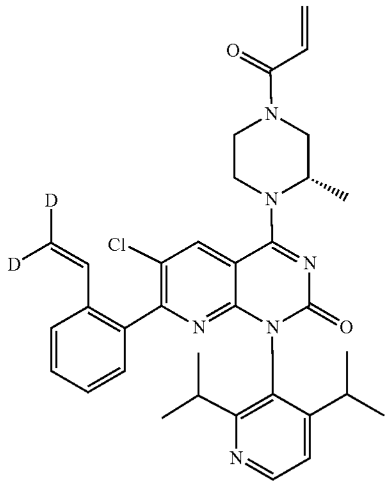

Referring to the preparation method of Example 17, Compound 5-8 was prepared by using methyl-$d_3$-triphenylphosphonium iodide instead of methyltriphenylphosphonium bromide. $R_f$: 0.56 (DCM:MeOH=10:1). The specific preparation method was as follows:

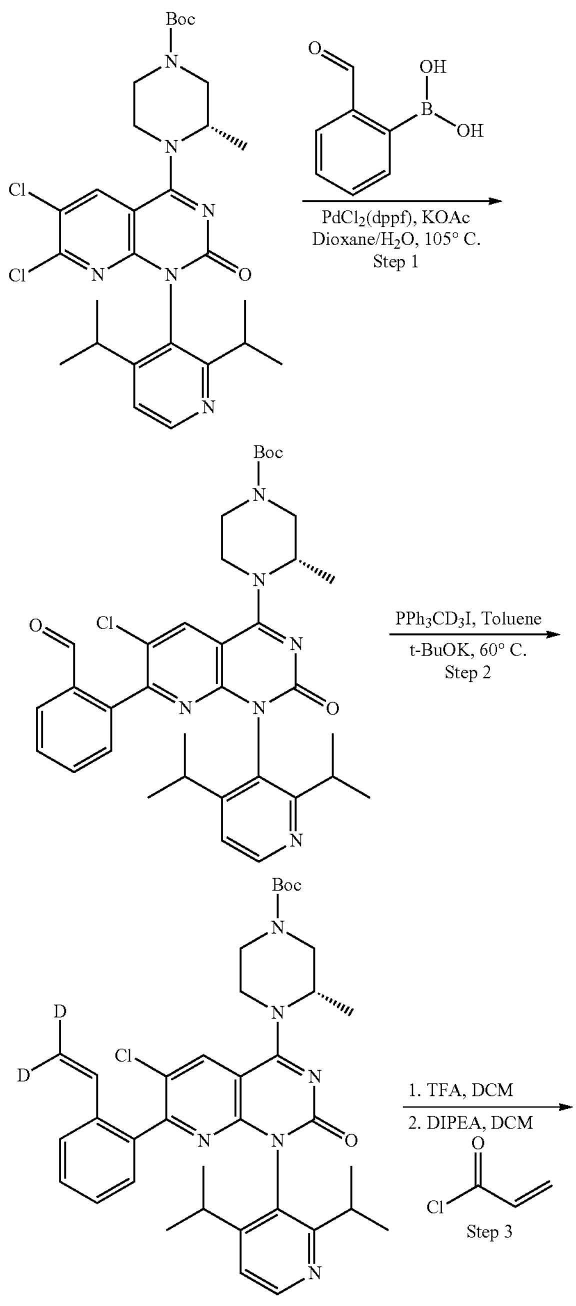

-continued

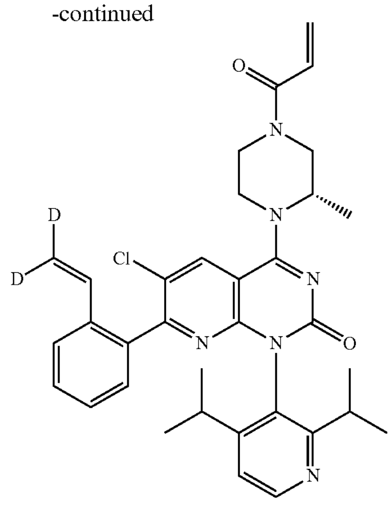

5-8

Step 1

Tert-butyl-(S)-4-(6,7-dichloro-1-(2,4-diisopropylpyridin-3-yl)-2-oxo-1,2-dihydropyrido[2,3-d]pyrimidin-4-yl)-3-methylpiperazine-1-carboxylate (1.65 g), 2-formylphenylboronic acid (650 mg), potassium acetate (843 mg), 1,4-dioxane (50 ml), water (5 ml) and [1,1'-bis(diphenylphosphino)ferrocene] palladium dichloride (212 mg) were added into a 100 ml single-necked flask, warmed to 105° C. after nitrogen gas replacement and stirred for 2.5 h. After the reaction, the resulting solution was diluted with water and extracted with ethyl acetate. The organic layers were combined, washed with saturated salt solution, dried over anhydrous sodium sulfate, filtered, concentrated under reduced pressure and purified by silica gel column chromatography to obtain 1.66 g of a yellow solid. MS: m/z 645.3, $[M+H]^+$.

Step 2

Methyl-$d_3$-triphenylphosphonium iodide (568 mg), potassium tert-butoxide (146 mg) and toluene (20 ml) were added into a 50 ml three-necked flask, warmed to 60° C. after nitrogen gas replacement, and stirred for 1.5 h. A solution of the product from the previous step (300 mg) in toluene (5 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 256 mg of a light-yellow solid. MS: m/z 645.3, $[M+H]^+$.

Step 3

The product from the previous step (256 mg) and dichloromethane (15 ml) were added into a 50 ml single-necked flask, dropwise added with trifluoroacetic acid (6 ml) at 10° C.~15° C. and stirred at room temperature for 1 h after the addition. The reaction solution was concentrated to dryness, and the residue was added with dichloromethane (15 ml), cooled to 0° C., added with N,N-diisopropylethylamine (258 mg), then slowly dropwise added with a solution of acryloyl chloride (38 mg) in dichloromethane (1 ml), and stirred for 10 min after the addition. The reaction was quenched by slowly pouring saturated aqueous solution of ammonium chloride, and the obtained solution was extracted with dichloromethane. The organic layers were combined, washed with saturated salt solution, dried over anhydrous sodium sulfate, filtered, concentrated under reduced pressure and purified by silica gel column chromatography to obtain 200 mg of an off-white solid. $^1$H NMR (400 MHz, $CDCl_3$): δ 8.56 (d, J=5.2 Hz, 1H), 8.12 (s, 1H), 7.58 (d, J=7.9 Hz, 1H), 7.40 (td, J=7.6, 0.8 Hz, 1H), 7.27 (td, J=7.5, 1.0 Hz, 1H), 7.14 (d, J=5.2 Hz, 1H), 7.01 (d, J=7.6 Hz, 1H), 6.76-6.52 (m, 1H), 6.43 (d, J=16.7 Hz, 1H), 6.35-6.23 (m, 1H), 5.84 (dd, J=10.4, 1.8 Hz, 1H), 5.25-4.26 (m, 3H), 4.10-3.53 (m, 3H), 3.46-2.99 (m, 1H), 2.81-2.42 (m, 2H), 1.63-1.45 (m, 3H), 1.29-1.17 (m, 6H), 1.09-0.94 (m, 6H); MS: m/z 599.2931, $[M+H]^+$.

Example 20

5-9

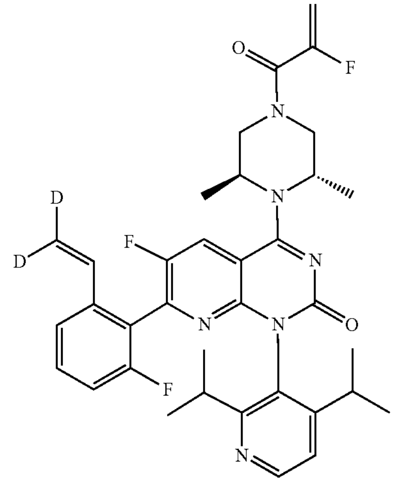

Referring to the preparation method of Example 3, Compound 5-9 was prepared by using methyl-$d_3$-triphenylphosphonium iodide instead of methyltriphenylphosphonium bromide and using fluorinated acrylic acid for the final amide bond construction. $R_f$: 0.54 (DCM:MeOH=10:1). The specific preparation method was as follows:

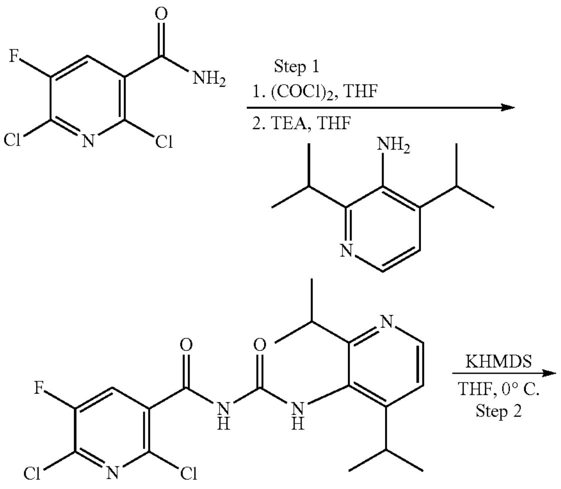

-continued

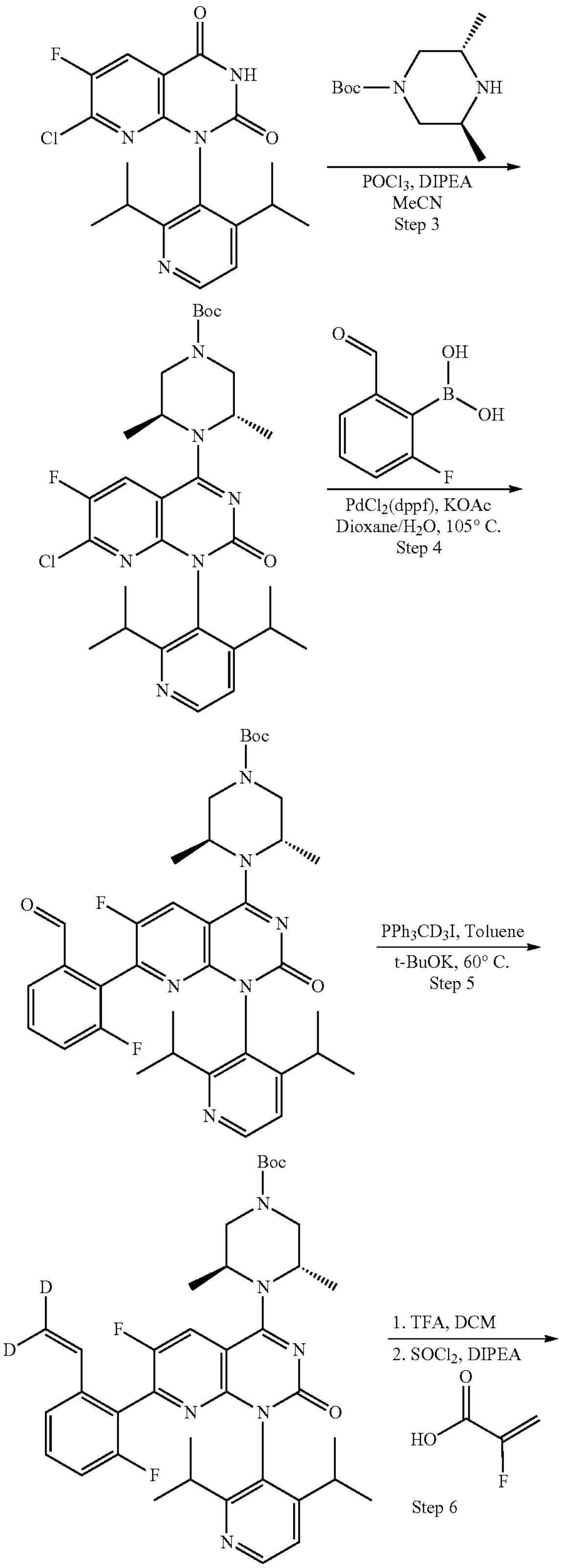

-continued

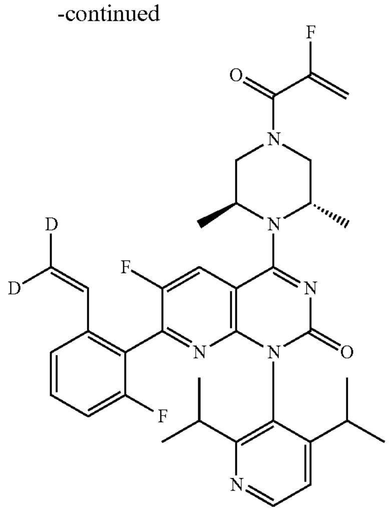

5-9

Step 1

2,6-Dichloro-5-fluoronicotinamide (4.3 g) and tetrahydrofuran (100 ml) were added into a 250 ml reaction flask, cooled to 0° C., dropwise added with oxalyl chloride (3.0 g), warmed to 70° C. after the addition and stirred for 1 h. The reaction solution was concentrated to dryness, cooled to 0° C., added with tetrahydrofuran (30 ml), dropwise added with a solution of 2,4-diisopropyl-3 -aminopyridine (3.0 g) in tetrahydrofuran (20 ml), then added with triethylamine (2.1 g), and stirred at room temperature for another 0.5 h after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 6.8 g of a white solid. MS: m/z 413.1, $[M+H]^+$.

Step 2

The product from the previous step (6.8 g) and tetrahydrofuran (60 ml) were added into a 250 ml reaction flask, cooled to 0° C., dropwise added with potassium bis(trimethylsilyl)amide (33 ml), and stirred at room temperature for 1 h after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 3.1 g of a yellow solid. MS: m/z 377.1, $[M+H]^+$.

Step 3

The product from the previous step (700 mg), tert-butyl-(3S,5S)-3,5-dimethylpiperazine-1-carboxylate (418 mg), acetonitrile (20 ml) and N,N-diisopropylethylamine (1.45 g) were added into a 100 ml single-necked flask, dropwise added with phosphoryl trichloride (570 mg) at room temperature, and stirred for another 30 min after the addition. The reaction solution was poured into water and extracted with ethyl acetate. The organic layers were combined, washed with saturated sodium chloride solution, dried over anhydrous sodium sulfate, filtered, concentrated under reduced pressure and purified by silica gel column chromatography to obtain 540 mg of a yellow solid. MS: m/z 573.3, $[M+H]^+$.

Step 4

The product from the previous step (200 mg), 2-fluoro-6-formylphenylboronic acid (88 mg), potassium acetate (103 mg), 1,4-dioxane (10 ml), water (1 ml) and [1,1'-bis (diphenylphosphino)ferrocene] palladium dichloride (51 mg) were added into a 50 ml single-necked flask, warmed to 105° C. after nitrogen gas replacement, and stirred for 2.5 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 193 mg of a yellow solid. MS: m/z 661.3, $[M+H]^+$.

Step 5

Methyl-$d_3$-triphenylphosphonium iodide (357 mg), potassium tert-butoxide (99 mg) and toluene (10 ml) were added into a 50 ml three-necked flask, warmed to 60° C. after nitrogen gas replacement, and stirred for 1 h. A solution of the product from the previous step (193 mg) in toluene (5 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 134 mg of a light-yellow solid. MS: m/z 661.4, $[M+H]^+$.

Step 6

The product from the previous step (134 mg) and dichloromethane (5 ml) were added into a 50 ml single-necked flask, dropwise added with trifluoroacetic acid (3 ml) at room temperature, and stirred at room temperature for 1.5 h after the addition. After the reaction, the reaction solution was cooled to 0° C., slowly added with saturated aqueous solution of sodium bicarbonate to adjust the pH to alkalescence and extracted with dichloromethane. The organic layers were combined, dried over anhydrous sodium sulfate, filtered, and concentrated under reduced pressure to dryness. A light-yellow solid was obtained. 2-Fluoroacrylic acid (28 mg) and dichloromethane (10 ml) were added into another flask, slowly dropwise added with sulfoxide chloride (44 mg), and stirred at room temperature for 30 min after the addition.

The concentrate was added with dichloromethane (10 ml) and N,N-diisopropylethylamine (129 mg), cooled to 0° C. under nitrogen gas protection, then slowly dropwise added with above prepared 2-fluoroacryloyl chloride, and stirred for 30 min after the addition. After the reaction, the resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 44 mg of an off-white solid. $^1H$ NMR (400 MHz, $CDCl_3$): δ 8.57 (dd, J=5.0, 0.9 Hz, 1H), 7.98 (d, J=8.1 Hz, 1H), 7.42-7.34 (m, 2H), 7.16 (dd, J=5.1, 1.6 Hz, 1H), 7.07-6.98 (m, 1H), 6.33-6.14 (m, 1H), 5.42 (dd, J=47.4, 3.5 Hz, 1H), 5.24 (dd, J=16.8, 3.5 Hz, 1H), 4.44-4.26 (m, 2H), 4.06-3.55 (m, 4H), 2.74-2.42 (m, 2H), 1.47-1.38 (m, 6H), 1.25-1.14 (m, 6H), 1.08-0.92 (m, 6H). MS: m/z 633.3132, $[M+H]^+$.

Example 21

5-11

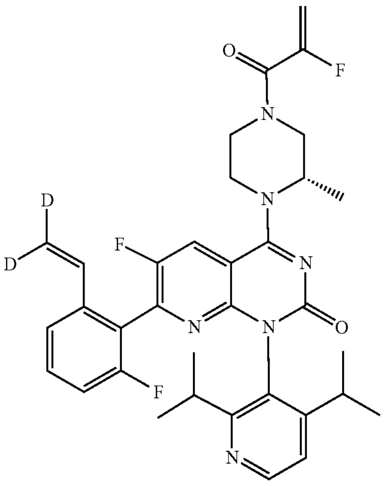

Referring to the preparation method of Example 3, Compound 5-11 was prepared by using methyl-$d_3$-triphenylphosphonium iodide instead of methyltriphenylphosphonium bromide and using fluorinated acrylic acid for the final amide bond construction. $R_f$: 0.53 (DCM:MeOH=10:1). The specific preparation method was as follows:

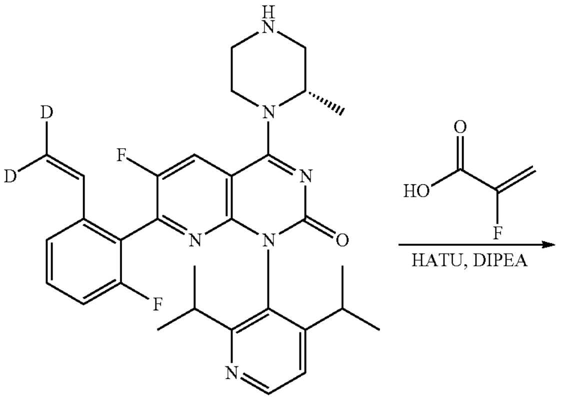

-continued

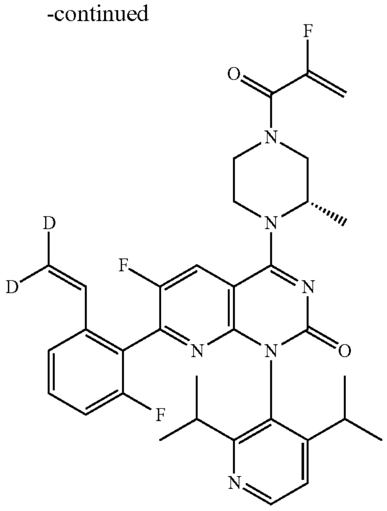

5-11

1-(2,4-Diisopropylpyridin-3-yl)-6-fluoro-7-(2-fluoro-6-(vinyl-2,2-$d_2$)phenyl)-4-((S)-2-methylpiperazin-1-yl)pyrido[2,3-d]pyrimidin-2(1H)-one (200 mg), dichloromethane (10 ml), 2-fluoroacrylic acid (50 mg, 0.56 mmol) and N,N-diisopropylethylamine (143 mg) were added into a 50 ml three-necked flask, stirred at room temperature for 10 min, then slowly added with 2-(7-azabenzotriazol-1-yl)-N,N,N',N'-tetramethyluronium hexafluorophosphate (156 mg), and stirred at room temperature to react for 1 h after the addition. The reaction solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 154 mg of a white solid. $^1H$ NMR (400 MHz, $CDCl_3$): δ 8.57 (d, J=5.1 Hz, 1H), 7.87 (d, J=8.3 Hz, 1H), 7.42-7.32 (m, 2H), 7.15 (d, J=5.1 Hz, 1H), 7.07-6.97 (m, 1H), 6.32-6.20 (m, 1H), 5.42 (dd, J=47.4, 3.5 Hz, 1H), 5.26 (dd, J=16.8, 3.6 Hz, 1H), 5.09-4.81 (m, 1H), 4.71-4.24 (m, 2H), 4.24-3.90 (m, 1H), 3.87-3.50 (m, 2H), 3.49-3.05 (m, 1H), 2.82-2.33 (m, 2H), 1.55 (d, J=5.6 Hz, 3H), 1.29-1.13 (m, 6H), 1.10-0.90 (m, 6H). MS: m/z 619.3006, $[M+H]^+$.

Example 22

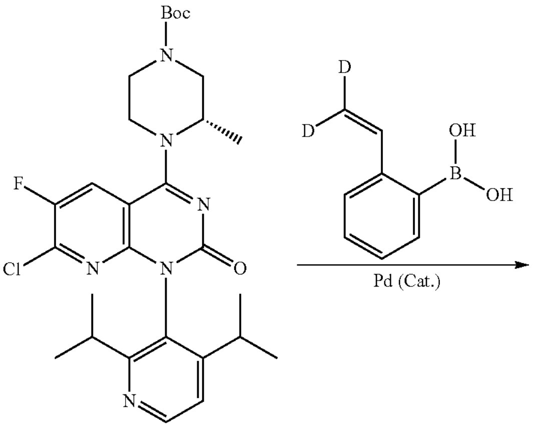

Intermediate 6

-continued

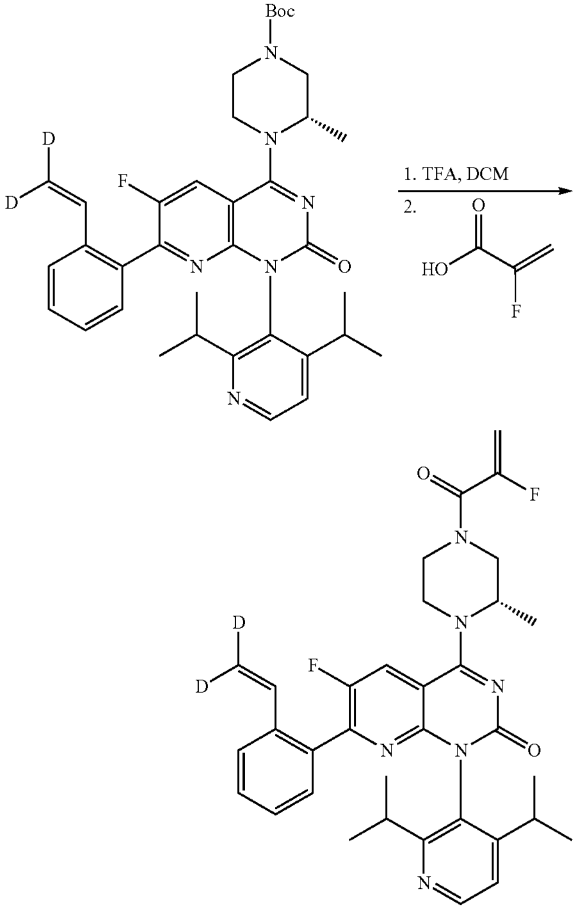

5-15

Referring to the preparation method of Example 1, Compound 5-15 was prepared by using fluorinated acrylic acid for the final amide bond construction. $R_f$: 0.54 (DCM:MeOH=10:1).

Example 23

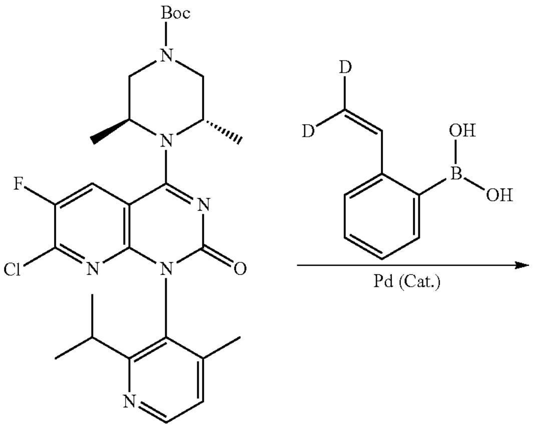

Intermediate 1

-continued

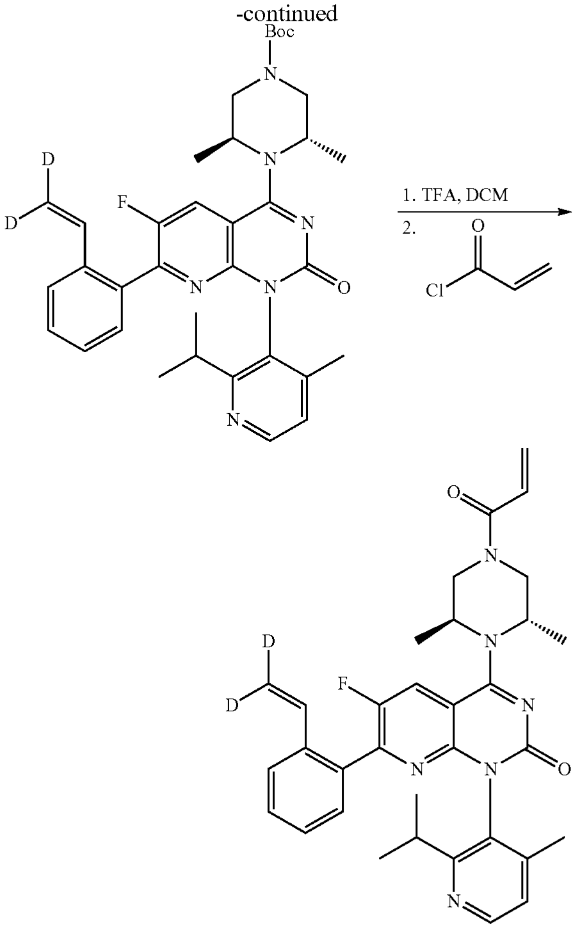

3-21

Referring to the preparation method of Example 1, Compound 3-21 was prepared by using acryloyl chloride for the final amide bond construction. $R_f$: 0.56 (DCM:MeOH=10:1). The specific preparation method was as follows:

Step 1

Tert-butyl-4-(6-fluoro-7-chloro-1-(2-isopropyl-4-methylpyridin-3-yl)-2-oxo-1,2-dihydropyrido[2,3-d]pyrimidin-4-yl)-dimethylpiperazine-1-carboxylate (Intermediate 1), cesium carbonate, toluene, [1,1'-bis(diphenylphosphino)ferrocene] palladium dichloride and 2-(6-vinyl-$d_2$-phenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7-8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 24

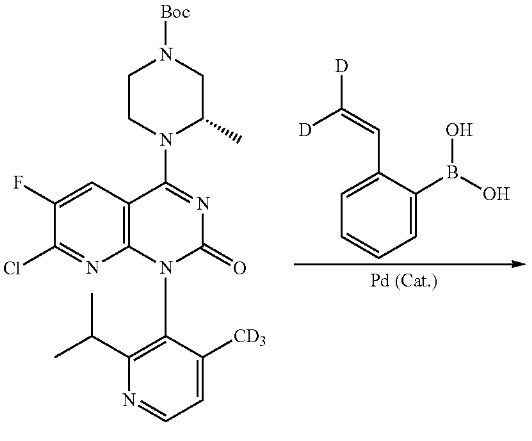

Intermediate 5

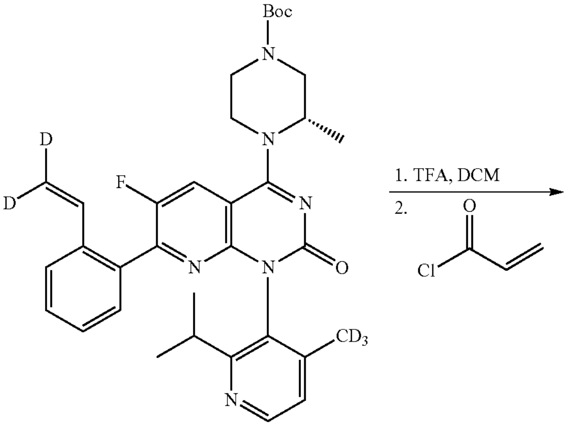

-continued

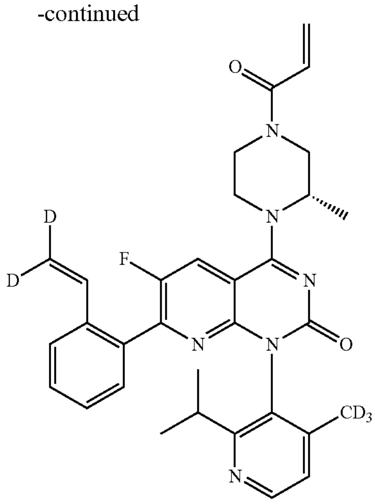

4-7

Referring to the preparation method of Example 1, Compound 4-7 was prepared by using acryloyl chloride for the final amide bond construction. $R_f$: 0.57 (DCM:MeOH=10:1). The specific preparation method was as follows:

Step 1

Tert-butyl-4-(6-fluoro-7-chloro-1-(2-isopropyl-4-methyl-$d_3$-pyridin-3-yl)-2-oxo-1,2-dihydropyrido[2,3-d]pyrimidin-4-yl)-dimethylpiperazine-1-carboxylate (Intermediate 5), cesium carbonate, toluene, [1,1'-bis(diphenylphosphino)ferrocene] palladium dichloride and 2-(6-vinyl-$d_2$-phenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7-8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of -acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 25

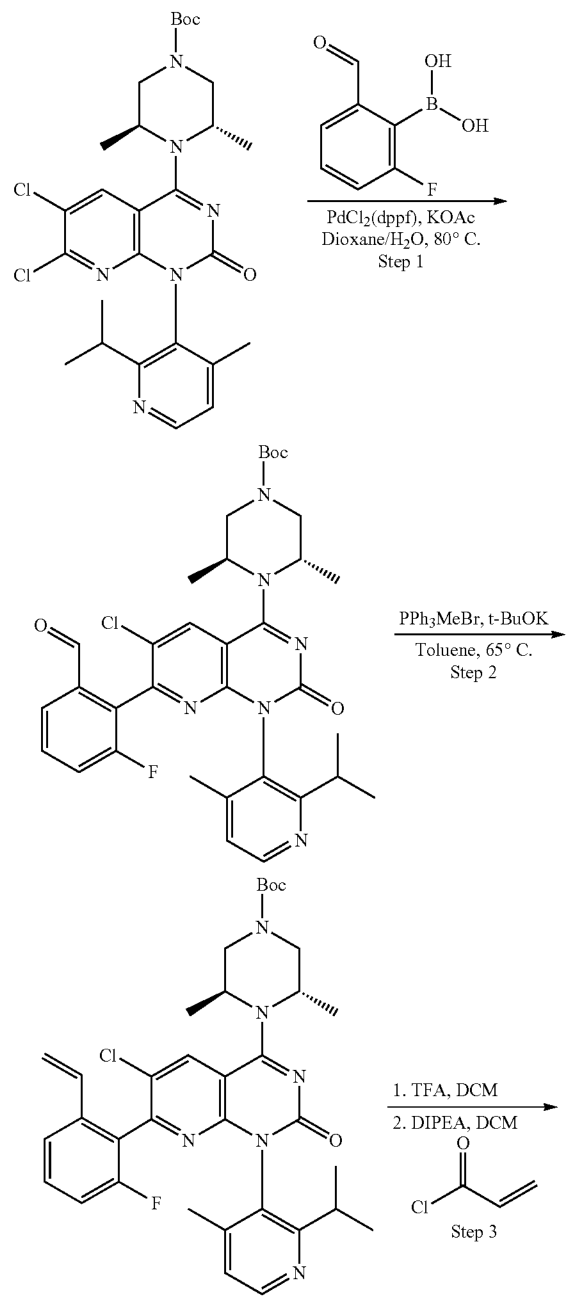

-continued

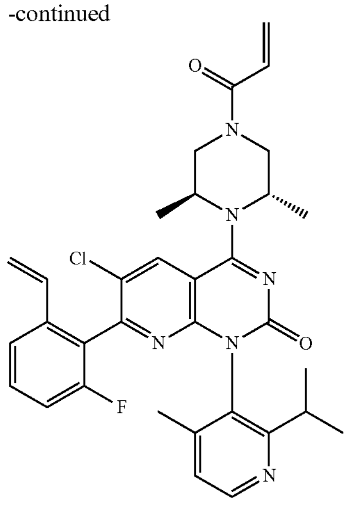

3-8

Step 1

Tert-butyl-(3S,5S)-4-(6,7-dichloro-1-(2-isopropyl-4-methylpyridin-3-yl)-2-oxo-1,2-dihydropyrido[2,3-d]pyrimidin-4-yl)-3,5-dimethylpiperazine-1-carboxylate (0.9 g), 2-fluoro-6-formylphenylboronic acid (405 mg), potassium acetate (473 mg), 1,4-dioxane (25 ml), water (4 ml) and [1,1'-bis(diphenylphosphino)ferrocene] palladium dichloride (117 mg) were added into a 100 ml single-necked flask, warmed to 80° C. after nitrogen gas replacement and stirred for 3 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 800 mg of a yellow solid. $^1$H NMR (400 MHz, $CDCl_3$): δ 9.77 (td, J=10.4, 1.5 Hz, 1H), 8.43 (d, J=4.9 Hz, 1H), 8.24 (dd, J=5.9, 1.7 Hz, 1H), 7.72-7.65 (m, 1H), 7.65-7.57 (m, 1H), 7.38 (td, J=8.6, 1.0 Hz, 1H), 7.09-6.99 (m, 1H), 4.43-4.22 (m, 2H), 3.92-3.74 (m, 2H), 3.74-3.40 (m, 2H), 2.78-2.61 (m, 1H), 2.02-1.92 (m, 3H), 1.52 (s, 9H), 1.46-1.40 (m, 3H), 1.40-1.34 (m, 3H), 1.23-1.17 (m, 3H), 1.04-0.92 (m, 3H). MS: m/z 649.3, $[M+H]^+$.

Step 2

Methyltriphenylphosphonium bromide (1.1 g), potassium tert-butoxide (344 mg) and toluene (30 ml) were added into a 50 ml three-necked flask, warmed to 65° C. after nitrogen gas replacement, and stirred for 1 h. A solution of the product from the previous step (800 mg) in toluene (10 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 600 mg of a light-yellow solid. $^1$H NMR (400 MHz, $CDCl_3$): δ 8.47 (d, J=4.8 Hz, 1H), 8.26 (d, J=3.0 Hz, 1H), 7.43-7.32 (m, 2H), 7.10-6.97 (m, 2H), 6.26-6.09 (m, 1H), 5.60 (dd, J=27.2, 17.4 Hz, 1H), 5.17 (dd, J=11.0, 5.7 Hz, 1H), 4.43-4.22 (m, 2H), 3.92-3.44 (m, 4H), 2.79-2.61 (m, 1H), 2.01 (d, J=9.1 Hz, 3H), 1.53 (s, 9H), 1.43 (t, J=6.1 Hz, 6H), 1.26-1.20 (m, 3H), 1.04 (dd, J=12.9, 6.8 Hz, 3H). MS: m/z 647.3, $[M+H]^+$.

Step 3

The product from the previous step (600 mg) and dichloromethane (10 ml) were added into a 50 ml single-necked flask, dropwise added with trifluoroacetic acid (10 ml) at 0° C., and stirred at room temperature for 1 h after the addition. After the reaction, the reaction solution was cooled to 0° C., slowly added with saturated aqueous solution of sodium bicarbonate to adjust the pH to alkalescence and extracted with dichloromethane. The organic layers were combined, dried over anhydrous sodium sulfate, filtered, and concentrated under reduced pressure to dryness. The concentrate was added with dichloromethane (30 ml) and N,N-diisopropylethylamine (0.8 ml), cooled to 0° C. under nitrogen gas protection, slowly dropwise added with acryloyl chloride (168 mg), and stirred for 30 min after the addition. After the reaction, the resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 430 mg of a yellow solid. $^1H$ NMR (400 MHz, $CDCl_3$): δ 8.47 (d, J=4.9 Hz, 1H), 8.26 (d, J=3.0 Hz, 1H), 7.42-7.30 (m, 2H), 7.11-6.94 (m, 2H), 6.70-6.55 (m, 1H), 6.48-6.34 (m, 1H), 6.25-6.09 (m, 1H), 5.82 (dd, J=10.4, 1.6 Hz, 1H), 5.67-5.51 (m, 1H), 5.21-5.10 (m, 1H), 4.50-4.27 (m, 2H), 4.08-3.54 (m, 4H), 2.77-2.57 (m, 1H), 2.04-1.94 (m, 3H), 1.50-1.34 (m, 6H), 1.26-1.16 (m, 3H), 1.07-0.97 (m, 3H). MS: m/z 601.2556, $[M+H]^+$.

Example 26

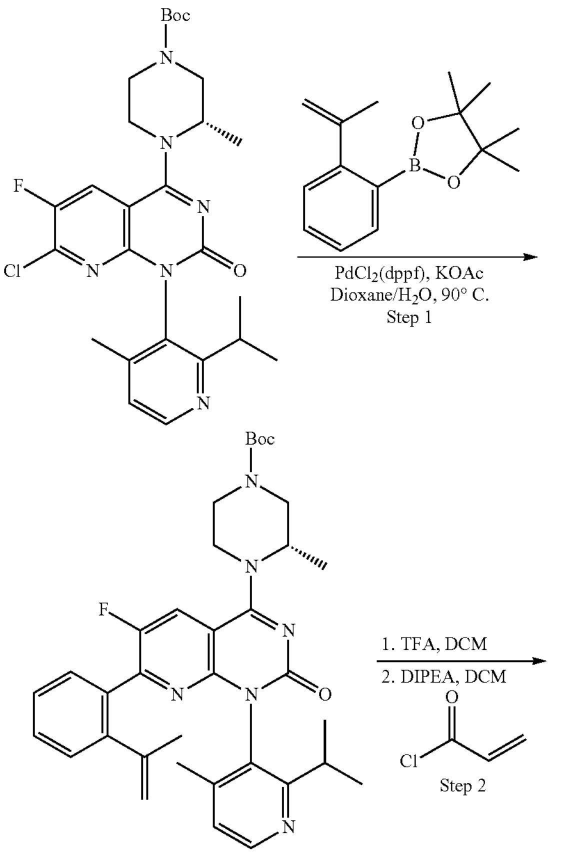

-continued

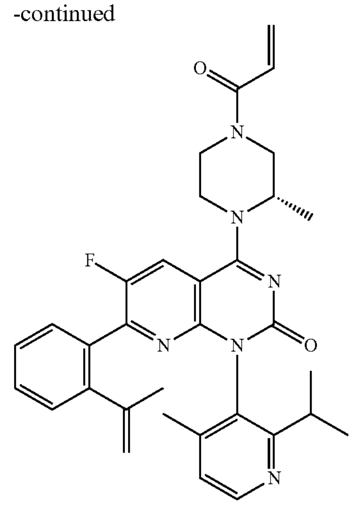

3-1a

Step 1

Tert-butyl-(S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (2.23 g), 2-isopropenylphenylboronic acid pinacol ester (1.2 g), potassium acetate (2.3 g), 1,4-dioxane (50 ml), water (2.5 ml) and [1,1'-bis(diphenylphosphino)ferrocene] palladium dichloride (307 mg) were added into a 100 ml single-necked flask, warmed to 90° C. after nitrogen gas replacement and stirred for 3 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 830 mg of a light colour solid. MS: m/z 613.3, $[M+H]^+$.

Step 2

The product from the previous step (830 mg), dichloromethane (20 ml) and trifluoroacetic acid (5 ml) were added into a 50 ml single-necked flask and stirred at room temperature for 1 h after the addition. After the reaction, the reaction solution was cooled to 0° C., slowly added with saturated aqueous solution of sodium bicarbonate to adjust the pH to alkalescence and extracted with dichloromethane. The organic layers were combined, dried over anhydrous sodium sulfate, filtered, and concentrated under reduced pressure to dryness. The concentrate was added with dichloromethane (30 ml) and N,N-diisopropylethylamine (476 mg), cooled to 0° C. under nitrogen gas protection, slowly dropwise added with a solution of acryloyl chloride (121 mg) in dichloromethane (5 ml), and stirred for 30 min after the addition. After the reaction, the resulting solution was diluted with water and extracted with dichloromethane. The organic layers were combined, washed once with saturated salt solution, dried over anhydrous sodium sulfate, filtered, concentrated under reduced pressure and purified by silica gel column chromatography to obtain 520 mg of a light-yellow solid. $^1H$ NMR (400 MHz, $CDCl_3$): δ 8.48 (d, J=4.9 Hz, 1H), 7.58-7.48 (m, 1H), 7.17 (d, J=7.2 Hz, 1H), 7.14-7.08 (m, 2H), 6.98 (d, J=4.9 Hz, 1H), 6.92-6.84 (m, 2H), 6.73-6.51 (m, 1H), 6.48-6.35 (m, 2H), 5.80 (dd, J=10.4, 1.8 Hz, 1H), 5.20-4.34 (m, 2H), 4.20-3.40 (m, 4H), 3.34-2.89 (m, 1H), 2.60-2.36 (m, 1H), 2.20 (d, J=1.2 Hz, 3H), 1.86-

1.79 (m, 3H), 1.35-1.22 (m, 3H), 1.19-1.11 (m, 3H), 1.10-1.01 (m, 3H). MS: m/z 567.2929, [M+H]+.

Example 27

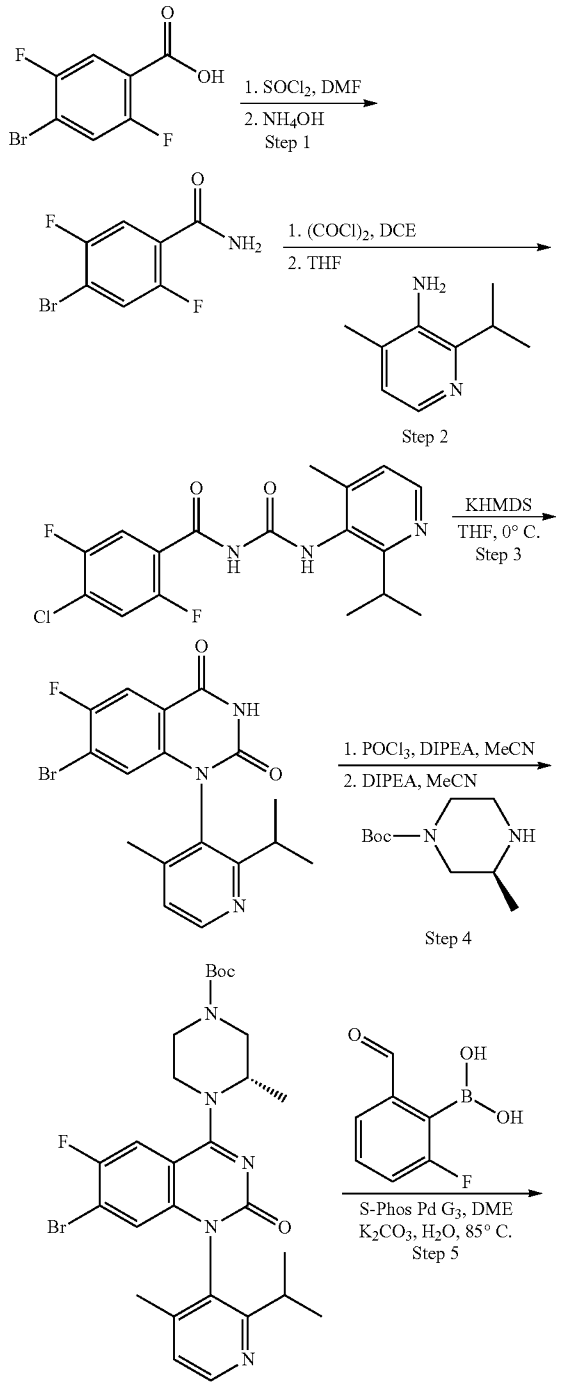

-continued

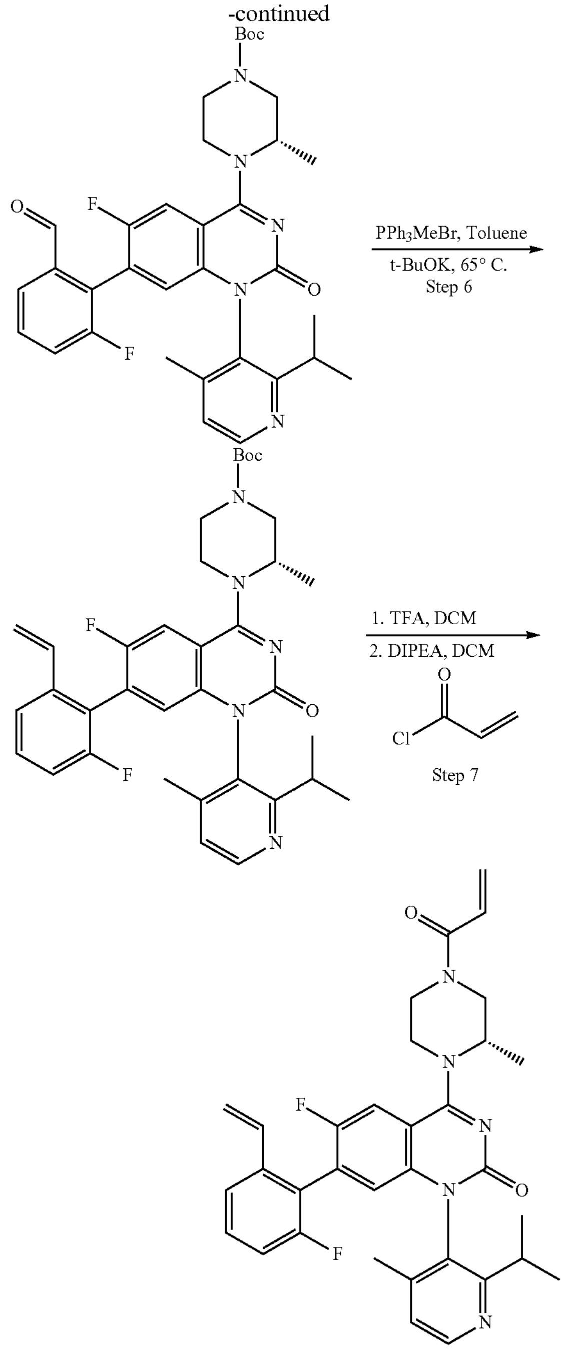

3-3Ca

4-Bromo-2,5-difluorobenzoic acid (50.0 g), thionyl chloride (150 ml) and N,N-dimethylformamide (0.5 ml) were added into a 1000 ml reaction flask, warmed to 70° C. after the addition and stirred for 1 h. The obtained mixture was concentrated under reduced pressure and subjected to azeotropy with toluene twice. The residue was added with 1,4-dioxane (500 ml), cooled to 0-5° C., dropwise added with aqueous ammonia (200 ml), and stirred for another 1 h after the addition while the temperature was maintained at 0° C. After the reaction, the reaction solution was added with saturated aqueous solution of ammonium chloride (200 ml), stirred for 10 min, and extracted with ethyl acetate. The organic phases were combined, washed once with saturated salt solution, dried over anhydrous sodium sulfate, filtered, and concentrated under reduced pressure to obtain 48.5 g of an off-white solid, which was directly used for the next reaction step. MS: m/z 236.0, $[M+H]^+$.

Step 2

The product from the previous step (48.5 g) and 1,2-dichloroethane (800 ml) were added into a 2000 ml reaction flask, cooled to 0° C., dropwise added with a solution of oxalyl chloride (31.3 g) in dichloromethane (200 ml), warmed to 45° C. after the addition and stirred for 1 h. The reaction solution was concentrated to dryness and subjected to azeotropy with toluene twice. The residue was added with tetrahydrofuran (400 ml), cooled to 0° C., dropwise added with a solution of 2-isopropyl-4-methylpyridin-3-amine (32.4 g) in tetrahydrofuran (150 ml), and stirred for another 16 h after the addition. After the reaction, the reaction solution was concentrated under reduced pressure to obtain an off-white solid, which was added with ethyl acetate (250 ml) and subjected to recrystallization to give 38.0 g of a white solid. $^1$H NMR (400 MHz, DMSO-$d_6$): δ 11.19 (s, 1H), 9.72 (s, 1H), 8.35 (d, J=4.8 Hz, 1H), 7.96 (dd, J=9.2, 5.5 Hz, 1H), 7.84 (dd, J=8.4, 5.9 Hz, 1H), 7.17 (d, J=4.9 Hz, 1H), 3.35-3.23 (m, 1H), 2.22 (s, 3H), 1.17 (d, J=6.8 Hz, 6H). MS: m/z 412.1, $[M+H]^+$.

Step 3

The product from the previous step (33.3 g) and tetrahydrofuran (1000 ml) were added into a 2000 ml single-necked flask, cooled to 0° C., dropwise added with potassium bis(trimethylsilyl)amide (202.0 ml), rewarmed to 10° C.~15° C. after the addition and stirred for 2 h. After the reaction, the reaction solution was poured into saturated aqueous solution of ammonium chloride and extracted with ethyl acetate. The organic layers were combined, washed once with saturated salt solution, dried over anhydrous sodium sulfate, filtered, and concentrated under reduced pressure. The residue was added with ethyl acetate (400 ml), heated to reflux for 30 min, naturally cooled to room temperature, and filtered. The filter cake was dried to obtain 16.0 g of a white solid. $^1$H NMR (400 MHz, $CDCl_3$): δ 8.94 (br s, 1H), 8.70 (d, J=4.8 Hz, 1H), 8.00 (d, J=7.5 Hz, 1H), 7.26 (d, J=4.8 Hz, 1H), 6.62 (d, J=5.2 Hz, 1H), 2.90-2.73 (m, 1H), 2.15 (s, 3H), 1.24 (d, J=6.7 Hz, 3H), 1.17 (d, J=6.7 Hz, 3H). MS: m/z 392.0, $[M+H]^+$.

Step 4

The product from the previous step (10.0 g), acetonitrile (300 ml) and N,N-diisopropylethylamine (19.8 g) were added into a 1000 ml single-necked flask, cooled to 0° C., dropwise added with phosphorus oxychloride (23.5 g), warmed to 80° C. after the addition and stirred for 1 h. The obtained mixture was concentrated under reduced pressure to dryness. The residue was added with acetonitrile (300 ml), cooled to 0° C., added with N,N-diisopropylethylamine (40.0 g), then dropwise added with a solution of (S)-4-N-tert-butoxycarbonyl-2-methylpiperazine (5.4 g, 27 mmol) in dichloromethane (60 ml), and stirred after the addition. After the reaction, the reaction solution was poured into saturated aqueous solution of ammonium chloride and extracted with ethyl acetate. The organic layers were combined, washed once with saturated salt solution, dried over anhydrous sodium sulfate, filtered, concentrated under reduced pressure and purified by silica gel column chromatography to obtain 13.0 g of an off-white solid. $^1$H NMR (400 MHz, DMSO-$d_6$): δ 8.58 (d, J=4.9 Hz, 1H), 7.83 (dd, J=9.2, 2.1 Hz, 1H), 7.36 (d, J=4.9 Hz, 1H), 6.56 (dd, J=5.9, 1.0 Hz, 1H), 4.76 (s, 1H), 4.18-3.89 (m, 2H), 3.82 (d, J=13.0 Hz, 1H), 3.66-3.52 (m, 1H), 3.38-2.97 (m, 2H), 2.66-2.54 (m, 1H), 1.96 (d, J=4.3 Hz, 3H), 1.45 (s, 9H), 1.30 (dd, J=6.5, 2.4 Hz, 3H), 1.06 (dd, J=6.7, 2.8 Hz, 3H), 1.02 (dd, J=6.7, 2.9 Hz, 3H). MS: m/z 574.2, $[M+H]^+$.

Step 5

The product from the previous step (2.6 g), 2-fluoro-6-formylbenzeneboronic acid (907 mg), potassium carbonate (1.9 g, 13.7 mmol), ethylene glycol dimethyl ether (30 ml), water (6 ml), SPhos Pd G3 (390 mg) and S-Phos (185 mg) were added into a 100 ml single-necked flask, warmed to 85° C. after nitrogen gas replacement, and stirred for 16 h. After the reaction, the resulting solution was diluted with water and extracted with ethyl acetate. The organic layers were combined, washed once with saturated salt solution, dried over anhydrous sodium sulfate, filtered, concentrated under reduced pressure and purified by silica gel column chromatography to obtain 1.9 g of a yellow solid. $^1$H NMR (400 MHz, $CDCl_3$): δ 9.84 (d, J=5.4 Hz, 1H), 8.58 (d, J=4.8 Hz, 1H), 7.78 (d, J=7.7 Hz, 1H), 7.66-7.53 (m, 2H), 7.42 (t, J=8.6 Hz, 1H), 7.18 (dd, J=9.8, 4.9 Hz, 1H), 6.37 (t, J=6.6 Hz, 1H), 5.05-4.76 (m, 1H), 4.46-3.86 (m, 3H), 3.85-3.57 (m, 1H), 3.48-3.03 (m, 2H), 2.91-2.73 (m, 1H), 2.12-2.05 (m, 3H), 1.57-1.46 (m, 3H), 1.54 (s, 9H), 1.29-1.22 (m, 3H), 1.18-1.03 (m, 3H). MS: m/z 618.3, $[M+H]^+$.

Step 6

Methyltriphenylphosphonium bromide (2.0 g), potassium tert-butoxide (620 mg) and toluene (60 ml) were added into a 100 ml three-necked flask, warmed to 65° C. under nitrogen gas protection and stirred, then dropwise added with a solution of the product from the previous step (1.9 g) in toluene (20 ml) and stirred for another 30 min after the addition. After the reaction, the reaction solution was poured into saturated aqueous solution of ammonium chloride and extracted with ethyl acetate. The organic layers were combined, washed once with saturated salt solution, dried over anhydrous sodium sulfate, filtered, concentrated under reduced pressure and purified by silica gel column chromatography to obtain 1.6 g of a light-yellow solid. MS: m/z 616.3, $[M+H]^+$.

Step 7

The product from the previous step (1.6 g) and dichloromethane (20 ml) were added into a 50 ml single-necked flask, dropwise added with trifluoroacetic acid (20 ml) at 0° C.~5° C. and rewarmed to 15° C.~20° C. for stirring after the addition. After the reaction, the reaction solution was concentrated to dryness. The residue was added with dichloromethane (20 ml), cooled to 0° C., added with N,N-diisopropylethylamine (2.6 ml), then slowly dropwise added with a solution of acryloyl chloride (353 mg) in dichloromethane (3 ml), and stirred for 30 min after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate, and filtered. The filtrate was concentrated and purified by silica gel column chromatography to obtain 280 mg of a white solid. $^1$H NMR (400 MHz, $CDCl_3$): δ 8.56 (dd, J=4.9, 2.7 Hz, 1H), 7.56 (d, J=9.1 Hz, 1H), 7.45-7.33 (m, 2H), 7.15 (t, J=5.1 Hz, 1H), 7.09-7.00 (m, 1H), 6.75-6.52 (m, 1H), 6.42 (d, J=16.8 Hz, 1H), 6.37-6.21 (m, 2H), 5.82 (dd, J=10.5, 1.7 Hz, 1H), 5.66 (dd, J=17.3, 10.0 Hz, 1H), 5.21 (dd, J=11.0, 5.0 Hz, 1H), 5.16-4.23 (m, 3H), 4.10-3.48 (m, 3H), 3.41-2.99 (m, 1H), 2.82 (br s, 1H), 2.11-2.00 (m, 3H), 1.61-1.40 (m, 3H), 1.28-1.19 (m, 3H), 1.14-1.04 (m, 3H). MS: m/z 570.2669, $[M+H]^+$.

Example 28

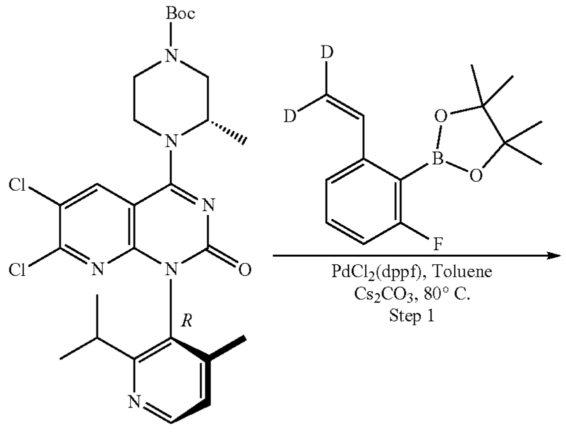

Intermediate 3M

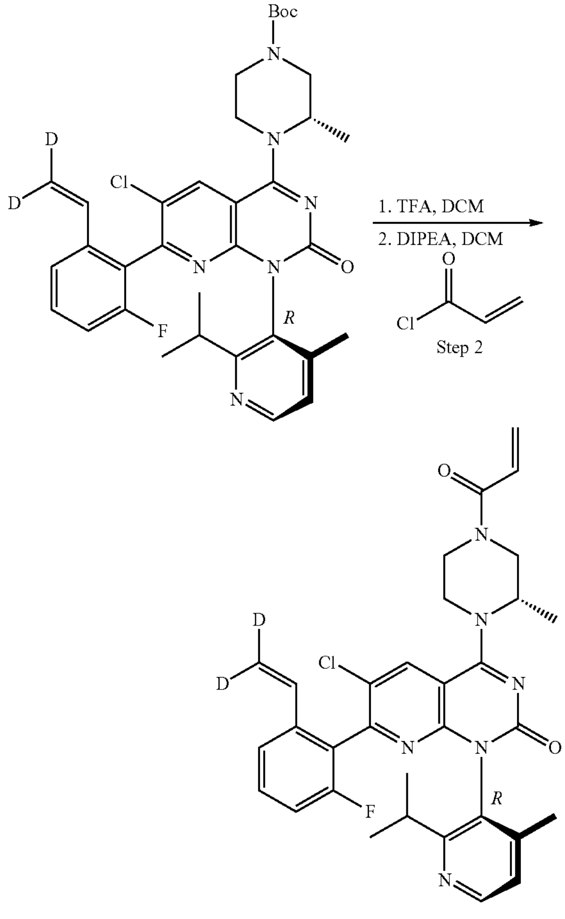

3-12M

Step 1

Tert-butyl-(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (Intermediate 3M) (824 mg), cesium carbonate (1.5 g), toluene (30 ml), [1,1'-bis(diphenylphosphino)ferrocene]palladium dichloride (110 mg) and 2-(2-fluoro-6-(vinyl-2,2-$d_2$)phenyl)-4,4,5,5-tetramethyl-1,3,2-dioxaborinane (45 mg) were added into a 100 ml single-necked flask, inside which nitrogen gas replacement was performed after the addition. The resulting mixture was warmed to 80° C. to react for 8 h. The reaction solution was poured into 50 ml of water, and the obtained solution was extracted with 50 ml of ethyl acetate. The organic layer was separated, dried over anhydrous sodium sulfate, filtered, concentrated under reduced pressure and purified by silica gel column chromatography to obtain 340 mg of a yellow solid. MS: m/z 635.3, $[M+H]^+$.

Step 2

The product from the previous step (340 mg) and dichloromethane (15 ml) were added into a 50 ml single-necked flask, dropwise added with trifluoroacetic acid (3.75 ml) at room temperature, and reacted at room temperature for 2 h after the addition. After the reaction, the reaction solution was cooled to 0° C., slowly added with saturated aqueous solution of sodium bicarbonate to adjust the pH to 7-8 and extracted with dichloromethane. The organic phases were combined, dried over anhydrous sodium sulfate, filtered, and concentrated under reduced pressure to dryness. The residue was added with dichloromethane (10 ml) and N,N-diisopropylethylamine (138 mg), cooled down by ice bath, slowly dropwise added with a solution of acryloyl chloride (50 mg) in dichloromethane (5 ml), and continued to react for 30 min after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain 170 mg of a yellow solid, which was then prepared and purified to give 100 mg of an off-white solid. $^1H$ NMR (400 MHz, $CDCl_3$): δ 8.48 (d, J=4.9 Hz, 1H), 8.15 (s, 1H), 7.43-7.32 (m, 2H), 7.06 (t, J=5.2 Hz, 1H), 7.05-6.97 (m, 1H), 6.75-6.54 (m, 1H), 6.44 (d, J=16.6 Hz, 1H), 6.17 (d, J=5.6 Hz, 1H), 5.84 (dd, J=10.4, 1.8 Hz, 1H), 5.33-4.22 (m, 3H), 4.12-3.52 (m, 3H), 3.46-2.99 (m, 1H), 2.91-2.60 (m, 1H), 2.06-1.93 (m, 3H), 1.59-1.41 (m, 3H), 1.27-1.18 (m, 3H), 1.10-0.97 (m, 3H). MS: m/z 589.2511, $[M+H]^+$. The specific rotation was +94.200 (determined according to Chinese Pharmacopoeia, 2020 Edition, Volume IV, General chapter 0621). The HPLC retention time (RT) was 13.6 min (column: CHIRALPAK IC (4.6×250 mm, 5 μm), mobile phase: ethanol-tert-butyl methyl ether (70:30), column temperature: 35° C., flow rate: 0.5 ml/min).

Example 28-2

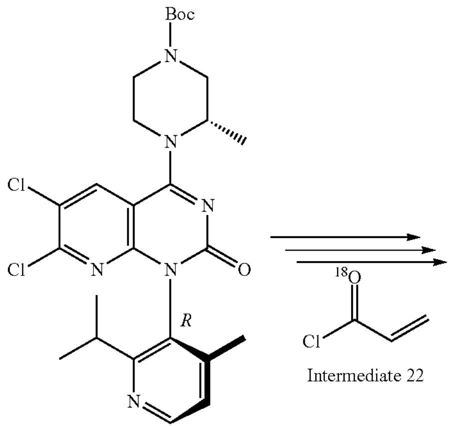

Intermediate 3M

Intermediate 22

-continued

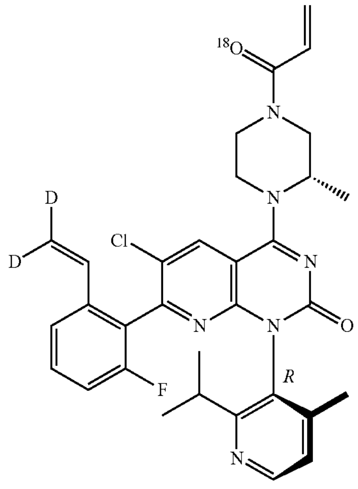

3-9MIS

-continued

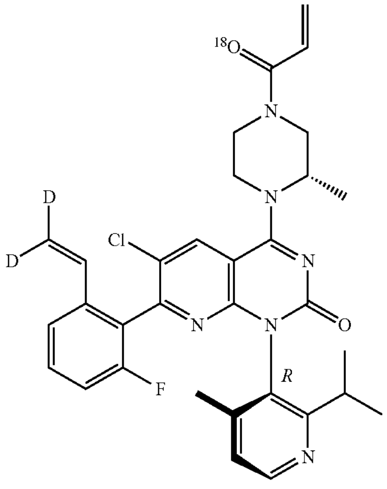

3-9MIS

Referring to the method of Example 28, Compound 3-9MIS was prepared by using Intermediate 3M and Intermediate 22 as the raw materials. $R_f$: 0.56 (DCM:MeOH=10:1). The specific preparation method was as follows:

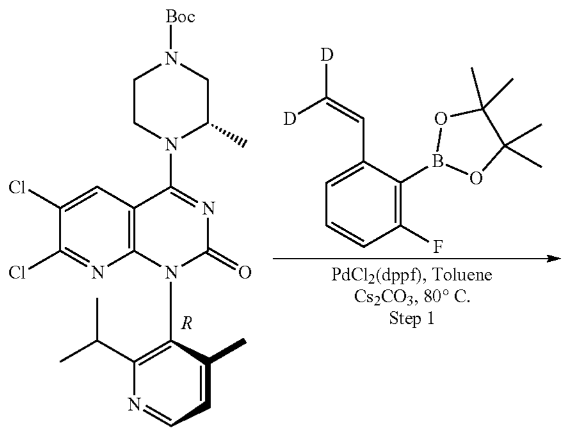

Intermediate 3M

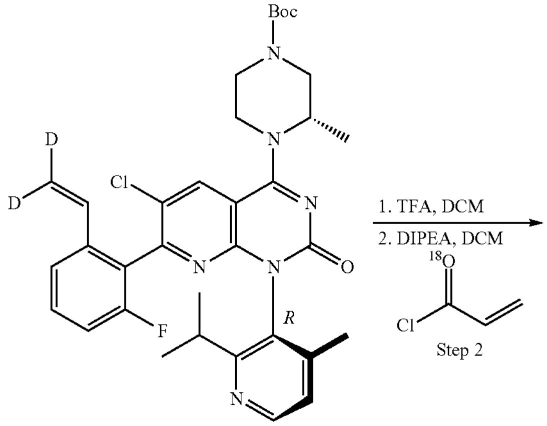

Step 1

Tert-butyl-(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (Intermediate 3M) (500 mg), cesium carbonate (1.0 g), toluene (30 ml), [1,1'-bis(diphenylphosphino)ferrocene]palladium dichloride (100 mg) and 2-(2-fluoro-6-(vinyl-2,2-$d_2$)phenyl)-4,4,5,5-tetramethyl-1,3,2-dioxaborinane (50 mg) were added into a single-necked flask, inside which nitrogen gas replacement was performed after the addition. The resulting mixture was warmed to 80° C. for reaction. The reaction solution was poured into 50 ml of water, and the obtained solution was extracted with 50 ml of ethyl acetate. The organic layer was separated, dried over anhydrous sodium sulfate, filtered, concentrated under reduced pressure and purified by silica gel column chromatography to obtain 240 mg of a yellow solid, which was directly used for the next reaction step.

Step 2

The product from the previous step (240 mg) and dichloromethane (15 ml) were added into a 50 ml single-necked flask, dropwise added with trifluoroacetic acid (2.5 ml) at room temperature, and reacted at room temperature after the addition. After the reaction, the reaction solution was cooled to 0° C., slowly added with saturated aqueous solution of sodium bicarbonate to adjust the pH to 7-8 and extracted with dichloromethane. The organic phases were combined, dried over anhydrous sodium sulfate, filtered, and concentrated under reduced pressure to dryness. The residue was added with dichloromethane (10 ml) and N,N-diisopropylethylamine (150 mg), cooled down by ice bath, slowly dropwise added with a solution of O-18 labeled acryloyl chloride (60 mg) in dichloromethane (5 ml), and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain 87 mg of an off-white solid. MS: m/z 591.2515, $[M+H]^+$.

Example 28-3

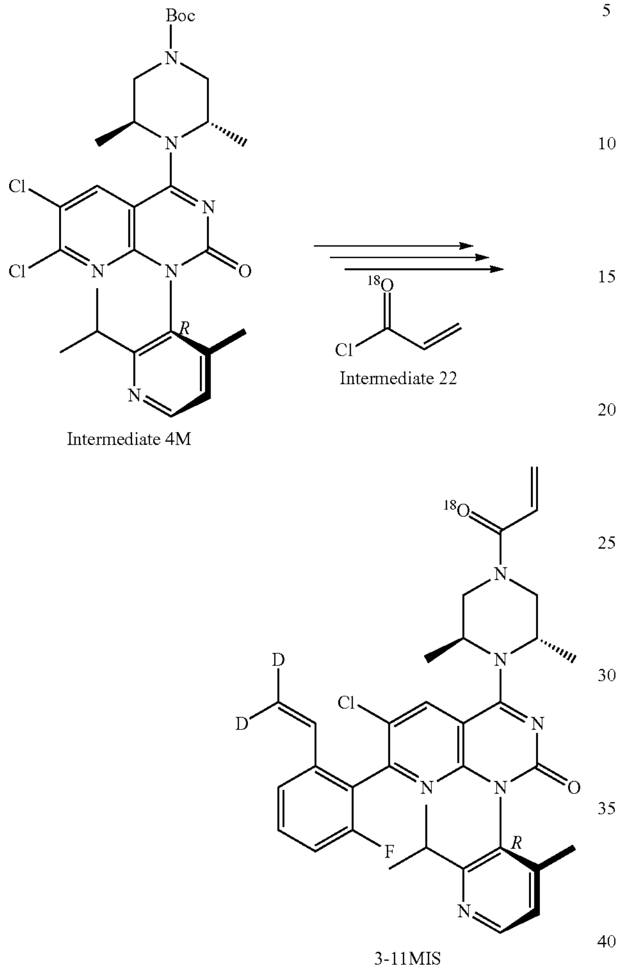
Intermediate 4M
Intermediate 22
3-11MIS

Referring to the method of Example 28, Compound 3-11MIS was prepared by using Intermediate 4M and Intermediate 22 as the raw materials. $R_f$: 0.57 (DCM:MeOH=10:1). The specific preparation method was as follows:

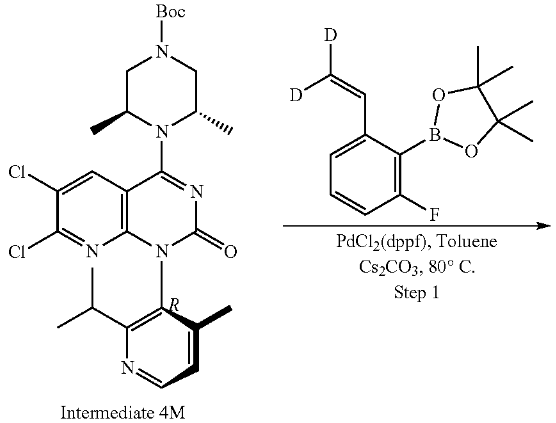

Intermediate 4M

-continued

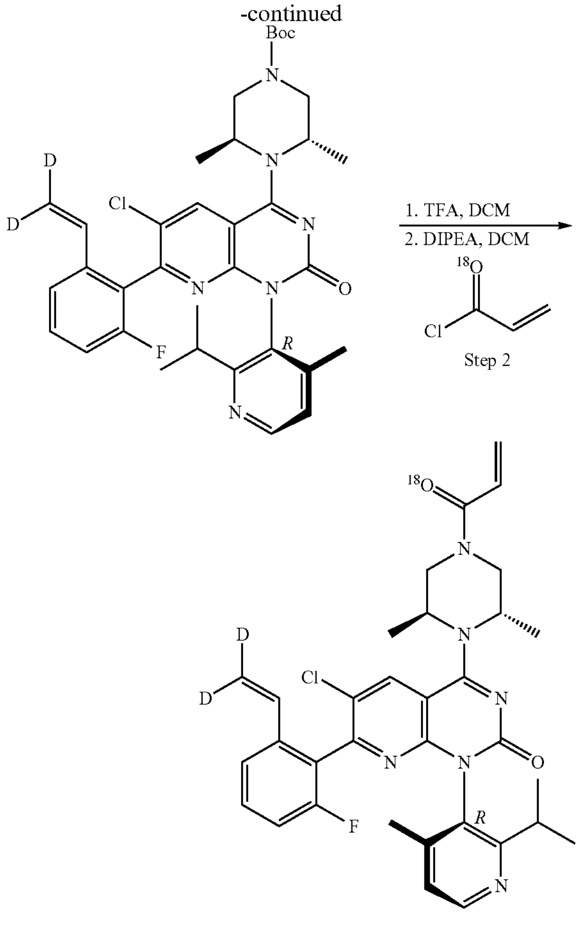

3-11MIS

Step 1

Tert-butyl-4-(6,7-dichloro-1-(2-isopropyl-4-methylpyridin-3-yl)-2-oxo-1,2-dihydropyrido[2,3-d]pyrimidin-4-yl)-dimethylpiperazine-1-carboxylate (Intermediate 4M), cesium carbonate, toluene, [1,1'-bis(diphenylphosphino)ferrocene] palladium dichloride and 2-(2-fluoro-6-(vinyl-2,2-$d_2$)phenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7~8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of O-18 labeled acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 28-4

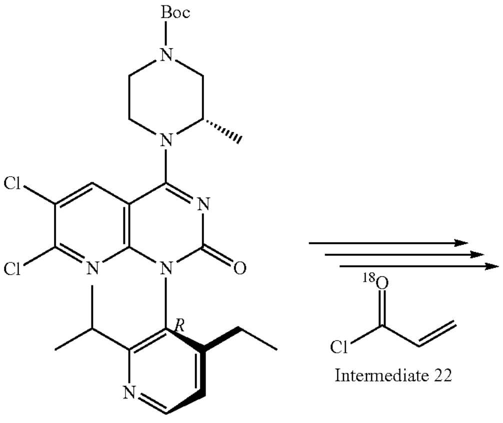

Intermediate 5M

Intermediate 22

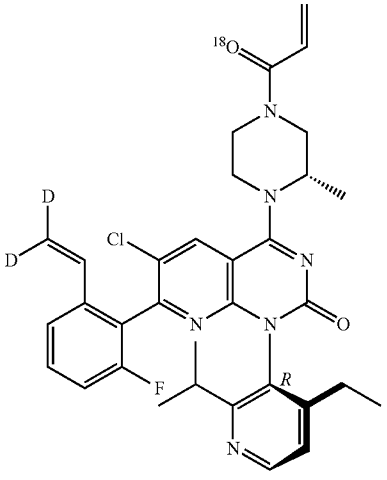

3-12MIS

Referring to the method of Example 28, Compound 3-12MIS was prepared by using Intermediate 5M and Intermediate 22 as the raw materials. $R_f$: 0.55 (DCM:MeOH=10:1). The specific preparation method was as follows:

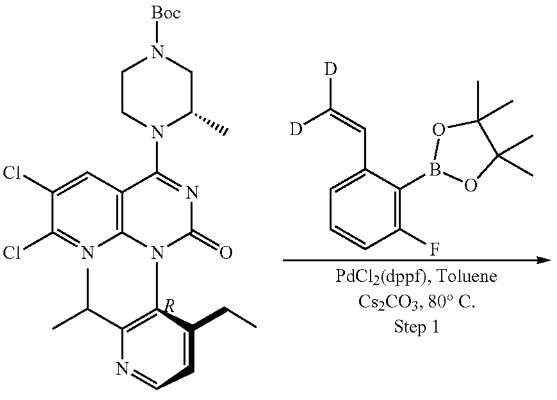

Intermediate 5M

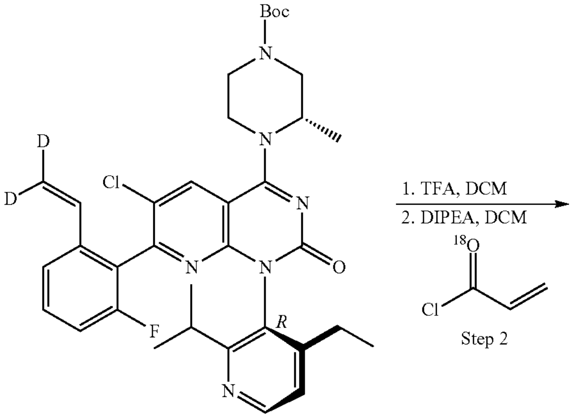

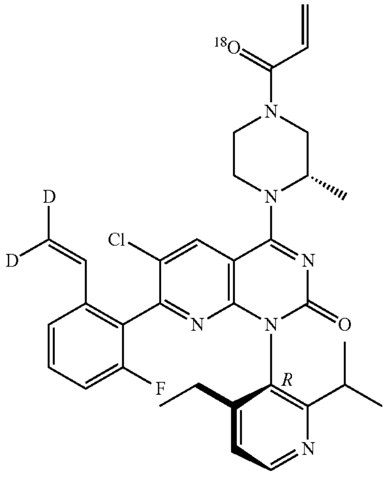

3-12MIS

Step 1

Tert-butyl-4-(6,7-dichloro-1-(2-isopropyl-4-ethylpyridin-3-yl)-2-oxo-1,2-dihydropyrido[2,3-d]pyrimidin-4-yl)-3-methylpiperazine-1-carboxylate (Intermediate 5M), cesium carbonate, toluene, [1,1'-bis(diphenylphosphino)ferrocene] palladium dichloride and 2-(2-fluoro-6-(vinyl-2,2-$d_2$)phenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7~8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of O-18 labeled acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 28-1P

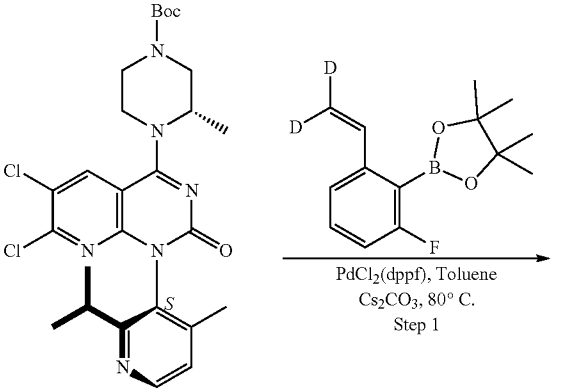

Intermediate 3P

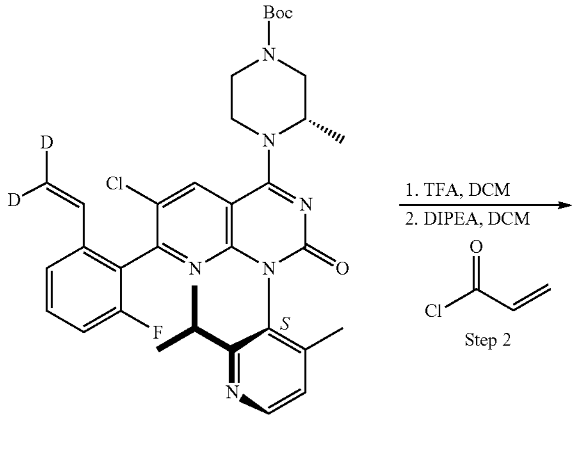

-continued

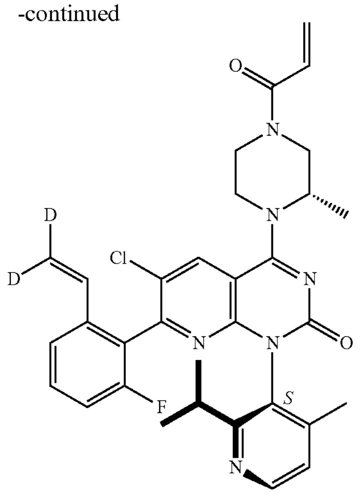

3-12P

Step 1

Tert-butyl-(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (6.1 g), potassium trifluoro-(2-fluoro-6-(vinyl-2,2-$d_2$)phenyl)borate (3.84 g), toluene (300 ml) and water (15 ml) were added into a 500 ml reaction flask, added with barium hydroxide octahydrate (14.1 g) and 1,1-bis(diphenylphosphino)ferrocene palladium dichloride dichloromethane complex (906 mg) after nitrogen gas replacement, and then warmed to 50° C. for reaction after nitrogen gas replacement for three times. After the reaction, the reaction solution was washed with subsaturated salt solution, and reextracted once with ethyl acetate. The organic phases were combined, dried over anhydrous sodium sulfate, and subjected to silica gel column chromatography to obtain 4.3 g of a product.

Step 2

Tert-butyl-(3S)-4-(6-chloro-7-(2-fluoro-6-(vinyl-2,2-$d_2$)phenyl)-1-(2-isopropyl-4-methylpyridin-3-yl)-2-oxo-1,2-dihydropyrido[2,3-d]pyrimidin-4-yl)-3-methylpiperazine-1-carboxylate (4.3 g) and dichloromethane (56 ml) were added into a 100 ml reaction flask, cooled to 0° C. under nitrogen gas protection, dropwise added with trifluoroacetic acid (15 ml), and rewarmed to room temperature for reaction after the addition. The reaction solution was added with saturated aqueous solution of sodium bicarbonate to adjust the pH to about 9, stirred and extracted with dichloromethane for three times. The organic phases were combined, washed once with saturated salt solution, dried over anhydrous sodium sulfate and concentrated under reduced pressure.

The residue was added with dichloromethane (40 ml) and DIPEA (10 ml), cooled to 0° C. under nitrogen gas protection, dropwise added with acryloyl chloride (871 mg), and subjected to heat preservation reaction after the addition. The reaction was quenched by adding saturated aqueous solution of ammonium chloride (30 ml), and the obtained solution was stirred at room temperature, and extracted with dichloromethane for three times. The organic phases were combined, washed once with saturated salt solution, dried over anhydrous sodium sulfate, subjected to rotary evaporation to remove the solvent and then subjected to silica gel column chromatography to obtain 2.46 g of a product. $^1$HNMR (400 MHz, Chloroform-d) δ 8.43 (dd, J=5.0, 2.2 Hz, 1H), 8.14 (s, 1H), 7.32 (tt, J=6.1, 3.7 Hz, 2H), 7.06-6.94 (m, 2H), 6.71-6.54 (m, 1H), 6.40 (d, J=16.7 Hz, 1H), 6.14 (d, J=6.0 Hz, 1H), 5.80 (dd, J=10.5, 1.9 Hz, 1H), 4.96-4.69 (m, 1H), 4.56-4.25 (m, 2H), 3.78 (dt, J=80.4, 17.6 Hz, 3H), 3.40-3.01 (m, 1H), 2.84-2.63 (m, 1H), 1.99 (t, J=9.0 Hz, 3H), 1.54-1.40 (m, 3H), 1.21 (dd, J=9.1, 4.1 Hz, 3H), 1.01 (dt, J=11.3, 5.5 Hz, 3H). MS: m/z 589.2515 [M+H]+.

Example 29

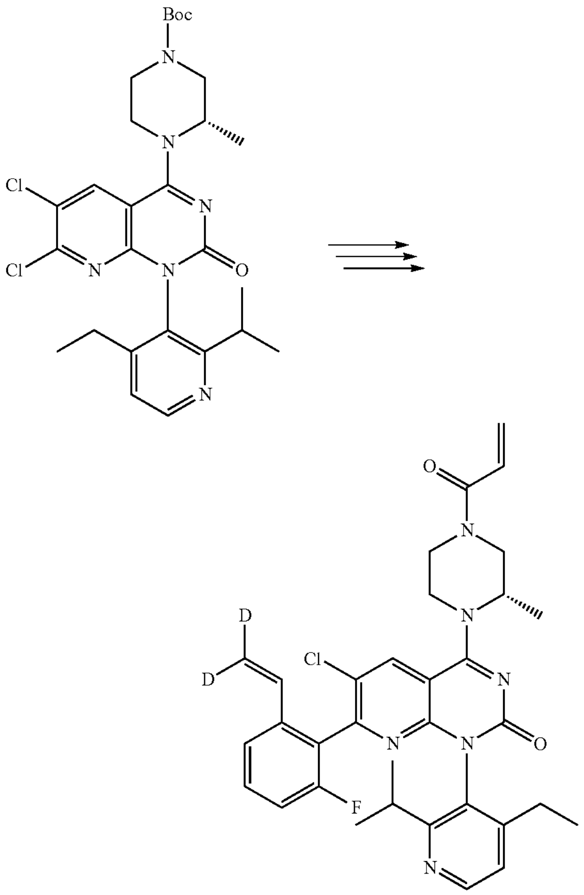

2-2

Referring to the preparation scheme of Example 28, Compound 2-2 was prepared. $R_f$: 0.53 ($CH_2Cl_2$:MeOH=10:1). The specific preparation method was as follows:

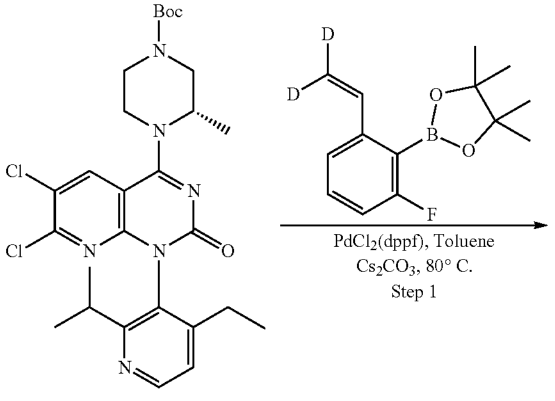

-continued

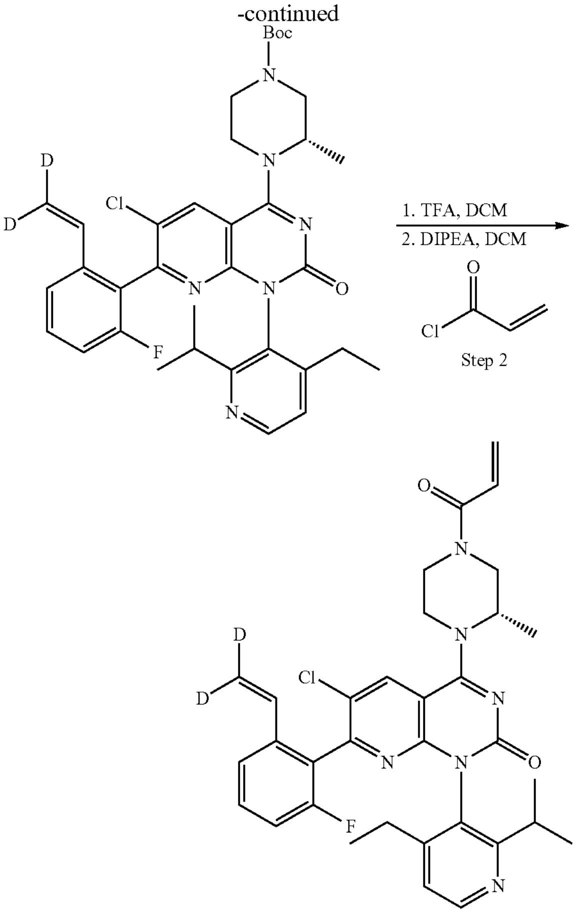

2-2

Step 1

Tert-butyl-4-(6,7-dichloro-1-(2-isopropyl-4-ethylpyridin-3-yl)-2-oxo-1,2-dihydropyrido[2,3-d]pyrimidin-4-yl)-3-methylpiperazine-1-carboxylate, cesium carbonate, toluene, [1,1'-bis(diphenylphosphino)ferrocene] palladium dichloride and 2-(2-fluoro-6-(vinyl-2,2-$d_2$)phenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7~8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 30

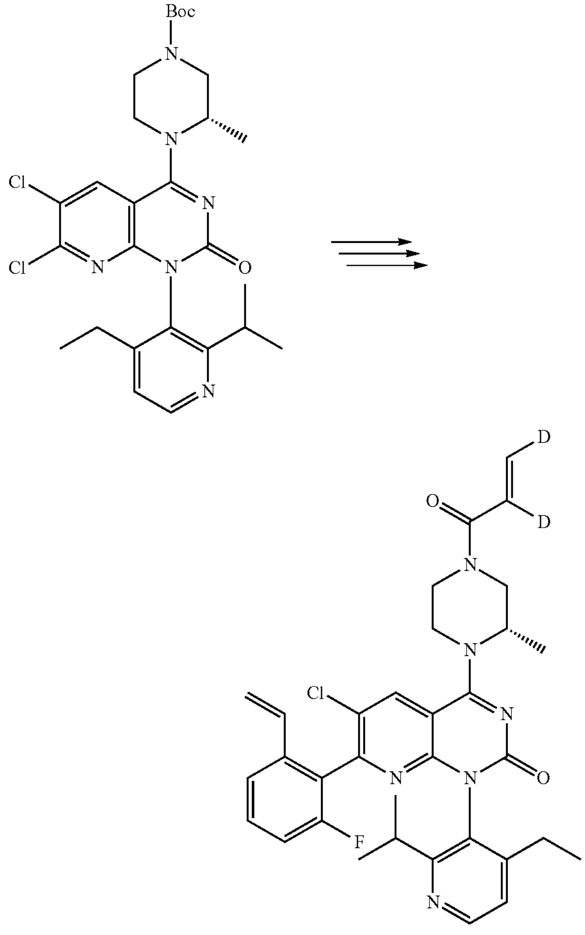

2-8

Referring to the preparation scheme of Example 28, Compound 2-8 was prepared. $R_f$: 0.54 ($CH_2Cl_2$:MeOH=10:1). The specific preparation method was as follows:

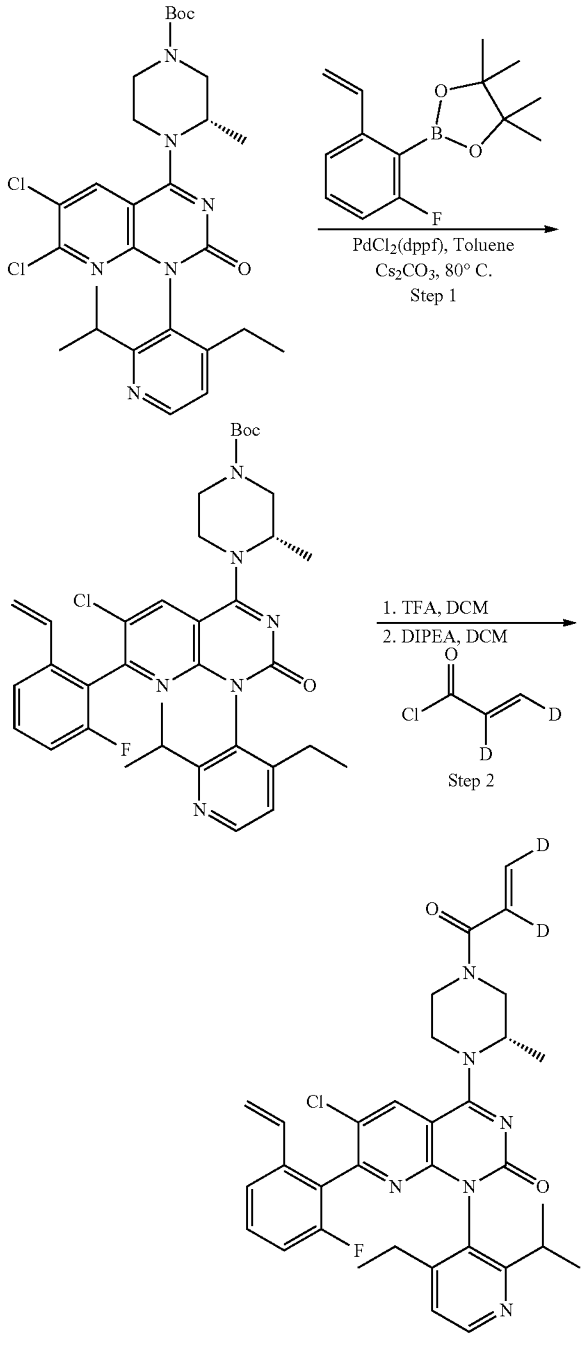

2-8

Step 1

Tert-butyl-4-(6,7-dichloro-1-(2-isopropyl-4-ethylpyridin-3-yl)-2-oxo-1,2-dihydropyrido[2,3-d]pyrimidin-4-yl)-3-methylpiperazine-1-carboxylate, cesium carbonate, toluene, [1,1'-bis(diphenylphosphino)ferrocene] palladium dichloride and 2-(2-fluoro-6-(vinyl)phenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7~8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of deuterium labeled acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain an off-white solid.

Example 31

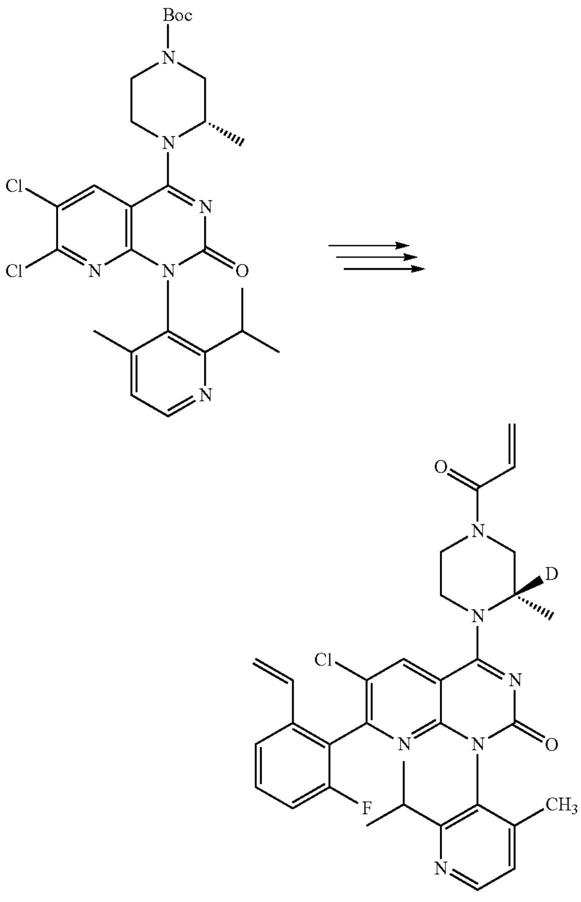

3-49

Referring to the preparation scheme of Example 28, Compound 3-49 was prepared. $R_f$: 0.53 ($CH_2Cl_2$: MeOH=10:1).

Example 32

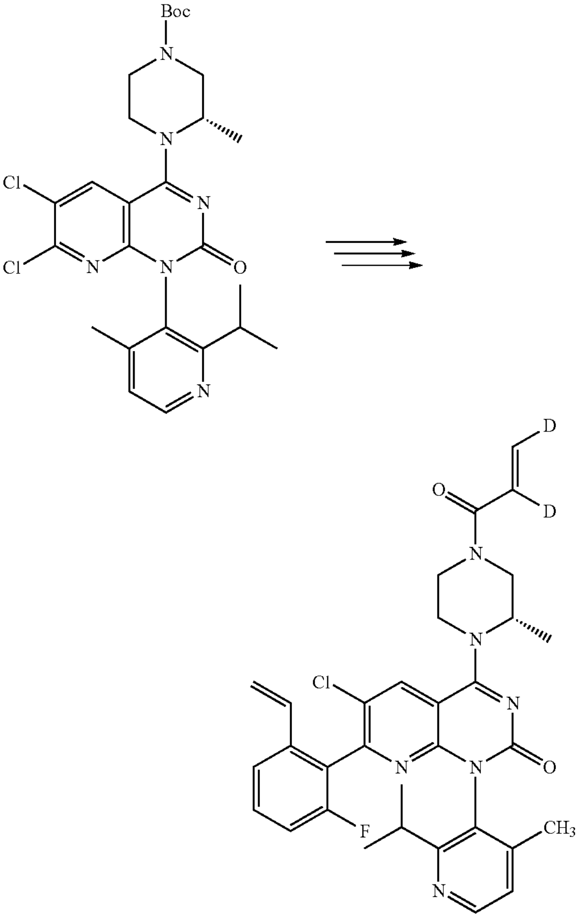

3-51

Referring to the preparation scheme of Example 28, Compound 3-51 was prepared. $R_f$: 0.55 ($CH_2Cl_2$: MeOH=10:1). The specific preparation method was as follows:

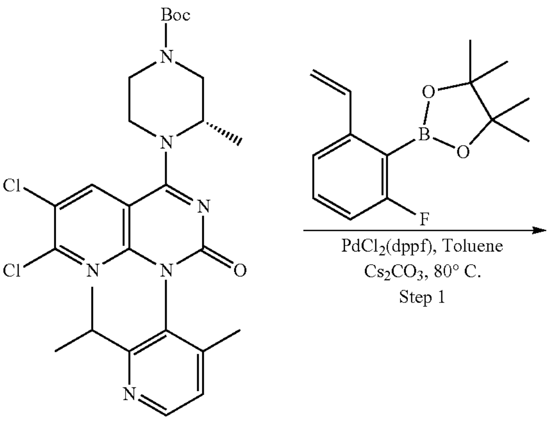

-continued

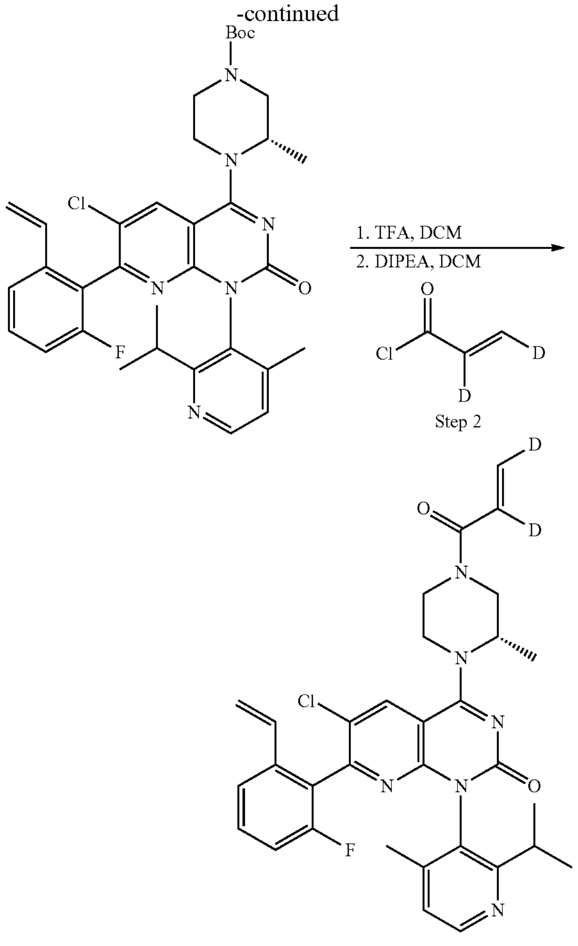

3-51

Step 1

Tert-butyl-4-(6,7-dichloro-1-(2-isopropyl-4-methylpyridin-3-yl)-2-oxo-1,2-dihydropyrido[2,3 -d]pyrimidin-4-yl)-3-methylpiperazine-1-carboxylate, cesium carbonate, toluene, [1,1'-bis(diphenylphosphino)ferrocene] palladium dichloride and 2-(2-fluoro-6-(vinyl)phenyl)-4,4,5,5-tetramethyl-1,3,2-dioxaborinane were added into a single-necked flask, inside which nitrogen gas replacement was performed after the addition. The mixture in the flask was warmed to 80° C. for reaction. The reaction solution was poured into water, and the obtained solution was extracted with ethyl acetate. The organic layer was separated, dried over anhydrous sodium sulfate, filtered, concentrated under reduced pressure and purified by silica gel column chromatography to obtain a yellow solid, which was directly used for the next reaction step.

Step 2

The product from the previous step and dichloromethane were added into a 50 ml single-necked flask, dropwise added with trifluoroacetic acid at room temperature, and reacted at room temperature after the addition. After the reaction, the reaction solution was cooled to 0° C., slowly added with saturated aqueous solution of sodium bicarbonate to adjust the pH to 7-8 and extracted with dichloromethane. The organic phases were combined, dried over anhydrous sodium sulfate, filtered, and concentrated under reduced pressure to dryness. The residue was added with dichloromethane and N,N-diisopropylethylamine, cooled down by ice bath, slowly dropwise added with a solution of deuterium labeled acryloyl chloride in dichloromethane, and continued to react after the addition. After the reaction, the reaction was quenched by slowly pouring saturated aqueous solution of ammonium chloride, and the obtained solution was extracted with dichloromethane. The organic layers were combined, washed with saturated salt solution, dried over anhydrous sodium sulfate and filtered. The filtrate was concentrated and purified by silica gel column chromatography to obtain an off-white solid.

Example 33

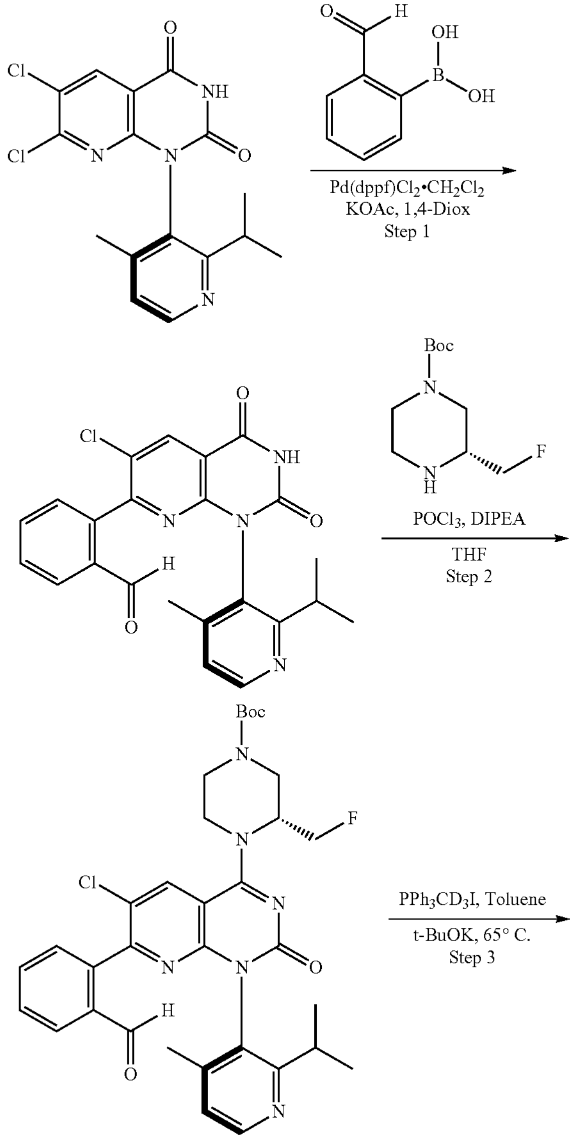

-continued

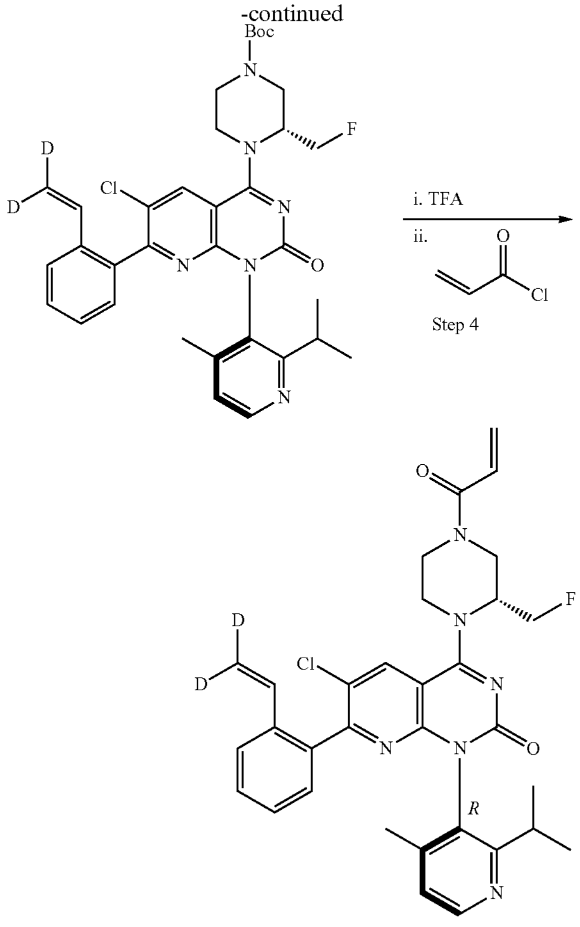

3K-4M

Step 1

(R)-6,7-dichloro-1-(2-isopropyl-4-methylpyridin-3-yl)-pyrido[2,3-d]pyrimidin-2,4(1H,3H)-dione (3 g), 2-formylphenylboronic acid (1.9 g), potassium acetate (2.4 g), Pd(dppf)$Cl_2$·$CH_2Cl_2$ (709 mg) and dioxane (30 ml) were added into a 100 ml single-necked flask, inside which nitrogen gas replacement was performed after the addition. The resulting mixture was warmed to 85° C. and stirred for 4 h. After the reaction, the reaction solution was filtered and the filtrate was added with saturated salt solution and extracted with ethyl acetate. The organic layers were combined, washed once with saturated salt solution, dried over anhydrous sodium sulfate and filtered. The filtrate was concentrated and purified by silica gel column chromatography to obtain 3.6 g of a white solid. $^1$HNMR (400 MHz, $CDCl_3$): δ 9.81 (s, 1H), 9.04 (s, 1H), 8.60 (s, 1H), 8.51 (d, J=4.9 Hz, 1H), 7.87-7.91 (m, 1H), 7.68-7.60 (m, 2H), 7.24-7.19 (m, 1H), 7.09 (d, J=5.0 Hz, 1H), 2.89-2.76 (m, 1H), 2.11 (s, 3H), 1.24 (d, J=6.8 Hz, 3H), 1.04 (d, J=6.7 Hz, 3H). MS: m/z 435.1, $[M+H]^+$.

Step 2

The product from the previous step (1.0 g), N,N-diisopropylethylamine (2.4 g), tert-butyl-(R)-3-(fluoromethyl) piperazine-1-carboxylate (753 mg) and tetrahydrofuran (40 ml) were added into a 100 ml three-necked flask, inside which nitrogen gas replacement was performed. The resulting mixture was slowly dropwise added with phosphoryl trichloride (705 mg) under the condition of ice bath, then rewarmed to room temperature and stirred. After the reaction, the reaction was quenched by slowly adding with saturated aqueous solution of ammonium chloride, and the obtained solution was extracted with ethyl acetate. The organic layers were combined, washed once with saturated salt solution, dried over anhydrous sodium sulfate and filtered. The filtrate was concentrated and purified by silica gel column chromatography to obtain 340 mg of a white solid. $^1$HNMR (400 MHz, $CDCl_3$): δ 9.82 (s, 1H), 8.47 (d, J=4.9 Hz, 1H), 8.25 (br s, 1H), 7.93-7.84 (m, 1H), 7.68-7.59 (m, 2H), 7.25-7.19 (m, 1H), 7.07 (d, J=5.0 Hz, 1H), 5.25-4.65 (m, 3H), 4.45-4.18 (m, 3H), 3.91-3.67 (m, 1H), 3.52-3.12 (m, 2H), 2.78-2.64 (m, 1H), 2.05 (s, 3H), 1.53 (s, 9H), 1.24 (d, J=6.7 Hz, 3H), 1.03 (d, J=6.7 Hz, 3H). MS: m/z 635.3, $[M+H]^+$.

Step 3

Methyl-$d_3$-triphenylphosphonium iodide (1.97 g), potassium tert-butoxide (543 mg) and toluene (40 ml) were added into a 100 ml reaction flask, warmed to 65° C. under nitrogen gas protection, and stirred for 1 h. A solution of the product from the previous step (1.2 g) in toluene (30 ml) was dropwise added into the reaction flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 700 mg of a light-yellow solid. MS: m/z 637.3, $[M+H]^+$.

Step 4

The product from the previous step (300 mg) and dichloromethane (5 ml) were added into a 50 ml single-necked flask, subjected to nitrogen gas replacement, slowly dropwise added with trifluoroacetic acid (1.2 ml) under the condition of ice bath and stirred at room temperature. After the reaction, the reaction solution was concentrated to dryness. The concentrate was added with dichloromethane (20 ml), subjected to nitrogen gas replacement, slowly dropwise added with an appropriate amount of DIPEA under the condition of ice bath to adjust the pH of the obtained solution to 7~8 and acryloyl chloride (54 mg), and stirred at 0° C. After the reaction, the reaction was quenched by adding with saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain 203 mg of a white solid. MS: m/z 591.2, $[M+H]^+$.

Example 34

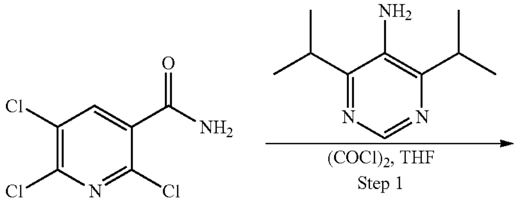

-continued

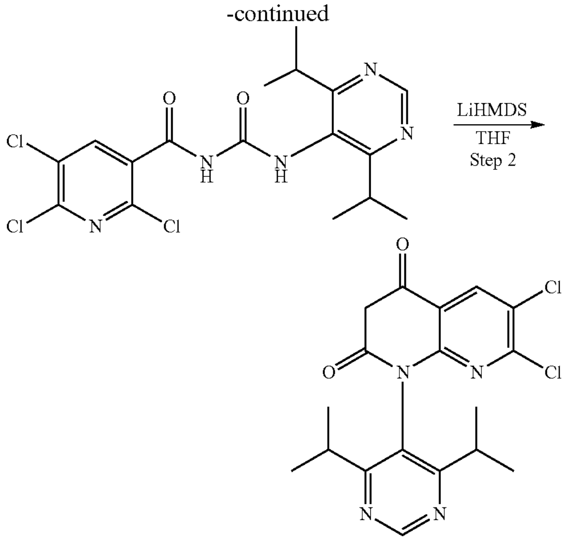

Step 1

Tetrahydrofuran (20 ml) was added into a 50 ml three-necked flask, subjected to nitrogen gas replacement, cooled to −5° C., slowly dropwise added with oxalyl chloride (1.3 g), stirred for 10 min, added with 2,5,6-trichloronicotinamide (2.0 g) in batches, warmed to 45° C. and stirred for 1 h. After the reaction, the reaction solution was concentrated to drying-up. The residue was added with tetrahydrofuran (15 ml), subjected to nitrogen gas replacement, cooled to −5° C., slowly dropwise added with a solution of 4,6-diisopropylpyridine-5-amine (1.1 g) in tetrahydrofuran (10 ml), and stirred at room temperature for 1 h. After the reaction, the reaction solution was added with water to quench the reaction, concentrated to remove tetrahydrofuran, added with saturated aqueous solution of sodium carbonate to adjust the pH of the aqueous phase to 7~8, stirred at room temperature for 10 min, and then filtered. The filter cake was dried to give 2.6 g of an off-white solid. MS: m/z 430.1, $[M+H]^+$.

Step 2

The product from the previous step (2.6 g) and tetrahydrofuran (100 ml) were added into a 250 ml three-necked flask, subjected to nitrogen gas replacement, cooled to 10-15° C., dropwise added with LiHMDS (1M in THF, 13.6 ml), and stirred at room temperature for 3 h. After the reaction, the reaction was quenched by adding with saturated aqueous solution of ammonium chloride, and the obtained solution was extracted with ethyl acetate. The organic layers were combined, washed once with saturated salt solution, dried over anhydrous sodium sulfate, and filtered. The filtrate was concentrated until a large amount of solid was precipitated, then added with methyl tertiary butyl ether (3 ml), stirred at room temperature for 10 min, and then filtered. The filter cake was dried to give 1.7 g of a white solid. MS: m/z 394.1, $[M+H]^+$.

Step 3

The product from the previous step (1.7 g), tetrahydrofuran (45 ml), DIPEA (3.3 g) and (S)-4-N-tert-butoxycarbonyl-2-methylpiperazine (861 mg) were added into a 100 ml three-necked flask, subjected to nitrogen gas replacement, slowly dropwise added with phosphorus oxychloride (1.3 g) under the condition of ice bath and stirred at room temperature for 30 min, then added with (S)-4-N-tert-butoxycarbonyl-2-methylpiperazine (430 mg) and stirred at room temperature for 30 min. After the reaction, the reaction was quenched by adding with saturated aqueous solution of ammonium chloride, and the obtained solution was extracted with ethyl acetate. The organic layers were combined, washed once with saturated salt solution, dried over anhydrous sodium sulfate and filtered. The filtrate was concentrated to obtain 2.5 g of a brown solid. MS: m/z 576.2, $[M+H]^+$.

Step 4

The product from the previous step (1.5 g), 2-formylbenzeneboronic acid (435 mg), potassium carbonate (765 mg), $Pd(dppf)Cl_2 \cdot CH_2Cl_2$ (245 mg), 1,4-dioxane (15 ml) and water (1.5 ml) were added into a 50 ml single-necked flask, subjected to nitrogen gas replacement, warmed to 80° C. and stirred. After the reaction, the reaction solution was filtered. The filtrate was concentrated and purified by silica gel column chromatography to obtain 1.3 g of a brown solid. MS: m/z 664.3, $[M+H]^+$.

Step 5

Methyl-$d_3$-triphenylphosphonium iodide (1.34 g), potassium tert-butoxide (513 mg) and toluene (40 ml) were added into a 100 ml reaction flask, warmed to 65° C. under nitrogen gas protection, and stirred for 1 h. A solution of the product from the previous step (1.0 g) in toluene (30 ml) was dropwise added into the reaction flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 453 mg of a light-yellow solid. MS: m/z 664.3, $[M+H]^+$.

Step 6

The product from the previous step (800 mg) and dichloromethane (10 ml) were added into a 50 ml single-necked flask, subjected to nitrogen gas replacement, slowly dropwise added with trifluoroacetic acid (4.1 g) under the condition of ice bath, warmed to 30° C. and stirred for 30 min. After the reaction, the reaction solution was concentrated to dryness. The concentrate was added with saturated $NaHCO_3$ aqueous solution to adjust the pH of the aqueous phase to 7~8, and then extracted with ethyl acetate. The organic layers were combined, washed once with saturated salt solution, dried over anhydrous sodium sulfate and filtered. The filtrate was concentrated until a large amount of solid was precipitated, then added with MTBE (5 ml), stirred at room temperature, and filtered. The filter cake was dried. The dried filter cake and dichloromethane (10 ml) were added into a 50 ml single-necked flask, slowly dropwise added with DIPEA (930 mg) and acryloyl chloride (163 mg) under the condition of ice bath, warmed to 30° C. and stirred. After the reaction, the reaction was quenched by adding with saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain 420 mg of a brown solid. MS: m/z 618.3, $[M+H]^+$.

For part of the compounds of the present invention, the advantages in synthesis and preparation are summarized as follows:

Reference WO2018217651A1 discloses two strategies to construct "carbon-carbon bond" through Suzuki reaction, which are summarized as follows:

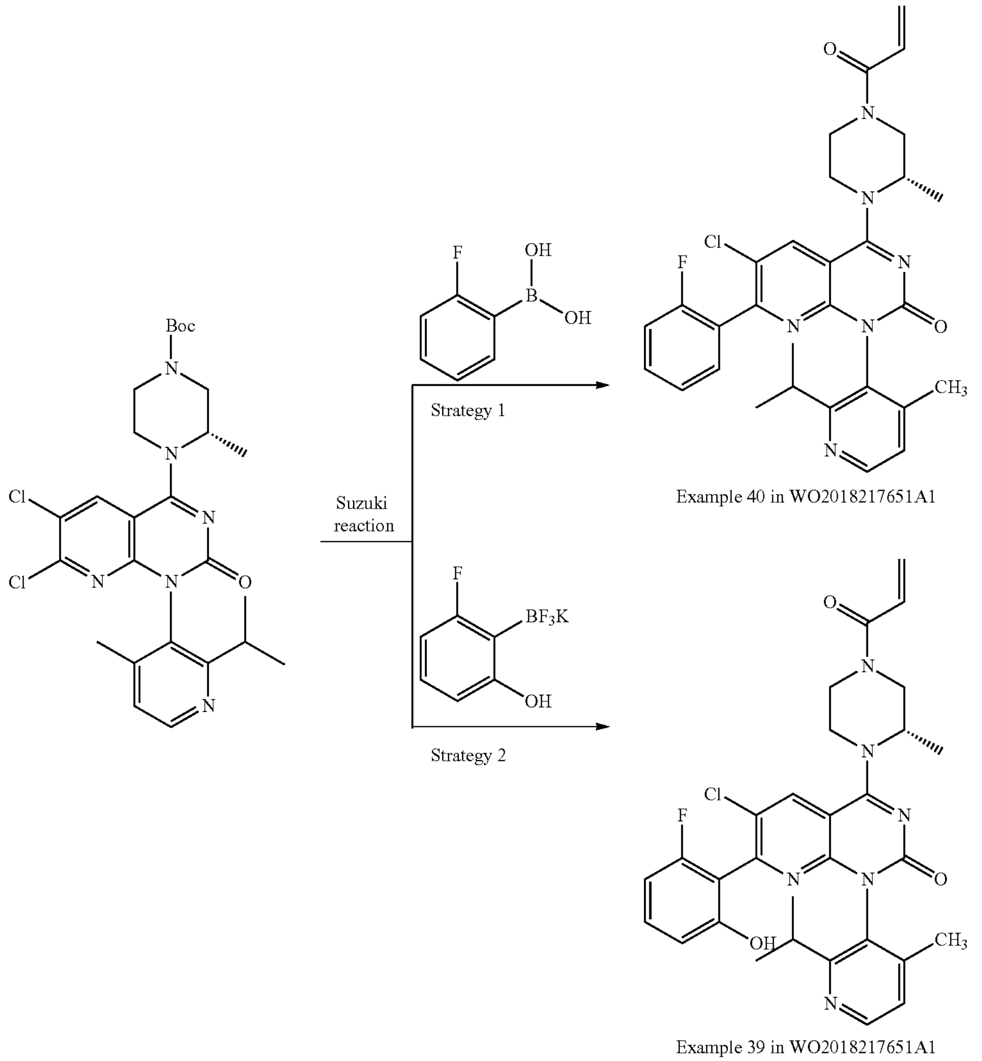

Wherein, "free boric acid" is used as the raw material for "carbon-carbon bond construction" in Suzuki reaction performed in Strategy 1. "Potassium fluoroborate" is used as the intermediate for "carbon-carbon bond construction" in Strategy 2. If the method recorded in Reference WO2018217651A1 is simply applied to the compounds of the present invention, the following side reaction during Suzuki reaction will occur when "chlorine substitution" is present at 6-position in the parent nuclear molecular structure:

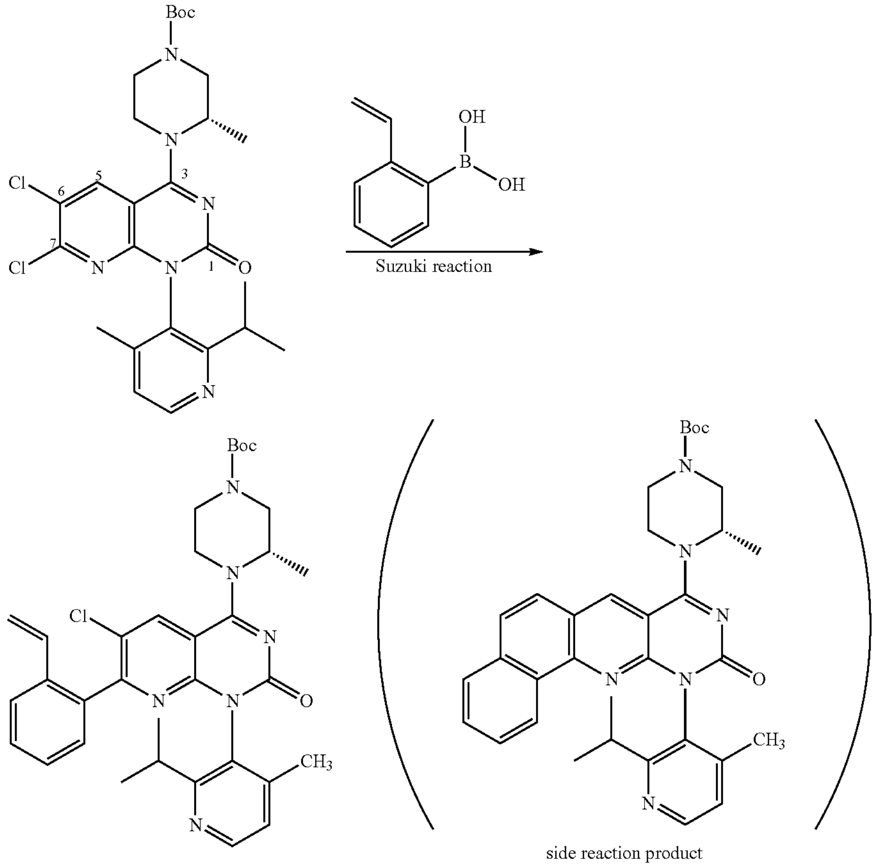

side reaction product

In order to avoid the above side reaction, the following two synthesis schemes for the construction of the molecules with “chlorine substitution present at 6-position in the parent nuclear molecular structure” are adopted in the present invention:

Scheme 1: the molecules with alkene substitution of the present invention are constructed by using the strategy of “Suzuki reaction” in combination with “Wittig” reaction. For example, for the preparation of Compound 3-6 in Example 2, in the first step, Suzuki reaction was performed at first by using the precursor compound for Wittig reaction, i.e., the boric acid intermediate with “aldehyde functional group”, then in the second step, “alkene functional group” was constructed by using “Wittig reaction”, so as to avoid the occurrence of the side reaction.

Scheme 2: “replacement between hydrogen and deuterium” for the terminal hydrogen of the alkene is used, and the occurrence of the side reaction is avoided by using “primary isotope effect of deuterium and hydrogen”. For example, for the synthesis of Compound 3-20 in Example 28, the intermediate with deuterated alkene terminal was used. When Suzuki reaction is carried out, the amount of the side reaction product is significantly reduced as compared with alkene which is not deuterated.

Based on the above analysis, the target molecules with alkenes are prepared in the present invention by adopting the synthesis strategies different from the existing public literature, so that the occurrence of the side reaction is avoided. It is beneficial to the control of product quality and to industrial production.

Preparation of Comparative Compound TM-1:

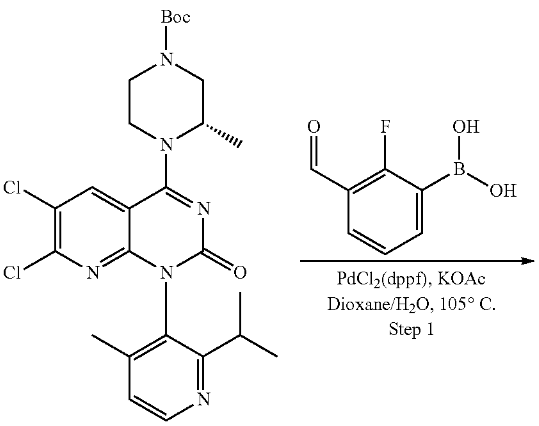

-continued

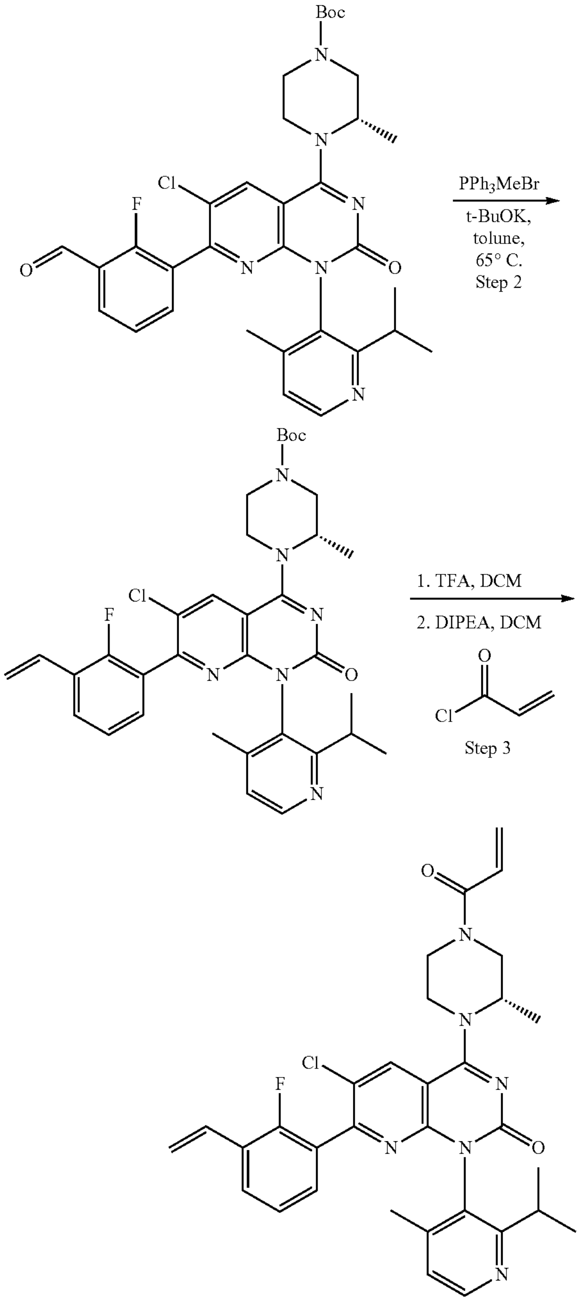

TM-1

Step 1

Tert-butyl-(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (2.0 g), 2-fluoro-3-formylphenylboronic acid (861 mg), potassium acetate (1.0 g), 1,4-dioxane (40 ml), water (8 ml) and [1,1'-bis(diphenylphosphino)ferrocene] palladium dichloride (249 mg) were added into a 50 ml single-necked flask, warmed to 105° C. after nitrogen gas replacement, and stirred for 2 h. After the reaction, the resulting solution was cooled to room temperature, diluted with water, and extracted with ethyl acetate. The organic layers were combined, washed with saturated salt solution, dried over anhydrous sodium sulfate, filtered, concentrated under reduced pressure and purified by silica gel column chromatography to obtain 1.2 g of a yellow solid.

Step 2

Methyltriphenylphosphonium bromide (1.7 g), potassium tert-butoxide (531 mg) and toluene (20 ml) were added into a 100 ml three-necked flask, warmed to 65° C. after nitrogen gas replacement, and stirred for 1 h. A solution of the product from the previous step (1.2 g) in toluene (30 ml) was dropwise added into the flask and the obtained mixture was stirred for another 30 min after the addition. The reaction solution was poured into saturated aqueous solution of ammonium chloride and extracted with ethyl acetate. The organic layers were combined, washed with saturated salt solution, dried over anhydrous sodium sulfate, filtered, concentrated under reduced pressure and purified by silica gel column chromatography to obtain 1.0 g of a light-yellow solid.

Step 3

The product from the previous step (1.0 g) and dichloromethane (10 ml) were added into a 50 ml single-necked flask, dropwise added with trifluoroacetic acid (10 ml) at 10° C.~15° C. and stirred for another 1 h after the addition. The reaction solution was concentrated to dryness. The residue was added with dichloromethane (10 ml), cooled to 0° C., added with N,N-diisopropylethylamine (1.6 ml), then slowly dropwise added with a solution of acryloyl chloride (214 mg) in dichloromethane (1 ml), and stirred for 30 min after the addition. The reaction was quenched by slowly pouring saturated aqueous solution of ammonium chloride, and the obtained solution was extracted with ethyl acetate. The organic layers were combined, washed with saturated salt solution, dried over anhydrous sodium sulfate, filtered, concentrated under reduced pressure and purified by silica gel column chromatography to obtain 800 mg of a light-yellow solid (namely Compound TM-1). $^{1}H$ NMR (400 MHz, DMSO-$d_6$): δ 8.56-8.45 (m, 2H), 7.75 (td, J=7.5, 1.5 Hz, 1H), 7.39 (d, J=4.9 Hz, 1H), 7.27 (t, J=7.7 Hz, 1H), 7.13 (td, J=7.1, 1.5 Hz, 1H), 6.95-6.75 (m, 2H), 6.22 (dd, J=16.6, 5.4 Hz, 1H), 5.95 (dd, J=17.7, 0.7 Hz, 1H), 5.78 (dd, J=10.3, 2.2 Hz, 1H), 5.48 (d, J=12.1 Hz, 1H), 4.98 (s, 1H), 4.50-4.24 (m, 2H), 4.23-4.04 (m, 1H), 3.91-3.72 (m, 1H), 3.72-3.41 (m, 1H), 3.34-3.04 (m, 1H), 2.90-2.72 (m, 1H), 2.02 (d, J=4.6 Hz, 3H), 1.35 (d, J=6.7 Hz, 3H), 1.12 (d, J=6.8 Hz, 3H), 1.00 (d, J=6.8 Hz, 3H); $^{13}C$ NMR (100 MHz, DMSO-$d_6$): δ 165.4, 163.0, 162.8, 162.5, 161.8, 158.9, 158.5, 158.2, 157.8, 155.3, 155.1, 153.9, 152.0, 151.9, 147.3, 137.5, 131.6, 130.2, 129.3, 128.6, 128.5, 128.33, 128.29, 128.2, 125.7, 125.58, 125.56, 125.4, 125.2, 125.1, 124.6, 123.9, 119.1, 119.0, 106.8, 51.5, 51.3, 49.2, 45.7, 45.2, 42.1, 30.0, 22.10, 22.08, 21.91, 21.88, 17.95, 17.90, 16.2, 15.5. MS: m/z 587.2, $[M+H]^+$.

Preparation of Comparative Compound TM-2:

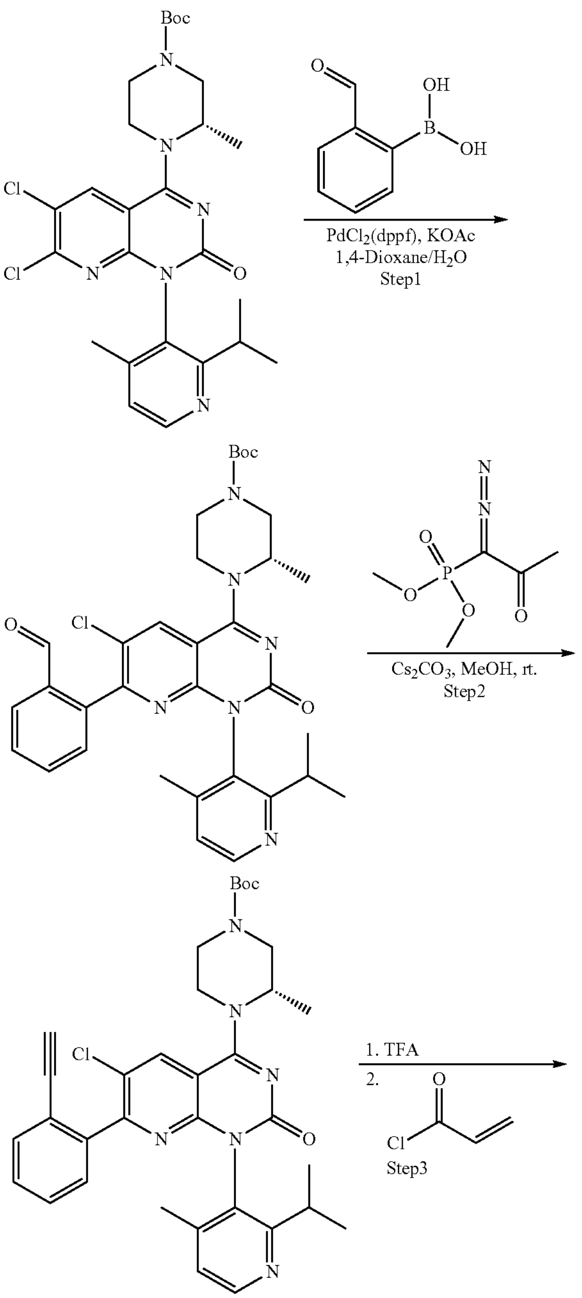

-continued

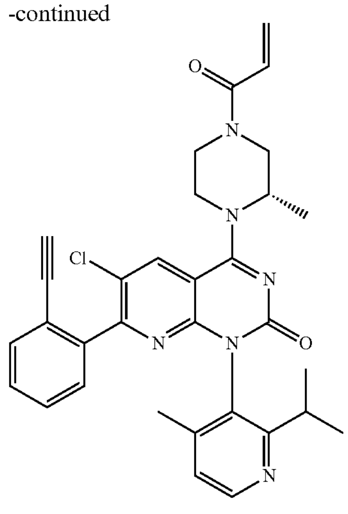

TM-2

Step 1

Tert-butyl-(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (2.0 g), 2-formylphenylboronic acid (1.1 g), potassium acetate (1.1 g), 1,4-dioxane (20 ml), water (2 ml) and [1,1'-bis(diphenylphosphino)ferrocene] palladium dichloride dichloromethane complex (132 mg) were added into a three-necked flask, inside which nitrogen gas replacement was performed. The mixture in the flask was warmed to 80° C. and stirred for 2 h. After the reaction, the resulting solution was cooled to room temperature and filtered. The filtrate was concentrated and purified by silica gel column chromatography to give 1.6 g of a yellow solid.

Step 2

The product from the previous step (1.6 g) and cesium carbonate (1.7 g) were added into a 500 ml dry single-necked flask, added with methanol (25 ml) for dissolution, dropwise added with dimethyl-(1-diazo-2-oxopropyl) phosphonate (1.0 g) at room temperature after nitrogen gas replacement, and reacted at room temperature for 2 h after the addition. The reaction solution was added with salt solution to quench the reaction and extracted with ethyl acetate (20 ml×3). The organic phases were combined, dried over anhydrous sodium sulfate, filtered, concentrated and purified by silica gel column chromatography to give 1.3 g of a luminous yellow solid. $^1$H NMR (400 MHz, $CDCl_3$): δ 8.47 (d, J=4.9 Hz, 1H), 8.11 (s, 1H), 7.57-7.50 (m, 1H), 7.42-7.33 (m, 2H), 7.13-7.08 (m, 1H), 7.06 (dd, J=4.9, 0.6 Hz, 1H), 4.92 (m, 1H), 4.53-3.89 (m, 3H), 3.81-3.56 (m, 1H), 3.44-3.04 (m, 2H), 2.94 (s, 1H), 2.84-2.69 (m, 1H), 2.03 (s, 3H), 1.59-1.49 (m, 12H), 1.24 (d, J=6.7 Hz, 3H), 1.05 (d, J=6.8 Hz, 3H). MS: m/z 613.3, $[M+H]^+$.

Step 3

The product from the previous step (1.3 g), dichloromethane (10 ml) and trifluoroacetic acid (1.8 g) were added into a 500 ml dry single-necked flask and stirred at room temperature for 2 h after the addition. The reaction solution was added with sodium hydroxide aqueous solution to adjust the pH thereof to 7~8, and extracted with dichloromethane (20 ml×3). The organic phases were combined, dried over anhydrous sodium sulfate, filtered and concentrated to dryness. The concentrate was added with DIPEA (415 mg, 3.2 mmol) and dichloromethane (15 ml), stirred for 10 min, then slowly dropwise added with acryloyl chloride (226 mg)

under the condition of ice bath, stirred and reacted for 30 min. The reaction solution was added with water to quench the reaction and extracted with dichloromethane (20 ml×3). The organic phases were combined, concentrated under reduced pressure and purified by silica gel column chromatography to give 910 mg of a light-yellow solid. $^1$H NMR (400 MHz, $CDCl_3$): δ 8.47 (d, J=4.9 Hz, 1H), 8.12 (s, 1H), 7.58-7.51 (m, 1H), 7.42-7.34 (m, 2H), 7.13-7.05 (m, 2H), 6.74-6.54 (m, 1H), 6.43 (dd, J=16.7, 1.4 Hz, 1H), 5.84 (dd, J=10.4, 1.8 Hz, 1H), 5.21-4.24 (m, 3H), 4.14-3.53 (m, 3H), 3.41-3.04 (m, 1H), 2.94 (s, 1H), 2.84-2.65 (m, 1H), 2.10-1.96 (m, 3H), 1.64-1.44 (m, 3H), 1.24 (d, J=6.8 Hz, 3H), 1.06 (d, J=6.7 Hz, 3H). MS: m/z 567.2, [M+H]$^+$.

Preparation of Comparative Compound TM-3:

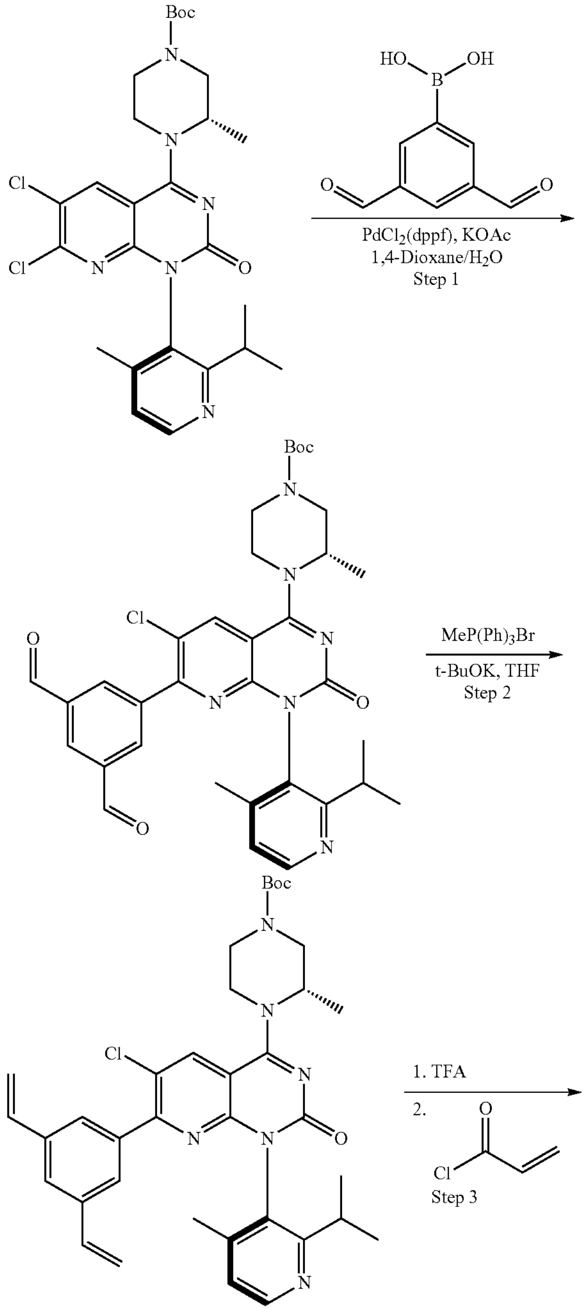

-continued

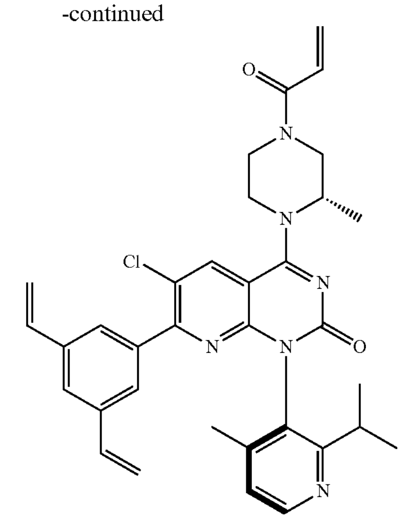

TM-3

Step 1

Tert-butyl-(R)—(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (7.1 g), (3,5-diformylphenyl) boronic acid (2.8 g), Pd(dppf)$Cl_2$ (0.95 g), potassium acetate (3.8 g), 1,4-dioxane (80 ml) and water (20 ml) were added into a 250 ml single-necked flask, inside which nitrogen gas replacement was performed. The resulting mixture was warmed to 90° C. and reacted for 2.5 h. After the reaction, the reaction solution was cooled to room temperature, added with water, and extracted with ethyl acetate. The organic layers were combined, washed once with saturated salt solution, dried over anhydrous sodium sulfate and filtered. The filtrate was concentrated and purified by silica gel column chromatography to obtain 4.0 g of a light-yellow white solid. $^1$H NMR (400 MHz, $CDCl_3$): δ 10.05 (s, 2H), 8.56 (d, J=4.9 Hz, 1H), 8.43 (m, 1H), 8.38 (d, J=1.4 Hz, 2H), 8.18 (s, 1H), 7.16 (d, J=4.9 Hz, 1H), 5.06-4.78 (m, 1H), 4.57-3.55 (m, 4H), 3.45-3.01 (m, 2H), 2.86-2.69 (m, 1H), 2.06 (s, 3H), 1.62-1.48 (m, 3H), 1.54 (s, 9H), 1.26 (d, J=6.8 Hz, 3H), 1.07 (d, J=6.7 Hz, 3H).

Step 2

Methyltriphenylphosphonium bromide (8.9 g), potassium tert-butoxide (3.5 g) and tetrahydrofuran (100 ml) were added into a 250 ml three-necked flask, subjected to nitrogen gas replacement, and stirred at room temperature for 1 h. The obtained mixture was slowly dropwise added with a solution of the product from the previous step (2.0 g) in tetrahydrofuran (20 ml), and stirred at room temperature for 1 h. After the reaction, the reaction solution was added with saturated aqueous solution of ammonium chloride to quench the reaction and extracted with dichloromethane. The organic layers were combined, washed once with saturated salt solution, dried over anhydrous sodium sulfate, and filtered. The filtrate was concentrated and purified by silica gel column chromatography to give 1.9 g of a light-yellow solid.

Step 3

The product from the previous step (1.9 g) and dichloromethane (20 ml) were added into a 100 ml single-necked flask, subjected to nitrogen gas replacement, slowly dropwise added with trifluoroacetic acid (10 ml) under the condition of ice bath and stirred at room temperature for 1 h. After the reaction, the reaction solution was concentrated to dryness. The concentrate was added with dichloromethane (20 ml) for dissolution, subjected to nitrogen gas replacement, slowly dropwise added with DIPEA (2.3 g) and acryloyl chloride (402 mg) under the condition of ice bath, and stirred at room temperature for 0.5 h. After the reaction, the reaction was quenched by adding with saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain 500 mg of a light-yellow solid. $^1$H NMR (400 MHz, DMSO-$d_6$): δ 8.49 (d, J=4.8 Hz, 2H), 7.67 (s, 1H), 7.56 (s, 2H), 7.27 (d, J=4.7 Hz, 1H), 6.99-6.82 (m, 1H), 6.81-6.65 (m, 2H), 6.32-6.19 (m, 1H), 5.85-5.73 (m, 3H), 5.36 (d, J=11.0 Hz, 2H), 5.00 (br s, 1H), 4.51-4.04 (m, 3H), 3.92-3.44 (m, 2H), 3.35-3.06 (m, 1H), 2.82-2.67 (m, 1H), 1.98 (s, 3H), 1.42-1.34 (m, 3H), 1.12 (d, J=6.6 Hz, 3H), 1.05-0.98 (m, 3H). MS: m/z 595.2676, [M+H]$^+$.

Preparation of Comparative Compound TM-4:

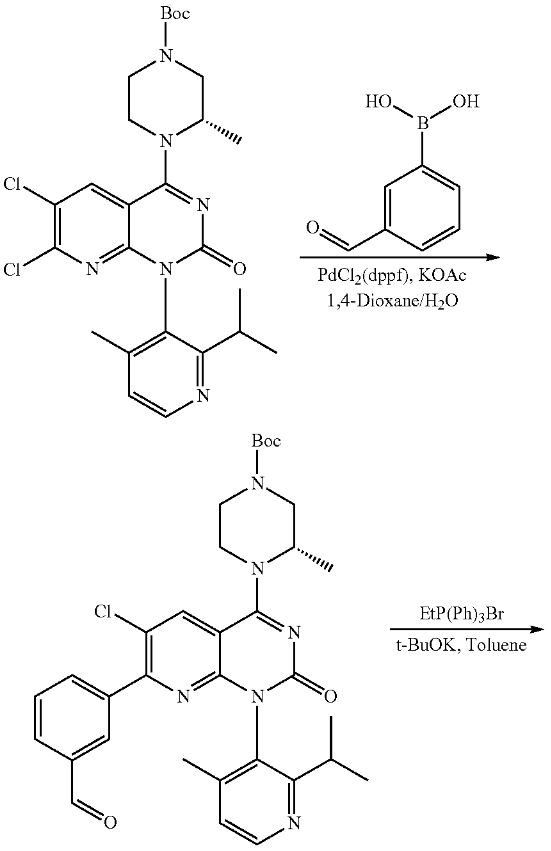

-continued

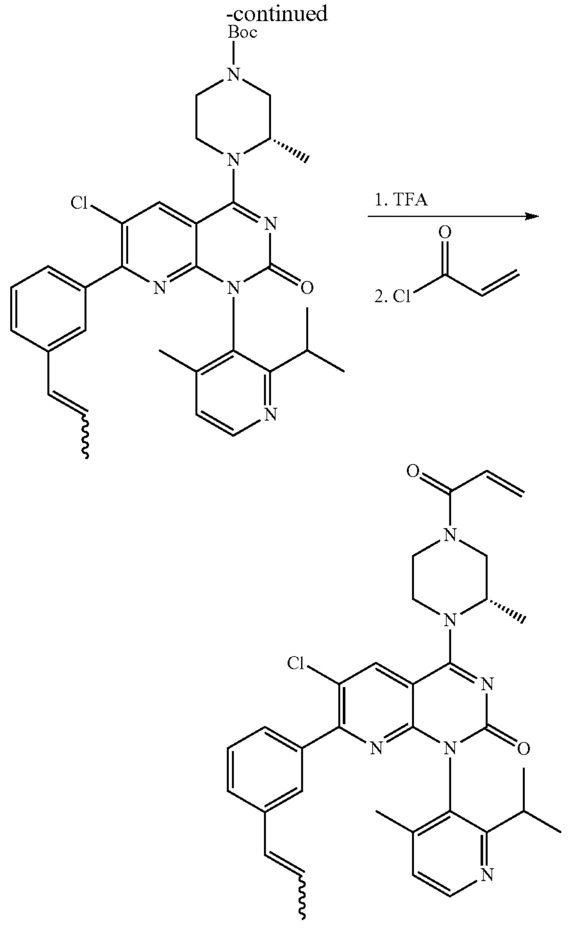

TM-4

Step 1

Tert-butyl-(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (10.0 g), potassium acetate (8.8 g), Pd(dppf)$Cl_2$ (1.3 g), 3-formylphenyl boronic acid (4.1 g), 1,4-dioxane (180 ml) and water (20 ml) were added into a 500 ml single-necked flask, inside which nitrogen gas replacement was performed. The resulting mixture was warmed to 90° C. and stirred for 2 h. After the reaction, the reaction solution was cooled to room temperature, added with water, and extracted with ethyl acetate. The organic layers were combined, washed once with saturated salt solution, dried over anhydrous sodium sulfate and filtered. The filtrate was concentrated and purified by silica gel column chromatography to obtain 9.0 g of a light-yellow solid. MS: m/z 617.2671, [M+H]$^+$.

Step 2

Ethyltriphenylphosphonium bromide (2.3 g), potassium tert-butoxide (685 mg) and toluene (30 ml) were added into a 250 ml three-necked flask, subjected to nitrogen gas replacement, warmed to 65° C. and stirred for 2 h. The obtained mixture was slowly dropwise added with a solution of the product from the previous step (1.5 g) in toluene (10 ml), warmed to 100° C. and reacted for 2 h. After the reaction, the reaction solution was cooled to room temperature, added with saturated aqueous solution of ammonium chloride to quench the reaction and extracted with dichloromethane. The organic layers were combined, washed once with saturated salt solution, dried over anhydrous sodium sulfate, and filtered. The filtrate was concentrated and purified by silica gel column chromatography to give 600 mg of a light-yellow solid.

Step 3

The product from the previous step (600 mg) and dichloromethane (6 ml) were added into a 50 ml single-necked flask, subjected to nitrogen gas replacement, slowly dropwise added with trifluoroacetic acid (3 ml) under the condition of ice bath and stirred at room temperature for 1 h. After the reaction, the reaction solution was concentrated to dryness. The concentrate was added with dichloromethane (6 ml), subjected to nitrogen gas replacement, slowly dropwise added with DIPEA (740 mg) and acryloyl chloride (173 mg) under the condition of ice bath, and stirred at room temperature for 0.5 h. After the reaction, the reaction was quenched by adding with saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain 250 mg of a light-yellow solid. MS: m/z 583.2686, $[M+H]^+$.

Preparation of Comparative Compound TM-5:

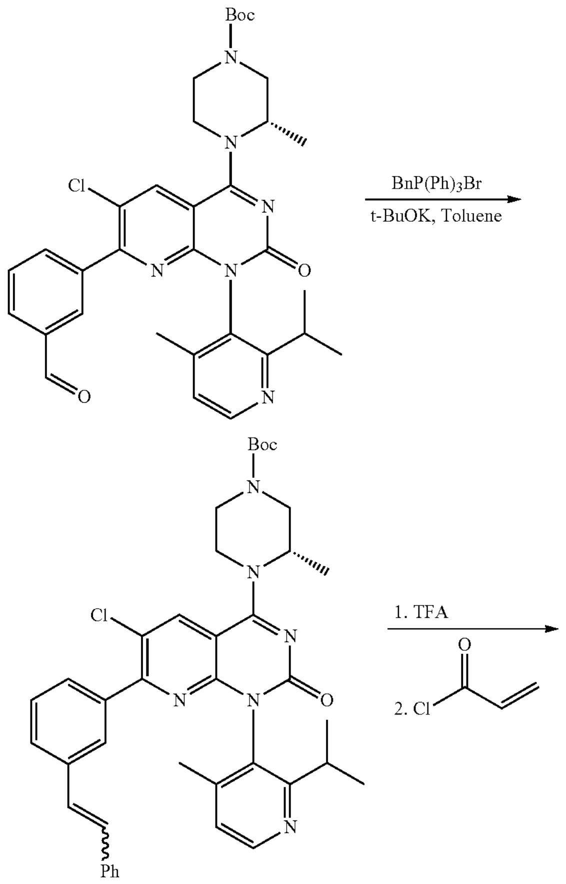

-continued

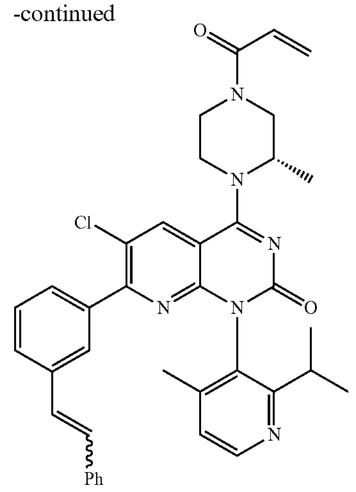

TM-5

Step 1

Benzyltriphenylphosphonium bromide (2.6 g), potassium tert-butoxide (682 mg) and toluene (15 ml) were added into a 250 ml three-necked flask, subjected to nitrogen gas replacement, warmed to 65° C. and stirred for 2 h. The obtained mixture was slowly dropwise added with a solution of tert-butyl-(S)-4-(6-chloro-7-(3-formylphenyl)-1-(2-isopropyl-4-methylpyridin-3-yl)-2-oxo-1,2-dihydropyrido[2,3-d]pyrimidin-4-yl)-3-methylpiperazine-1-carboxylate (1.5 g) in toluene, warmed to 100° C. and reacted for 2 h. After the reaction, the reaction solution was cooled to room temperature, added with saturated aqueous solution of ammonium chloride to quench the reaction and extracted with dichloromethane. The organic layers were combined, washed once with saturated salt solution, dried over anhydrous sodium sulfate, and filtered. The filtrate was concentrated and purified by silica gel column chromatography to give 800 mg of a light-yellow solid.

Step 2

The product from the previous step (800 mg) and dichloromethane (10 ml) were added into a 50 ml single-necked flask, subjected to nitrogen gas replacement, slowly dropwise added with trifluoroacetic acid (5 ml) under the condition of ice bath and stirred at room temperature for 1 h. After the reaction, the reaction solution was concentrated to dryness. The concentrate was added with dichloromethane (10 ml), subjected to nitrogen gas replacement, slowly dropwise added with DIPEA (897 mg) and acryloyl chloride (209 mg) under the condition of ice bath, and stirred at room temperature for 0.5 h. After the reaction, the reaction was quenched by adding with saturated aqueous solution of ammonium chloride, and the obtained solution was extracted with dichloromethane. The organic layers were combined, washed once with saturated salt solution, dried over anhydrous sodium sulfate and filtered. The filtrate was concentrated and purified by silica gel column chromatography to obtain 278 mg of a light-yellow solid. MS: m/z 645.2856, $[M+H]^+$.

Application of Compound 3-2 in Preparation of PROTAC (Proteolysis Targeting Chimeras) Molecule by Using "Alkene Metathesis Reaction":

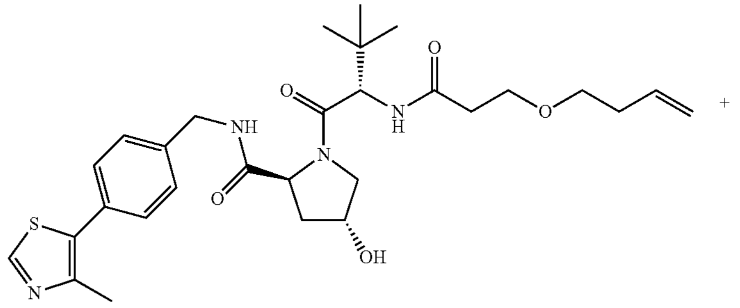

TM-P-1

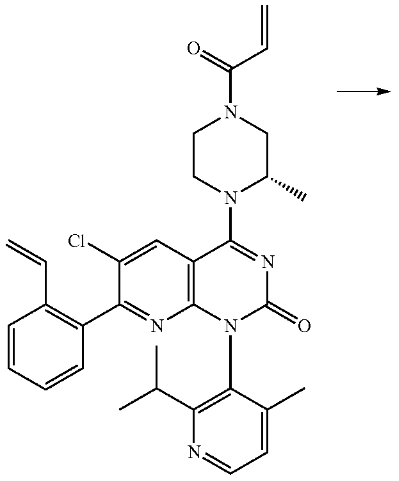

3-2

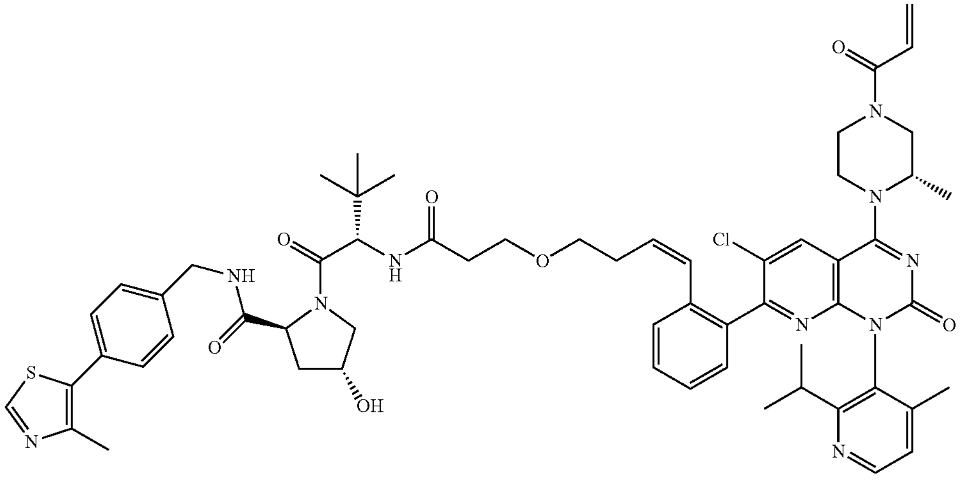

TM-P

TM-P-1 was prepared by referring to reference (Targeted Degradation of Oncogenic KRASG12C by VHL-Recruiting PROTACs; ACS Cent. Sci. 2020, 6, 1367-1375), which then was subjected to alkene metathesis reaction with Compound 3-2 (references: J. Am. Chem. Soc., 2005, 127, 17160-17161; Org. Lett., 2007, 9, 1203-1206; J. Am. Chem. Soc., 2013, 135, 1276-1279; J. Am. Chem. Soc., 2019, 141, 6791-6796; J. Am. Chem. Soc., 2006, 128, 13652-13653; Org. Lett., 2007, 9, 769-771; J. Am. Chem. Soc., 2006, 128, 4079-4089), followed by purification to yield Compound TM-P.

Biological Tests

1. $IC_{50}$ Value of Cell Proliferation Inhibitory Activity on NCI-H358 [3D Model Test]

100 μl of agarose gel with a high concentration was spread in a 96-well plate as the bottom agarose gel layer. Agarose with a low concentration and growth medium containing cells were mixed and then spread on the bottom agar layer, cooled and solidified, then incubated overnight at 37° C. Mother solutions were prepared from the test compounds by using DMSO, and then subjected to gradient elution with RPMI 1640 growth medium. The solutions of test compounds with different concentrations after gradient elution were added to the 96-well plate comprising an upper layer of agar gel-cells. Solvent control well was set up and the plate was incubated in a $CO_2$ incubator. The drug-containing medium was changed during the incubation period and the cell growth situation was observed. After the incubation, the cells were stained with NBT and the number of cell colony formation was counted, and the $IC_{50}$ values of the compounds inhibiting cell proliferation were derived.

The activity data of part of the representative compounds of the present invention are as follows: wherein "A" represents an $IC_{50}$ value (nM) of <50;

"B" represents an $IC_{50}$ value (nM) of 50~150 (150 is not included);

"C" represents an $IC_{50}$ value (nM) of 150~300;

"D" represents an $IC_{50}$ value (nM) of >300.

| Compound No. | $IC_{50}$ value of cell proliferation inhibitory activity on NCI-H358 [3D model test] |
|---|---|
| 3-1 | A |
| 3-2 | A |
| 3-5 | A |
| 3-6 | A |

-continued

| Compound No. | $IC_{50}$ value of cell proliferation inhibitory activity on NCI-H358 [3D model test] |
|---|---|
| 3-19 | A |
| 3-20 | A |
| 3-23 | A |
| 3-24 | A |
| 3-25 | A |
| 3-27 | A |
| 4-3 | A |
| 4-8 | A |
| 4-9 | A |
| 4-11 | A |
| 4-16 | A |
| 4-23 | A |
| 5-3 | A |
| 5-8 | A |
| 5-9 | A |
| 5-11 | A |
| 5-24 | A |

The compounds such as Compound 3-1, Compound 3-2, Compound 3-5, Compound 3-6, Compound 3-19, and Compound 3-20 show significant anti-cell proliferation activity against KRAS G12C mutant type cells NCI-H358.

2. Test of Cell Proliferation Activity of MIA PaCa-2 by CellTiter-Glo Reagent

MIA PaCa-2 cells in exponential growth phase were digested with trypsin-EDTA, plated in a 96-well plate with 2000-3000 cells per well, and incubated overnight at 37° C. with 5% $CO_2$. Mother solutions were prepared from the test compounds by using DMSO, subjected to gradient elution with DMEM growth medium, and then added into the 96-well plate and incubated in an incubator for 72 h at 37° C. with 5% $CO_2$. After the incubation, CellTiter-Glo test reagent with an equal volume was added into each well and the obtained 96-well plate was incubated after shaking. The chemiluminescence values were determined by microplate reader, and the $IC_{50}$ values of the test compounds inhibiting the proliferation of MIA PaCa-2 cells were fitted and calculated by GraphPad Prism software.

Wherein "A" represents an $IC_{50}$ value (nM) of <50; "B" represents an $IC_{50}$ value (nM) of 50~150 (150 is not included); "C" represents an $IC_{50}$ value (nM) of 150~300; "D" represents an $IC_{50}$ value (nM) of >300.

| Compound No. | $IC_{50}$ value of cell proliferation inhibitory activity of the compound on MIA PaCa-2 |
|---|---|
| 3-1 | A |
| 3-2 | A |
| 3-5 | A |
| 3-6 | A |
| 3-8 | A |
| 3-19 | A |
| 3-20 | A |
| 3-23 | A |
| 3-24 | A |
| 4-3 | A |
| 4-8 | A |
| 4-23 | A |
| 5-3 | A |
| 5-8 | A |
| 5-24 | A |

The compounds such as Compound 3-1, Compound 3-2, Compound 3-5, Compound 3-6, Compound 3-19, and Compound 3-20 show significant anti-cell proliferation activity against KRAS G12C mutant type cells MIA PaCa-2.

3. Test of Cell Proliferation Activity of NCI-H358 by CellTiter-Glo Reagent

NCI-H358 cells in exponential growth phase were digested with trypsin-EDTA, plated in a 96-well plate with 2000-3000 cells per well, and incubated overnight at 37° C. with 5% $CO_2$. Mother solutions were prepared from the test compounds by using DMSO, subjected to gradient elution with RPMI 1640 growth medium, and then added into the 96-well plate and incubated in an incubator for 72 h at 37° C. with 5% $CO_2$. After the incubation, CellTiter-Glo test reagent with an equal volume was added into each well and the obtained 96-well plate was incubated after shaking. The chemiluminescence values were determined by microplate reader, and the $IC_{50}$ values of the test compounds inhibiting the proliferation of NCI-H358 cells were fitted and calculated by GraphPad Prism software.

Wherein "A" represents an $IC_{50}$ value (nM) of less than or equal to 50; "B" represents an $IC_{50}$ value (nM) of more than 50.

| Compound No. | $IC_{50}$ value of cell proliferation inhibitory activity of NCI-H358 |
|---|---|
| 2-3 | A |
| 2-8 | A |
| 3-49 | A |
| 3-51 | A |
| 3-12M | A |
| 3-12P | B |
| 3-16M | A |
| 3-16P | B |

Test results demonstrate that: Compound 2-3, Compound 2-8, Compound 3-49, Compound 3-51, Compound 3-12M and Compound 3-16M show significant anti-cell proliferation activity against KRAS G12C mutant type cells NCI-H358.

Compound 3-12M with axial chiral R configuration shows significantly better cell proliferation inhibitory activity on NCI-H358 than the corresponding Compound 3-12P with axial chiral S configuration. The cell proliferation inhibitory activity of Compound 3-12M with R-configuration is more than 5 times that of the corresponding Compound 3-12P with axial chiral S-configuration.

Compound 3-16M with axial chiral R configuration shows significantly better cell proliferation inhibitory activity on NCI-H358 than the corresponding Compound 3-16P with axial chiral S configuration.

4. Inhibition Test of the Compounds on Cell Proliferation Activity of NCI-H358

The inhibition effects of the compounds on proliferation activity of NCI-H358 cells were tested with reference to the method of bioassay test 3, and the test results are as follows.

Wherein "A" represents an $IC_{50}$ value (nM) of less than or equal to 50; "B" represents an $IC_{50}$ value (nM) of more than 50.

| Compound No. | $IC_{50}$ value of cell proliferation inhibitory activity of NCI-H358 |
|---|---|
| 3-1MIS | A |
| 3-3MIS | A |
| 3-4MIS | A |

-continued

| Compound No. | $IC_{50}$ value of cell proliferation inhibitory activity of NCI-H358 |
|---|---|
| 3-5MIS | A |
| 3-7MIS | A |
| 3-8MIS | A |
| 3-9MIS | A |
| 3-11MIS | A |
| 3-12MIS | A |

Test results demonstrate that: Compound 3-1MIS, Compound 3-3MIS, Compound 3-4MIS, Compound 3-5MIS, Compound 3-7MIS, Compound 3-8MIS, Compound 3-9MIS, Compound 3-11MIS and Compound 3-12MIS show significant anti-cell proliferation activity against KRAS G12C mutant type cells NCI-H358.

5. Preliminary Safety Test of the Compounds

Test samples: Compound 3-2, Compound 3-6, Compound 3-12M, Compound 3-20, and Compound 4-8.

Animal species and number: Balb/c; 6 animals per group (half male and half female).

Administration mode: oral administration by gavage.

Animal grouping and administration dose: vehicle blank group, Compound 3-2 group (200 mg/kg, 400 mg/kg, 800 mg/kg), Compound 3-6 group (200 mg/kg, 400 mg/kg, 800 mg/kg), Compound 3-12M group (200 mg/kg, 400 mg/kg, 800 mg/kg), Compound 3-20 group (200 mg/kg, 400 mg/kg, 800 mg/kg), Compound 4-8 group (200 mg/kg, 400 mg/kg, 800 mg/kg).

Administration frequency: once a day for 5 days.

Test Procedure:

after the administration, acute toxic reactions were observed by the cage side for 4 h, and detailed clinical observations were made for those animals that showed obvious abnormalities. General clinical observations were performed 2 times a day (once in the morning and once in the afternoon) during the test period. Death, morbidity, respiration, secretions, feces, and diet, drinking situation and so on were observed, and the changes in body weight of the mice during the administration period were recorded. The animals in each group were euthanized after the administration, and all animals were dissected and subjected to gross observation.

| Group | Day 1 | Day 2 | Day 3 | Day 4 | Day 5 |
|---|---|---|---|---|---|
| Vehicle group | / | / | / | / | / |
| Compound 3-2 group | 200 mg/kg | 200 mg/kg | 400 mg/kg | 400 mg/kg | 800 mg/kg |
| Compound 3-6 group | 200 mg/kg | 200 mg/kg | 400 mg/kg | 400 mg/kg | 800 mg/kg |
| Compound 3-12M group | 200 mg/kg | 200 mg/kg | 400 mg/kg | 400 mg/kg | 800 mg/kg |
| Compound 3-20 group | 200 mg/kg | 200 mg/kg | 400 mg/kg | 400 mg/kg | 800 mg/kg |
| Compound 4-8 group | 200 mg/kg | 200 mg/kg | 400 mg/kg | 400 mg/kg | 800 mg/kg |

Test results: during the administration period, for Compound 3-2, Compound 3-6, Compound 3-12M, Compound 3-20, and Compound 4-8, all animals in the dose groups were normal in water and food intake, activity and body weight, and no significant abnormality was showed. The maximum tolerated doses of Compound 3-2, Compound 3-6, Compound 3-12M, Compound 3-20, and Compound 4-8 are initially suggested to be greater than 800 mg/kg.

6. Pharmacodynamics Test of Tumor Cells MIA PaCa-2-Derived Xenograft Tumor Model in Nude Mice Model establishment and administration regimen:

Animal species and number: Balb/c Nude; 6 animals per group.

Test samples: Compound 3-2, Compound 3-6, Compound 3-20, Compound 3-12M.

Test groups: blank solvent control group; Compound 3-2 (10 mg/kg, QD×15 days), Compound 3-6 (10 mg/kg, QD×15 days), Compound 3-20 (10 mg/kg, QD×15 days), Compound 3-12M (10 mg/kg, QD×15 days).

Animal model establishment: MIA paca-2 tumor cells in logarithmic growth phase were cultured in vitro and collected, and inoculated subcutaneously into the right back of nude mice at a quantity of $5\times10^6$ cells/each. When the tumor volume reached 150~300 $mm^3$, the tumor-bearing nude mice were randomly grouped. Subsequently, the animals in each group were administered, and the day of the first administration was defined as day 1 of the test.

Administration route and frequency: oral administration by gavage; once a day.

General state observation: observation time and frequency: once a day; observation indexes or contents: including but not limited to administration location, appearance and signs, general behavioral activities, mental status, death and other abnormal performance of the animals. The animals were euthanized at the end of the test.

Tumor volume calculation: V=½×long diameter×short diameter$^2$ ($mm^3$). Tumor growth inhibition rate TGI (%) is used to evaluate the tumor inhibition efficacy of the compounds. TGI (%)=[1−(mean tumor volume in treatment group at the end of administration−mean tumor volume in treatment group at the beginning of administration)/(mean tumor volume in control group at the end of administration−mean tumor volume in control group at the beginning of administration)]×100%.

"+" represents a tumor inhibition rate of <60%; "++" represents a tumor inhibition rate of 60%~80%; "+++" represents a tumor inhibition rate of >80%.

| Compound | Tumor inhibition rate (%) |
|---|---|
| 3-2 | +++ |
| 3-6 | +++ |
| 3-12M | +++ |
| 3-20 | +++ |

Test Results:

(1) Compound 3-2, Compound 3-6, Compound 3-12M, and Compound 3-20 show significant inhibition effect on the growth of subcutaneously transplanted tumors derived from pancreatic cancer MIA paca-2 cells in nude mice, and the tumor inhibition rate of Compound 3-12M is higher than that of Compound 3-20.

(2) During the administration period, all the test animals were normal in water and food intake, activity and body weight, and no toxicity was exhibited.

7. Effect of the Compounds on KRAS(G12C) Enzyme Activity

Test principle: Eu-tagged GST antibody binds to $KRAS^{G12C}$ protein with GST tag. $d_2$-tagged 6HIS antibody binds to c-Raf protein with 6HIS tag. When $KRAS^{G12C}$ protein is activated by binding to GTP, it binds to c-Raf protein, thus pulling Eu and $d_2$ closer. After Eu as a donor is excited by light source (320 nm), through resonance transfer the energy is transferred to the adjacent acceptor $d_2$, which emits 665 nm emission light. The signal intensity at 665 nm wave length is directly proportional to the amount of $KRAS^{G12C}$ protein binding to c-Raf protein. When an inhibitor is added, the binding of $KRAS^{G12C}$ and c-Raf is inhibited. The level of a compound inhibiting $KRAS^{G12C}$ enzyme activity is evaluated in this way.

Wherein the compound AMG510 was prepared according to the literature method (Journal. Medicinal. Chemistry. 2020, 63, 52-65).

Compound Dilution:

Compound stock solution was taken, and the test compound was subjected to gradient elution in DMSO. The above diluted compound was added into a quantitative volume of enzyme reaction buffer and subjected to oscillation on a microplate oscillator for 20 min.

Compound Test:

4 μL of enzyme was transferred to a 384-well reaction plate. 1 μL of the test compound was added into the 384-well reaction plate. The plate was sealed with sealing film, and the reaction plate with the compound was centrifuged at 1000 rpm for 1 min and incubated for 60 min. 5 μL of a mixture of substrate and antibody was transferred to the 384-well reaction plate. The plate was sealed with sealing film, then centrifuged at 1000 rpm for 1 min and incubated for 120 min at room temperature. By using a multifunctional microplate reader with excitation light set to 320 nm and emission light set to 615 nm and 665 nm, the fluorescence signals at 615 nm (Eu) and 665 nm (d2) were read.

Data Analysis:

$$\% \text{ inhibition rate} = 100 - \left[\frac{\overline{Ratio}_{test\ compound} - \overline{Ratio}_{positive\ control}}{\overline{Ratio}_{negative\ control} - \overline{Ratio}_{positive\ control}}\right] * 100$$

$\overline{\text{Ratio}}_{positive\ control}$: average value of the ratios of 10 positive control wells; $\overline{\text{Ratio}}_{negative\ control}$: average value of the ratios of 10 negative control wells.

Test Results:

| Compound | $IC_{50}$ value of the compound on KRAS G12C enzyme activity (nM) |
|---|---|
| 3-12M | 9.7 |
| 3-20 | 19.0 |
| AMG510 | 42.1 |

The test results show that both Compound 3-12M and Compound 3-20 have remarkable better inhibitory activity on $KRAS^{G12C}$ enzyme than AMG510.

8. Test of Proliferation Inhibition of the Compounds on Tumor Cells NCI-H358

Test samples: Compound 3-2, Compound 3-6, Compound 3-20, and Compound 3-12M.

The test method of inhibitory activity was the same as that in Test 3 in "Biological Tests" part.

Test Results:

| Compound | $IC_{50}$ of proliferation inhibitory activity of the compound on NCI-H358 cell line (nM) |
|---|---|
| 3-2 | 10 |
| 3-6 | 11 |
| 3-20 | 10 |
| 3-12M | 8 |
| AMG510 | 41 |

The test results show that both Compound 3-12M and Compound 3-20 are better than AMG510 in cell proliferation inhibitory activity of NCI-H358.

9. Pharmacodynamics Study of Tumor Cells H358-Derived Xenograft Tumor Model

Model establishment and administration regimen:

Animal species and number: Balb/c Nude; 10 animals per group.

Test samples: Compound ARS1620 (the representative inhibitor targeting KRAS G12C tumor target, acquired by purchase) and Compound 3-12M.

Test groups: blank solvent control group;

Compound ARS1620 (100 mg/kg, i.g., QD×28 days);

Compound 3-12M (20 mg/kg, i.g., QD×28 days);

Compound 3-12M (100 mg/kg, i.g., QD×28 days).

Animal Model Establishment:

NCI-H358 tumor cells in logarithmic growth phase were cultured in vitro and collected, and inoculated subcutaneously into the right back of nude mice at a quantity of $5\times10^6$ cells/each. When the tumor volume reached 150~300 $mm^3$, the tumor-bearing nude mice were randomly grouped. Subsequently, the animals in each group were administered, and the day of the first administration was defined as day 1 of the test.

Administration route and frequency: oral administration by gavage; once a day.

General state observation: observation time and frequency: once a day; observation indexes or contents: including but not limited to administration location, appearance and signs, general behavioral activities, mental status, death and other abnormal performance of the animals. The animals were euthanized at the end of the test.

Tumor volume calculation: V=½×long diameter×short diameter$^2$ ($mm^3$).

Figure 2:
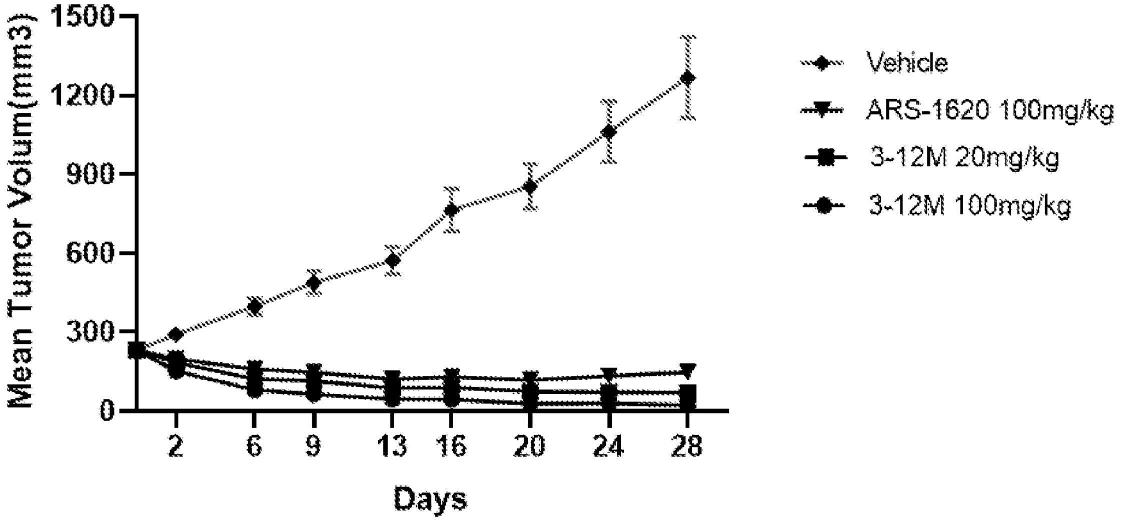
FIG. 2 shows tumor volume growth curve of NCI-H358 tumor cells xenograft tumor models in vivo for Compound 3-12M and ARS1620.

Test Results:

the compound shows significant inhibition effect on the growth of subcutaneously transplanted tumors derived from lung cancer NCI-H358 cells in nude mice, see FIG. 2. The inhibitory activity of Compound 3-12M on tumor growth in vivo is significantly better than that of ARS1620.

10. Pharmacodynamics Study of Tumor Cells NCI-H358-Derived Xenograft Tumor Model Model establishment and administration regimen:

Animal species and number: Balb/c Nude; 6 animals per group.

Test samples: Compound 3-2, Afatinib (acquired by purchase), and Trametinib (acquired by purchase).

Test groups: blank solvent control group;

Compound 3-2 (10 mg/kg, i.g., QD×21 days);

Afatinib (10 mg/kg, i.g., QD×21 days);

Trametinib (0.1 mg/kg, i.g., QD×21 days);

Compound 3-2 (10 mg/kg) in combination with Afatinib (10 mg/kg), once a day for 21 days continuously;

Compound 3-2 (10 mg/kg) in combination with Trametinib (0.1 mg/kg), once a day for 21 days continuously.

Animal Model Establishment:

NCI-H358 tumor cells in logarithmic growth phase were cultured in vitro and collected, and inoculated subcutaneously into the right back of nude mice at a quantity of $5\times10^6$ cells/each. When the tumor volume reached 150-300 $mm^3$, the tumor-bearing nude mice were randomly grouped. Subsequently, the animals in each group were administered, and the day of the first administration was defined as day 1 of the test.

Administration frequency: once a day.

General state observation: observation time and frequency: once a day; observation indexes or contents: including but not limited to administration location, appearance and signs, general behavioral activities, mental status, death and other abnormal performance of the animals. The animals were euthanized at the end of the test.

Tumor volume calculation: V=½×long diameter×short diameter$^2$ ($mm^3$).

Test Results:

"+" represents a tumor inhibition rate of <130%; "++" represents a tumor inhibition rate of 130%~200%; "+++" represents a tumor inhibition rate of >200%.

| Compound | Tumor inhibition rate (%) |
|---|---|
| 3-2 | ++ |
| Afatinib | + |
| 3-2 + Afatinib | +++ |
| Trametinib | + |
| 3-2 + Trametinib | +++ |

In respect to NCI-H358-derived xenograft tumor model, Compound 3-2 in combination with marketed drugs Afatinib and Trametinib respectively are used and significant synergistic inhibition effect on tumor growth is achieved.

11. Pharmacodynamic Effect Study of Tumor Cells MIA PaCa-2-Derived Xenograft Tumor Model Model establishment and administration regimen:

Animal species and number: Balb/c Nude; 6 animals per group.

Test samples: Compound 3-2, and Compound TM-1.

Test groups: blank solvent control group;

Compound 3-2 (20 mg/kg, i.g., QD×21 days);

Compound TM-1 (20 mg/kg, i.g., QD×21 days).

Animal model establishment: MIA PaCa-2 tumor cells in logarithmic growth phase were cultured in vitro and collected, and inoculated subcutaneously into the right back of nude mice at a quantity of $5\times10^6$ cells/each. When the tumor volume reached 150-300 $mm^3$, the tumor-bearing nude mice were randomly grouped. Subsequently, the animals in each group were administered, and the day of the first administration was defined as day 1 of the test.

Administration frequency: once a day.

General state observation: observation time and frequency: once a day; observation indexes or contents: including but not limited to administration location, appearance and signs, general behavioral activities, mental status, death and other abnormal performance of the animals. The animals were euthanized at the end of the test.

Tumor volume calculation: V=½×long diameter×short diameter$^2$ ($mm^3$).

Test Results:

in the following table, "+" represents a tumor inhibition rate of <100%; "++" represents a tumor inhibition rate of 100%~140%; "+++" represents a tumor inhibition rate of >140%.

| Compound | Tumor inhibition rate (%) |
|---|---|
| 3-2 | +++ |
| TM-1 | + |

12. Test of Proliferation Inhibitory Activity of the Compounds on MIA Paca-2 Cells Test samples: Compound 3-2 and Compound TM-2.

The test method of inhibitory activity was the same as that in Test 2 in "Biological Tests" part.

Test Results:

in the following table, "A" represents an $IC_{50}$ value (nM) of ≤15; "B" represents an $IC_{50}$ value (nM) of 15~45; "C" represents an $IC_{50}$ value (nM) of ≥45.

| Compound | $IC_{50}$ of proliferation inhibitory activity of the compound on MIA Paca-2 cell line |
|---|---|
| 3-2 | A |
| TM-2 | C |

Compound 3-2 has remarkable better proliferation inhibitory activity on MIA Paca-2 cell line than Compound TM-2.

13. Analysis Regarding Therapeutic Safety Window

A continuous administration safety test reveals that for Compound 3-2, Compound 3-6, Compound 3-12M, Compound 3-20 and Compound 4-8, the dose was gradually increased from 200 mg/kg to 800 mg/kg in the five-day continuous administration test, and all animals in dose groups were normal in water and food intake, activity and body weight, and no significant abnormality was showed.

On the other hand, a pharmacodynamic test in vivo reveals that the effective dose of Compound 3-2, Compound 3-6 and Compound 3-12M for tumor inhibition is less than 10 mg/kg, and these compounds have a wide therapeutic safety window (the ratio of toxic dose to effective dose is greater than 80), thus have significant potential for application.

14. Genotoxicity Study—Test of Effect on Chromosomal Aberration in Chinese Hamster Lung Fibroblasts Test objective: the objective was to evaluate the potential genotoxicity of Compound 3-12M of the present invention and to evaluate whether the test sample was able to induce chromosomal aberrations in Chinese hamster lung fibroblasts in presence or absence of rat liver S9 metabolic activation system.

Cell line: Chinese hamster lung fibroblasts (CHL cells), obtained from ATCC.

Test regimen: in addition to a test compound group, a vehicle control group (DMSO) and positive control groups (0.1 μg/mL of direct-acting mutagen mitomycin C, 10 μg/mL of indirect-acting mutagen cyclophosphamide) were also set in this test. After the addition of 3-12M or control substances, the cells were incubated for 24 h under the condition of non-metabolic activation (the concentration of Compound 3-12M was 0.75-10 μg/ml) or for 4 h under the condition of non-metabolic activation or metabolic activation (the concentration of Compound 3-12M was 3-40 μg/ml) and then incubated for another 20 h after the replacement of fresh normal culture solution. 4 h before the collection of cells, colchicine (0.01 mg/mL, 0.1 mL) was added into the cells in each vial for incubation. After the incubation, the cells in each vial were collected for counting, and treated with hypotonic solution (0.075 mol/L of KCl). The cells were fixed and then prepared into a chromosome spread with Giemsa staining. 100 cells were observed in mitomycin group and in cyclophosphamide group under the condition of metabolic activation, and 300 cells were observed in each of the remaining test sites, and chromosome aberration rate for each test site was calculated.

Test results: Compound 3-12M has no teratogenic effect on the chromosomes in Chinese hamster lung fibroblasts, indicating that compound 3-12M has no potential genotoxic risk.

However, supporting information in the appendix of the reference (The New England Journal of Medicine, 2020; 383:1207-1217; DOI: 10.1056/NEJMoa1917239) (page 23) reveals that the chromosome aberration effect test of AMG510 shows a positive result, indicating that AMG510 has potential genotoxicity.

15. Study of Transport Effect of Transporter MDR1 on the Compound

Whether the compound is a substrate for P-gp was assessed by testing the uptake ratio of the compound in vesicles expressing human-derived MDR1 (MDR1 coding P-gp) transporter protein. For this test, fluorescein and N-methylquinidine were used as the probe substrates in positive control group. ATP-containing test sample or positive control samples were prepared and pre-incubated with MDR1 vesicles at 37° C. After the pre-incubation, the two kinds of samples were mixed and co-incubated at 37° C. The samples were then transferred to a 96-well filter plate, and washed by suction filtration. The vesicles on the filter plate were lysed by using 80% of methanol, and then centrifuged to collect the filtrate. The filtrate was added with pre-cooled methanol containing internal standard. After the centrifugation, the obtained supernatant was taken and the test sample or positive control samples were detected. The test results indicate that Compound 3-12M is not a substrate for P-gp. According to the report (supporting information in the appendix of the reference: The New England Journal of Medicine, 2020; 383:1207-1217; DOI: 10.1056/NEJMoa1917239), AMG510 is a substrate for resistance mechanism transport protein P-gp, and AMG510 may have drug resistance to tumor cells triggered by drug efflux mediated by multidrug resistance protein P-glycoprotein (P-gp). In contrast, Compounds 3-12M does not have such efflux effect.

16. Acute Toxicity Test for Compound 3-2 and Compound 3-6

Test samples: Compound 3-2, and Compound 3-6.

Animal species and number: SD rat; 6 animals per group (half male and half female).

Administration mode: oral administration by gavage.

Animal grouping and administration dose: vehicle blank group, Compound 3-2 group (500 mg/kg, 1000 mg/kg, 2000 mg/kg), Compound 3-6 group (500 mg/kg, 1000 mg/kg, 2000 mg/kg).

Administration frequency: once.

Test Procedure:

observation by the cage side after the administration on the day of administration (D1): frequency and time of the observation: for the animals in each group, acute toxic reactions were observed by the cage side for 4 h after the administration, and detailed clinical observations were made for those animals that showed obvious abnormalities. Death, morbidity, respiration, secretions, feces, and diet, drinking situation and so on were observed, and the changes in body weight of the rats during the administration period were recorded. The contents of detailed clinical observation included but were not limited to behavioral activity, skin, coat, eyes, ears, nose, abdomen, external genitalia, anus, extremities, feet, and respiration. The animals in each group were euthanized at the end of observation period, and all animals were dissected and subjected to gross observation.

Test results: Compound 3-2 and Compound 3-6 were administered to SD rats by gavage once at the doses of 500 mg/kg, 1000 mg/kg and 2000 mg/kg. No animals in each group were dead or close to death. No changes related to the test samples were found in the gross observation of the animals in each dose group. Under the present test conditions, the maximum tolerated dose (MTD) of Compound 3-2 and Compound 3-6 is greater than or equal to 2000 mg/kg respectively.

17. Safety Test for Repeated Administration for 14 Days of Compound 3-2 and Compound 3-6

Test samples: Compound 3-2, and Compound 3-6.

Animal species and number: SD rat; 6 animals per group (half male and half female).

Administration mode: oral administration by gavage.

Animal grouping and administration dose: vehicle blank group, Compound 3-2 group (50 mg/kg, 150 mg/kg, 400 mg/kg), Compound 3-6 group (50 mg/kg, 150 mg/kg, 400 mg/kg).

Administration frequency: once a day for 14 days.

Test Procedure:

after the administration, acute toxic reactions were observed by the cage side for 4 h, and detailed clinical observations were made for those animals that showed obvious abnormalities. General clinical observations were performed 2 times a day (once in the morning and once in the afternoon) during the test period. Death, morbidity, respiration, secretions, feces, and diet, drinking situation and so on were observed, and the changes in body weight of the rats during the administration period were recorded. The contents of detailed clinical observation included but were not limited to behavioral activity, skin, coat, eyes, ears, nose, abdomen, external genitalia, anus, extremities, feet, and respiration. The animals in each group were euthanized at the end of administration period, and all animals were dissected and subjected to gross observation.

Test results: during the administration period (14 days), for Compound 3-2 and Compound 3-6, all animals in the dose groups were normal in water and food intake, activity and body weight, and no significant abnormality was showed.

18. Preliminary Study of Capsule Product of Compound 3-6

Formulation:

| Ingredient | Function | Dosage per capsule (mg) |
|---|---|---|
| Compound 3-6 | Main ingredient | 100 |
| Starch | Diluent | 50 |
| Starch slurry | Adhesive | appropriate amount |
| Sodium carboxymethyl starch | Disintegrant | 10 |
| Magnesium stearate | Lubricant | 2 |
| Gelatin hollow capsule | Capsule shell | 1 capsule |

Preparation Method of the Capsule:

Mixing: weighed Compounds 3-6, starch and sodium carboxymethyl starch were added into a wet mixing granulator for mixing.

Adhesive solution preparation: purified water was weighted, slowly added with an appropriate amount of starch under stirring condition, and stirred to disperse evenly to prepare the adhesive-starch slurry.

Soft material preparation: by using the wet mixing granulator and controlling the stirring speed and shearing speed, the starch slurry was slowly added, stirred and sheared to prepare soft material.

Granulation: the prepared soft material was granulated by using an oscillating granulator with 24-mesh sieve to obtain wet granules.

Drying: the wet granules were added into a fluidized bed granulator to obtain dried granules.

Sieving: the dried granules were sieved by the sieve of the oscillating granulator to obtain sieved granules, which were then weighed.

Mixing: the sieved granules were added into a three-dimensional multi-directional motion mixer, after the mixing added with magnesium stearate, and then subjected to final mixing to obtain the final mixed granules.

Filling: by using a filling machine, the final mixed granules were filled into 1 #gelatin hollow capsules, and the qualified capsules were screened to obtain capsules to be packed. The capsule samples with neat appearance were then obtained.

The invention claimed is:

1. A compound of formula (I), or a stereoisomer, a tautomer or a pharmaceutically acceptable salt thereof,

I

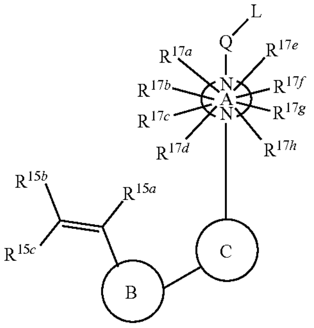

wherein,

Ring B is an aryl or a heteroaryl;

Ring C is any one of the following groups:

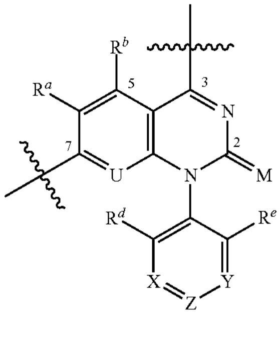

or

-continued

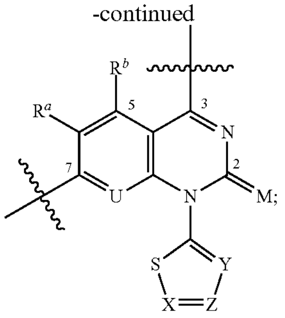

wherein, the carbon atom at the "3" position is connected with Ring A, and the carbon atom at the "7" position is connected with Ring B;

U is nitrogen or $CR^U$, wherein $R^U$ is hydrogen or deuterium;

M is oxygen or sulfur;

X is nitrogen or $CR^1$, Y is nitrogen or $CR^2$, Z is nitrogen or $CR^3$;

$R^a$ and $R^b$ are each independently hydrogen, deuterium, or a halogen; and $R^d$ and $R^e$ are each independently hydrogen, deuterium, a halogen, an alkyl, a deuterated alkyl, a haloalkyl, hydroxyl, amino, sulfonyl, sulfonamido, an alkenyl, or an alkynyl;

Ring A is a 5 to 7-membered nitrogen-containing heterocyclyl;

$R^1$, $R^2$, $R^3$, $R^{15a}$, $R^{15b}$, $R^{15c}$, $R^{17a}$, $R^{17b}$, $R^{17c}$, $R^{17d}$, $R^{17e}$, $R^{17f}$, $R^{17g}$, and $R^{17h}$ are each independently hydrogen, deuterium, a halogen, an alkyl, a deuterated alkyl, a haloalkyl, an alkenyl, or an alkynyl;

Q is —C(O)—, —C(S)—, —S(O)—, or —$S(O)_2$—;

L is an alkynyl, an alkenyl, or a haloalkyl;

the following structural fragment:

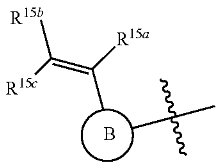

is any one of the following groups:

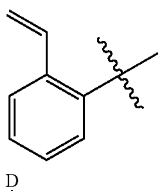

;

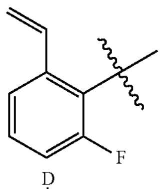

;

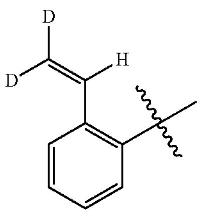

;

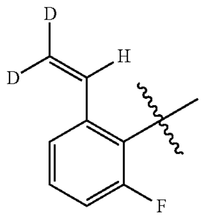

;

-continued
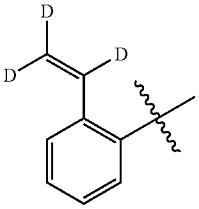 ; 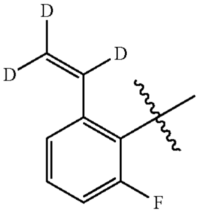 ;
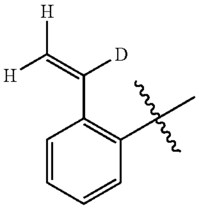 ; 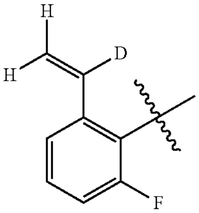 ;
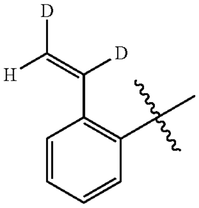 ; 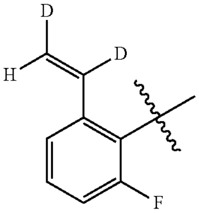 ;
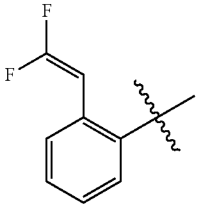 ; 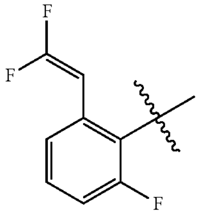 ;
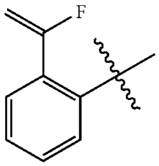 ; 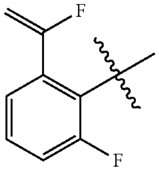 ;
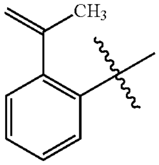 ; 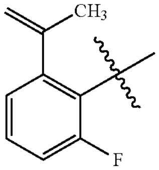 ;
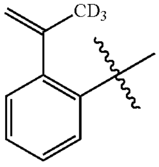 ; 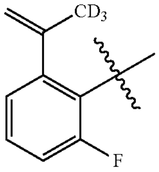 ;
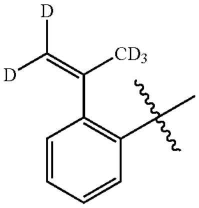 ; 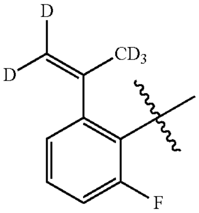 ;
-continued
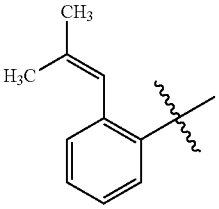 ; 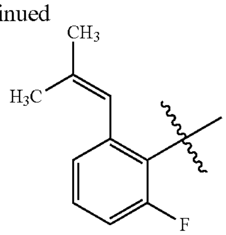 ;
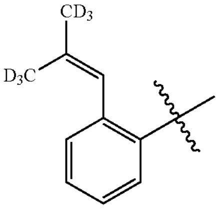 ; or 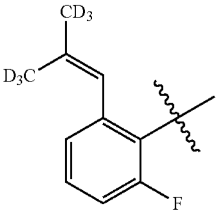 ;
the following structural fragment:
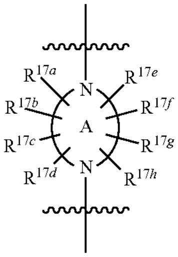
is any one of the following groups:
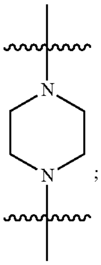 ; 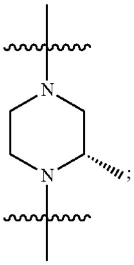 ; 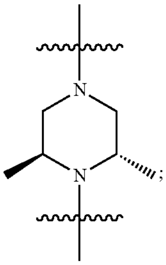 ;
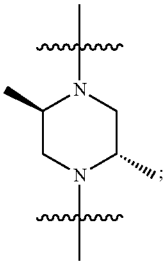 ; 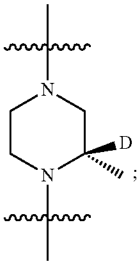 ;
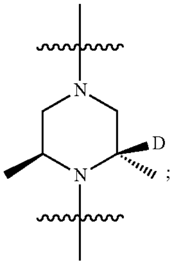 ; or 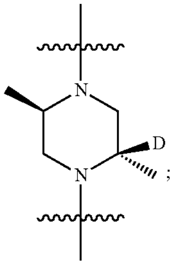 ;

the following structural fragment:

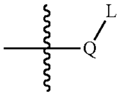

is any one of the following groups:

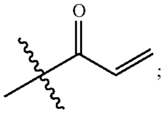 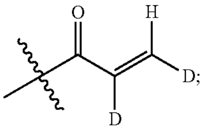 or

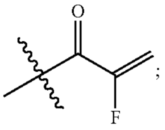

and the following structural fragments:

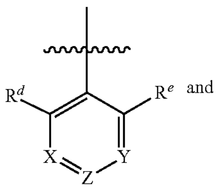 and 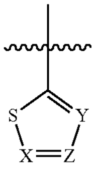

are each independently any one of the following groups:

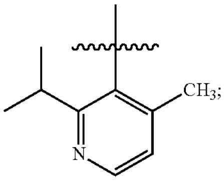 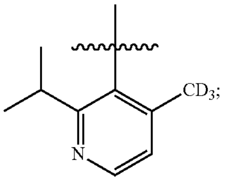

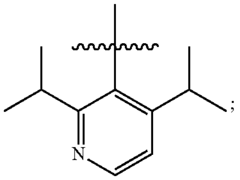 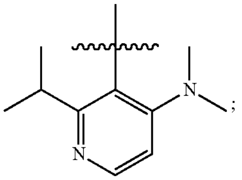

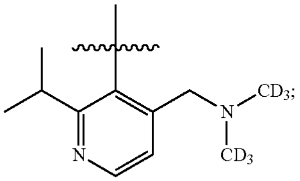 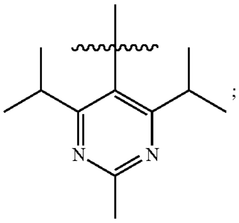

-continued

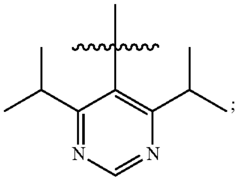 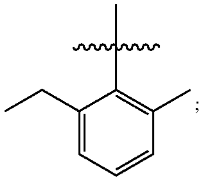

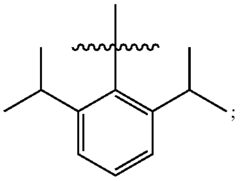 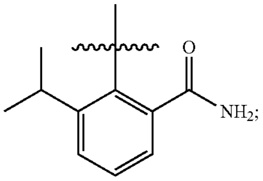

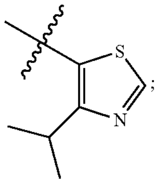 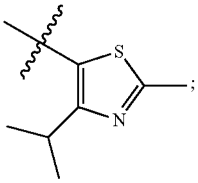 or

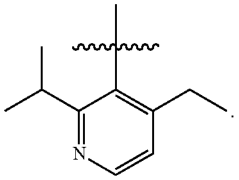

2. The compound of formula (I), or the stereoisomer, the tautomer or the pharmaceutically acceptable salt thereof according to claim 1, wherein the compound is any one selected from the group consisting of 1-1

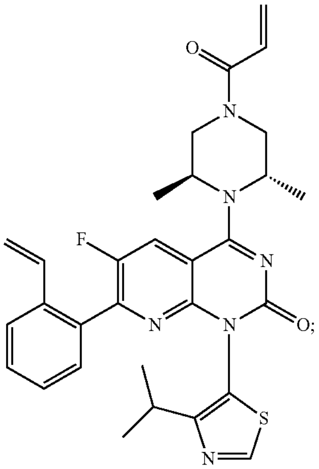

-continued
1-2
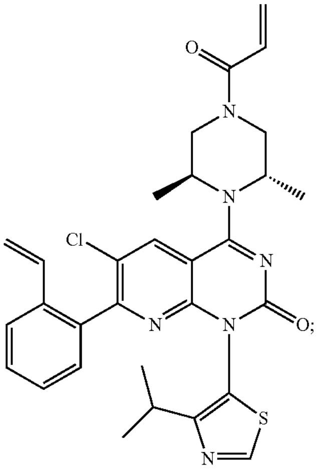
1-3
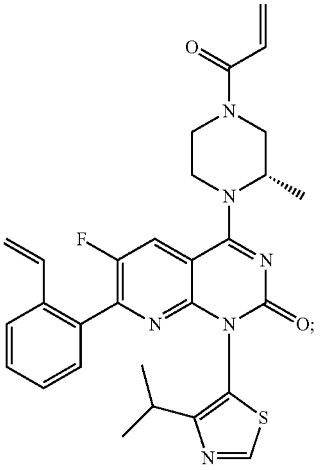
1-4
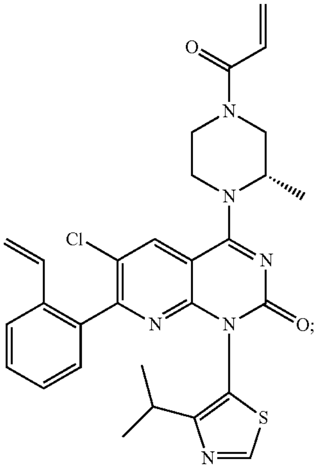
-continued
1-5
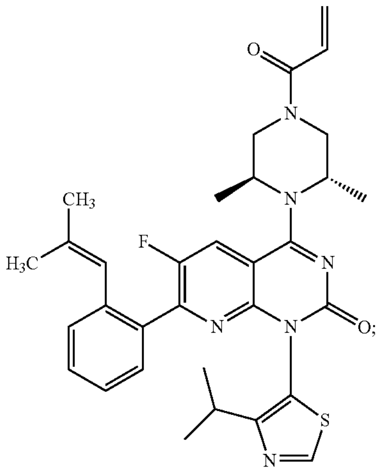
1-6
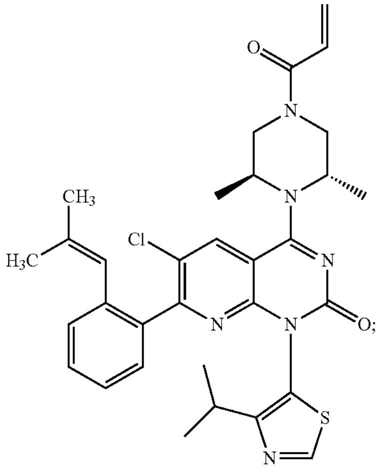
1-7
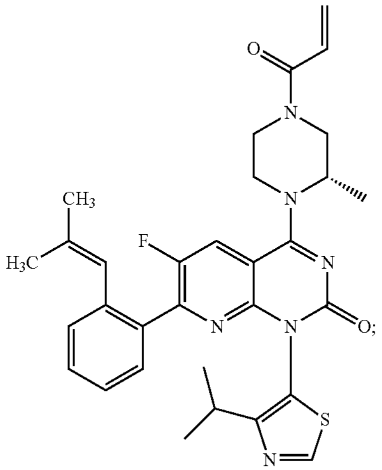

-continued
1-8
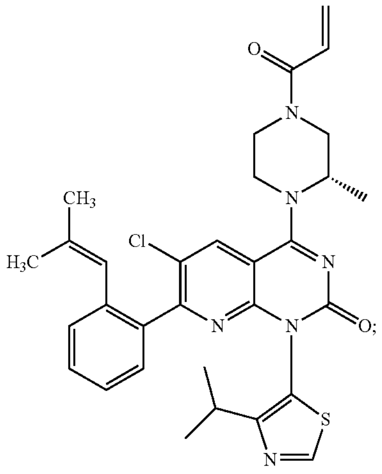
1-9
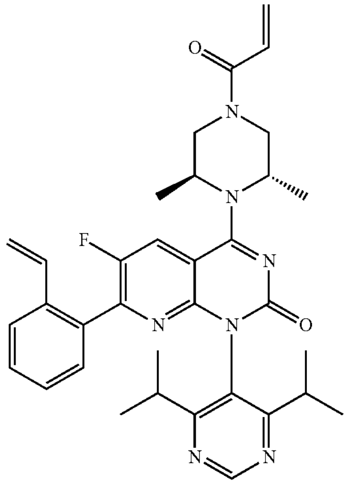
;
1-10
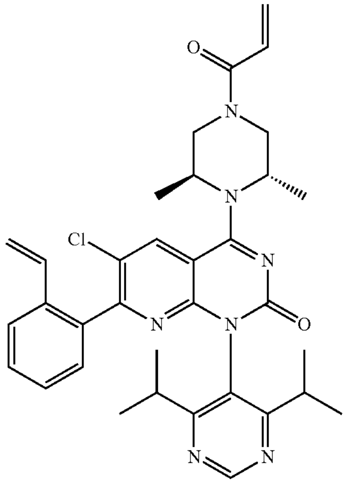
;
-continued
1-11
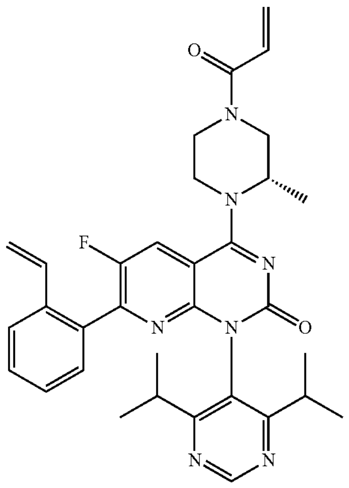
;
1-12
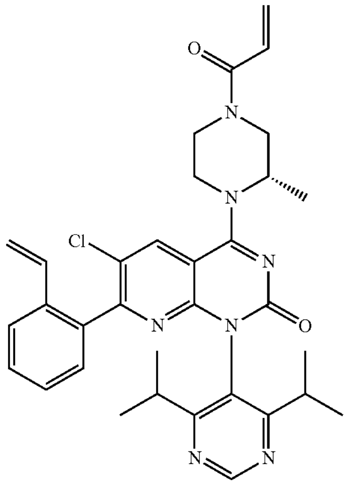
;
1-13
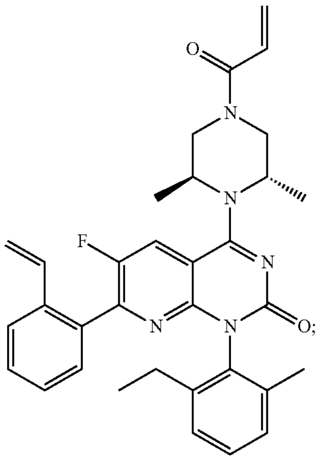

-continued
1-14
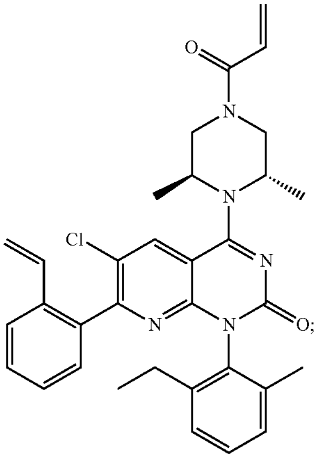
1-15
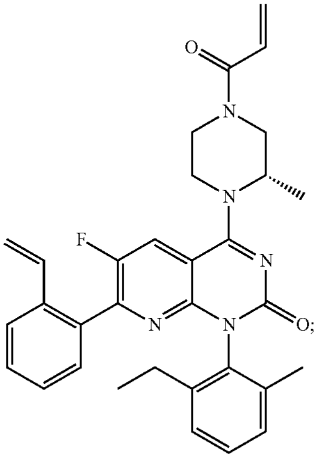
1-16
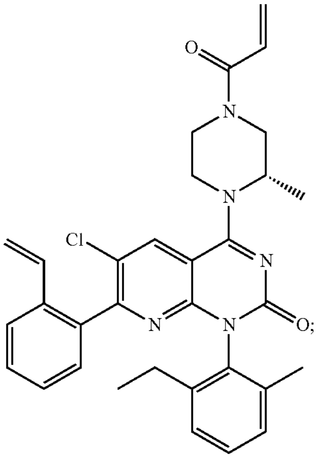
-continued
1-17
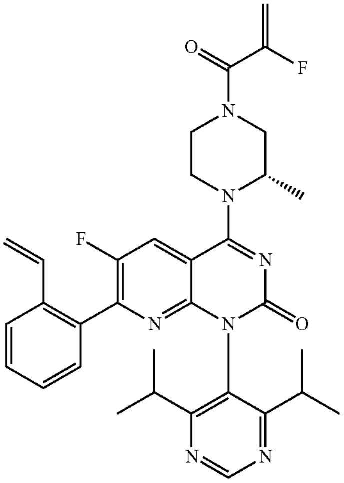
;
1-18
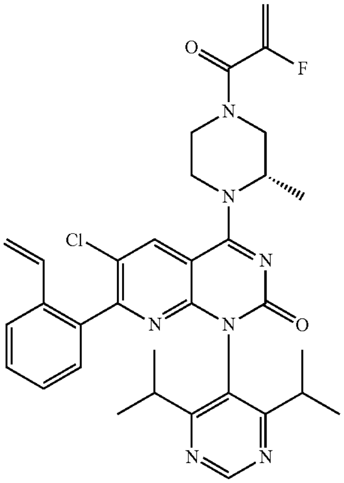
;
1-19
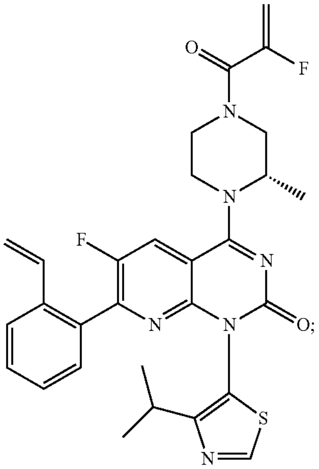

-continued
1-20
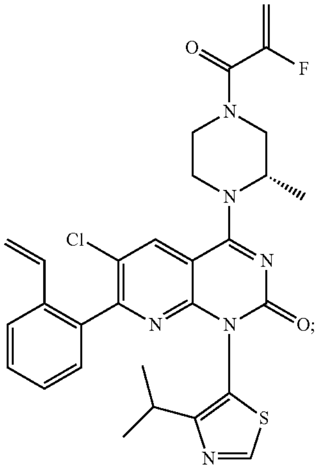
1-21
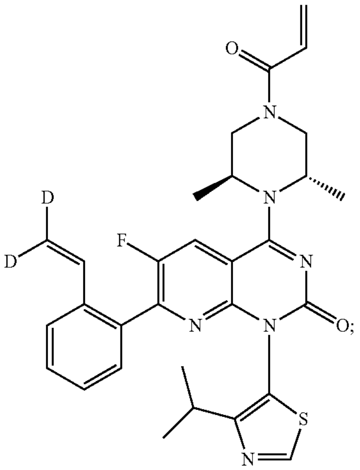
1-22
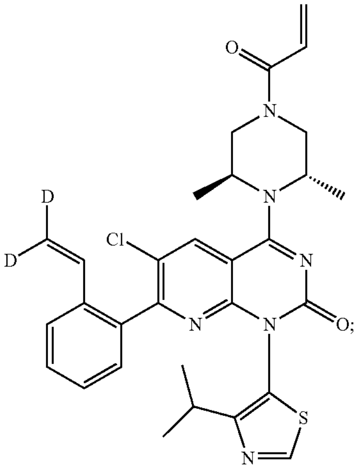
-continued
1-23
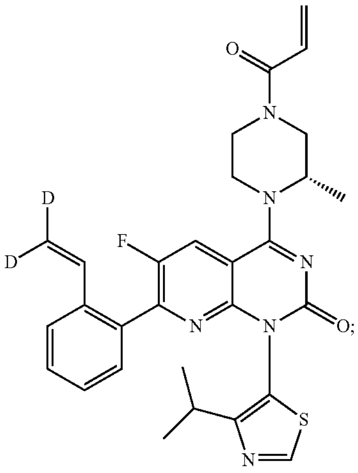
1-24
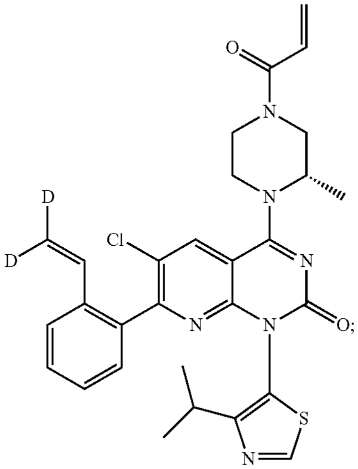
1-25
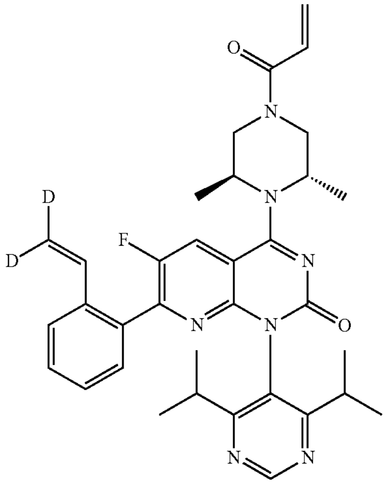
;

-continued
1-26
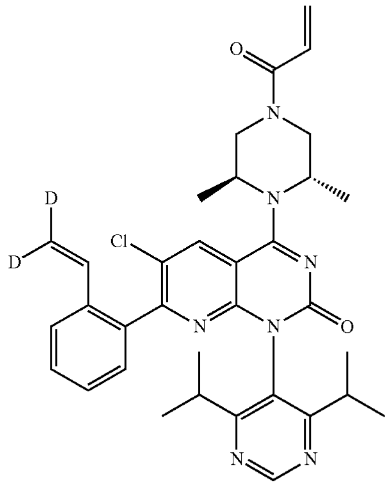
;
1-27
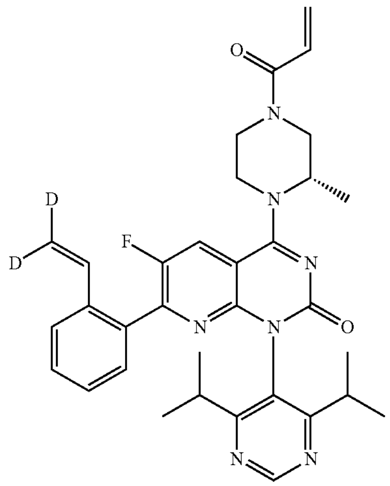
and
1-28
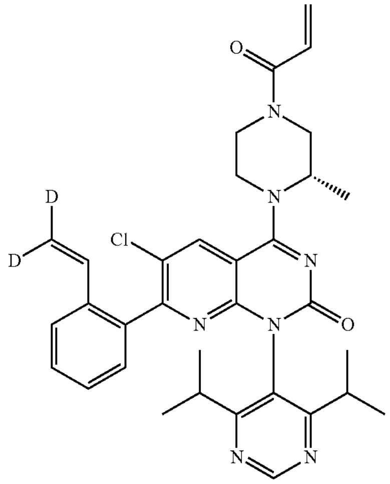
.
3. The compound of formula (I), or the stereoisomer, the tautomer or the pharmaceutically acceptable salt thereof according to claim 1, wherein the compound is any one selected from the group consisting of
3K-1
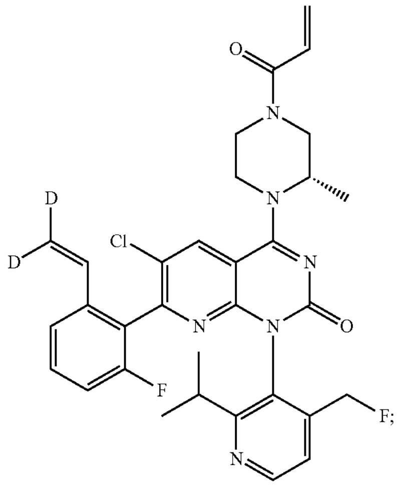
3K-2
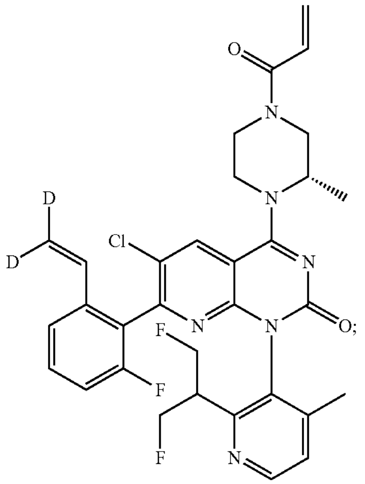
3K-3
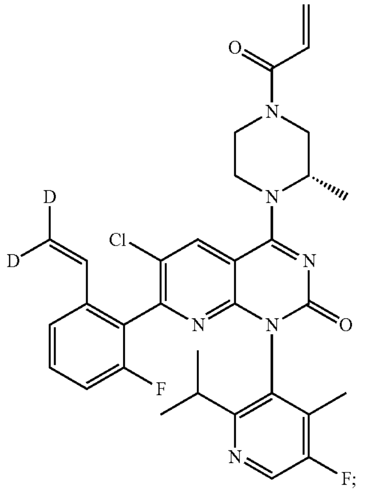

-continued
3K-4
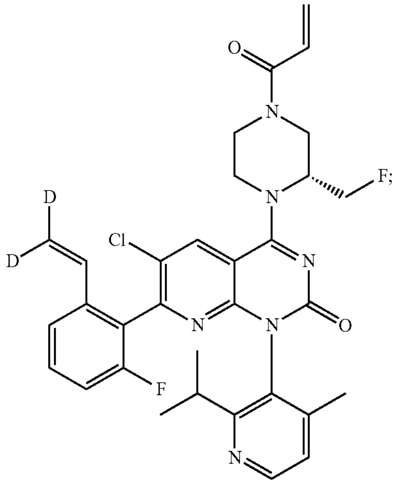
3K-5
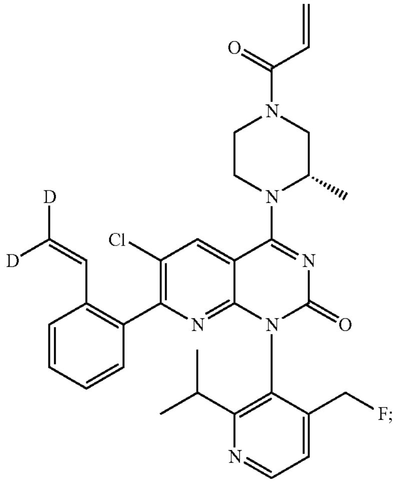
3K-6
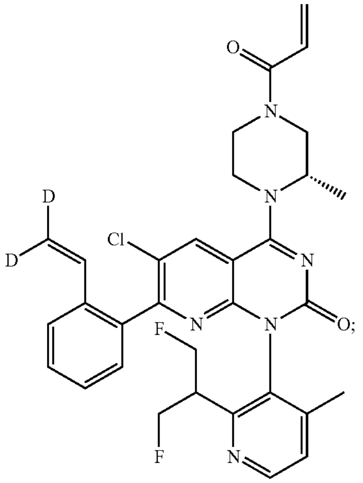
-continued
3K-7
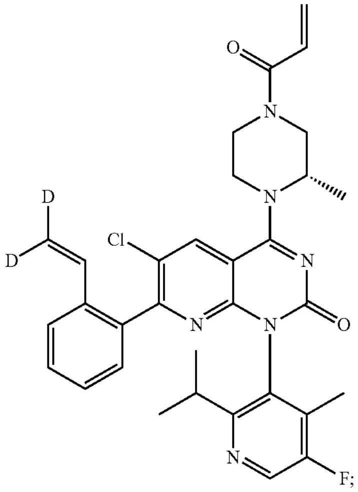
3K-8
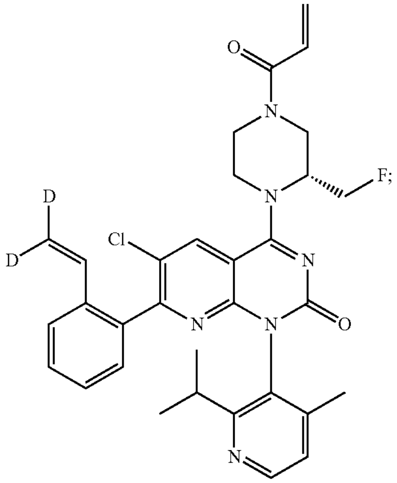
3-1MS
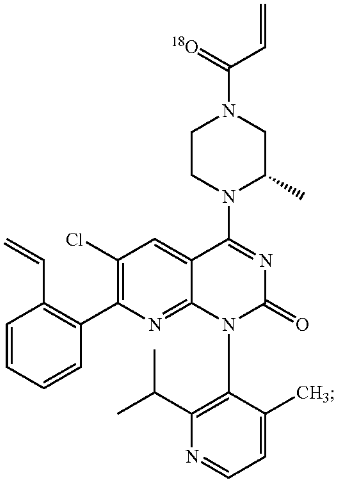

-continued
3-3MS
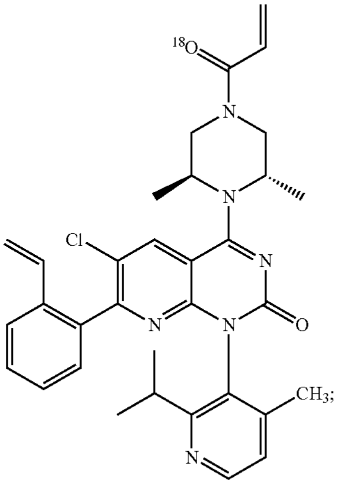
3-4MS
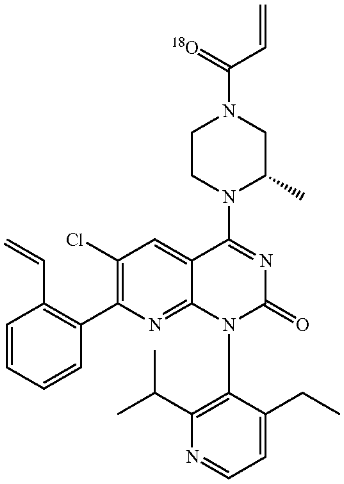
;
3-5MS
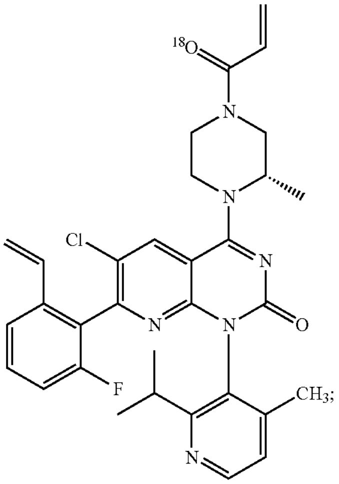
-continued
3-7MS
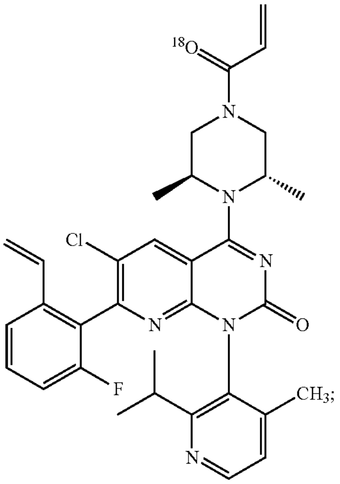
3-8MS
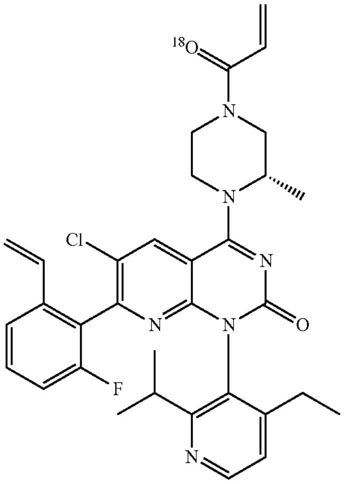
;
3-9MS
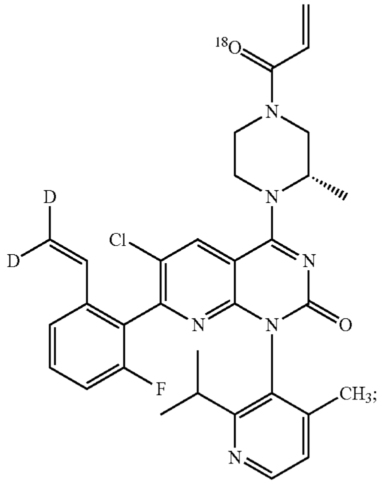

-continued
3-11MS
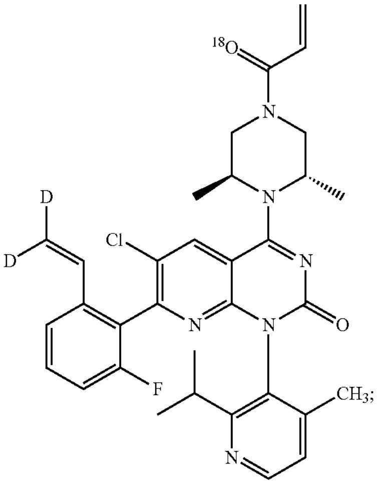
3-12MS
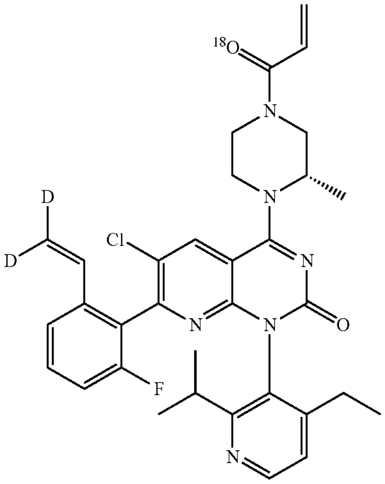
;
3-1MIS
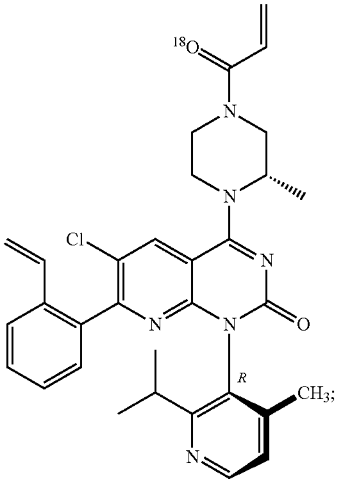
-continued
3-3MIS
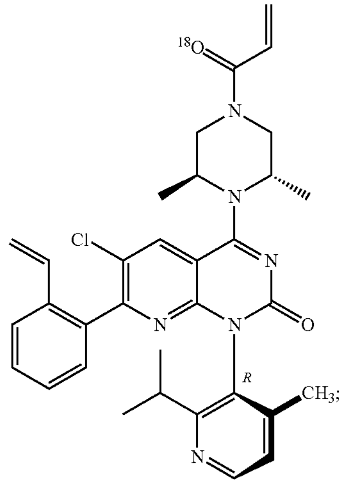
3-4MIS
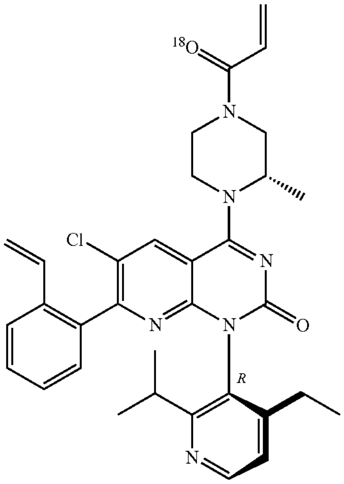
;
3-5MIS
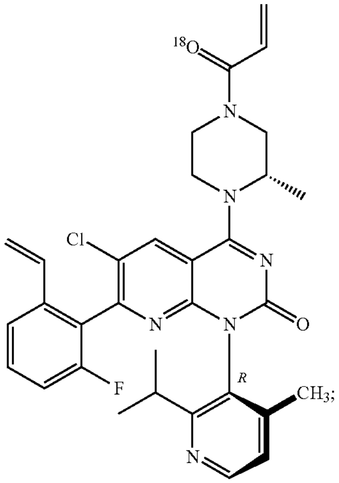

3-7MIS
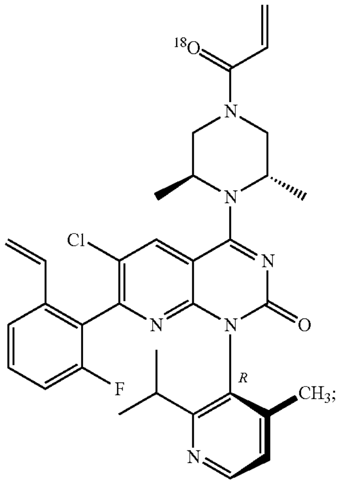
3-8MIS
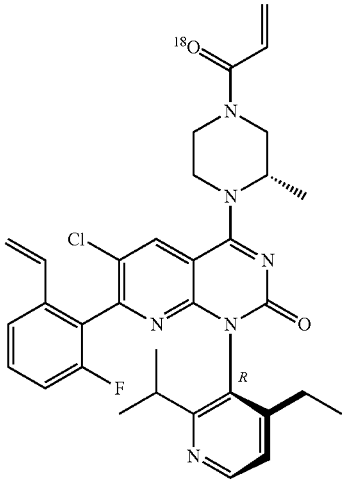
;
3-9MIS
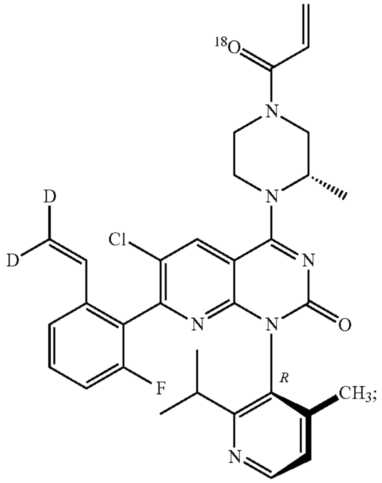
3-11MIS
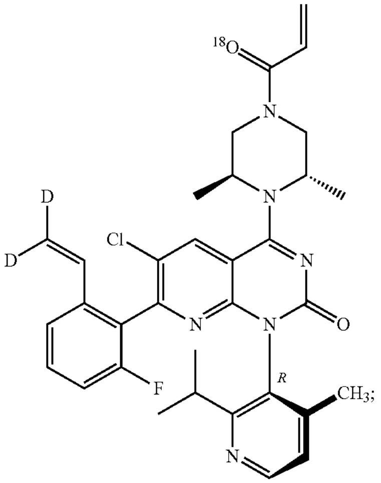
3-12MIS
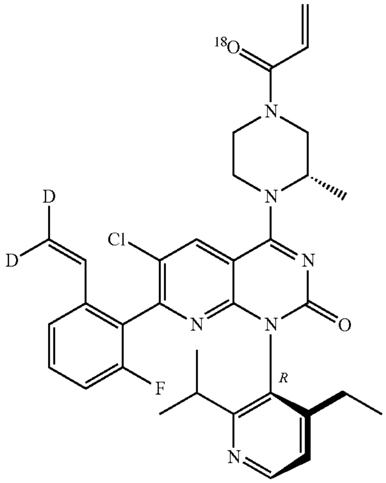
;
3K-1M
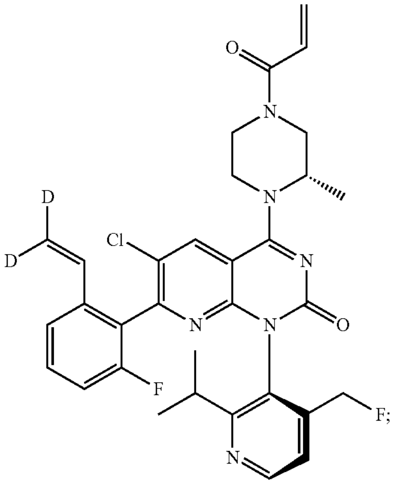

-continued
3K-2M
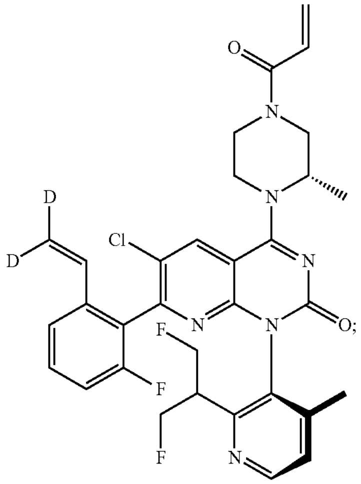
3K-3M
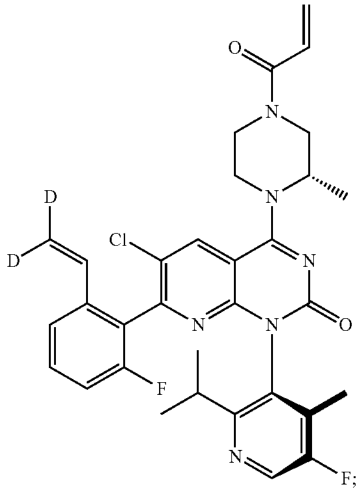
3K-5M
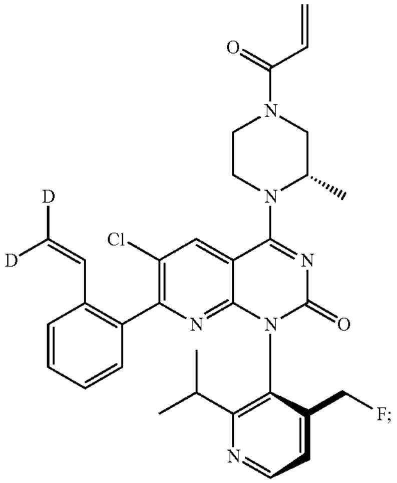
-continued
3K-6M
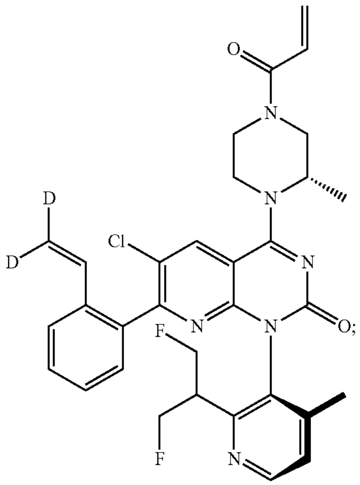
3K-7M
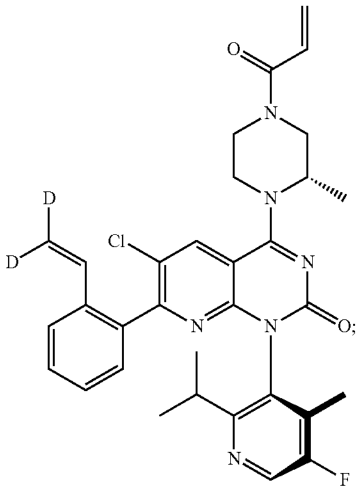
3K-9M
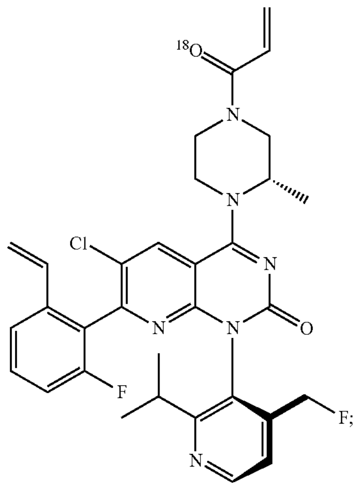

-continued 3K-10M

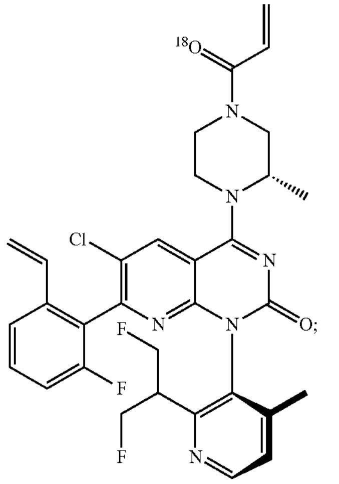

;

3K-11M

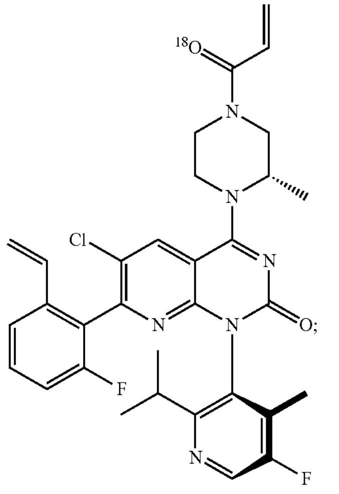

;

3K-13M

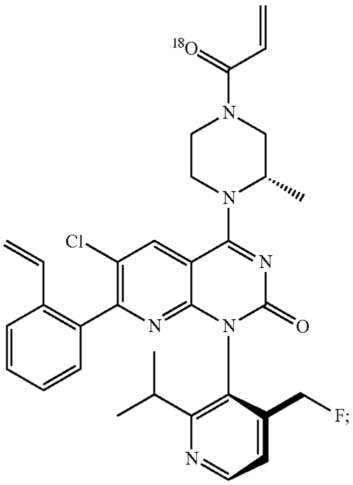

;

-continued 3K-14M

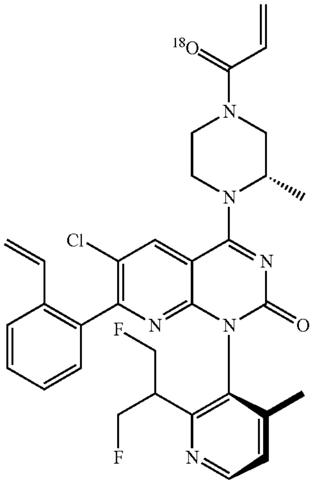

and 3K-15M

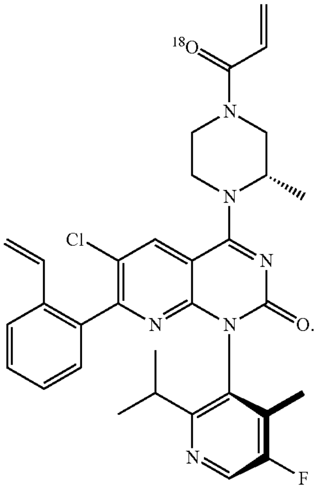

.

4. A pharmaceutical composition, comprising a therapeutically effective amount of the compound, or the stereoisomer, the tautomer or the pharmaceutically acceptable salt thereof according to claim 1 and pharmaceutically available carriers.

5. A method for preventing and/or treating diseases associated with KRAS mutation mediated cancers or associated with KRAS G12C mutation mediated cancers, comprising administering a therapeutically effective amount of the compound, or the stereoisomer, the tautomer or the pharmaceutically acceptable salt thereof according to claim 1 or a pharmaceutical composition comprising the compound, or the stereoisomer, the tautomer or the pharmaceutically acceptable salt thereof according to claim 1 to a subject in need thereof, wherein the compound, or the stereoisomer, the tautomer or the pharmaceutically acceptable salt thereof is used alone or used in combination with other therapeutic methods including immunotherapy.

6. The method according to claim 5, wherein the diseases associated with KRAS mutation mediated cancers or associated with KRAS G12C mutation mediated cancers are liver cancer, esophageal cancer, gastric cancer, renal cell cancer, sarcoma, bile duct cancer, colon cancer, prostate cancer, ovarian cancer, breast cancer, hematological cancer, pancreatic cancer, MYH-associated polyposis, colorectal cancer, lung cancer, uterine cancer, mesothelioma, cervical cancer, or bladder cancer.

7. A compound of formula (II), or a stereoisomer, a tautomer or a pharmaceutically acceptable salt thereof,

II

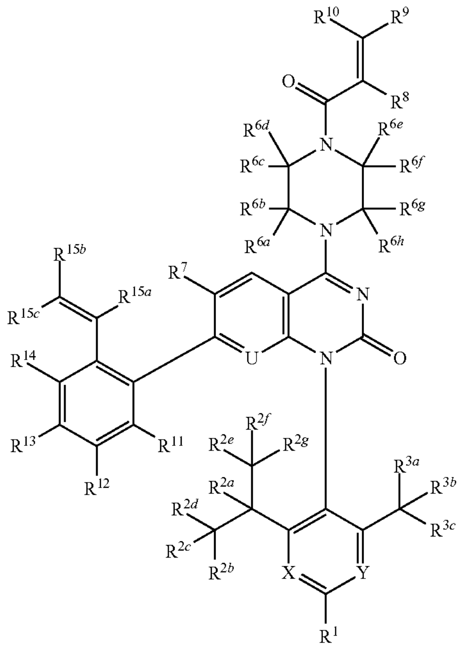

wherein,

X is nitrogen or $CR^4$, Y is nitrogen or $CR^5$;

U is nitrogen or $CR^U$, wherein $R^U$ is hydrogen or deuterium;

$R^1$, $R^{2a}$, $R^{2b}$, $R^{2c}$, $R^{2d}$, $R^{2e}$, $R^{2f}$, $R^{2g}$, $R^{3a}$, $R^{3b}$, $R^{3c}$, $R^4$, $R^5$, $R^{12}$, $R^{13}$, $R^{14}$, $R^{15a}$, $R^{15b}$, and $R^{15c}$ are each independently hydrogen, deuterium, an alkyl, or a deuterated alkyl;

$R^{6a}$, $R^{6b}$, $R^{6c}$, $R^{6d}$, $R^{6e}$, $R^{6f}$, $R^{6g}$, and $R^{6h}$ are each independently hydrogen, deuterium, methyl, or methyl-$d_3$;

$R^7$ is fluorine, or chlorine;

$R^8$, $R^9$, $R^{10}$, and $R^{11}$ are each independently hydrogen, deuterium, or fluorine;

the structural fragment

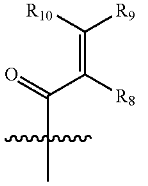

is any one of the following groups:

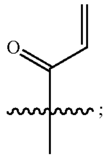 ; 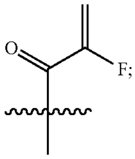 ; or 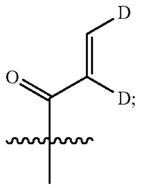 ;

the structural fragment

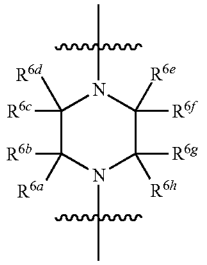

is any one of the following groups:

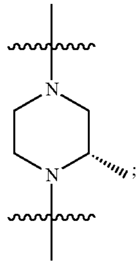 ; 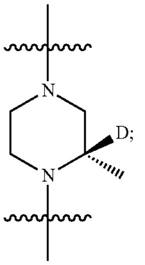 ; 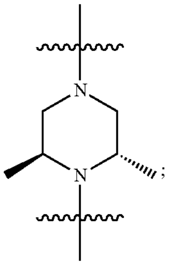 ;

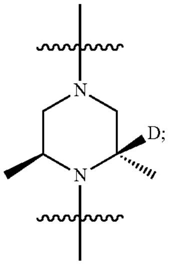 ; or 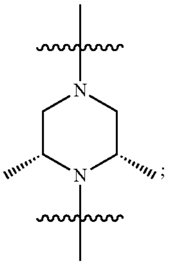 ;

the structural fragment

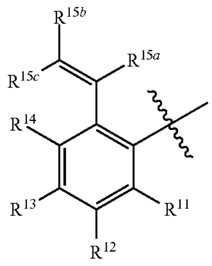

is any one of the following groups:

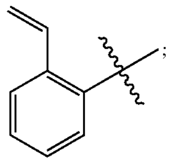
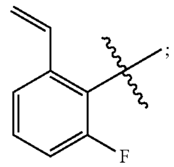
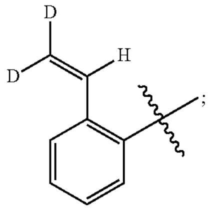
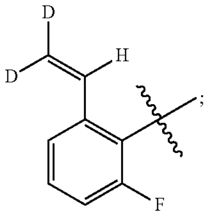
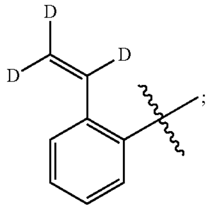
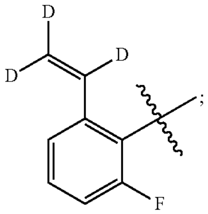
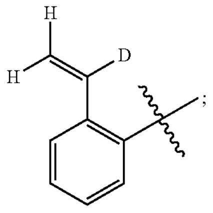
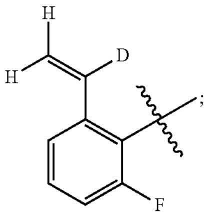
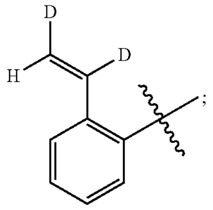
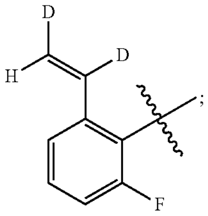
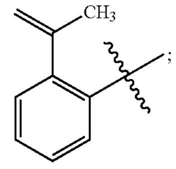
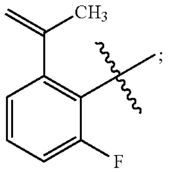
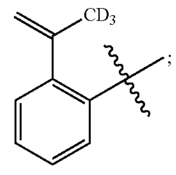
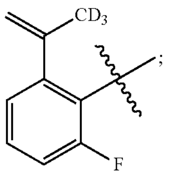
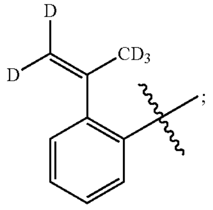
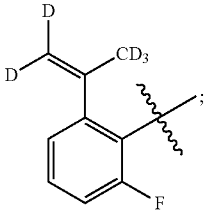
-continued
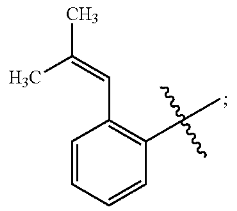
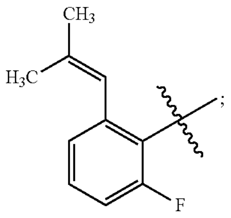
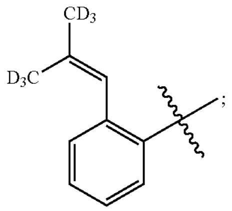
or
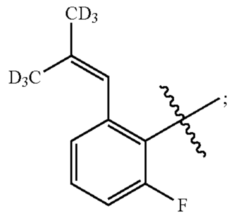
and
the structural fragment
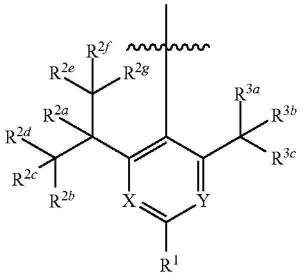
is any one of the following groups:
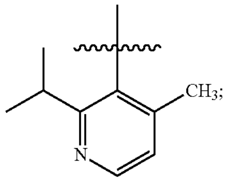
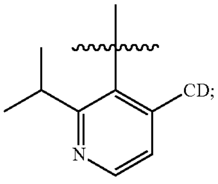
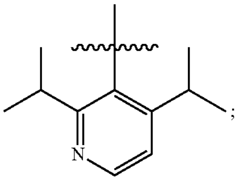
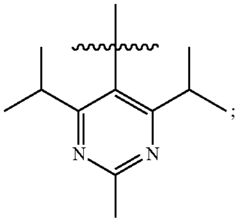
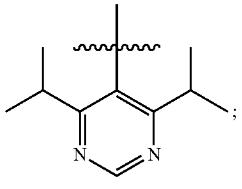
or
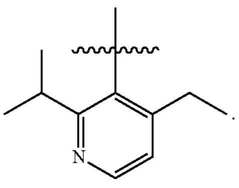
8. The compound of formula (II), or the stereoisomer, the tautomer or the pharmaceutically acceptable salt thereof according to claim 7, wherein the compound is represented by formula (II-1),

II-1

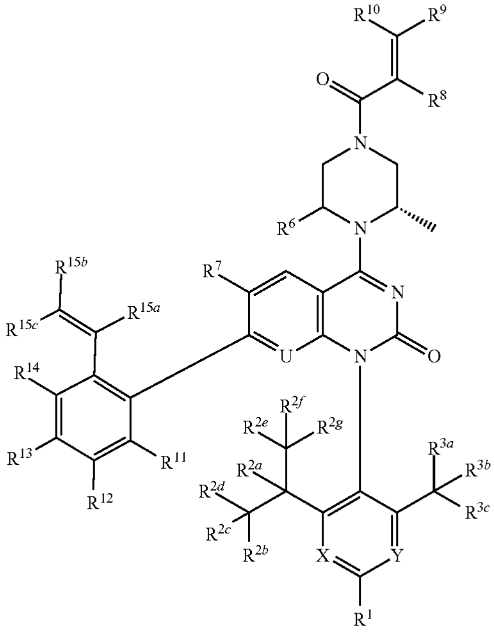

wherein,

X is nitrogen or $CR^4$, Y is nitrogen or $CR^5$;

U is nitrogen or $CR^U$, wherein $R^U$ is hydrogen or deuterium;

$R^1$, $R^{2a}$, $R^{2b}$, $R^{2c}$, $R^{2d}$, $R^{2e}$, $R^{2f}$, $R^{2g}$, $R^{3a}$, $R^{3b}$, $R^{3c}$, $R^4$, $R^5$, $R^{12}$, $R^{13}$, $R^{14}$, $R^{15a}$, $R^{15b}$, and $R^{15c}$ are each independently hydrogen, deuterium, an alkyl, or a deuterated alkyl;

$R^6$ is hydrogen, deuterium, methyl, or methyl-$d_3$;

$R^7$ is fluorine, or chlorine;

$R^8$, $R^9$, $R^{10}$, and $R^{11}$ are each independently hydrogen, deuterium, or fluorine;

the structural fragment

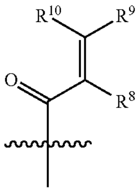

is any one of the following groups:

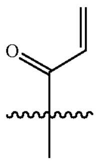
; or
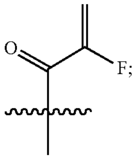

the structural fragment

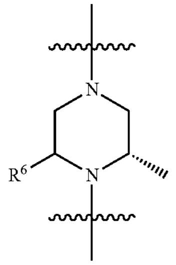

is any one of the following groups:

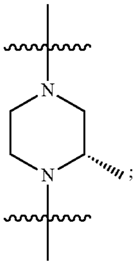
;
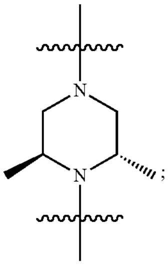
; or
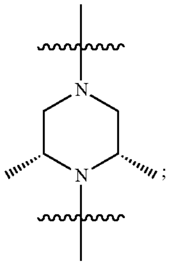
;

the structural fragment

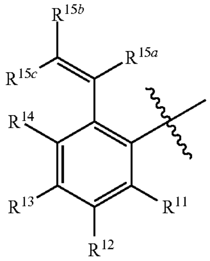

is any one of the following groups:

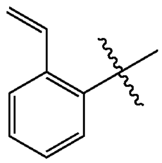
;
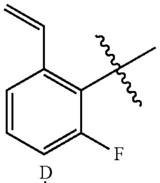
;
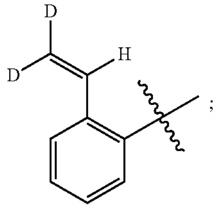
;
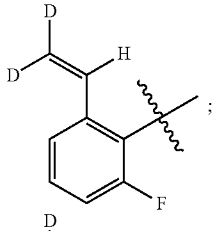
;
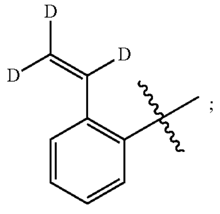
;
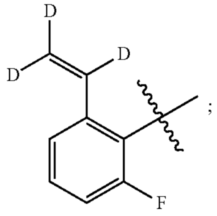
;

-continued
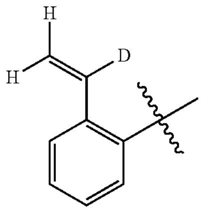;
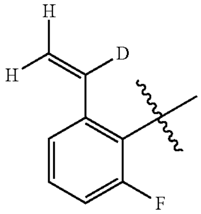;
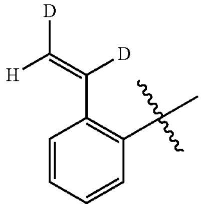;
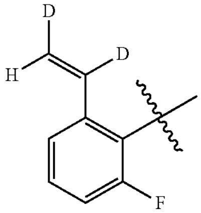;
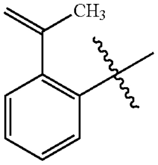;
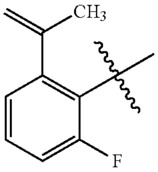;
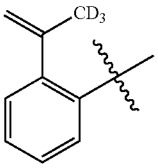;
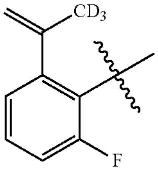;
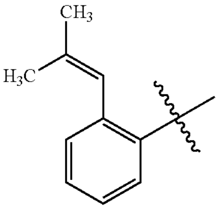;
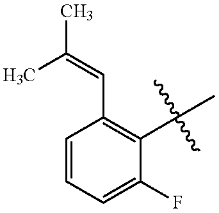;
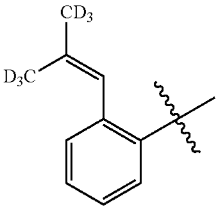; or
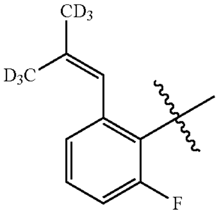;
and
the structural fragment
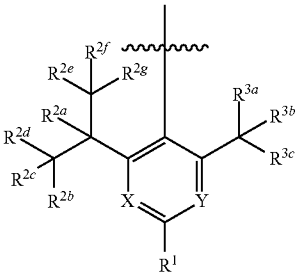
is any one of the following groups:
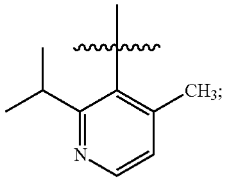
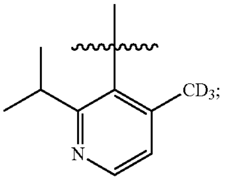
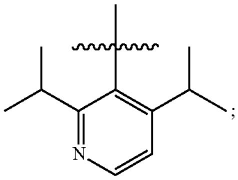;
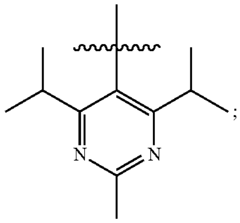; or
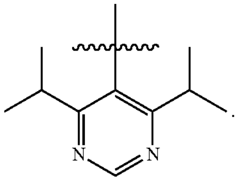.
9. The compound of formula (II), or the stereoisomer, the tautomer or the pharmaceutically acceptable salt thereof according to claim 7, wherein the compound is any one selected from the group consisting of
2-1
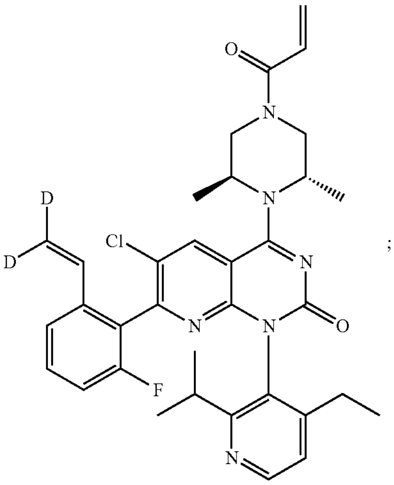;

-continued
2-2
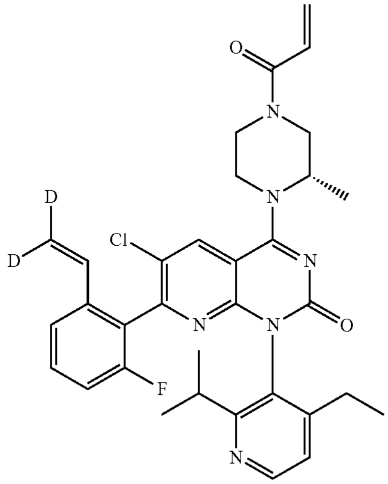
;
2-3
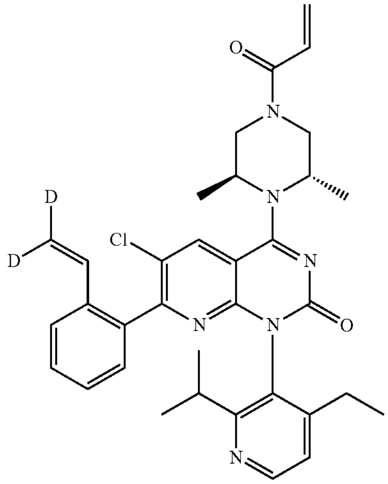
;
2-4
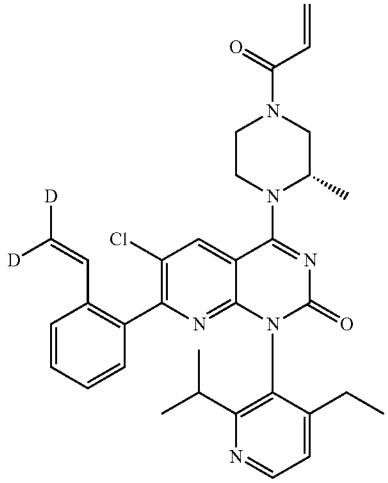
;
-continued
2-5
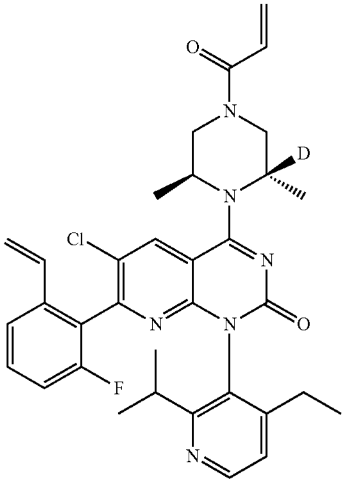
;
2-6
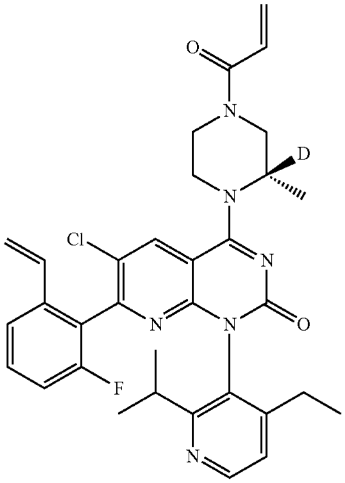
;
2-7
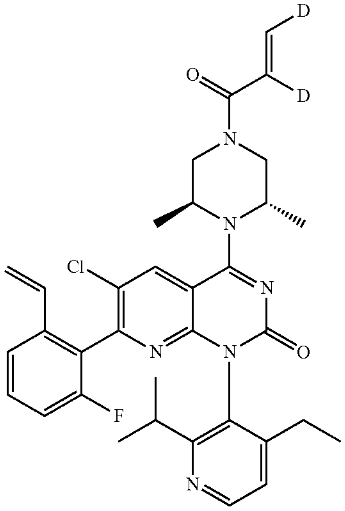
;

2-8
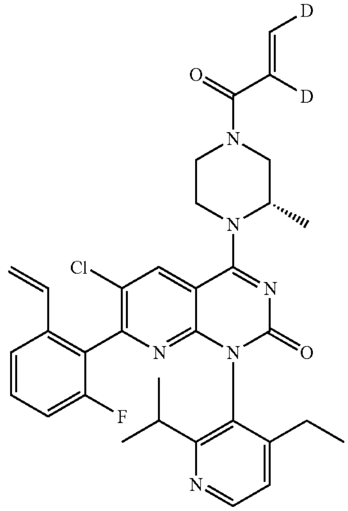
;
2-9
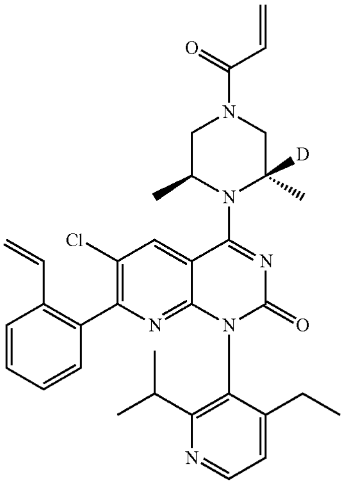
;
2-10
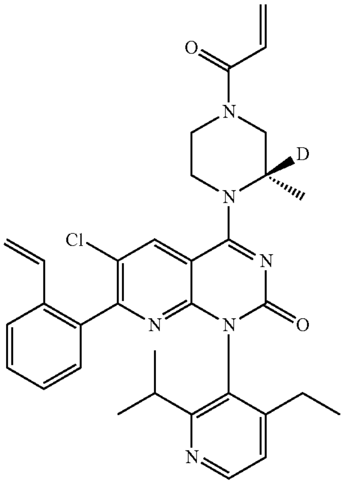
;
2-11
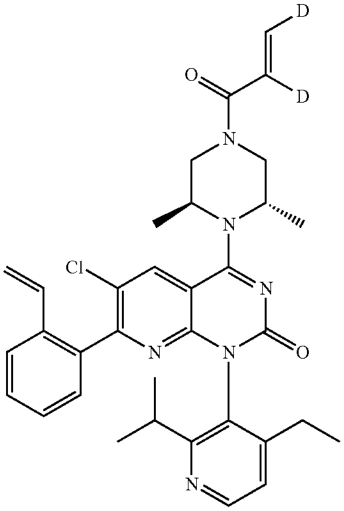
;
2-12
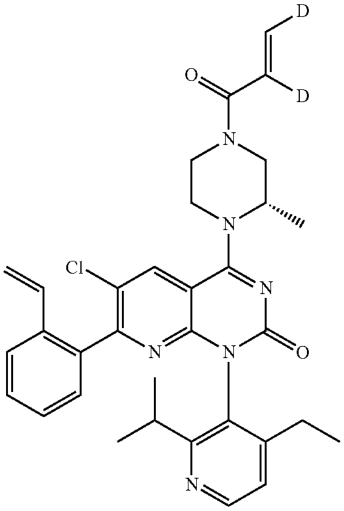
;
2-13
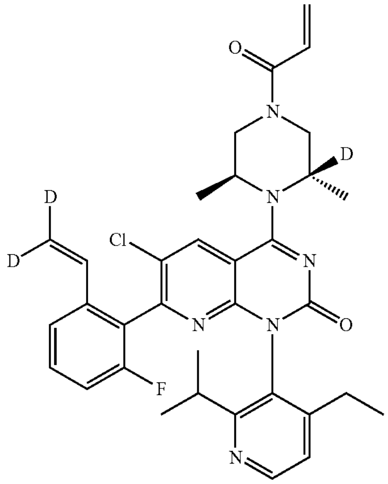
;

-continued
2-14
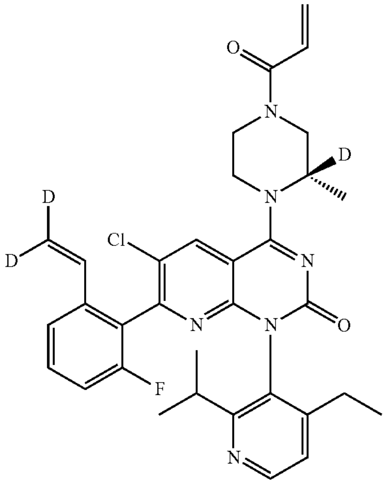
;
2-15
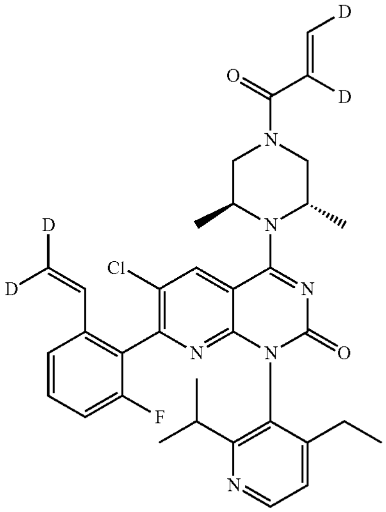
;
2-16
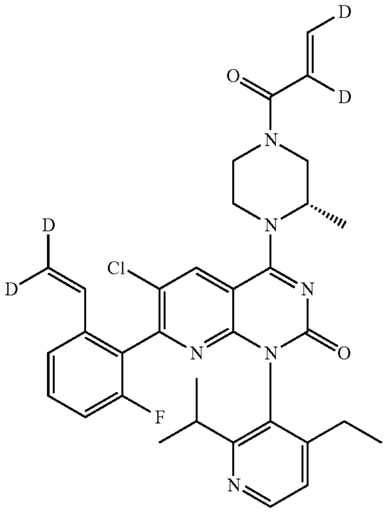
;
-continued
2-17
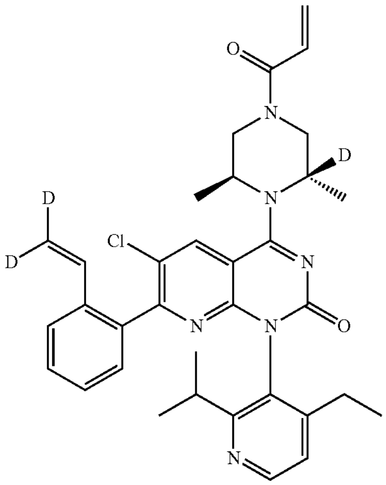
;
2-18
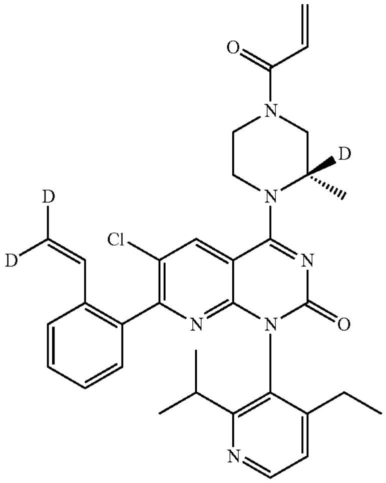
;
2-19
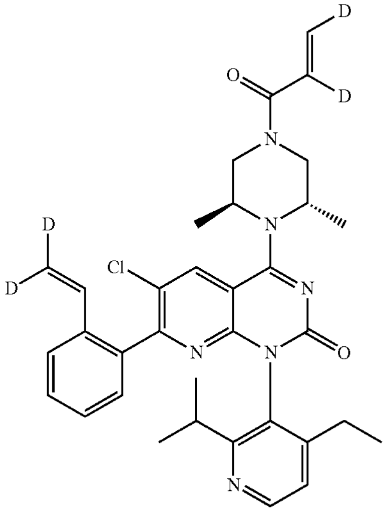
;

-continued
2-20
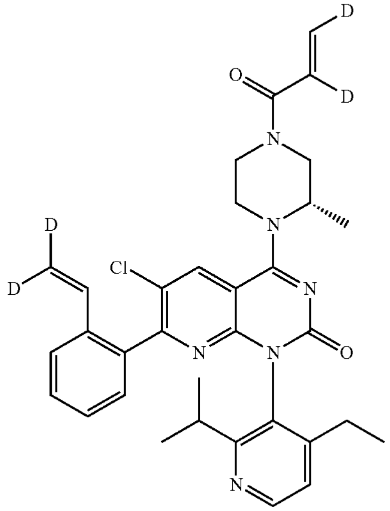
;
3-1
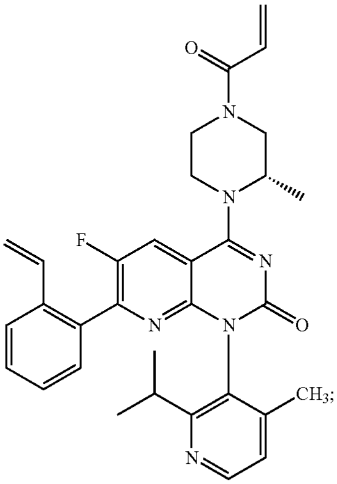
3-2
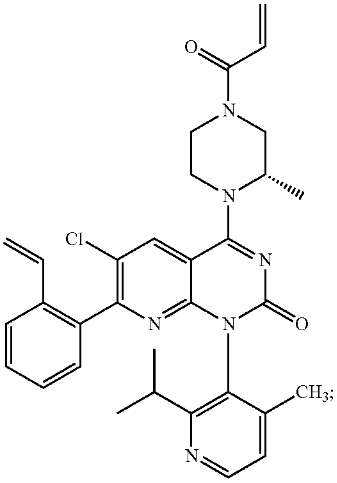
-continued
3-3
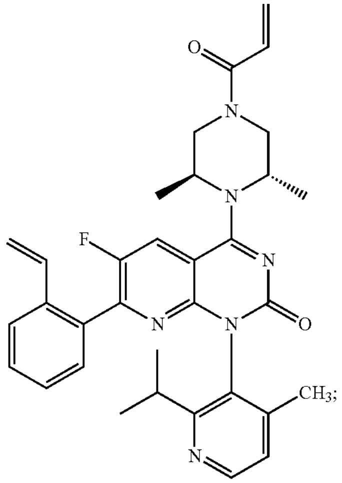
3-4
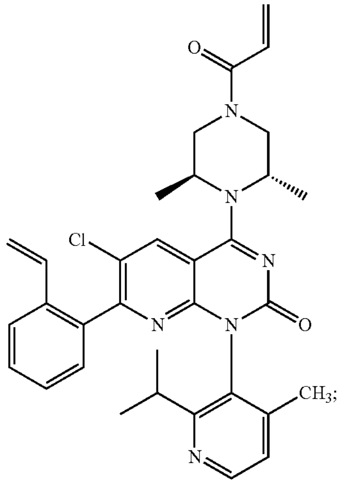
3-1a
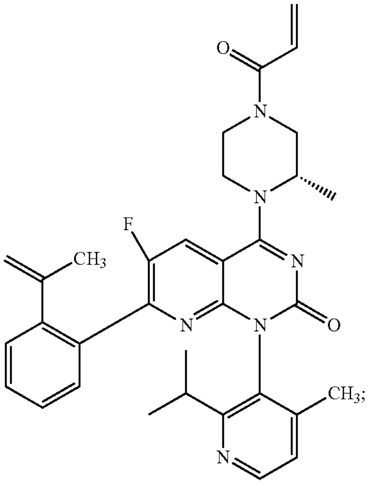

-continued
3-2a
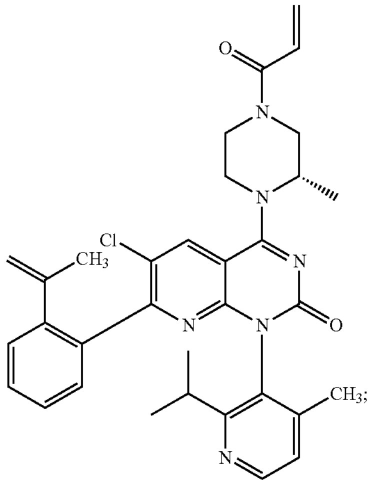
3-3a
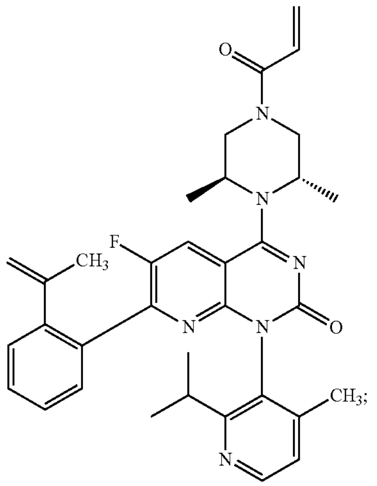
3-4a
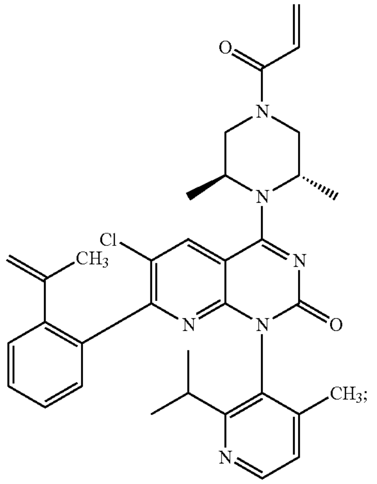
-continued
3-5
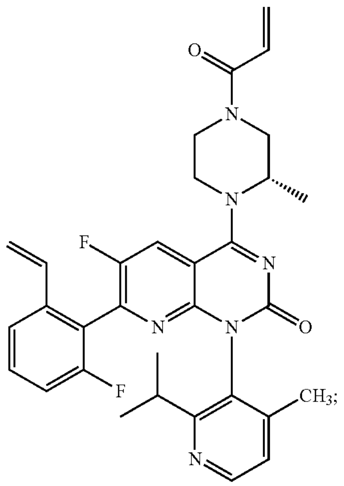
3-6
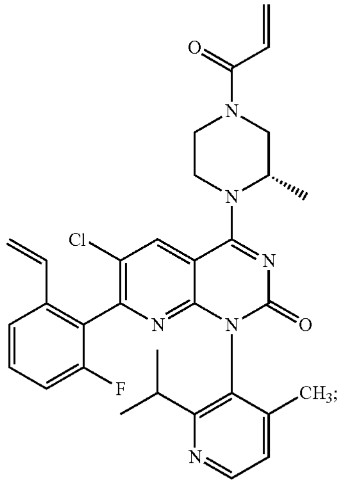
3-7
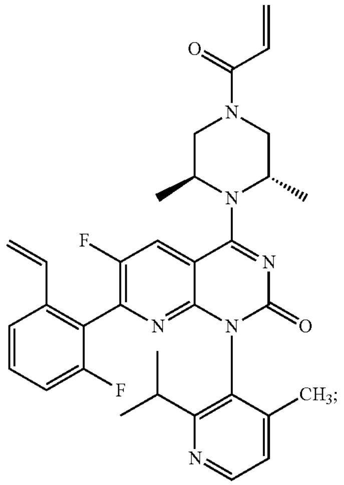

3-8
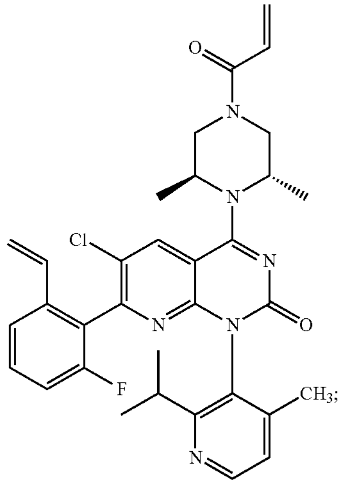
3-17
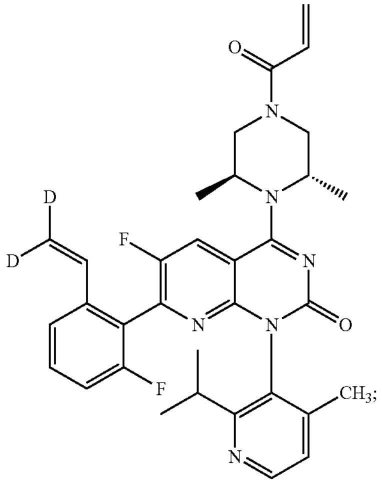
3-18
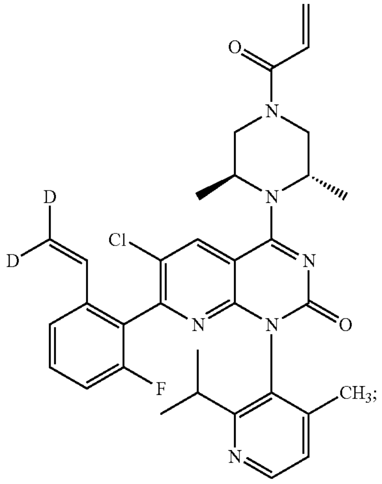
3-19
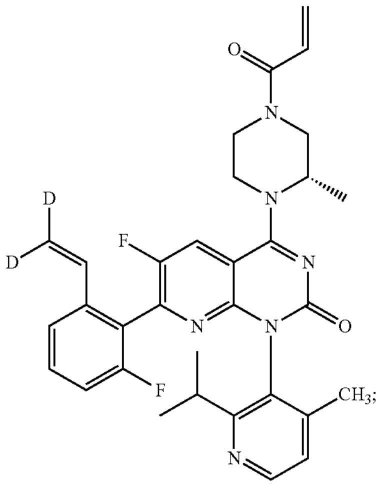
3-20
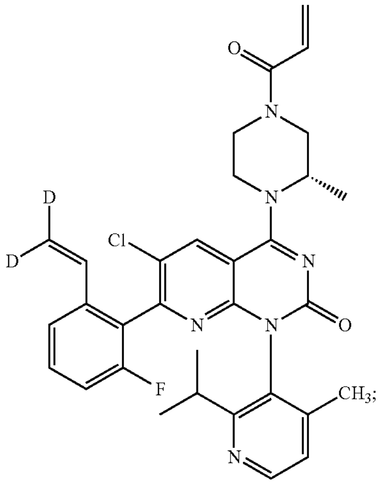
3-21
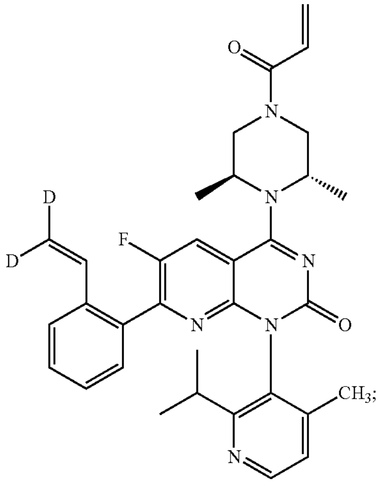

3-22
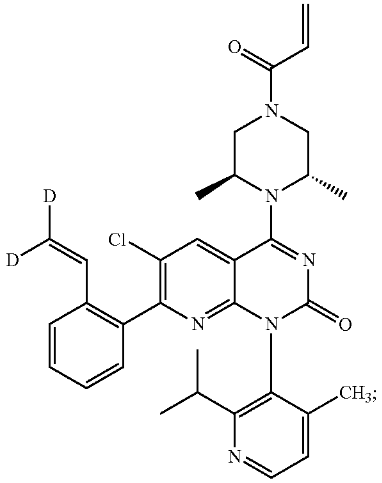
3-23
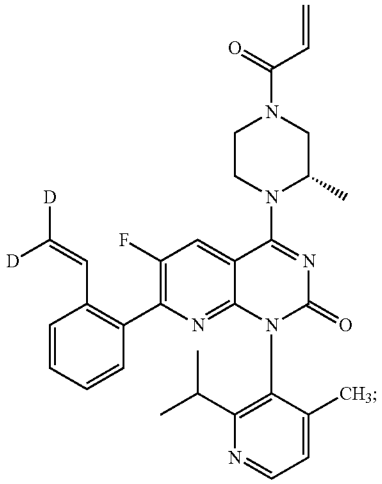
3-24
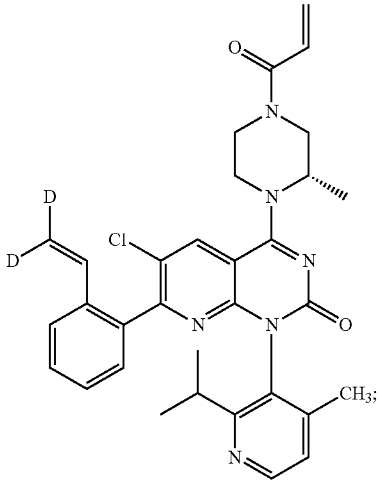
3-25
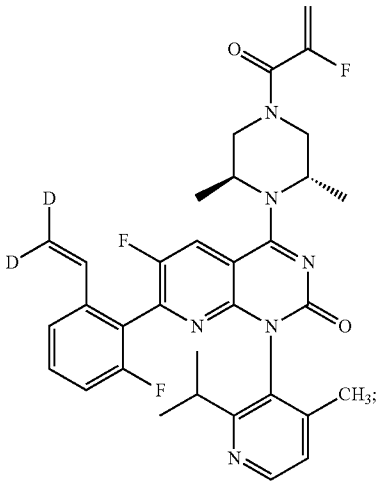
3-26
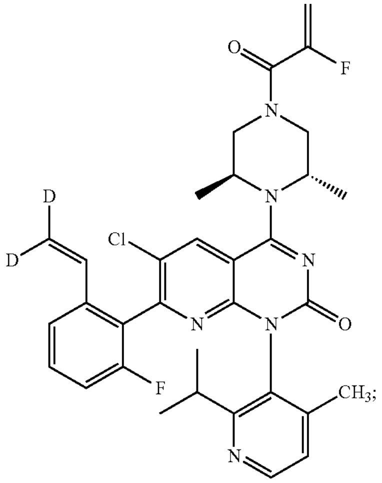
3-27
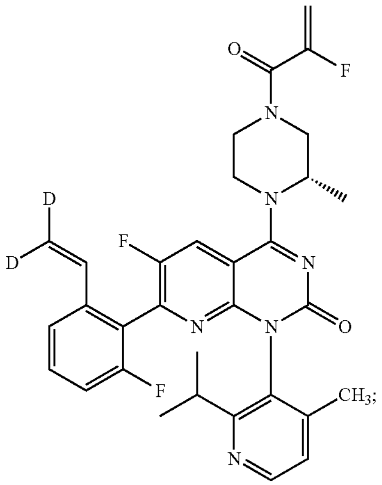

-continued
3-28
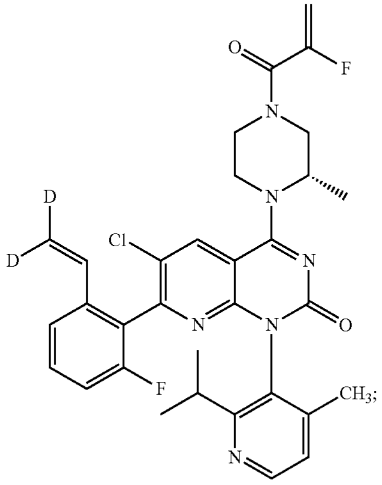
3-29
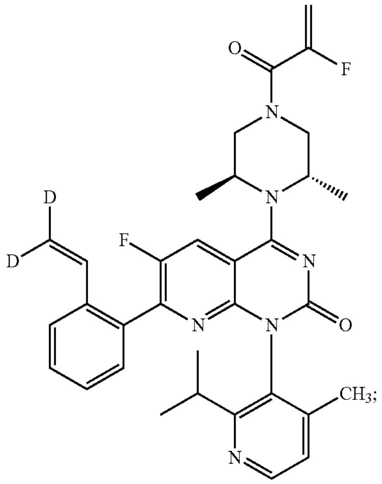
3-30
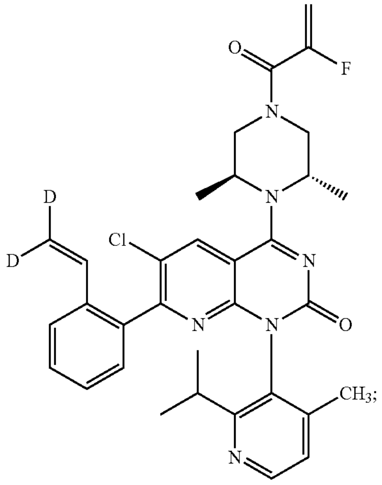
-continued
3-31
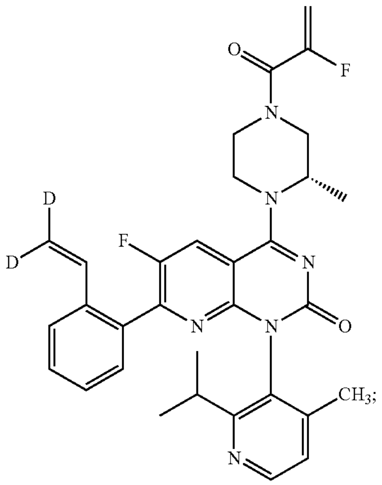
3-32
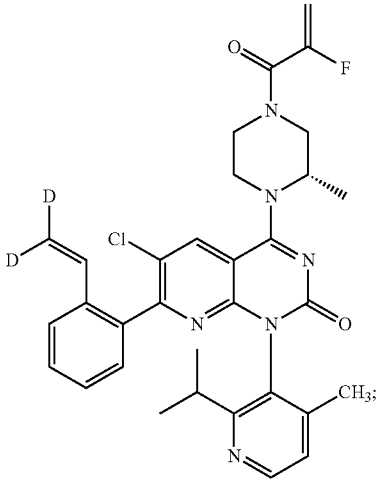
3-33
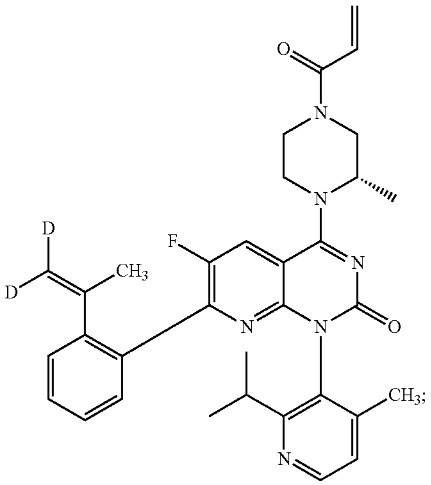

-continued
3-34
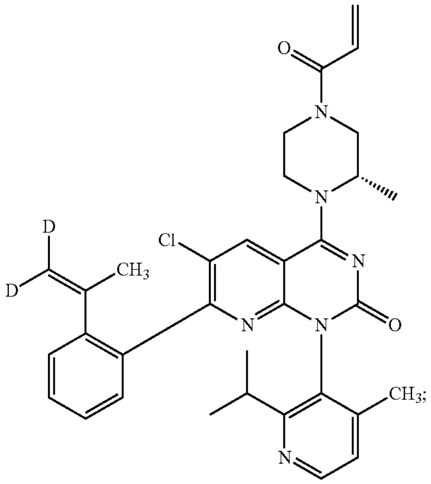
3-35
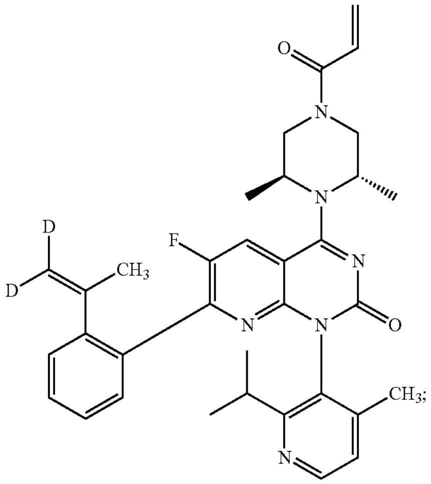
3-36
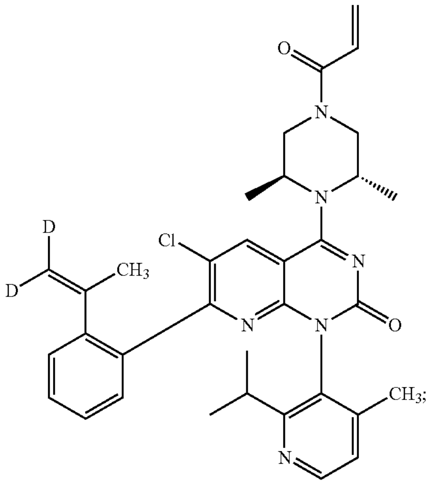
-continued
3-37
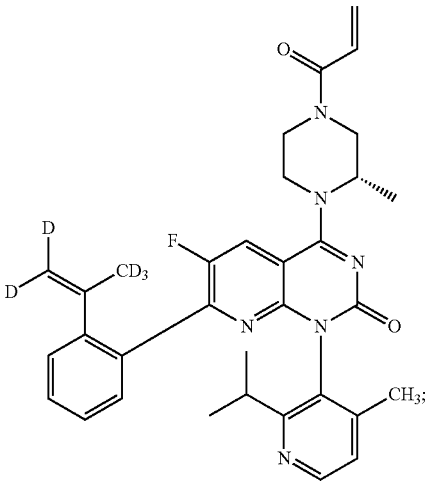
3-38
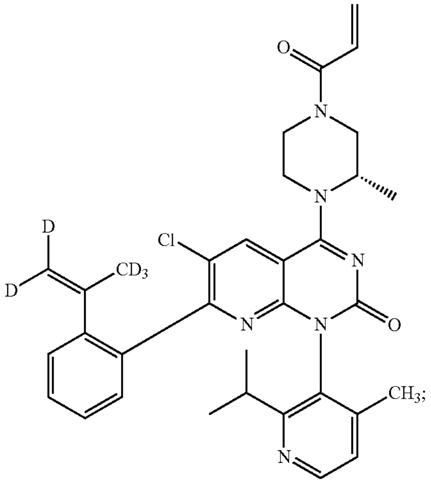
3-39
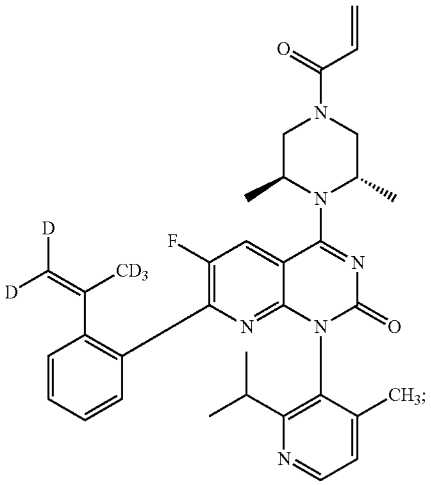

3-40
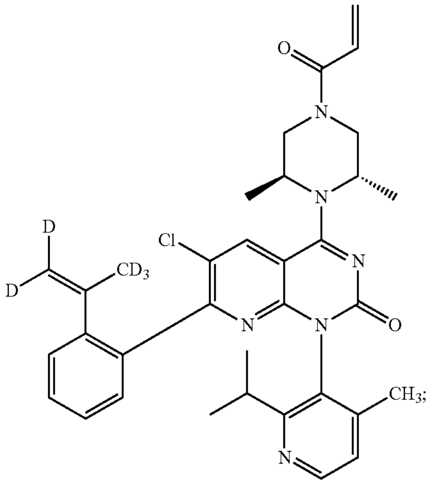
3-41
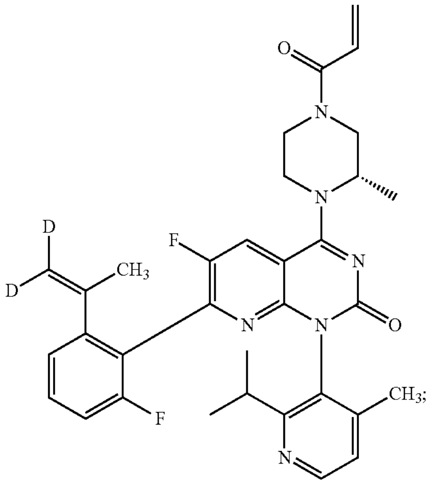
3-42
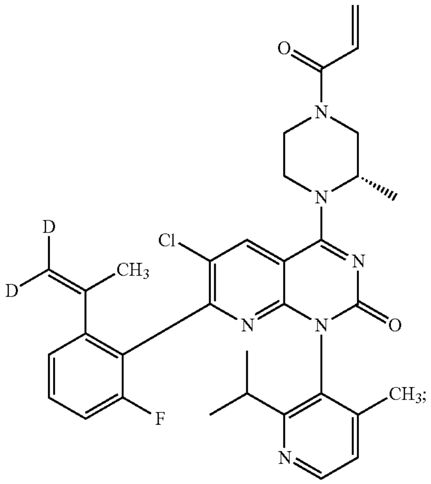
3-43
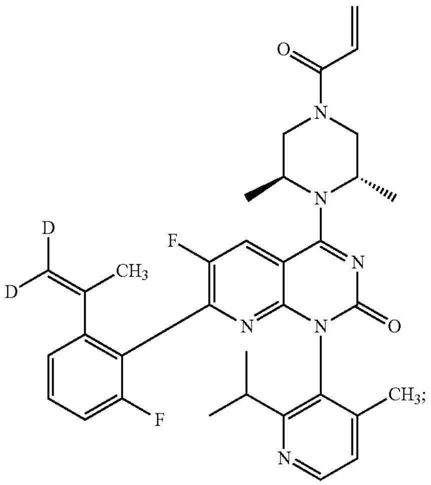
3-44
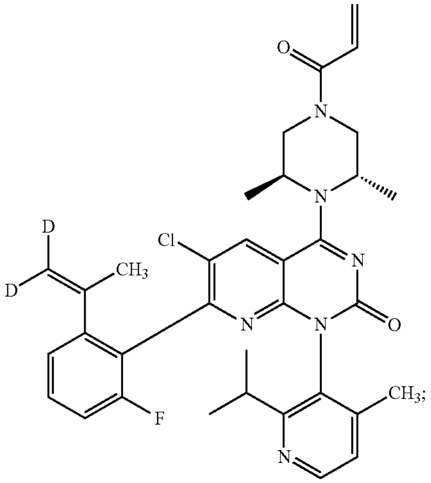
3-45
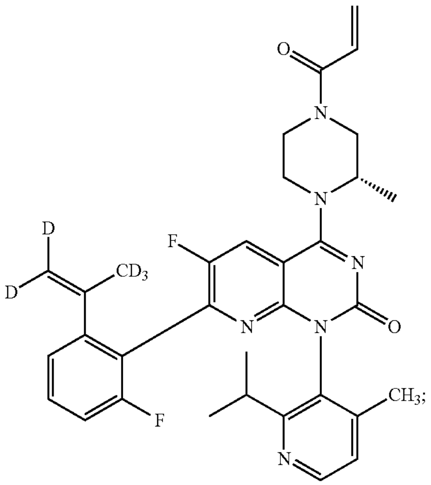

-continued 3-46

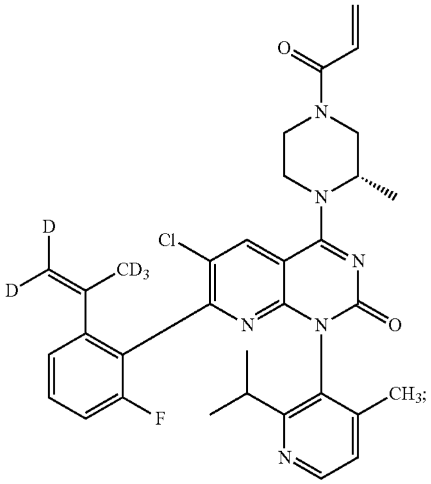

3-47

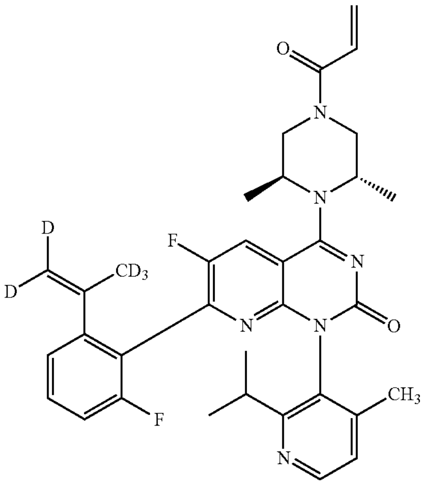

and 3-48

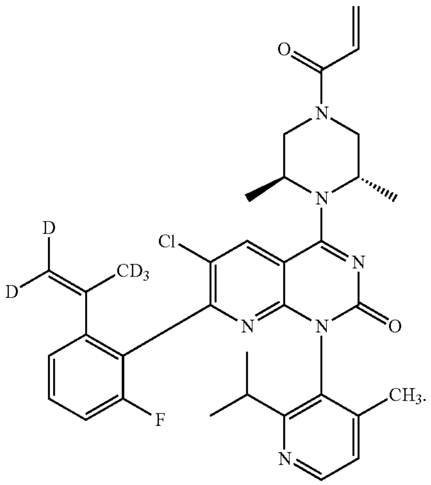

10. The compound of formula (II), or the stereoisomer, the tautomer or the pharmaceutically acceptable salt thereof according to claim 7, wherein the compound is represented by formula (III),

III

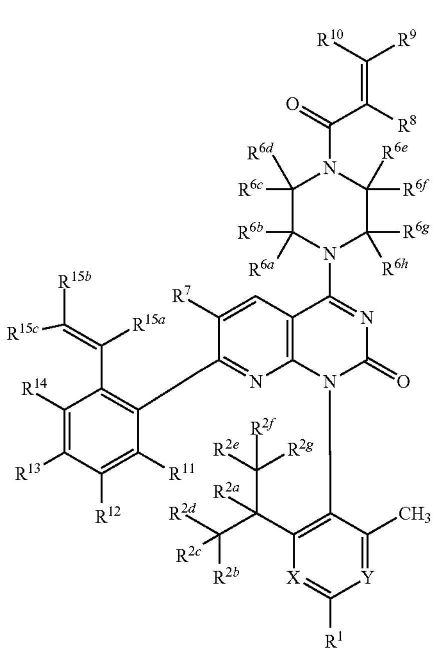

wherein,

X is nitrogen or $CR^4$, Y is nitrogen or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, and $R^{15c}$ are each independently hydrogen, deuterium, an alkyl, or a deuterated alkyl;

$R^{6a}$, $R^{6b}$, $R^{6c}$, $R^{6d}$, $R^{6e}$, $R^{6f}$, $R^{6g}$, and $R^{6h}$ are each independently hydrogen, deuterium, methyl, or methyl-$d_3$;

$R^7$ is fluorine or chlorine;

$R^8$, $R^9$, $R^{10}$, and $R^{11}$ are each independently hydrogen, deuterium, or fluorine;

the structural fragment

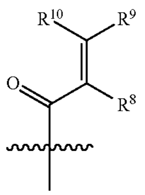

is any one of the following groups:

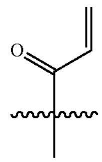

;

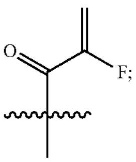

or

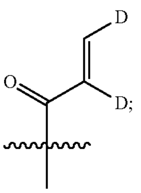

the structural fragment

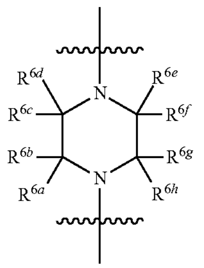
is any one of the following groups:
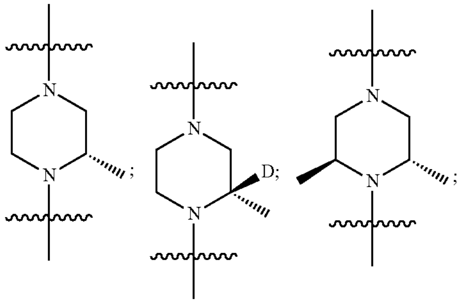
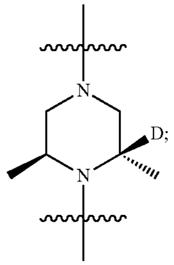
or
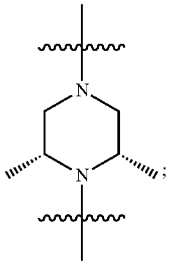
and
the structural fragment
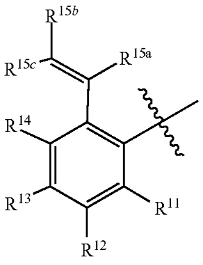
is any one of the following groups:
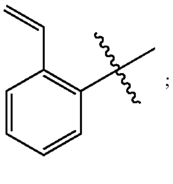
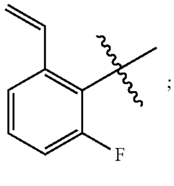
-continued
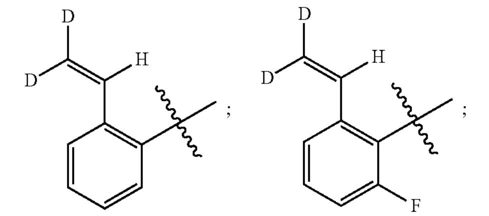
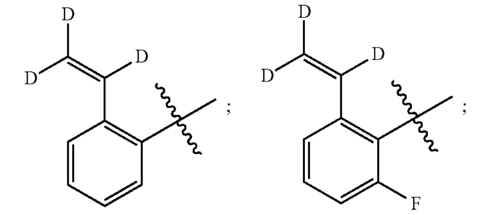
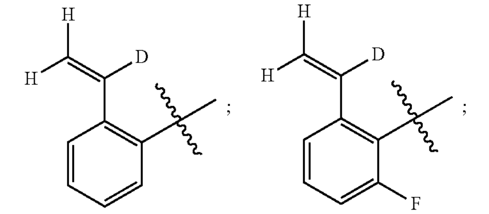
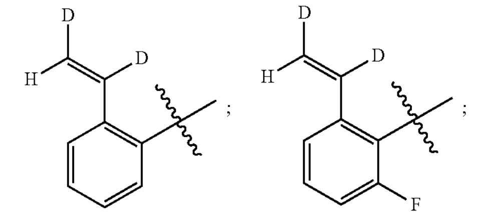
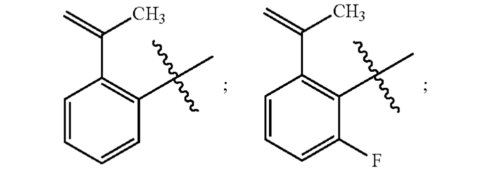
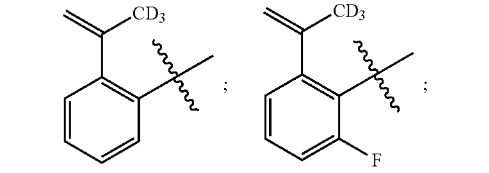
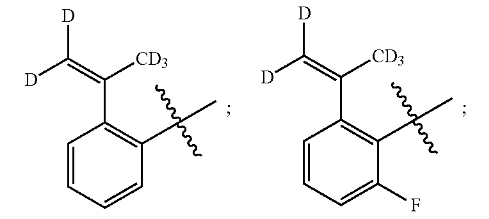
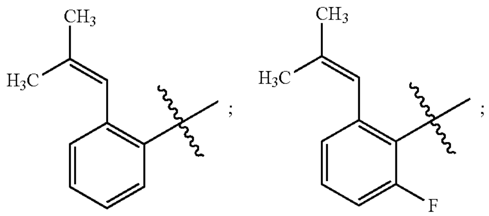

-continued
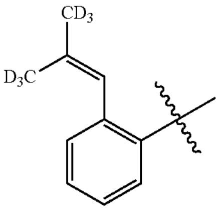
; or
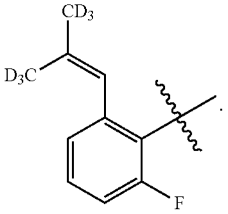
.
11. The compound of formula (II), or the stereoisomer, the tautomer or the pharmaceutically acceptable salt thereof according to claim 7, wherein the compound is any one selected from the group consisting of
3-49
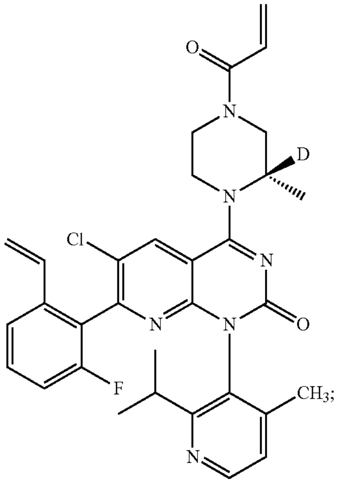
;
3-50
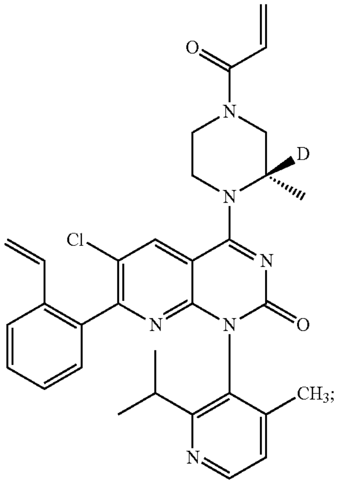
;
-continued
3-51
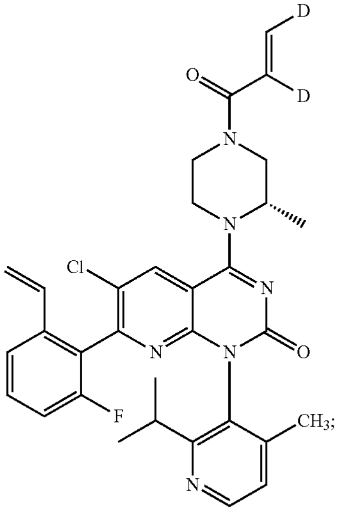
;
3-52
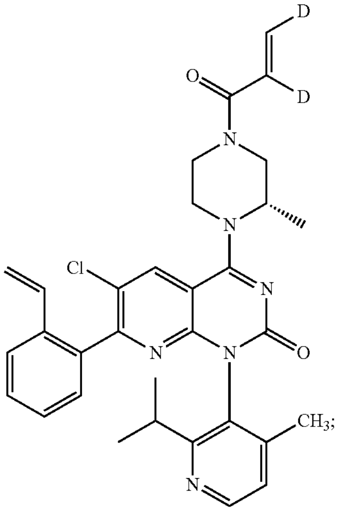
;
3-53
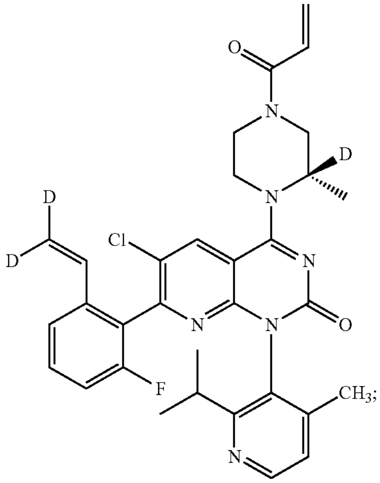
;

-continued
3-54
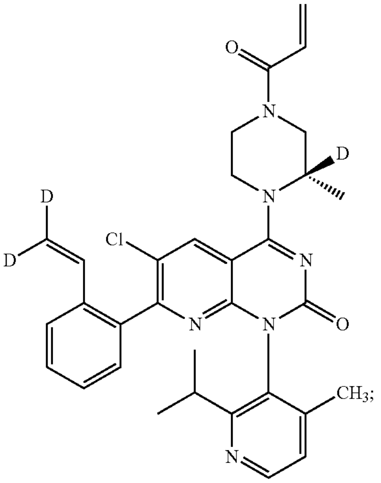
3-55
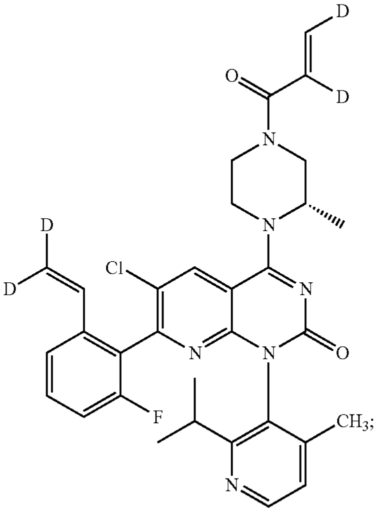
3-56
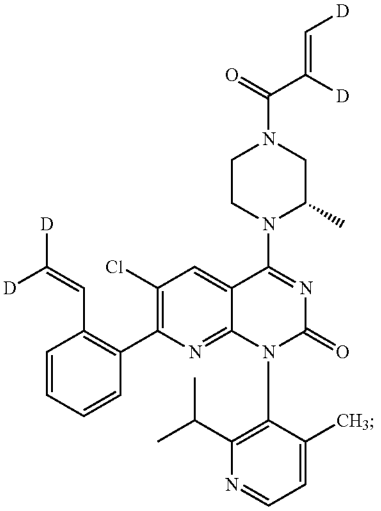
-continued
4-1
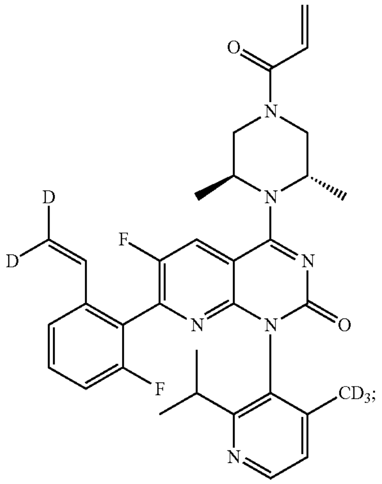
4-2
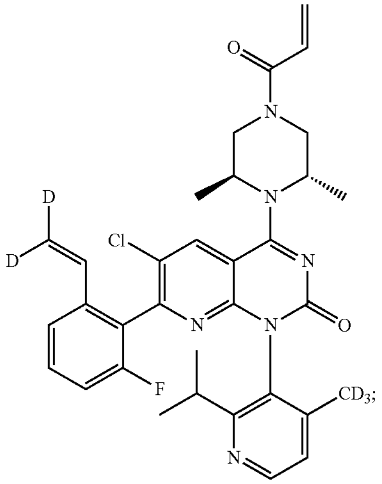
4-3
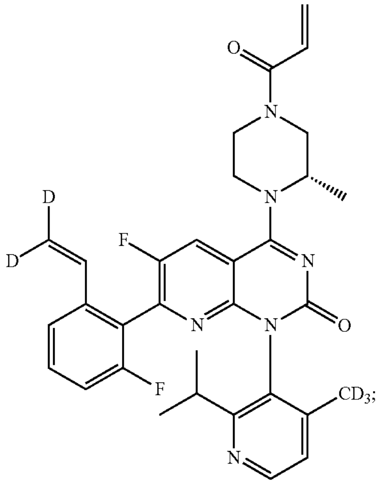

-continued
4-4
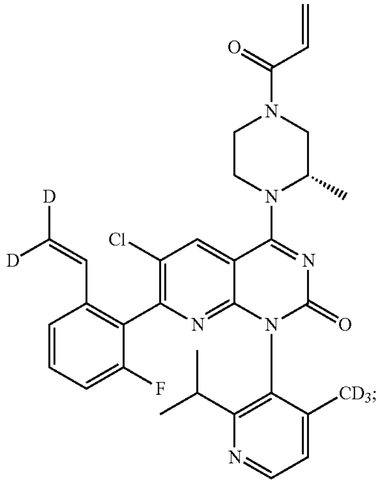
4-5
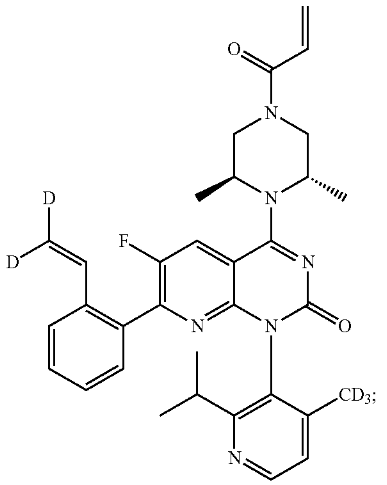
4-6
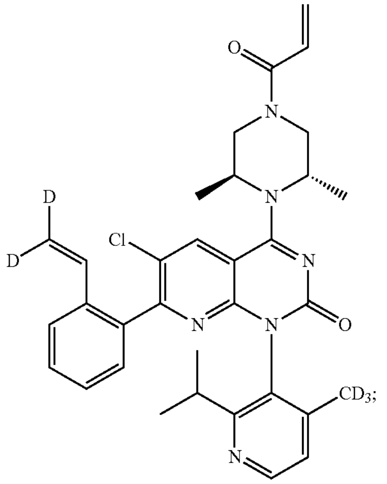
-continued
4-7
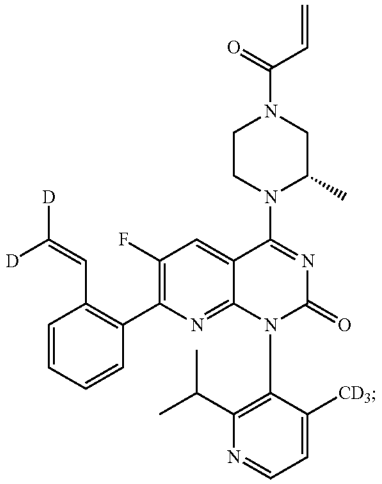
4-8
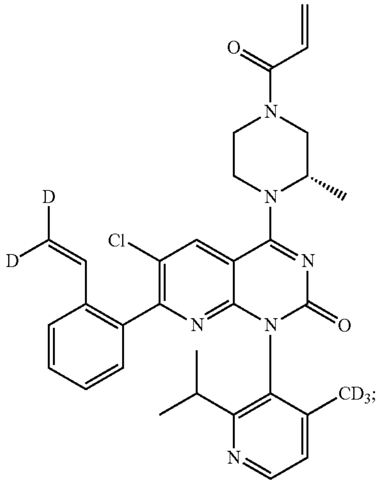
4-9
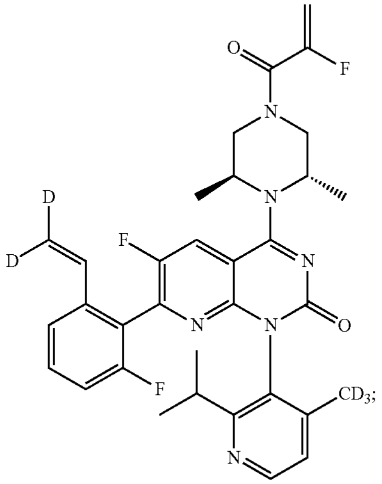

-continued
4-10
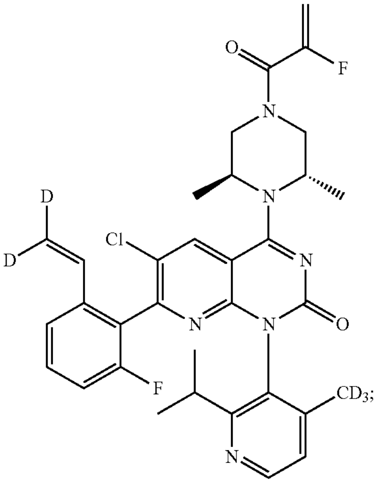
4-11
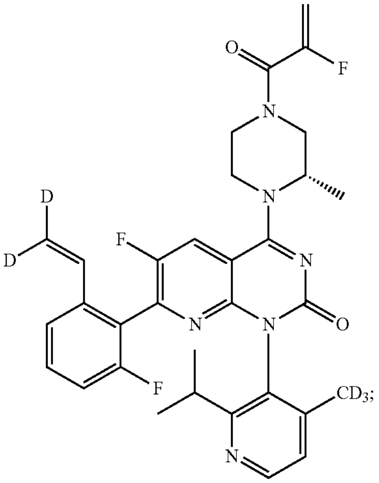
4-12
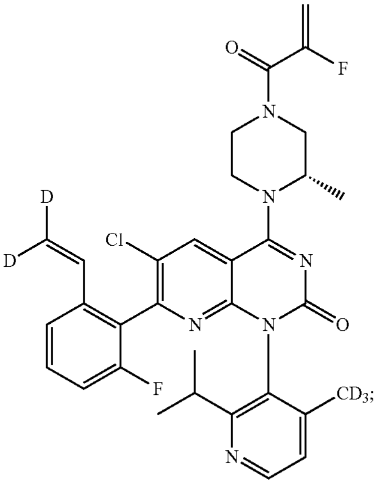
-continued
4-13
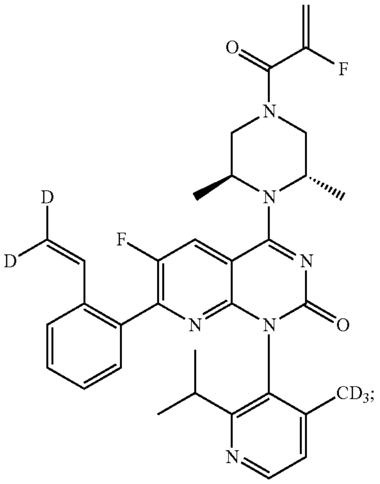
4-14
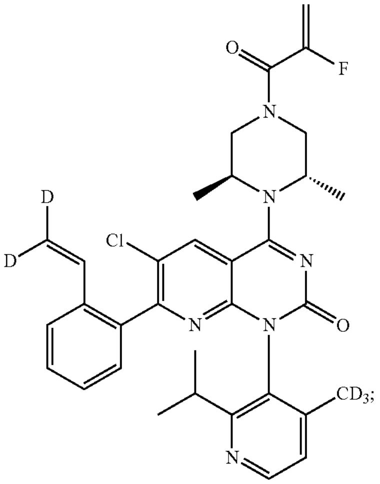
4-15
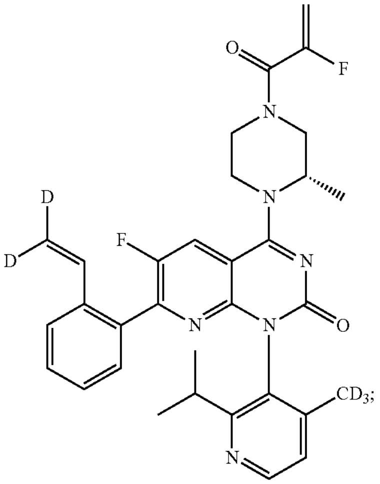

-continued
4-16
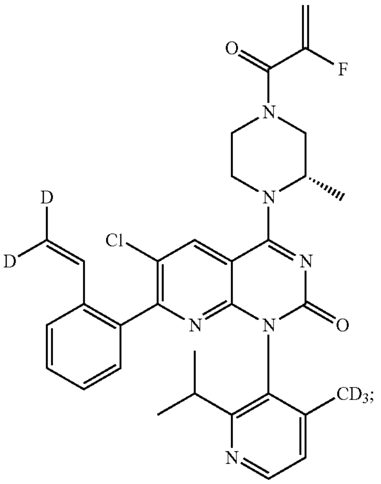
4-17
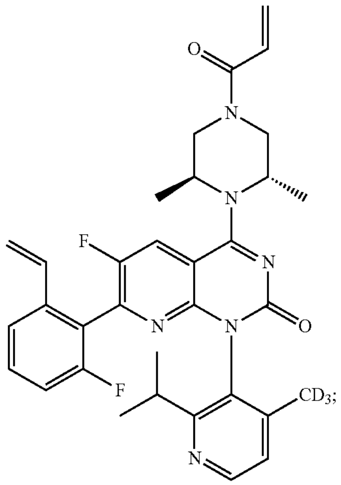
4-18
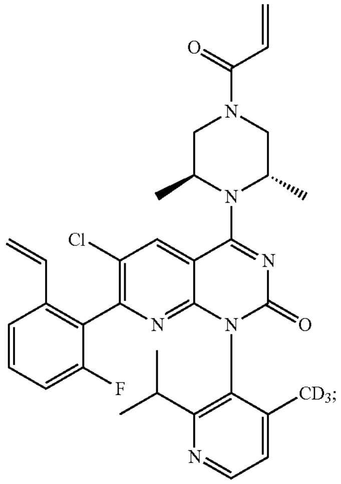
-continued
4-19
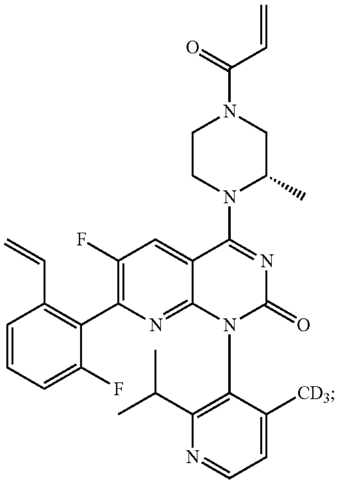
4-20
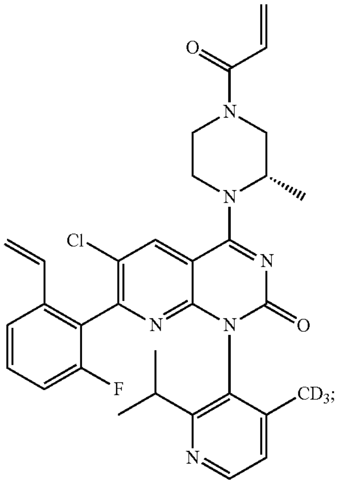
4-21
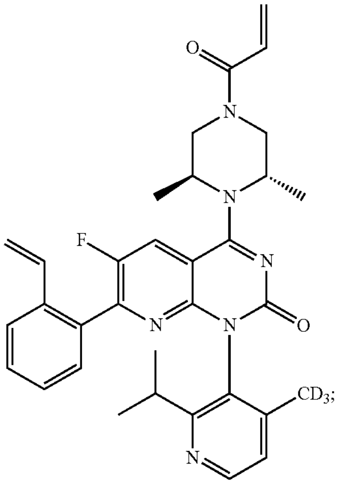

-continued
4-22
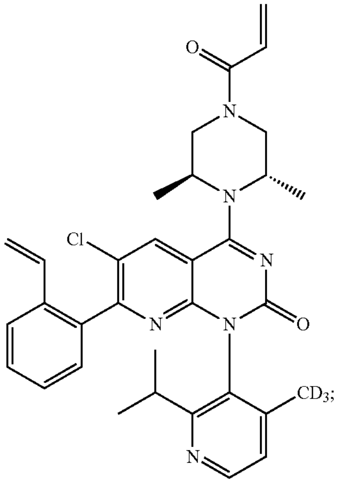
4-23
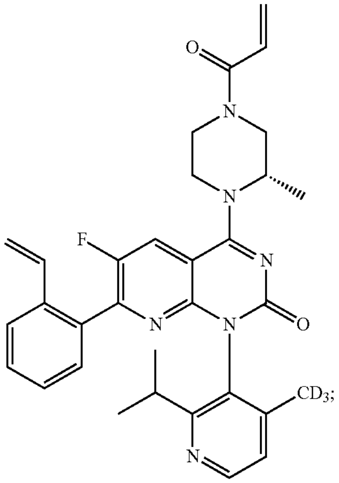
4-24
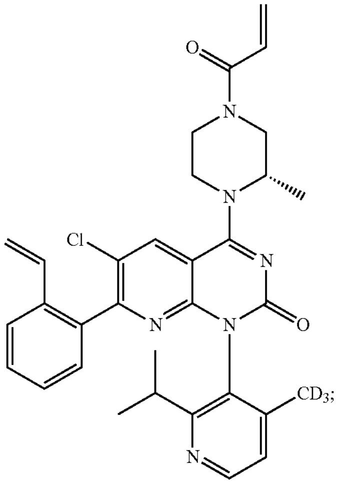
-continued
4-25
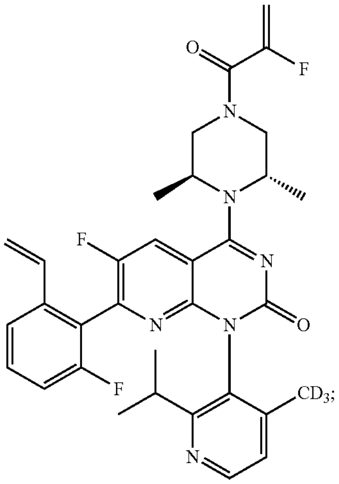
4-26
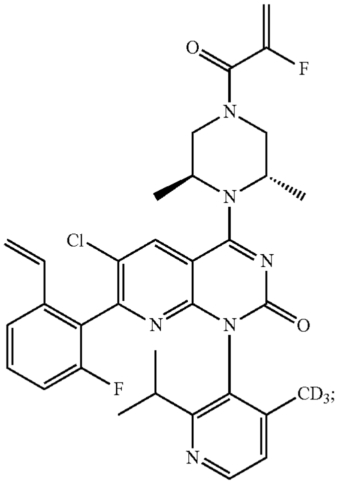
4-27
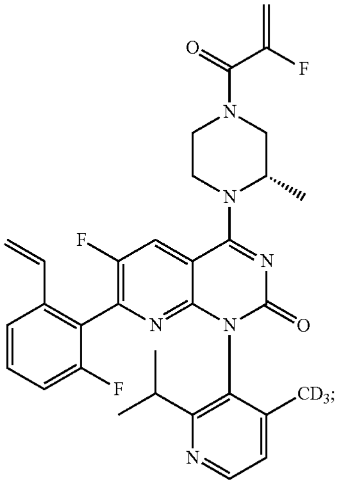

-continued
4-28
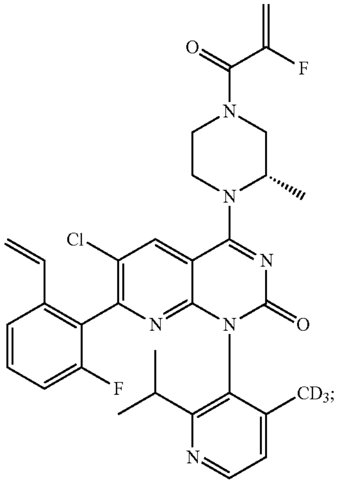
4-29
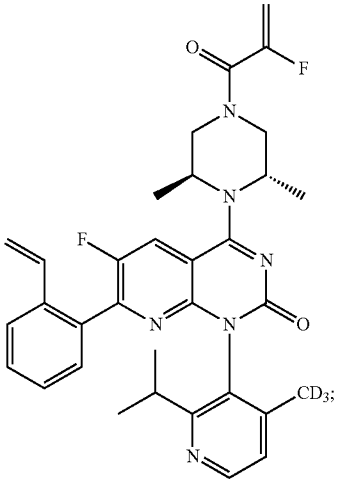
4-30
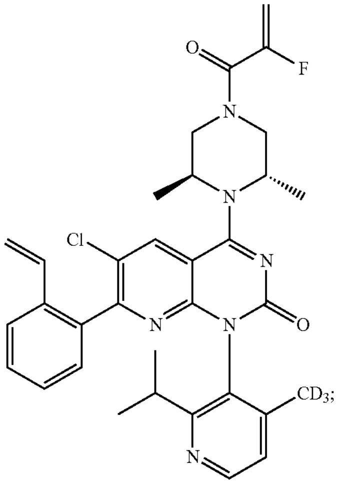
-continued
4-31
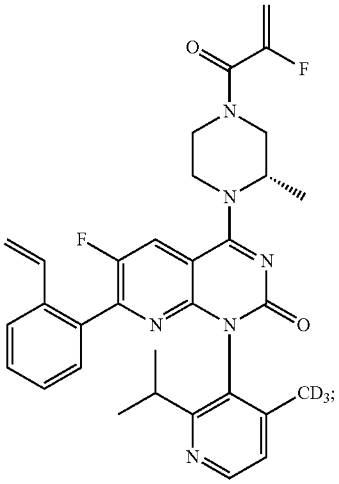
4-32
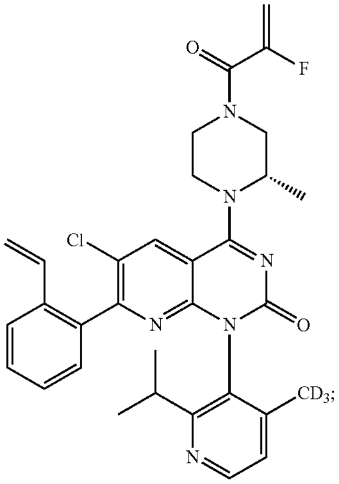
4-33
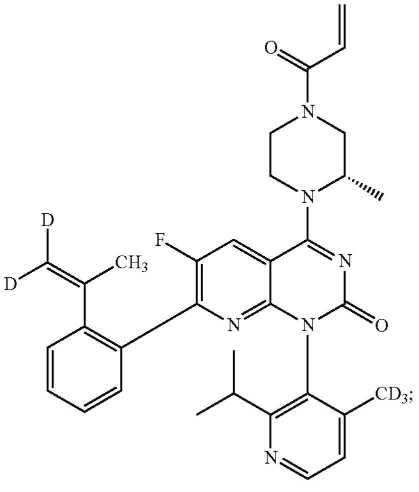

-continued
4-34
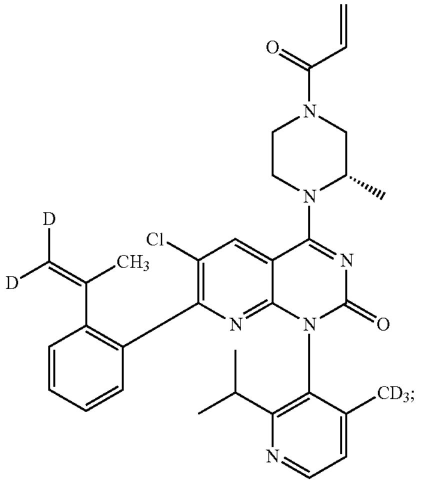
4-35
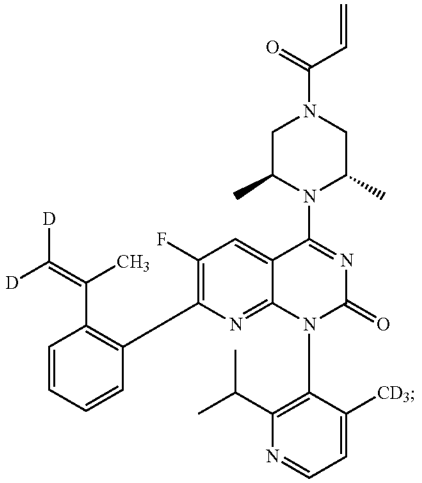
4-36
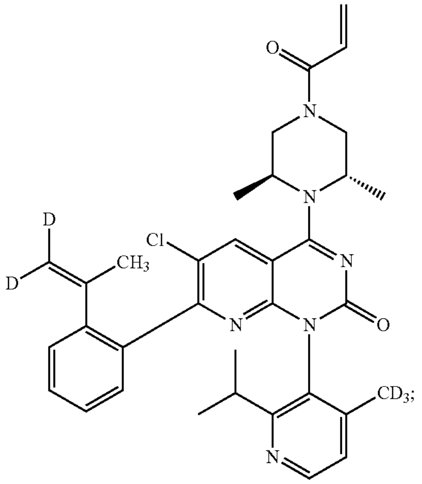
-continued
4-37
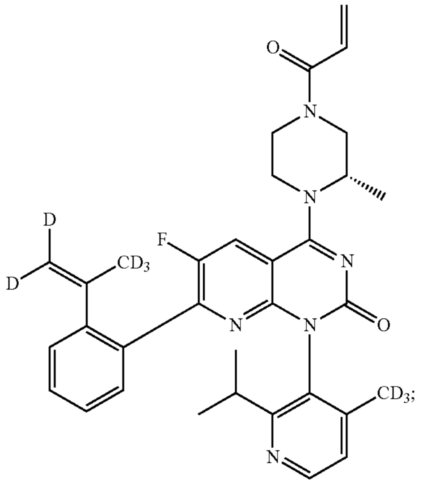
4-38
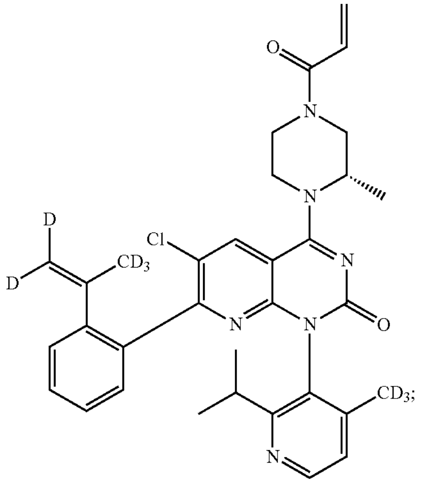
4-39
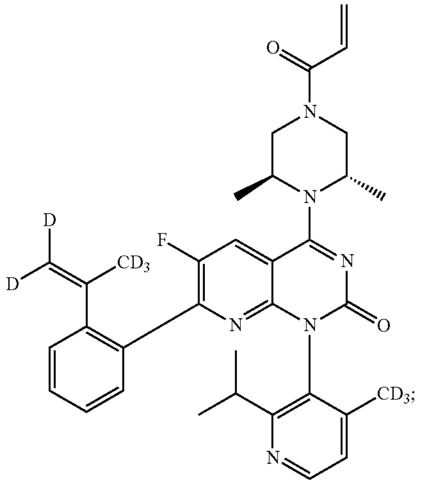

-continued
4-40
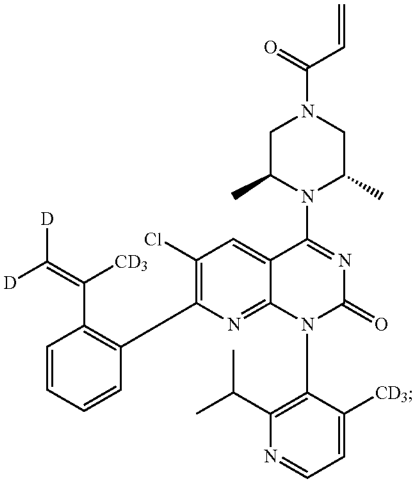
4-41
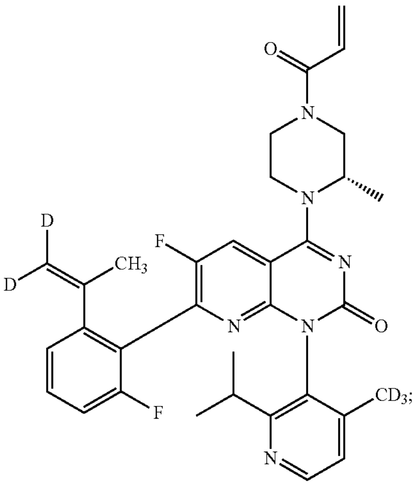
4-42
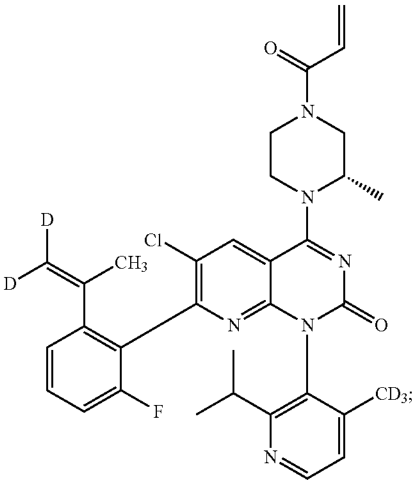
-continued
4-43
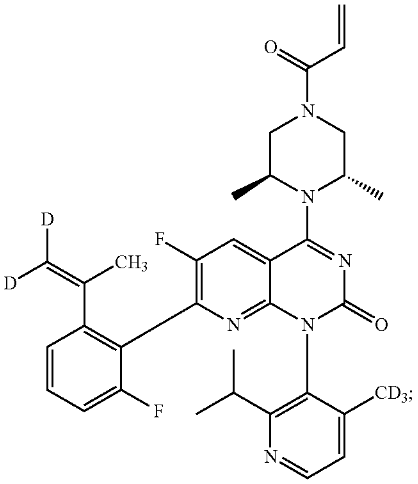
4-44
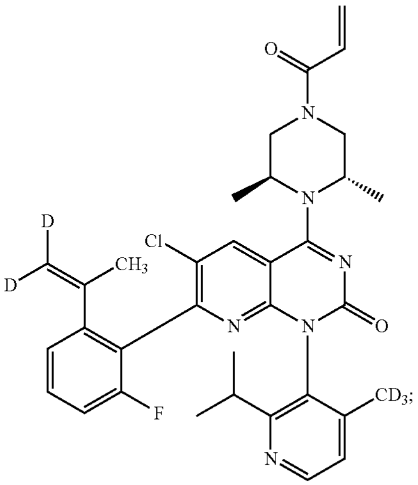
4-45
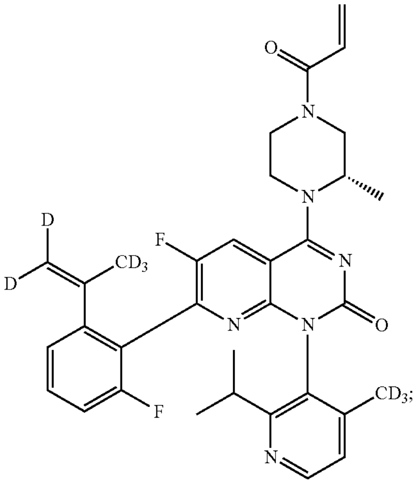

-continued
4-46
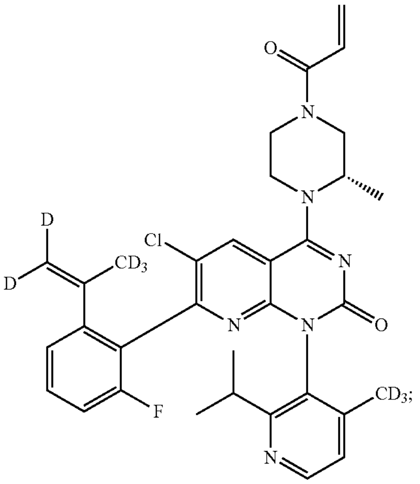
4-47
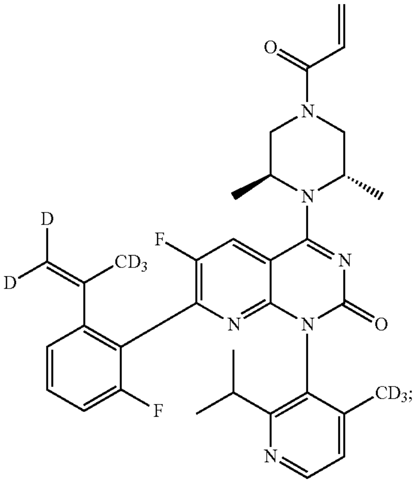
4-48
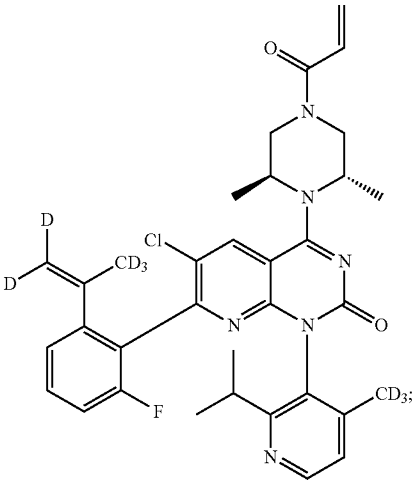
-continued
5-1
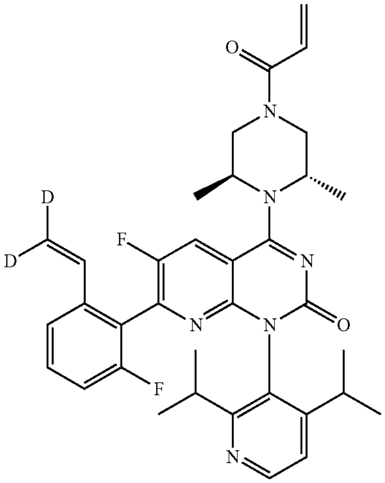
;
5-2
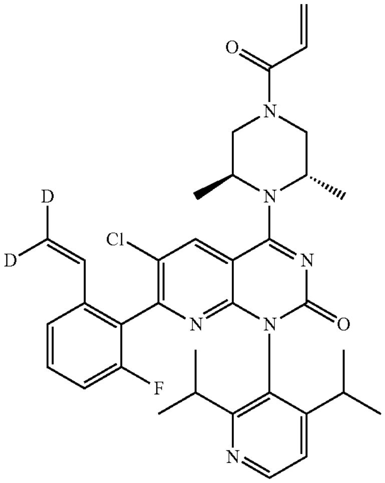
;
5-3
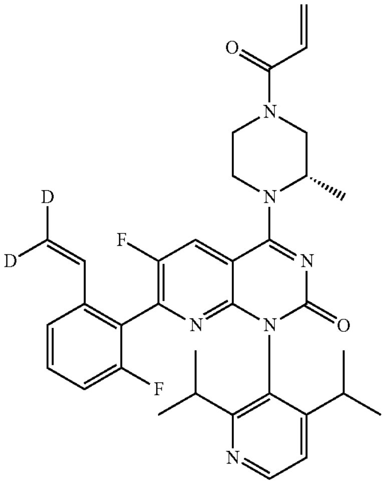
;

-continued
5-4
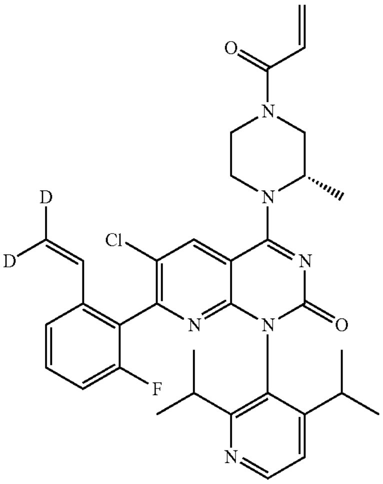
;
5-5
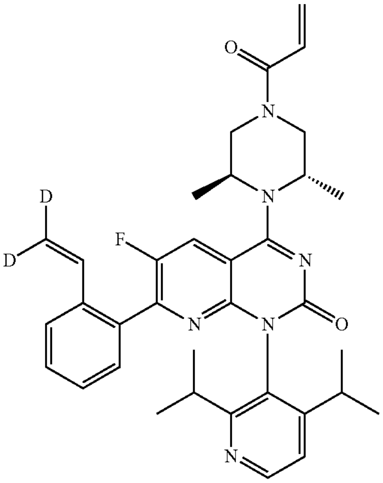
;
5-6
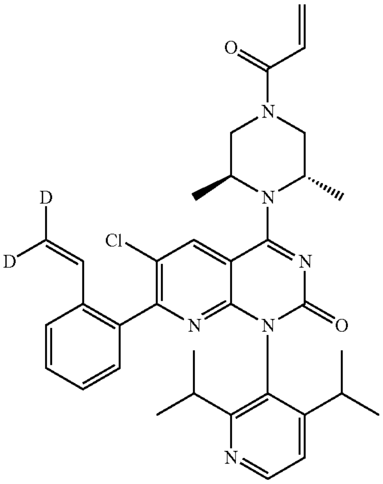
;
-continued
5-7
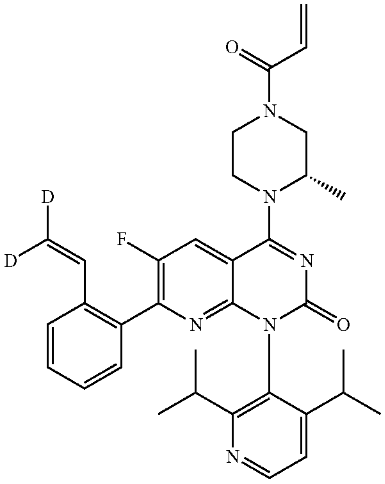
;
5-8
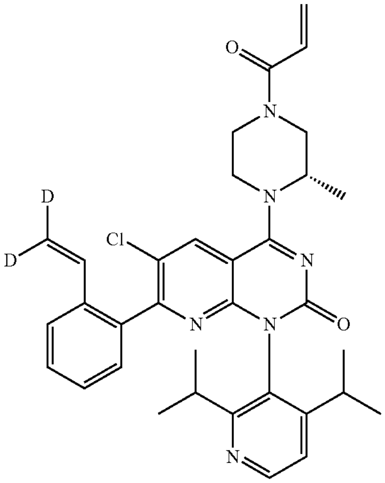
;
5-9
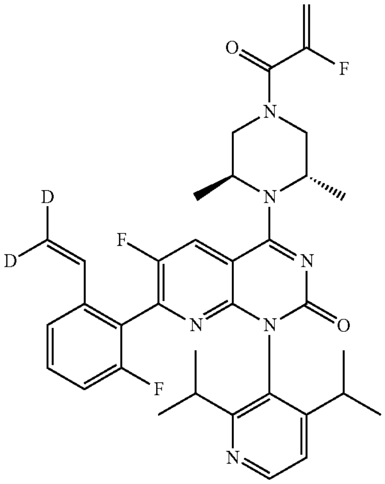
;

-continued
5-10
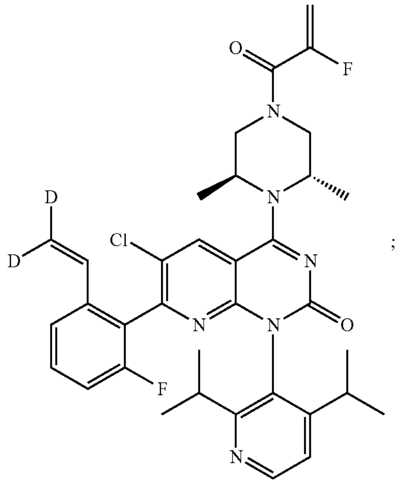
;
5-11
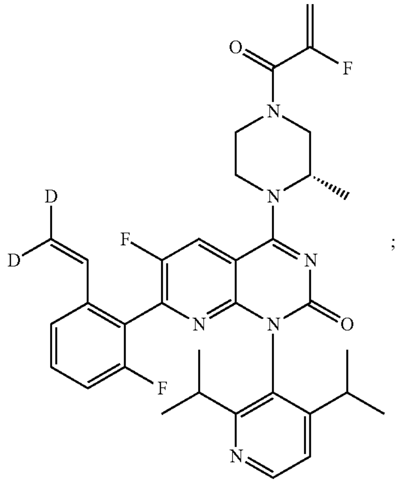
;
5-12
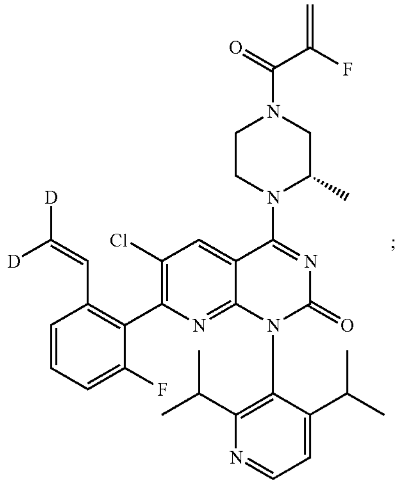
;
-continued
5-13
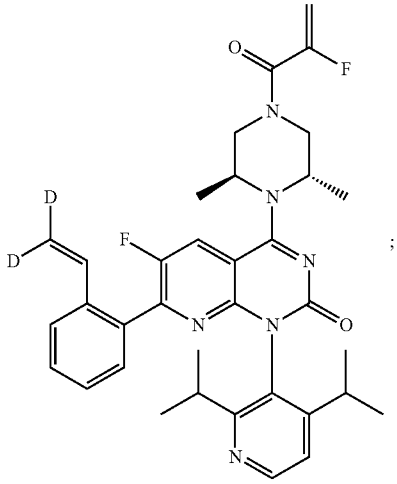
;
5-14
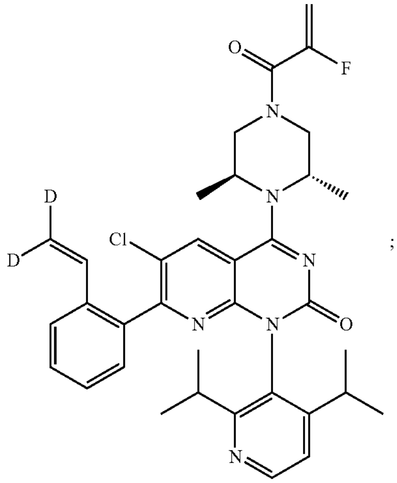
;
5-15
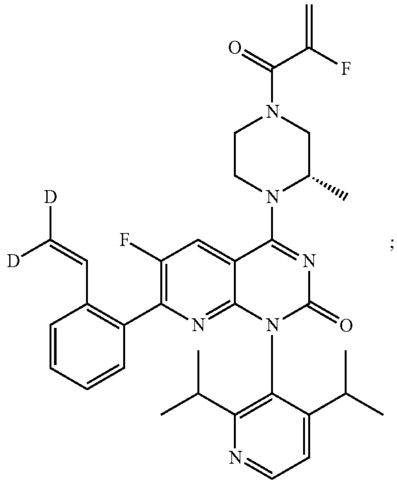
;

-continued
5-16
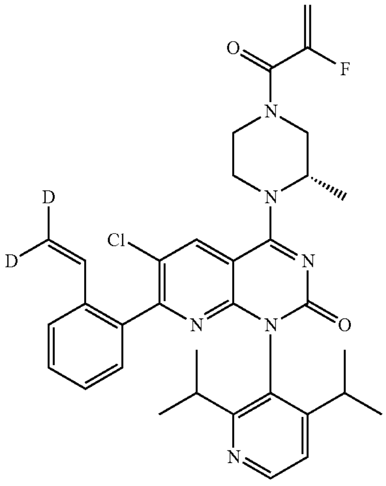
;
5-17
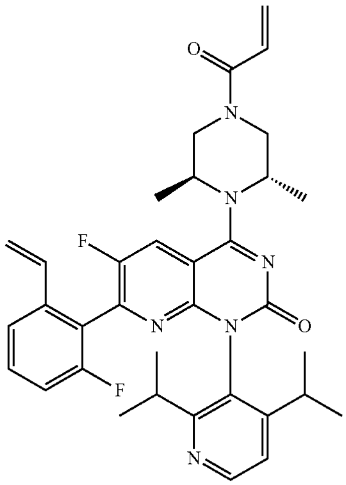
;
5-18
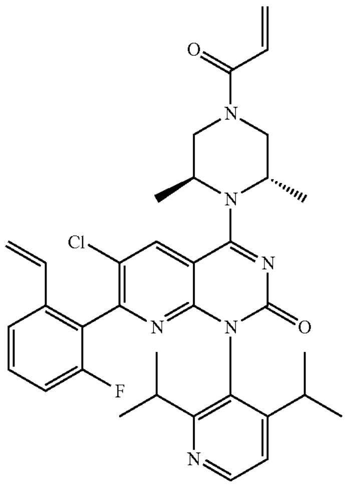
;
-continued
5-19
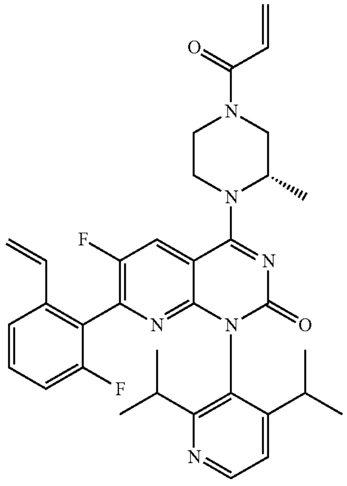
;
5-20
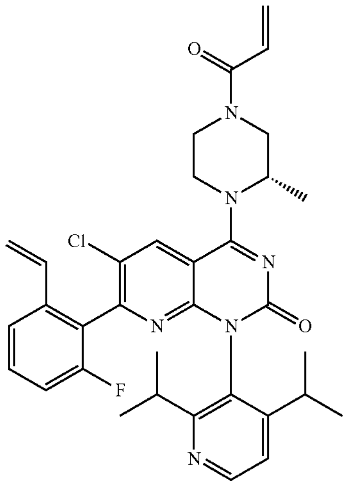
;
5-21
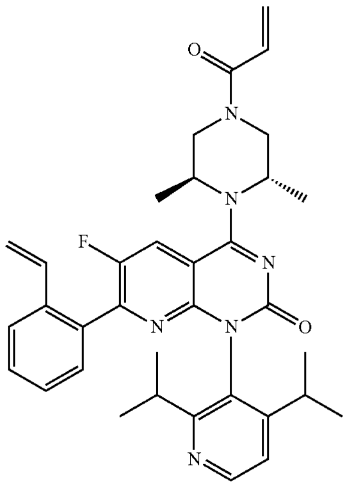
;

-continued
5-22
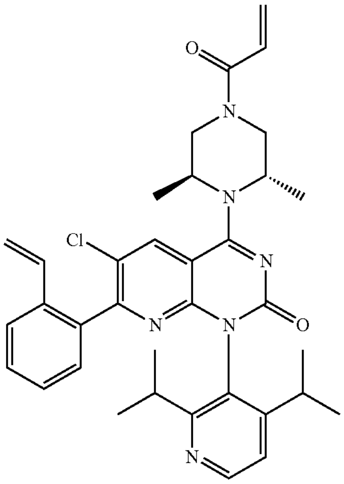
;
5-23
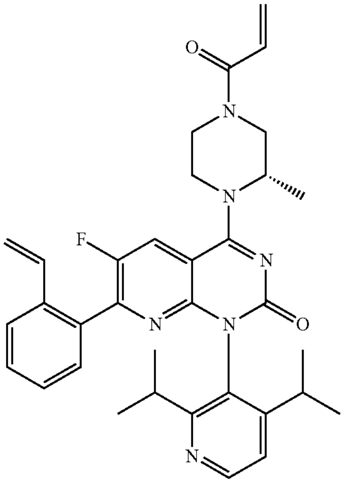
;
5-24
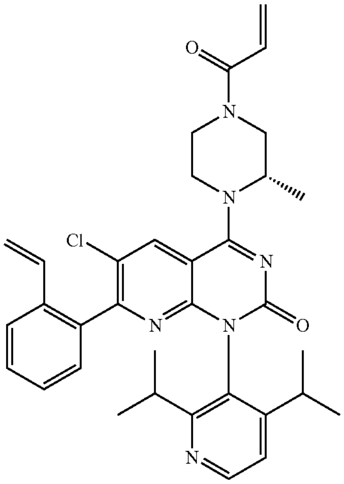
;
-continued
5-25
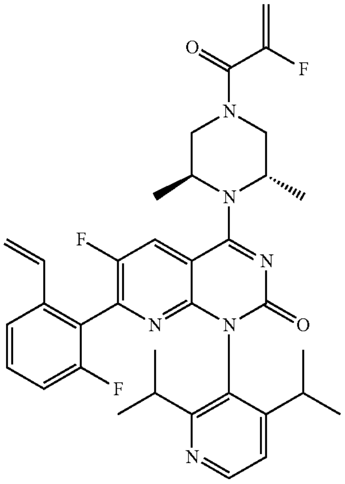
;
5-26
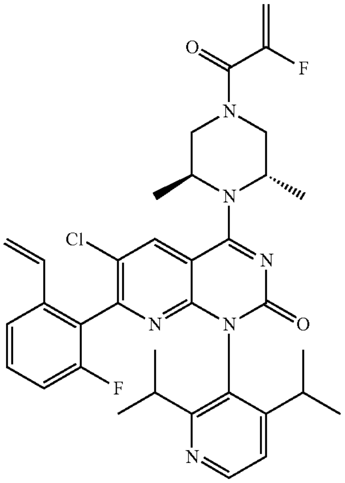
;
5-27
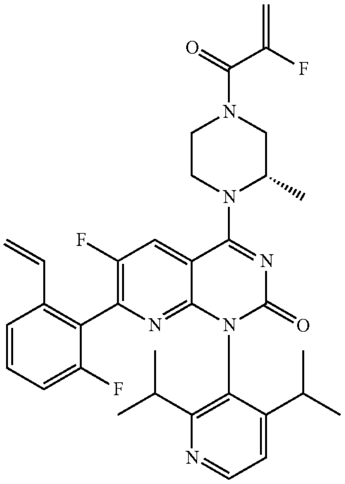
;

-continued
5-28
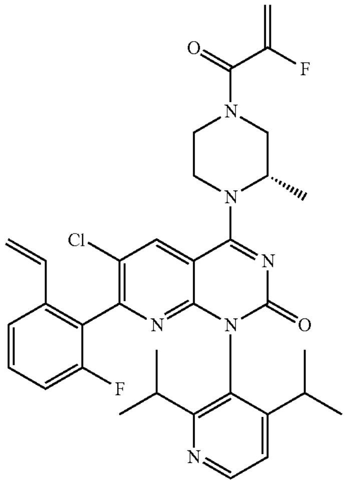
;
5-29
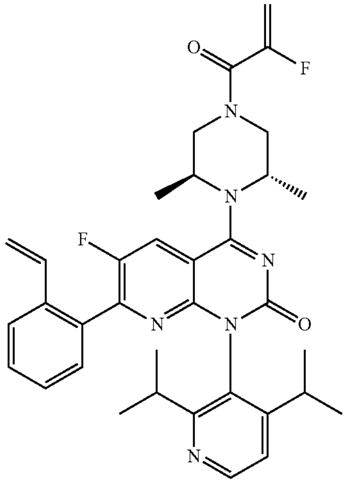
;
5-30
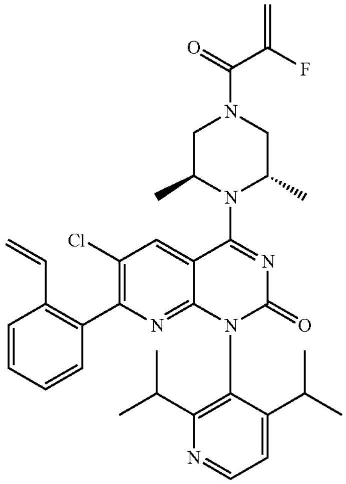
;
-continued
5-31
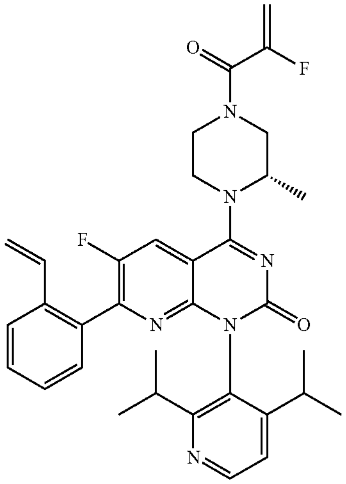
and
5-32
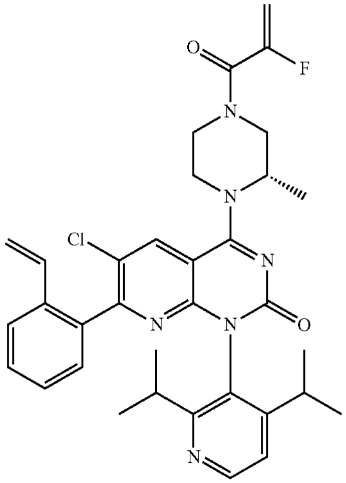
.
12. The compound of formula (II), or the stereoisomer, the tautomer or the pharmaceutically acceptable salt thereof according to claim 7, wherein the compound is any one selected from the group consisting of
3-1Ca
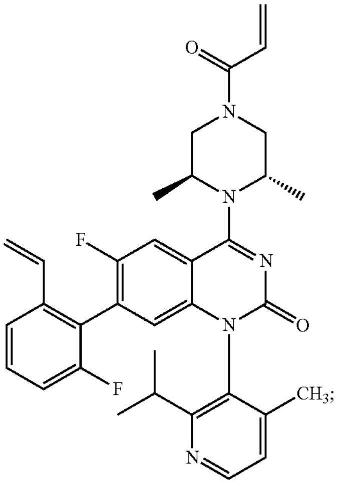

-continued
3-2Ca
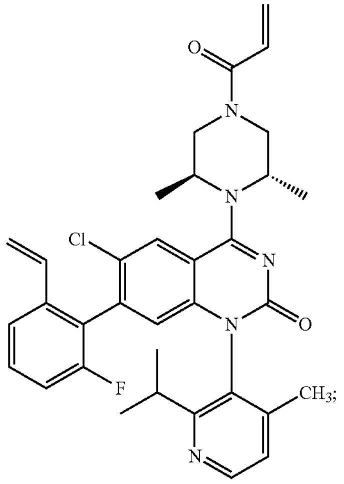
3-3Ca
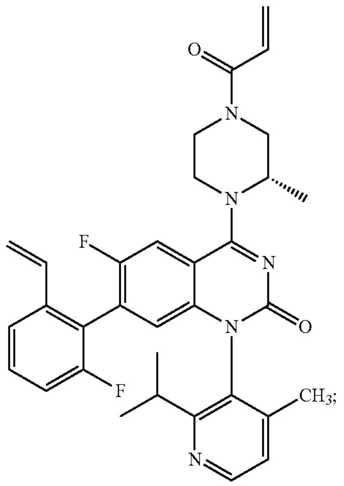
3-4Ca
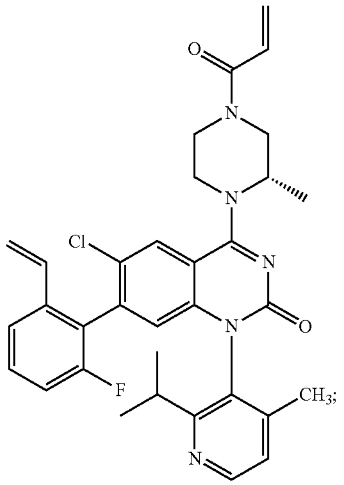
-continued
3-1C
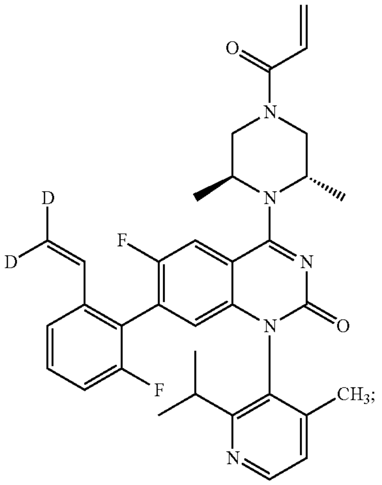
3-2C
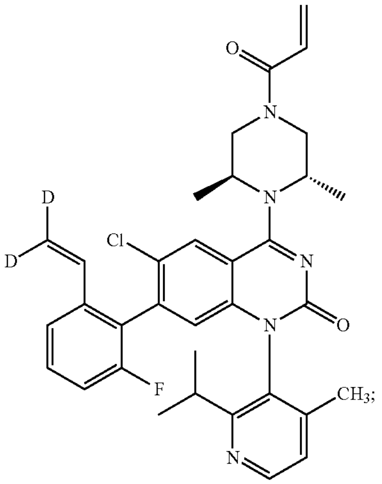
3-3C
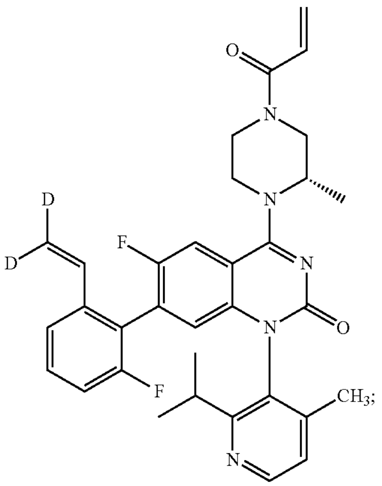

-continued
3-4C
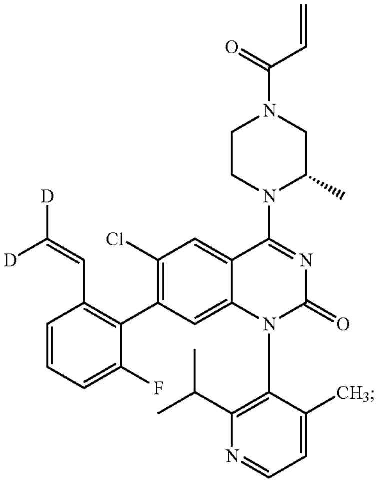
3-5C
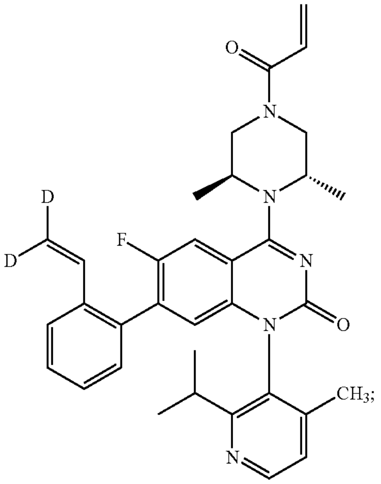
3-6C
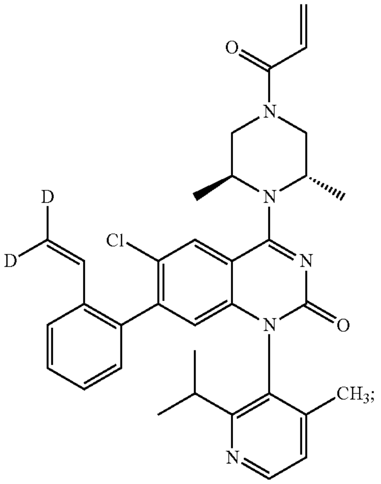
-continued
3-7C
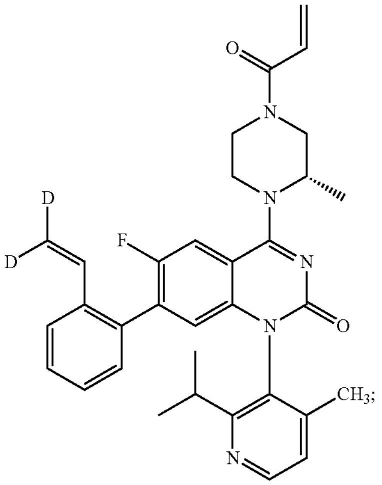
3-8C
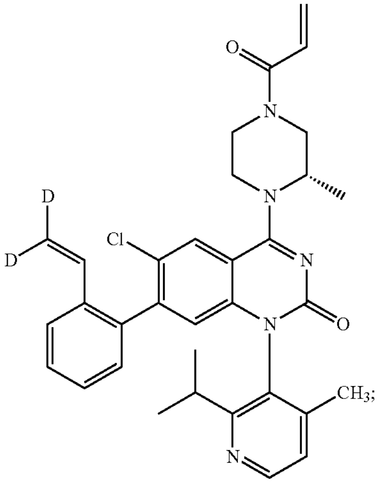
3-9C
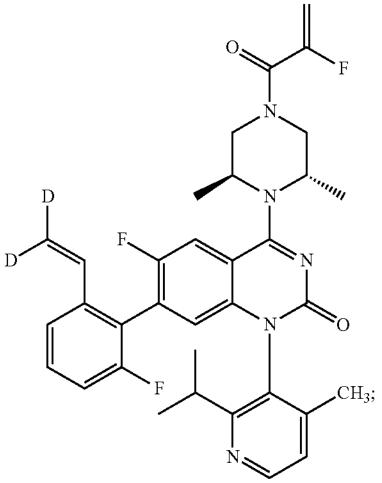

-continued
3-10C
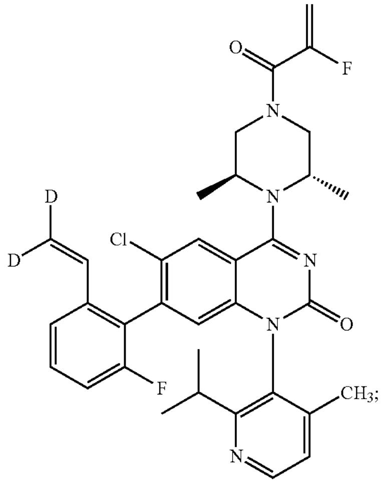
3-11C
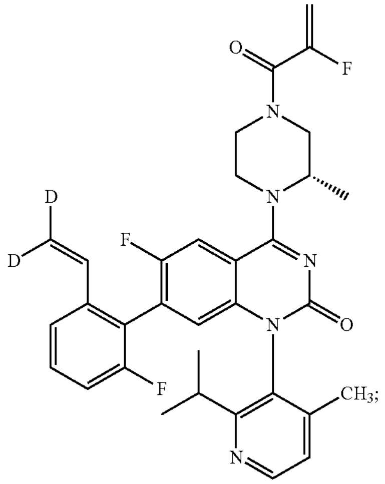
3-12C
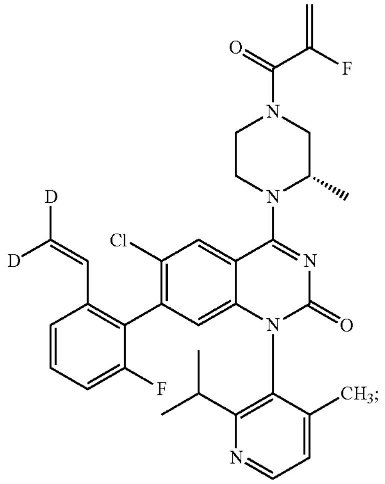
3-13C
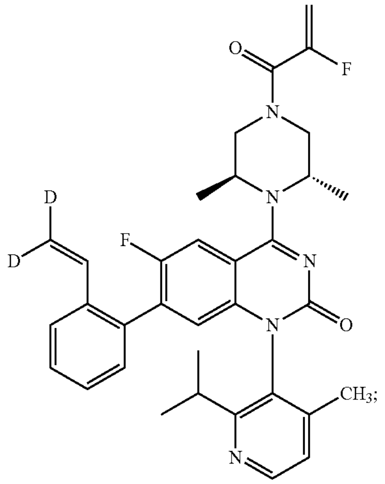
3-14C
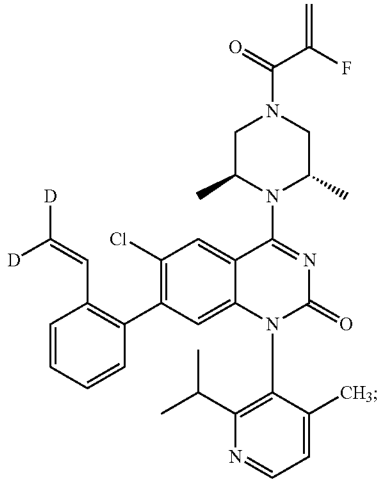
3-15C
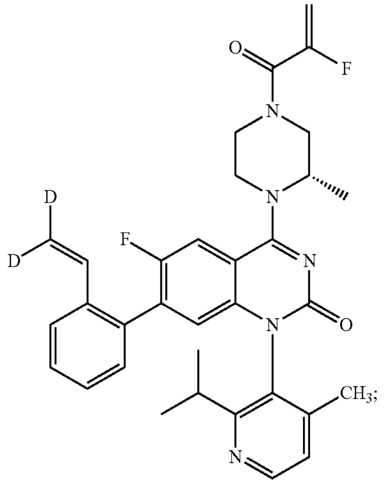

-continued
3-16C
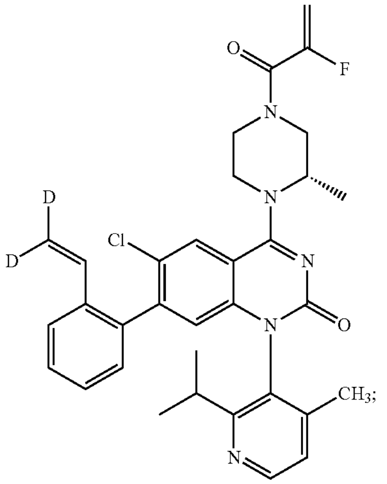
4-1C
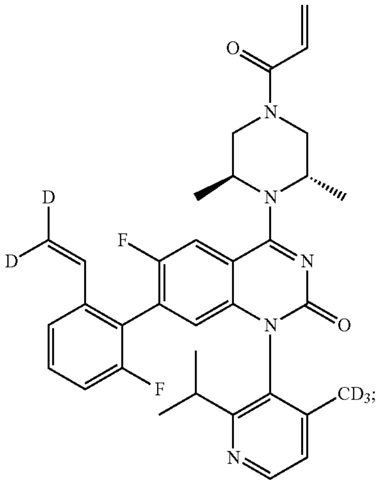
4-2C
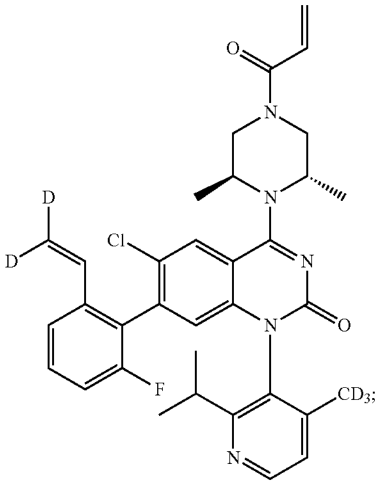
-continued
4-3C
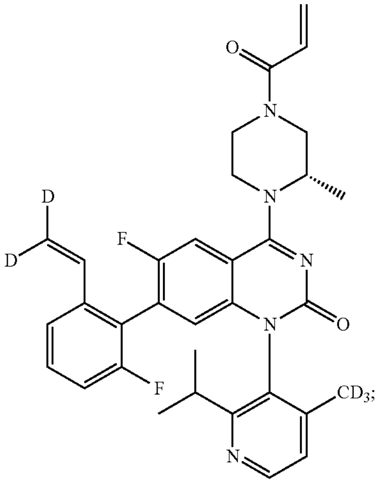
4-4C
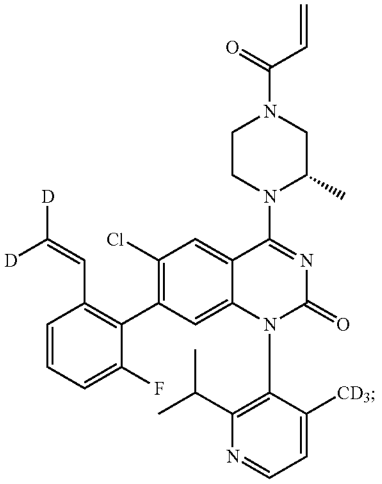
4-5C
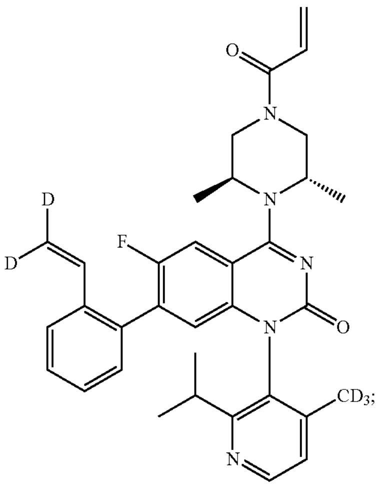

-continued
4-6C
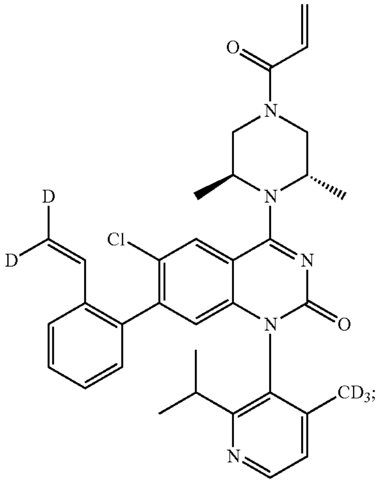
4-7C
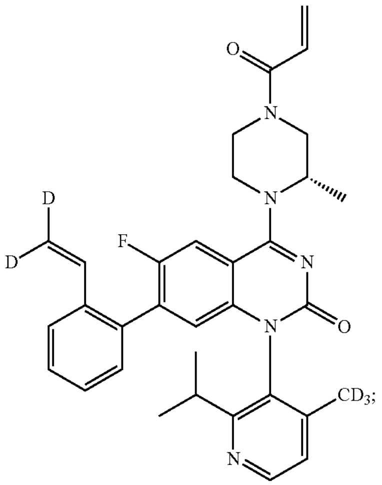
4-8C
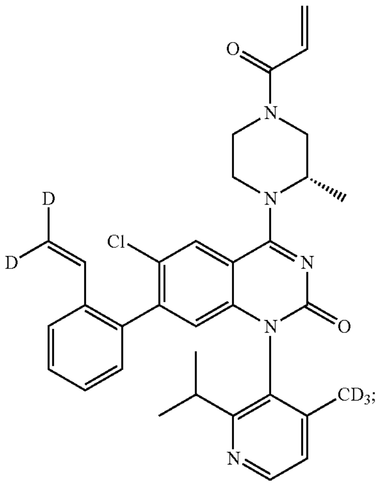
-continued
4-9C
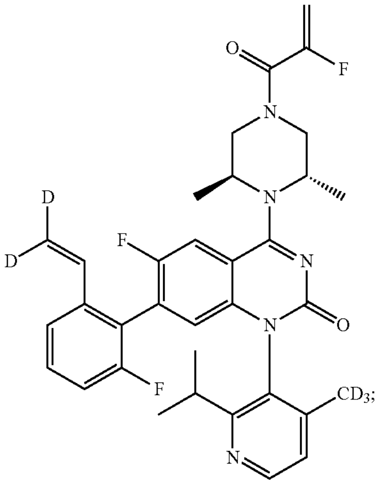
4-10C
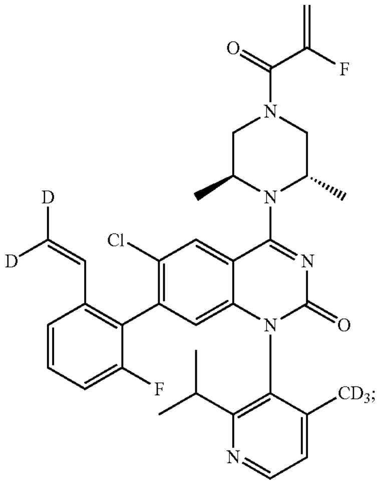
4-11C
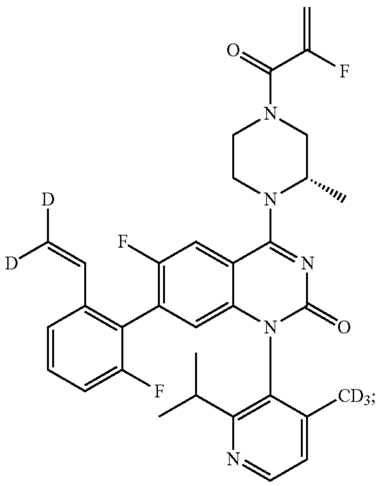

-continued
4-12C
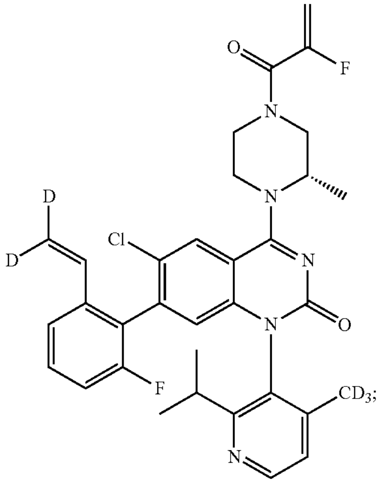
4-13C
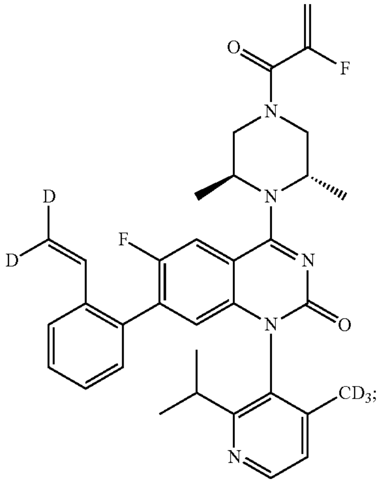
4-14C
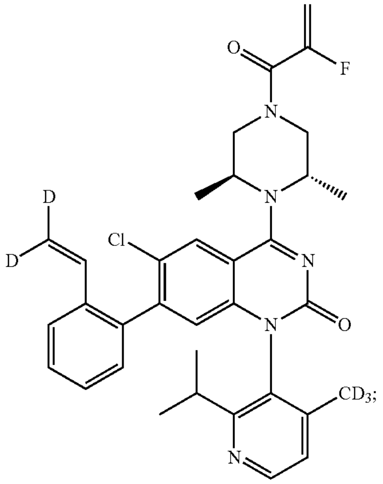
-continued
4-15C
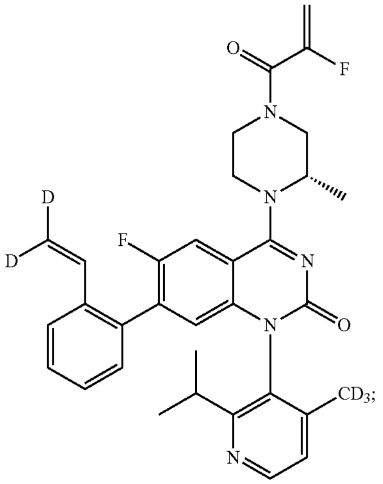
4-16C
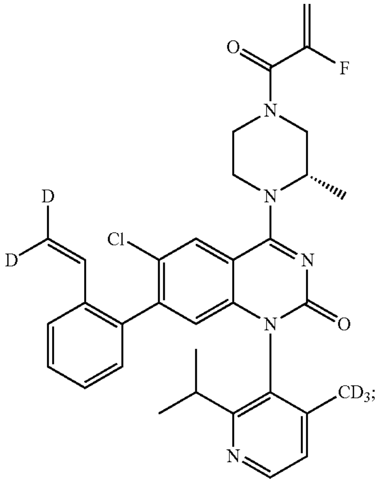
5-1C
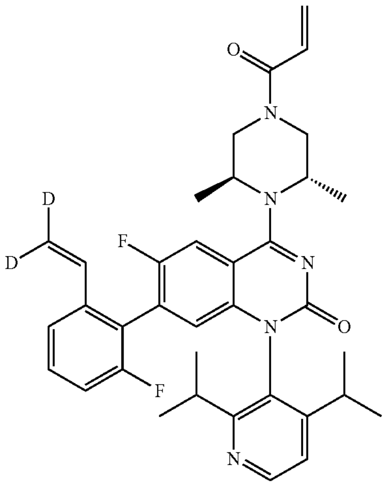
;

-continued
5-2C
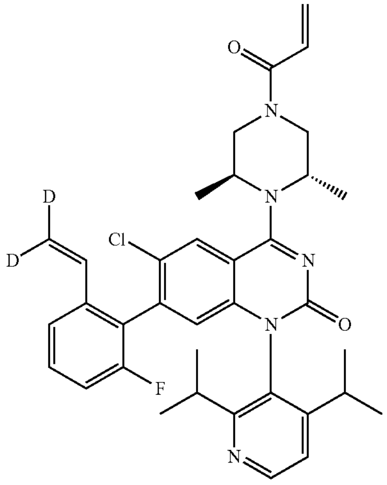
;
5-3C
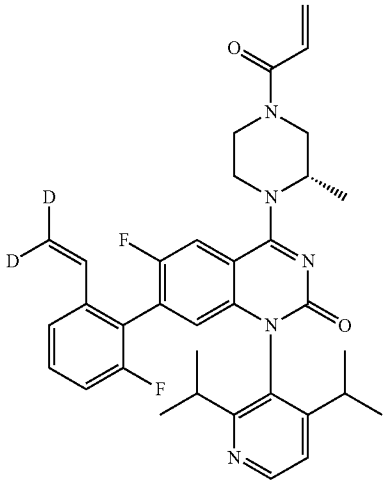
;
5-4C
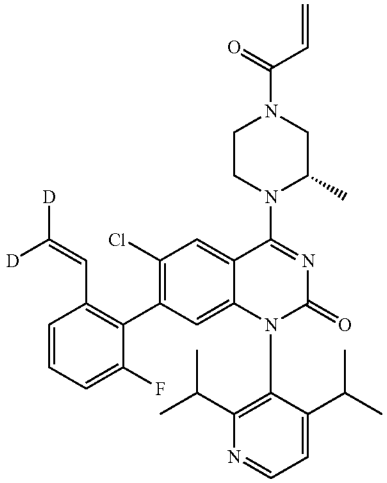
;
-continued
5-5C
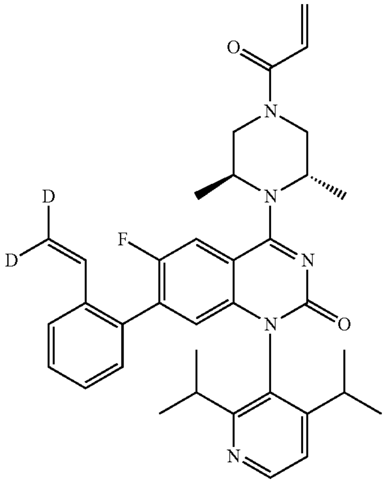
;
5-6C
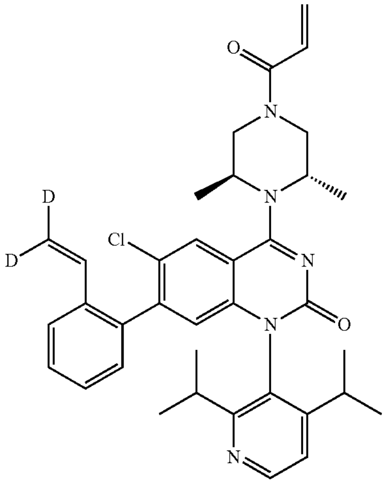
;
5-7C
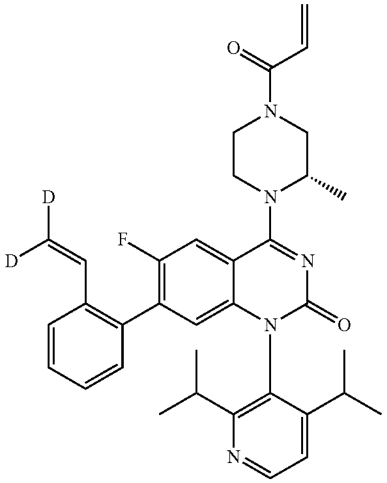
;

-continued
5-8C
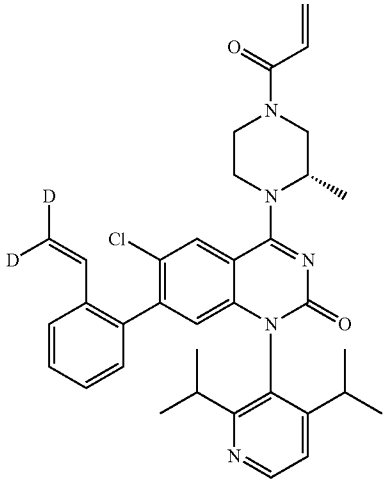
;
5-9C
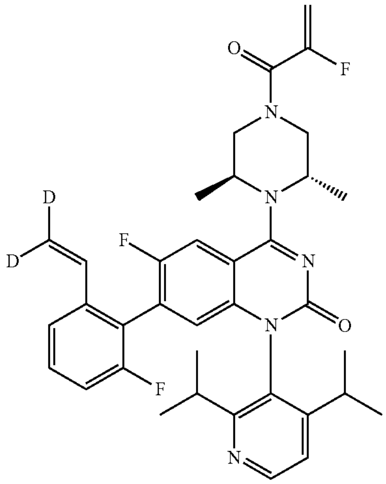
;
5-10C
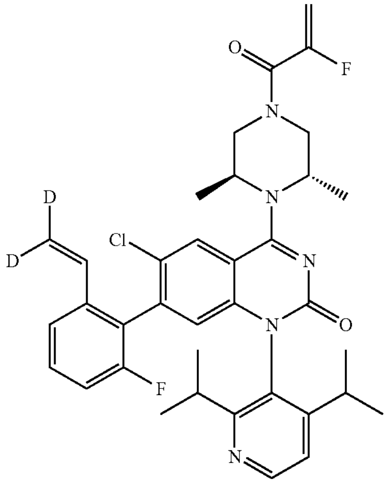
;
-continued
5-11C
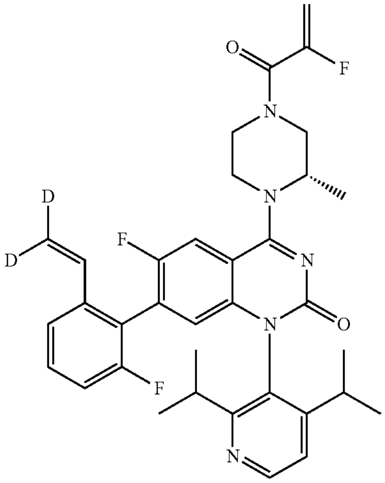
;
5-12C
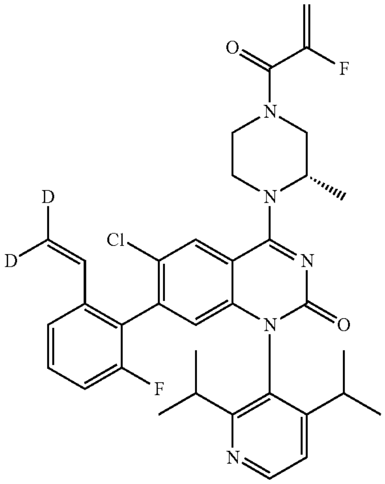
;
5-13C
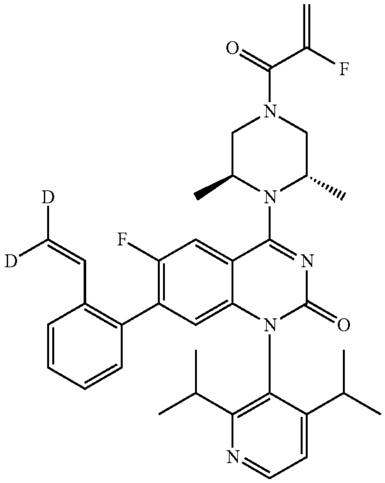
;

-continued 5-14C

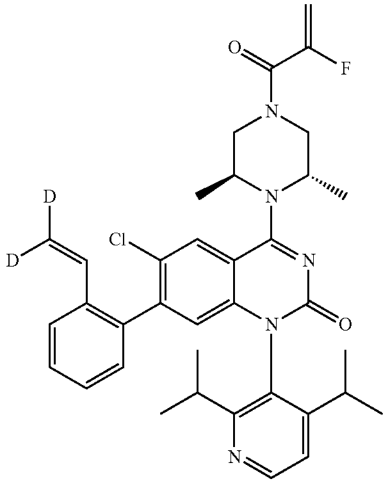

;

5-15C

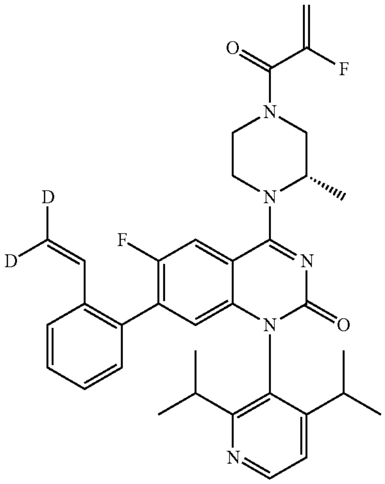

; and 5-16C

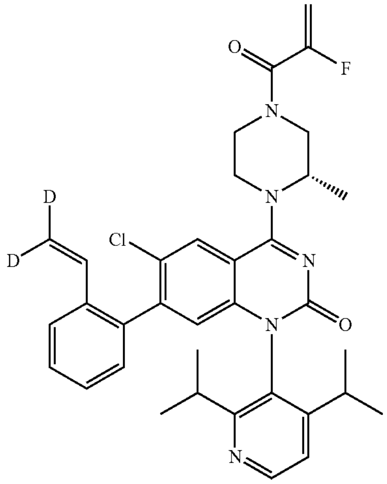

.

13. A pharmaceutical composition, comprising a therapeutically effective amount of the compound, or the stereoisomer, the tautomer, or the pharmaceutically acceptable salt thereof according to claim 7 and pharmaceutically available carriers.

14. A method for preventing and/or treating diseases associated with KRAS mutation mediated cancers or associated with KRAS G12C mutation mediated cancers, comprising administering a therapeutically effective amount of the compound, or the stereoisomer, the tautomer or the pharmaceutically acceptable salt thereof according to claim 7 or a pharmaceutical composition comprising the compound, or the stereoisomer, the tautomer or the pharmaceutically acceptable salt thereof according to claim 7 to a subject in need thereof, wherein the compound, or the stereoisomer, the tautomer or the pharmaceutically acceptable salt thereof is used alone or used in combination with other therapeutic methods including immunotherapy.

15. The method according to claim 14, wherein the diseases associated with KRAS mutation mediated cancers or associated with KRAS G12C mutation mediated cancers are liver cancer, esophageal cancer, gastric cancer, renal cell cancer, sarcoma, bile duct cancer, colon cancer, prostate cancer, ovarian cancer, breast cancer, hematological cancer, pancreatic cancer, MYH-associated polyposis, colorectal cancer, lung cancer, uterine cancer, mesothelioma, cervical cancer, or bladder cancer.

16. The compound of formula (II), or the stereoisomer, the tautomer or the pharmaceutically acceptable salt thereof according to claim 7, wherein the compound is represented by formula (IV),

IV

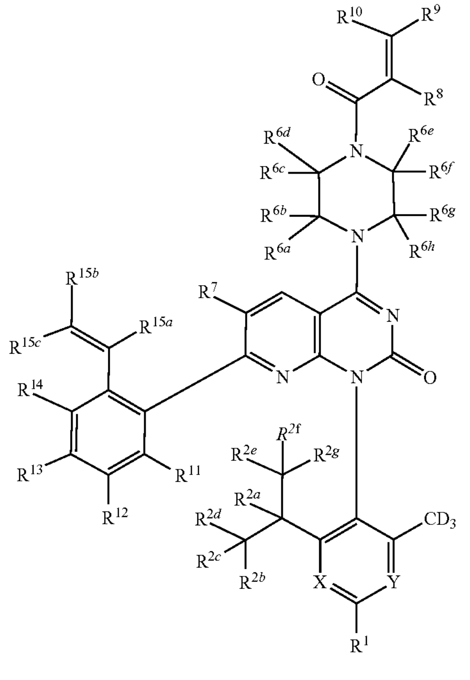

wherein,

X is nitrogen or $CR^4$, Y is nitrogen or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, and $R^{15c}$ are each independently hydrogen, deuterium, an alkyl, or a deuterated alkyl;

$R^{6a}$, $R^{6b}$, $R^{6c}$, $R^{6d}$, $R^{6e}$, $R^{6f}$, $R^{6g}$, and $R^{6h}$ are each independently hydrogen, deuterium, methyl, or methyl-$d_3$;

$R^7$ is fluorine or chlorine;

$R^8$, $R^9$, $R^{10}$, and $R^{11}$ are each independently hydrogen, deuterium, or fluorine;

the structural fragment

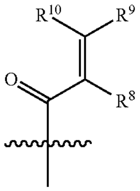
is any one of the following groups:
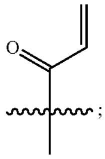 ; 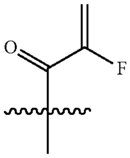 or 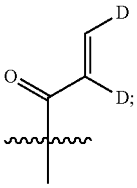 ;
the structural fragment
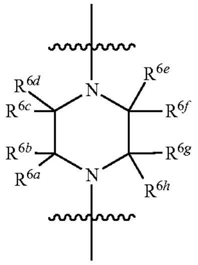
is any one of the following groups:
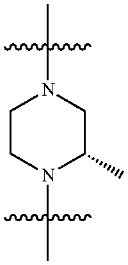 ; 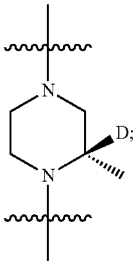 ; 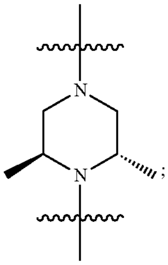 ;
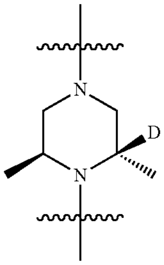 or 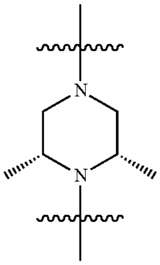 ;
and
the structural fragment
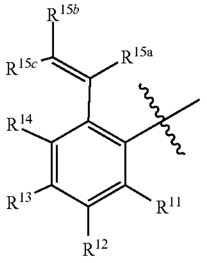
is any one of the following groups:
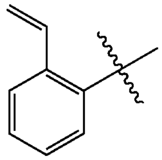 ; 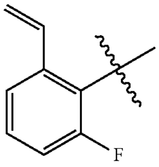 ;
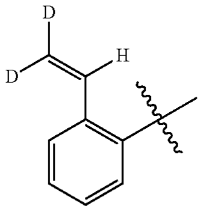 ; 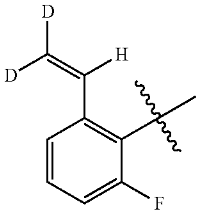 ;
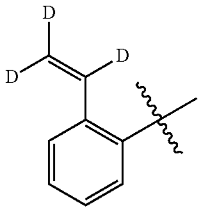 ; 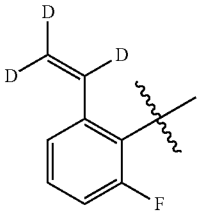 ;
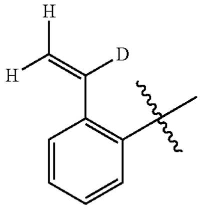 ; 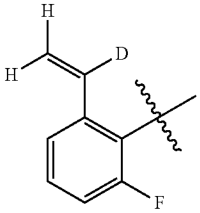 ;
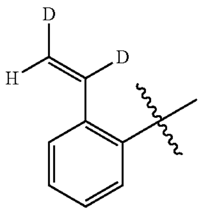 ; 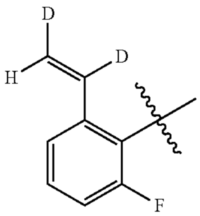 ;
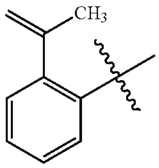 ; 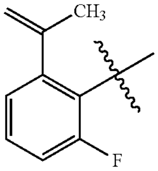 ;

-continued

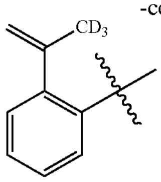 ; 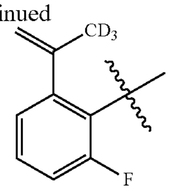 ;

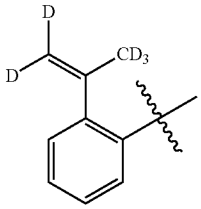 ; 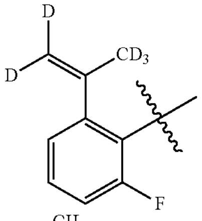

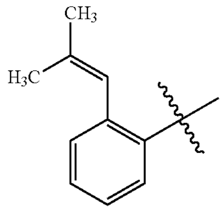 ; 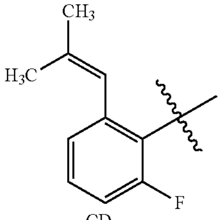 ;

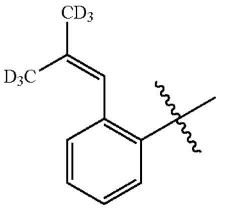 ; or 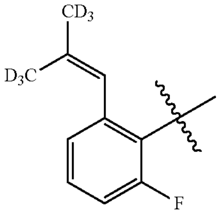 .

17. The compound of formula (II), or the stereoisomer, the tautomer or the pharmaceutically acceptable salt thereof according to claim 7, wherein the compound is represented by formula (V),

V

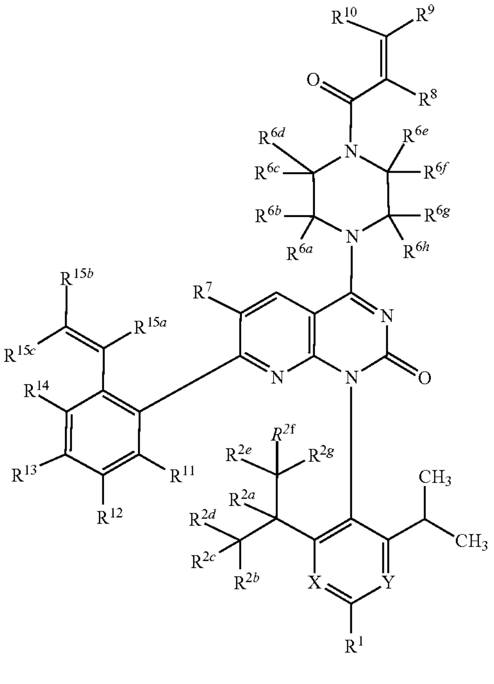

wherein,

X is nitrogen or $CR^4$, Y is nitrogen or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, and $R^{15c}$ are each independently hydrogen, deuterium, an alkyl, or a deuterated alkyl;

$R^{6a}$, $R^{6b}$, $R^{6c}$, $R^{6d}$, $R^{6e}$, $R^{6f}$, $R^{6g}$, and $R^{6h}$ are each independently hydrogen, deuterium, methyl, or methyl-$d_3$;

$R^7$ is fluorine or chlorine;

$R^8$, $R^9$, $R^{10}$, and $R^{11}$ are each independently hydrogen, deuterium, or fluorine;

the structural fragment

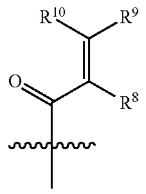

is any one of the following groups:

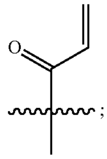 ; 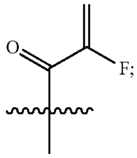 ; or 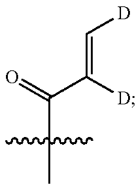 ;

the structural fragment

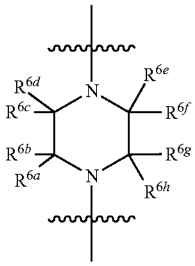

is any one of the following groups:

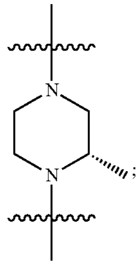 ; 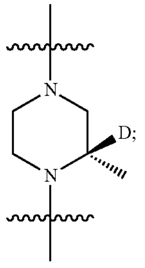 ; 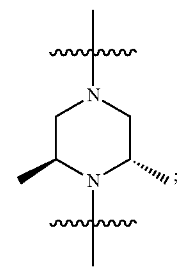 ;

-continued
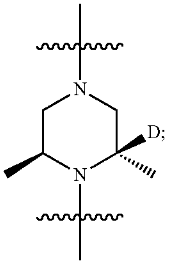
or
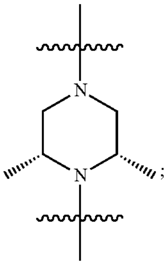
;
and
the structural fragment
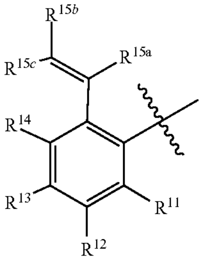
is any one of the following groups:
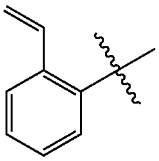
;
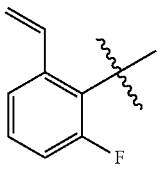
;
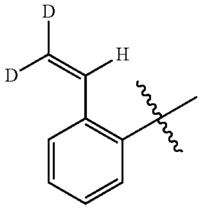
;
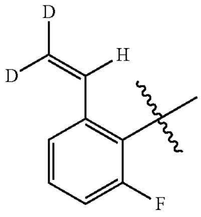
;
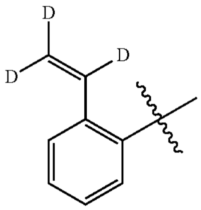
;
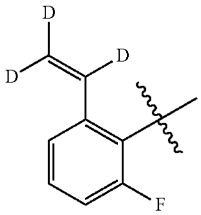
;
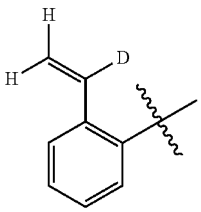
;
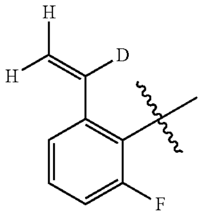
;
-continued
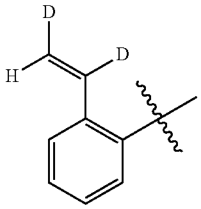
;
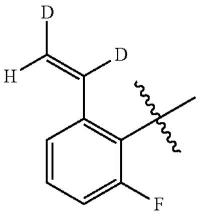
;
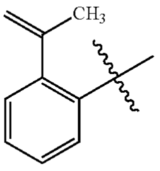
;
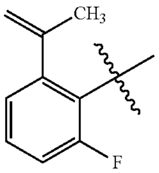
;
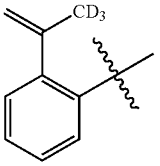
;
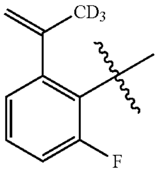
;
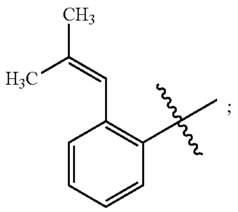
;
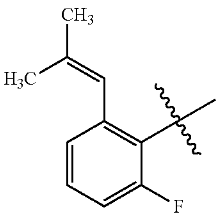
;
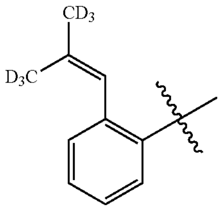
; or
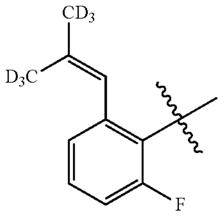
.
18. The compound of formula (II), or the stereoisomer, the tautomer or the pharmaceutically acceptable salt thereof according to claim 7, wherein the compound is any one selected from the group consisting of
3-1
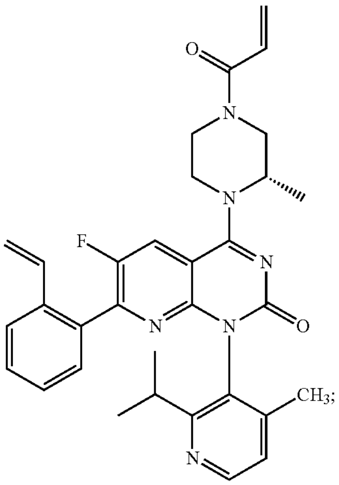

-continued
3-2
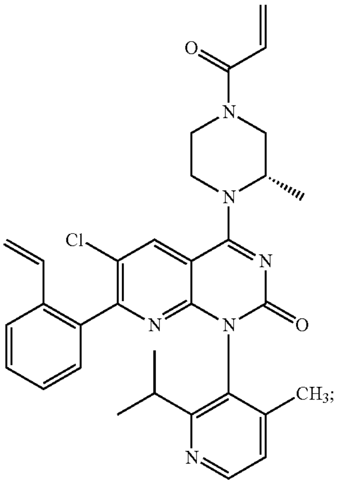
3-5
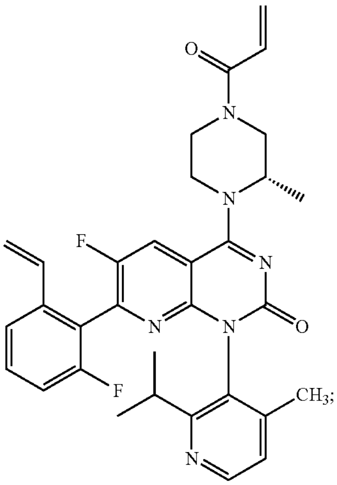
3-6
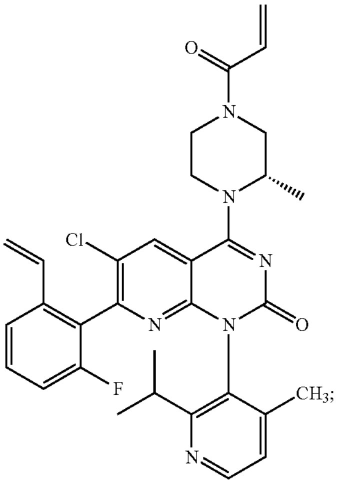
-continued
3-8
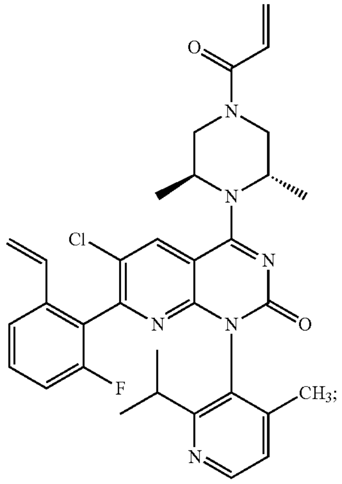
4-17
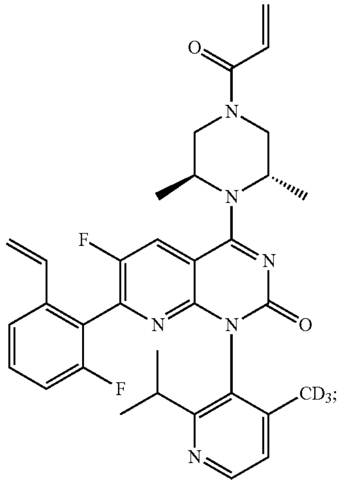
3-20
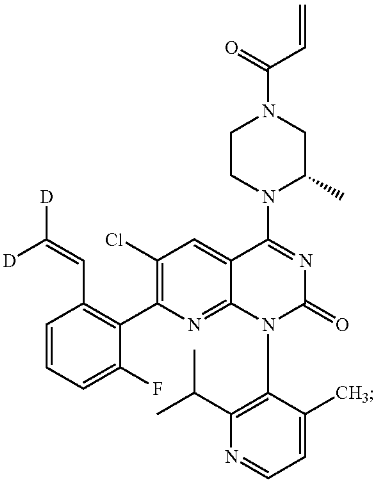

-continued
3-21
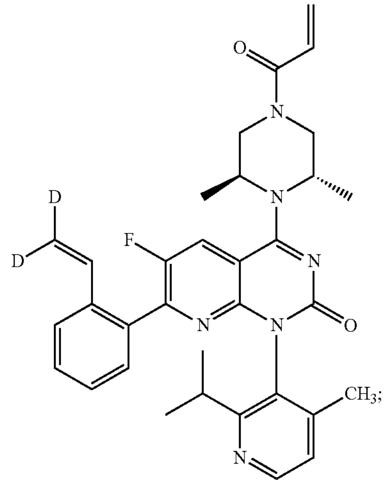
3-6M
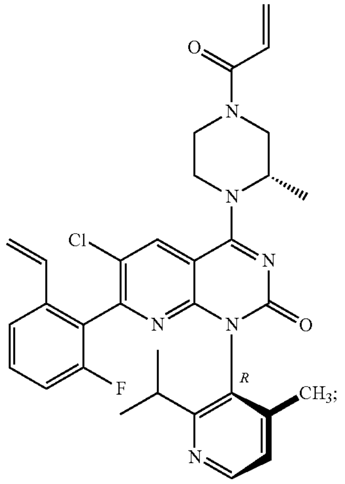
3-2M
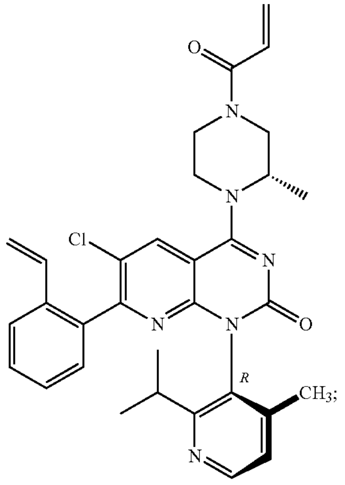
-continued
3-12M
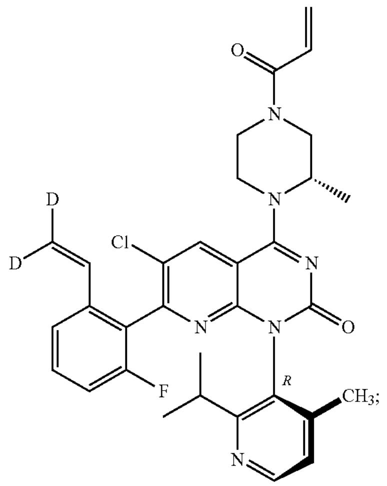
3-16M
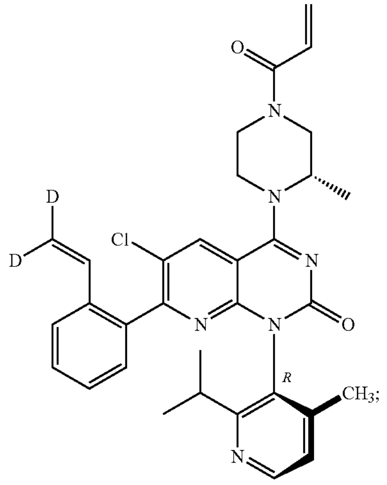
1-11
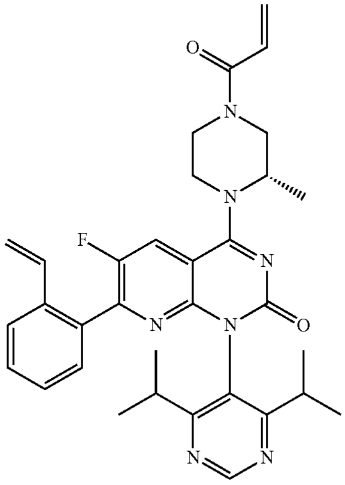
;

-continued 1-12

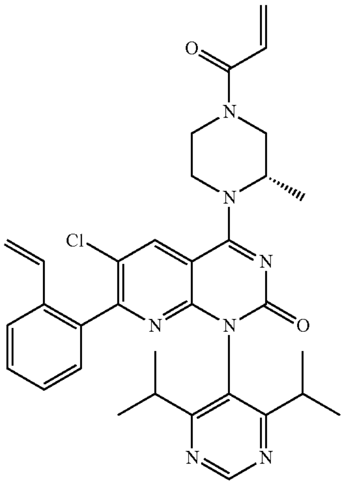

;

1-27

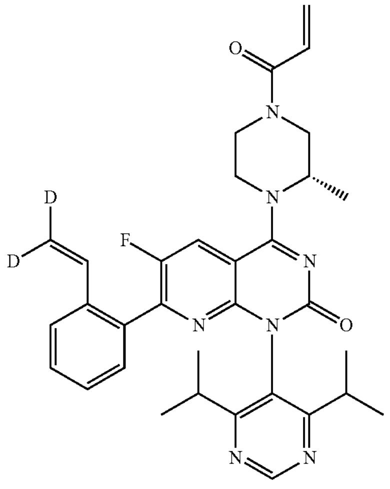

and 1-28

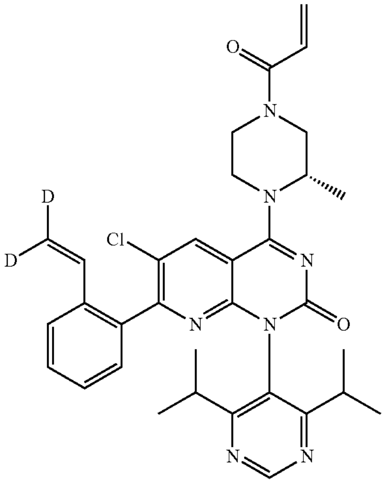

.

19. A compound of formula (VI), or a stereoisomer, a tautomer or a pharmaceutically acceptable salt thereof,

VI

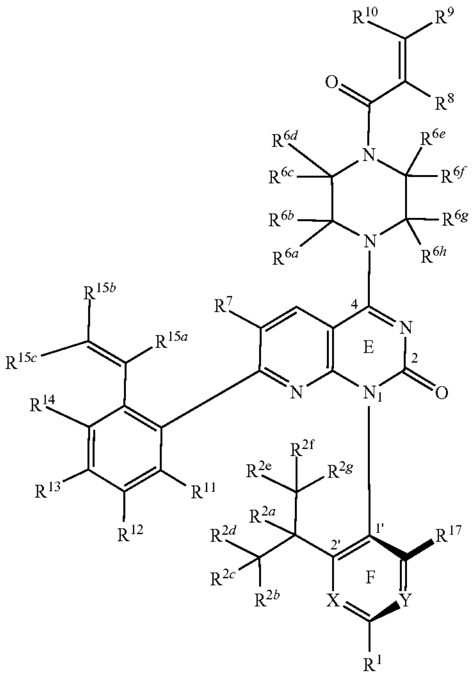

wherein, the axial chiral stereoscopic configuration formed by the connection between the nitrogen atom at the position 1 of Ring E and the carbon atom at the position 1' of Ring F is optically pure;

X is nitrogen or $CR^4$, Y is nitrogen or $CR^5$;

$R^1$, $R^{2a}$, $R^{2b}$, $R^{2c}$, $R^{2d}$, $R^{2e}$, $R^{2f}$, $R^{2g}$, $R^4$, $R^5$, $R^{12}$, $R^{13}$, $R^{14}$, $R^{15a}$, $R^{15b}$, and $R^{15c}$ are each independently hydrogen, deuterium, an alkyl, a deuterated alkyl, or a halogen;

$R^{6a}$, $R^{6b}$, $R^{6c}$, $R^{6d}$, $R^{6e}$, $R^{6f}$, $R^{6g}$, and $R^{6h}$ are each independently selected from the group consisting of hydrogen, deuterium, methyl, or methyl-$d_3$;

$R^7$ is fluorine or chlorine;

$R^8$, $R^9$, $R^{10}$, and $R^{11}$ are each independently hydrogen, deuterium, or fluorine; and $R^{17}$ is hydrogen, an alkyl, a deuterated alkyl, a haloalkyl, cyclopropyl, or deuterated cyclopropyl.

20. The compound of formula (VI), or the stereoisomer, the tautomer or the pharmaceutically acceptable salt thereof according to claim 19, wherein the compound is represented by formula (IIIM) with R axial chiral stereoscopic configuration,

IIIM

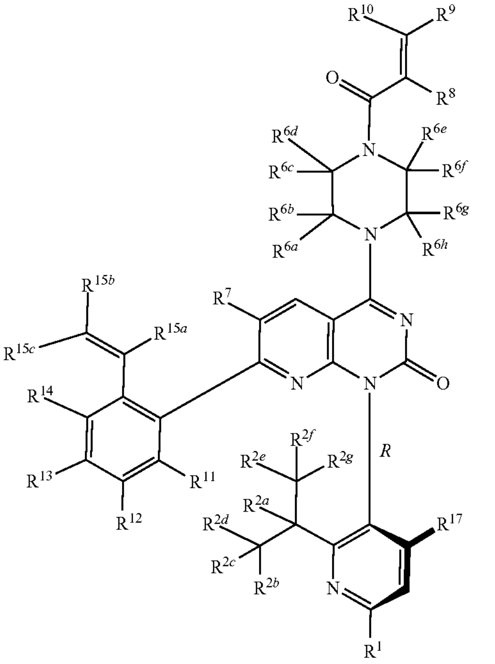

wherein, $R^1$, $R^{2a}$, $R^{2b}$, $R^{2c}$, $R^{2d}$, $R^{2e}$, $R^{2f}$, $R^{2g}$, $R^{12}$, $R^{13}$, $R^{14}$, $R^{15a}$, $R^{15b}$, and $R^{15c}$ are each independently hydrogen, deuterium, an alkyl, a deuterated alkyl, an alkenyl alkyl, an alkynyl alkyl, a deuterated alkenyl alkyl, a deuterated alkynyl alkyl, or a halogen;

$R^{6a}$, $R^{6b}$, $R^{6c}$, $R^{6d}$, $R^{6e}$, $R^{6f}$, $R^{6g}$, and $R^{6h}$ are each independently hydrogen, deuterium, methyl, or methyl-$d_3$;

$R^7$ is hydrogen, fluorine, or chlorine;

$R^8$, $R^9$, $R^{10}$, and $R^{11}$ are each independently hydrogen, deuterium, or fluorine;

$R^{17}$ is hydrogen, deuterium, fluorine, chlorine, bromine, iodine, methyl, ethyl, deuterated methyl, or deuterated ethyl;

the structural fragment

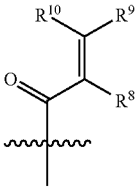

is any one of the following groups:

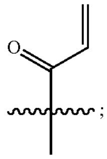 ; 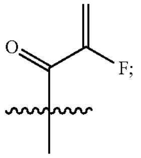 or 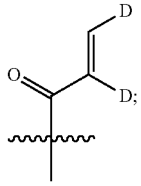

the structural fragment

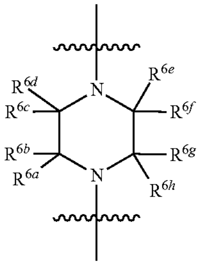

is any one of the following groups:

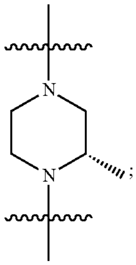 ; 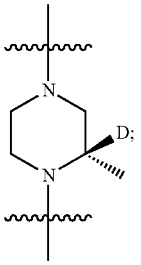 ; 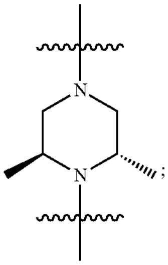 ;

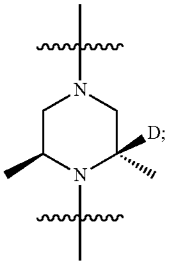 or 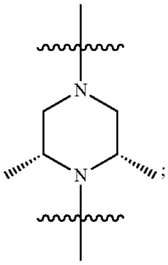 ;

and the structural fragment

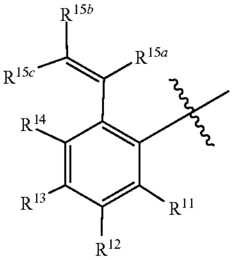

is any one of the following groups:

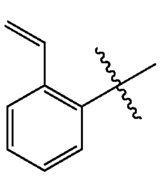 ; 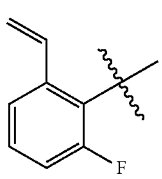 ;

-continued
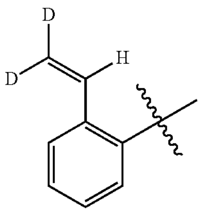 ; 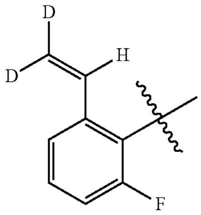 ;
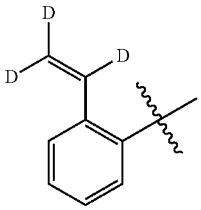 ; 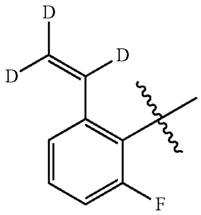 ;
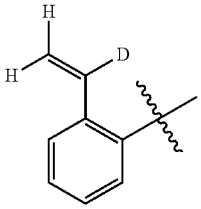 ; 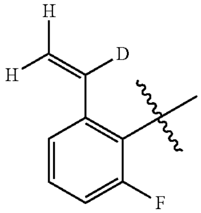 ;
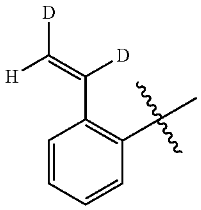 ; 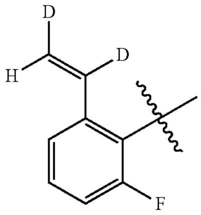 ;
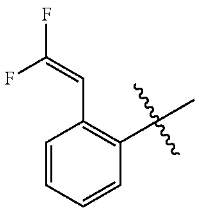 ; 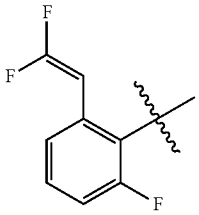 ;
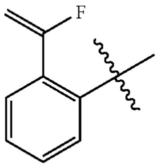 ; 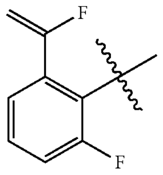 ;
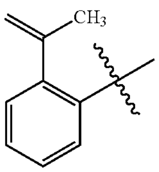 ; 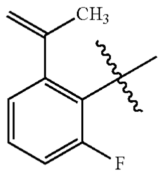 ;
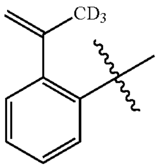 ; 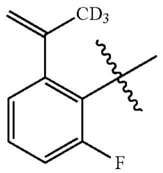 ;
-continued
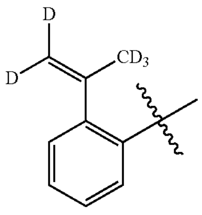 ; 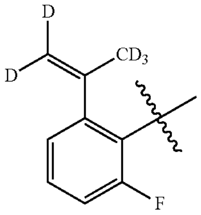 ;
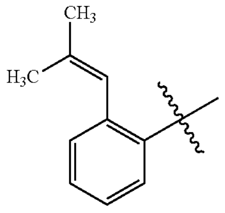 ; 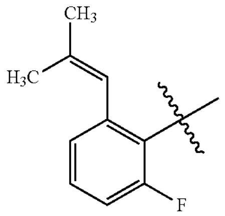 ;
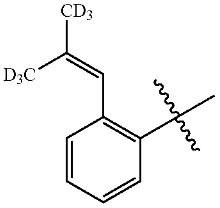 ; or 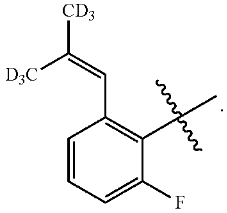
21. The compound of formula (VI), or the stereoisomer, the tautomer or the pharmaceutically acceptable salt thereof according to claim 19, wherein the compound is represented by any one selected from the group consisting of the following compounds with R axial chiral stereoscopic configuration;
3-1M
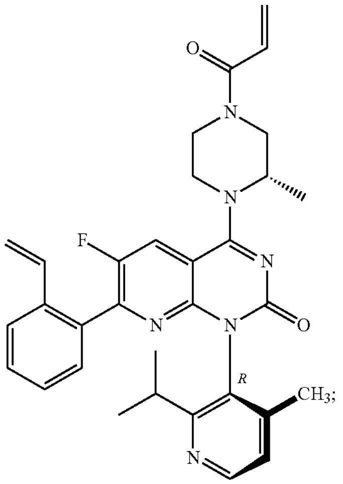

-continued
3-2M
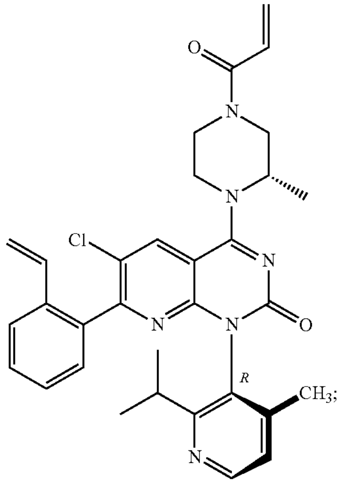
3-3M
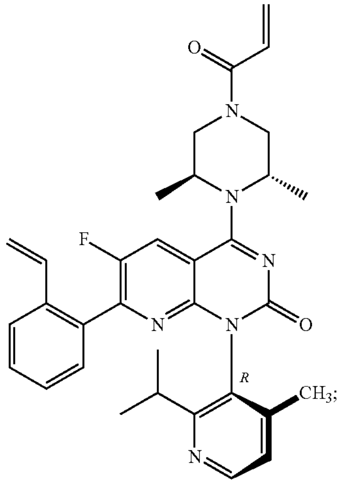
3-4M
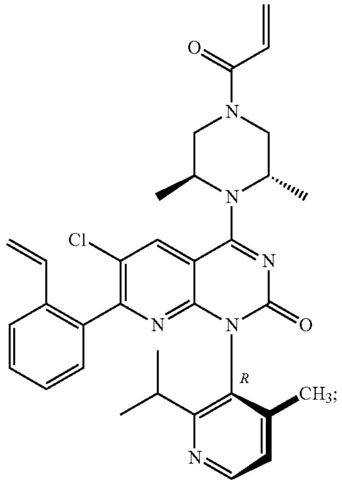
-continued
3-5M
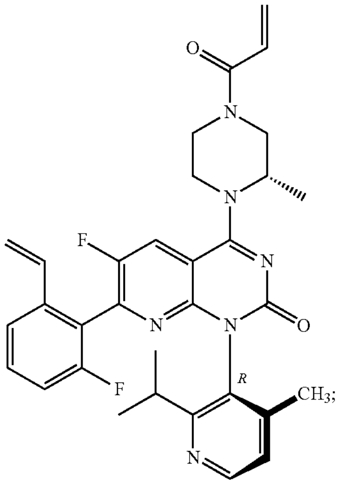
3-6M
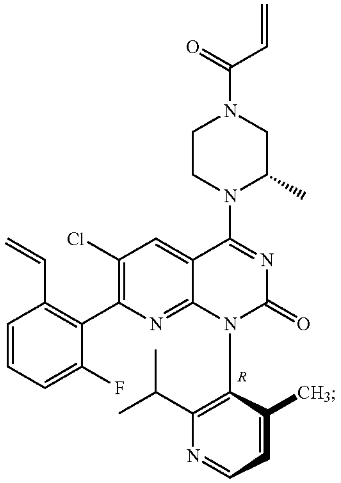
3-7M
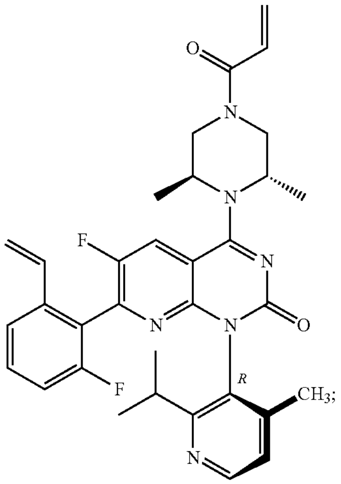

-continued
3-8M
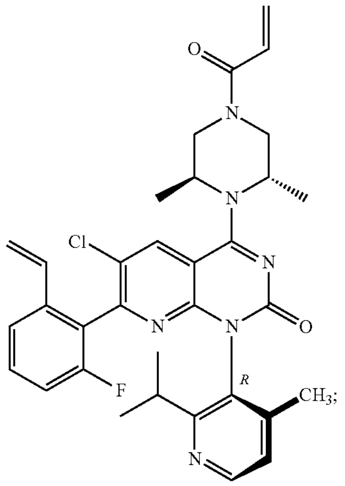
3-9M
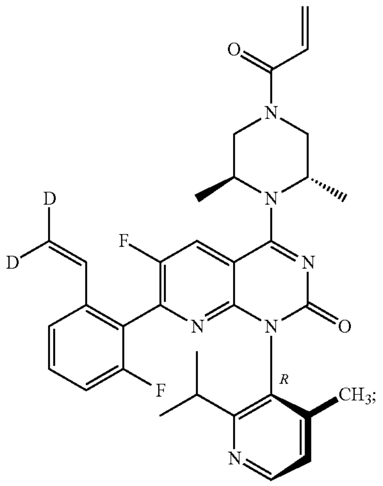
3-10M
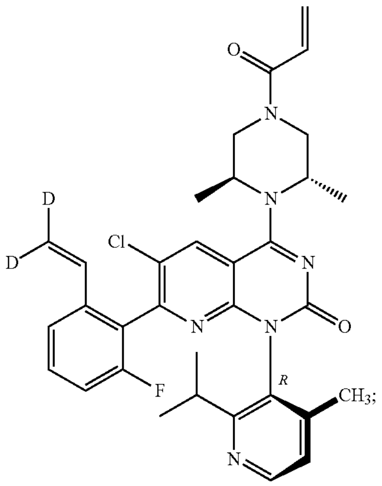
-continued
3-11M
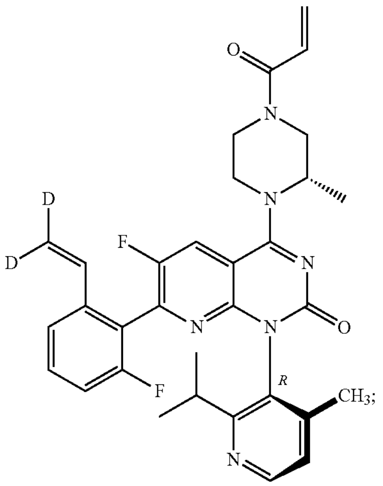
3-12M
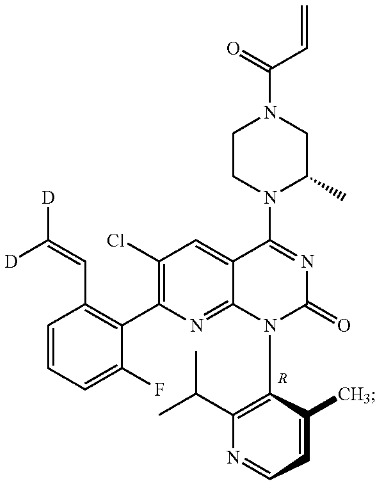
3-13M
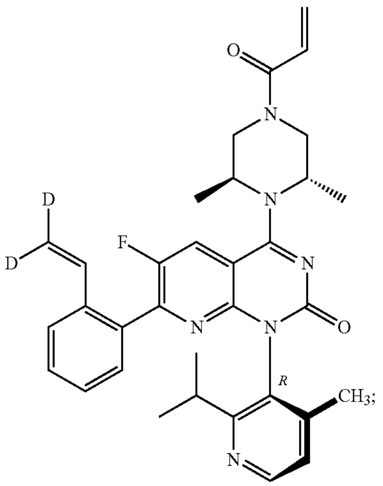

-continued
3-14M
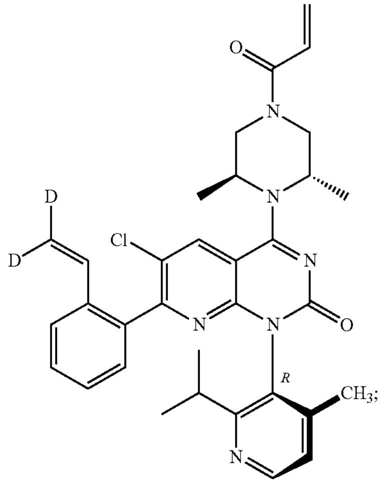
3-15M
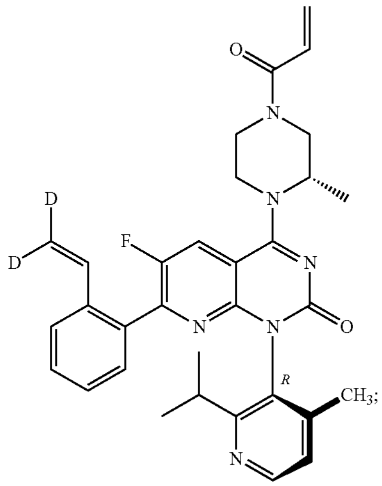
3-16M
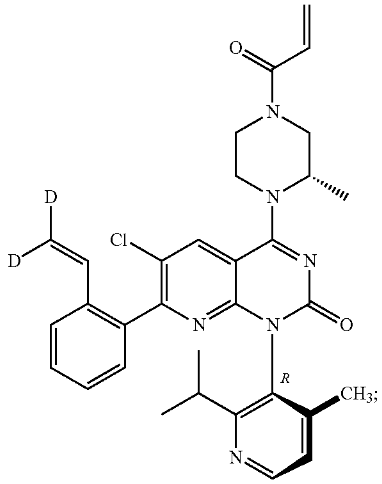
-continued
3-17M
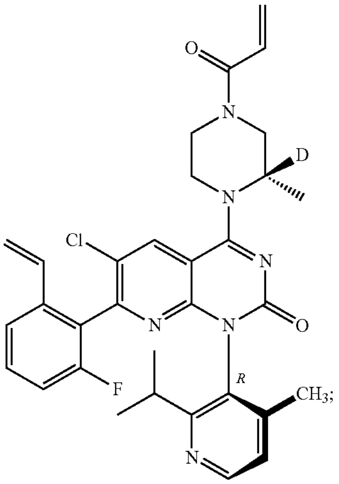
3-18M
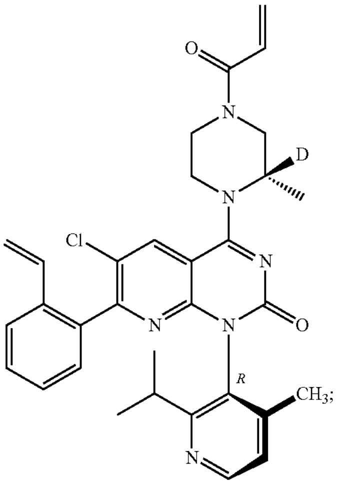
3-19M
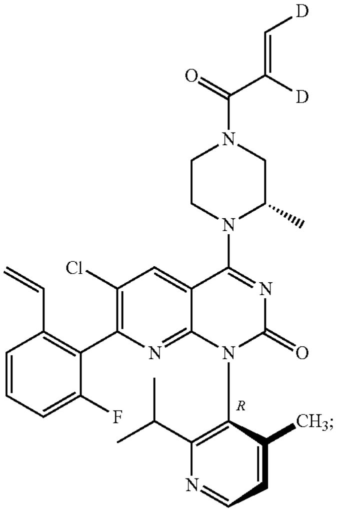

3-20M
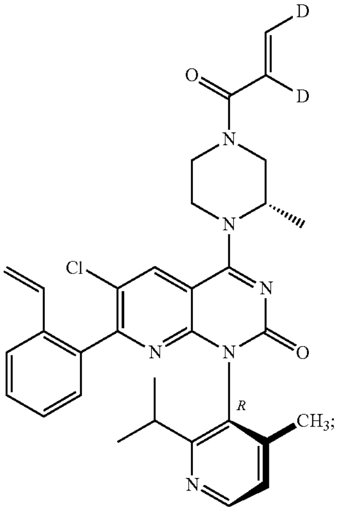
3-21M
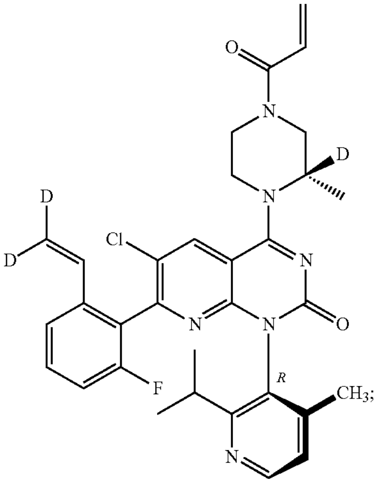
3-22M
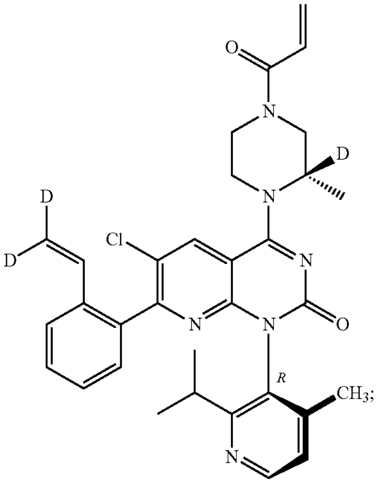
3-23M
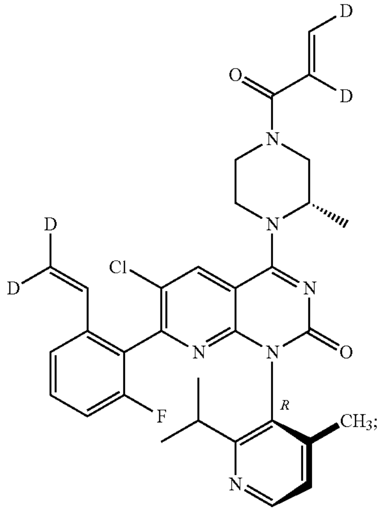
3-24M
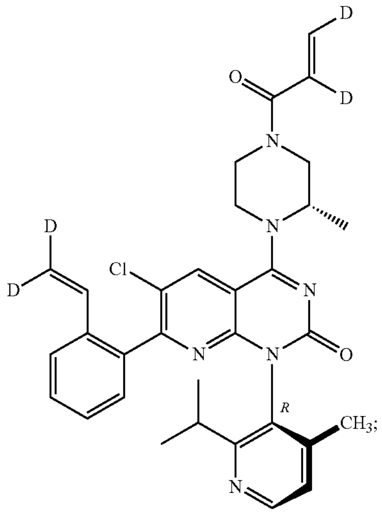
3-25M
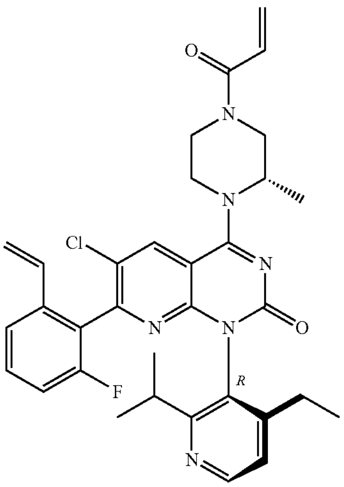
;

-continued
3-26M
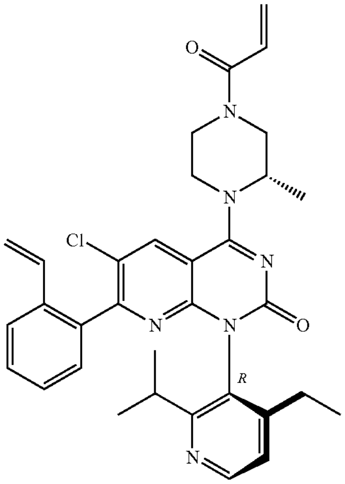
;
3-27M
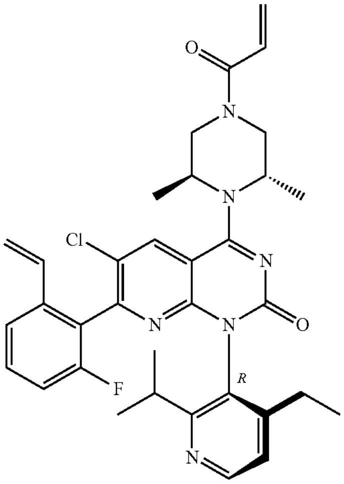
;
3-28M
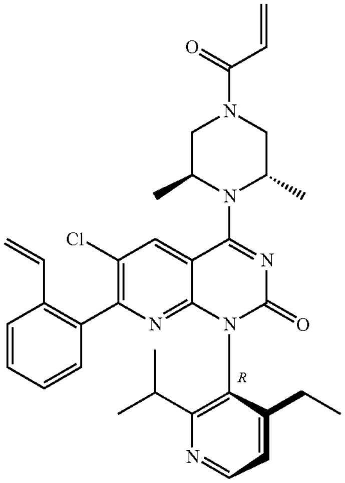
;
3-29M
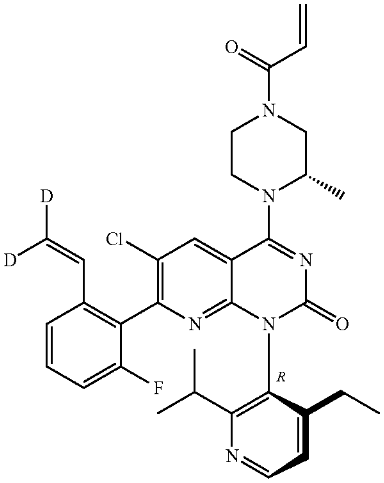
;
3-30M
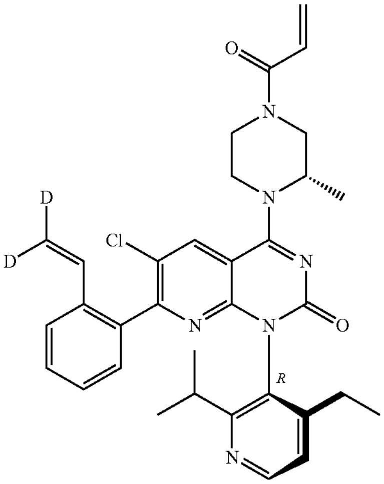
;
3-31M
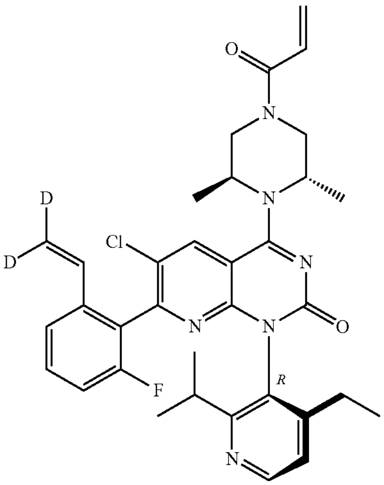
;

-continued
3-32M
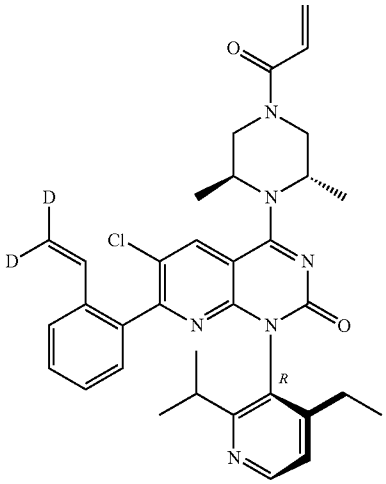
;
4-1M
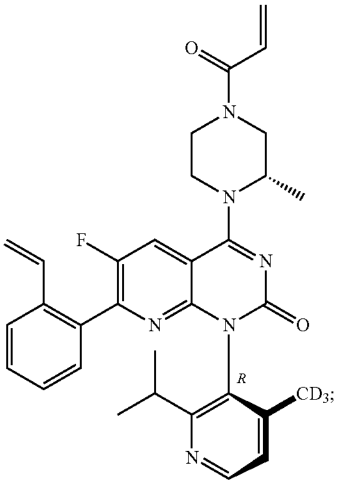
4-2M
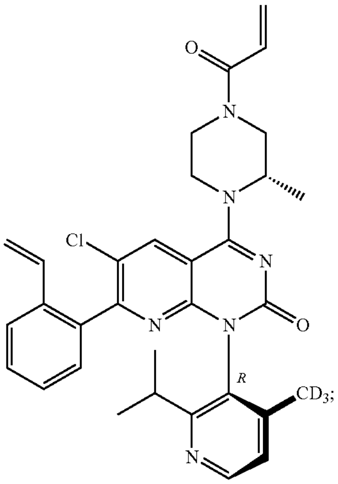
-continued
4-3M
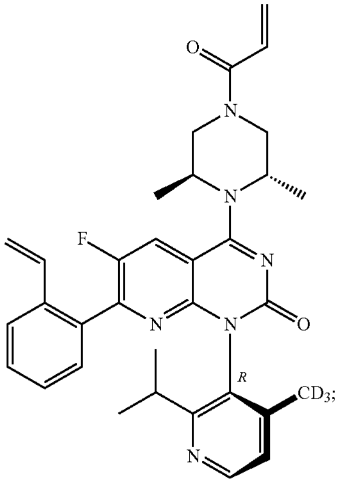
4-4M
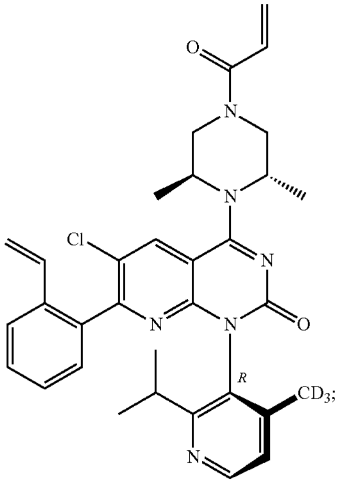
4-5M
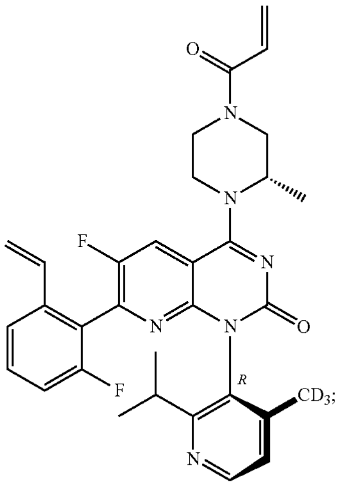

-continued
4-6M
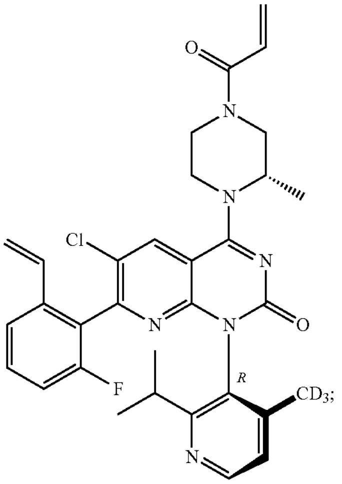
4-7M
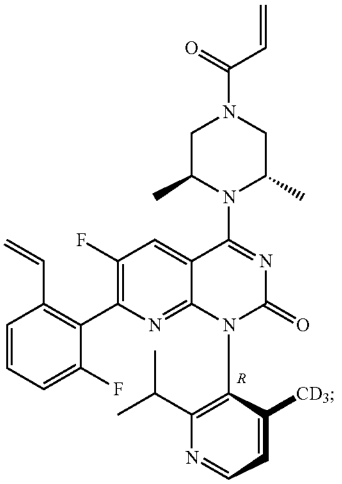
4-8M
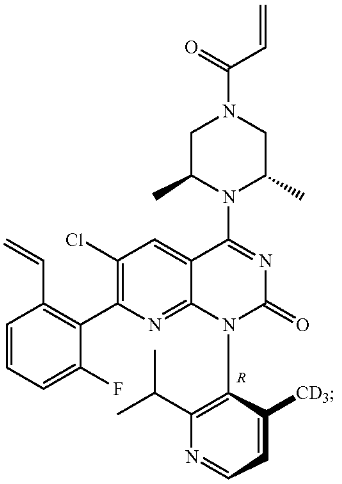
-continued
4-9M
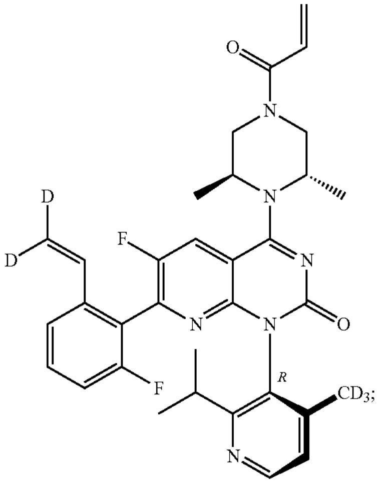
4-10M
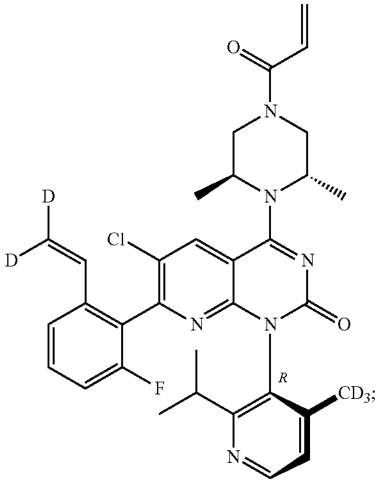
4-11M
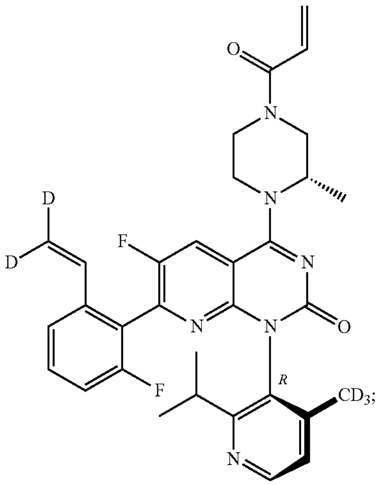

-continued
4-12M
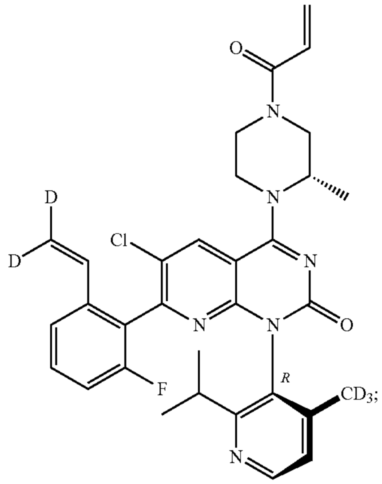
4-13M
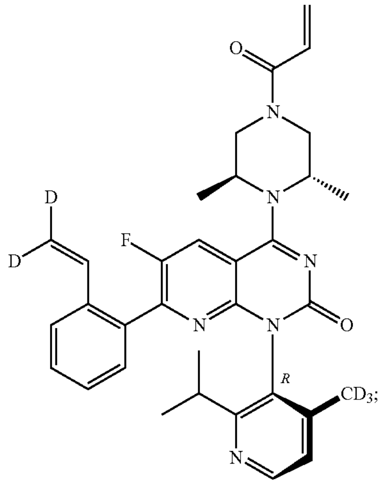
4-14M
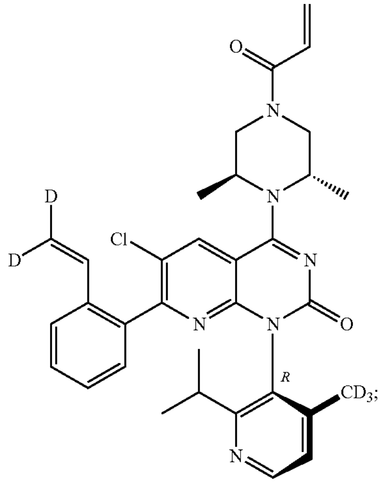
-continued
4-15M
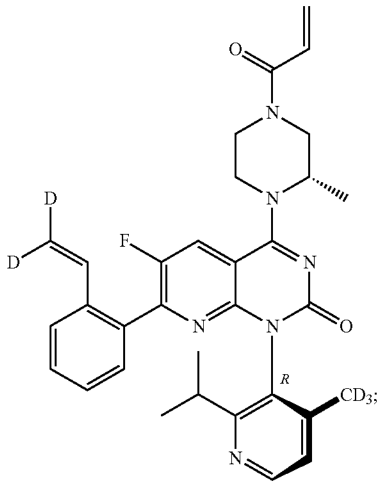
4-16M
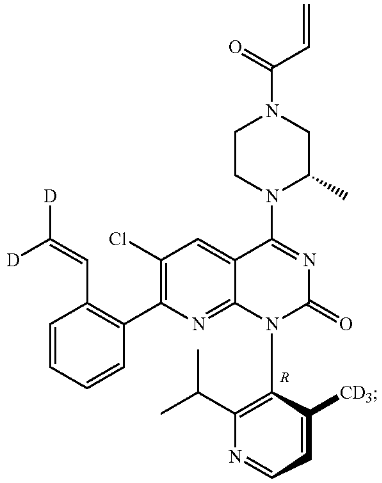
4-17M
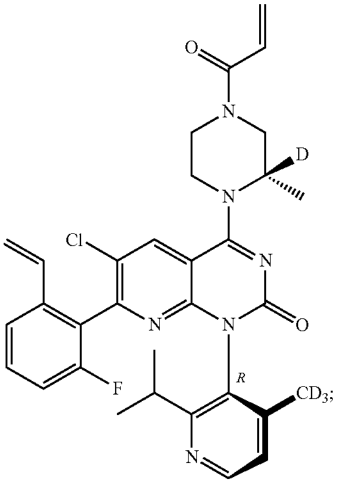

-continued
4-18M
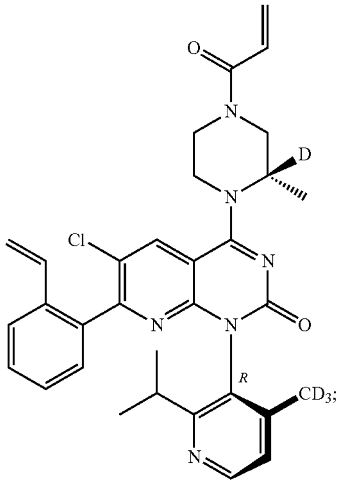
4-19M
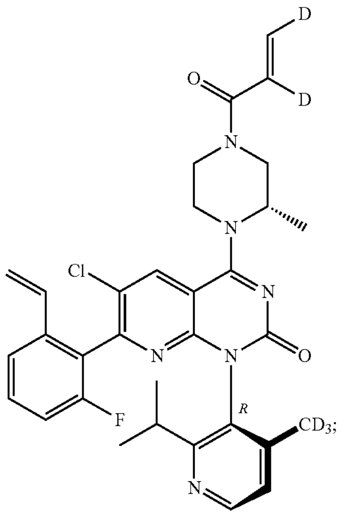
4-20M
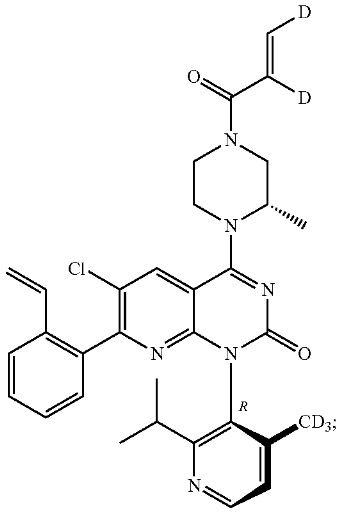
-continued
4-21M
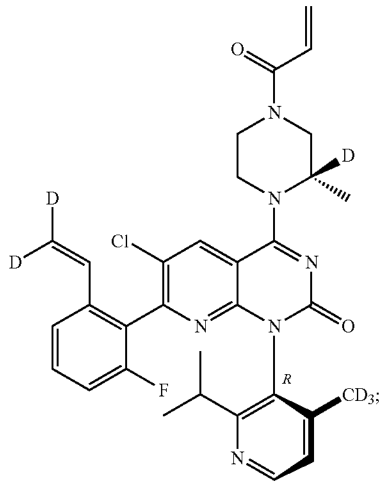
4-22M
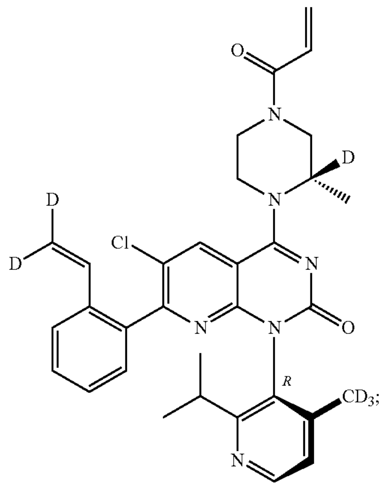
4-23M
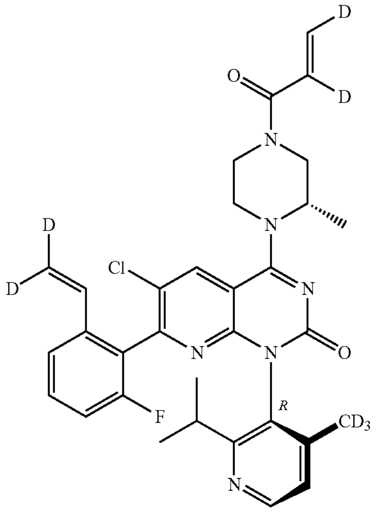
and -continued 4-24M

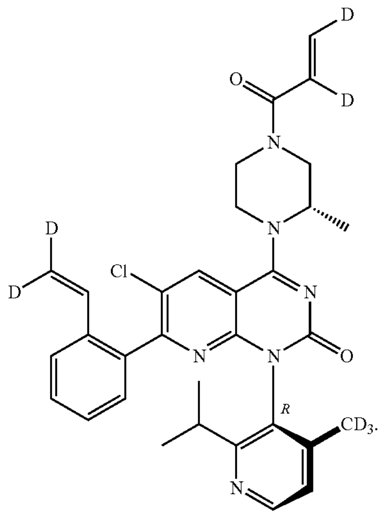

22. A pharmaceutical composition, comprising a therapeutically effective amount of the compound, or the stereoisomer, the tautomer, or the pharmaceutically acceptable salt thereof according to claim 19 and pharmaceutically available carriers.

23. A method for preventing and/or treating diseases associated with KRAS mutation mediated cancers or associated with KRAS G12C mutation mediated cancers, comprising administering a therapeutically effective amount of the compound, or the stereoisomer, the tautomer or the pharmaceutically acceptable salt thereof according to claim 19 or a pharmaceutical composition comprising the compound, or the stereoisomer, the tautomer or the pharmaceutically acceptable salt thereof according to claim 19 to a subject in need thereof, wherein the compound, or the stereoisomer, the tautomer or the pharmaceutically acceptable salt thereof is used alone or used in combination with other therapeutic methods including immunotherapy.

24. The method according to claim 23, wherein the diseases associated with KRAS mutation mediated cancers or associated with KRAS G12C mutation mediated cancers are liver cancer, esophageal cancer, gastric cancer, renal cell cancer, sarcoma, bile duct cancer, colon cancer, prostate cancer, ovarian cancer, breast cancer, hematological cancer, pancreatic cancer, MYH-associated polyposis, colorectal cancer, lung cancer, uterine cancer, mesothelioma, cervical cancer, or bladder cancer.

* * * * *